(12) United States Patent
Wurtz et al.

(10) Patent No.: US 8,420,830 B2
(45) Date of Patent: Apr. 16, 2013

(54) MACROCYCLIC FACTOR VIIA INHIBITORS USEFUL AS ANTICOAGULANTS

(75) Inventors: Nicholas Ronald Wurtz, Pennington, NJ (US); Eldon Scott Priestley, Yardley, PA (US); Daniel L. Cheney, Ringoes, NJ (US); Peter W. Glunz, Yardley, PA (US); Xiaojun Zhang, Furlong, PA (US); Brandon Parkhurst, Twin Rivers, NJ (US); Vladimir Ladziata, Ewing, NJ (US); Luciano Mueller, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 787 days.

(21) Appl. No.: 12/519,376

(22) PCT Filed: Dec. 19, 2007

(86) PCT No.: PCT/US2007/088032
§ 371 (c)(1),
(2), (4) Date: Sep. 24, 2009

(87) PCT Pub. No.: WO2008/079836
PCT Pub. Date: Jul. 3, 2008

(65) Prior Publication Data
US 2010/0113488 A1 May 6, 2010

Related U.S. Application Data

(60) Provisional application No. 60/870,864, filed on Dec. 20, 2006, provisional application No. 60/984,460, filed on Nov. 1, 2007.

(51) Int. Cl.
*A61K 31/405* (2006.01)

(52) U.S. Cl.
USPC ........... 548/454; 548/452; 548/416; 548/400; 514/415; 514/412; 514/410; 514/408; 514/359

(58) Field of Classification Search .................. None
See application file for complete search history.

(56) References Cited

U.S. PATENT DOCUMENTS

| 6,642,252 | B2 | 11/2003 | Bisacchi et al. |
| 7,122,559 | B2 | 10/2006 | Glunz et al. |
| 7,144,895 | B2 | 12/2006 | Bisacchi et al. |
| 7,456,195 | B2 | 11/2008 | Zhang et al. |
| 7,592,331 | B2 * | 9/2009 | Priestley et al. ............. 514/183 |

| 2006/0166997 | A1 | 7/2006 | Zhang et al. |
| 2007/0208054 | A1 | 9/2007 | Priestley et al. |
| 2009/0131473 | A1 | 5/2009 | Nirschl et al. |

FOREIGN PATENT DOCUMENTS

| WO | WO03/011222 A2 | 2/2003 |
| WO | WO2007/076431 A1 | 7/2007 |
| WO | WO2008/079759 A1 | 7/2008 |

OTHER PUBLICATIONS

U.S. Appl. No. 12/303,571.
U.S. Appl. No. 12/519,365.
Carson, S.D., "The role of tissue factor in the production of thrombin", Blood Coagulation and Fibrinolysis, vol. 4, pp. 281-292 (1993).
Giesen, P. et al., "Blood-borne tissue factor: Another view of thrombosis", PNAS, vol. 96, pp. 2311-2315 (1999).
Himber, J. et al., "Inhibition of tissue factor limits the growth of venous thrombus in the rabbit", J. of Thrombosis and Haemostasis, vol. 1, pp. 889-895 (2003).
Hoffman, M., "A cell-based model of coagulation and the role of factor VIIa", Blood Reviews, vol. 17, pp. S1-S5 (2003).
Morrissey, J.H., "Quantitation of activated factor VII levels in plasma using a tissue factor mutant selectively deficient in promoting factor VII activation", Blood, vol. 81, pp. 734-744 (1993).
Morrissey, J.H., "Tissue factor: in at the start . . . and the finish?", J. of Thrombosis and Haemostasis, vol. 1, pp. 878-880 (2003).

* cited by examiner

*Primary Examiner* — Brandon Fetterolf
*Assistant Examiner* — Theodore R West
(74) *Attorney, Agent, or Firm* — Jing G. Sun

(57) ABSTRACT

The present invention relates generally to novel macrocycles of Formula (I):

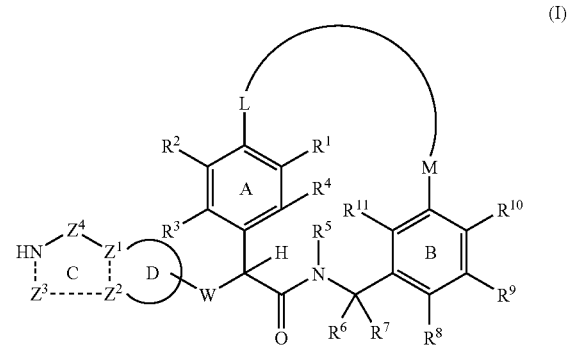

(I)

or stereoisomers, tautomers, pharmaceutically acceptable salts, solvates, or prodrugs thereof, wherein the variables A, B, C, D, L, M, W, $Z^1$, $Z^2$, $Z^3$, $Z^4$, $R^1$, $R^2$, $R^3$, $R^4$, $R^5$, $R^6$, $R^7$, $R^8$, $R^9$, and $R^{10}$ are as defined herein. These compounds are selective inhibitors of factor VIIa which can be used as medicaments.

17 Claims, No Drawings

MACROCYCLIC FACTOR VIIA INHIBITORS USEFUL AS ANTICOAGULANTS

CROSS-REFERENCE TO RELATED APPLICATIONS

The present application is a 371 application of PCT/US2007/088032 filed Dec. 19, 2007, which claims priority benefit of U.S. provisional applications Ser. No. 60/870,864, filed Dec. 20, 2006, and priority benefit of Ser. No. 60/984,460, filed Nov. 1, 2007, each of which is incorporated by reference herein.

FIELD OF THE INVENTION

The present invention provides novel macrocycles, and analogues thereof, which are selective inhibitors of the serine protease coagulation factor VIIa. This invention also relates to pharmaceutical compositions comprising these compounds and methods of using the same.

BACKGROUND OF THE INVENTION

Thromboembolic diseases remain the leading cause of death in developed countries despite the availability of anticoagulants such as warfarin (Coumadin®), heparin, low molecular weight heparins (LMWH), and synthetic pentasaccharides and antiplatelet agents such as aspirin and clopidogrel (Plavix®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor VIIa (FVIIa). Factor VII is a plasma serine protease involved in the initiation of the coagulation cascade. It is present in human blood at a concentration of approximately 500 ng/mL, with about 1% of the total amount in the proteolytically active form factor VIIIa (Morrissey, J. H. et al. *Blood* 1993, 81, 734-744). Factor VIIa binds with high affinity to its cofactor, tissue factor, in the presence of calcium ions to form a complex with enhanced proteolytic activity (Carson, S. D. and Brozna, J. P. *Blood Coag. Fibrinol.* 1993, 4, 281-292). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted form that is de-encrypted during clot formation. (Giesen, P. L. A. et al. *Proc. Natl. Acad. Sci.* 1999, 96, 2311-2315; Himber, J. et al. *J. Thromb. Haemost.* 2003, 1, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880). Therefore, factor VIIa plays a key role in propagating this amplification loop and is thus an attractive target for anti-thrombotic therapy.

SUMMARY OF THE INVENTION

The present invention provides novel macrocycles, and analogues thereof, which are useful as selective inhibitors of serine protease enzymes, especially factor VIIa, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of a thromboembolic disorder comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

These and other features of the invention will be set forth in expanded form as the disclosure continues.

DETAILED DESCRIPTION OF THE INVENTION

In a first aspect, the present invention provides, inter alia, a compound of Formula (I):

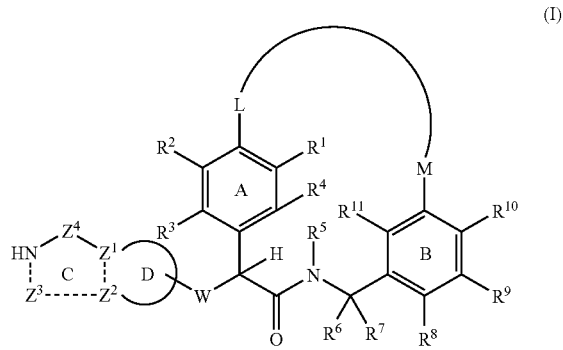

(I)

or stereoisomers, tautomers, pharmaceutically acceptable salts, solvates, or prodrugs thereof, wherein:

ring A is phenyl or a pyridyl isomer defined by replacing one of $CR^1$, $CR^2$, $CR^3$, or $CR^4$ in ring A of formula (I) with N;

ring B is phenyl or a pyridyl isomer defined by replacing one of $CR^8$, $CR^9$, $CR^{10}$, or $CR^{11}$ in ring B of formula (I) with N;

$Z^1$ is C or N;

$Z^2$ is C or N;

provided that when $Z^1$ is N, then $Z^2$ is C; or $Z^2$ is N, then $Z^1$ is C;

for the definition of $Z^3$, as they are written from left to right, the atom connectivity is in the order —NH—$Z^3$—$Z^2$—;

$Z^3$ is —$CR^{18}R^{18}$—, —$NR^{19}$—, —O—, $S(O)_p$—, —C(=O)—, —C(=NH)—, —$CR^{18}$=$CR^{18}$—, —$CR^{18}R^{18}CR^{18}R^{18}$—, —$CR^{18}$=N—, —$CR^{18}R^{18}NR^{19}$—, —$NR^{19}CR^{18}R^{18}$—, —$C(O)CR^{18}R^{18}$—, —$C(O)NR^{19}$—, —$CR^{18}R^{18}C(O)$—, —$C(O)C(O)$—, —$SO_2$—, —$SO_2CR^{18}R^{18}$—, —$CR^{18}R^{18}SO_2$—, —$CR^{18}R^{18}CR^{18}R^{18}CR^{18}R^{18}$—, —$CR^{18}$=$CR^{18}CR^{18}R^{18}$—, —$CR^{18}R^{18}CR^{18}$=$CR^{18}$—, —N=$CR^{18}CR^{18}R^{18}$—, —$CR^{18}R^{18}CR^{18}$=N—, —$CR^{18}R^{18}CR^{18}R^{18}O$—, —$NR^{19}CR^{18}R^{18}CR^{18}R^{18}$—, —$CR^{18}R^{18}CR^{18}R^{18}NR^{19}$—, —$C(O)CR^{18}R^{18}CR^{18}R^{18}$—, —$CR^{18}R^{18}C(O)CR^{18}R^{18}$—, —$CR^{18}R^{18}CR^{18}R^{18}C(O)$—, —$CR^{18}$=$CR^{18}C(O)$—, —$C(O)CR^{18}$=$CR^{18}$—, —N=$CR^{18}C(O)$—, —$C(O)CR^{18}$=N—, —$C(O)CR^{18}R^{18}O$—, —$NR^{19}C(O)CR^{18}R^{18}$—, —$CR^{18}R^{18}C(O)NR^{19}$—, —$NR^{19}CR^{18}R^{18}C(O)$—, —$C(O)CR^{18}R^{18}NR^{19}$—, —$C(O)NR^{19}CR^{18}R^{18}$—, —$SO_2CR^{18}R^{18}CR^{18}R^{18}$—, —$CR^{18}R^{18}SO_2CR^{18}R^{18}$—, —$CR^{18}R^{18}CR^{18}R^{18}SO_2$—, —$CR^{18}$=$CR^{18}SO_2$—, —$SO_2CR^{18}$=$CR^{18}$—, —N=$CR^{18}SO_2$—, —$SO_2CR^{18}$=N—, —$SO_2CR^{18}R^{18}O$—, —$NR^{19}SO_2CR^{18}R^{18}$—, —$CR^{18}R^{18}SO_2NR^{19}$—, —$NR^{19}CR^{18}R^{18}SO_2$—, —$SO_2CR^{18}R^{18}NR^{19}$—, or —$SO_2NR^{19}CR^{18}R^{18}$—;

provided that is other than:

$Z^4$ is C(O), $CR^{20}R^{20}$ or $SO_2$;

ring D, including the two atoms $Z^1$ and $Z^2$ which are fused to ring C, is phenyl substituted with 0-3 $R^{21}$ or a 5-6 membered heteroaryl consisting of: carbon atoms and 1-4 heteroatoms selected from the group consisting of N, O, and S, wherein said heteroaryl is substituted with 0-3 $R^{21}$;

for the definitions of L and M, as they are written from left to right, the atom connectivity is in the order (ring A)-L-M-(ring B);

M is —CONH—, —$SO_2NH$—, —NHCO—, or —$NHSO_2$—;

when M is —CONH—, L is selected from —$C(R^{12}R^{13})C(R^{12}R^{13})$—, —$XC(R^{12}R^{13})$—, —$C(R^{12}R^{13})_y$—, —$C(R^{12}R^{13})C(R^{12}R^{13})C(R^{12}R^{13})$—, —$XC(R^{12}R^{13})C(R^{12}R^{13})$—, —$C(R^{12}R^{13})XC(R^{12}R^{13})$—, —$C(R^{12}R^{13})C(R^{12}R^{13})Y$—, —$XC(R^{12}R^{13})Y$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, —$C(R^{12}R^{13})XC(R^{12}R^{13})C(R^{12}R^{13})$—, —$C(R^{12}R^{13})C(R^{12}R^{13})XC(R^{12}R^{13})$—, —$C(R^{12}R^{13})C(R^{12}R^{13})C(R^{12}R^{13})Y$—, —$XC(R^{12}R^{13})C(R^{12}R^{13})Y$—, and —$C(R^{12}R^{13})XC(R^{12}R^{13})Y$—;

when M is —$SO_2NH$—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})C(R^{12}R^{13})$—, —$C(R^{12}R^{13})XC(R^{12}R^{13})C(R^{12}R^{13})$—, —$C(R^{12}R^{13})C(R^{12}R^{13})$—, —$C(R^{12}R^{13})_y$—, —$C(R^{12}R^{13})C(R^{12}R^{13})C(R^{12}R^{13})Y$—, —$XC(R^{12}R^{13})C(R^{12}R^{13})Y$—, and —$C(R^{12}R^{13})XC(R^{12}R^{13})Y$—;

when M is —NHCO—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—;

when M is —$NHSO_2$—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—;

W is $NR^h$, O or S;

X is O, $S(O)_p$, or $NR^{16}$;

Y is O or $NR^{16a}$;

$R^1$ is H, F, Cl, Br, I, $C_{1-4}$ alkyl substituted with 0-1 OH, $C_{1-4}$ fluoroalkyl, $C_{2-4}$ alkenyl, $C_{2-4}$ alkynyl, $C_{1-4}$ alkoxy, $C_{1-4}$ alkylthio, or $C_{3-6}$ cycloalkyl;

$R^2$ is H, F, Cl, Br, I, —$(CH_2)_sOR^a$, —$(CH_2)_sSR^b$, —$(CH_2)_sCF_3$, —$(CH_2)_sOCF_3$, —$(CH_2)_sOCHF_2$, —$(CH_2)_sOCH_2F$, —$(CH_2)_sCN$, —$(CH_2)_sNO_2$, —$(CH_2)_sNR^cR^d$, —$(CH_2)_sC(O)R^a$, —$(CH_2)_sCO_2R^a$, —$(CH_2)_sNR^cC(O)R^a$, —$(CH_2)_sC(O)NR^cR^d$, —$(CH_2)_sNR^cC(O)OR^b$, —$(CH_2)_sOC(O)OR^b$, —$(CH_2)_sNR^cC(O)NR^cR^d$, —$(CH_2)_sOC(O)NR^cR^d$, —$(CH_2)_sSO_2NR^cR^d$, —$(CH_2)_sNR^cSO_2NR^cR^d$, —$(CH_2)_sNR^cSO_2R^b$, —$(CH_2)_sNR^cSO_2CF_3$, —$(CH_2)_sSO_2CF_3$, —$(CH_2)_sS(O)_2R^b$, $C_{1-6}$ alkyl substituted with 0-2 $R^e$, $C_{1-4}$ fluoroalkyl, $C_{2-4}$ alkenyl substituted with 0-2 $R^e$, $C_{2-4}$ alkynyl substituted with 0-2 $R^e$, —$(CH_2)_sC_{3-6}$ carbocycle substituted with 0-2 $R^f$—$(CH_2)_s$-(5- to 6-membered heterocycle), —$(CH_2)_s$—$NR^C$—(5- to 6-membered heterocycle), or —$(CH_2)_s$—O-(5- to 6-membered heterocycle); wherein said heterocycle comprises carbon atoms and 1-3 heteroatoms selected from N, $NR^c$, O, and $S(O)_p$ and is substituted with 0-2 $R^g$;

$R^3$ is H, F, Cl, Br, I, —$(CH_2)_sOR^a$, —$(CH_2)_sSR^b$, —$(CH_2)_sCF_3$, —$(CH_2)_sOCF_3$, —$(CH_2)_sOCHF_2$, —$(CH_2)_sOCH_2F$, —$(CH_2)_sCN$, —$(CH_2)_sNO_2$, —$(CH_2)_sNR^cR^d$, —$(CH_2)_sC(O)R^a$, —$(CH_2)_sCO_2R^a$, —$(CH_2)_sNR^cC(O)R^a$, —$(CH_2)_sC(O)NR^cR^d$, —$(CH_2)_sNR^cC(O)OR^b$, —$(CH_2)_sOC(O)OR^b$, —$(CH_2)_sNR^cC(O)NR^cR^d$, —$(CH_2)_sOC(O)NR^cR^d$, —$(CH_2)_sSO_2NR^cR^d$, —$(CH_2)_sNR^cSO_2NR^cR^d$, —$(CH_2)_sNR^cSO_2R^b$, —$(CH_2)_sNR^cSO_2CF_3$, —$(CH_2)_sSO_2CF_3$, —$(CH_2)_sS(O)_2R^b$, —$O(CH_2)_nCO_2R^a$, —$(CH_2)_sSO_2NHCOR^b$,

—(CH$_2$)$_s$CONHSO$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —O(benzyl substituted with CO$_2$R$^a$), —(CH$_2$)$_s$tetrazolyl, —(CH$_2$)$_s$—C$_{3-6}$ carbocycle substituted with 0-2 R$^{f1}$, —(CH$_2$)$_s$-(5- to 6-membered heterocycle), —(CH$_2$)$_s$—NR$^c$-(5- to 6-membered heterocycle), or —(CH$_2$)$_s$—O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;

alternatively, R$^2$ and R$^3$ may combine to form a 5- to 7-membered carbocycle or heterocycle comprising: carbon atoms and 0-2 heteroatoms selected from N, NR$^c$, O, and S(O)$_p$; wherein said carbocycle and heterocycle are substituted with 0-3 R$^{g1}$;

R$^4$ is H, F, Cl, Br, I, or C$_{1-4}$ alkyl;

R$^5$ is H, —(CH$_2$)$_q$OR$^a$, —(CH$_2$)$_q$SR$^b$, —(CH$_2$)$_r$CF$_3$, —(CH$_2$)$_q$OCF$_3$, —(CH$_2$)$_q$OCHF$_2$, —(CH$_2$)$_q$OCH$_2$F, —(CH$_2$)$_q$CN, —(CH$_2$)$_q$NO$_2$, —(CH$_2$)$_q$NR$^c$R$^d$, —(CH$_2$)$_s$C(O)R$^a$, —(CH$_2$)$_s$CO$_2$R$^a$, —(CH$_2$)NR$^c$C(O)R$^a$, —(CH$_2$)$_s$C(O)NR$^c$R$^d$, —(CH$_2$)$_q$NR$^c$C(O)OR$^b$, —(CH$_2$)$_q$OC(O)OR$^b$, —(CH$_2$)$_q$NR$^c$C(O)NR$^c$R$^d$, —(CH$_2$)$_q$OC(O)NR$^c$R$^d$, —(CH$_2$)$_q$SO$_2$NR$^c$R$^d$, —(CH$_2$)$_q$NR$^c$SO$_2$NR$^c$R$^d$, —(CH$_2$)$_q$NR$^c$SO$_2$R$^b$, —(CH$_2$)$_q$NR$^c$SO$_2$CF$_3$, —(CH$_2$)$_q$SO$_2$CF$_3$, —(CH$_2$)$_q$S(O)$_2$R$^b$, —(CH$_2$)$_q$SO$_2$NHCOR$^b$, —(CH$_2$)$_s$CONHSO$_2$R$^b$, —O(benzyl substituted with CO$_2$R$^a$), —(CH$_2$)$_s$tetrazolyl, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^{g1}$;

R$^6$ is H, —(CH$_2$)$_r$OR$^a$, —(CH$_2$)$_r$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, —(CH$_2$)$_r$NR$^c$R$^d$, —(CH$_2$)$_s$C(O)R$^a$, —(CH$_2$)$_s$CO$_2$R$^a$, —(CH$_2$)$_r$NR$^c$C(O)R$^a$, —(CH$_2$)$_s$C(O)NR$^c$R$^d$, —(CH$_2$)$_r$NR$^c$C(O)OR$^b$, —(CH$_2$)$_r$OC(O)OR$^b$, —(CH$_2$)$_r$NR$^c$C(O)NR$^c$R$^d$, —(CH$_2$)$_r$OC(O)NR$^c$R$^d$, —(CH$_2$)$_r$SO$_2$NR$^c$R$^d$, —(CH$_2$)$_r$NR$^c$SO$_2$NR$^c$R$^d$, —(CH$_2$)$_r$NR$^c$SO$_2$R$^b$, —(CH$_2$)$_r$NR$^c$SO$_2$CF$_3$, —(CH$_2$)$_r$SO$_2$CF$_3$, —(CH$_2$)$_r$S(O)$_2$R$^b$, —(CH$_2$)$_r$SO$_2$NHCOR$^b$, —(CH$_2$)$_s$CONHSO$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^{g1}$;

alternatively, R$^5$ and R$^6$ can be joined to form a 2 to 5-membered alkylene chain, which may be substituted with 0-1 R$^{f1}$;

R$^7$ is H or C$_{1-6}$ alkyl;

alternatively, R$^6$ and R$^7$ can be joined to form a 3-7 membered carbocycle or heterocycle; wherein said carbocycle may be substituted with 0-2 R$^{f1}$; and said heterocycle comprises carbon atoms and 1-3 heteroatoms selected from N, NR$^c$, O, and S(O)$_p$ and is substituted with 0-2 R$^{g1}$;

R$^8$ is H, F, Cl, Br, CN, CH$_2$F, CHF$_2$, —(CH$_2$)$_s$CF$_3$, —(CH$_2$)$_s$CN, —(CH$_2$)$_s$NO$_2$, C$_{1-6}$ alkyl, C$_{2-6}$ alkenyl, C$_{2-6}$ alkynyl, —(CH$_2$)$_n$—OR$^i$, —(CH$_2$)$_n$—SR$^j$, —(CH$_2$)$_n$—NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$CONR$^c$R$^d$, —(CH$_2$)$_s$SO$_2$R$^j$, —(CH$_2$)$_s$SO$_2$NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$^c$R$^d$, —(CH$_2$)$_s$NR$^c$SO$_2$NR$^c$R$^d$, —(CH$_2$)$_s$NR$^c$SO$_2$RJ, —(CH$_2$)$_s$NR$^c$SO$_2$CF$_3$, —(CH$_2$)$_s$SO$_2$CF$_3$, —O(CH$_2$)$_n$CO$_2$R$^a$, —(CH$_2$)$_s$SO$_2$NHCOR$^b$, —(CH$_2$)$_s$CONHSO$_2$R$^j$, —O(benzyl substituted with CO$_2$R$^a$), —(CH$_2$)$_s$tetrazolyl, C$_{1-6}$ alkyl substituted with 0-3 R$^e$, C$_{1-4}$ fluoroalkyl, C$_{2-4}$ alkenyl substituted with 0-3 R$^e$, C$_{2-4}$ alkynyl substituted with 0-3 R$^e$, —(CH$_2$)$_s$—C$_{3-6}$ carbocycle substituted with 0-3 R$^{f1}$, —(CH$_2$)$_n$-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$, or —O-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$;

R$^9$, R$^{10}$, and R$^{11}$ are, independently at each occurrence, H, F, Cl, Br, I, C$_{1-4}$ alkyl, or C$_{1-4}$ alkoxy;

R$^{12}$ and R$^{13}$ are, independently at each occurrence, H, F, Cl, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —OC(O)OR$^a$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, —(CH$_2$)$_s$-(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;

alternatively, any two R$^{12}$ or R$^{13}$ attached to either the same carbon or to two adjacent carbons may combine to form a 3- to 7-membered carbocycle or heterocycle comprising: carbon atoms and 0-3 heteroatoms selected from N, NR$^c$, O, and S(O)$_p$, wherein said carbocycle or heterocycle is substituted with 0-3 R$^g$;

alternately, two R$^{12}$ or R$^{13}$ on the same carbon atom can be replaced with oxo;

optionally, two R$^{12}$ or R$^{13}$ on adjacent carbon atoms in L may be replaced with a double bond between the two carbon atoms or four R$^{12}$ or R$^{13}$ on adjacent carbon atoms in L may be replaced with a triple bond between the two carbon atoms;

R$^{16}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —CH$_2$C(O)OR$^b$, —SO$_2$NR$^c$R$^d$, —SO$_2$CF$_3$, —S(O)$_2$R$^b$, or —(CH$_2$)$_s$-(5- to 6-membered heterocycle); wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{16a}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —CH$_2$C(O)OR$^b$, —SO$_2$NR$^c$R$^d$, —SO$_2$CF$_3$, —S(O)$_2$R$^b$, or 5- to 6-membered heterocycle; wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{17}$ is, independently at each occurrence, H or Me;

R$^{18}$ is, independently at each occurrence, H, F, Cl, Br, I, CF$_3$, OCF$_3$, OCHF$_2$, OCH$_2$F, CN, C$_{1-4}$ alkoxy, C$_{1-4}$ haloalkyl, C$_{1-4}$ alkyl, C$_{2-4}$ alkenyl, C$_{2-4}$ alkynyl, or C$_{3-6}$ cycloalkyl;

R$^{19}$ is, independently at each occurrence, is, independently at each occurrence, H, C$_{1-4}$ alkyl, C$_{2-4}$ alkenyl, or C$_{2-4}$ alkynyl;

R$^{20}$ is, independently at each occurrence, H, CF$_3$, C$_{1-6}$ alkyl substituted with 0-2 R$^e$, C$_{1-4}$haloalkyl, C$_{2-4}$ alkenyl substituted with 0-2 R$^e$, C$_{2-4}$ alkynyl substituted with 0-2 R$^e$, or —(CH$_2$)$_s$-(5- to 6-membered heterocycle); wherein said heterocycle comprises carbon atoms and 1-3 heteroatoms selected from N, $NR^c$, O, and $S(O)_p$ and is substituted with 0-2 $R^{g1}$;

$R^{21}$ is, independently at each occurrence, F, Cl, Br, I, CN, OH, $CF_3$, $C_{1-4}$ alkyl, $C_{1-4}$ haloalkyl, $C_{1-4}$ alkoxy, or $C_{3-6}$ cycloalkyl;

$R^a$ is, independently at each occurrence, H, $C_{1-4}$ alkyl, $C_{3-6}$ cycloalkyl, fluoroalkyl, phenyl, or benzyl; wherein said alkyl and cycloalkyl are optionally substituted with 0-2 $R^e$, and said phenyl and benzyl are optionally substituted with 0-2 $R^f$;

$R^b$ is, independently at each occurrence, $C_{1-4}$ alkyl, $C_{3-6}$ cycloalkyl, fluoroalkyl, phenyl, or benzyl; wherein said alkyl and cycloalkyl are optionally substituted with 0-2 $R^e$, and said phenyl and benzyl are optionally substituted with 0-2 $R^f$;

$R^c$ and $R^d$ are, independently at each occurrence, H, $C_{1-4}$ alkyl, $C_{3-6}$ cycloalkyl, fluoroalkyl, phenyl, or benzyl;

alternatively, $R^c$ and $R^d$, when attached to the same nitrogen atom, combine to form a 4- to 7-membered heterocycle comprising: carbon atoms and 0-2 additional heteroatoms selected from N, O, and $S(O)_p$; wherein said heterocycle is substituted with 0-2 $R^g$;

$R^e$ is, independently at each occurrence, F, $CF_3$, OH, or $C_{1-3}$ alkoxy;

$R^f$ is, independently at each occurrence, F, Cl, Br, $CF_3$, OH, $C_{1-3}$ alkyl, or $C_{1-3}$ alkoxy;

$R^{f1}$ is, independently at each occurrence, $R^f$, $-CO_2R^a$, $-C(O)NR^cR^d$, $-CONHSO_2R^b$, or $-CH_2CONHSO_2Rb$;

$R^g$ is, independently at each occurrence, =O, F, Cl, Br, $CF_3$, OH, $C_{1-3}$ alkyl, $C_{1-3}$ fluoroalkyl, $C_{1-3}$ alkoxy or $C_{1-3}$ fluoroalkoxy;

$R^{g1}$ is, independently at each occurrence, $R^g$, $-CO_2R^a$, $-C(O)NR^cR^d$, $-CONHSO_2R^b$, or $-CH_2CONHSO_2Rb$;

$R^h$ is, independently at each occurrence, H or $C_{1-3}$ alkyl;

$R^i$ is, independently at each occurrence, H, $C_{1-4}$ alkyl, $C_{3-6}$ cycloalkyl, phenyl, or benzyl; wherein said alkyl and cycloalkyl are optionally substituted with 0-2 $R^k$ and 0-5 F; and said phenyl and benzyl are optionally substituted with 0-2 $R^f$;

$R^j$ is, independently at each occurrence, $C_{1-4}$ alkyl, $C_{3-6}$ cycloalkyl, phenyl, or benzyl; wherein said alkyl and cycloalkyl are optionally substituted with 0-2 $R^k$ and 0-5 F, and said phenyl and benzyl are optionally substituted with 0-2 $R^f$;

$R^k$ is, independently at each occurrence, $CF_3$, OH, or $C_{1-3}$ alkoxy;

n, at each occurrence, is selected from 0, 1, 2, 3, and 4;
p, at each occurrence, is selected from 0, 1, and 2;
q, at each occurrence is selected from 2 or 3;
r, at each occurrence is selected from 1, 2, or 3; and
s, at each occurrence, is selected from 0, 1, and 2.

In another aspect, the present invention includes the compounds of Formula (I) or stereoisomers, tautomers, pharmaceutically acceptable salts, solvates, or prodrugs thereof, within the scope of the first aspect wherein:

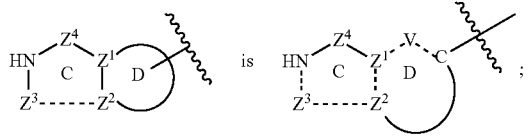

wherein V is selected from $CR^{21}$, S, O and N when $Z^1$=C; alternatively, V=$CR^{21}$ when $Z^1$=N.

In a second aspect, the present invention includes the compounds of Formula (I) or stereoisomers, tautomers, pharmaceutically acceptable salts, solvates, or prodrugs thereof, within the scope of the first aspect wherein:

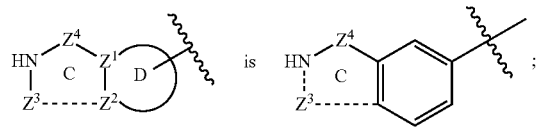

wherein the phenyl ring is substituted with 0-3 $R^{21}$.

In a third aspect, the present invention includes the compounds of Formula (I), or stereoisomers, tautomers, pharmaceutically acceptable salts, solvates, or prodrugs thereof, within the scope of the first aspect wherein:

is selected from:

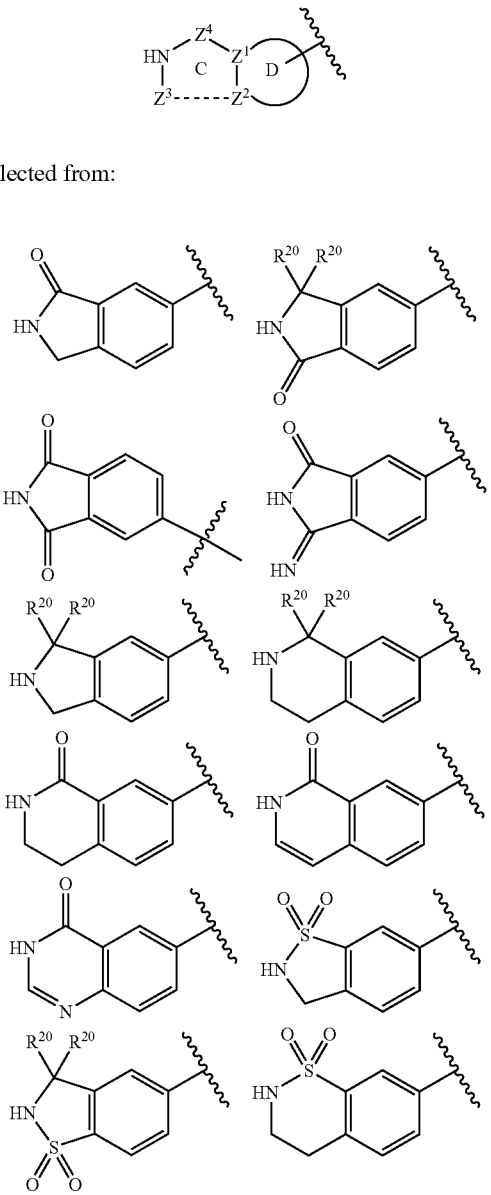

-continued

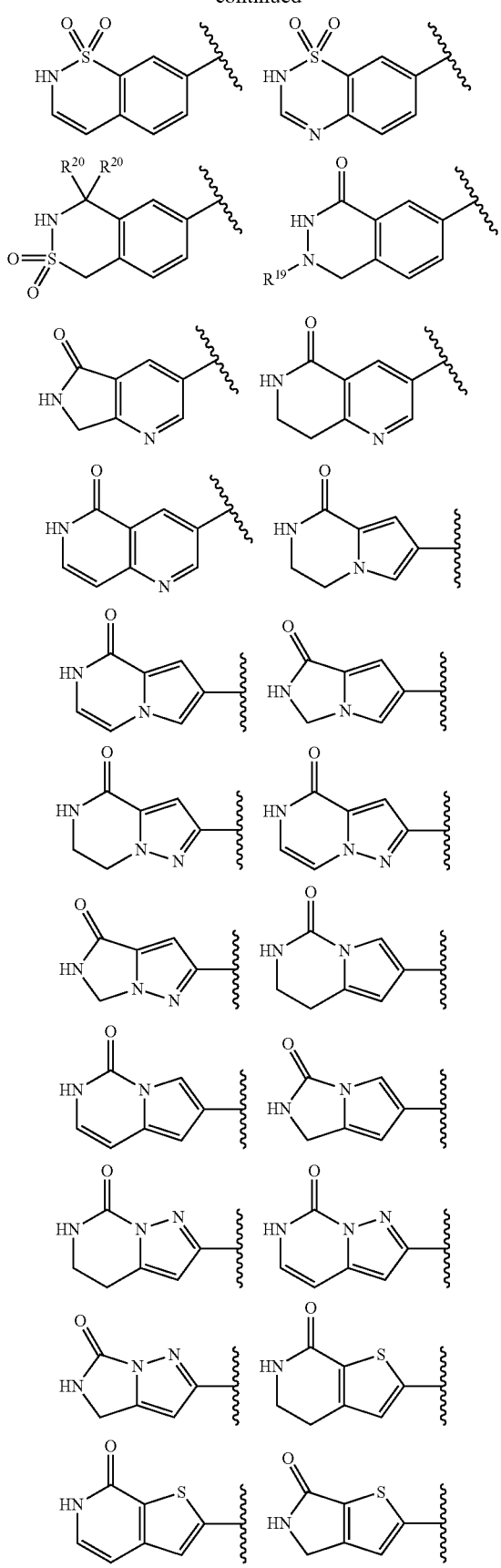

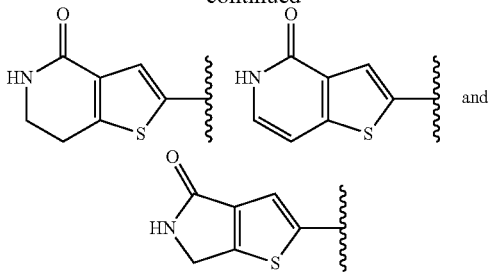

and wherein ring C is substituted with 0-2 $R^{18}$; and ring D is substituted with 0-2 $R^{21}$;

M is —CONH—, —SO$_2$NH—, —NHCO—, or —NHSO$_2$—;

when M is —CONH—, L is selected from —C($R^{12}R^{13}$)C($R^{12}R^{13}$)—, —XC($R^{12}R^{13}$)—, —C($R^{12}R^{13}$)Y—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)XC($R^{12}R^{13}$), —C($R^{12}R^{13}$)C($R^{12}R^{13}$)Y—, —XC($R^{12}R^{13}$)Y—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, —C($R^{12}R^{13}$)XC($R^{12}R^{13}$)C($R^{12}R^{13}$)—, —C($R^{12}R^{13}$)C($R^{12}R^{13}$)XC($R^{12}R^{13}$)—, —C($R^{12}R^{13}$)C($R^{12}R^{13}$)C($R^{12}R^{13}$)Y—, and —XC($R^{12}R^{13}$)C($R^{12}R^{13}$)Y—;

when M is —SO$_2$NH—, L is selected from —C($R^{12}R^{13}$)C($R^{12}R^{13}$)—, —C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

when M is —NHCO—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

when M is —NHSO$_2$—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

X is O, S, or $NR^{16}$;

W is NH or O;

$R^2$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, $C_{1-6}$ alkyl substituted with 0-2 R$^e$, $C_{2-4}$ alkenyl substituted with 0-2 R$^e$, $C_{2-4}$ alkynyl substituted with 0-2 R$^e$, $C_{3-6}$ carbocycle substituted with 0-2 R$^f$, —(CH$_2$)$_s$-(5- to 6-membered heterocycle), —NR$^c$—(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^g$;

$R^3$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, —O(CH$_2$)$_n$CO$_2$R$^a$, —SO$_2$NHCOR$^b$, —CONHSO$_2$R$^b$, $C_{1-6}$ alkyl substituted with 0-2 R$^e$, $C_{2-4}$ alkenyl substituted with 0-2 R$^e$, $C_{2-4}$ alkynyl substituted with 0-2 R$^e$, —O(benzyl substituted with CO$_2$R$^a$), or tetrazolyl;

alternatively, $R^2$ and $R^3$ may combine to form a 5- to 7-membered carbocycle or heterocycle comprising: carbon atoms and 0-2 heteroatoms selected from N, NR$^c$, O, and S(O)$_p$; wherein said carbocycle and heterocycle are substituted with 0-3 R$^g$;

R$^5$ is H, —CH$_2$CH$_2$OR$^a$, —CH$_2$CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$CH$_2$NR$^c$R$^d$, —CH$_2$C(O)NR$^c$R$^d$, —CH$_2$CH$_2$C(O)NR$^c$R$^d$, —CH$_2$CONHSO$_2$R$^b$, —CH$_2$CH$_2$CONHSO$_2$R$^b$, C$_{1-6}$ alkyl substituted with 0-2 R$^e$, —(CH$_2$)$_s$—C$_{3-6}$ carbocycle substituted with 0-2 R$^f$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^g$;

R$^6$ is H, —CH$_2$OR$^a$, —CH$_2$CH$_2$OR$^a$, CN, —CO$_2$R$^a$, —C(O)NR$^c$R$^d$, —CH$_2$CO$_2$R$^a$, —CH$_2$C(O)NR$^c$R$^d$, —CONHSO$_2$R$^b$, —CH$_2$CONHSO$_2$R$^b$, C$_{1-6}$ alkyl substituted with 0-2 R$^e$, —(CH$_2$)$_s$—C$_{3-6}$ carbocycle substituted with 0-2 R$^f$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^g$;

alternatively, R$^5$ and R$^6$ can be joined to form a 2 to 5-membered alkylene chain, which may be substituted with 0-1 R$^{f1}$;

R$^7$ is H or C$_{1-6}$ alkyl;

alternatively, R$^6$ and R$^7$ can be joined to form a 3-7 membered carbocycle or heterocycle; wherein said carbocycle may be substituted with 0-2 R$^f$1; and said heterocycle comprises carbon atoms and 1-3 heteroatoms selected from N, NR$^c$, O, and S(O)$_p$ and is substituted with 0-2 R$^{g1}$;

R$^9$ is H, F, Cl, Br, I, C$_{1-4}$ alkyl, or C$_{1-4}$ alkoxy;

R$^{10}$ and R$^{11}$ are, independently at each occurrence, H, F, Cl, Br, I, or C$_{1-4}$ alkyl;

R$^{12}$ and R$^{13}$ are, independently at each occurrence, H, F, Cl, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^f$, —(CH$_2$)$_s$-(5- to 6-membered heterocycle), —NR$^C$—(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;

alternatively, any two R$^{12}$ or R$^{13}$ attached to either the same carbon or to two adjacent carbons may combine to form a 5- to 7-membered carbocycle or heterocycle comprising: carbon atoms and 0-3 heteroatoms selected from N, NR$^c$, O, and S(O)$_p$, wherein said carbocycle or heterocycle is substituted with 0-3 R$^g$; and optionally, two R$^{12}$ or R$^{13}$ on adjacent carbon atoms in L may be replaced with a double bond between the two carbon atoms, In a fourth aspect, the present invention includes the compounds of Formula (I), or stereoisomers, tautomers, pharmaceutically acceptable salts, solvates, or prodrugs thereof, within the scope of the first, second, or third aspect wherein:

ring A is phenyl or a pyridyl isomer defined by replacing one of CR$^1$, CR$^2$, CR$^3$, or CR$^4$ in ring A of formula (I) with N;

ring B is phenyl or a pyridyl isomer defined by replacing one of CR$^8$, CR$^9$, CR$^{10}$, or CR$^{11}$ in ring B of formula (I) with N;

with the proviso that when ring A is pyridyl, then ring B is not pyridyl;

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, XC(R$^{12}$R$^{13}$)Y—, and —C(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$), —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

W is NH or O; and

R$^4$ is H or F.

In a fifth aspect, the present invention includes the compounds of Formula (I), or stereoisomers, tautomers, pharmaceutically acceptable salts, solvates, or prodrugs thereof, within the scope of the first, second, third, or fourth aspect wherein:

ring A is phenyl;

ring B is phenyl;

M is —CONH— or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, and —C(R$^{12}$R$^{13}$)C(R$^{12}$R$^{13}$)Y—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, and —XC(R$^{12}$R$^{13}$)C(R$^{12}$R$^{13}$)—;

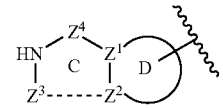

is selected from:

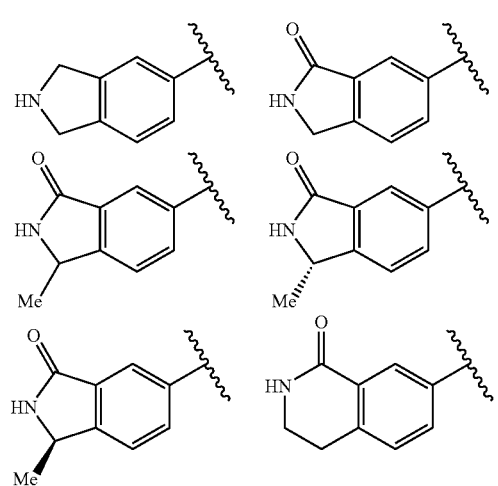

-continued

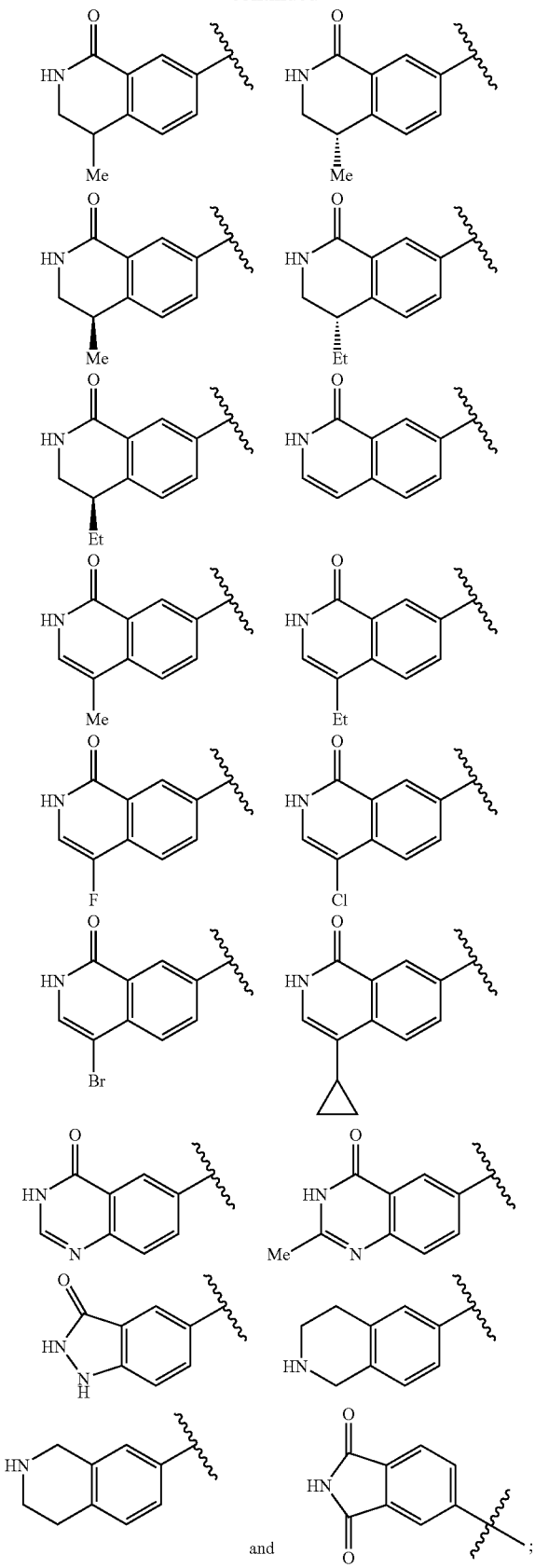

wherein ring D is optionally substituted with 0-1 F;

W is NH;

$R^1$ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl;

$R^2$ is H, F, Cl, $OR^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O-(5- to 6-membered heterocycle); wherein said heterocycle comprises carbon atoms and 1-3 heteroatoms selected from N, $NR^c$, O, and $S(O)_p$ and is substituted with 0-2 $R^g$;

$R^3$ is H, F, Cl, $OR^a$, —$O(CH_2)_nCO_2R^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O(benzyl substituted with $CO_2R^a$);

$R^4$ is H;

$R^5$ is H, $C_{1-4}$ alkyl, —$CH_2CH_2OR^a$, —$CH_2CH_2CH_2OR^a$, —$CH_2CO_2R^a$, —$CH_2CH_2CO_2R^a$, —$CH_2CH_2CH_2CO_2R^a$, —$CH_2CH_2NHCO_2R^b$, —$CH_2CH_2NR^cR^d$, —$CH_2C(O)NR^cR^d$, or —$CH_2CH_2C(O)NR^cR^d$;

$R^6$ is H, —$CH_2OR^a$, —$CH_2CH_2OR^a$, CN, $C_{1-4}$ alkyl, —$CO_2R^a$, —$C(O)NR^cR^d$, —$CH_2CO_2R^a$, or —$CH_2C(O)NR^cR^d$;

$R^7$ is H;

$R^8$ is H, F, Cl, Br, CN, $CH_2F$, $CHF_2$, —$(CH_2)_sCF_3$, $C_{1-6}$ alkyl, $C_{2-6}$ alkenyl, $C_{2-6}$ alkynyl, —$(CH_2)_n$—$OR^i$, —$(CH_2)_n$—$SR^j$, —$(CH_2)_n$—$NR^cR^d$, —$(CH_2)_sCO_2R^a$, —$(CH_2)_sNR^cC(O)R^a$, —$(CH_2)_sCONR^cR^d$, —$(CH_2)_sSO_2R^1$, —$(CH_2)_sSO_2NR^cR^d$, $NR^cSO_2RJ$, $NR^cSO_2CF_3$, —$SO_2CF_3$, —O(benzyl substituted with $CO_2R^a$), $C_{1-6}$ alkyl substituted with 0-3 $R^e$, $C_{1-4}$ fluoroalkyl, $C_{2-4}$ alkenyl substituted with 0-3 $R^e$, $C_{2-4}$ alkynyl substituted with 0-3 $R^e$, —$(CH_2)_s$—$C_{3-6}$ carbocycle substituted with 0-3 $R^{f1}$, —$(CH_2)_n$-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$, or —O-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$; and $R^9$, $R^{10}$ and $R^{11}$ are, independently at each occurrence, H, F, or Cl.

In a sixth aspect, the present invention includes the compounds of Formula (I), or stereoisomers, tautomers, pharmaceutically acceptable salts, solvates, or prodrugs thereof, within the scope of any one of the above aspects, wherein:

ring A is phenyl;

ring B is phenyl;

M is —CONH—;

L is selected from —$C(R^{12}R^{13})C(R^{12}R^{13})$—, —XC$(R^{12}R^{13})$—, —$C(R^{12}R^{13})_y$—, —$C(R^{12}R^{13})C(R^{12}R^{13})C(R^{12}R^{13})$—, —$C(R^{12}R^{13})XC(R^{12}R^{13})$—, and —$C(R^{12}R^{13})C(R^{12}R^{13})Y$—;

W is NH;

$R^1$ is H, Cl, Br, methyl, ethyl, vinyl, 2-propenyl, allyl, ethynyl, 1-propynyl, methoxy, ethoxy, or cyclopropyl;

$R^8$ is H, F, Cl, Br, CN, —$(CH_2)_n$—$OR^i$, —$(CH_2)_n$—$SR^j$, —$(CH_2)_n$—$NR^cR^d$, $NR^cC(O)R^a$, $CONR^cR^d$, —$(CH_2)_sSO_2R^j$, —$(CH_2)_sSO_2NR^cR^d$, $NR^cSO_2R^j$, $NR^cSO_2CF_3$, —$SO_2CF_3$, —O(benzyl substituted with $CO_2R^a$), $C_{1-6}$ alkyl substituted with 0-3 $R^e$, $C_{1-4}$ fluoroalkyl, $C_{2-4}$ alkenyl substituted with 0-3 $R^e$, $C_{2-4}$ alkynyl substituted with 0-3 $R^e$, —$(CH_2)_s$—$C_{3-6}$ carbocycle substituted with 0-3 $R^{f1}$, —$(CH_2)_n$-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$, or —O-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$.

In a seventh aspect, the present invention includes the compounds of Formula (I), or stereoisomers, tautomers, pharmaceutically acceptable salts, solvates, or prodrugs thereof, within the scope of any one of the above aspects, wherein:

L is selected from —C(R$^{12}$R$^{13}$)C(R$^{12}$R$^{13}$)C(R$^{12}$R$^{13}$)—, —C(R$^{12}$R$^{13}$)NR$^{16}$C(R$^{12}$R$^{13}$), —C(R$^{12}$R$^{13}$)C(R$^{12}$R$^{13}$)Y—, —C(R$^{12}$R$^{13}$)C(R$^{12}$R$^{13}$)—, —C(R$^{12}$R$^{13}$)NR$^{16}$— or —OC(R$^{13}$)—;

is selected from:

Y is O or NMe;
R$^1$ is H, Cl, Br, methyl, ethyl, vinyl, 2-propenyl, ethynyl, methoxy, or ethoxy;
R$^3$ is H, F, Cl, Me, OCH$_2$CO$_2$H;
R$^5$ is H, C$_{1-4}$ alkyl, —CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$NR$^c$R$^d$, —CH$_2$C(O)NR$^c$R$^d$, or —CH$_2$CH$_2$C(O)NR$^c$R$^d$;
R$^6$ is H, C$_{1-4}$ alkyl, —CO$_2$R$^a$, —C(O)NR$^c$R$^d$, —CH$_2$CO$_2$R$^a$, or —CH$_2$C(O)NR$^c$R$^d$;
R$^{12}$ and R$^{13}$ are, independently at each occurrence, H, methyl, ethyl, propyl, isopropyl, cyclopropyl, t-butyl, methoxy, ethoxy, propoxy, isopropoxy, cyclopropoxy, OH, CH$_2$OH, OCH$_2$OMe, or NHCO$_2$Bn, with the proviso that no more than two of R$^{12}$ and R$^{13}$ in L are other than H; and
R$^{16}$ is H, C$_{1-4}$ alkyl, —C(O)R$^a$, —C(O)NR$^c$R$^d$, —C(O)OR$^b$, —CH$_2$C(O)OR$^b$, or —S(O)$_2$Rb.

In an eighth aspect, the present invention includes the compounds of Formula (I), or stereoisomers, tautomers, pharmaceutically acceptable salts, solvates, or prodrugs thereof, within the scope of any one of the above aspects, wherein:

L is —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)NR$^{16}$C(R$^{12}$R$^{13}$)—, —C(R$^{12}$R$^{13}$)C(R$^{12}$R$^{13}$)NH—, —C(R$^{12}$R$^{13}$)C(R$^{12}$R$^{13}$)NMe-, —C(R$^{12}$R$^{13}$)NHCH$_2$—, —C(R$^{12}$R$^{13}$)CH$_2$—, —CH$_2$NMe-, or —OCH$_2$—;

R$^1$ is H, Cl, Br, methyl, ethyl, methoxy, or ethoxy;
R$^2$ is H, Cl, Br, methyl, ethyl, methoxy, or ethoxy;
R$^3$ is H or F;
R$^5$ is H, C$_{1-4}$ alkyl, —CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$CH$_2$NR$^c$R$^d$, —CH$_2$C(O)NR$^c$R$^d$, or —CH$_2$CH$_2$C(O)NR$^c$R$^d$;
R$^6$ is H, methyl, ethyl, —CO$_2$H or —CH$_2$CO$_2$H;
R$^7$ is H; and
R$^8$ is H, F, Cl, Br, CN, C$_{1-6}$ alkyl substituted with 0-3 R$^e$, OR$^i$, —CH$_2$OR$^i$, —CONR$^c$R$^d$, —SO$_2$RJ, —SO$_2$NR$^c$R$^d$, phenyl, O-phenyl, a 5- to 10-membered heterocycle selected from: morpholinyl, pyrrolidinyl, piperidinyl, pyrazolyl, oxazolyl, isoxazolyl, thiazolyl, imidazolyl, pyridyl, dihydroisoquinolinyl, or O-5- to –10-membered heterocycle selected from: imidazolyl, oxadiazolyl, pyrazinyl, pyrazolyl, pyridazinyl, pyridyl, pyrimidinyl, pyrrolidinyl, pyrrolyl, tetrahydrofuranyl, thiadiazolyl, thiazolyl, thiophenyl, or triazolyl wherein said phenyl and heterocycle are substituted with 0-2 R$^g$; and
R$^9$, R$^{10}$ and R$^{11}$ are, independently at each occurrence, H, F, or Cl.

In a ninth aspect, the present invention includes the compounds of Formula (I), or stereoisomers, tautomers, pharmaceutically acceptable salts, solvates, or prodrugs thereof, wherein:

ring A is phenyl;
ring B is phenyl;
M is —CONH—;
L is —CH$_2$CH$_2$CH$_2$—, —CH(Me)CH$_2$CH$_2$—, —CH$_2$CH$_2$O—, —CHFCH$_2$O—, —CH(Me)CH$_2$O—, —CH(Et)CH$_2$O—, —CH(OH)CH$_2$O—, —CH(OMe)CH$_2$O—, —CH(OEt)CH$_2$O—, —CH(CH$_2$OH)CH$_2$O—, —CH(OCH$_2$OMe)CH$_2$O—, —CH(NHCO$_2$Bn)CH$_2$O—, —CH(Me)CH$_2$NH—, —CH(Me)CH$_2$N(Me)—, —CH$_2$N(Me)—, —CH$_2$NHCH$_2$—, —CH$_2$N(Me)CH$_2$—, —CH$_2$N(Et)CH$_2$—, —CH$_2$N(Pr)CH$_2$—, —CH$_2$N(i-Pr)CH$_2$—, —CH$_2$N(COMe)CH$_2$—, —CH$_2$N(COEt)CH$_2$—, —CH$_2$N(CO(i-Pr))CH$_2$—, —CH$_2$N(CO$_2$Me)CH$_2$—, —CH$_2$N(CH$_2$CO$_2$H)CH$_2$—, —CH(Me)NHCH$_2$—, —CH(Me)N(COMe)CH$_2$—, —CH(Me)N(CO$_2$Me)CH$_2$—, or —CH(Me)N(CO$_2$Bn)CH$_2$—;

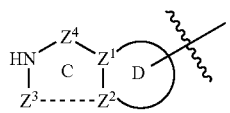

is selected from:

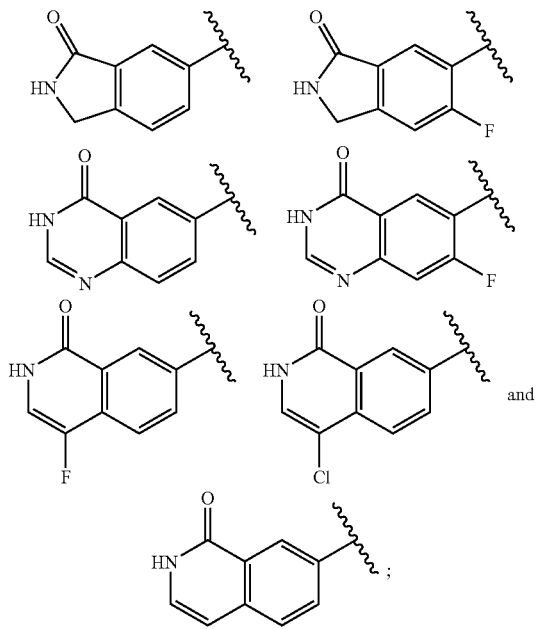

$R^1$ is H, Cl, Br, methyl, ethyl, methoxy, or ethoxy;
$R^2$ is H, Cl, Br, methyl, ethyl, methoxy, or ethoxy;
$R^3$ is H or F;
$R^4$ is H;
$R^5$ is H, methyl, ethyl, propyl, —CH$_2$CO$_2$H, —CH$_2$CH$_2$CO$_2$H, —CH$_2$CH$_2$CO$_2$Et, —CH$_2$CH$_2$CH$_2$CO$_2$H, —CH$_2$CH$_2$NHCO$_2$Me, —CH$_2$CH$_2$NHCO$_2$(t-Bu), —CH$_2$CH$_2$OH, —CH$_2$CH$_2$OMe, —CH$_2$CH$_2$NH$_2$, —CH$_2$CH$_2$CONH$_2$, or —CH$_2$CH$_2$CONHMe;
$R^6$ is H, methyl, ethyl, —CO$_2$H or —CH$_2$CO$_2$H;
$R^7$ is H;
$R^8$ is H, F, Cl, Br, CN, OH, —CH$_2$OH, —CH$_2$OMe, —OCF$_2$H, —OCF$_3$, —OCF$_2$CF$_2$H, CO$_2$H, —SO$_2$Et, —SO$_2$(i-Pr), —SO$_2$-cyclopropyl, phenyl, 2-OCF$_3$-phenyl, 3-CO$_2$H-phenyl, 3-CO$_2$Me-phenyl, 2,6-diF-phenyl, 2-F-5-CO$_2$H-phenyl, 1H-pyrazol-1-yl, 1-Me-1H-pyrazol-4-yl, 1-Me-1H-pyrazol-5-yl, 1-Et-1H-pyrazol-5-yl, oxazol-2-yl, 3,5-diMe-isoxazol-4-yl, 2-thiazolyl, 1H-imidazol-1-yl, 1-Me-1H-imidazol-2-yl, 1,2-dimethyl-1H-imidazol-5-yl, 2-pyridyl, 3-pyridyl, 4-pyridyl,

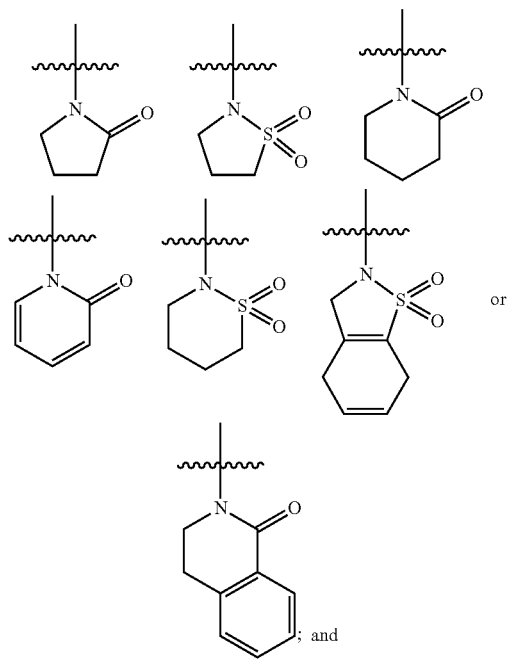

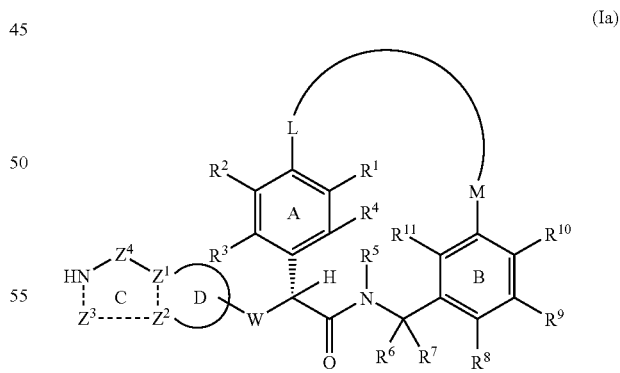

$R^9$, $R^{10}$, and $R^{11}$ are H.

In a tenth aspect, the present invention includes a compound of Formula (Ia):

(Ia)

or stereoisomers, tautomers, pharmaceutically acceptable salts, solvates, or prodrugs thereof, within the scope of any of the above aspects, wherein all variables are the same as defined in the corresponding aspect.

In an eleventh aspect, the present invention provides a compound selected from one or more exemplified Examples or stereoisomers, tautomers, pharmaceutically acceptable salts, solvates, or prodrugs thereof.

In another embodiment, the present invention includes a compound of Formula (I) or stereoisomers, tautomers, pharmaceutically acceptable salts, solvates, or prodrugs thereof, wherein:

M is —CONH—;
L is —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)C(R$^{12}$R$^{13}$)NMe-, —C(R$^{12}$R$^{13}$)N(C═OCH$_3$)CH$_2$—, —C(R$^{12}$R$^{13}$)NHCH$_2$—, —C(R$^{12}$R$^{13}$)CH$_2$—, —CH$_2$NMe-, or —OCH$_2$—;
R$^1$ is H, Cl, Br, methyl, ethyl, methoxy, or ethoxy;
R$^2$ is H, Cl, Br, methyl, ethyl, methoxy, or ethoxy;
R$^3$ is H;
R$^4$ is H;
R$^5$ is H, methyl, ethyl, or —CH$_2$CO$_2$H;
R$^6$ is H, methyl, ethyl, —CO$_2$H or —CH$_2$CO$_2$H;
R$^7$ is H; and
R$^8$ is —CONR$^c$R$^d$ or —SO$_2$Rb.

In another embodiment,

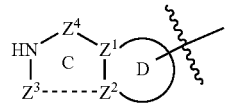

is selected from:

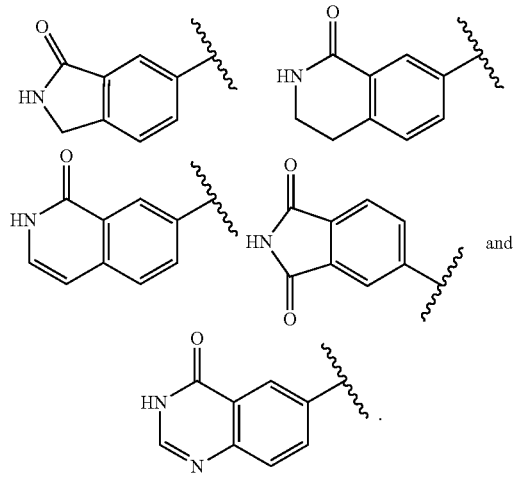

In another embodiment, ring A is phenyl or a pyridyl isomer defined by replacing one of CR$^1$, CR$^2$, CR$^3$, or CR$^4$ in ring A of formula (I) with N; and ring B is phenyl. Preferably ring A is phenyl and ring B is phenyl.

In another embodiment, M is —CONH— or —NHSO$_2$—;
when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, and —C(R$^{12}$R$^{13}$)C(R$^{12}$R$^{13}$)Y—;
when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, and —XC(R$^{12}$R$^{13}$)C(R$^{12}$R$^{13}$)—.

In another embodiment, M is —CONH—; and L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, and —C(R$^{12}$R$^{13}$)C(R$^{12}$R$^{13}$)Y—; preferably L is selected from —C(R$^{12}$R$^{13}$)C(R$^{12}$R$^{13}$)C(R$^{12}$R$^{13}$)—, —C(R$^{12}$R$^{13}$)NR$^{16}$C(R$^{12}$R$^{13}$), —C(R$^{12}$R$^{13}$)C(R$^{12}$R$^{13}$)Y—, —C(R$^{12}$R$^{13}$)C(R$^{12}$R$^{13}$)—, —C(R$^{12}$R$^{13}$)NR$^{16}$— or —OC(R$^{12}$R$^{13}$)—; preferably L is —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)NR$^{16}$C(R$^{12}$R$^{13}$)—, —C(R$^{12}$R$^{13}$)C(R$^{12}$R$^{13}$)NH—, —C(R$^{12}$R$^{13}$)C(R$^{12}$R$^{13}$)NMe-, —C(R$^{12}$R$^{13}$)NHCH$_2$—, —C(R$^{12}$R$^{13}$)CH$_2$—, —CH$_2$NMe-, or —OCH$_2$—; preferably L is —CH$_2$CH$_2$CH$_2$—, —CH(Me)CH$_2$CH$_2$—, —CH$_2$CH$_2$O—, —CHFCH$_2$O—, —CH(Me)CH$_2$O—, —CH(Et)CH$_2$O—, —CH(OMe)CH$_2$O—, —CH(OEt)CH$_2$O—, —CH(OCH$_2$OMe)CH$_2$O—, —CH(NHCO$_2$Bn)CH$_2$O—, —CH(Me)CH$_2$NH—, —CH(Me)CH$_2$N(Me)—, —CH$_2$N(Me)—, —CH$_2$NHCH$_2$—, —CH$_2$N(Me)CH$_2$—, —CH$_2$N(Et)CH$_2$—, —CH$_2$N(Pr)CH$_2$—, —CH$_2$N(i-Pr)CH$_2$—, —CH$_2$N(COMe)CH$_2$—, —CH$_2$N(COEt)CH$_2$—, —CH$_2$N(CO(i-Pr))CH$_2$—, —CH$_2$N(CO$_2$Me)CH$_2$—, —CH$_2$N(CH$_2$CO$_2$H)CH$_2$—, —CH(Me)NHCH$_2$—, —CH(Me)N(COMe)CH$_2$—, —CH(Me)N(CO$_2$Me)CH$_2$—, or —CH(Me)N(CO$_2$Bn)CH$_2$—.

In another embodiment,

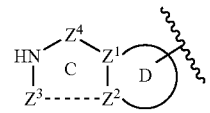

is selected from:

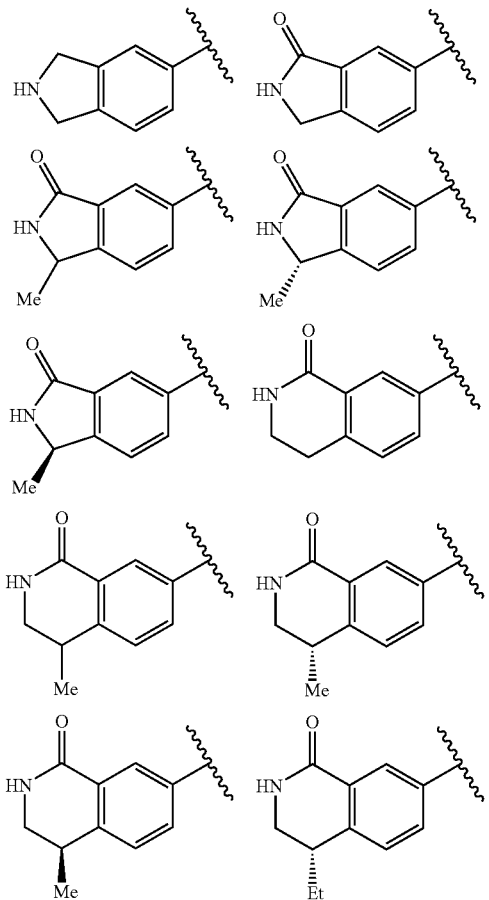

-continued

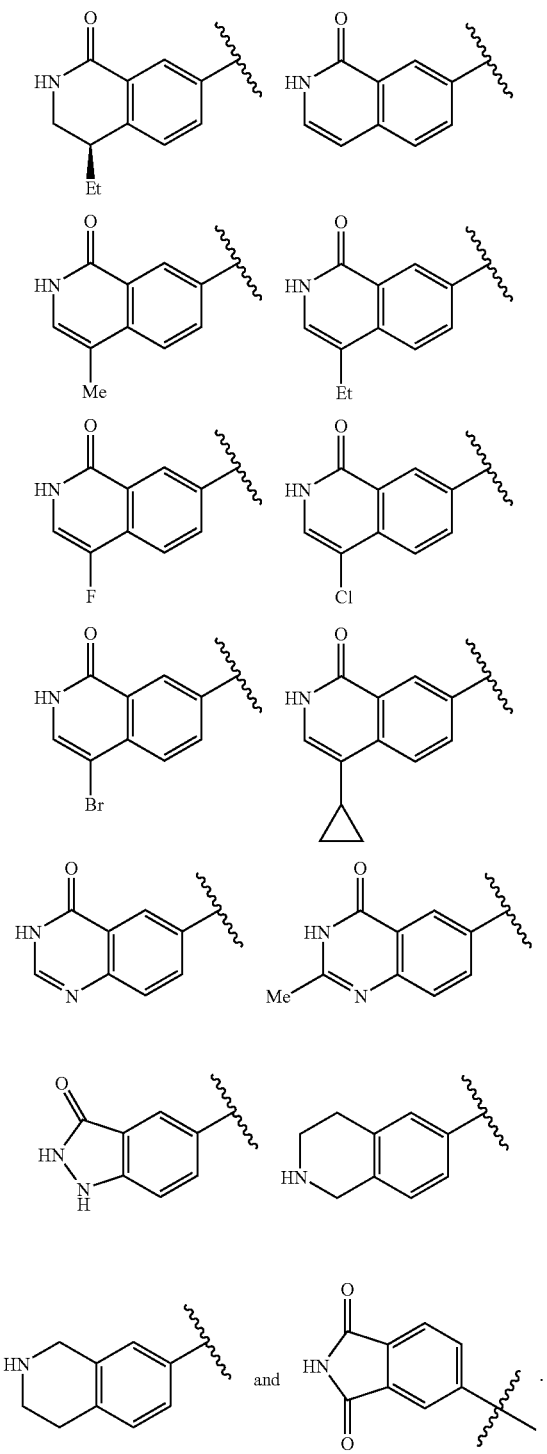

In another embodiment

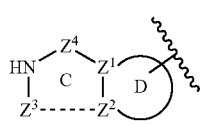

is selected from:

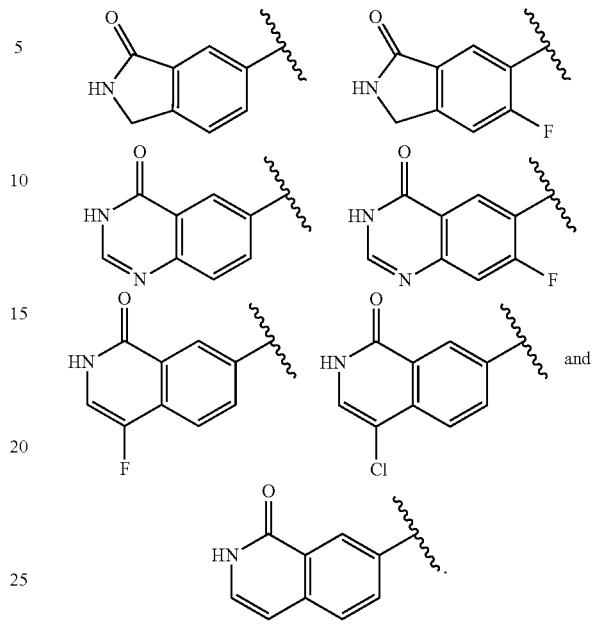

In another embodiment,

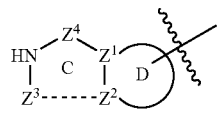

is selected from:

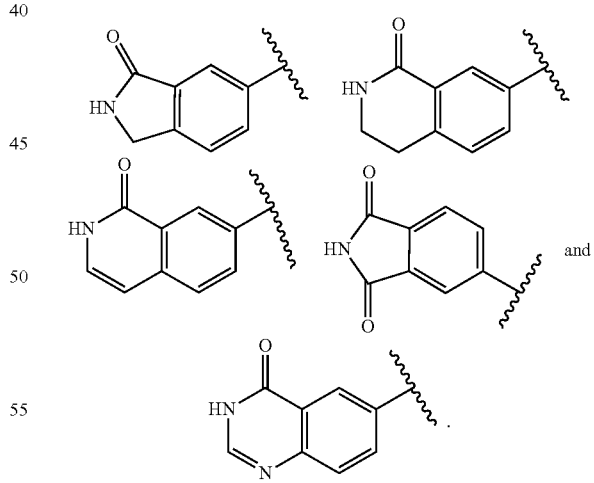

In another embodiment, R¹ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl. Preferably, R¹ is H, Cl, Br, methyl, ethyl, vinyl, 2-propenyl, allyl, ethynyl, 1-propynyl, methoxy, ethoxy, or cyclopropyl. Preferably, R¹ is H, Cl, Br, methyl, ethyl, vinyl, 2-propenyl, ethynyl, methoxy, or ethoxy. Preferably, R¹ is H, Cl, Br, methyl, ethyl, methoxy, or ethoxy.

In another embodiment, $R^2$ is H, F, Cl, $OR^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O-(5- to 6-membered heterocycle); wherein said heterocycle comprises carbon atoms and 1-3 heteroatoms selected from N, $NR^c$, O, and $S(O)_p$ and is substituted with 0-2 $R^g$. Preferably, $R^2$ is H, Cl, Br, methyl, ethyl, methoxy, or ethoxy.

In another embodiment, $R^3$ is H, F, Cl, $OR^a$, —O(CH$_2$)$_n$CO$_2$R$^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O(benzyl substituted with CO$_2$R$^a$). Preferably, $R^3$ is H, F, Cl, Me, OCH$_2$CO$_2$H. Preferably, $R^3$ is H or F. Preferably, $R^3$ is H.

In another embodiment, $R^4$ is H.

In another embodiment, $R^5$ is H, —CH$_2$CH$_2$OR$^a$, —CH$_2$CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$CH$_2$NR$^c$R$^d$, —CH$_2$C(O)NR$^c$R$^d$, —CH$_2$CH$_2$C(O)NR$^c$R$^d$, —CH$_2$CONHSO$_2$R$^b$, —CH$_2$CH$_2$CONHSO$_2$R$^b$, $C_{1-6}$ alkyl substituted with 0-2 $R^e$, —(CH$_2$)$_s$—C$_{3-6}$ carbocycle substituted with 0-2 $R^f$, or —(CH$_2$)$_s$-5- to 6-membered heterocycle; wherein said heterocycle comprises carbon atoms and 1-3 heteroatoms selected from N, $NR^c$, O, and $S(O)_p$ and is substituted with 0-2 $R^g$. Preferably, $R^5$ is H, $C_{1-4}$ alkyl, —CH$_2$CH$_2$OR$^a$, —CH$_2$CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$CH$_2$NR$^c$R$^d$, —CH$_2$C(O)NR$^c$R$^d$, or —CH$_2$CH$_2$C(O)NR$^c$R$^d$. Preferably, $R^5$ is H, $C_{1-4}$ alkyl, —CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$NR$^c$R$^d$, —CH$_2$C(O)NR$^c$R$^d$, or —CH$_2$CH$_2$C(O)NR$^c$R$^d$. Preferably, $R^5$ is H, methyl, ethyl, propyl, —CH$_2$CO$_2$H, —CH$_2$CH$_2$CO$_2$H, —CH$_2$CH$_2$CO$_2$Et, —CH$_2$CH$_2$CH$_2$CO$_2$H, —CH$_2$CH$_2$NHCO$_2$Me, —CH$_2$CH$_2$NHCO$_2$(t-Bu), —CH$_2$CH$_2$OH, —CH$_2$CH$_2$OMe, —CH$_2$CH$_2$NH$_2$, —CH$_2$CH$_2$CONH$_2$, or —CH$_2$CH$_2$CONHMe.

In another embodiment, $R^6$ is H, —CH$_2$OR$^a$, —CH$_2$CH$_2$OR$^a$, CN, —CO$_2$R$^a$, —C(O)NR$^c$R$^d$, —CH$_2$CO$_2$R$^a$, —CH$_2$C(O)NR$^c$R$^d$, —CONHSO$_2$R$^b$, —CH$_2$CONHSO$_2$R$^b$, $C_{1-6}$ alkyl substituted with 0-2 $R^e$, —(CH$_2$)$_s$—C$_{3-6}$ carbocycle substituted with 0-2 $R^f$, or —(CH$_2$)$_s$-5- to 6-membered heterocycle; wherein said heterocycle comprises carbon atoms and 1-3 heteroatoms selected from N, $NR^c$, O, and $S(O)_p$ and is substituted with 0-2 $R^g$. Preferably, $R^6$ is H, —CH$_2$OR$^a$, —CH$_2$CH$_2$OR$^a$, CN, $C_{1-4}$ alkyl, —CO$_2$R$^a$, —C(O)NR$^c$R$^d$, —CH$_2$CO$_2$R$^a$, or —CH$_2$C(O)NR$^c$R$^d$. Preferably, $R^6$ is H, $C_{1-4}$ alkyl, —CO$_2$R$^a$, —C(O)NR$^c$R$^d$, —CH$_2$CO$_2$R$^a$, or —CH$_2$C(O)NR$^c$R$^d$. Preferably, $R^6$ is H, methyl, ethyl, —CO$_2$H or —CH$_2$CO$_2$H.

In another embodiment, $R^6$ is H, —CH$_2$OR$^a$, —CH$_2$CH$_2$OR$^a$, CN, —CO$_2$R$^a$, —C(O)NR$^c$R$^d$, —CH$_2$CO$_2$R$^a$, —CH$_2$C(O)NR$^c$R$^d$, —CONHSO$_2$R$^b$, —CH$_2$CONHSO$_2$R$^b$, $C_{1-6}$ alkyl substituted with 0-2 $R^e$, —(CH$_2$)$_s$—C$_{3-6}$ carbocycle substituted with 0-2 $R^f$, or —(CH$_2$)$_s$-5- to 6-membered heterocycle; wherein said heterocycle comprises carbon atoms and 1-3 heteroatoms selected from N, $NR^c$, O, and $S(O)_p$ and is substituted with 0-2 $R^g$. Preferably, $R^6$ is H, —CH$_2$OR$^a$, —CH$_2$CH$_2$OR$^a$, CN, $C_{1-4}$ alkyl, —CO$_2$R$^a$, —C(O)NR$^c$R$^d$, —CH$_2$CO$_2$R$^a$, or —CH$_2$C(O)NR$^c$R$^d$. Preferably, $R^6$ is H, $C_{1-4}$ alkyl, —CO$_2$R$^a$, —C(O)NR$^c$R$^d$, —CH$_2$CO$_2$R$^a$, or —CH$_2$C(O)NR$^c$R$^d$. Preferably, $R^6$ is H, methyl, ethyl, —CO$_2$H or —CH$_2$CO$_2$H.

In another embodiment, $R^7$ is H.

In another embodiment, $R^8$ is H, F, Cl, Br, CN, $C_{1-6}$ alkyl substituted with 0-3 $R^e$, $OR^i$, —CH$_2$OR^i$, —CONR$^c$R$^d$, —SO$_2$R$^j$, —SO$_2$NR$^c$R$^d$, phenyl, O-phenyl, a 5- to 10-membered heterocycle selected from: morpholinyl, pyrrolidinyl, piperidinyl, pyrazolyl, oxazolyl, isoxazolyl, thiazolyl, imidazolyl, pyridyl, dihydroisoquinolinyl,

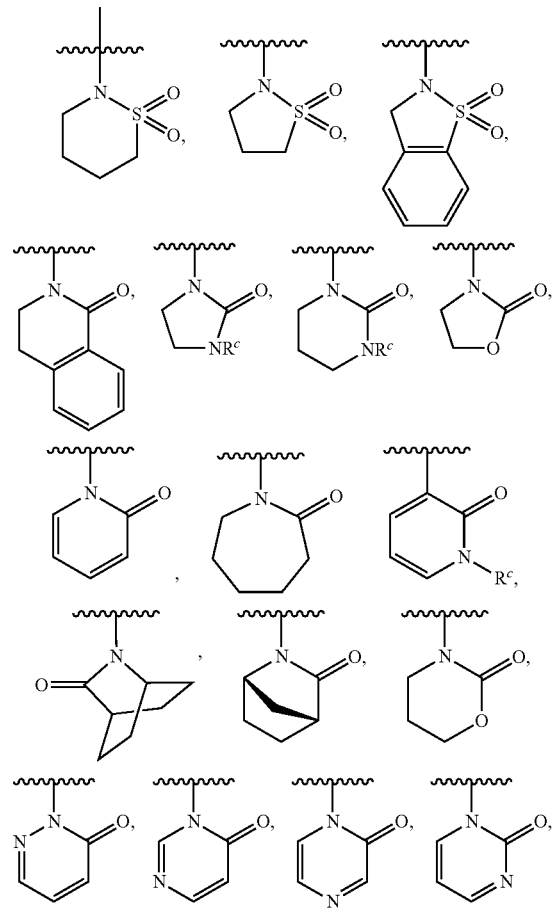

or O-5- to –10-membered heterocycle selected from: imidazolyl, oxadiazolyl, pyrazinyl, pyrazolyl, pyridazinyl, pyridyl, pyrimidinyl, pyrrolidinyl, pyrrolyl, tetrahydrofuranyl, thiadiazolyl, thiazolyl, thiophenyl, or triazolyl wherein said phenyl and heterocycle are substituted with 0-2 $R^g$. Preferably, $R^8$ is H, F, Cl, Br, CN, OH, —CH$_2$OH, —CH$_2$OMe, —OCF$_2$H, —OCF$_3$, —OCF$_2$CF$_2$H, CO$_2$H, —SO$_2$Et, —SO$_2$(i-Pr), —SO$_2$-cyclopropyl, phenyl, 2-OCF$_3$-phenyl, 3-CO$_2$H-phenyl, 3-CO$_2$Me-phenyl, 2,6-diF-phenyl, 2-F-5-CO$_2$H-phenyl, 1H-pyrazol-1-yl, 1-Me-1H-pyrazol-4-yl, 1-Me-1H-pyrazol-5-yl, 1-Et-1H-pyrazol-5-yl, oxazol-2-yl, 3,5-diMe-isoxazol-4-yl, 2-thiazolyl, 1H-imidazol-1-yl, 1-Me-1H-imidazol-2-yl, 1,2-dimethyl-1H-imidazol-5-yl, 2-pyridyl, 3-pyridyl, 4-pyridyl,

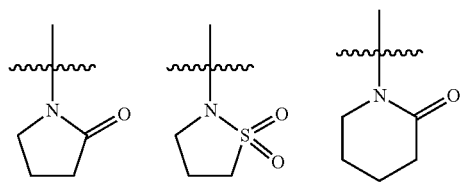

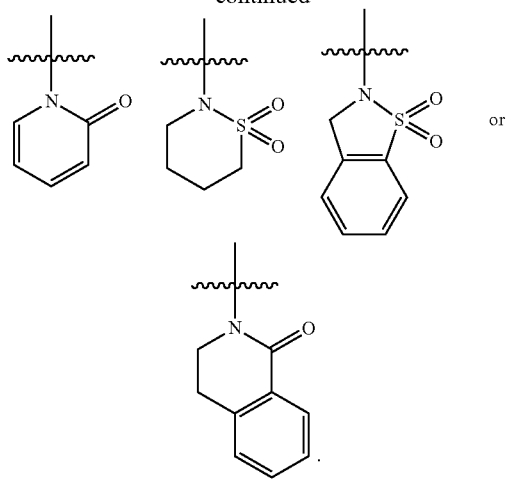

In another embodiment, $R^9$ is H, F, Cl, Br, I, or $C_{1-4}$ alkyl. Preferably, $R^9$, is H, F, or Cl. Preferably, $R^9$, is H or F. Preferably, $R^9$, is H.

In another embodiment, $R^{10}$ is H, F, Cl, Br, I, or $C_{1-4}$ alkyl. Preferably, $R^{10}$, is H, F, or Cl. Preferably, $R^{10}$, is H or F. Preferably, $R^{10}$, is H.

In another embodiment, $R^{11}$ is H, F, Cl, Br, I, or $C_{1-4}$ alkyl. Preferably, $R^{11}$, is H, F, or Cl. Preferably, $R^{11}$, is H or F. Preferably, $R^{11}$, is H.

II. OTHER EMBODIMENTS OF THE INVENTION

In another embodiment the present invention provides a composition comprising at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a process for making a compound of the present invention or a stereoisomer, tautomer, pharmaceutically acceptable salt, solvate or prodrug thereof.

In another embodiment, the present invention provides an intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agent(s). In a preferred embodiment, the present invention provides a pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment or prophylaxis of a thromboembolic disorder comprising: administering to a patient in need of such treatment or prophylaxis a therapeutically effective amount of at least one of the compounds of the present invention or a stereoisomer, tautomer, pharmaceutically acceptable salt, solvate, or prodrug thereof. In another embodiment, the present invention provides a compound of the present invention or a stereoisomer, tautomer, pharmaceutically acceptable salt, solvate or prodrug thereof, for use in therapy for the treatment or prophylaxis of a thromboembolic disorder. In another embodiment, the present invention also provides the use of a compound of the present invention or a stereoisomer, tautomer, pharmaceutically acceptable salt, solvate or prodrug thereof, for the manufacture of a medicament for the treatment or prophylaxis of a thromboembolic disorder. Preferably, in these embodiments, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a compound of the present invention or a stereoisomer, tautomer, pharmaceutically acceptable salt, solvate or prodrug thereof, for use in therapy.

In another embodiment, the present invention provides a method for treating a thromboembolic disorder, comprising: administering to a patient in need thereof a therapeutically effective amount of a first and second therapeutic agent, wherein the first therapeutic agent is a compound of the present invention or a stereoisomer, tautomer, pharmaceutically acceptable salt, solvate or prodrug thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. In another embodiment, the present invention provides a first and second therapeutic agent for use in treating a thromboembolic disorder, wherein the first therapeutic agent is a compound of the present invention or a stereoisomer, tautomer, pharmaceutically acceptable salt, solvate or prodrug thereof, and the second therapeutic agent is at least one agent selected from a second factor VIIa inhibitor, an anti-coagulant agent, an anti-platelet agent, a thrombin inhibiting agent, a thrombolytic agent, and a fibrinolytic agent. Preferably, in these embodiments, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

III. CHEMISTRY

Compounds of this invention may have one or more asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, (enantiomeric and diastereomeric) racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl group can be unsubstituted or substituted with at least one hydrogen being replaced by another chemical group. Examples of alkyl include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration having one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, and ethyl-S—.

"Halo" or "halogen" as used herein refers to fluoro, chloro, bromo, and iodo. "Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" is intended to mean any stable 3-, 4-, 5-, 6-, 7-, or 8-membered monocyclic or bicyclic or 7-, 8-, 9-, 10-, 11-, 12-, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13 ed.), R. J. Lewis, ed., J. Wiley & Sons; Inc., New York (1997). "$C_{6-10}$ aryl" refers to phenyl or naphthyl. Unless otherwise specified, "aryl", "$C_{6-10}$ aryl" or "aromatic residue" may be unsubstituted or substituted with 1 to 3 groups selected from H, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O) CH$_3$, S(=O)$_2$CH$_3$, CH$_3$, CH$_2$CH$_3$, CO$_2$H, and CO$_2$CH$_3$.

As used herein, the term "heterocycle" or "heterocyclic group" is intended to mean a stable 3-, 4-, 5-, 6-, or 7-membered monocyclic or polycyclic or 7-, 8-, 9-, 10-, 11-, 12-, 13-, or 14-membered polycyclic heterocyclic ring that is saturated, partially unsaturated or fully unsaturated, and that consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —SO$_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl; thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

Bridged rings are also included in the definition of heterocycle. A bridged ring occurs when one or more atoms (i.e., C, O, N, or S) link two non-adjacent carbon or nitrogen atoms. Examples of bridge rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

When a dotted ring is used within a ring structure, this indicates that the ring structure may be saturated, partially saturated or unsaturated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quarternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^f$, then said group may optionally be substituted with up to three $R^f$ groups and $R^f$ at each occurrence is selected independently from the definition of $R^f$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "*Design and Application of Prodrugs*," by H. Bundgaard, at pp. 113-191 (1991);
c) H. Bundgaard, *Advanced Drug Delivery Reviews*, Vol. 8, p. 1-38 (1992);
d) H. Bundgaard, et al., *Journal of Pharmaceutical Sciences*, Vol. 77, p. 285 (1988); and
e) N. Kakeya, et. al., *Chem Phar Bull*., Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-16}$alkyl, $C_{1-6}$ alkylbenzyl, 4-methoxybenzyl, indanyl, phthalyl, methoxymethyl, $C_{1-6}$ alkanoyloxy-$C_{1-6}$ alkyl (e.g. acetoxymethyl, pivaloyloxymethyl or propionyloxymethyl), $C_{1-6}$ alkoxycarbonyloxy-$C_{1-6}$ alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, ed. F. D. King, The Royal Society of Chemistry, Cambridge, UK, 1994.

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

ACN is acetonitrile,
AcOH or HOAc is acetic acid,
AD-mix-beta contains potassium osmate, potassium ferricyanide, potassium carbonate and hydroquinidine 1,4-phthalazinediyl diether,
AIBN is azo-bis-isobutyrlnitrile,
9-BBN is 9-borabicyclo[3.3.1]nonane,
BINAP is 2,2'-bis(diphenylphosphino)-1,1'-binaphthalene,
Bn is benzyl,
Boc is tert-butyl oxycarbonyl,
BOM is benzyloxymethyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
DCE is 1,2-dichloroethane,
DCM or $CH_2Cl_2$ is dichloromethane,
DIBAH is diisobutylaluminum hydride,
DIC is 1,3-diisopropylcarbodiimide,
DIEA is diethylpropyl amine,
DMAP is dimethylaminopyridine,
DME is dimethyl ether,
DMF is dimethylformamide,
DMPU is 1,3-dimethyl-3,4,5,6-tetrahydro-2(1H)-pyrimidinone,
DMSO is dimethyl sulfoxide,
DPPA is diphenylphosphoryl azide,
EDCI is 1-(3-dimethylaminopropyl)-3-ethylcarbodiimide hydrochloride,
Et is ethyl,
EtOH is ethanol,
EtOAc is ethyl acetate,
$Et_2O$ is diethyl ether
HCl is hydrochloric acid
HEPES is 4-(2-hydroxyethyl)piperaxine-1-ethanesulfonic acid,
HOAt or HOAT is 1-hydroxy-7-azabenzotriazole,
HOBt is 1-hydroxybenzotriaole hydrate
LAH is lithium aluminum hydride
LDA is lithium diisopropylamide,
LiHMDS is bis(trimethylsilyl)amide,
mCPBA or MCPBA is meta-chloroperbenzoic acid,
Me is methyl,
MeOH is methanol, MsCl is methanesulfonyl chloride,
NaHMDS is sodium hexamethyldisilazane,
NaOAc is sodium acetate,
NBS is N-bromosuccinimide,
OAc is acetate,
Pd$_2$(dba)$_3$ is tris(dibenzylideneacetone)dipalladium(0),
Pd(PPh$_3$)$_4$ is tetraks (triphenylphosphine) palladium,
Ph is phenyl,
PMDTA is N,N,N',N',N,N"-pentamethyldiethylenetriamine,
Pr is propyl,
PyBOP is benzotriazol-1-yl-oxytripyrrolidinophosphonium hexafluorophosphate,
iPr or i-Pr is isopropyl,
i-PrOH or IPA is isopropanol,
TBAF is tetrabutylammoniumfluoride,
TBAI is tetrabutylammonium iodide,
TBS is tert-butyldimethylsilyl,
TBDMS-Cl is tert-butyldiphenylchlorosilane,
TBDPS-Cl is tert-butyldimethylchlorosilane,
TBSCl is tert-butyldimethylsilyl chloride,
TEA is triethylamine,
TEMPO is 2,2,6,6-tetramethylpiperidine-1-oxyl,
TFA is trifluoroacetic acid,
TFAA is trifluoroacetic anhydride,
THE is tetrahydrofuran,
TrCl is trityl chloride,
TRIS is tris(hydroxymethyl)aminomethane,
Tr is trityl,
Xantphos is 4,5-bis(diphenylphosphino)-9,9-dimethylxanthene.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (I) can be prepared according to the general methods shown in the schemes below. Compounds of formula (I) where Z=NH can be prepared using the general method shown in Scheme 1. Using the Petasis boronic acid Mannich reaction (Petasis, N. A., Zavialov, I. A. *J. Am. Chem. Soc.* 1997, 119, 445-446; Petasis, N. A., Goodman, A., Zavialov, I. A. *Tetrahedron* 1997, 53, 16463-16470.), amines 1 are reacted with glyoxylic acid and phenyl boronic acids 2 to afford arylglycines 3. This reaction is typically conducted in a solvent such as, but not limited to, toluene, dichloromethane, 1,2-dichloroethane, methanol, ethanol, dimethylformamide, or acetonitrile, or appropriate mixtures thereof. In some cases, mixtures of acetonitrile and dimethylformamide are preferred. Fluorinated alcohols such as hexafluoroisopropanol are useful additives that may improve the rate and or yield of the reaction. If necessary, the reaction is heated conventionally or in a microwave reactor to achieve a practical reaction rate.

The preparation of amines 1 is described in the experimental procedures for Intermediates 1-7 and 12. Additionally, preparation of primary amines is well known in the art of organic synthesis and many primary amines are commercially available. Preparation of phenylboronic acids 2, which contain a protected benzylamine (PG=protecting group) is described in the synthesis of examples and in Schemes 8 and 9. Additionally, preparation of phenylboronic acids 2 can be achieved through methods known to one skilled in the art of organic synthesis. The protecting group PG in 2 may be, for instance, a carbamate such as Boc or Cbz, or the entire PGNR$^5$CR$^6$R$^7$ group may be a nitrile, which may be deprotected by catalytic hydrogenation to an unsubstituted benzylamine. The protecting group is removed under appropriate conditions from arylglycines 3 to provide amino acids 4. Amino acids 4 can be cyclized to macrocycles 5 under conditions suitable for forming an amide bond between the acid and the amine. Coupling reagents and conditions can be found in Bodanszky, "Principles of Peptide Synthesis, Second Edition" Springer Verlag Ed, Berlin (1993) and in a recent review (Montalbetti, C. A. G. N., Falque, V. *Tetrahedron* 2005, 61, 10819-11046). Coupling reagents include, but not limited to, CDI, DIC, and EDCI. Optionally, an intermediate activated ester can be prepared by adding one equivalent of 1-hydroxybenzotriazole or 1-hydroxy-7-azabenzotriazole. Other coupling reagents include, but not limited to, BOP or HATU, which are usually reacted in the presence of a tertiary base such as DIEA or TEA. BOP is a preferred reagent for preparation of compounds of Formula (I). Addition of catalytic or stoichiometric DMAP may improve the reaction rate or yield. The reaction may be conducted in solvents such as, but not limited to, DCE, DCM, DMF, or mixtures thereof. Finally, it may be necessary to run the macrocyclization reaction under dilute conditions (initial concentration of 4<0.1 M) to favor macrocyclization over dimerization. Depending on the particular substituent groups present in the final compounds, deprotection steps may be required before or after the macrocyclization step to afford compounds of Formula (I).

Scheme 1

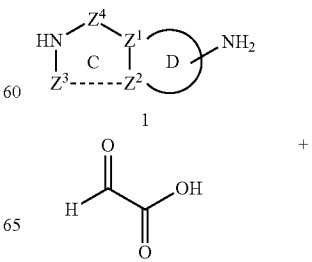

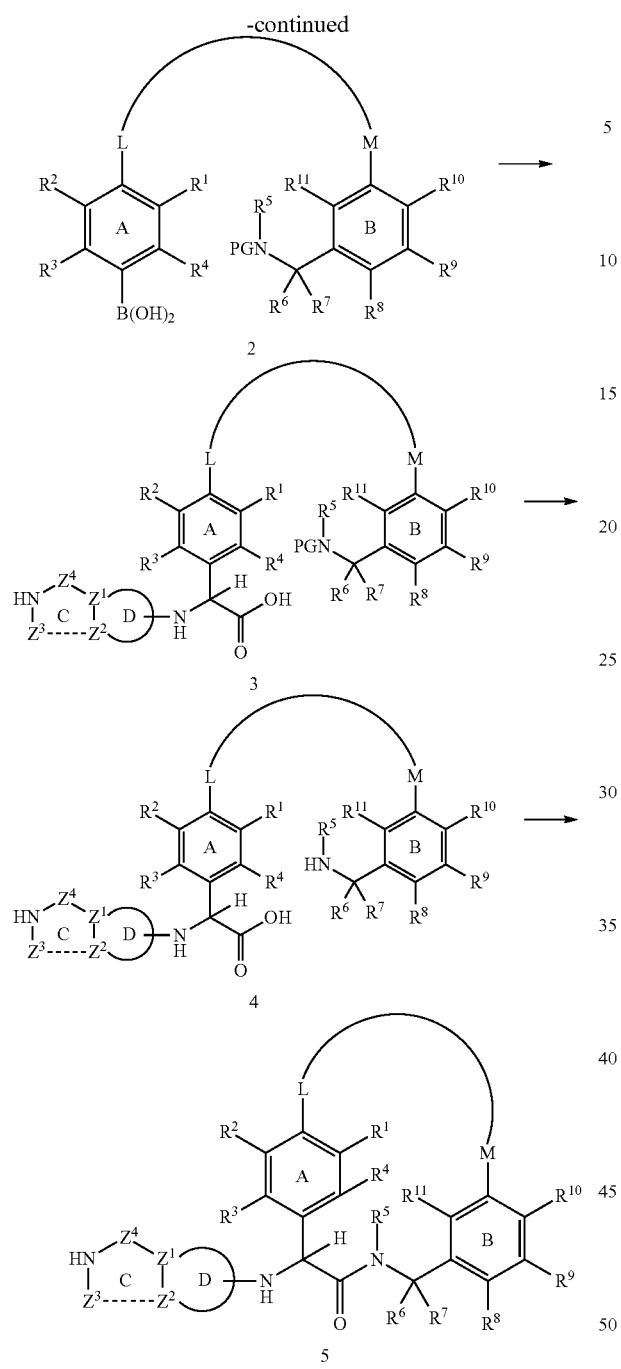

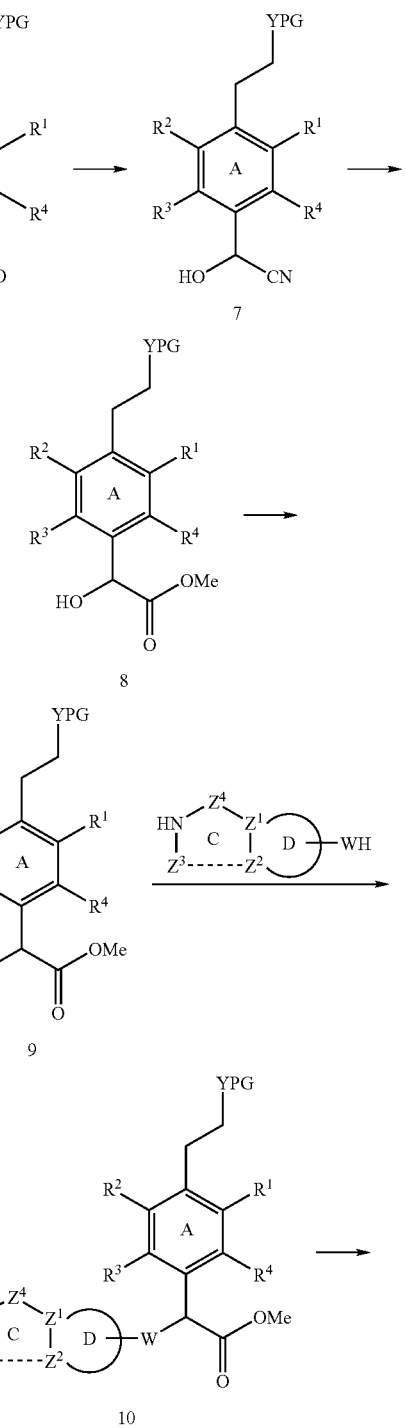

reacted with 9 in a solvent such as DCM or DMF and in presence of a base such as 2,6-lutidine, TEA, or DIEA to afford 10. The protecting group in 10 is removed and 11, containing nucleophilic groups YH is reacted with phenyl carbamates 12, or their synthetic equivalent isocyanate or carbamoyl halide to give 13. The methyl ester in 13 is hydrolyzed and the nitrogen protecting group (PG) is removed to give amino acids 14. Subsequent cyclization as described in Scheme 1 affords macrocycles 15.

Scheme 2

An alternative to the Petasis chemistry, enabling the synthesis of compounds of Formula (I) where Z is either NH or O is shown in Scheme 2. This scheme shows an explicit subset of L amd M groups, but the chemistry shown can be readily modified by one skilled in the art to prepare compounds containing other combinations of L and M. Starting aldehydes 6 are commercially available or can be readily prepared by methods known to one skilled in the art of organic synthesis. The aldehydes are converted to the cyanohydrins 7 by treatment, for instance, with potassium cyanide and sodium hydrogensulfite in a mixture of EtOAc and water. The cyanohydrins are reacted with hydrogen chloride in methanol, and the intermediate imidates are hydrolyzed to afford methyl esters 8. The hydroxyl group in 8 is converted to a leaving group (LG) such as halogen or sulfonate. Chloride and triflate are preferred LGs for this reaction, Nucleophiles W—ZH are

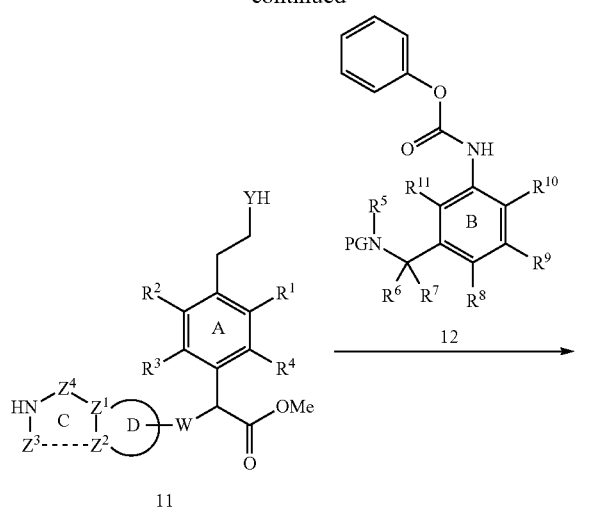
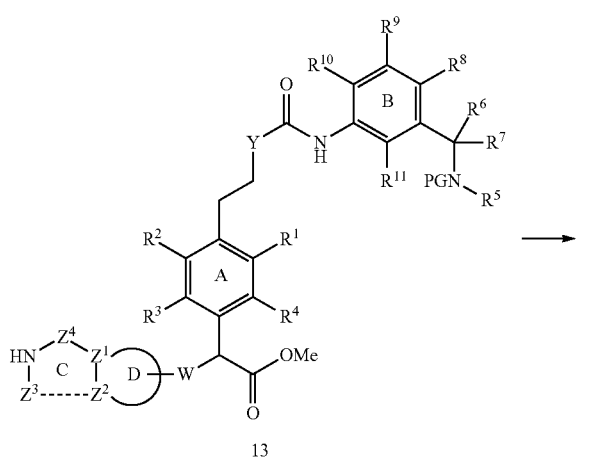
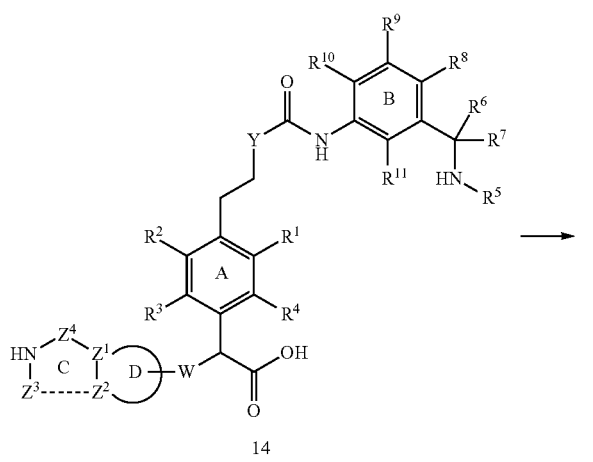
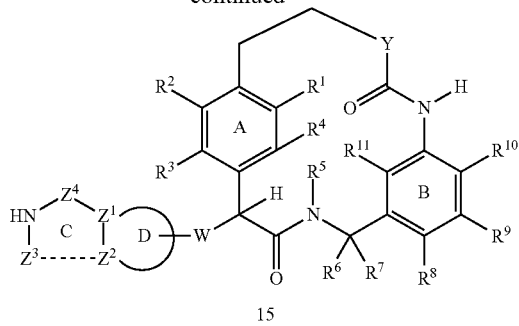

Alternatively to Schemes 1 and 2, as exemplified in Scheme 3, aldehydes 6 can be condensed with trimethylsilylcyanide in presence of ammonia to give aminonitriles 16. Treatment of 16 with hydrogen chloride in MeOH, followed by hydrolysis on aqueous workup gives amino esters 17. Amino esters 17 may be coupled with aryl or heteroaryl halides or sulfonates W-LG by methods known in the art. For example, amino esters 17 may be coupled to W-LG in the presence of a palladium catalyst, an appropriate ligand, for example, BINAP, using a base such as cesium carbonate to provide esters 18. Esters 18 are a subset of esters 10 in Scheme 2, and can be converted to compounds of Formula (I) using the subsequent methods described in Scheme 2.

Scheme 3

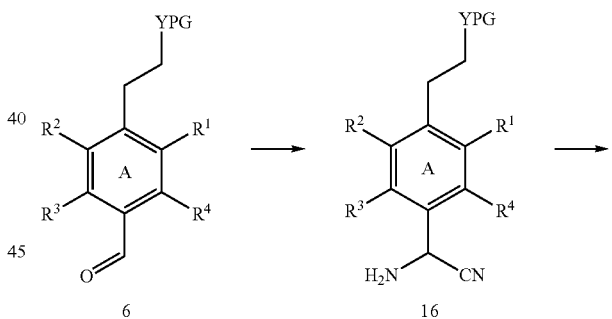
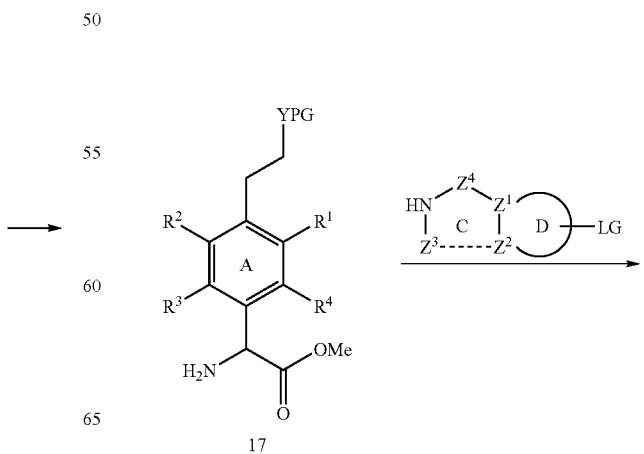

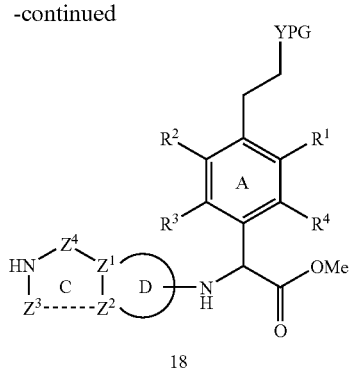

Another alternative for the introduction of the Z group is shown in Scheme 4. Hydroxy esters 8 are oxidized to keto esters 19, using, for instance, Swern conditions or MnO$_2$. Subsequent reductive amination with primary amines W—NH$_2$, using, for instance, sodium cyanoborohydride or sodium triacetoxyborohydride in a solvent such as DCM or acetonitrile, affords amino esters 18. As indicated in Schemes 2 and 3, compounds 18 may be converted to compounds of Formula (I).

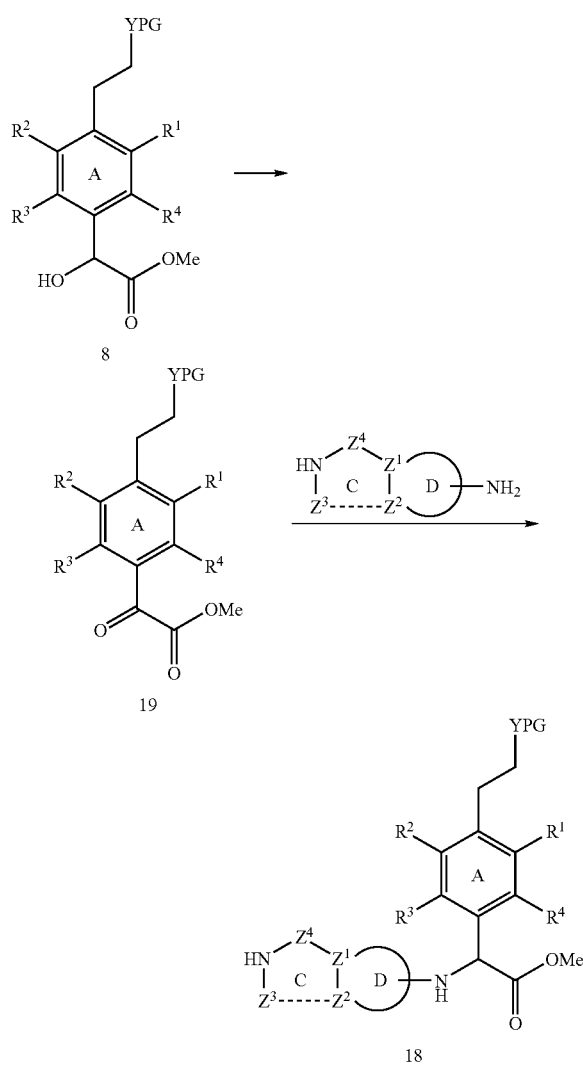

Another synthetic approaches to compounds of Formula (I) are those based on olefin metathesis, as shown in Schemes 5. For reviews of olefin metathesis, see: Trnka, T. M., Grubbs, R. H. *Acc. Chem. Res.* 2001, 34, 18-29, and Connon, S. J., Blechert, S. *Ang. Chem., Int. Ed.* 2003, 42, 1900-1923. Scheme 5 shows a cross methathesis strategy, where allyl (m=1) or vinyl (m=0) derivatives 20 are coupled to vinylacetamide (q=1) or acrylamide (q=0) derivatives 21 using an olefin methathesis catalyst, for instance, the Grubb's second generation ruthenium catalyst (Cl$_2$(PCY$_3$)(IMes) Ru═CHPh). Hydrolysis of the ester and removal of the amine protecting group affords amino acids 23. Subsequent amide coupling as described in Scheme 1 affords macrocycles 24. The double bond may be reduced by catalytic hydrogenation to afford macrocycles 25 with a saturated L group.

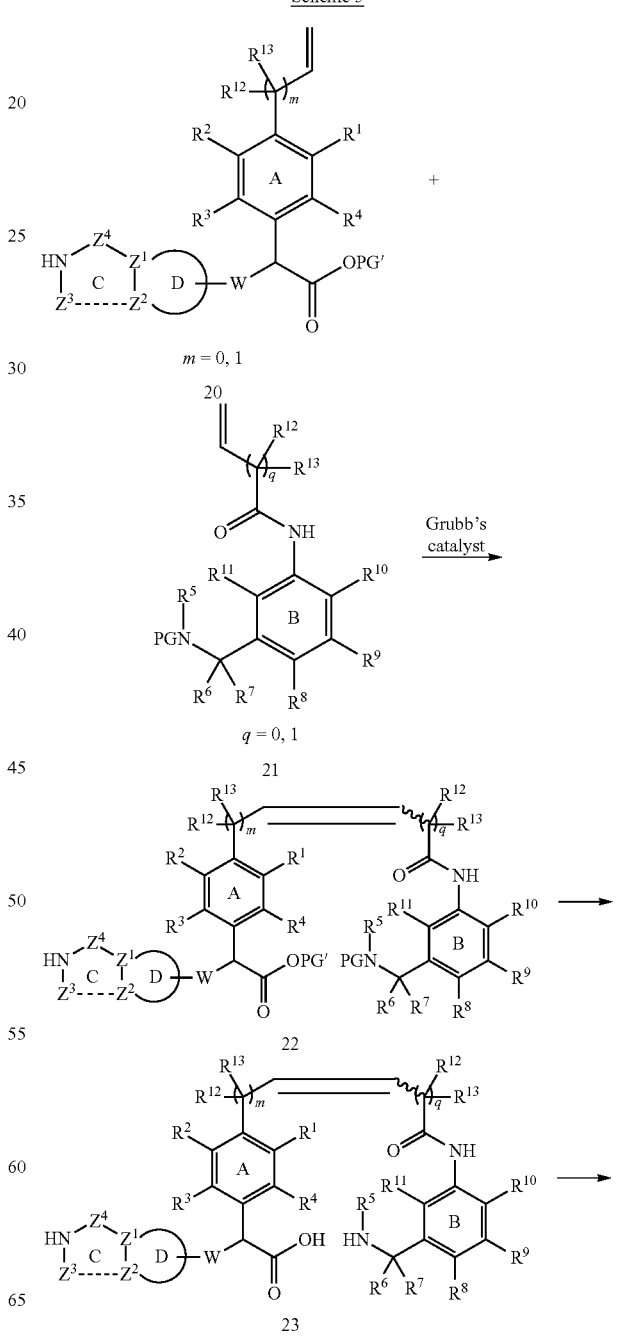

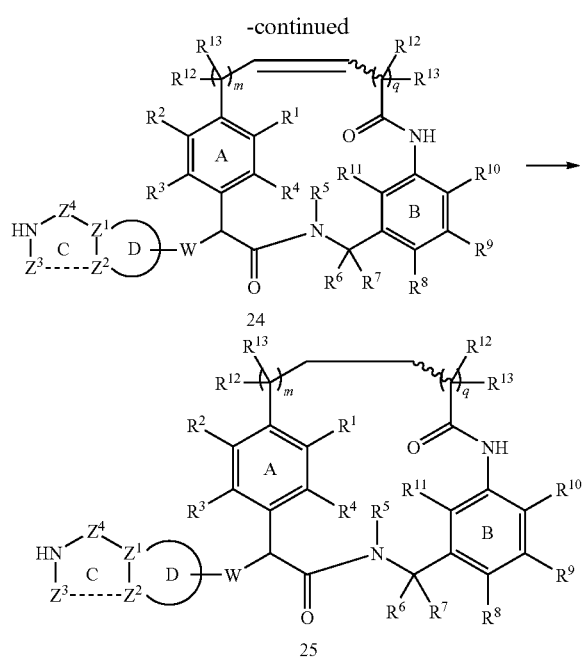

Synthesis of benzylamine intermediates with $R^5$ substituents other than H can be achieved as shown in Scheme 9. Nitro fluoride 43 may be treated with thiols to afford sulfides. The acid can then be converted to methyl amides 44 through the acid chloride. Subsequent reductions with iron/acetic acid and borane give benzyl amines 46. These may be protected, for instance as the Cbz derivatives 47, which are useful intermediates in the synthesis of macrocycles where M=—CONH— and —SO$_2$NH—. Oxidation of the sulfide to the sulfone can be achieved at a later stage in the synthesis using mCPBA.

Scheme 9

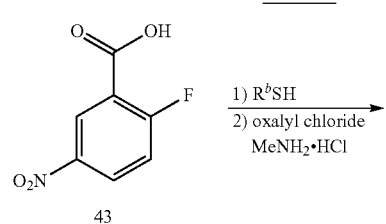

Synthesis of benzylamine intermediates for preparation of compounds of Formula (I) is shown in Schemes 8 and 9. Scheme 8 shows the preparation of benzylamine intermediates where $R^5$=H. Nitro fluoride 36 may be treated with thiols to afford sulfides 37. Compounds 37 can be oxidized with mCPBA to sulfones 38. Subsequent catalytic hydrogenation affords anilines 39, which are useful intermediates in the synthesis of macrocycles where M=—CONH— and —SO$_2$NH—. Alternatively, iron/acetic acid reduction of 37 to aniline 40, followed by borane reduction gives benzylamine 41. Subsequent protection, for instance, with Cbz-Cl and base, gives intermediates 42, which are also useful for the synthesis of macrocycles where M=—CONH— and —SO$_2$NH—. Oxidation of the sulfide to the sulfone can be achieved at a later stage in the synthesis using mCPBA. Methods for coupling these benzylamine intermediates to A ring intermediates to afford key intermediates 2 are given in the Examples.

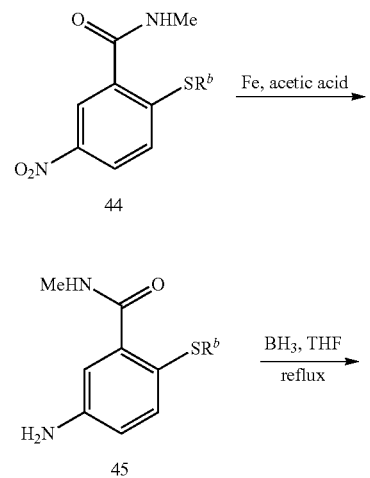

Scheme 8

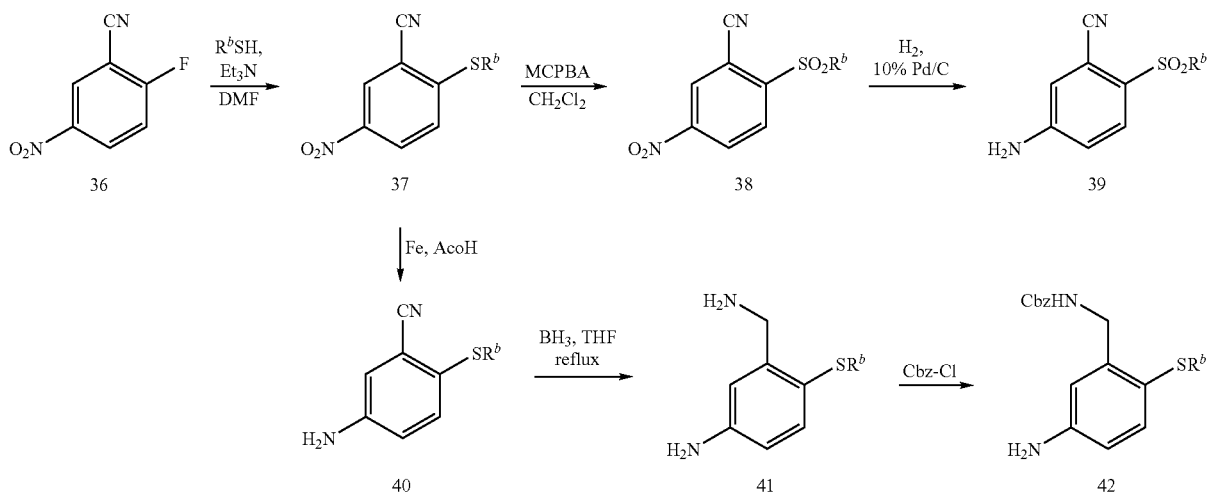

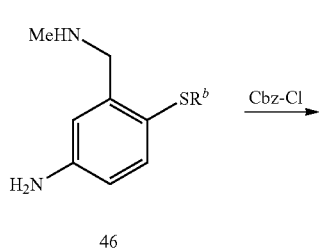

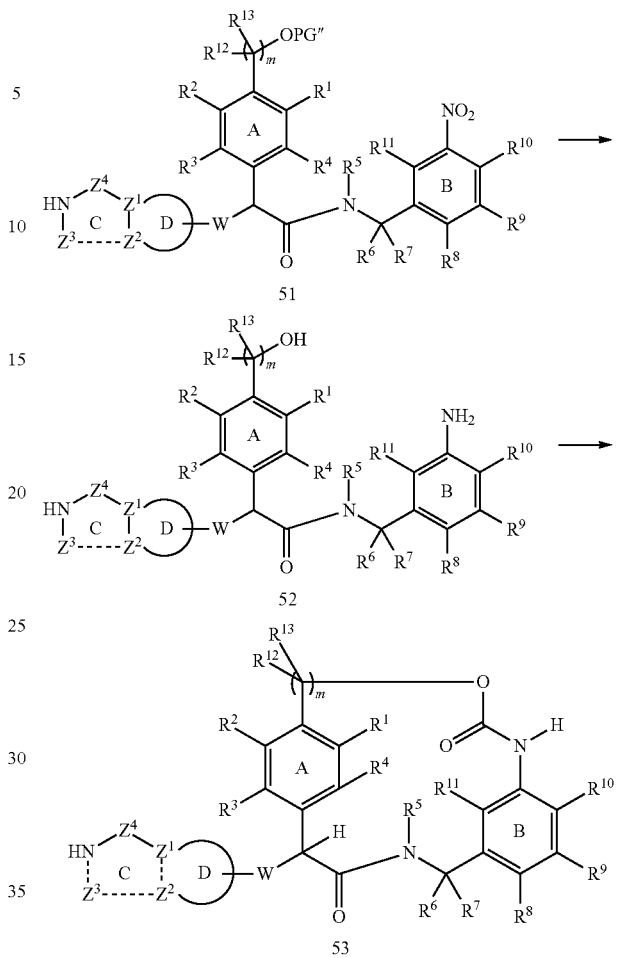

Scheme 10 depicts an alternate approach to compounds where Y=O and M=—CONH—; ring closure is accomplished via carbamate formation. Compounds 48 (prepared according to the Schemes 1-4) are deprotected (PG' protecting group) to afford acids 49, which in turn are coupled with amines 50 to afford amides 51. Following amide bond formation, a second protecting group removal (PG' protecting group) and the nitro functional group reduction (reducing conditions, such as $H_2$, Pd—C or Fe, AcOH) afford amino alcohols 52. Treatment of these intermediates with phosgene (or a phosgene equivalent such as triphosgene) to generate the carbamic chloride intermediate in situ, followed by slow addition of this intermediate into a basic reaction mixture, such as triethylamine or Hunig's base in DCM or acetonitrile, effects macrocyclization to yield compounds 53.

Scheme 10

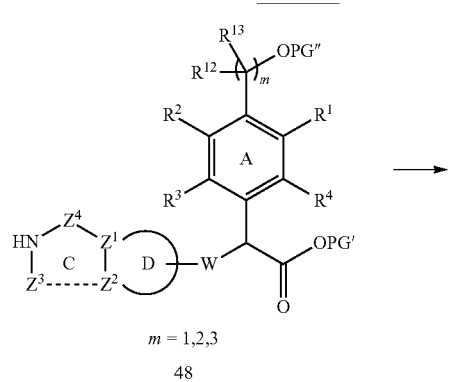

The compounds of the instant invention herein described may have asymmetric centers. For example, the chiral carbon atom in Formula (I) (indicated with an asterisk below) exists either in the S or R configuration. Thus, the stereoisomeric configurations of each compound of Formula (I) are considered part of the invention. In a preferred stereoisomeric embodiment, the present invention provides for the R configuration at the indicated chiral carbon for all embodiments of Formula (I), or tautomers, pharmaceutically acceptable salts, solvates, or prodrug forms thereof.

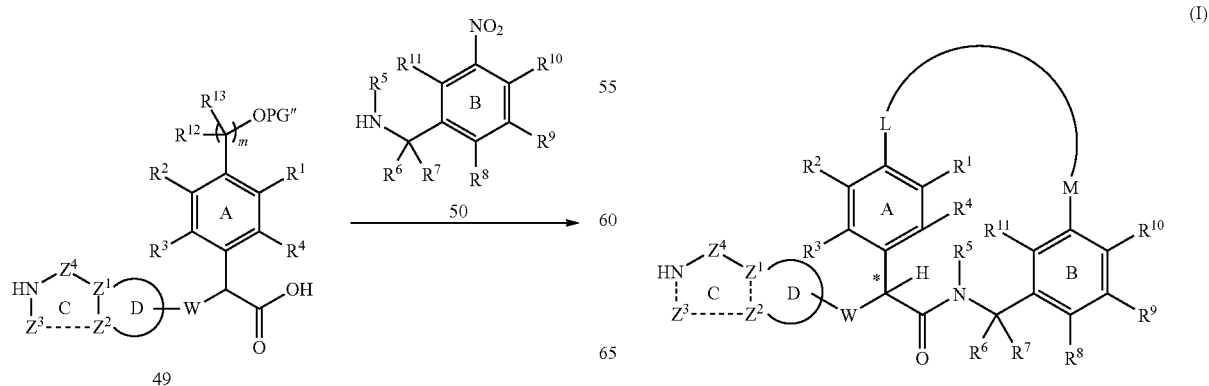

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running DiscoveryVP software using Column 1 (SunFire C18; 3.5 um; 4.6×150 mm) and Column 2 (XBridge Phenyl 3.5 um; 4.6×150 mm) eluted at 1 mL/min with a 10 min gradient from 100% A to 100% B and holding 100% B for 5 min while monitoring at 220 nM and 254 nM. Purities are reported at 254 nM. The following solvent systems were used for Method A: Solvent A: 10% methanol, 90% water, 0.05% TFA; Solvent B: 10% water, 90% methanol, 0.05% TFA, UV 254 nm) and Method B: Solvent A: 5% acetonitrile, 95% water, 0.05% $NH_4HCO_3$. Solvent B: 95% acetonitrile, 5% water, 0.05% $NH_4HCO_3$. Purification of intermediates and final products was carried out via either normal or reverse phase chromatography. Normal phase chromatography was carried out on an ISCO CombiFlash™ System using prepacked $SiO_2$ cartridges eluted with gradients of hexanes and ethyl acetate. Reverse phase preparative HPLC was carried out using a Shimadzu Preparative HPLC system running DiscoveryVP software using Method A: Waters Sunfire 5 µm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 µm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 µm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 µm C18 30×100 mm column with a min gradient at 40 mL/min from 100% A to 100% B (A: 10% methanol, 89.9% water, 0.1% TFA; B: 10% water, 89.9% methanol, 0.1% TFA, UV 220 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

IV. BIOLOGY

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, and artificial heart valves.

Some conditions contribute to the risk of developing thrombosis. For example, alterations of the vessel wall, changes in the flow of blood, and alterations in the composition of the vascular compartment. These risk factors are collectively known as Virchow's triad. (Hemostasis and Thrombosis, Basic Principles and Clinical practice, page 853, $5^{th}$ Edition, 2006, edited by Colman, R. W. et al. Published by Lippincott Williams & Wilkins)

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e. heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al. *Blood* 2005, 105, 453-463).

Because of its key role in the coagulation cascade, researchers have postulated that inhibition of factor VIIa could be used to treat or prevent thromboembolic diseases. (Girard, T. J.; Nicholson, N. S. *Curr. Opin. Pharmacol.* 2001, 1, 159-163; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al. *J. Thrombosis and Thrombolysis* 2002, 14, 113-121). In addition, small molecule active site directed factor VIIa inhibitors have demonstrated antithrombotic efficacy in animal models of arterial thrombosis (Suleymanov, O., et al. *J Pharmacology and Experimental Therapeutics* 2003, 306, 1115-1121; Olivero, A. G. et al. *J. Biol. Chem.* 2005, 280, 9160-9169; Young, W. B., et al. *Bioorg. Med. Chem. Lett.* 2006, 16, 2037-2041; Zbinden, K. G. et al. *Bioorg. Med. Chem.* 2006, 14, 5357-5369) and venous thrombosis (Szalony, J. A., et al. Thrombosis Research 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 prevents deep vein thrombosis in patients undergoing total knee replacement (Lee, A., et al. *Circulation* 2001, 104, 74-78), reduces systemic thrombin generation in patients undergoing coronary angioplasty (Moons, A. H. M. *J. Am. Coll. Cardiol.* 2003, 41, 2147-2153) and reduces magnitude and duration of ischemic events in patients with acute coronary syndromes (Giugliano, R. P. et al. World Congress of Cardiology 2006, Barcelona, Poster #3897).

Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

While a number of factor VIIa inhibitors have been discussed in the art, improved inhibitors, especially non-peptide inhibitors, of serine proteases for the treatment of thromboembolic disorders are always desirable. The present invention discloses bicyclic lactam derivatives, and analogues thereof, as inhibitors of coagulation Factor VIIa and, as such, their utility in the treatment of thromboembolic disorders.

Also, it is preferred to find new compounds with improved activity in in vitro clotting assays, compared with known serine protease inhibitors, such as the activated partial thromboplastin time (aPTT) or the prothrombin time (PT) assay. (For a description of the aPTT and PT assays see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51).

It is also desirable to find new compounds with improved pharmacological characteristics compared with known factor VIIa inhibitors. For example, it is preferred to find new compounds with improved factor VIIa inhibitory activity and improved selectivity for factor VIIa versus other serine proteases. It is also desirable and preferable to find compounds with advantageous and improved characteristics in one or more of the following categories that are given as examples, and not intended to be limiting: (a) pharmacokinetic properties, including oral bioavailability, half life, and clearance; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

As used herein, the term "patient" encompasses all mammalian species.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurance of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurance of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination with other active ingredients to inhibit factor VIIa or to prevent or treat the disorders listed herein. When applied to a combination, the term refers to combined amounts of the active ingredients that result in the preventive or therapeutic effect, whether administered in combination, serially or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined vide supra).

The term "thromboembolic disorders (or conditions)" as used herein includes arterial or venous cardiovascular or cerebovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke; atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a 'big baby', hypertension, low HDL cholesterol, and polycystic ovary syndrome.

Risk factor for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al. *Medicine* (Baltimore) 1999, 78(5):285-291; Levine M. et al. *N Engl J Med* 1996, 334(11):677-681; Blom, J. W. et al. *JAMA:* 2005, 293(6):715-722.) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e. presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al. *British Journal of Surgery* 2001, 88:913-930.)

A. In Vitro Assays

The effectiveness of compounds of the present invention as inhibitors of the coagulation factors VIIa, IXa, Xa, XIa, XIIa or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.00035 M.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.001 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate Spectrozyme #312 (pyroGlu-Pro-Arg-pNA; American Diagnostica) at a concentration of 0.00015 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002-0.00026 M.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_m$ values:

$(v_o - v_s)/v_s = I/(K_i(1 + S/K_m))$ for a competitive inhibitor with one binding site; or $v_s/v_o = A + ((B-A)/1 + ((IC_{50}/(I)^n)))$ and
$K_i = IC_{50}/(1 + S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using Alexin (Trinity Biotech, Ireland) following the directions in the package insert. Plasma (0.05 mL) is warmed to 37° C. for 1 minute. Alexin (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-induced Carotid Artery Thrombosis (ECAT) Model

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The ED50 (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

V. PHARMACEUTICAL COMPOSITIONS, FORMULATIONS AND COMBINATIONS

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutical acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18 th Edition, 1990.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intra-musculary, or sub-cutaneously). When administered intra-venous or intra-arterial, the dose can be given continuously or intermittend. Furthermore, formulation can be developed for intramuscular and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA) and piroxicam are preferred. Other suitable platelet inhibitory agents include glycoprotein IIb/IIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g. pravastatin, lovastatin, simvastatin, fluvastatin, atorvsatatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor VIIa in serum samples could be determined by careful titration of protease activity in the presence of the relevant chromogenic substrate, S2366, with a potent and selective Factor VIIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof

EXAMPLES

The following Examples have been prepared, isolated and characterized using the methods disclosed herein. The following Examples demonstrate a partial scope of the invention and are not meant to be limiting of the scope of the invention.

Intermediate 1:
7-Amino-3,4-dihydroisoquinolin-1(2H)-one

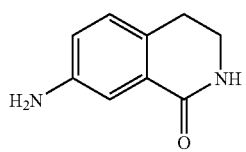

Intermediate 1A

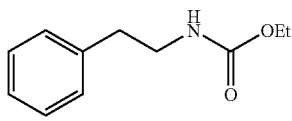 [SMILES: CCOC(=O)NCCc1ccccc1]

Ethyl chloroformate (20.8 g, 0.192 mol) was added dropwise to a solution of phenethylamine (15.5 g, 0.128 mol) and triethylamine (180 mL) in diethyl ether (500 mL) while maintaining the internal temperature of the reaction below 10° C. The reaction mixture was stirred two additional hours at ambient temperature and then filtered. The filtrate was concentrated in vacuo and the resulting oil was purified by flash chromatography (0-100% EtOAc in hexane) to yield Intermediate 1A (23.1 g, 94%). MS (ESI) m/z 193.4 $(M+H)^+$.

Intermediate 1B

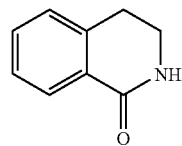 [SMILES: O=C1NCCc2ccccc21]

Intermediate 1A (4 g, 0.02 mol) was refluxed in a mixture of phosphorous pentoxide (5 g) and phosphorous oxychloride (25 mL) for 2 h. The reaction mixture was concentrated in vacuo to an oil, carefully quenched with wet ice followed by neutralization with sodium bicarbonate and extracted with diethyl ether. The combined organics were washed with water (2×50 mL), brine, dried ($MgSO_4$) and concentrated in vacuo. The crude product was purified by flash chromatography (0-100% EtOAc in hexane) to yield Intermediate 1B (1.1 g, 38%).

Intermediate 1C

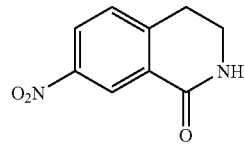

Intermediate 1B (1.1 g, 7.48 mmol) was added portionwise to a mixture of sulfuric acid (1 mL) and fuming nitric acid (5 mL) at 0° C. with stirring. Reaction was allowed to warm to ambient temperature and stirred for 2.5 h before pouring onto ice. The precipitate was collected by filtration and dried in vacuo to yield Intermediate 1C (770 mg, 55% yield) as a white solid.

Intermediate 1

Intermediate 1C (700 mg, 3.6 mmol) was stirred in MeOH (25 ml) with 10% Pd/C (cat.) under $H_2$ (60 psi) for 1 h. The reaction mixture was filtered through Celite® and concentrated in vacuo to give Intermediate 1 (500 mg, 86% yield). $^1$H NMR (400 MHz, $CD_3OD$) δ ppm 2.81 (t, J=6.59 Hz, 2H) 3.42

(t, J=6.55 Hz, 2H) 6.84 (dd, J=8.13, 2.42 Hz, 26H) 7.02 (d, J=7.91 Hz, 1H) 7.26 (d, J=2.64 Hz, 1H).

Intermediate 2: 6-aminoisoindolin-1-one

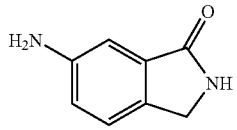

Intermediate 2A

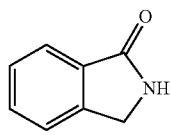

A solution of methyl 2-cyanobenzoate (9.2 g, 57 mmol) and Raney Ni (~1 g) in MeOH (200 mL) was stirred under H$_2$ (60 psi) for 16 h. The reaction mixture was filtered through Celite® and concentrated in vacuo to yield Intermediate 2A (7.5 g, 99% yield) as a white solid.
Intermediate 2B

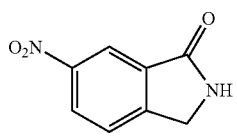 [SMILES: O=C1NCc2ccc([N+](=O)[O-])cc21]

Potassium nitrate (1.215 g, 12.02 mmol) was added portionwise to a solution of Intermediate 2A (1.6 g, 12.02 mmol) in sulfuric acid (24 mL) at 0° C. over 10 min. The reaction mixture was stirred for 3 h at ambient temperature. The reaction mixture was poured onto ice and the resulting precipitate was washed with water and dried in vacuo to yield Intermediate 2B (1.85 g, 10.38 mmol, 86% yield) as a beige solid.
Intermediate 2

A suspension of Intermediate 2B (1.6 g, 8.98 mmol) and Pd/C (0.18 g) in MeOH (100 mL) was stirred under H$_2$ (1 atm) for 4 h. The reaction mixture was filtered and the filter cake was washed with MeOH. The combined filtrates were concentrated in vacuo. The crude solid was triturated with MeOH (10 mL) and dried in vacuo to yield Intermediate 2 (800 mg, 5.40 mmol, 60.1% yield) as a beige solid. $^1$H NMR (400 MHz, DMSO-d$_6$) δ ppm 4.15 (s, 2H) 5.26 (s, 2H) 6.77 (dd, J=8.25, 2.20 Hz, 1H) 6.80 (s, 1H) 7.16 (d, J=8.79 Hz, 1H) 8.29 (s, 1H). MS (ESI) m/z 149.2 (M+H)$^+$.

Intermediate 3: 7-aminoisoquinolin-1(2H)-one

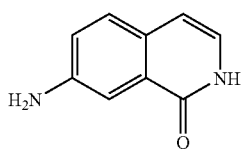

Intermediate 3A

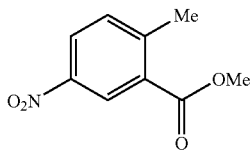 [SMILES: COC(=O)c1cc([N+](=O)[O-])ccc1C]

To 2-methyl-5-nitrobenzoic acid (2.69 g, 14.85 mmol) in CH$_2$Cl$_2$ (40 mL) was added thionyl chloride (5.42 mL, 74.2 mmol) and DMF (0.5 mL). The mixture was stirred at 80° C. (oil bath) for 3.5 h. After it was cooled to rt, the solvent was removed and the residue was azeotroped with toluene. The crude solid acyl chloride was dried in vacuo for 20 min. It was then dissolved in CH$_2$Cl$_2$ (20 mL) and MeOH (10 mL) and stirred at rt for 30 min. Solvent was removed and the residue was diluted in EtOAc/hexanes, washed with sat. NaHCO$_3$, brine, dried over Na$_2$SO$_4$. After evaporation of the solvent, Intermediate 3A (2.8 g) was obtained as a white solid that was used for next step without purification.
Intermediate 3B

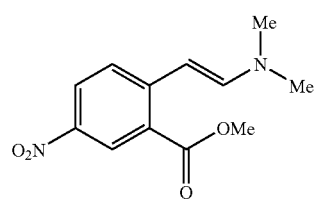 [SMILES: COC(=O)c1cc([N+](=O)[O-])ccc1/C=C/N(C)C]

A mixture of Intermediate 3A (2.38 g, 12.19 mmol) and 1-tert-butoxy-N,N,N',N'-tetramethylmethanediamine (5.79 mL, 28.0 mmol) was heated at 115° C. (no solvent) for 3.5 h. After the mixture was cooled to rt, it was triturated with hexanes/EtOAc (6:1). After over night standing at rt, the precipitate was collected by filtration to give solid Intermediate 3B (2.73 g, 90% yield).
Intermediate 3C

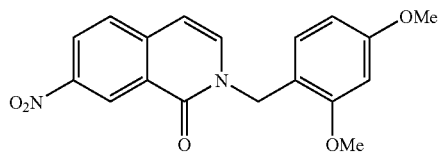 [SMILES: COc1ccc(Cn2ccc3ccc([N+](=O)[O-])cc3c2=O)c(OC)c1]

To Intermediate 3B (3.0 g, 11.99 mmol) in toluene (18 mL) was added (2,4-dimethoxyphenyl)methanamine (2.476 mL, 16.48 mmol). The mixture was stirred at 125° C. (oil bath) for 3.5 h. The color changed from deep red to yellow. After the mixture cooled to rt, it was triturated with EtOAc/hexanes (1:2) and left standing overnight. The yellow precipitate was collected by filtration to give Intermediate 3C (3.92 g, 96% yield).
Intermediate 3D

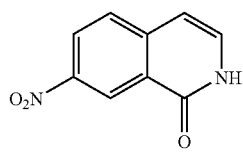 [SMILES: O=c1[nH]ccc2ccc([N+](=O)[O-])cc12]

Intermediate 3C (1.2 g, 3.53 mmol) in TFA (20.0 mL) was stirred at 85° C. for 2.5 h. After the mixture cooled to rt, TFA was removed under vacuum. The crude was chased with methanol once and dried under high vacuum to give a deep purple solid. The solid was further triturated with EtOAc and collected by filtration to give Intermediate 3D (1.0 g, 100%) as TFA solvate.

Intermediate 3

To Intermediate 3D (710 mg, 3.73 mmol) was added tetrahydrofuran (160 mL, stabilized with 25 ppm BHT) and water (0.95 mL). The solution was sonicated to near complete dissolution and 10% Pd/C (290 mg) was added. This solution was then hydrogenated with a hydrogen balloon for 50 min. Pd/C was removed by filtration and the filtrate was condensed to give a slightly yellow solid Intermediate 3 (570 mg, 95% yield). $^1$H NMR (400 MHz, DMSO-$d_6$) δ ppm 5.47 (s, 2H) 6.32 (d, J=7.15 Hz, 1H) 6.78 (d, J=4.95 Hz, 1H) 6.95 (dd, J=8.52, 2.47 Hz, 1H) 7.27-7.32 (m, 2H) 10.81 (s, 1H); LC-MS 161 (M+H).

Intermediate 4: 6-aminoquinazolin-4(3H)-one

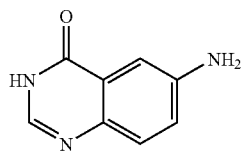 [SMILES: Nc1ccc2nc[nH]c(=O)c2c1]

Intermediate 4A

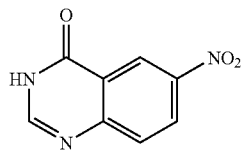 [SMILES: O=c1[nH]cnc2ccc([N+](=O)[O-])cc12]

In a 2 mL microwave vial was placed formamide (1.5 mL, 37.8 mmol) and 5-nitroanthranilic acid (917 mg, 5.04 mmol) to give a yellow suspension. The mixture was heated under microwave at 150° C. for 60 min. The mixture was diluted with EtOAc (1 L) and washed with NaHCO$_3$ (Sat. 200 mL) and brine (200 mL). The organic layer was dried by MgSO$_4$ and concentrated to yield Intermediate 4A (760 mg, 79% yield).

Intermediate 4

In a 1 L flask was added Intermediate 4A (1 g, 5.23 mmol) in MeOH (500 mL) to give a yellow suspension. 10% Pd/C (0.056 g, 0.523 mmol) was added. The mixture was stirred at rt under a hydrogen balloon for 4 h. The reaction mixture was filtered and concentrated to a yellow solid 0.84 g (100%). $^1$H NMR (500 MHz, DMSO-$d_6$) δ ppm 5.60 (s, 2H) 7.05 (dd, J=8.80, 2.75 Hz, 1H) 7.16 (d, J=2.75 Hz, 1H) 7.36 (d, J=8.80 Hz, 1H) 7.74 (s, 1H) 11.80 (s, 1H).

Intermediate 5:
7-amino-4-chloroisoquinolin-1(2H)-one

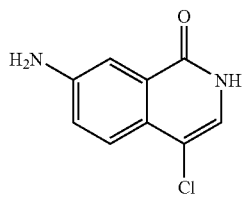

Intermediate 5A

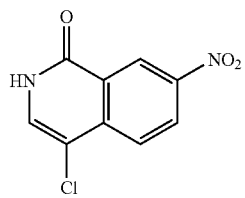 [SMILES: O=c1[nH]cc(Cl)c2ccc([N+](=O)[O-])cc12]

A solution of Intermediate 3D (299.7 mg, 1.576 mmol) and N-chlorosuccinimide (235 mg, 1.760 mmol) in DMA (4.5 mL) was heated by microwave at 200° C. for 10 min. The reaction mixture was poured into water (40 mL). The product was isolated by filtration, air dried, and then dried under vacuum to give Intermediate 5A as a yellow green solid (328.3 mg, 93%). LC/MS: RT=0.99 min, [M+H]$^+$=225.1, 227.1. Gradient: 0 to 100% Solvent B in 2 min, hold 1 min. Flow rate: 5 mL/min. Solvent A: 10% acetonitrile, 90% water, 0.1% trifluoroacetic acid. Solvent B: 90% acetonitrile, 10% water, 0.1% trifluoroacetic acid. UV: 220 nM. Column: Phenomenex Luna C18, 30×4.6 mm, 5 micron.

Intermediate 5

Tin(II) chloride dihydrate (1.25 g, 5.54 mmol) was added to a suspension of 31A (312 mg, 1.389 mmol) and ammonium chloride (370 mg, 6.92 mmol) in MeOH (10 mL) and the reaction mixture was stirred at rt for 7 h. The reaction mixture was then placed in a 50° C. oil bath overnight. Sat'd sodium bicarbonate was added and the mixture was extracted with ethyl acetate (4×). The combined organic layers were washed with brine, dried (MgSO$_4$) and then concentrated in vacuo to give Intermediate 5 as a brown solid (244 mg, 90%). MS (ESI) m/z 195.2, 197.1 (M+H)$^+$.

Intermediate 6:
7-amino-4-fluoroisoquinolin-1(2H)-one

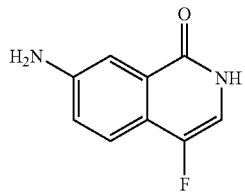

Intermediate 6A

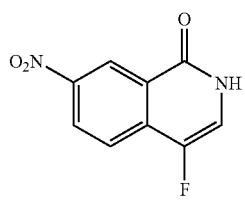 [SMILES: O=c1[nH]cc(F)c2ccc([N+](=O)[O-])cc12]

A 20 mL microwave tube was charged with Intermediate 3D (1.0 g, 5.25 mmol), Selectflor (1.86 g, 5.25 mmol) and dimethylacetamide (10 mL). The brown solution was microwaved at 150° C. for 15 min. The reaction mixture was cooled to rt and concentrated in vacuo. Twenty 1.0 g scale reactions were carried out and purified by preparative HPLC to give Intermediate 6A (5.0 g, 23% yield) as a yellow solid. MS (ESI) m/z 208.8 (M+H)$^+$.

Intermediate 6

A solution of Intermediate 6A (1.5 g, 7.2 mmol) in methanol/THF (1:1, 20 ml) was added to palladium on carbon (150 mg) and the resulting mixture was stirred for 3 h under $H_2$ (1 atm). The reaction mixture was filtered and concentrated. The crude product was purified by silica gel coloum chromatography to give Intermediate 6 as a yellow solid. Yield: 1.2 g, 88%. $^1$H NMR (400 MHz, DMSO-$d_6$) δ 10.7 (s, 1H), 7.5 (d, 1H), 7.3 (d, 1H), 7.2 (d, 1H), 6.9 (d, 1H), 5.8 (s, 1H). LCMS- $(M+1)^+$ 178.8.

Intermediate 7: 6-amino-5-fluoroisoindolin-1-one

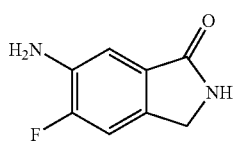 [SMILES: Nc1cc2c(cc1F)CNC2=O]

Intermediate 7A

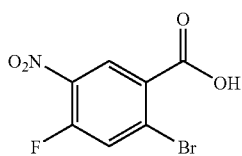

Potassium nitrate (11.54 g, 114 mmol) was added portionwise to a solution of 2-bromo-4-fluorobenzoic acid (25 g, 114 mmol) in sulfuric acid (228 mL) at 0° C. over 10 min. The reaction mixture was stirred for 3 h at ambient temperature. The reaction mixture was poured onto ice. The resulting precipitate was washed with water and dried in vacuo to yield a mixture of Intermediate 7A and 2-Br-4-F-6-nitrobenzoic acid (9:1) as a white solid (19.5 g). 7 g of this solid was purified by prep HPLC (0.1% TFA, $H_2O$/MeOH, 35% to 60%) to yield Intermediate 7A (5.6 g, 21.21 mmol) as a white solid. MS (ESI) m/z 262.1/264.1 (M–H)$^-$.

Intermediate 7B

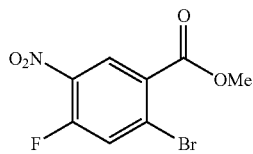 [SMILES: COC(=O)c1cc([N+](=O)[O-])c(F)cc1Br]

Thionyl chloride (1.673 mL, 22.92 mmol) was added to methanol (100 mL) at 0° C. and stirred for 30 min. Intermediate 7A (5.5 g, 20.83 mmol) was added and the mixture was heated at 60° C. for 18 h. The reaction mixture was concentrated to a white solid and purified by column chromatography (0 to 50% EtOAc in hexanes, 120 g column) to yield Intermediate 7B (5.03 g, 18.09 mmol, 87% yield) as a white solid. MS (ESI) m/z 279.0/281.0 (M+H)$^+$.

Intermediate 7C

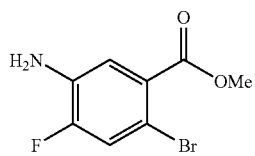

Iron (5.02 g, 90 mmol) was added portionwise to a solution of Intermediate 7B (5.0 g, 17.98 mmol) in ethanol (138 mL)/water (34.6 mL)/AcOH (6.92 mL) at 110° C. (bath temp). The reaction mixture was refluxed for 1 h. The reaction mixture was neutralized with NaHCO$_3$ (aq, sat'd), diluted with $H_2O$ (250 mL) and extracted with EtOAc (2×400 mL). The organics were combined, washed with brine, dried over Na$_2$SO$_4$ and concentrated to yield Intermediate 7C (2.45 g, 9.88 mmol, 54.9% yield) as a white solid. MS (ESI) m/z 248.1/250.1 (M+H)$^+$.

Intermediate 7D

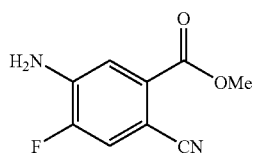

A solution of copper (I) cyanide (0.812 g, 9.07 mmol) and Intermediate 7C (1.5 g, 6.05 mmol) in DMF (24.19 mL) was divided into two vessels and microwaved at 180° C. for 10 min. The reaction mixture was diluted with NH$_4$OH (50 mL) and $H_2O$ (50 mL) and extracted with EtOAc (1×200 mL). The organics were washed with NaHCO$_3$, brine, dried over Na$_2$SO$_4$ and concentrated. Purification by column chromatography (0 to 100% EtOAc in Hexanes) yielded Intermediate 7D (650 mg, 3.35 mmol, 55.4% yield) as a yellow solid. MS (ESI) m/z 195.2 (M+H)$^+$.

Intermediate 7

A mixture of Intermediate 7D (200 mg, 1.030 mmol) and Raney Ni in MeOH and NH$_3$ (20 mL, 7.0 M) was stirred under $H_2$ (50 psi) for 16 h. The reaction mixture was diluted with acteone (100 mL), filtered through Celite and concentrated. The resulting solid was titurated with $H_2O$ (20 mL) and dried in vacuo to yield Intermediate 7 (100 mg, 0.602 mmol, 58.4% yield) as a white solid. MS (ESI) m/z 166.9 (M+H)$^+$. $^1$H NMR (400 MHz, DMSO-$d_6$) δ ppm 5.14-5.43 (m, 2H) 6.92-7.11 (m, 1H) 7.10-7.28 (m, 1H) 8.17-8.46 (m, 1H).

Intermediate 8: (R)-2-(4-bromo-2-methylphenyl)propan-1-ol

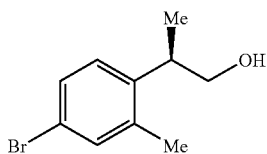 [SMILES: Cc1cc(Br)ccc1[C@@H](C)CO]

Intermediate 8A

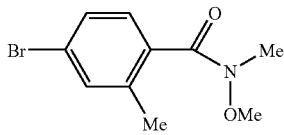 [SMILES: CON(C)C(=O)c1ccc(Br)cc1C]

To a suspension of 4-bromo-2-methylbenzoic acid (30.5 g, 142 mmol) in DCM (250 mL), were added oxalyl chloride (14.9 mL, 170 mmol) and DMF (20 μL, 0.258 mmol). The suspension was stirred at rt for 9 h, then concentrated to afford the acid chloride (33.1 g, quantitative) as an off-white crystalline solid. To a mixture of N,O-Dimethylhydroxylamine hydrochloride (16.60 g, 170 mmol) and pyridine (34.4 mL, 425 mmol) in DCM (250 mL) and acetonitrile (50 mL) at 0° C., was added a solution of the acid chloride prepared above in DCM (100 mL), dropwise over 20 min. The resultant suspension was removed from the ice bath and was stirred at rt for 6 h. The reaction mixture was washed with 2N HCl (2×), H$_2$O and brine, dried (Na$_2$SO$_4$), filtered through 1" SiO$_2$ and concentrated to afford Intermediate 8A (34.6 g, 134 mmol, 95% yield) as a light brown oil. MS (ESI) m/z 258.1 (M+H)$^+$.

Intermediate 8B

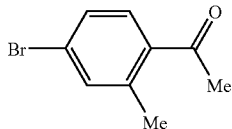 [SMILES: CC(=O)c1ccc(Br)cc1C]

To a round bottom. flask containing 3M methylmagnesium iodide in Et$_2$O (62.6 mL, 188 mmol), was added a solution of Intermediate 8A (34.6 g, 134 mmol) in Et$_2$O (200 mL) at rt, dropwise via a canulla over 30 min. The resulting suspension was stirred at rt. Additional 3 M methylmagnesium iodide in Et$_2$O (20 mL, 60 mmol) was added and the gray solution was stirred at rt for 5 h. The reaction was cooled to 0° C., then was carefully quenched with H$_2$O. The thick mixture was acidified with 1N HCl, then was extracted with Et$_2$O (2×). The combined organic was washed with 1N HCl and brine, dried (Na$_2$SO$_4$), filtered through 2" SiO$_2$ (eluting with Et$_2$O) and concentrated. The crude product was dissolved in hexanes, loaded onto a 330 g column and eluted with a gradient from 0 to 30% ethyl acetate/hexanes to afford Intermediate 8B (20.2 g, 94 mmol, 70.0% yield) as a colorless crystalline solid. MS (ESI) m/z 213.1 (M+H)$^+$.

Intermediate 8C

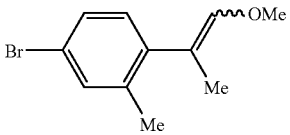

To a suspension of (methoxymethyl)triphenylphosphonium chloride (14.56 g, 42.5 mmol) in THF (100 mL) was added potassium tert-butoxide (4.77 g, 42.5 mmol) in THF (50 mL) at rt under argon. The red suspension was stirred at rt for min, then a solution of Intermediate 8B (5.485 g, 25.7 mmol) in THF (50 ml) was added. The resulting suspension allowed to stir overnight at rt. THF was removed under reduced pressure, and hexanes (300 mL) was added to the residue. The resulting suspension was sonicated and then stirred for 30 minutes. Ph$_3$PO was removed by filtration and the filtrate was concentrated. The residue was dissolved in acetone (50.00 ml), and iodomethane (8.05 ml, 129 mmol) was added. The reaction mixture was stirred at it for 3 h. Solvent was removed under reduced pressure, and the residue was sonicated in EtOAc/hex (2/8; 250 mL). The resulting suspension was filtered through a small pad of silica, silica washed with EtOAc/hex (2/8; 3×50 mL). The solvent was removed under reduced pressure and the residue was purified by ISCO: (120 g) 0 to 15% EtOAc/hexanes gradient, eluted at ~7% EtOAc. Fractions were combined and concentrated under reduced pressure to give Intermediate 8C (5.770 g, 23.93 mmol, 93% yield) (mixture of E- and Z-isomers) as a colorless oil.

Intermediate 8D

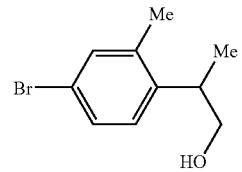 [SMILES: Cc1cc(Br)ccc1C(C)CO]

A mixture containing Intermediate 8C (6.740 g, 28.0 mmol), dioxane (70 mL) and HCl (conc.) (25 mL) was heated at 60° C. for 1 h. The dioxane was removed under reduced pressure, and the residue was partitioned between EtOAc (150 mL) and water (100 mL). The EtOAc phase was washed with water (2×100 mL), brine (1×100 mL) and dried (Na$_2$SO$_4$). Solvent was removed under reduced pressure, and the crude aldehyde was dissolved in MeOH (50 mL) and cooled to 0° C. To this solution, sodium borohydride (2.12 g, 55.9 mmol) was added, and the reaction was allowed to stir at 0° C. for 15 min, and then at rt for 5 min. MeOH was removed under reduced pressure. The residue was dissolved in EtOAc (150 mL), washed with water (2×), brine (1×) and dried (Na$_2$SO$_4$). The resulting EtOAc suspension was filtered through a pad of silica, pad washed with EtOAc (3×), EtOAc fraction concentrated to give Intermediate 8D (5.531 g, 24.14 mmol, 86% yield) as a brownish oil. MS (ESI) m/z 211.1 (M+H)$^+$.

Intermediate 8

Chiral separation of Intermediate 8D to afford Intermediate 8, was accomplished by SFC using a Regis Whelk-01 (R,R) column, 500×21 mm ID, 10 μm; temperature: rt; 5% Isopropanol: 95% CO$_2$; Flow rate: 65 ml/min; UV Detection: 220 nm; RT$_1$: 12.10 (R-stereoisomer) RT$_2$: 15.12 (S-stereoisomer). MS (ESI) m/z 211.1 (M+H)$^+$—H$_2$O. $^1$H-NMR: (Jeol ECX-400) (400 MHz, CDCl$_3$) δ ppm 1.22 (d, J=7.15 Hz, 3H) 1.32 (t, J=5.77 Hz, 1H) 2.34 (s, 3H) 3.14-3.28 (m, 1H) 3.63-3.77 (m, 2H) 7.04-7.11 (m, 1H) 7.32 (d, J=5.50 Hz, 2H).

Intermediate 9: (R)-2-(4-bromo-2-methoxyphenyl)propan-1-ol

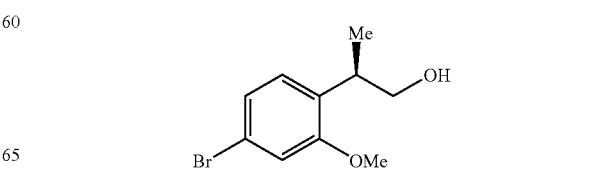

Intermediate 9A

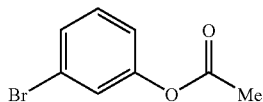 [SMILES: CC(=O)Oc1cccc(Br)c1]

Sulfuric acid (0.3 mL, 5.63 mmol) was added to a well stirred mixture of 3-bromophenol (26.2 g, 152 mmol) and acetic anhydride (15.3 mL, 162 mmol), cooled with a rt water bath. After 30 min, the volatiles were removed on a rotovap. Ice was added to the residue, which was then extracted with ether (3×). The combined organic layers were washed with brine, dried (MgSO$_4$) and concentrated in vacuo to give Intermediate 9A (32.0 g, 149 mmol, 98% yield) as an amber colored oil. ~95% pure.

Intermediate 9B

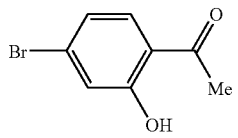

Aluminum chloride (36 g, 270 mmol) was added to Intermediate 9A (32.0 g, 149 mmol) in a round bottom flask fitted with a reflux condenser, nitrogen gas inlet, and sodium hydroxide solution to scrub the HCl(g) effluent. The reaction flask was place in a 120° C. oil bath. The reaction mixture become fluid, then was warmed to 165° C. over 1 h. The temperature was maintained at this temperature for 1 h, then was allowed to cool to rt. To the solid reaction mixture was added dichloromethane (~200 mL) to form a slurry. The slurry was added to ice. This process was repeated multiple times to process the entire reaction mixture. The dichloromethane/water mixture was stirred until both phases were fairly clear, then the phase were separated. The organic phase was washed with brine, dried (MgSO$_4$) and then concentrated in vacuo to obtain Intermediate 9B (30.14 g, 140 mmol, 94% yield) as a dark red oil. MS (ESI) m/z 213, 215.3 (M+H)$^+$. ~90% pure.

Intermediate 9C

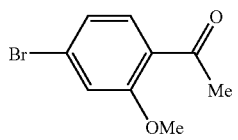

Iodomethane (10.5 mL, 168 mmol) was added dropwise over 30 min to a solution of Intermediate 9B (30.14 g, 140 mmol) in DMF (100 mL) at 0° C. After min, the reaction was warmed to rt for 2.5 h. Water (250 mL) was added and the resulting tan precipitate was filtered and washed with water to give Intermediate 9C (29.64 g, 129 mmol, 92% yield). MS (ESI) m/z 229. 231 (M+H)$^+$.

Intermediate 9D

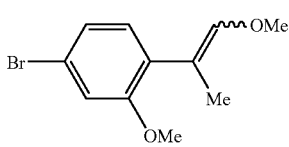 [SMILES: COC=C(C)c1ccc(Br)cc1OC]

Using a procedure analogous to that used to prepare Intermediate 8C, Intermediate 9C (0.32 g, 0.633 mmol) was reacted potassium tert-butoxide and methoxymethyl)triphenylphosphonium chloride (53.7 g, 157 mmol) to give Intermediate 9D (18.965 g, 73.8 mmol, 77% yield) as a yellow oil. MS (ESI) m/z 257.1, 259.1 (M+H)$^+$. 1:1 mixture of olefin isomers. ~95% pure.

Intermediate 9E

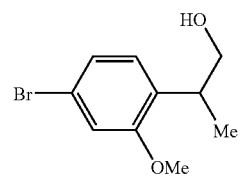 [SMILES: COc1cc(Br)ccc1C(C)CO]

Using a procedure analogous to that used to prepare Intermediate 8D, Intermediate 9D (19.0 g, 73.8 mmol) was reacted with HCl and then sodium borohydride to give Intermediate 9E (16.4 g, 66.8 mmol, 91% yield) as a pale yellow oil.

Intermediate 9

Chiral separation of Intermediate 9E to afford Intermediate 9 was accomplished by SFC using a Regis Whelk-01 (R,R) column, 500×21 mm ID, 10 μm; temperature: 35° C.; 5% Isopropanol: 95% CO$_2$; Flow rate: 70 ml/min; UV Detection: 276 nm; RT$_1$: 9.9 (R-stereoisomer) RT$_2$: 11.3 (S-stereoisomer). MS (ESI) m/z 227, 229 (M-OH)$^+$.

Intermediate 10: (R)-4-(1-(tert-butyldimethylsilyloxy)propan-2-yl)-3-methylphenylboronic acid

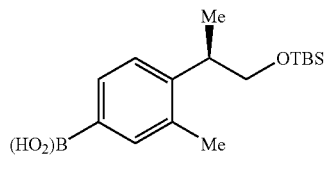

Intermediate 10A

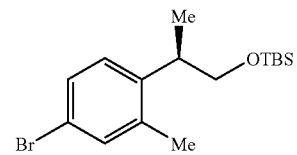 [SMILES: Cc1cc(Br)ccc1[C@@H](C)CO[Si](C)(C)C(C)(C)C]

tert-Butyldimethylchlorosilane (0.724 g, 4.80 mmol) was added to a solution of Intermediate 8 (1 g, 4.36 mmol) and imidazole (0.594 g, 8.73 mmol) in CH$_2$Cl$_2$ (25 mL) and stirred at rt for 3 h. The reaction was diluted with CH$_2$Cl$_2$ (75 mL), washed with water and brine, and concentrated. The crude material was purified by flash chromatography (80 g column, 0 to 25% EtOAc in Hexanes) to yield Intermediate 10A (1.39 g, 4.05 mmol, 93% yield) as a clear oil.

Intermediate 10

BuLi (2.70 mL, 4.32 mmol) was added dropwise to a solution of Intermediate 10A (1.35 g, 3.93 mmol) in THF (40 mL) at −78° C. After stirring for 5 min, trimethyl borate (0.879 mL, 7.86 mmol) was added and the cooling bath was removed. The reaction mixture was stirred for 14 h at rt. The reaction mixture was diluted with Et$_2$O (100 mL) and washed for 5 min with 0.5 M HCl (50 mL). The organic phase was separated, washed with H$_2$O and brine (50 mL each) and concentrated. The crude oil was purified by column chromatography (0 to 100% EtOAc in Hexanes, 40 g column) to yield Intermediate 10 (795 mg, 2.58 mmol, 65.6% yield) as a clear solid. MS (ESI) m/z 307.7 (M−H)$^-$.

Intermediate 11: tert-butyl 5-amino-2-(cyclopropylsulfonyl)benzyl (methyl)carbamate

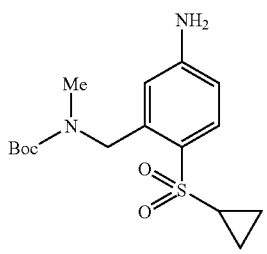 [SMILES: CN(Cc1cc(N)ccc1S(=O)(=O)C1CC1)C(=O)OC(C)(C)C]

Intermediate 11A

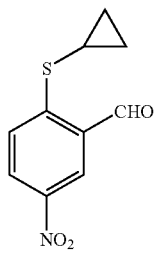 [SMILES: O=Cc1cc([N+](=O)[O-])ccc1SC1CC1]

Sulphur powder (3.5 g, 11 mmol) was added portionwise to a solution of cyclopropyl magnesium bromide (220 mL, 0.5 M in THF). The reaction mixture was heated at 50° C. for 1 h. The brown solution was then cooled to 0° C., and LAH (2.3 g, 6 mmol) was added portionwise (frothing was observed). The resulting green suspension was heated to 50° C. for 30 min. Again, it was cooled to 0° C., quenched with 4 mL of water, 200 mL of 5% $H_2SO_4$ and allowed to stir for 10 min. The layers were separated and extracted with $Et_2O$ (2×50 mL). The combined organic layers were washed with sat. $NH_4Cl$ solution (2×100 mL), 10% $NaHCO_3$ solution (2×100 mL), water (1×100 mL), brine, and dried over sodium sulphate. The above organic layer was decanted to a mixture of 2-chloro-5-nitrobenzaldehyde (10 g, 5.3 mmol) and anhydrous $K_2CO_3$ (11.2 g, 8.1 mmol) in DMF (100 ml). The reaction mixture was heated at 85° C. overnight. The reaction mixture was filtered through Celite®, and concentrated in vacuo. The residue dissolved in ethyl acetate, washed with water, brine, dried over sodium sulphate and concentrated. The crude was crystallized from hexane. Yield: 11 g, 92%.

Intermediate 11B

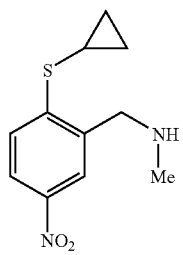 [SMILES: CNCc1cc([N+](=O)[O-])ccc1SC1CC1]

To stirred solution of compound Intermediate 11A (10.0 g, 4.4 mmol) in methanol (100 mL) was added 30% methanolic methyl amine solution (14 mL, 13 mmol) dropwise and stirred for 1 h. The reaction mixture was cooled to 0° C., sodium borohydride (3.4 g, 8.9 mmol) was added portionwise and the mixture was stirred at rt for over night. The reaction mixture was concentrated, diluted with ethyl acetate washed with water, brine dried over sodium sulphate and concentrated. Recrystallization from hexane (10 g, 94%) yielded Intermediate 11B. LC-MS=238.

Intermediate 11C

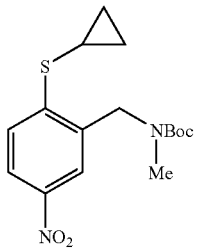

To a stirred solution of compound Intermediate 11B (10 g, 4.1 mmol) and triethyl amine (12 mL, 8.3 mmol) in THF (100 mL) was added boc anhydride (10 g, 4.6 mmol) and stirred at rt overnight. The reaction mass was diluted with water extracted with ethyl acetate, washed with, water brine, dried over sodium sulphate, concentrated and crystallized to give Intermediate 11C (13 g, 92%). LC-MS (M−Boc) 238.

Intermediate 11D

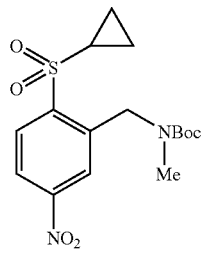

mCPBA (10 g, 57.9 mmol) was added to a solution of Intermediate 11C (10.7 g, 31.6 mmol) in $CH_2Cl_2$ (90 mL) at 0° C. After 4 h an addition 2.0 g of mCPBA was added to the mixture and stirred for 1 h. The mixture was diluted with dichloromethane and then washed with satd $NaHCO_3$ and brine, The organic layer was separated, dried over sodium sulfate, filtered and concentrated. The crude product was dissolved in a small amount of dichloromethane and charged to a 120 g silica gel cartridge which was eluted with 0-50% ethyl acetate/hexanes over a period of 50 mins to yield Intermediate 11D (11.1 g, 30 mmol, 95% yield). MS (ESI) m/z 315 (M+H)−tBu$^+$.

Intermediate 11

To a solution of Intermediate 11D (2.33 g, 6.29 mmol) in methanol (50 mL), was added 10% Pd—C (200 mg, 0.188 mmol). The mixture was stirred overnight under an atmosphere of $H_2$ (1 atm). The reaction was filtered over Celite and concentrated to yield Intermediate 11 (2.16 g, 6.03 mmol, 96% yield) as a tan foam. MS (ESI) m/z 341 (M+H)$^+$. $^1$H NMR (400 MHz, DMSO-$d_6$) δ ppm 0.85-1.08 (m, 4H) 1.38

(d, J=48.37 Hz, 9H) 2.67-2.78 (m, J=4.40 Hz, 1H) 2.84 (s, 3H) 4.68 (s, 2H) 5.94-6.30 (m, 2H) 6.39 (s, 1H) 7.44 (d, J=8.79 Hz, 1H).

Intermediate 12:
6-amino-7-fluoroquinazolin-4(3H)-one

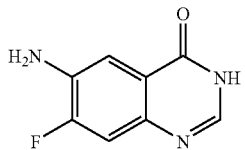 [SMILES: Nc1cc2c(=O)[nH]cnc2cc1F]

Intermediate 12A

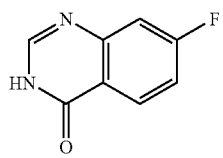

2-amino-4-fluorobenzoic acid (0.3 g, 1.934 mmol) in methoxyethanol (2.0 mL) in a microwave vessel was irradiated at 210° C. for 20 min. After cooling white crystals were observed. The sample was concentrated and diluted with 0.01M ammonia. The white solid was filtered and washed with 0.01M ammonia. The brown solid was collected and dried to give Intermediate 12A (0.24 g, 75% yield). MS (ESI) m/z 164.9 (M+H)$^+$.

Intermediate 12B

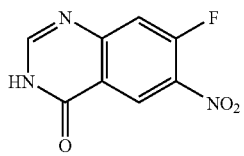 [SMILES: O=c1[nH]cnc2cc(F)c([N+](=O)[O-])cc12]

To Intermediate 12A (0.2 g, 1.218 mmol) at 0° C. in sulfuric acid (4.87 mL, 1.218 mmol) was added potassium nitrate (0.058 mL, 1.218 mmol) portion wise over 10 minutes. The reaction was then allowed to warm to room temp and stirred overnight. LCMS showed mostly starting material and about 10% product. More potassium nitrate (0.058 mL, 1.218 mmol) was added and reaction was heated to 80° C. for 1 h. LCMS showed mostly product. Saturated sodium bicarbonate was slowly added in the cooled reaction (ice water bath) and yellow solid precipitate was observed. This was filtered and washed with water. The solid was dried to give Intermediate 12B (0.14 g, 55% yield) as a yellow solid. (ESI) (m/z) 209.9[M+H]$^+$.

Intermediate 12

A solution of Intermediate 12B (0.12 g, 0.574 mmol) in methanol (5 mL) with a few drops of HCl was stirred until hydrogen at atmospheric pressure with palladium on carbon (0.02 g, 0.188 mmol) for 1.5 h. The catalyst was filtered off and washed with methanol. The filtrate was evaporated and dried under vacuum overnight to give Intermediate 12 (0.1 g, 97% yield) as a yellow solid. $^1$H NMR (400 MHz, DMSO-d$_6$) δ ppm 7.39-7.51 (m, 2H) 8.57 (s, 1H), MS (ESI) m/z 180 (M+H)$^+$.

Intermediate 13: (R)-4-(1-(tert-butyldimethylsilyloxy)propan-2-yl)-3-methoxyphenylboronic acid

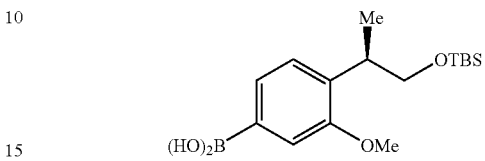

Using procedure analogous to that used to prepare Intermediate 10, Intermediate 9 (7.8 g, 158 mmol) was protected with tert-Butyldimethylchlorosilane to yield (R)-(2-(4-bromo-2-methoxyphenyl)propoxy)(tert-butyl)dimethylsilane (9.2 g, 81% yield) as a clear oil. The protected alcohol (3.00 g, 8.35 mmol) was reacted with BuLi and trimethyl borate to yield Intermediate 10 (1.87 g, 5.77 mmol, 69.1% yield) as a colorless oil. $^1$H NMR (400 MHz, methanol-d$_3$) δ ppm 7.12-7.19 (m, 2H) 7.12 (s, 1H) 3.82 (s, 3H) 3.75 (dd, J=9.89, 5.50 Hz, 1H) 3.52-3.58 (m, 0H) 3.32-3.37 (m, 0H) 1.23 (d, J=6.60 Hz, 3H) 0.84 (s, 9H) −0.04 (d, J=2.20 Hz, 6H).

Intermediate 14: tert-butyl methyl(5-nitro-2-(trifluoromethoxy)benzyl)carbamate

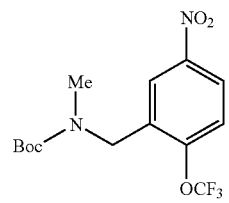 [SMILES: CN(Cc1cc([N+](=O)[O-])ccc1OC(F)(F)F)C(=O)OC(C)(C)C]

Intermediate 14A

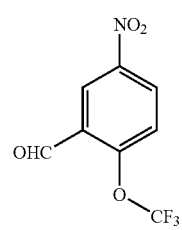 [SMILES: O=Cc1cc([N+](=O)[O-])ccc1OC(F)(F)F]

To a mixture of nitric acid (1.6 mL, 35.8 mmol) and sulfuric acid (8 mL, 150 mmol) at 0° C., was added 2-(trifluoromethoxy)benzaldehyde (1.881 mL, 13.15 mmol), dropwise over 10 min. The brown mixture was stirred at 0° C. for 1 h, then was poured onto 100 mL ice. The suspension was stirred, then the precipitate was collected by filtration, rinsed with H$_2$O and sucked dry. The product was dissolved with EtOAc (20 mL), dried (Na$_2$SO$_4$) and concentrated to afford Intermediate 14A (2.10 g, 8.93 mmol, 67.9% yield) as a yellow oil.

Intermediate 14

To a stirred solution of Intermediate 14A (1 g, 4.25 mmol) in MeOH (20 mL) was added methylamine (33% in EtOH)

(0.662 mL, 5.32 mmol) dropwise and stirred for 1 h at 25° C. (white solid formed). Then, the reaction mixture was cooled to 0° C. and sodium borohydride (0.322 g, 8.51 mmol) was added portionwise with stirring. The reaction mixture was allowed to reach rt and stirred for 3 h. The reaction mixture was concentrated under reduced pressure, then was partitioned between EtOAc and H$_2$O. The aqueous phase was extracted with EtOAc. The combined organic extract was washed with brine, dried (Na$_2$SO$_4$), and concentrated. Solvent was removed under reduced pressure to give the amine as a brown oil. MS (ESI) m/z 251.2 (M+H)$^+$. To a solution of the amine in THF (20 mL), was added Boc$_2$O (1.114 g, 5.10 mmol), followed by TEA (0.1 mL). The mixture was stirred at rt for 15 h, then was concentrated. The crude product was dissolved in hexanes, loaded onto a 40 g column and eluted with a gradient from 0 to 50% ethyl acetate/hexanes to afford Intermediate 14 (1.23 g, 3.51 mmol, 83% yield) as a pale yellow oil. MS (ESI) m/z 295.2 (M+H)$^+$.

Intermediate 15: tert-butyl 2-(difluoromethoxy)-5-nitrobenzyl(methyl)carbamate

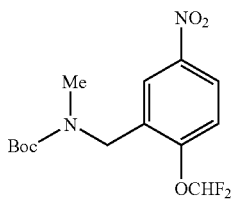 [SMILES: CN(Cc1cc([N+](=O)[O-])ccc1OC(F)F)C(=O)OC(C)(C)C]

Intermediate 15A

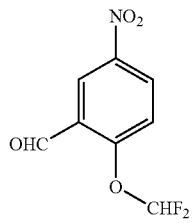 [SMILES: O=Cc1cc([N+](=O)[O-])ccc1OC(F)F]

To a mixture of nitric acid (1.6 mL, 35.8 mmol) and sulfuric acid (8 mL, 150 mmol) at 0° C., was added 2-(difluoromethoxy)benzaldehyde (2.5 g, 14.52 mmol), dropwise over 5 min. The brown mixture was stirred at 0° C. for 1 h, then was poured onto 100 mL ice. The suspension was stirred, then the precipitate was collected by filtration, rinsed with H$_2$O and sucked dry. The product was dissolved with EtOAc (20 mL), dried (Na$_2$SO$_4$) and concentrated to afford Intermediate 15A (2.78 g, 12.80 mmol, 88% yield) as a yellow solid.
Intermediate 15

To a stirred solution of Intermediate 15A (1 g, 4.61 mmol) in MeOH (20 mL) was added methylamine (33% in EtOH) (0.717 mL, 5.76 mmol) dropwise and stirred for 1 h at 25° C. (white solid formed). Then, the reaction mixture was cooled to 0° C. and sodium borohydride (0.348 g, 9.21 mmol) was added portionwise with stirring. The reaction mixture was allowed to reach rt and was stirred for 15 h. The reaction mixture was concentrated under reduced pressure, then was partitioned between EtOAc and H$_2$O. The aqueous phase was extracted with EtOAc. The combined organic extract was washed with brine, dried (Na$_2$SO$_4$), and concentrated. Solvent was removed under reduced pressure to give the amine as a yellow oil (1.04 g). (MS (ESI) m/z 233.3 (M+H)$^+$). To a solution of the amine in THF (20 mL), was added Boc$_2$O (1.206 g, 5.53 mmol), followed by TEA (0.1 mL). The mixture was stirred at rt for 15 h, then was concentrated. The crude product was dissolved in chloroform and hexanes, loaded onto a 40 g column and eluted with a gradient from 0 to 50% ethyl acetate/hexanes to afford Intermediate 15 (1.43 g, 4.30 mmol, 93% yield) as a colorless solid. MS (ESI) m/z 277.2 (M+H)$^+$. $^1$H NMR (400 MHz, CHLOROFORM-d) δ ppm 8.05-8.23 (m, 2H) 7.24 (s, 1H) 6.66 (t, J=72.14 Hz, 1H) 4.53 (d, J=17.61 Hz, 2H) 2.93 (br. s., 3H) 1.48 (d, J=23.96 Hz, 9H).

Intermediate 16: Methyl 2-(4-((R)-1-hydroxypropan-2-yl)-3-methylphenyl)-2-(1-oxo-1,2-dihydroisoquinolin-7-ylamino)acetate

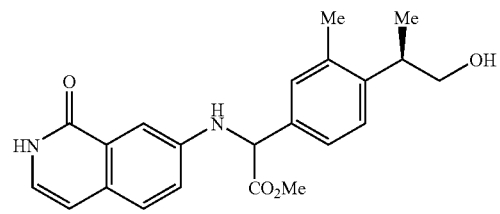 [SMILES: COC(=O)C(Nc1ccc2cc[nH]c(=O)c2c1)c1ccc([C@@H](C)CO)c(C)c1]

In a reaction vial, Intermediate 10 (1.256 g, 4.07 mmol), Intermediate 3 (0.653 g, 4.07 mmol), and glyoxylic acid monohydrate (0.375 g, 4.07 mmol) were dissolved in acetonitrile (20 mL) and DMF (5 mL). The mixture was heated in an oil bath at 80° C. for 2 h. Solvent was removed under reduced pressure, the residue was dissolved in MeOH (5 mL), and benzene (15 mL) was added. To this solution, TMS-Diazomethane (2 M in ether) (5.09 mL, 10.19 mmol) was added dropwise at rt. The mixture was stirred for 15 min at rt, then was evaporated. The residue was purified by flash chromatography: (120 g) 50-100% EtOAc/hex. Eluted at ~100% EtOAc. Fractions were combined and concentrated under reduced pressure to give Intermediate 16 (1.026 g, 2.70 mmol, 66.2% yield) as a yellow powder. MS (ESI) m/z 381.3. $^1$H-NMR: (Jeol ECX-400) (400 MHz, CDCl$_3$) δ ppm 1.22 (d, J=7.15 Hz, 3H) 1.53-1.64 (m, 1H) 2.34 (d, J=3.30 Hz, 3H) 3.17-3.28 (m, 1H) 3.64-3.69 (m, 1H) 3.76 (s, 3H) 5.21 (s, 2H) 6.42 (d, J=7.15 Hz, 1H) 6.86-6.92 (m, 1H) 7.03 (d, J=6.05 Hz, 1H) 7.20 (dd, J=7.97, 3.02 Hz, 1H) 7.29 (s, 1H) 7.31-7.39 (m, 2H) 7.43 (d, J=3.30 Hz, 1H).

Intermediate 17: 1-(2-bromo-5-nitrophenyl)-N-methylmethanamine

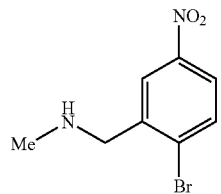 [SMILES: CNCc1cc([N+](=O)[O-])ccc1Br]

Intermediate 17A

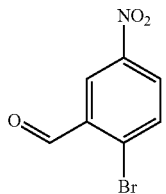 [SMILES: O=Cc1cc([N+](=O)[O-])ccc1Br]

Potassium nitrate (2.59 mL, 54.0 mmol) was added portionwise to a stirred and chilled (ice bath) solution of 2-bromobenzaldehyde (10 g, 54.0 mmol) in sulfuric acid (50 mL, 938 mmol) over 1 h. After 40 min an additional portion of KNO3 (0.72 g) was added. After 3 h stirring at 0° C., the mixture was poured over ice water, and the product was filtered and washed with water. The crude pale yellow solid was recrystallized from 1:1 ethyl acetate/hexane (~60 mL) to give Intermediate 17A (6.789 g, 29.5 mmol, 54.6% yield). MS (ESI) m/z 230, 232 (M+H)$^+$.

Intermediate 17

To a stirred solution of Intermediate 17A (17.768 g, 77 mmol) in MeOH (200 mL) was added methylamine (33 wt. % in EtOH) (21.81 mL, 232 mmol) dropwise and stirred for 1 h at 25° C. Then, the reaction mixture was cooled to 0° C. and sodium borohydride (5.84 g, 154 mmol) was added portionwise with stirring. The reaction mixture was allowed to reach rt and stirred overnight. The reaction mixture was concentrated under reduced pressure, diluted with EtOAc (250 mL), washed with water (2×100 mL), brine (1×100 mL) and dried (Na$_2$SO$_4$). The solvent was removed under reduced pressure to give Intermediate 17 (18.134 g, 74.0 mmol, 96% yield) as a yellow oil. Compound was pure (>95% by NMR) and utilized in the subsequent step without any further purification. MS (ESI) m/z 245.1 (M+H)$^+$. $^1$H-NMR: (500 MHz, CDCl$_3$) δ ppm 2.51 (s, 3H), 3.90 (s, 2H), 7.73 (d, J=8.8 Hz, 1H), 7.99 (dd, J=8.8, 2.7 Hz, 1H), 8.32 (d, J=2.7 Hz, 1H).

Intermediate 18: tert-butyl 2-bromo-5-nitrobenzyl(methyl)carbamate

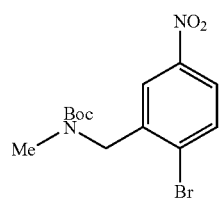 [SMILES: CN(Cc1cc([N+](=O)[O-])ccc1Br)C(=O)OC(C)(C)C]

Intermediate 17 (10 g, 40.8 mmol) was dissolved in THF (50 mL), Boc$_2$O (17.81 g, 82 mmol) was added, and the reaction mixture was stirred at 40° C. overnight. Imidazole (5.56 g, 82 mmol) was added to the reaction mixture and it was stirred for 15 min at rt. THF was removed under reduced pressure, and the residue was redissolved in CHCl$_3$ (100 mL). The solution was washed with 0.5% HCl (2×25 mL), water (2×25 mL), brine (1×25 mL), dried (Na$_2$SO$_4$) and concentrated. The residue was purified by flash chromatograpy (0-50% EtOAc/hexanes) to give Intermediate 18 (13.512 g, 39.1 mmol, 96% yield) as a yellowish solid. $^1$H-NMR: (400 MHz, CDCl$_3$) δ ppm 1.48 (d, J=40.43 Hz, 9H) 2.97 (s, 3H) 4.55 (d, J=8.35 Hz, 2H) 7.74 (d, J=8.79 Hz, 1H) 7.91-8.13 (m, 2H).

Example 1

(R)-7-Ethanesulfonyl-2-(3-oxo-2,3-dihydro-1H-isoindol-5-ylamino)-4,11-diaza-tricyclo[14.2.2.1$^{6,10}$]henicosa-1(19),6,8,10(21),16(20),17-hexaene-3,12-dione

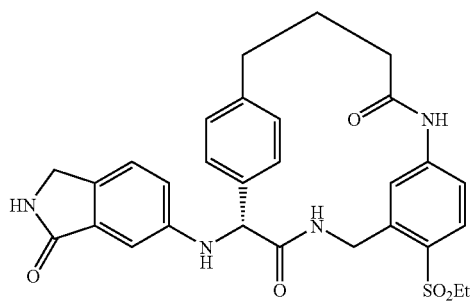

1A

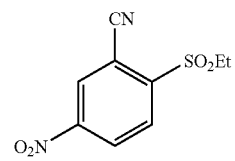

Ethanethiol (2.8 mL, 38 mmol) was added to a solution of 2-fluoro-5-nitrobenzonitrile (5.00 g, 30.1 mmol) and triethylamine (9.3 mL, 67 mmol) in DMF (100 mL). The reaction mixture was stirred for 1 h and then poured into water (500 mL). The resulting precipitate was isolated by filtration, dissolved in DCM, washed with water and brine, dried (MgSO$_4$), and concentrated under reduced pressure. The residue (6.14 g) was dissolved in DCM (100 mL), cooled to 0° C., and treated with mCPBA (16.0 g, 71 mmol) in one portion. The reaction mixture was allowed to stir at rt overnight, and then was extracted with sodium bicarbonate solution (saturated), sodium bisulfite solution (10%), and brine. The organic layer was dried (MgSO$_4$) and concentrated under reduced pressure to afford 1A (5.6 g, 80%) as a pale yellow solid. $^1$H NMR (400 MHz, CDCl$_3$) δ 1.02 (s, 6H), 1.97 (m, 2H), 2.36 (t, J=7.5 Hz, 2H), 2.68 (t, J=7.7 Hz, 2H), 3.76 (s, 4H), 7.18 (d, J=7.9 Hz, 2H), 7.72 (d, J=7.5 Hz, 2H).

1B

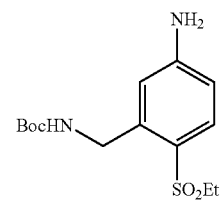

A solution of 1A (2.0 g, 8.32 mmol) in MeOH (100 mL) and hydrochloric acid (1 N, 20 mL) was hydrogenated (60 psi) over 20% Pd(OH)$_2$ (380 mg) for three days. The reaction mixture was filtered and hydrogenated twice more for three days each time over fresh catalyst. The reaction mixture was filtered and then concentrated in vacuo to give a white solid (2.15 g) after trituration with ethyl acetate and ether. 1.0 g of the solid was dissolved in THF (25 mL) and triethylamine (1 mL) and treated with 2-(tert-butoxycarbonyloxyimino)-2-phenylacetonitrile (0.905 g, 3.67 mmol). The reaction mixture was stirred overnight at rt. The reaction mixture was concentrated in vacuo and the residue was extracted twice with DCM and saturated sodium bicarbonate. The combined organics were extracted with brine, dried, and concentrated in vacuo. The residue was purified by silica gel chromatography (gradient from 0 to 50% ethyl acetate in hexanes) to give 1B (1.07 g, 88%) as a clear oil. MS (ESI) m/z 315.12 (M+H)$^+$.

1C

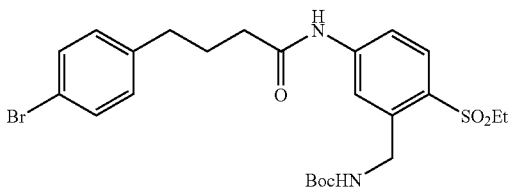

Oxalyl chloride (8.35 mL, 16.70 mmol) was added dropwise to a solution –+ of 4-(4-bromophenyl)butanoic acid (2.03 g, 8.35 mmol) and DMF (0.030 mL, 0.398 mmol) in CH$_2$Cl$_2$ (16 mL) at 25° C. over 10 min. The reaction mixture was stirred for 2 h, concentrated in vacuo and azeoptroped with toluene (2×25 mL). The crude brown oil was dissolved in DCM and added dropwise to a solution of 1B (2.5 g, 7.95 mmol) and pyridine (1.929 mL, 23.85 mmol) in DCM (30 mL) at 0° C. After stirring 2 h at 25° C. the reaction mixture was diluted with EtOAc (200 mL), washed with 1.0 M HCl, saturated NaHCO$_3$, and brine (100 mL), dried over Na$_2$SO$_4$ and concentrated in vacuo. The crude material was purified by flash chromatography (0 to 100% EtOAc in hexanes) to yield 1C (3.78 g, 7.01 mmol, 88% yield) as a white foam. $^1$H NMR (400 MHz, CDCl$_3$) δ ppm 1.27 (t, J=7.97 Hz, 3H) 1.40 (s, 9H) 1.96-2.08 (m, 2H) 2.36 (t, J=7.42 Hz, 2H) 2.65 (t, J=7.42 Hz, 2H) 3.14 (q, J=7.70 Hz, 2H) 4.48 (d, J=6.60 Hz, 2H) 7.06 (d, J=8.25 Hz, 2H) 7.34-7.43 (m, J=8.24 Hz, 3H) 7.52 (s, 1H) 7.82-7.92 (m, J=8.79 Hz, 1H) 7.92-8.02 (m, 1H).

1D

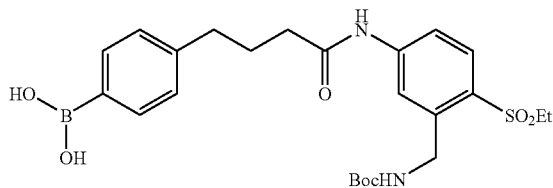

A mixture of bis(neopentyl glycolato)diboron (2.324 g, 10.29 mmol), potassium acetate (2.019 g, 20.58 mmol), 1C (3.7 g, 6.86 mmol) and (1,1'-bis(diphenylphosphino)ferrocene)-dichloropalladium(II) (0.282 g, 0.343 mmol) in dioxane (25 mL) was sparged with argon and stirred at 80° C. for 2 h. The mixture was diluted with EtOAc (150 mL), washed with water (100 mL), brine (100 mL), dried over Na$_2$SO$_4$ and concentrated in vacuo. The crude boronic ester was hydrolyzed during purification by prep HPLC (MeOH/H$_2$O, 0.1% TFA) to yield 1D (2.59 g, 5.13 mmol, 74.9% yield) as a clear oil. MS (ESI) m/z 505.2 (M+H)$^+$. $^1$H NMR (400 MHz, CD$_3$OD) δ ppm 1.22 (t, J=7.42 Hz, 3H) 1.45 (s, 9H) 1.96-2.06 (m, 2H) 2.41 (t, J=7.42 Hz, 2H) 2.69 (t, J=7.70 Hz, 2H) 4.56 (s, 2H) 7.21 (d, J=7.70 Hz, 2H) 7.53 (d, J=8.24 Hz, 2H) 7.74 (dd, J=8.79, 2.20 Hz, 1H) 7.78-7.89 (m, 2H).

1E

A solution of ID (500 mg, 0.99 mmol), Intermediate 2 (147 mg, 0.99 mmol) and glyoxylic acid monohydrate (91 mg, 0.99 mmol) in acetonitrile (2 mL) and DMF (2 mL) was microwaved at 100° C. for 10 min. The reaction mixture was concentrated in vacuo and purified by flash chromatography (0% to 20% MeOH in CH$_2$Cl$_2$) to yield 1E (540 mg, 0.812 mmol, 82% yield) as a yellow foam. MS (ESI) m/z 665.6 (M+H)$^+$.

Example 1

A solution of 1E (540 mg, 0.693 mmol) in TFA (5 mL) and dioxane (5 mL) was stirred at rt for 4 h. The reaction mixture was concentrated, redissolved in acetonitrile/water (1:1, 20 mL) and lyophilized. A solution of the resulting benzylamine in DMF (5.0 mL) was added via syringe pump over 6 h to a solution of BOP (920 mg, 2.08 mmol), DMAP (424 mg, 3.47 mmol), and triethylamine (0.48 mL, 3.47 mmol) in CH$_2$Cl$_2$ (100 mL) at 40° C. The reaction mixture was concentrated in vacuo and purified by prep HPLC to yield the racemic macrocycle (105 mg). The racemate was separated into peak 1 (30 mg) and Example 1 (30 mg) using with a Chiralcel OD-H (2.0 cm×25 cm, 5 micron, Chiral Technologies, Inc.), 50% MeOH/EtOH (1:1)/50% Heptane, 20 mL/min flow rate, and uv detection at 220 nm. Example 1: $^1$H MS (ESI) m/z 547.5 (M+H)$^+$. 1H NMR (400 MHz, CD$_3$OD) δ ppm 1.24 (t, J=7.42 Hz, 3H) 2.00-2.16 (m, 1H) 2.24-2.47 (m, 3H) 2.54-2.69 (m, 1H) 2.83-2.98 (m, 1H) 3.34-3.46 (m, 2H) 4.15-4.24 (m, J=17.04 Hz, 1H) 4.28 (s, 2H) 4.98-5.07 (m, 2H) 6.60-6.65 (m, 1H) 6.87-6.93 (m, 1H) 6.91-7.00 (m, 1H) 7.03-7.15 (m, 2H) 7.26 (d, J=7.70 Hz, 1H) 7.32-7.40 (m, J=8.24 Hz, 1H) 7.52-7.59 (m, J=8.25 Hz, 1H) 7.75 (d, J=8.79 Hz, 1H). Chiral analytical HPLC retention times: peak 1, 5.69 min; peak 2, 9.70 min using the following chromatography conditions: Chiral OD (4.6×250 mm, 10 micron), 50% (1:1 ethanol/methanol)/50% heptane as eluent, 1 mL/min flow rate and uv

Example 2

(R)-7-Ethanesulfonyl-2-(1-oxo-1,2,3,4-tetrahydro-isoquinolin-7-ylamino)-4,11-diaza-tricyclo[14.2.2.1$^{6,10}$]henicosa-1(19),6,8,10(21),16(20),17-hexaene-3,12-dione

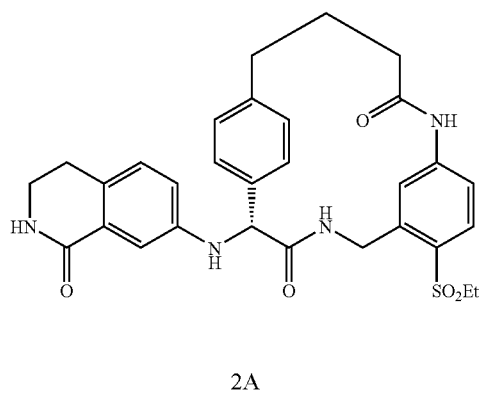

2A

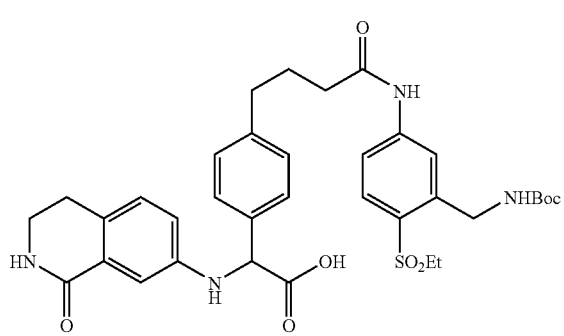

Using a procedure analogous to that used to prepare 1E, 1D (500 mg, 0.99 mmol) and Intermediate 1 (161 mg, 0.99 mmol) were reacted with glyoxylic acid monohydrate (91 mg, 0.99 mmol) to yield 2A (643 mg, 0.812 mmol, 96% yield) as a yellow foam. MS (ESI) m/z 679.5 (M+H)$^+$.

Example 2

Using a procedure analogous to that used to prepare Example 1, 2A (640 mg, 0.943 mmol) was deprotected with TFA and cyclized with BOP to yield the racemic macrocycle (150 mg, 28.4% yield) as a yellow solid. The racemate was separated into peak 1 (28 mg, 0.050 mmol) and Example 2 (25 mg, 0.045 mmol) using with a Chiralcel OD-H (2.0 cm×25 cm, 5 micron, Chiral Technologies, Inc.), 50% MeOH/EtOH (1:1)/50% Heptane, 20 mL/min flow rate, and uv detection at 220 nm. Example 2: LC/MS (ESI) m/z 547.5 (M+H)$^+$. $^1$H NMR (400 MHz, CD$_3$OD) δ ppm 1.24 (t, J=7.42 Hz, 3H) 2.02-2.16 (m, 1H) 2.24-2.46 (m, 3H) 2.54-2.67 (m, 1H) 2.79 (t, J=6.60 Hz, 2H) 2.85-2.96 (m, 1H) 3.32-3.47 (m, 4H) 4.94-5.05 (m, 2H) 6.60 (d, J=1.65 Hz, 1H) 6.80 (dd, J=8.24, 2.20 Hz, 1H) 6.89 (dd, J=8.24, 2.20 Hz, 1H) 7.01 (d, J=8.24 Hz, 1H) 7.04-7.14 (m, 2H) 7.19-7.24 (m, J=2.75 Hz, 1H) 7.34 (d, J=7.70 Hz, 1H) 7.52 (dd, J=7.70, 1.65 Hz, 1H) 7.75 (d, J=8.79 Hz, 1H). Chiral analytical HPLC retention times: peak 1, 5.99 min; peak 2, 8.36 min using the following chromatography conditions: Chiral OD (4.6×250 mm, 10 micron), 50% (1:1 ethanol/methanol)/50% heptane as eluent, 1 mL/min flow rate and uv detection at 254 nm. Analytical HPLC (Method A): Col A: 7.76 min, 97%; Col B: 7.75 min, 97%.

Example 3

(R)-4-Methyl-2-(3-oxo-2,3-dihydro-1H-isoindol-5-ylamino)-7-(propane-2-sulfonyl)-4,11-diaza-tricyclo[14.2.2.1$^{6,10}$]henicosa-1(19),6,8,10(21),16(20),17-hexaene-3,12-dione trifluoroacetic acid salt

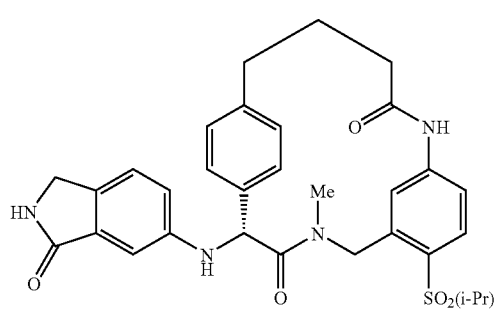

3A

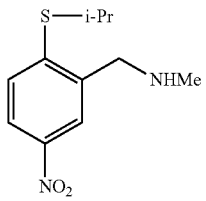 [SMILES: CNCc1cc([N+](=O)[O-])ccc1SC(C)C]

To a stirred solution of 2-chloro-5-nitro-benzaldehyde (2 g, 0.011 mol) and potassium carbonate (1.9 g, 0.0141 mol) in DMF (20 ml), was added 2-propane thiol (1.3 ml, 0.0141 mol) drop wise. The reaction mixture was refluxed at 80° C. for overnight. The reaction mass was diluted with water extracted with ethyl acetate washed with water and brine, dried over sodium sulfate and concentrated. After column purification, compound 3A (2.2 g, 84%) obtained as pale yellow liquid. $^1$H-NMR (400 MHz, CDCl$_3$) δ 1.48 (6H, d), 3.65-3.72 (1H, q), 7.56 (1H, d), 8.33-8.34. (1H, d), 8.67 (1H, s), 10.35 (1H, s). (ESI) m/z 226 (M+H)$^+$.

3B

To stirred solution of compound 3A (25.5 g, 0.1133 mol) in methanol (150 mL), was added 30% methanolic methyl amine solution (35 mL, 0.3399 mol) drop wise. The mixture was stirred for 1 h. The reaction mixture was cooled to 0° C., sodium borohydride (8.6 g, 0.2266 mol) was added portion wise, then the reaction was stirred at rt overnight. The reaction mass was concentrated diluted with ethyl acetate, washed with water and brine, dried over sodium sulfate and concentrated. After column purification (23 g, 85%) of pure compound 3B obtained. $^1$H-NMR (400 MHz, CDCl$_3$) δ 1.43 (6H, d), 2.49 (3H, s), 3.61-3.67 (1H, m), 3.85 (2H, s), 7.37-7.40 (1H, d), 8.07-8.10 (1H, d), 8.23 (1H, s). (ESI) m/z 241 (M+H)$^+$.

3C

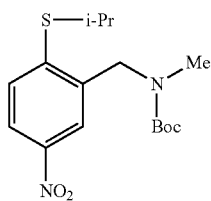 [SMILES: CC(C)Sc1ccc([N+](=O)[O-])cc1CN(C)C(=O)OC(C)(C)C]

To a stirred solution of compound 3B (4 g, 0.0166 mmol) and triethylamine (4.6 mL, 0.0333 mol) in THF (40 mL), was added Boc$_2$O (3.9 g, 0.0183 mmol). The reaction was stirred at rt overnight, then was diluted with water and extracted with ethyl acetate. The organic phase was washed with water and brine, dried over sodium sulfate and concentrated to afford 3C (4.3 g, 76%). $^1$H-NMR (400 MHz, CDCl$_3$) δ 1.41-1.44 (6H, d), 1.54-1.57 (9H, bs), 2.92 (3H, s), 3.59-3.66 (1H, m), 4.49-4.52 (2H, d), 7.40-7.42 (1H, d), 7.95 (1H, d), 8.08-8.10 (1H, d). (ESI) m/z 241 (M−Boc+2H)$^+$.

3D

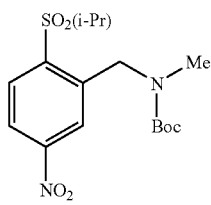

To a solution of 3C (3.00 g, 8.81 mmol) in DCM (50 mL) at 0° C., was added m-CPBA (4.94 g, 22.0 mmol). The suspension was stirred at rt for 1.5 h. The mixture was filtered and the precipitate was rinsed with CH$_2$Cl$_2$ (3×10 mL). The combined DCM solution was washed with 10% aq. K$_2$CO$_3$ (3×) and brine, dried (Na$_2$SO$_4$) and concentrated. The crude product was purified by flash chromatography (0 to 60% ethyl acetate/hexanes gradient) to afford 3.18 g of 3D as a yellow foam. MS (ESI) m/z 373.2 (M+H)$^+$.

3E

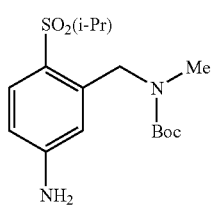

To a solution of 3D (3.18 g, 8.54 mmol) in methanol (30 mL), was added 10% Pd—C (100 mg). The mixture was evacuated and flushed with H$_2$ (3×), then was stirred under an atmosphere of H$_2$ for 16 h. The reaction was filtered, concentrated, then coevaporated with toluene to afford 2.92 g of 3E as a white solid. MS (ESI) m/z 343.2 (M+H)$^+$.

3F

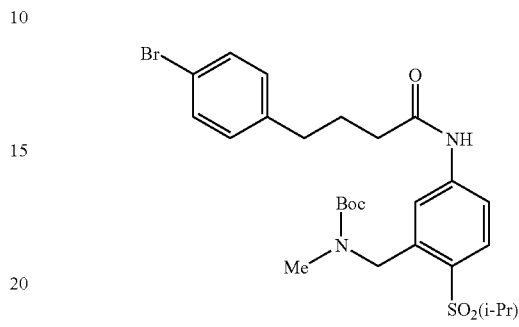

To a solution of 4-(4-Bromophenyl)butanoic acid (2.28 g, 9.39 mmol) in CH$_2$Cl$_2$ (30 mL), were added oxalyl chloride (0.93 mL, 10.7 mmol) and DMF (2 drops). The mixture was stirred at rt for 2 h, then was concentrated. The resultant oil was co-evaporated with toluene to afford the acid chloride as a yellow oil. To a solution of 3E (2.92 g, 8.54 mmol) and DMAP (209 mg, 1.71 mmol) in 5:1 DCM/pyridine (30 mL) at 0° C., was added a solution of the acid chloride in DCM (5 mL). The mixture was stirred at 0° C. for 1 h, then was quenched with water. The mixture was diluted with EtOAc, then was washed with H$_2$O (2×), 0.2 N HCl and brine, dried (Na$_2$SO$_4$) and concentrated. The crude product was purified by flash chromatography (0-100% EtOAc/hexanes gradient) to afford 4.84 g of 3F (100%) as a colorless crystalline solid. MS (ESI) m/z 567.2 (M+H)$^+$.

3G

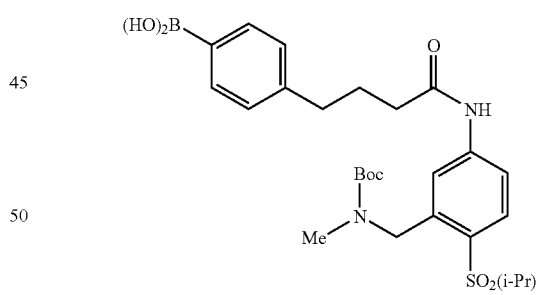

In a sealed tube were added 3F (3.00 g, 5.30 mmol), bis(neopentyl glycolato)diboron (1.32 g, 5.82 mmol), and KOAc (1.30 g, 13.3 mmol). DMSO (10 mL) was added, then the suspension was degassed by evacuating and flushing with argon (4×). (1,1′-bis(diphenylphosphino)ferrocene)-dichloropalladium(II) (194 mg, 0.265 mmol) was added, the mixture was degassed (1×) and sealed. The reaction was lowered into an 80° C. oil bath and stirred for 4 h. The reaction mixture was diluted with EtOAc, washed with H$_2$O (2×) and brine, dried (Na$_2$SO$_4$), filtered through a 1″ pad of silica gel and concentrated. The crude product was purified by preparative HPLC to afford 1.55 g of 3G as an off-white solid. MS (ESI) m/z 533.4 (M+H)$^+$.

3H

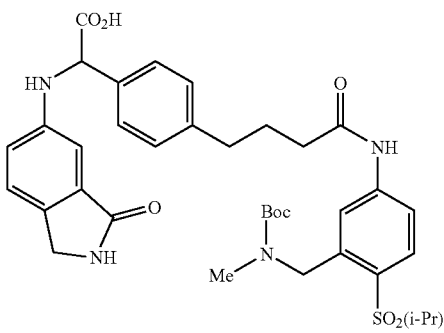

Intermediate 2 (164 mg, 1.11 mmol), 3G (535 mg, 1.00 mmol), and glyoxylic acid monohydrate (111 mg, 1.21 mmol) were taken up in CH$_3$CN (3 mL) and DMF (2 ml). The mixture was stirred at 60° C. for 48 h, then was concentrated. The crude product was purified by flash chromatography (1 to 20% MeOH/CH$_2$Cl$_2$ gradient) to afford 313 mg of 3H as a pale yellow solid. MS (ESI) m/z 693.3 (M+H)$^+$.

3I

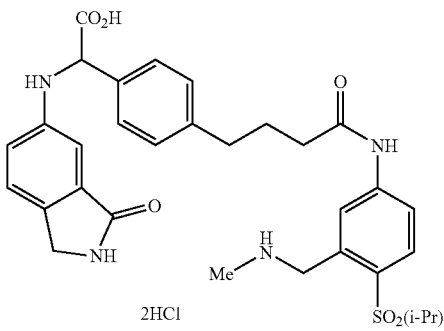

To a solution of 3H (313 mg, 0.452 mmol) in 5 mL EtOAc, was added a solution of 4N HCl in dioxane (5 mL). The resultant suspension was stirred at rt for 1 h, then was concentrated to afford 295 mg (98%) of 3I as a pale yellow solid. MS (ESI) m/z 593.3 (M+H)$^+$.

Example 3

To a solution of BOP (392 mg, 0.886 mmol), DIEA (0.386 mL, 2.22 mmol) and DMAP (271 mg, 2.22 mmol) in DCM (50 mL) at 40° C., was added a solution of 3I (295 mg, 0.443 mmol) and DIEA (0.154 mL, 0.886 mmol) in DMF (5 mL), dropwise via a syringe pump over 3 h, stirred 13 h. The mixture was diluted with DCM, then was washed with H$_2$O (2×) and brine, dried (Na$_2$SO$_4$) and concentrated. The crude product was purified by preparative HPLC, followed by flash chromatography (1 to 20% MeOH/CH$_2$Cl$_2$ gradient) to afford the 81 mg of the racemic macrocycle as a pale yellow solid. The racemate (48 mg) was separated via chiral chromatography (Chiralpak AD-H (20×250 mm) 90:10 EtOH/heptane (20 mL/min) for 10 min to elute the less active enantiomer, followed by 100% MeOH for min to elute the more active enantiomer). The second peak was re-purified by preparative HPLC (CH$_3$CN/H$_2$O) to afford 23.4 mg of Example 3.

$^1$H-NMR: (400 MHz, MeOD) δ ppm 7.77 (d, J=8.59 Hz, 1H) 7.63 (dd, J=7.83, 2.02 Hz, 1H) 7.36 (dd, J=7.71, 1.64 Hz, 1H) 7.29 (d, J=8.08 Hz, 1H) 7.02-7.11 (m, 3H) 6.99 (dd, J=7.83, 1.77 Hz, 1H) 6.91 (dd, J=8.59, 2.02 Hz, 1H) 6.58 (d, J=1.77 Hz, 1H) 5.61 (t, J=8.59 Hz, 2H) 4.29 (s, 2H) 4.12 (d, J=17.18 Hz, 1H) 3.62 (dt, J=13.64, 6.82 Hz, 1H) 3.40 (s, 3H) 2.97 (ddd, J=13.64, 5.81, 2.53 Hz, 1H) 2.52 (ddd, J=13.58, 11.18, 2.27 Hz, 1H) 2.37-2.46 (m, 2H) 2.22-2.33 (m, 1H) 1.99-2.08 (m, 1H) 1.35 (d, J=6.82 Hz, 3H) 1.21 (d, J=6.82 Hz, 3H). (ESI) m/z 575.2 (M+H)$^+$.

Example 4

(R)-4-Methyl-2-(1-oxo-1,2,3,4-tetrahydro-isoquinolin-7-ylamino)-7-(propane-2-sulfonyl)-4,11-diazatricyclo[14.2.2.1$^{6,10}$]henicosa-1(19),6,8,10(21),16(20),17-hexaene-3,12-dione trifluoroacetic acid salt

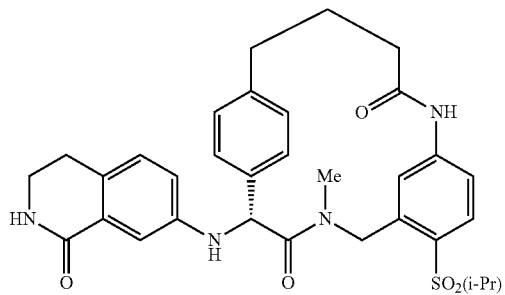

4A

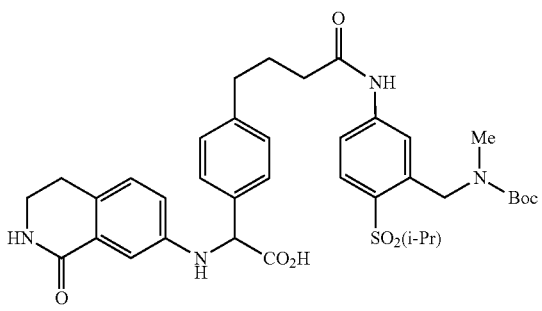

In a microwave reaction vial Intermediate 1 (128 mg, 0.789 mmol), 3G (400 mg, 0.751 mmol), and glyoxylic acid monohydrate (69.2 mg, 0.751 mmol) were dissolved in acetonitrile (2.25 mL) and DMF (1.75 mL) to give a yellow solution. The mixture was irradiated in a microwave reactor at 100° C. for 10 min, then was concentrated. The crude product was purified by flash chromatography (1 to 20% MeOH/CH$_2$Cl$_2$ gradient) to afford 380 mg (71.6%) of 4A as a yellow glass. (ESI) m/z 707.2 (M+H)$^+$.

4B

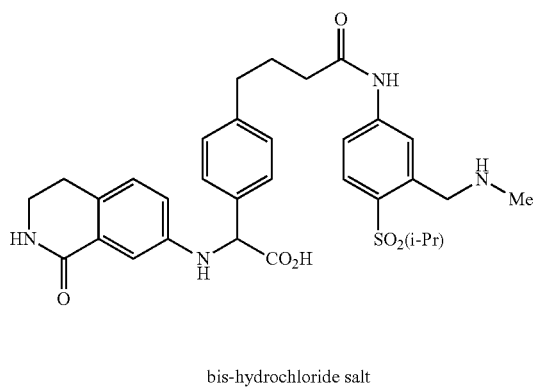

bis-hydrochloride salt

To a solution of 4A (380 mg, 0.538 mmol) in ethyl acetate (5 mL), was added 4N HCl in dioxane (5 mL, 20 mmol) to give a suspension. The suspension was stirred at rt for 1 h, then concentrated. The solid residue was co-evaporated with EtOAc (3×) and toluene to afford 365 mg (100%) of 4B as a pale yellow solid. (ESI) m/z 607.2 (M+H)$^+$.

Example 4

To a solution of BOP (475 mg, 1.074 mmol) and DMAP (328 mg, 2.69 mmol) in CH$_2$Cl$_2$ (80 mL) and DMF (20 mL) at 40° C., was added a solution of 4B (365 mg, 0.537 mmol) and DIEA (0.188 mL, 1.07 mmol) in DMF (5 mL) via syringe pump over 7 h. The reaction mixture was then placed in a freezer and allowed to stand overnight. Water (2 mL) was added to the reaction and the mixture was concentrated to a brown oil. H$_2$O (10 mL) was added and the resultant solid was collected by filtration and sucked dry. The crude product was purified by preparative HPLC, followed by recrystallization from methanol to afford 63 mg of the racemic macrocycle as a colorless solid. The enantiomers were separated via chiral chromatography (Chiralpak AD-H (20×250 mm), 1:1 MeOH/EtOH+0.1% DEA (20 mL/min) for 15 min to elute the less active enantiomer, then 100% MeOH for 25 min to elute the more active enantiomer). The second peak was purified by preparative HPLC (CH$_3$CN/H$_2$O) to afford 28 mg of Example 4. $^1$H NMR (400 MHz, CD$_3$OD) δ ppm 7.77 (d, J=8.25 Hz, 1H) 7.57 (dd, J=7.70, 1.65 Hz, 1H) 7.38 (d, J=2.20 Hz, 1H) 7.33-7.37 (m, 1H) 7.07-7.13 (m, 2H) 6.95-7.02 (m, 2H) 6.91 (dd, J=8.52, 1.92 Hz, 1H) 6.59 (d, J=1.10 Hz, 1H) 5.57-5.65 (m, 2H) 4.11 (d, J=17.04 Hz, 1H) 3.62 (dt, J=13.60, 6.66 Hz, 1H) 3.42 (t, J=6.60 Hz, 2H) 3.36 (s, 3H) 2.93-3.01 (m, 1H) 2.84 (t, J=6.60 Hz, 2H) 2.48-2.56 (m, 1H) 2.37-2.46 (m, 2H) 2.21-2.32 (m, 1H) 1.97-2.07 (m, 1H) 1.35 (d, J=6.60 Hz, 3H) 1.21 (d, J=6.60 Hz, 3H). (ESI) m/z 589.2 (M+H)$^+$. Analytical HPLC (Method A): Col A: 10.71 min, 99%; Col B: 10.63 min, 98%.

Example 5

(R)-4-Methyl-2-(1-oxo-1,2-dihydro-isoquinolin-7-ylamino)-7-(propane-2-sulfonyl)-4,11-diaza-tricyclo[14.2.2.1 6,10]henicosa-1(19),6,8,10(21),16(20),17-hexaene-3,12-dione

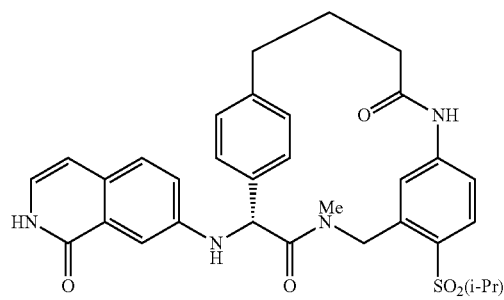

5A

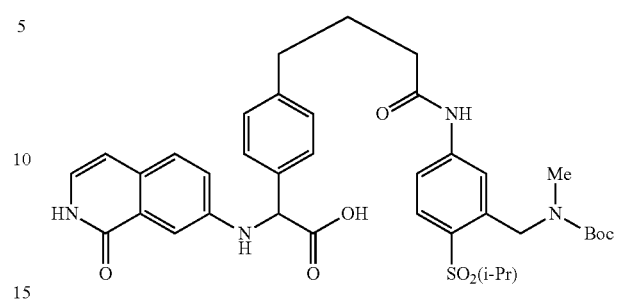

To 3G (500 mg, 0.939 mmol), Intermediate 3 (165 mg, 1.033 mmol) and glyoxylic acid monohydrate (95 mg, 1.033 mmol) was added acetonitrile (5.0 mL), and DMF (2.5 mL). The mixture was stirred at 70° C. for 4.0 h. Solvent was removed and the crude was added to a silica gel column (40 g) and was eluted with CH$_2$Cl$_2$/MeOH (2% to 25%) to give 5A (440 mg, 67% yield). $^1$H NMR (400 MHz, methanol-d$_4$) δ ppm 1.25 (d, J=7.03 Hz, 6H) 1.40-1.48 (br, 9H) 1.93-2.03 (m, 2H) 2.38 (t, J=7.47 Hz, 2H) 2.67 (t, J=7.47 Hz, 2H) 2.95 (s, 3H) 4.82 (s, 2H) 5.15 (s, 1H) 6.54 (d, J=7.03 Hz, 1H) 6.89 (d, J=7.03 Hz, 1H) 7.16-7.24 (m, 3H) 7.29 (d, J=2.64 Hz, 1H) 7.42 (d, J=8.35 Hz, 1H) 7.48 (d, J=7.91 Hz, 2H) 7.70 (s, 1H) 7.80-7.87 (m, 1H); LC-MS 705 (M+H)$^+$.

5B

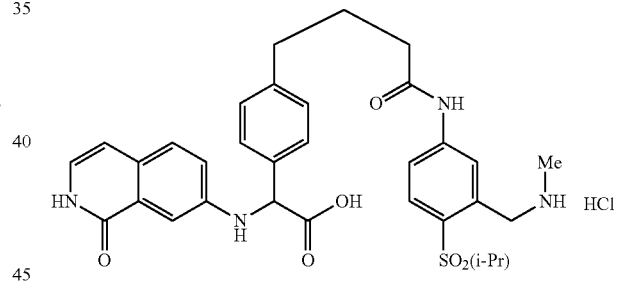

To a suspension of 5A (340 mg, 0.482 mmol) was added 4.0 N HCl in dioxane (10 mL, 40.0 mmol). The mixture was stirred at rt for 2.5 h. Solvent was removed and chased twice with EtOAc to give brown solid 5B (340 mg, 100% yield). $^1$H NMR (400 MHz, methanol-d$_4$) δ ppm 1.28 (d, J=6.59 Hz, 6H) 1.99-2.05 (m, 3H) 2.43 (t, J=7.47 Hz, 2H) 2.71 (t, J=7.47 Hz, 2H) 2.78 (s, 3H) 4.42 (s, 2H) 5.33 (s, 1H) 6.65 (d, J=7.03 Hz, 1H) 7.08 (d, J=7.03 Hz, 1H) 7.25 (d, J=8.35 Hz, 2H) 7.39-7.45 (m, 3H) 7.59 (d, J=8.79 Hz, 2H) 7.79 (dd, J=8.79, 2.20 Hz, 1H) 7.96 (d, J=8.79 Hz, 1H) 8.16 (d, J=2.20 Hz, 1H); LC-MS 605 (M+H)$^+$.

Example 5

To a solution of BOP (207 mg, 0.468 mmol) and DMAP (143 mg, 1.170 mmol) in CH$_2$Cl$_2$ (35 ml) and DMF (4.0 mL) at 40° C. was added a solution of 5G (150 mg, 0.234 mmol) and DIEA (0.082 mL, 0.468 mmol) in DMF (4.0 mL) via a syringe pump over 4.0 h. Right after addition of 5B, solvent was removed. The residue was redissolved in CHCl$_3$ (60 mL) and to this solution was added water (20 mL) and brine (20 mL). The layers were separated, the aqueous was extracted with CHCl₃ (20 mL). The combined organic layers were dried over Na₂SO₄. After evaporation of solvent, the crude product was dissolved in MeOH/DMSO (4.0 mL, 1:1) and purified by prep HPLC using AXIA column eluting with 90% water to 10% water in Acetonitrile with 0.1% TFA to give the crude cycle (62 mg, 42% yield). The crude produce and material from another synthesis (110 mg) were dissolved in 16 mL of 85:15 IPA-0.1% DEA:Heptane-0.1% DEA and 0.1 mL DEA and separated by a Chiral PAK AD-H 250 mm×20 mm column eluting with 85:15 IPA-0.1% DEA:Heptane-0.1% DEA for 25 min at 10 mL/min to obtain the first enantiomer (RT=12 min, 36 mg), then eluting with 100% 1:1 EtOH:MeOH-0.1% DEA from 10 ml/min to ml/min for 40 min to obtain the second enantiomer (RT=38 min, 39 mg). Peak 2 was identified to be Example 5: ¹H NMR (400 MHz, methanol-d₄) δ ppm 1.16 (d, J=7.15 Hz, 3H) 1.30 (d, J=6.60 Hz, 3H) 1.93-2.04 (m, 1H) 2.23 (d, J=10.99 Hz, 1H) 2.38-2.48 (m, 3H) 2.86-2.96 (m, 1H) 3.36 (s, 3H) 3.57 (m, J=6.60 Hz, 1H) 4.08 (d, J=17.04 Hz, 1H) 5.61 (d, J=17.59 Hz, 1H) 5.65 (s, 1H) 6.52 (d, J=7.15 Hz, 1H) 6.58 (s, 1H) 6.88-6.96 (m, 2H) 6.98-7.03 (m, 1H) 7.03-7.07 (m, 1H) 7.23 (dd, J=8.52, 2.47 Hz, 1H) 7.32 (d, J=8.25 Hz, 1H) 7.41 (d, J=8.79 Hz, 1H) 7.52 (s, 1H) 7.61 (d, J=6.60 Hz, 1H) 7.74 (d, J=8.24 Hz, 1H); LC-MS 587 (M+H)⁺.

Example 6

(R)-7-Ethanesulfonyl-2-(1-oxo-1,2-dihydro-isoquinolin-7-ylamino)-4,11-diaza-tricyclo[14.2.2.1⁶,¹⁰]henicosa-1(19),6,8,10(21),16(20),17-hexaene-3,12-dione

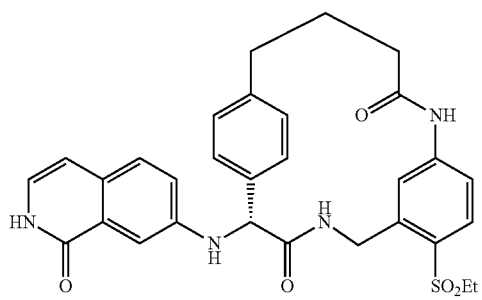

6A

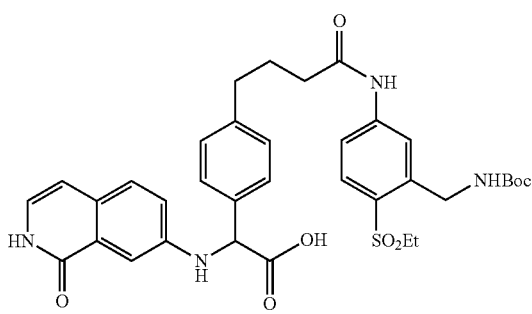

Using a procedure analogous to that used to prepare 1E, 1D (500 mg, 0.99 mmol) and Intermediate 3 (159 mg, 0.99 mmol) were reacted with glyoxylic acid monohydrate (91 mg, 0.99 mmol) to yield 6A (580 mg, 0.857 mmol, 86% yield) as a yellow foam. MS (ESI) m/z 677.6 (M+H)⁺.

6B

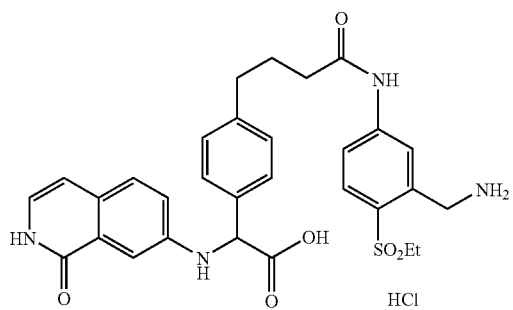

6A (580 mg, 0.857 mmol) was dissolved in dioxane (5 mL) and 4.0 M HCl in dioxane was added. The reaction mixture was stirred for 2 h at ambient temperature. The liquid was decanted off of a brown solid and concentrated. The brown solid was dissolved in MeOH (50 mL) and concentrated in vacuo to yield 6B (330 mg, 0.538 mmol, 62.8% yield) as a yellow solid. MS (ESI) m/z 577.5 (M+H)⁺

Example 6

A solution of 6B (330 mg, 0.538 mmol) in DMF (5.0 mL) was added via syringe pump over 6 h to a solution of BOP (714 mg, 1.615 mmol), DMAP (329 mg, 2.69 mmol), and triethylamine (0.375 mL, 2.69 mmol) in CH₂Cl₂ (100 mL) at 40° C. The reaction mixture was concentrated in vacuo and purified by prep HPLC to yield 330 mg of a brown oil. 150 mg of this oil was separated into enantiomer 1 (10 mg, 0.018 mmol, 6.67% yield) and Example 6 (7 mg, 0.013 mmol, 4.67% yield) using an Chiralcel OD-H (2.0 cm×25 cm, 5 micron, Chiral Technologies, Inc.), 50% MeOH/EtOH (1:1)/50% Heptane, 20 mL/min flow rate, and uv detection at 220 nm and then a second purification using Phenom. Luna C18, 21.2×100 mm, 10 micron, flow rate 20 mL/min, A: H₂O/MeOH (9:1), B: H₂O/MeOH (1:9), 0.1% TFA, 20 to 100% B, 10 min gradient uv detection at 220 nm. Characterization for Example 6: LC/MS (ESI) m/z 559.2.5 (M+H)⁺. ¹H NMR (400 MHz, CD₃OD) δ ppm 1.23 (t, J=7.42 Hz, 3H) 2.00-2.17 (m, 1H) 2.26-2.46 (m, 3H) 2.54-2.64 (m, 1H) 2.83-2.97 (m, 1H) 3.32-3.52 (m, 2H) 4.18 (dd, J=17.04, 5.50 Hz, 1H) 5.00-5.20 (m, 2H) 6.54 (d, J=7.15 Hz, 1H) 6.64 (d, J=1.65 Hz, 1H) 6.85-6.94 (m, 2H) 7.02-7.14 (m, 2H) 7.19 (dd, J=8.79, 2.20 Hz, 1H) 7.29-7.46 (m, 3H) 7.59 (dd, J=7.97, 1.37 Hz, 1H) 7.75 (d, J=8.79 Hz, 1H) 8.98 (t, J=6.05 Hz, 1H). Analytical HPLC (Method A): Col A: 6.42 min, 95%; Col B: 6.45 min, 99%.

Example 7

[(2R,5R)-17,20-Dimethyl-3,12-dioxo-2-(4-oxo-3,4-dihydro-quinazolin-6-ylamino)-13-oxa-4,11-diaza-tricyclo[14.2.2.1⁶,¹⁰]henicosa-1(19),6,8,10(21),16(20),17-hexaen-5-yl]-acetic acid

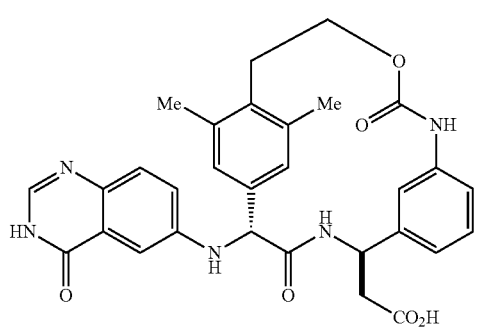 [SMILES: Cc1cc2cc(C)c1CCOC(=O)Nc1cccc(c1)[C@@H](CC(=O)O)NC(=O)[C@@H]2Nc1ccc2nc[nH]c(=O)c2c1]

7A

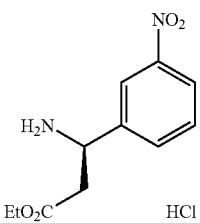 [SMILES: CCOC(=O)C[C@@H](N)c1cccc([N+](=O)[O-])c1 ; Cl]

4.0 M HCl in dioxane (5 mL) was added to a solution of (R)-3-amino-3-(3-nitrophenyl)propanoic acid (2.88 g, 13.70 mmol) in acetonitrile (10 mL) and the solvent was removed in vacuo. In a separate flask, thionyl chloride (1.150 mL, 15.76 mmol) was added dropwise to ethanol (55 mL) at −5° C. and stirred for 30 min. The solution was added to the HCl salt and stirred at 40° C. for 15 h and then concentrated in vacuo to yield 7A (3.23 g, 13.57 mmol, 99% yield) as a white solid. MS (ESI) m/z 239.3 (M+H)$^+$.

7B

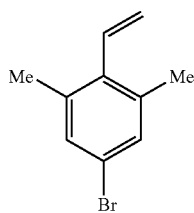

KF (8.70 g, 150 mmol), n-Bu$_4$NCl (27.7 g, 100 mmol), Pd(dba)$_2$ (290 mg, 0.5 mmol), 5-bromo-2-iodo-1-methylbenzene (15.55 g, 50 mmol), trimethyl(vinyl)silane (27 mL, 200 mmol), and toluene (100 mL) were added to a pressure vessel and sparged with argon. The vessel was sealed and heated at 160° C. for 60 min. The mixture was cooled to ambient temperature, diluted with dichloromethane, filtered and concentrated. The crude oil was purified by flash chromatography (100% hexanes) to yield 7B (10 g, 47 mmol, 95% yield) as a clear oil. $^1$H NMR (400 MHz, CDCl$_3$) b ppm 2.26 (s, 6H) 5.24 (dd, J=17.86, 1.92 Hz, 1H) 5.55 (dd, J=11.54, 2.20 Hz, 1H) 7.18 (s, 2H).

7C: Br

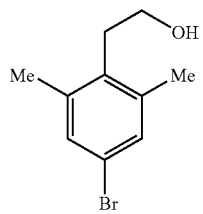 [SMILES: Cc1cc(Br)cc(C)c1CCO]

A solution of 7B (1.5 g, 7.6 mmol) in 0.5 M 9-BBN in THF (200 mL, 100 mmol) was heated at 100° C. in a sealed tube for 10 h. The mixture was cooled to 0 C in a 250 mL. Erlenmeyer flask. NaOH (1.0 M, 200 mL) then H$_2$O$_2$ (50%, 200 mL) were added slowly dropwise while maintaining the internal temperature below 30° C. HCl (1.0 M, 200 mL) was added and the mixture was extracted with Et$_2$O (2 X). The organics were combined, washed with NaHCO$_3$, brine, dried over Na$_2$SO$_4$ and concentrated in vacuo. The crude oil was purified by flash chromatography (0% to 30% hexanes in EtOAc) to yield 7C (6.7 g, 62%) as a clear oil. $^1$H NMR (400 MHz, CDCl$_3$) δ ppm 2.31 (s, 6H) 2.89 (t, J=7.33 Hz, 2H) 3.73 (t, J=7.33 Hz, 2H) 7.16 (s, 2H).

7D

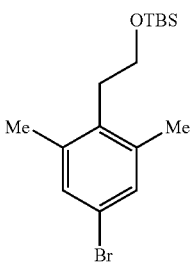

tert-Butyldimethylsilyl chloride (1.483 g, 9.84 mmol) was added to a solution of 7C (2.05 g, 8.95 mmol) and imidazole (0.914 g, 13.42 mmol) in DCM (45 mL) and stirred for 4 h at rt. The reaction was diluted with DCM (100 mL), washed with 0.5 M HCl (100 mL), brine, dried over Na$_2$SO$_4$ and concentrated. The crude oil was purified by column chromatography (0 to 40% EtOAc in Hexanes, 120 g column) to yield 7D (3.05 g, 8.88 mmol, 99% yield) as a colorless oil. $^1$H NMR (400 MHz, CHLOROFORM-D) δ ppm −0.01 (s, 6H) 0.86 (s, 9H) 2.30 (s, 6H) 2.84 (t, J=7.58 Hz, 2H) 3.66 (t, 2H) 7.13 (s, 2H).

7E

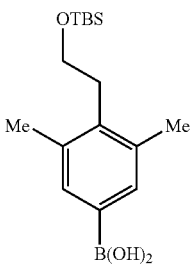

BuLi (6.11 mL, 9.77 mmol) was added dropwise to a solution of 7D (3.05 g, 8.88 mmol) in THF (89 mL) at −78° C. After stirring for 5 min, trimethyl borate (2.0 mL, 17.8 mmol) was added and the cooling bath was removed. The reaction mixture was stirred for 14 h at rt. The reaction mixture was diluted with Et$_2$O (200 mL) and washed for 5 min with 0.5 M HCl (100 mL). The organic phase was separated, washed with H$_2$O and brine (50 mL each) and concentrated. The crude oil was purified by column chromatography (0 to 100% over 20 min, EtOAc in Hexanes, 80 g column) to yield 7E (1.7 g, 5.51 mmol, 62.1% yield) as a whte solid. $^1$H NMR (400 MHz, MeOD) δ ppm −0.03 (s, 6H) 0.85 (s, 9H) 2.33 (s, 6H) 2.92 (t, J=7.07 Hz, 2H) 3.74 (t, J=7.20 Hz, 2H) 7.20 (s, 2H).

7F

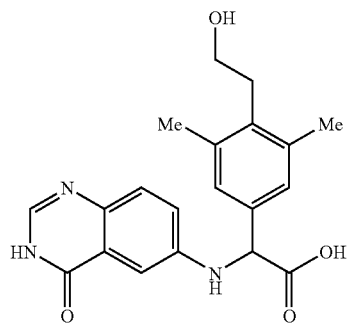 [SMILES: Cc1cc(C(Nc2ccc3nc[nH]c(=O)c3c2)C(=O)O)cc(C)c1CCO]

Using a procedure analogous to that used to prepare 1E, 7E (250 mg, 0.811 mmol), was reacted with Intermediate 4 (145 mg, 0.892 mmol), and glyoxylic acid monohydrate. 7F (167 mg) was obtained as a brown solid after tituration of the crude product with MeOH. MS (ESI) m/z 368.3 (M+H)⁺.

7G

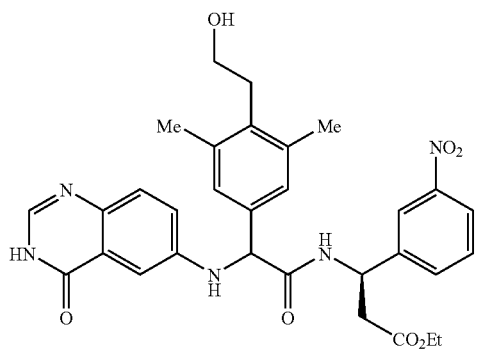 [SMILES: CCOC(=O)C[C@@H](NC(=O)C(Nc1ccc2nc[nH]c(=O)c2c1)c1cc(C)c(CCO)c(C)c1)c1cccc([N+](=O)[O-])c1]

A cloudy solution of 7A (125 mg, 0.455 mmol) and triethylamine (0.380 mL, 2.73 mmol) in DMF (2 mL) was added to a solution of 7F (167 mg, 0.455 mmol) and 1-hydroxy-7-azabenzotriazole (61.9 mg, 0.455 mmol) in DMF (2 mL). 1-(3-(dimethylamino)propyl)-3-ethyl-carbodiimide hydrochloride (174 mg, 0.909 mmol) was added and the reaction mixture was stirred for 15 h at 40° C. The reaction mixture was diluted with EtOAc (100 mL), washed with brine, dried over Na₂SO₄ and concentrated. The crude product was purified by flash chromatography (0 to 20% MeOH in CH₂Cl₂, 40 g column) to yield 7G (162 mg, 0.276 mmol, 60.7% yield) as an orange solid. ¹H NMR (400 MHz, MeOH) δ ppm 0.94-1.18 (m, 3H) 2.34 (s, 6H) 2.83-3.05 (m, 4H) 3.60 (t, J=7.42 Hz, 2H) 3.75-3.87 (m, 1H) 3.99-4.11 (m, 1H) 4.96 (s, 1H) 5.44-5.58 (m, 1H) 7.11-7.21 (m, 2H) 7.23-7.44 (m, 2H) 7.48 (dd, J=8.79, 5.50 Hz, 1H) 7.51-7.59 (m, 1H) 7.76-7.92 (m, 2H) 7.98-8.29 (m, 2H). MS (ESI) m/z 588.3 (M+H)⁺.

7H

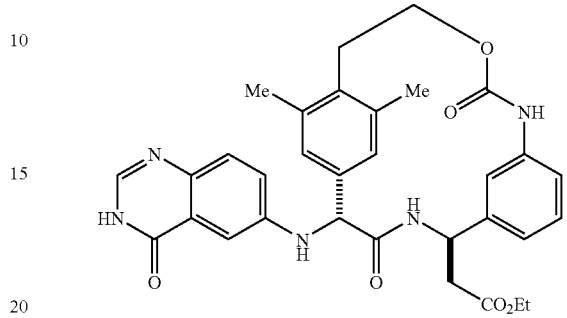

A solution of 7G (150 mg, 0.255 mmol) in methanol (10 mL) with Pd/C (27.2 mg, 0.026 mmol) was stirred under H₂ (50 psi) for 4 h. The reaction was filtered, and concentrated. The crude product was purified by column chromatography (0 to 20% MeOH in CH₂Cl₂) to yield the aniline (122 mg, 0.219 mmol, 86% yield) as a yellow solid. A phosgene solution (20% in toluene, 58.5 mg, 0.118 mmol) was added dropwise to a solution of the yellow solid (66 mg, 0.118 mmol) in acetonitrilte (10 mL) at 0° C. The cooling bath was removed and the cloudy mixture was stirred for 1 h at rt. Argon was bubbled though the solution and then 0.5 mL DBU was added. The solution was added dropwise over 2 h to a solution of triethylamine (165 μL, 1.184 mmol) in CH₂Cl₂ (30 mL) at 40° C. The reaction mixture was concentrated and purified by prep HPLC (Phenom. Luna C18, 21.2×100 mm, 10 micron, flow rate 20 mL/min, A: H₂O/MeOH (9:1), B: H₂O/MeOH (1:9), 0.1% TFA, 20 to 90% B, 10 min gradient.) to yield 7I (15 mg) and diastereomer 2 (9 mg). ¹H NMR (400 MHz, CD₃OD) δ ppm 1.24 (t, J=7.15 Hz, 3H) 2.29 (s, 3H) 2.31-2.39 (m, 1H) 2.50 (s, 3H) 2.69-3.01 (m, 4H) 3.10-3.26 (m, 2H) 4.18 (q, J=7.15 Hz, 2H) 5.05 (s, 1H) 5.29 (dd, J=8.79, 4.95 Hz, 1H) 6.26 (s, 1H) 6.65 (d, J=7.70 Hz, 1H) 6.86-6.95 (m, 2H) 7.14 (t, J=7.70 Hz, 1H) 7.28 (d, J=2.75 Hz, 1H) 7.33-7.42 (m, 2H) 7.44-7.51 (m, 1H) 8.71 (s, 1H). MS (ESI) m/z 584.5 (M+H)⁺.

Example 7

LiOH (1.0 M, 1 mL) was added to a solution of 7I1 (15 mg, 0.026 mmol) in THF (1 mL) and stirred for 2 h at rt. The reaction mixture was concentrated and purified by HPLC (Phenom. Luna C18, 21.2×100 mm, 10 micron, flow rate 20 mL/min, A: H₂O/MeOH (9:1), B: H₂O/MeOH (1:9), 0.1% TFA, 20 to 100% B, 10 min gradient.) to yield Example 7 (6 mg, 10.80 μmol, 42.0% yield) as a white solid. ¹H NMR (400 MHz, CD₃OD) δ ppm 2.28 (s, 3H) 2.50 (s, 2H) 2.61-2.95 (m, 4H) 3.10-3.24 (m, 2H) 5.04 (s, 1H) 5.29 (dd, J=8.79, 5.50 Hz, 1H) 6.26 (s, 1H) 6.65 (d, J=7.70 Hz, 1H) 6.88-6.98 (m, 2H) 7.09-7.19 (m, J=7.97, 7.97 Hz, 1H) 7.27 (d, J=2.20 Hz, 1H) 7.33 (dd, J=9.07, 2.47 Hz, 1H) 7.39 (s, 1H) 7.46 (d, J=9.34 Hz, 1H) 8.48 (s, 1H). MS (ESI) m/z 556.4 (M+H)⁺. Analytical HPLC (Method A): Col A: 5.54 min, 95%; Col B: 5.98 min, 90%.

Example 8

[(2R,5R)-17,20-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid ethyl ester

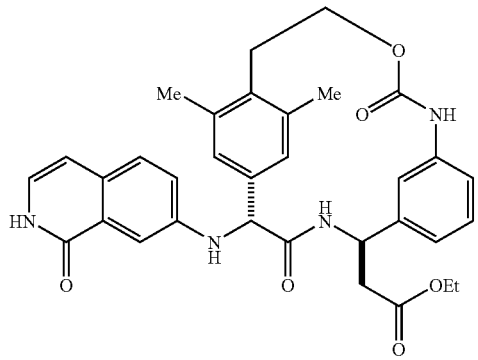 [SMILES: CCOC(=O)C[C@H]1NC(=O)[C@H](Nc2ccc3cc[nH]c(=O)c3c2)c2cc(C)c(c(C)c2)CCOC(=O)Nc2cccc1c2]

8A

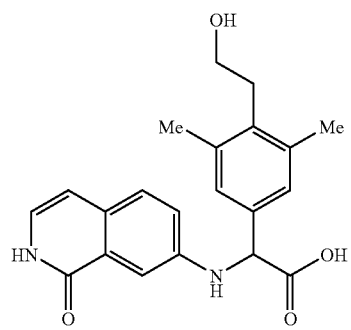 [SMILES: Cc1cc(C(Nc2ccc3cc[nH]c(=O)c3c2)C(=O)O)cc(C)c1CCO]

Using a procedure analogous to that used to prepare 1E, 7E (250 mg, 0.811 mmol), was reacted with Intermediate 3, and glyoxylic acid monohydrate. The reaction mixture was concentrated and purified by column chromatography (5 to 20% MeOH in CH$_2$Cl$_2$, 40 g column) to yield 8A (247 mg, 0.674 mmol, 83% yield) as a yellow solid.

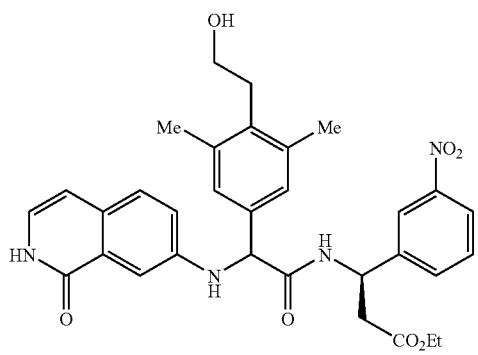 [SMILES: CCOC(=O)C[C@@H](NC(=O)C(Nc1ccc2cc[nH]c(=O)c2c1)c1cc(C)c(CCO)c(C)c1)c1cccc([N+](=O)[O-])c1]

Using a procedure analogous to that used to prepare 7G, 7A (185 mg, 0.674 mmol) was coupling to 8A using triethy-lamine, 1-hydroxy-7-azabenzotriazole, and 1-(3-(dimethylamino)propyl)-ethyl-carbodiimide HCl and purified by column chromatography (0 to 20% MeOH in CH$_2$Cl$_2$, 40 g column) to yield 8B (375 mg, 0.639 mmol, 95% yield) as a yellow solid. MS (ESI) m/z 587.4 (M+H)$^+$.

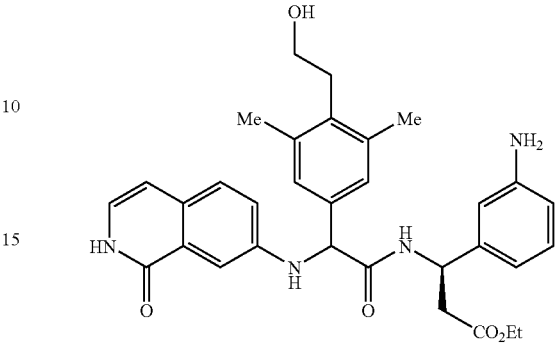

A solution of 8B (375 mg, 0.639 mmol) with Pd/C (68.0 mg, 0.064 mmol) in methanol (10 mL) was stirred under an atmosphere of H$_2$ (1 atm) for 4 h. The reaction mixture was filtered, concentrated and purified by column chromatography (0 to 20% MeOH in CH$_2$Cl$_2$, 40 g column) to yield 8C (245 mg, 0.440 mmol, 68.9% yield) as a yellow solid. MS (ESI) m/z 557.4 (M+H)$^+$.

Example 8

Using a procedure analogous to that used to prepare 7H, 8C (230 mg, 0.413 mmol) was reacted with Phosegene and purified by prep HPLC (Phenom. Luna C18, 21.2×100 mm, 10 micron, flow rate 20 mL/min, A: H$_2$O/MeOH (9:1), B: H$_2$O/MeOH (1:9), 0.1% TFA, 20 to 90% B, 10 min gradient.) to yield a mixture of diastereomers (50 mg). A small amount (10 mg) was separated by prep HPLC (Phenom. AXIA Luna, 100×30 mm, 5 micron, flow rate 40 mL/min, A: H$_2$O/Acn (9:1), B: H$_2$O/Acn (1:9), 0.1% TFA, 30 to 40% B, 10 min gradient) to yield Example 8 (4 mg) and its diastereomer (2.5 mg). $^1$H NMR (400 MHz, CD$_3$OD) δ ppm 0.97 (t, J=7.15 Hz, 3H) 2.40 (s, 3H) 2.46 (s, 3H) 2.70-2.96 (m, 2H) 3.07 (s, 2H) 3.74 (d, J=2.75 Hz, 2H) 4.95 (s, 1H) 5.05-5.17 (m, 1H) 6.32 (s, 1H) 6.58 (d, J=7.15 Hz, 1H) 6.67 (d, J=7.70 Hz, 1H) 6.89 (d, J=6.60 Hz, 1H) 6.95 (d, J=7.15 Hz, 1H) 7.08-7.20 (m, 2H) 7.27 (dd, J=8.79, 2.20 Hz, 1H) 7.32 (s, 1H) 7.47-7.60 (m, 2H). MS (ESI) m/z 583.5 (M+H)$_i$. Analytical HPLC (Method A): Col A: 7.88 min, 96%; Col B: 7.76 min, 96%.

Example 9

[(2R,5R)-17,20-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid

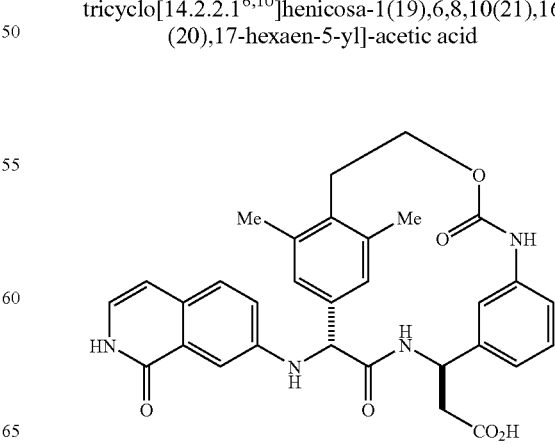

LiOH (1.0 M, 2 mL) was added to a mixture of Example 8 and its diastereomer (40 mg) in THF (2 mL) and stirred for 2 h at rt. The reaction mixture was concentrated and purified by HPLC (Phenom. Luna C18, 21.2×100 mm, 10 micron, flow rate 20 mL/min, A: $H_2O$/MeOH (9:1), B: $H_2O$/MeOH (1:9), 0.1% TFA, to 100% B, 10 min gradient.) to yield Example 9 (15 mg) and its diastereomer (7 mg) as a white solid. $^1H$ NMR (400 MHz, $CD_3OD$) δ ppm 2.31 (s, 3H) 2.49 (s, 3H) 2.61-2.97 (m, 4H) 3.08-3.26 (m, 2H) 5.05 (s, 1H) 5.26-5.39 (m, 1H) 6.28 (s, 1H) 6.55 (d, J=6.60 Hz, 1H) 6.66 (dd, J=7.70, 1.65 Hz, 1H) 6.87-7.00 (m, 3H) 7.14 (t, J=7.97 Hz, 1H) 7.22 (dd, J=8.79, 2.75 Hz, 1H) 7.33-7.49 (m, 3H). MS (ESI) m/z 555.09 $(M+H)^+$. Analytical HPLC (Method A): Col A: 6.86 min, 95%; Col B: 6.87 min, 95%.

Example 10

[(2R,5R)-17,20-Dimethoxy-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid ethyl ester

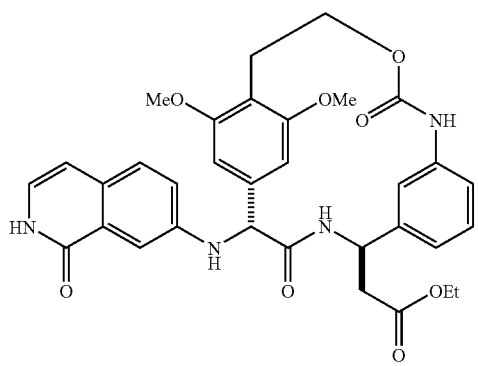 [SMILES: CCOC(=O)C[C@H]1NC(=O)[C@H](Nc2ccc3cc[nH]c(=O)c3c2)c2cc(OC)c(c(OC)c2)CCOC(=O)Nc2cccc1c2]

10A

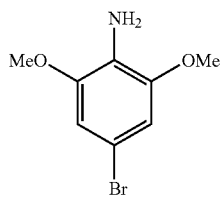 [SMILES: COc1cc(Br)cc(OC)c1N]

A solution of bromine (6.6 mL, 127 mmol) in $CH_2Cl_2$ (100 mL) was added dropwise to a solution of 2,6-dimethoxyaniline (19.5 g, 127 mmol) in $CH_2Cl_2$ (1273 mL) at 0° C. over 5 h. The reaction mixture was stirred for an additional 30 min and then NaOH (1.0 M, 500 mL) was added. The phases were separated and the organic phase was washed with $H_2O$ (1×250 mL), brine (1×250 mL), dried over $Na_2SO_4$ and concentrated. The crude brown oil was purified by column chromatography (0 to 50% EtOAc in hexanes) to yield 10A (20 g, 69.8 mmol, 54.8% yield) as a white solid.

10B

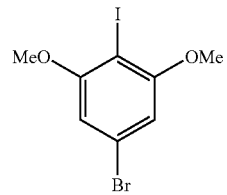 [SMILES: COc1cc(Br)cc(OC)c1I]

Sodium nitrite (0.713 mL, 22.41 mmol) in $H_2O$ (20 mL) was added dropwise to a solution of 10A (5 g, 21.54 mmol) in HCl (6.0 M, 40 mL) while maintaining the temperature below 5° C. The resulting solution was added to KI (3.58 g, 21.54 mmol) in $H_2O$ (2 mL) slowly followed by addition of tetrabutylammonium iodide (3.98 g, 10.77 mmol) and then heated at 60° C. for 3 h and stirred overnight at rt. The reaction mixture was diluted with $H_2O$ (200 mL) and extracted with $Et_2O$ (1×400 mL). The organic layer was washed with brine, dried over $Na_2SO_4$ and concentrated. The crude product was purified by column chromatography (0 to 15% EtOAc in Hexanes, 40 g column) to yield 10B (2.5 g, 7.29 mmol, 33.8% yield) as a white solid.

10C

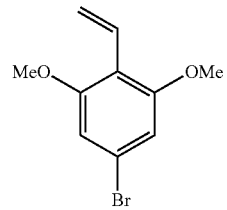

Using a procedure analogous to that used to prepare 7B, 10B (0.87 g, 2.54 mmol), was reacted with KF, n-$Bu_4NCl$, Pd(dba)$_2$ and trimethyl(vinyl)silane and purified by column chromatography (0 to 20% EtOAc in Hexanes) to yield 1° C. (480 mg, 1.975 mmol, 78% yield) as a clear solid. (Repeated multiple times.)

10D

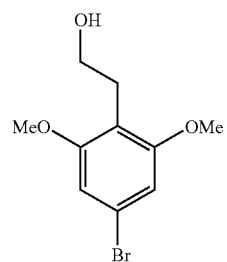 [SMILES: COc1cc(Br)cc(OC)c1CCO]

Using a procedure analogous to that used to prepare 7C, 1° C. (2.25 g, 9.26 mmol) was reacted with 9-BBN and purified by column chromatography to yield 10D (850 mg, 3.26 mmol, 35.2% yield) as a white solid.

10E

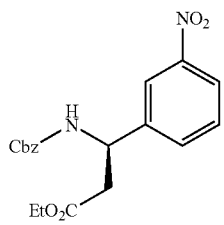 [SMILES: CCOC(=O)C[C@@H](NC(=O)OCc1ccccc1)c1cccc([N+](=O)[O-])c1]

N-(Benzyloxycarbonyloxy)succinimide (2.6 g, 10.6 mmol) and DIEA (3.81 mL, 21.84 mmol) were added to a solution of 7A (2.4 g, 8.74 mmol) in $CH_2Cl_2$ (60 mL) and stirred for 15 h at rt. The reaction mixture was diluted with EtOAc (100 mL), washed with 0.25 M HCl (50 mL), $NaHCO_3$ (50 mL), brine (50 mL), dried over $Na_2SO_4$ and concentrated. The crude oil was purified by column chromatography (0 to 100% EtOAc in Hexanes, 80 g column) to yield 10E (3.05 g, 8.19 mmol, 94% yield) as a white solid.

10F

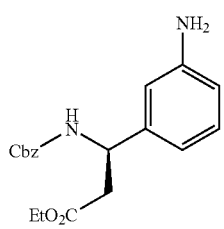 [SMILES: CCOC(=O)C[C@@H](NC(=O)OCc1ccccc1)c1cccc(N)c1]

A solution of 10E (3.05 g, 8.19 mmol) in ethanol (150 mL), water (37.5 mL), and acetic acid (7.5 mL) was heated to reflux (bath=110° C.). Iron (2.287 g, 41.0 mmol) was added portionwise over 10 min. The reaction mixture was refluxed for an additional 1 h and cooled to rt. The mixture was neutralized with sat'd $NaHCO_3$ (50 mL), diluted with $H_2O$ (200 mL) and extracted with EtOAc (3×100 mL). The organics were combined, washed with brine, dried over $Na_2SO_4$ and concentrated to yield 10F (2.25 g, 6.57 mmol, 80% yield) as a white solid. MS (ESI) m/z 343.3 $(M+H)^+$.

10G

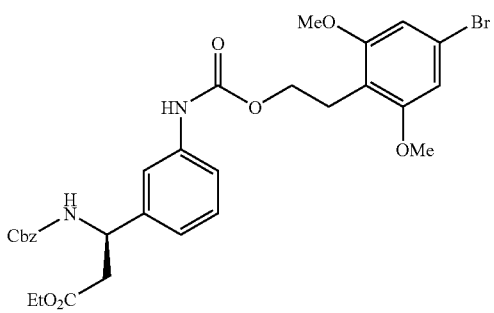 [SMILES: CCOC(=O)C[C@@H](NC(=O)OCc1ccccc1)c1cccc(NC(=O)OCCc2c(OC)cc(Br)cc2OC)c1]

Phosgene (2460 mg, 4.98 mmol) was added to a solution of 10F (852 mg, 2.489 mmol) in DCM (25 mL) with sodium bicarbonate (1046 mg, 12.45 mmol) dropwise at 0° C. The cooling bath was removed and the reaction mixture was stirred for 1 h at rt, filtered and concentrated in vacuo. The oil and 100D (650 mg, 2.489 mmol) were dissolved in THF (25 mL) and cooled to −40° C. NaH was added in one portion, the cooling bath was removed and the reaction mixture was stirred for 15 h. The reaction was quenched with citric acid (5 mL, sat'd), diluted with $H_2O$ (100 mL) and extracted with EtOAc (2×100 mL). The combined organics were washed with brine, dried over $Na_2SO_4$ and concentrated. The crude product was purified by flash chromatography (0 to 80% EtOAc in Hexanes, 80 g column) to yield 100G (1.2 g, 1.906 mmol, 77% yield) as a white foam. MS (ESI) m/z 629.2/631.2 $(M+H)^+$.

10H

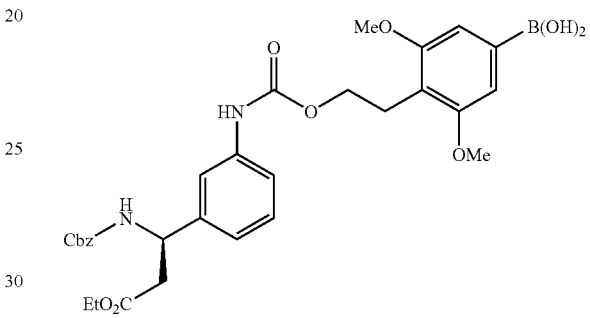

Using a procedure analogous to that used to prepare 1D, 10G (1.2 g, 1.906 mmol) was reacted with bis(neopentyl glycolato)diboron, potassium acetate, 1C (3.7 g, 6.86 mmol) and (1,1'-bis(diphenylphosphino)ferrocene)-dichloropalladium(II) and purified by prep HPLC ($H_2O$, MeOH, 0.1% TFA) to yield 10H (750 mg, 1.262 mmol, 66.2% yield) as a yellow solid. MS (ESI) m/z 593.3 $(M-H)^-$.

10I

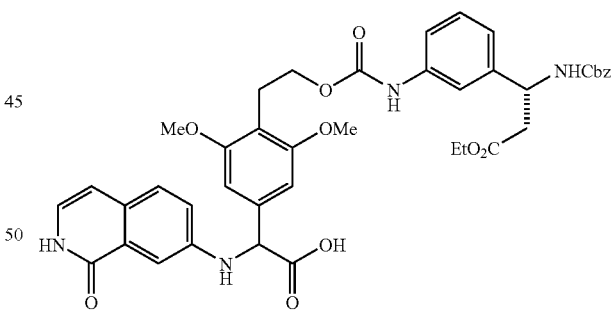

Using a procedure analogous to that used to prepare 1E, 10H (250 mg, 0.421 mmol), Intermediate 3, and glyoxylic acid monohydrate were reacted and purified by flash chromatography (0% to 20% MeOH in $CH_2Cl_2$) to yield 10I (310 mg, 0.404 mmol, 96% yield) as a yellow solid. MS (ESI) m/z 767.3 $(M+H)^+$.

Example 10

A solution of 10I (322 mg, 0.420 mmol) in MeOH (5 mL) was stirred with Pd/C under $H_2$ (60 psi) for 4 h. The reaction was filtered and concentrated to yield the crude deprotected amine (194 mg, 0.307 mmol, 73.0% yield) as a yellow glass. A solution of the crude product in DMF (4 mL) was added via syringe pump over 5 h to a solution of BOP (271 mg, 0.613 mmol), DMAP (187 mg, 1.533 mmol), and TEA (0.214 mL, 1.533 mmol) at 35° C. The reaction was concentrated and purified by prep HPLC to yield Example 10 (30 mg, 0.049 mmol, 15.92% yield) as a 2.6:1 mixture of diastereomers. $^1$H NMR (400 MHz, CD$_3$OD) δ ppm 0.93-1.27 (m, 3H) 2.68-2.91 (m, 3H) 3.08-3.22 (m, 1H) 3.52-3.63 (m, 2H) 3.72-3.86 (m, 3H) 3.98 (d, J=7.15 Hz, 3H) 4.03-4.20 (m, 2H) 4.44-4.52 (m, 1H) 5.08-5.16 (m, 1H) 5.27-5.37 (m, 1H) 6.42-6.51 (m, 1H) 6.51-6.61 (m, 2H) 6.66 (d, J=7.70 Hz, 1H) 6.86-6.97 (m, 2H) 7.01 (s, 1H) 7.13 (t, J=7.70 Hz, 1H) 7.22-7.32 (m, 1H) 7.41-7.61 (m, 2H). MS (ESI) m/z 615.4 (M+H)$^+$. Analytical HPLC (Method A): Col A: 7.61 (minor), 7.75 (major) min, 99%; Col B: 7.52 (minor), 7.65 (major) min, 99%.

Example 11

[(2R,5R)-17,20-Dimethoxy-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid

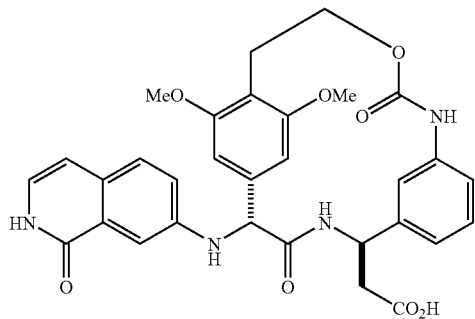 [SMILES: COc1cc2cc(OC)c1CCOC(=O)Nc1cccc(c1)[C@@H](CC(=O)O)NC(=O)[C@@H]2Nc1ccc2cc[nH]c(=O)c2c1]

A 1.0 M solution of LiOH (2 mL) was added to a solution of Example (25 mg, 0.041 mmol) in THF (2 mL) and stirred at rt for 2 h. 1.0 M HCl (2 mL) was added and the reaction mixture was concentrated in vacuo. The crude product was purified by prep HPLC to yield Example 11 as a white solid. (10 mg, 4:1 mix of diasteromers). MS (ESI) m/z 587.3 (M+H)$^+$. Analytical HPLC (Method A): Col A: 6.84 min, 99%; Col B: 6.82 min, 99%.

Example 12

[(2R,5R)-17,20-Dimethoxy-3,12-dioxo-2-(4-oxo-3,4-dihydro-quinazolin-6-ylamino)-13-oxa-4,11-diaza-tricyclo[14.2.2.1$^{6,10}$]henicosa-1(19),6,8,10(21),16(20),17-hexaen-5-yl]-acetic acid ethyl ester

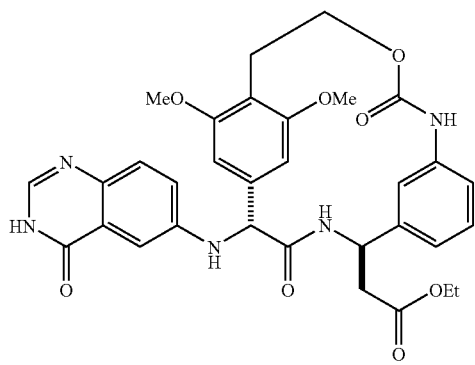 [SMILES: CCOC(=O)C[C@H]1NC(=O)[C@H](Nc2ccc3nc[nH]c(=O)c3c2)c2cc(OC)c(c(OC)c2)CCOC(=O)Nc2cccc1c2]

12A

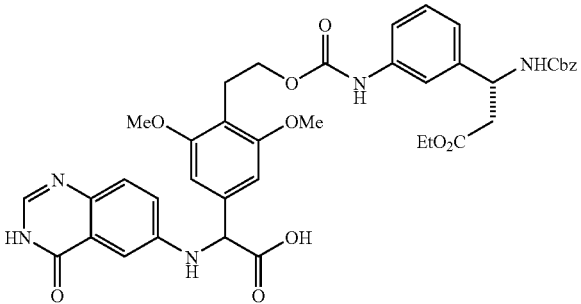 [SMILES: CCOC(=O)C[C@@H](NC(=O)OCc1ccccc1)c1cccc(NC(=O)OCCc2c(OC)cc(C(Nc3ccc4nc[nH]c(=O)c4c3)C(=O)O)cc2OC)c1]

Using a procedure analogous to that used to prepare 1E, 10H (200 mg, 0.336 mmol), Intermediate 4, and glyoxylic acid monohydrate were reacted and purified by flash chromatography (0% to 20% MeOH in CH$_2$Cl$_2$) to yield 12A (200 mg, 0.260 mmol, 77% yield) as a yellow solid. MS (ESI) m/z 768.4 (M+H)$^+$.

Example 12

A solution of 12A in methanol (5 mL) was stirred with Pd/C under H$_2$ (60 psi) for 4 h. The reaction was filtered and concentrated to yield the crude unprotected benzylamine (125 mg, 0.197 mmol, 76% yield) as a yellow glass. A solution of the crude material (125 mg, 0.197 mmol) in DMF (4 mL) was added via syringe pump over 5 h to a solution of BOP (174 mg, 0.395 mmol), DMAP (121 mg, 0.986 mmol) and TEA (0.137 mL, 0.986 mmol) in CH$_2$Cl$_2$ (40 mL) at 35° C. The reaction was concentrated and purified by prep HPLC to yield Example 12 (25 mg, 0.041 mmol, 20.59% yield) as a white solid. $^1$H NMR (400 MHz, CD$_3$OD) δ ppm 1.23 (t, J=7.15 Hz, 3H) 2.67-2.93 (m, 3H) 3.14 (s, 1H) 3.54 (s, 3H) 4.00 (s, 3H) 4.02-4.08 (m, J=2.20 Hz, 1H) 4.18 (q, J=7.15 Hz, 2H) 4.92-5.03 (m, 1H) 5.10 (s, 1H) 5.33 (d, J=4.40 Hz, 1H) 6.43 (s, 1H) 6.50 (s, 1H) 6.66 (d, J=7.70 Hz, 1H) 6.92 (d, J=7.70 Hz, 1H) 7.02 (s, 1H) 7.14 (t, J=7.70 Hz, 1H) 7.30-7.41 (m, 2H) 7.44-7.55 (m, 1H) 8.57 (s, 1H). MS (ESI) m/z 616.4 (M+H)$^+$. Analytical HPLC (Method A): Col A: 6.30 min, 91%; Col B: 6.81 min, 91%.

Example 13

[(2R,5R)-17,20-Dimethoxy-3,12-dioxo-2-(4-oxo-3,4-dihydro-quinazolin-6-ylamino)-13-oxa-4,11-diaza-tricyclo[14.2.2.1$^{6,10}$]henicosa-1(19),6,8,10(21),16(20),17-hexaen-5-yl]-acetic acid

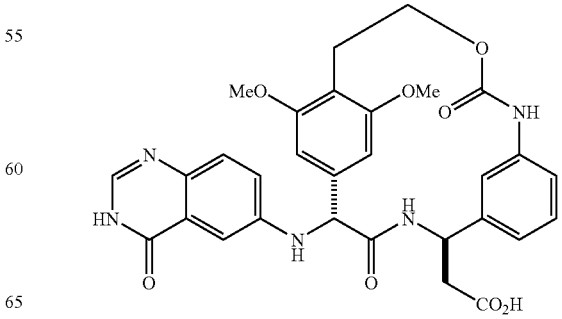

LiOH (1.0 M, 2 mL) was added to a solution of Example 12 (22 mg, 0.036 mmol) in THF (2 mL) and stirred for 1 h at rt. HCl (1.0 M, 2 mL) was added to the mixture and it was concentrated in vacuo. The crude solid was purified by pre HPLC (Phenom. Luna Axia, 30×100 mm, 5 micron, flow rate 40 mL/min, A: H$_2$O/MeOH (9:1), B: H$_2$O/MeOH (1:9), 0.1% TFA, 0 to 75% B, 10 min gradient) to yield Example 13 (19 mg, 0.032 mmol, 90% yield) as a yellow solid. MS (ESI) m/z 588.3 (M+H)$^+$. $^1$H NMR (400 MHz, CD$_3$OD) δ ppm 2.67-2.92 (m, 3H) 3.07-3.22 (m, 1H) 3.53 (s, 3H) 4.00 (s, 3H) 4.02-4.09 (m, J=7.15 Hz, 1H) 4.96-5.02 (m, 1H) 5.11 (s, 1H) 5.28-5.40 (m, 1H) 6.43 (s, 1H) 6.50 (s, 1H) 6.66 (d, J=7.70 Hz, 1H) 6.95 (d, J=7.70 Hz, 1H) 7.04 (s, 1H) 7.14 (t, J=7.70 Hz, 1H) 7.29-7.40 (m, 2H) 7.43-7.51 (m, 1H) 8.63 (s, 1H). Analytical HPLC (Method A): Col A: 5.49 min, 90%; Col B: 5.80 min, 98%.

Example 14

4,17,20-Trimethyl-2-(1-oxo-1,2-dihydro-isoquinolin-7-ylamino)-13-oxa-4,11-diaza-tricyclo[14.2.2.1$^{6,10}$] henicosa-1(19),6,8,10(21),16(20),17-hexaene-3,12-dione

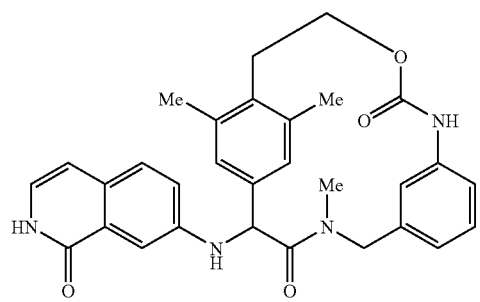 [SMILES: Cc1cc2cc(C)c1CCOC(=O)Nc1cccc(c1)CN(C)C(=O)C2Nc1ccc2cc[nH]c(=O)c2c1]

14A

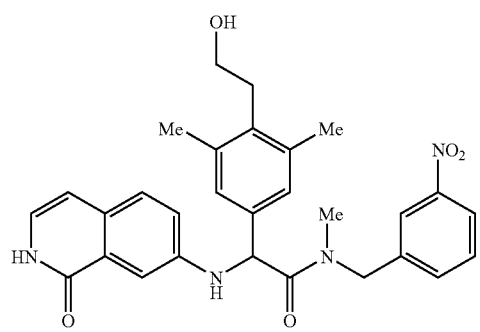 [SMILES: Cc1cc(C(Nc2ccc3cc[nH]c(=O)c3c2)C(=O)N(C)Cc2cccc([N+](=O)[O-])c2)cc(C)c1CCO]

A (100 mg, 0.273 mmol) was coupled to N-methyl-1-(3-nitrophenyl)methanamine (45.4 mg, 0.273 mmol) using triethylamine, 1-hydroxy-7-azabenzotriazole and 1-(3-(dimethylamino)propyl)-3-ethyl-carbodiimide hydrochloride. The crude solid was purified by column chromatography (0 to 20% MeOH in CH$_2$Cl$_2$) to yield 14A (135 mg, 0.262 mmol, 96% yield) as a yellow solid, MS (ESI) m/z 515.3 (M+H)$^+$.

14B

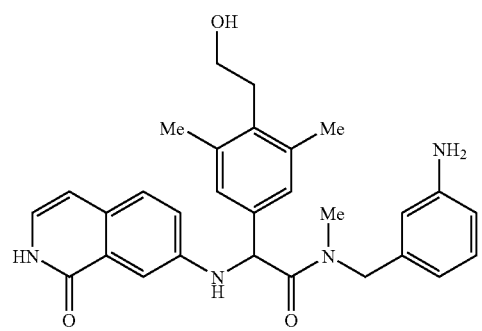 [SMILES: Cc1cc(C(Nc2ccc3cc[nH]c(=O)c3c2)C(=O)N(C)Cc2cccc(N)c2)cc(C)c1CCO]

A solution of 14A (130 mg, 0.253 mmol) in MeOH (5 mL) with Pd/C (20 mg) was stirred overnight under H$_2$ (1 atm). The reaction was filter and concentrated. The crude product was purified by column chromatography (0 to 20% MeOH in CH$_2$Cl$_2$, 12 g column) to yield 14B (105 mg, 0.217 mmol, 86% yield) as a yellow solid. MS (ESI) m/z 485.3 (M+H)$^+$.

Example 14

Using a procedure analogous to that used to prepare 7H, 14B (100 mg, 0.206 mmol) was reacted with Phosegene and Et$_3$N and purified by prep HPLC (Phenom. Luna Axia, 30×100 mm, 5 micron, flow rate 40 mL/min, A: H$_2$O/MeOH (9:1), B: H$_2$O/MeOH (1:9), 0.1% TFA, 40 to 80% B, 10 min gradient to yield Example 14 as a white solid. MS (ESI) m/z 511.3 (M+H)$^+$. $^1$H NMR (400 MHz, DMSO-d$_6$) δ ppm 2.20-2.27 (m, 3H) 2.37 (s, 3H) 2.69-2.87 (m, 2H) 2.89-3.09 (m, 2H) 3.16 (s, 3H) 3.82 (d, J=16.49 Hz, 1H) 5.27 (d, J=15.94 Hz, 1H) 5.60 (s, 1H) 5.86 (s, 1H) 6.33 (d, J=7.15 Hz, 1H) 6.61 (d, J=7.70 Hz, 1H) 6.76-6.87 (m, 1H) 6.94 (s, 1H) 7.13 (t, J=7.70 Hz, 1H) 7.22-7.31 (m, 1H) 7.34 (t, J=8.24 Hz, 2H) 9.04 (s, 1H) 10.86 (d, J=5.50 Hz, 1H). Analytical HPLC (Method A): Col A: 7.47 min, 99%; Col B: 7.42 min, 99%.

Example 15

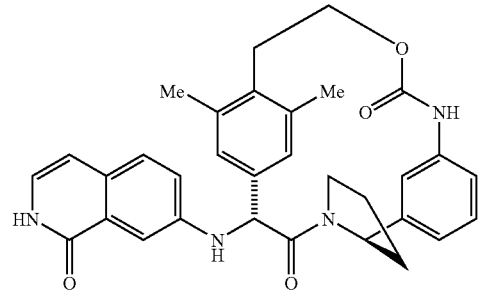 [SMILES: Cc1cc2cc(C)c1CCOC(=O)Nc1cccc(c1)[C@H]1CCCN1C(=O)[C@@H]2Nc1ccc2cc[nH]c(=O)c2c1]

15A

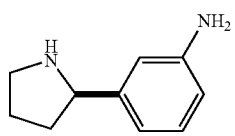 [SMILES: Nc1cccc([C@H]2CCCN2)c1]

3-(Pyrrolidin-2-yl)aniline hydrochloride (5 g) was separated into 15A (2 g, 98% recovery, >99.9% ee) and enantiomer 2 (2 g, 98% recovery, >99.6% ee) using the following method: Chiralpak AD-H (30×250 mm, 5 micron, Chiral Technologies, Inc.), $CO_2$/MeOH/DEA (85:15:0.1), 65 mL/min flow rate, and uv detection at 220 nm. MS (ESI) m/z 163.3 $(M+H)^+$. Chiral analytical retentions, 15A: 8.18 min, enantiomer 2: 11.19 min (Chiralpak AD-H (4.6×250 mm, 10 micron, Chiral Technologies, Inc.), $CO_2$/MeOH/DEA (70:30:0.1), 3 mL/min flow rate, and uv detection at 220 nm).

15B

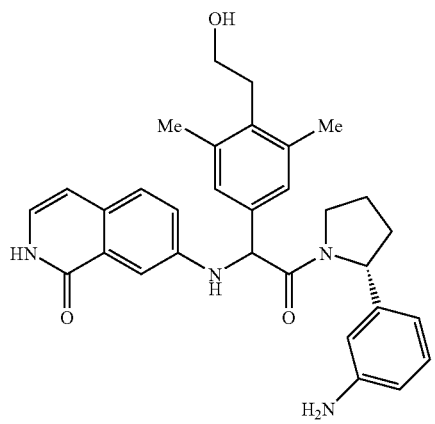 [SMILES: Cc1cc(C(Nc2ccc3cc[nH]c(=O)c3c2)C(=O)N2CCC[C@@H]2c2cccc(N)c2)cc(C)c1CCO]

A (66.4 mg, 0.409 mmol) and 8A (150 mg, 0.409 mmol) were coupled using triethylamine, 1-hydroxy-7-azabenzotriazole, and 1-(3-(dimethylamino)propyl)-ethyl-carbodiimide HCl and purified by flash chromatography (0 to 20% MeOH in $CH_2Cl_2$) to yield 15B (150 mg, 0.294 mmol, 71.8% yield) as a yellow solid. MS (ESI) m/z 511.4 $(M+H)^+$.

Example 15

Using a procedure analogous to that used to prepare 7H, 15B (150 mg, 0.294 mmol) was reacted with Phosgene and $Et_3N$ and purified by prep HPLC (Phenom. Luna Axia, 30×100 mm, 5 micron, flow rate 40 mL/min, A: $H_2O$/MeOH (9:1), B: $H_2O$/MeOH (1:9), 0.1% TFA, 40 to 90% B, 10 min gradient) to yield Example 15 (14 mg, 0.026 mmol, 8.88% yield) as a yellow solid. MS (ESI) m/z 537.3 $(M+H)^+$. $^1H$ NMR (400 MHz, $CD_3OD$) δ ppm 1.68-1.81 (m, 1H) 1.82-2.07 (m, 2H) 2.24-2.30 (m, 1H) 2.31 (s, 3H) 2.47 (s, 3H) 2.81-2.93 (m, 1H) 3.14-3.27 (m, 1H) 3.79-3.93 (m, 1H) 3.96-4.10 (m, 1H) 5.01-5.14 (m, 1H) 5.18-5.26 (m, 1H) 5.35 (s, 1H) 6.08 (s, 1H) 6.55 (d, J=7.15 Hz, 1H) 6.62 (d, J=8.25 Hz, 1H) 6.86 (d, J=7.70 Hz, 1H) 6.95 (d, J=7.15 Hz, 1H) 7.04 (s, 1H) 7.13 (t, J=7.70 Hz, 1H) 7.28 (dd, J=8.79, 2.75 Hz, 1H) 7.36 (s, 1H) 7.45 (d, J=8.79 Hz, 1H) 7.53 (d, J=2.20 Hz, 1H). Analytical HPLC (Method A): Col A: 7.78 min, 98%; Col B: 7.69 min, 98%.

Example 16

[(2R,5R,15R)-15,20-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid

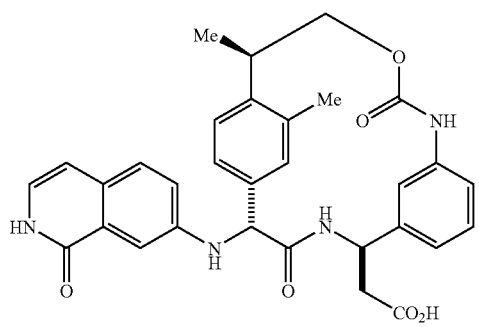 [SMILES: Cc1cc2ccc1[C@@H](C)COC(=O)Nc1cccc(c1)[C@@H](CC(=O)O)NC(=O)[C@@H]2Nc1ccc2cc[nH]c(=O)c2c1]

16A

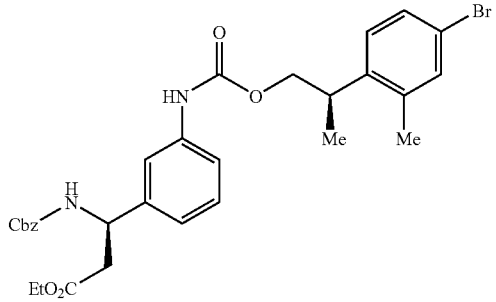 [SMILES: CCOC(=O)C[C@@H](NC(=O)OCc1ccccc1)c1cccc(NC(=O)OC[C@H](C)c2ccc(Br)cc2C)c1]

Using a procedure analogous to that used to prepare 10G, 10F (239 mg, 0.698 mmol) was reacted with sodium bicarbonate and Phosgene followed by Intermediate 8 and NaH. The crude product was purified by flash chromatography (0 to 80% EtOAc in Hexanes, 40 g column) to yield 16A (15 mg, 0.192 mmol, 27.6% yield) as a white foam. MS (ESI) m/z 597.22/599.23 $(M+H)^+$.

16B

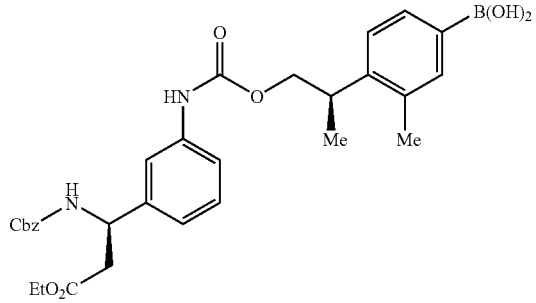 [SMILES: CCOC(=O)C[C@@H](NC(=O)OCc1ccccc1)c1cccc(NC(=O)OC[C@H](C)c2ccc(B(O)O)cc2C)c1]

Using a procedure analogous to that used to prepare 29B, 16A (115 mg, 0.192 mmol) was reacted with bis(neopentyl glycolato)diboron, potassium acetate and (1,1'-bis(diphenylphosphino)ferrocene)-dichloropalladium(II). The crude ester was purified by prep HPLC ($H_2O$/MeOH, 0.1% TFA) to yield 16B (78 mg, 0.139 mmol, 72.1% yield) as a brown oil. MS (ESI) m/z 580.4 $(M+NH_4)$.

16C

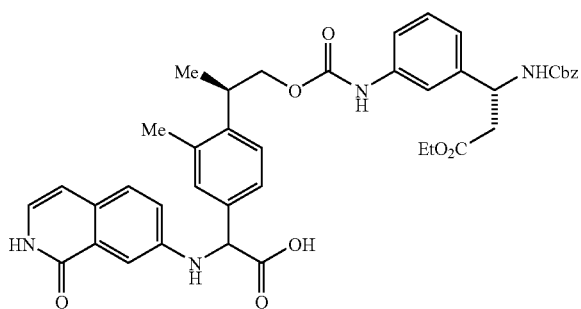 [SMILES: CCOC(=O)C[C@@H](NC(=O)OCc1ccccc1)c1cccc(NC(=O)OC[C@H](C)c2ccc(C(Nc3ccc4cc[nH]c(=O)c4c3)C(=O)O)cc2C)c1]

Using a procedure analogous to that used to prepare 1E, 16B (78 mg, 0.139 mmol), Intermediate 3, and glyoxylic acid monohydrate were reacted and purified by flash chromatography (0% to 20% MeOH in $CH_2Cl_2$) to yield 16C (85 mg, 0.116 mmol, 83% yield) as a yellow solid. MS (ESI) m/z 735.4 $(M+H)^+$.

16D

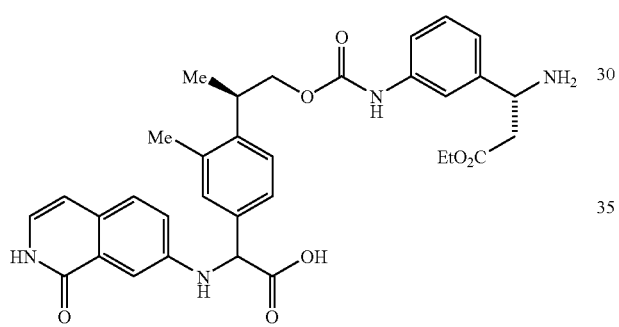

A solution of 16C (78 mg, 0.106 mmol) in MeOH (5 mL) with Pd/C (20 mg) was stirred under $H_2$ (50 psi) for 6 h. The reaction was filtered and concentrated to yield 16D (60 mg, 0.100 mmol, 94% yield) as a yellow solid. MS (ESI) m/z 601.5 $(M+H)^+$.

16E

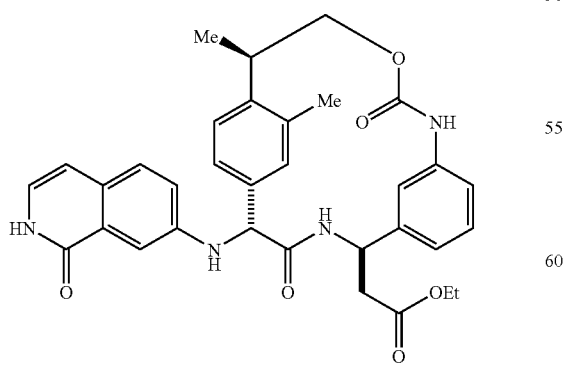

A solution of 16D (60 mg, 0.100 mmol) in DMF (2 mL) was added via syringe pump over 5 h to a solution of BOP (88 mg, 0.200 mmol), DMAP (61.0 mg, 0.499 mmol) and TEA (0.070 mL, 0.499 mmol) in $CH_2Cl_2$ (10 mL) at 35° C. over 4 h. The reaction was concentrated and purified by prep HPLC to yield 16E (3 mg, 5.15 μmol, 5.15% yield) and diastereomer 2 (3 mg, 5.15 μmol, 5.15% yield) as white solids. The compounds were repurified by WELKO column (60% EtOH/MeOH, 40% Heptane). MS (ESI) m/z 583.4 $(M+H)^+$.

Example 16

LiOH (1 mL, 1.0 M, aq) was added to a solution of 16E (3 mg, 5.15 μmol) in THF (1 mL) and stirred for 1 h at rt. HCl (1 mL, 1.0 M, aq) was added and the reaction mixture was concentrated. Purification by prep HPLC yielded Example 16 (1.3 mg, 2.344 μmol, 45.5% yield) as a white solid. MS (ESI) m/z 555.3 $(M+H)^+$. $^1$H NMR (400 MHz, $CD_3OD$) δ ppm 1.28 (d, J=7.15 Hz, 3H) 2.29 (s, 3H) 2.67-2.89 (m, 2H) 3.40-3.54 (m, 1H) 4.03 (dd, J=10.99, 4.40 Hz, 1H) 4.62-4.76 (m, 1H) 5.11 (s, 1H) 5.23-5.36 (m, J=9.34, 4.95 Hz, 1H) 6.25 (s, 1H) 6.55 (d, J=7.15 Hz, 1H) 6.65 (d, J=7.70 Hz, 1H) 6.91 (d, J=7.15 Hz, 1H) 6.95 (d, J=7.70 Hz, 1H) 7.08-7.17 (m, 1H) 7.21 (dd, J=8.52, 2.47 Hz, 1H) 7.37 (s, 1H) 7.42 (d, J=8.79 Hz, 1H) 7.57 (d, J=8.24 Hz, 1H). Analytical HPLC (Method A): Col A: 6.97 min, 99%; Col B: 8.01 min, 98%.

Example 17

(2R,15R)-17-Ethyl-4,15-dimethyl-2-(1-oxo-1,2-dihydro-isoquinolin-7-ylamino)-13-oxa-4,11-diazatricyclo[14.2.2.1$^{6,10}$]henicosa-1(19),6,8,10(21),16(20),17-hexaene-3,12-dione

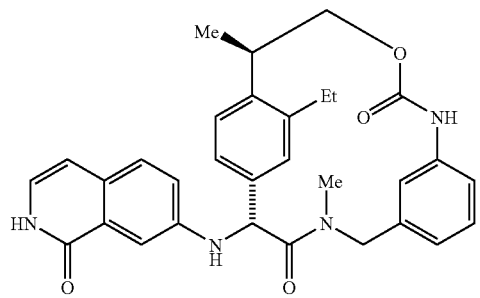 [SMILES: CCc1cc2ccc1[C@@H](C)COC(=O)Nc1cccc(c1)CN(C)C(=O)[C@@H]2Nc1ccc2cc[nH]c(=O)c2c1]

17A

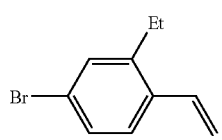

Using a procedure analogous to that used to prepare 7B, 4-bromo-2-ethyl-1-iodobenzene (2.1 g, 6.9 mmol) was reacted with trimethyl(vinyl)silane in a pressure vessel at 175° C. for 45 min to yield 17A (1.1 g, 77%) as a clear oil. $^1$H NMR (400 MHz, $CDCl_3$) δ ppm 1.03 (t, J=7.58 Hz, 3H) 2.51

(q, J=7.66 Hz, 2H) 5.15 (dd, J=10.99, 1.14 Hz, 1H) 5.47 (dd, J=17.31, 1.14 Hz, 1H) 6.74 (dd, J=17.43, 11.12 Hz, 1H) 7.08-7.20 (m, 3H).

17B

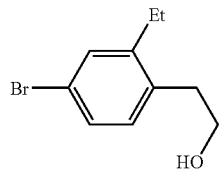 [SMILES: CCc1cc(Br)ccc1CCO]

Using a procedure analogous to that used to prepare 7C, 17A (1.98 g, 5.1 mmol) was heated in a pressure vessel with 9-BBN at 100° C. for 15 h to yield 17B (0.95 g, 81%) as a clear oil. $^1$H NMR (400 MHz, CDCl$_3$) δ ppm 1.23 (t, J=7.58 Hz, 3H) 2.66 (q, J=7.58 Hz, 2H) 2.87 (t, J=6.82 Hz, 2H) 3.83 (t, J=6.82 Hz, 2H) 7.06 (d, J=8.08 Hz, 1H) 7.25-7.31 (m, 1H) 7.32-7.37 (m, 1H).

17C

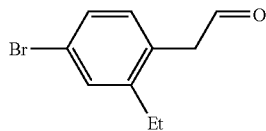

TEMPO (0.034 g, 0.218 mmol) added to a solution of 17B in CH$_2$Cl$_2$ (43.6 mL) and cooled to 0° C. Trichlorocyanuric acid (5.58 g, 24.01 mmol) was added over 30 min portionwise while maintaining a reaction temperature of 0° C. The reaction mixture stirred for 1 h at rt and then filtered through Celite®. The filtrated was washed with Na$_2$CO$_3$ (20 mL, sat'd), HCl (20 mL, 1.0 M) and brine (20 mL), dried over Na$_2$SO$_4$ and concentrated. The crude 17C used in the subsequent step without purification. $^1$H NMR (400 MHz, CDCl$_3$) δ ppm 1.19 (t, J=7.70 Hz, 3H) 2.56 (q, J=7.33 Hz, 2H) 3.67 (d, J=2.20 Hz, 2H) 7.01 (d, J=8.25 Hz, 1H) 7.32 (dd, J=8.24, 2.20 Hz, 1H) 7.38 (d, J=2.20 Hz, 1H) 9.69 (t, J=2.20 Hz, 1H).

17D

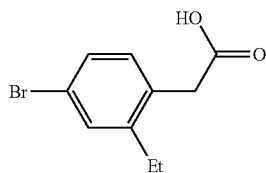

To a solution of 17C (5 g, 22.02 mmol) in t-butanol (150 mL), acetonitrile (25 mL) and water (50.0 mL) at rt, was added 2-methyl-2-butene (11.70 mL, 110 mmol), sodium chlorite (7.96 g, 88 mmol) and sodium phosphate monobasic monohydrate (3.49 g, 25.3 mmol). The mixture was stirred at rt for 1 h. The mixture was diluted with EtOAc and washed with 0.1 N HCl, H$_2$O and brine. The organic phase was dried (Na$_2$SO$_4$) and concentrated. The crude product was purified by flash chromatography (0 to 100% EtOAc in hexanes) to yield 17D (2.25 g, 9.26 mmol, 42.0% yield) as a clear oil. MS (ESI) m/z 241.1/243.1 (M−H)$^−$. $^1$H NMR (400 MHz, CHLOROFORM-d) δ ppm 1.21 (t, J=7.45 Hz, 3H) 2.62 (q, J=7.58 Hz, 2H) 3.63 (s, 2H) 7.07 (d, J=8.08 Hz, 1H) 7.29 (dd, J=8.21, 2.15 Hz, 1H) 7.35 (d, J=2.02 Hz, 1H).

17E

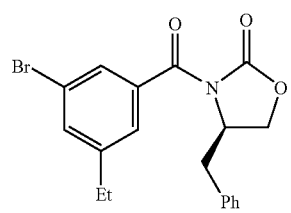 [SMILES: CCc1cc(Br)cc(C(=O)N2C(=O)OC[C@H]2Cc2ccccc2)c1]

Oxalyl chloride (5.09 mL, 10.18 mmol) and then DMF (7.17 μL, 0.093 mmol) were added to a solution of 17D (2.25 g, 9.26 mmol) in CH$_2$Cl$_2$ (50 mL) at rt. After stirring for 2.5 h, the reaction was concentrated to a red oil. BuLi (6.36 mL, 10.18 mmol) was added to a solution of (R)-(+)-4-benzyl-2-oxazolidinone (1.804 g, 10.18 mmol) in THF (50 mL) at −78° C. and stirred for 5 min. A solution of the red oil previously isolated in THF (10 mL) was added dropwise and the reaction mixture was stirred for 1 h at −78° C. The reaction was quench with sat'd NH$_4$Cl (5 mL) and warmed to rt. The mixture was diluted with EtOAc (200 mL) washed with brine, dried over Na$_2$SO$_4$ and concentrated. The crude product was purified by column chromatrography (0 to 50% EtOAc in Hexanes, 120 g column) to yield 17E (3.14 g, 7.81 mmol, 84% yield) as a pale yellow oil. MS (ESI) m/z 402.1/404.1 (M+H)$^+$. 1H NMR (400 MHz, CDCl$_3$) δ ppm 1.21 (t, J=7.42 Hz, 3H) 2.59 (q, J=7.70 Hz, 1H) 2.77 (dd, J=13.19, 9.89 Hz, 1H) 3.30 (dd, J=13.19, 3.30 Hz, 1H) 4.1.6-4.36 (m, 4H) 4.63-4.74 (m, 1H) 7.04 (d, J=8.24 Hz, 1H) 7.18 (d, J=6.60 Hz, 2H) 7.26-7.34 (m, 4H) 7.37-7.43 (m, 1H).

17F

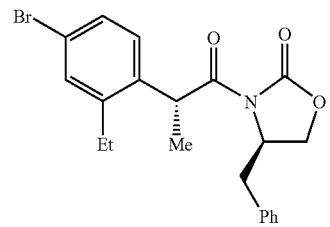 [SMILES: CCc1cc(Br)ccc1[C@@H](C)C(=O)N1C(=O)OC[C@H]1Cc1ccccc1]

Sodium bis(trimethylsilyl)amide (8.59 mL, 8.59 mmol) was added to a solution of 17E (3.14 g, 7.81 mmol) in THF (30 mL) at −78° C. After stirring for 1 h at −78° C., MeI (2.440 mL, 39.0 mmol) was added. The reaction mixture was stirred for 2 h at −78° C. and then allowed to warm to rt over 4 h. The reaction was quenched with sat. NH$_4$Cl. The mixture was diluted with EtOAc and washed with H$_2$O, sat. Na$_2$SO$_3$ and brine. The organic phase was dried over Na$_2$SO$_4$ and concentrated. The crude product purified by column chromatography (0 to 35% ethyl acetate/hexanes) to yield 17F (2.06 g, 4.95 mmol, 63.4% yield) as a clear oil. MS (ESI) m/z 416.2/418.2 (M+H)$^+$. $^1$H NMR (400 MHz, CDCl$_3$) δ ppm 1.24 (t, J=7.42 Hz, 3H) 1.48 (d, J=7.15 Hz, 3H) 2.70-2.85 (m, 3H) 3.35 (dd, J=13.19, 3.30 Hz, 1H) 4.04-4.17 (m, 2H) 4.58-4.67 (m, 1H) 5.19 (q, J=6.96 Hz, 1H) 7.10 (d, J=8.24 Hz, 1H) 7.20-7.24 (m, 2H) 7.26-7.37 (m, 4H).

17G

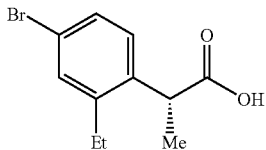

To a solution of 17F (2.05 g, 4.92 mmol) in THF (25 mL) and Water (8 mL) at 0° C., was added a solution of lithium peroxide (prepared by adding hydrogen peroxide (2.156 mL, 24.62 mmol) to lithium hydroxide monohydrate (0.137 mL, 4.92 mmol) in water (8 mL)), dropwise. The mixture was stirred at 0° C., for 1 h. The reaction was quenched with sat. $Na_2SO_3$ (~15 mL), and then the volatiles were removed in vacuo. The mixture was diluted with $H_2O$ and the aqueous solution was extracted with DCM (2×). The aqueous was acidified with conc. HCl, and extracted with EtOAc (2×). The combined organic extracts were washed with brine, dried ($Na_2SO_4$) and concentrated to yield 17G (1.25 g, 4.82 mmol, 98% yield) as a white solid. $^1$H NMR (400 MHz, $CDCl_3$) δ ppm 1.22 (t, J=7.70 Hz, 3H) 1.46 (d, J=7.15 Hz, 3H) 2.59-2.75 (m, 2H) 3.95 (q, J=7.15 Hz, 1H) 7.17 (d, J=8.25 Hz, 1H) 7.28-7.39 (m, 2H).

17H

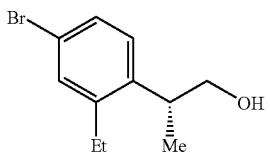

$BH_3$-THF (14.47 mL, 14.47 mmol) was added to a solution of 17G (1.24 g, 4.82 mmol) in THF (25 mL) dropwise at 0° C. The bath was removed and the reaction mixture was stirred overnight. The reaction mixture was cooled to 0° C. and water (75 mL) followed by 1N HCl (10 mL) were added. After stirring for 1 h, the mixture was extracted with EtOAc (2×100 mL). The organics were combined, washed with 0.1 N HCl, water and brine (100 mL each), dried over $Na_2SO_4$ and concentrated. The crude product was purified by column chromatography (0 to 60% EtOAc in Hexanes) to yield 17H (1.1 g, 4.52 mmol, 94% yield) as a clear oil. $^1$H NMR (400 MHz, CHLOROFORM-d) δ ppm 1.17-1.25 (m, 6H) 1.32 (dd, J=6.69, 5.43 Hz, 1H) 2.56-2.79 (m, 2H) 3.16-3.29 (m, 1H) 3.61-3.78 (m, 2H) 7.08 (d, J=8.59 Hz, 1H) 7.27-7.35 (m, 2H).

17I

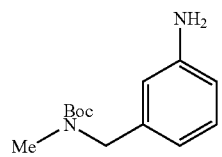

BOC-anhydride (4.61 mL, 19.86 mmol) and triethylamine (5.03 mL, 36.1 mmol) were added to a solution of N-methyl-1-(3-nitrophenyl)methanamine (3 g, 18.05 mmol) in $CH_2Cl_2$ (72.2 mL) and stirred for 30 min. The reaction was diluted with EtOAc (200 mL), washed with 1.0 M HCl, water and brine (100 mL each), dried over $Na_2SO_4$ and concentrated. A solution of the crude product in MeOH (100 mL) with Pd/C (50 mg, 0.047 mmol) was stirred under $H_2$ (50 psi) for 30 min. The reaction was filtered through Celite and concentrated. The crude product was purified by column chromatography (0 to 100% EtOAc in Hexanes, 120 g column) to yield 17I (3.5 g, 14.81 mmol, 75% yield) as a clear yellow oil. MS (ESI) m/z 237.24 (M+H)$^+$. $^1$H NMR (400 MHz, $CD_3OD$) δ ppm 1.46 (s, 9H) 2.79 (s, 3H) 4.31 (s, 2H) 6.54 (d, J=7.15 Hz, 1H) 6.57-6.65 (m, 2H) 6.87 (none, 1H) 7.05 (t, J=7.70 Hz, 1H).

17J

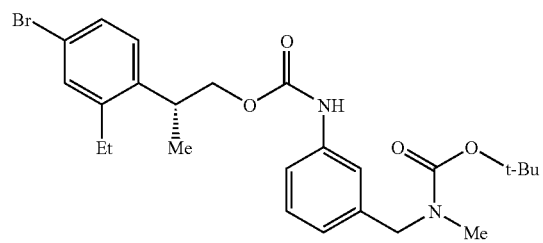 [SMILES: CCc1cc(Br)ccc1[C@@H](C)COC(=O)Nc1cccc(CN(C)C(=O)OC(C)(C)C)c1]

Using a procedure analogous to that used to prepare 10G, 17I (214 mg, 0.905 mmol) was reacted with sodium bicarbonate and Phosgene followed by Intermediate 8 and NaH. The crude product was purified by column chromatography (0 to 60% EtOAc in Hexanes, 40 g column) to yield 17J (400 mg, 0.791 mmol, 96% yield) as a clear oil. MS (ESI) m/z 503.4/505.4 (M+H)$^+$. $^1$H NMR (400 MHz, $CDCl_3$) 86 ppm 1.20 (t, J=7.42 Hz, 3H) 1.27 (d, J=7.15 Hz, 3H) 1.47 (s, 9H) 2.56-2.73 (m, 2H) 2.80 (d, J=14.84 Hz, 3H) 3.32-3.50 (m, 1H) 4.21 (d, J=7.15 Hz, 2H) 4.37 (s, 1H) 6.50 (s, 1H) 6.91 (s, 1H) 7.10 (d, J=9.34 Hz, 1H) 7.15-7.28 (m, 2H) 7.28-7.35 (m, 2H).

17K

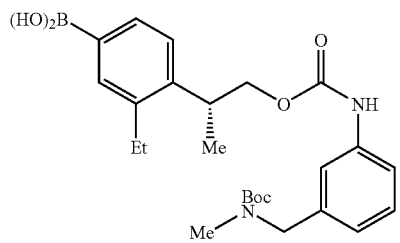 [SMILES: CCc1cc(B(O)O)ccc1[C@@H](C)COC(=O)Nc1cccc(CN(C)C(=O)OC(C)(C)C)c1]

Using a procedure analogous to that used to prepare 29B, 17J (400 mg, 0.791 mmol) was reacted with bis(neopentyl glycolato)diboron), potassium acetate and (1,1'-bis(diphenylphosphino)ferrocene)-dichloropalladium(II). The crude boronic ester was purified by prep HPLC (MeOH/$H_2O$, 0.1% TFA) to yield 17K (330 mg, 0.702 mmol, 89% yield) as a beige solid. MS (ESI) m/z 469.4 (M-H)$^-$.

117

17L

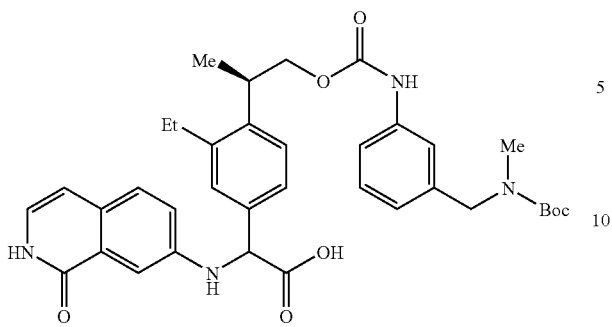

Using a procedure analogous to that used to prepare 1E, 17K (300 mg, 0.638 mmol), Intermediate 3, and glyoxylic acid monohydrate were reacted and purified by flash chromatography (0% to 20% MeOH in CH$_2$Cl$_2$) to yield 17L (350 mg, 0.545 mmol, 85% yield) as a yellow solid. MS (ESI) m/z 643.5 (M+H)$^+$. $^1$H NMR (400 MHz, CD$_3$OD) δ ppm 1.19 (t, J=7.70 Hz, 3H) 1.28 (dd, J=6.87, 2.47 Hz, 3H) 1.46 (d, J=10.99 Hz, 9H) 2.57-2.83 (m, 5H) 3.40-3.51 (m, 1H) 4.21 (d, J=7.70 Hz, 2H) 4.36 (s, 2H) 5.14 (s, 1H) 6.53 (d, J=7.15 Hz, 1H) 6.81-6.94 (m, 2H) 7.12-7.52 (m, 9H) 7.97 (s, 1H).

Example 17

HCl (2.0 M in dioxane, 2 mL) was added to a solution of 17L (350 mg, 0.545 mmol) in dioxane (2 mL). The reaction was stirred for 2 h and then concentrated in vacuo. A solution of the benzylamine and TEA (0.152 mL, 1.089 mmol) in DMF (4 mL) was added via syringe pump over 5 h to a solution of BOP (482 mg, 1.089 mmol) and DMAP (333 mg, 2.72 mmol) in DCM (60 mL) at 35° C. over 4 h. The reaction was concentrated and purified by prep HPLC to yield Example 17 (36 mg, 0.069 mmol, 12.60% yield) and diastereomer 2 (14 mg, 0.027 mmol, 4.90% yield) as a white solid. MS (ESI) m/z 525.5 (M+H)$^+$. $^1$H NMR (400 MHz, CD$_3$OD) δ ppm 1.09 (t, J=7.70 Hz, 3H) 1.30 (d, J=7.15 Hz, 3H) 2.47-2.61 (m, 1H) 2.88-3.05 (m, 1H) 3.43-3.59 (m, 1H) 3.80-4.03 (m, 2H) 4.64 (t, J=10.72 Hz, 1H) 5.45 (d, J=16.49 Hz, 1H) 5.66-5.74 (m, 1H) 5.92 (s, 1H) 6.53-6.61 (m, 1H) 6.67 (d, J=7.70 Hz, 1H) 6.88 (d, J=7.70 Hz, 1H) 6.95-7.04 (m, 1H) 7.16 (t, J=7.97 Hz, 1H) 7.29-7.57 (m, 5H) 7.63 (s, 1H). Analytical HPLC (Method A): Col A: 7.85 min, 99%; Col B: 7.77 min, 99%.

Example 18

(2R,15R)-7-Cyclopropanesulfonyl-17-ethyl-4,15-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

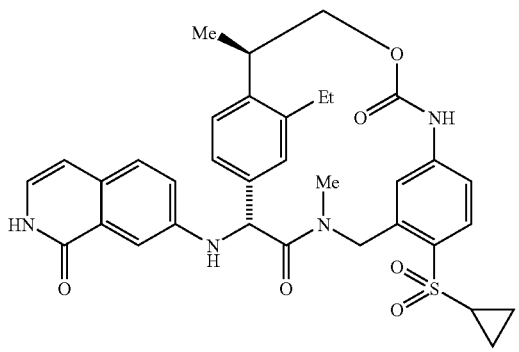 [SMILES: CCc1cc2ccc1[C@@H](C)COC(=O)Nc1ccc(S(=O)(=O)C3CC3)c(c1)CN(C)C(=O)[C@@H]2Nc1ccc2cc[nH]c(=O)c2c1]

118

18A

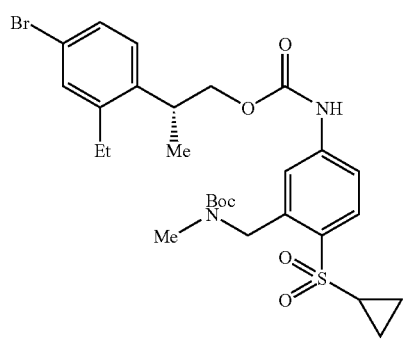 [SMILES: CCc1cc(Br)ccc1[C@@H](C)COC(=O)Nc1ccc(S(=O)(=O)C2CC2)c(CN(C)C(=O)OC(C)(C)C)c1]

Using a procedure analogous to that used to prepare 10G, Intermediate 11 (308 mg, 0.905 mmol) was reacted with sodium bicarbonate and Phosgene followed by 17H and NaH. The crude product was purified by column chromatography (0 to 60% EtOAc in Hexanes, 40 g column) to yield 18A (380 mg, 0.623 mmol, 76% yield). MS (ESI) m/z 609.3/611.3 (M+H)$^+$.

18B

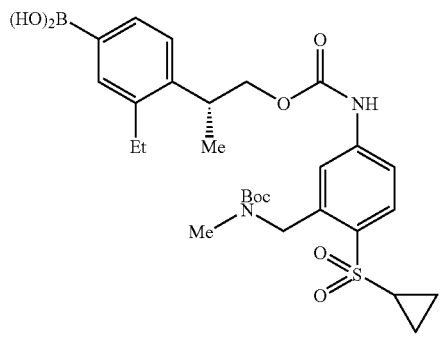 [SMILES: CCc1cc(B(O)O)ccc1[C@@H](C)COC(=O)Nc1ccc(S(=O)(=O)C2CC2)c(CN(C)C(=O)OC(C)(C)C)c1]

A mixture of 18A (350 mg, 0.572 mmol), (1,1'-bis(diphenylphosphino)ferrocene)-dichloropalladium(II) (23.54 mg, 0.029 mmol), potassium acetate (169 mg, 1.717 mmol) and bis(neopentyl glycolato)diboron (194 mg, 0.859 mmol) in dioxane (4 mL) was degassed and stirred for 2 h at 80° C. in a sealed tube. The reaction mixture was diluted with EtOAc (25 mL), filtered and concentrated. The crude boronic ester was purified by prep HPLC (MeOH/H$_2$O, 0.1% TFA) to yield 18B (270 mg, 0.468 mmol, 82% yield) as a beige solid. MS (ESI) m/z 575.7 (M+H)$^+$. $^1$H NMR (400 MHz, MeOD) δ ppm 1.15 (t, J=7.20 Hz, 3H) 1.20 (t, J=7.58 Hz, 3H) 1.31 (d, J=6.82 Hz, 3H) 2.57-2.95 (m, 4H) 3.49 (q, J=6.91 Hz, 1H) 4.06 (q, J=7.07 Hz, 2H) 4.17-4.32 (m, 2H) 4.97-5.16 (m, J=12.38, 12.38, 12.38 Hz, 3H) 6.99 (d, J=7.33 Hz, 1H) 7.14-7.46 (m, 11H).

119

18C

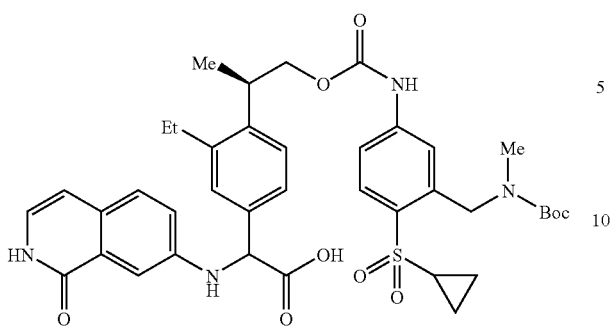

Using a procedure analogous to that used to prepare 1E, 18B (250 mg, 0.435 mmol) Intermediate 3, and glyoxylic acid monohydrate were reacted and purified by flash chromatography (0% to 20% MeOH in $CH_2Cl_2$) to yield 18C (280 mg, 0.375 mmol, 86% yield) as a yellow solid. MS (ESI) m/z 745.4 $(M+H)^+$.

Example 18

HCl (2.0 M in dioxane, 2 mL) was added to a solution of 18C (280 mg, 0.375 mmol) in dioxane (2 mL). The reaction was stirred for 2 hi and then concentrated in vacuo. A solution of the benzylamine and TEA (0.105 mL, 0.750 mmol) in DMF (4 mL) was added via syringe pump over 5 h to a solution of BOP (332 mg, 0.750 mmol) and DMAP (229 mg, 1.874 mmol) in DCM (60 mL) at 35° C. over 4 h. The reaction was concentrated and purified by prep HPLC to yield Example 18 (6.5 mg, 10.34 μmol, 2.76% yield) as a white solid. MS (ESI) m/z 629.5 $(M+H)^+$. $^1$H NMR (400 MHz, acetonitrile-$d_6$) δ ppm 0.96 (t, J=7.42 Hz, 3H) 1.00-1.24 (m, 4H) 1.29 (d, J=7.15 Hz, 3H) 2.33-2.49 (m, 1H) 2.63-2.91 (m, 3H) 3.28 (s, 3H) 3.35-3.63 (m, 2H) 3.91 (dd, J=10.72, 4.12 Hz, 1H) 4.19 (d, J=17.59 Hz, 1H) 4.59 (t, J=11.27 Hz, 1H) 5.62 (s, 1H) 5.71 (d, J=17.59 Hz, 1H) 6.26-6.41 (m, 2H) 6.76-6.87 (m, 2H) 7.05 (s, 1H) 7.16 (dd, J=8.52, 2.47 Hz, 1H) 7.34 (d, J=8.79 Hz, 1H) 7.40-7.50 (m, 2H) 7.57-7.67 (m, 1H) 7.69-7.78 (m, 2H) 9.13 (s, 1H). Analytical HPLC (Method A): Col A: 8.02 min, 99%; Col B: 8.03 min, 98%.

Example 19

[(2R,5R,15R)-17-Ethyl-15-methyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid ethyl ester

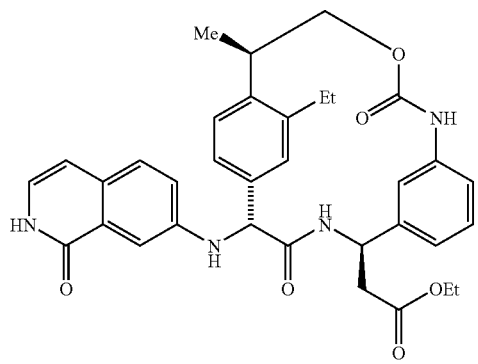 [SMILES: CCOC(=O)C[C@H]1NC(=O)[C@H](Nc2ccc3cc[nH]c(=O)c3c2)c2ccc(c(CC)c2)[C@@H](C)COC(=O)Nc2cccc1c2]

120

19A

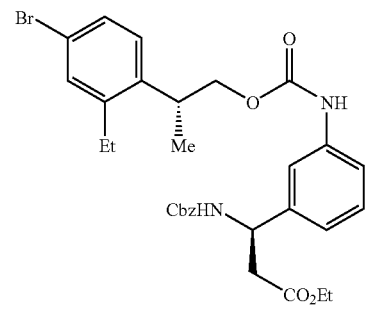 [SMILES: CCOC(=O)C[C@@H](NC(=O)OCc1ccccc1)c1cccc(NC(=O)OC[C@H](C)c2ccc(Br)cc2CC)c1]

Using a procedure analogous to that used to prepare 10G, 10F (310 mg, 0.905 mmol) was reacted with sodium bicarbonate and Phosgene followed by 17H and NaH. The crude product was purified by column chromatography (0 to 60% EtOAc in Hexanes, 40 g column) to yield 19A (350 mg, 0.572 mmol, 69.6% yield) as a clear oil. MS (ESI) m/z 611.3/613.3 $(M+H)^+$.

19B

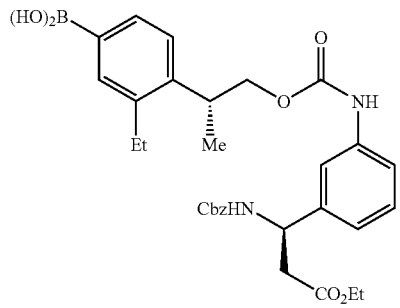 [SMILES: CCOC(=O)C[C@@H](NC(=O)OCc1ccccc1)c1cccc(NC(=O)OC[C@H](C)c2ccc(B(O)O)cc2CC)c1]

A mixture of 19A (350 mg, 0.572 mmol), (1,1'-bis(diphenylphosphino)ferrocene)-dichloropalladium(II) (23.54 mg, 0.029 mmol), potassium acetate (169 mg, 1.717 mmol) and bis(neopentyl glycolato)diboron (194 mg, 0.859 mmol) in dioxane (4 mL) was degassed and stirred for 2 h at 80° C. in a sealed tube. The reaction mixture was diluted with EtOAc (25 mL), filtered and concentrated. The crude boronic ester was purified by prep HPLC (MeOH/$H_2O$, 0.1% TFA) to yield 19B (270 mg, 0.468 mmol, 82% yield) as a beige solid. MS (ESI) m/z 575.7 (M–H)$^-$. $^1$H NMR (400 MHz, MeOD) δ ppm 1.15 (t, J=7.20 Hz, 3H) 1.20 (t, J=7.58 Hz, 3H) 1.31 (d, J=6.82 Hz, 3H) 2.57-2.95 (m, 4H) 3.49 (q, J=6.91 Hz, 1H) 4.06 (q, J=7.07 Hz, 2H) 4.17-4.32 (m, 2H) 4.97-5.16 (m, J=12.38, 12.38, 12.38 Hz, 3H) 6.99 (d, J=7.33 Hz, 1H) 7.14-7.46 (m, 11H).

19C

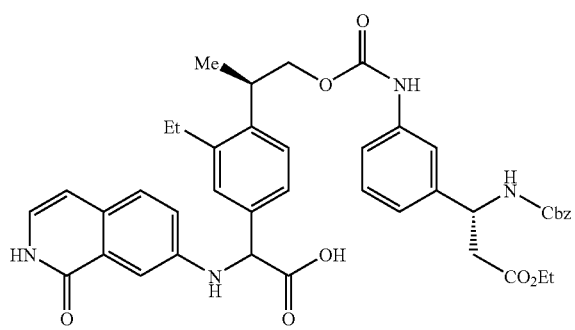 [SMILES: CCOC(=O)C[C@@H](NC(=O)OCc1ccccc1)c1cccc(NC(=O)OC[C@H](C)c2ccc(C(Nc3ccc4cc[nH]c(=O)c4c3)C(=O)O)cc2CC)c1]

Using a procedure analogous to that used to prepare 1E, 19B (270 mg, 0.468 mmol), Intermediate 3, and glyoxylic acid monohydrate were reacted and purified by flash chromatography (0% to 20% MeOH in $CH_2Cl_2$) to yield 19C (340 mg, 0.454 mmol, 97% yield) as a yellow solid. MS (ESI) m/z 749.6 $(M+H)^+$.

Example 19

19C (340 mg, 0.454 mmol) was stirred with Pd/C (25 mg) in MeOH (20 mL) under $H_2$ (60 psi) for 5 h. The reaction mixture was filtered and concentrated to yield the crude benzyl amine (236 mg, 0.384 mmol, 85% yield) as a yellow glass. A solution of the benzyl amine (236 mg, 0.384 mmol) and TEA (0.107 mL, 0.768 mmol) in DMF (4 mL) was added via syringe pump over 5 h to a solution of BOP (340 mg, 0.768 mmol) and DMAP (235 mg, 1.920 mmol) in DCM (60 mL) at 35° C. over 4 h. The reaction was concentrated and purified by prep HPLC to yield Example 19 (65 mg, 0.109 mmol, 28.4% yield) and diastereomer 2 (30 mg, 0.050 mmol, 13.10% yield). MS (ESI) m/z 597.3 $(M+H)^+$. $^1$H NMR (400 MHz, $CD_3OD$) δ ppm 1.04 (t, J=7.70 Hz, 3H) 1.20 (t, J=7.15 Hz, 3H) 1.28 (d, J=7.15 Hz, 3H) 2.39-2.55 (m, 1H) 2.61-2.99 (m, 4H) 3.41-3.54 (m, 1H) 3.99 (dd, J=10.99, 3.85 Hz, 1H) 4.14 (q, J=7.15 Hz, 2H) 4.74 (t, J=10.44 Hz, 1H) 5.14 (s, 1H) 5.23-5.36 (m, 1H) 6.24 (s, 1H) 6.53 (d, J=7.15 Hz, 1H) 6.63 (d, J=7.70 Hz, 1H) 6.91 (dd, J=7.15, 3.30 Hz, 2H) 7.05-7.16 (m, 2H) 7.22 (dd, J=8.52, 2.47 Hz, 1H) 7.43 (dd, J=12.09, 8.24 Hz, 3H) 7.57 (dd, J=7.70, 1.65 Hz, 1H). Analytical HPLC (Method A): Col A: 8.38, 96%; Col B: 8.23 min, 95%.

Example 20

[(2R,5R,15R)-17-Ethyl-15-methyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-5-yl]-acetic acid

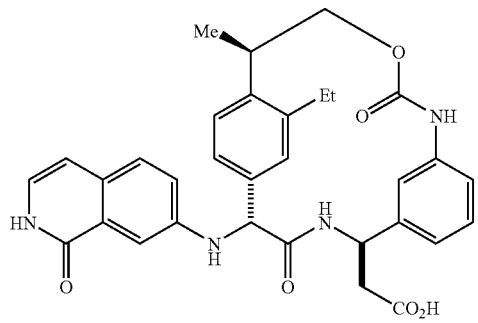

LiOH (2 mL, 1.0 M, aq) was added to a solution of Example 19 (30 mg, 0.050 mmol) in THF (2 mL) and stirred for 1 h at rt. HCl (2 mL, 1.0 M, aq) was added and the reaction mixture was concentrated. Purification by prep HPLC yielded Example 20 (21 mg, 0.037 mmol, 73.5% yield) as a white solid. MS (ESI) m/z 569.2 $(M+H)^+$. $^1$H NMR (400 MHz, $CD_3OD$) δ ppm 1.06 (t, J=7.42 Hz, 3H) 1.29 (d, J=6.60 Hz, 3H) 2.43-2.58 (m, 1H) 2.64-2.95 (m, 3H) 3.42-3.55 (m, 1H) 3.98 (dd, J=10.44, 3.85 Hz, 1H) 4.74 (t, J=10.44 Hz, 1H) 5.13 (s, 1H) 5.32 (dd, J=9.34, 4.95 Hz, 1H) 6.24 (s, 1H) 6.56 (d, J=7.15 Hz, 1H) 6.64 (d, J=7.70 Hz, 1H) 6.94 (t, J=6.87 Hz, 2H) 7.09-7.18 (m, 2H) 7.25 (dd, J=8.79, 2.20 Hz, 1H) 7.41- 7.47 (m, 3H) 7.50-7.59 (m, 1H). Analytical HPLC (Method A): Col A: 7.46 min, 99%; Col B: 7.45 min, 98%.

Example 21

(2R,15R)-7-Methoxymethyl-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

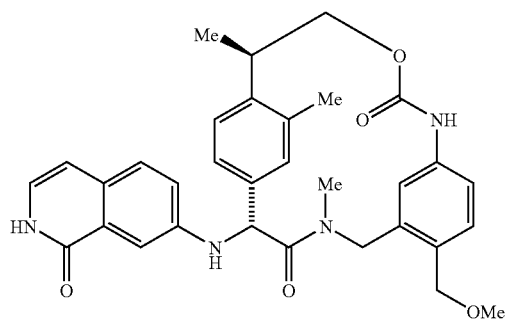 [SMILES: COCc1ccc2cc1CN(C)C(=O)[C@H](Nc1ccc3cc[nH]c(=O)c3c1)c1ccc(c(C)c1)[C@@H](C)COC(=O)N2]

21A

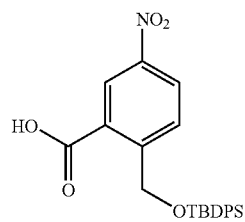

6-Nitroisobenzofuran-1(3H)-one (25 g, 140 mmol), and potassium hydroxide (7.83 g, 140 mmol), were dissolved in MeOH/water (300 mL/50 mL) to give a brown solution. The reaction mixture was heated to 95° C. and stirred under argon for 1.5 h. The reaction was concentrated in vacuo to a red oily solid. TBDPS-Cl (77 mL, 301 mmol) was added to solution of the oily solid in toluene (600 mL) and pyridine (300 mL) and stirred at rt 72 h. The reaction mixture was heated at 50° C. for 4 h and then quenched with sat. $NaHCO_3$ and extracted with DCM (3×3000 mL) and concentrated to an oily residue. The residue was dissolved in MeOH (500 mL) and THF (200 mL) and treated with an aqueous solution of $K_2CO_3$ (200 mL). After stirring for 30 min the mixture was concentrated to one quarter volume and diluted with brine (200 mL). The resulting mixture was cooled to 0° C. and adjusted to pH 4-5 with 1N $KHSO_4$ and extracted with ethyl acetate (3×200 mL). The combined organics were washed with brine, dried ($MgSO_4$) and concentrated in vacuo to a red oily residue which was purified on silica eluting with Hex/EtOAc 0-100% to yield 21A (17 g, 29% yield) as a clear, colorless oil. MS (ESI) m/z 436.2 $(M+H)^+$. $^1$H NMR (400 MHz, MeOD) δ ppm 1.10 (s, 9H) 5.24 (s, 2H) 7.32-7.44 (m, 6H) 7.65 (d, J=6.60 Hz, 4H) 8.23 (d, J=8.79 Hz, 1H) 8.43 (dd, J=8.79, 2.75 Hz, 1H) 8.74 (d, J=2.20 Hz, 1H).

21B

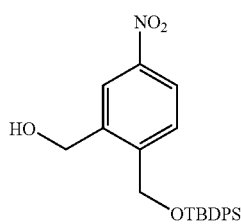

21A (17 g, 39.0 mmol) and borane-THF complex (195 mL, 195 mmol) were dissolved in THF (500 mL) to give a yellow solution. The solution was warmed to 60° C. and stirred for 5 h. The reaction mixture was cooled to rt, poured into water (200 mL), and acidified with 1N HCl and extracted with EtOAc (3×200 mL). The combined organics were washed with brine, dried (MgSO$_4$) and concentrated in vacuo to yield 21B (16 g, 38 mmol, 97% yield) and as an oil. MS (ESI) m/z 420.3 (M+H)$^+$.

21C

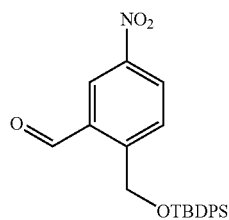

In a 1 L round-bottomed flask 21B (16 g, 38.0 mmol) and manganese dioxide (16.50 g, 190 mmol) were mixed in DCM (500 mL) to give a black suspension. The reaction mixture stirred at rt for 18 h under argon. The reaction mixture was filtered through a silica gel plug (4 in.) washing with DCM (500 mL). The filtrate was concentrated to yield 21C as an orange oil. $^1$H NMR (400 MHz, CDCl$_3$) δ ppm 1.13 (s, 9H) 5.25 (s, 2H) 7.35-7.46 (m, 6H) 7.66 (d, J=6.60 Hz, 4H) 8.12 (d, J=8.79 Hz, 1H) 8.46 (dd, J=8.52, 2.47 Hz, 1H) 8.65 (d, J=2.75 Hz, 1H) 10.14 (s, 1H).

21D

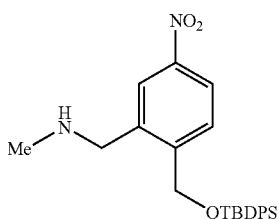

In a 500 mL round-bottomed flask 21C (15 g, 35.8 mmol) was dissolved in methanol (400 mL) to give a yellow solution. Methylamine (33% wt in EtOH, 10.09 mL, 107 mmol) was added and the solution was stirred at rt for 1 h before cooling to 0° C. and adding sodium borohydride (2.71 g, 71.5 mmol) portionwise and allowing to warm to rt. and stir for 2 h. The reaction mixture was quenched with water (400 mL) and diluted with ethyl acetate (500 mL). The organics were separated, washed with 1N HCl (1×100 mL), brine, dried (MgSO$_4$) and conc. in vacuo to yield 21D (14 g, 32 mmol, 90% yield) as an orange oil. MS (ESI) m/z 435.3 (M+H)$^+$.

21E

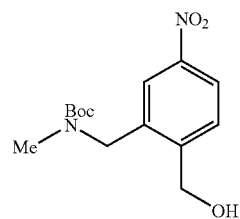

Boc$_2$O (0.539 mL, 2.319 mmol) was added to a solution of 21D (960 mg, 2.209 mmol) and TEA (0.616 mL, 4.42 mmol) in CH$_2$Cl$_2$ (20 mL) and stirred at rt overnight. The reaction was diluted with CH$_2$Cl$_2$ (80 mL), washed with 0.1 M HCl, sat'd NaHCO$_3$ and brine (50 mL each), dried over Na$_2$SO$_4$ and concentrated. TBAF (4.42 mL, 4.42 mmol) was added to a solution of the crude product in THF (20 mL) and stirred for 1 h. The reaction was diluted with EtOAc (100 mL), washed with H$_2$O and brine (50 mL) each, dried over Na$_2$SO$_4$ and concentrated. The crude oil of purified by column chromatography (40 g column, 0 to 100% EtOAc in hexanes) to yield 21E (480 mg, 1.620 mmol, 73.3% yield) as a yellow solid. MS (ESI) m/z 295.3 (M+H)$^+$. $^1$H NMR (400 MHz, CDCl$_3$) δ ppm 1.46 (s, 9H) 2.88 (s, 3H) 4.55 (s, 2H) 4.75 (d, J=4.95 Hz, 2H) 7.60 (d, J=8.25 Hz, 1H) 8.03 (d, J=2.75 Hz, 1H) 8.12 (dd, J=8.52, 2.47 Hz, 1H),

21F

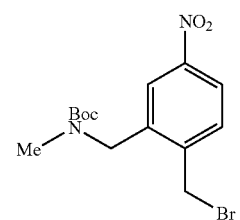

Methanesulfonic anhydride (529 mg, 3.04 mmol) was added in one portion to a solution of 21E (600 mg, 2.025 mmol) and pyridine (0.409 mL, 5.06 mmol) in THF (20 mL) and stirred for 2 h. Lithium bromide (352 mg, 4.05 mmol) was added and the reaction mixture was stirred for 3 h. The mixture was diluted with EtOAc (100 mL), washed with water and brine (50 mL each), dried over Na$_2$SO$_4$ and concentrated. The crude product was purified by column chromatography (0 to 75% EtOAc in hexanes) to yield 21F (450 mg, 1.253 mmol, 61.9% yield) as a clear yellow oil. $^1$H NMR (400 MHz, CD$_3$OD) δ ppm 1.47 (d, J=34.63 Hz, 9H) 2.90 (s, 3H) 4.70 (s, 2H) 4.80 (s, 2H) 7.67 (d, J=8.24 Hz, 1H) 8.03 (d, J=2.20 Hz, 1H) 8.14 (dd, J=8.52, 2.47 Hz, 1H).

21G

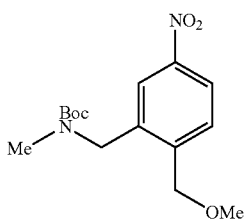

Sodium methoxide (529 mg, 2.450 mmol) was added to a solution of 21F (440 mg, 1.225 mmol) in MeOH (10 mL) and stirred at rt for 3 days. Solid ammonium chloride (131 mg, 2.450 mmol) was added to the reaction mixture and it was concentrated. The residue was dissolved in EtOAc (75 mL)/H₂O (50 mL). The organic phase was separated, washed with brine, dried over Na₂SO₄ and concentrated. The crude product was purified by flash chromatography (0 to 50% EtOAc in hexanes) to yield 21G (340 mg, 1.096 mmol, 89% yield) as a pale yellow oil. ¹H NMR (400 MHz, CDCl₃) δ ppm 1.47 (none, 26H) 2.86 (s, 3H) 3.43 (s, 3H) 4.44-4.59 (m, 4H) 7.58 (d, J=8.25 Hz, 1H) 7.98-8.07 (m, 1H) 8.11 (dd, J=8.52, 2.47 Hz, 1H).

21H

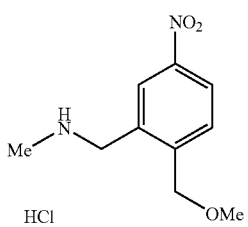 [SMILES: CNCc1cc([N+](=O)[O-])ccc1COC ; Cl]

21G (400 mg, 1.289 mmol) was dissolved in dioxane (5 mL). HCl in dioxane (4.0 M, 5 mL) was added and the reaction mixture was stirred for 8 h at it. The reaction was concentrated to yield 21H (315 mg, 1.277 mmol, 99% yield) as a purple powder. MS (ESI) m/z 211.3 (M+H)⁺. ¹H NMR (400 MHz, DMSO-d₆) δ ppm 2.63 (s, 3H) 3.38 (s, 3H) 4.25 (s, 2H) 4.70 (s, 2H) 7.72 (d, J=8.59 Hz, 1H) 8.26 (dd, J=8.46, 2.40 Hz, 1H) 8.50 (d, J=2.27 Hz, 1H) 9.20 (s, 2H).

21I

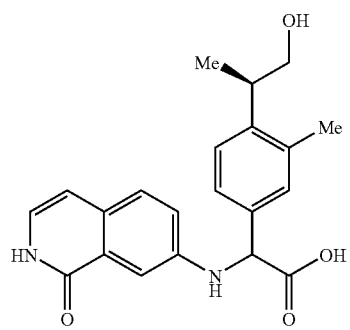 [SMILES: Cc1cc(C(Nc2ccc3cc[nH]c(=O)c3c2)C(=O)O)ccc1[C@@H](C)CO]

Intermediate 10 (150 mg, 0.487 mmol), Intermediate 3 and glyoxylic acid monohydrate (44.8 mg, 0.487 mmol) were dissolved in acetonitrile (1.6 mL)/DMF (400 μL) and heated at 100° C. in the microwave for 10 min. The reaction mixture was concentrated in vacuo and triturated with Et₂O to yield 21I (130 mg, 0.36 mmol, 76% yield). MS (ESI) m/z 367.5 (M+H)⁺.

21J

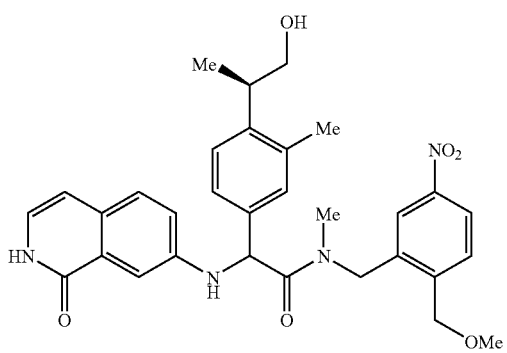 [SMILES: COCc1ccc([N+](=O)[O-])cc1CN(C)C(=O)C(Nc1ccc2cc[nH]c(=O)c2c1)c1ccc([C@@H](C)CO)c(C)c1]

A solution of 21H and 21I (260 mg, 0.710 mmol) were coupled using triethylamine, 1-hydroxy-7-azabenzotriazole, and 1-(3-(dimethylamino)propyl)-ethyl-carbodiimide HCl and purified by column chromatography (0 to 20% MeOH in CH₂Cl₂) to yield 21J (176 mg, 0.315 mmol, 44.4% yield) as a yellow solid. MS (ESI) m/z 559.3 (M+H)*.

21K

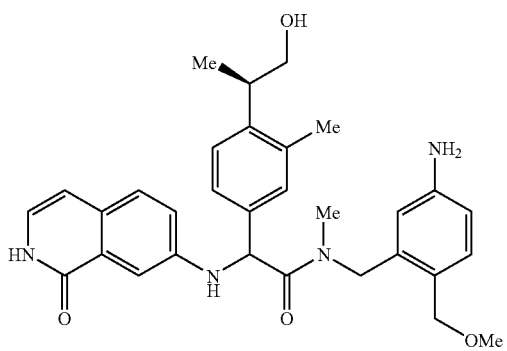 [SMILES: COCc1ccc(N)cc1CN(C)C(=O)C(Nc1ccc2cc[nH]c(=O)c2c1)c1ccc([C@@H](C)CO)c(C)c1]

A solution of 21J (176 mg, 0.315 mmol) in MeOH (5 mL) with Pd/C (20 mg) was stirred under H₂ (1 atm) at rt for 14 h. The reaction was filtered and concentrated to yield 21K (154 mg, 0.291 mmol, 92% yield). MS (ESI) m/z 527.5 (M+H)⁺.

Example 21

Using a procedure analogous to that used to prepare 7H, 21K (154 mg, 0.291 mmol) was reacted with Phosegene and Et₃N and purified by prep HPLC (Phenom. Luna Axia, 30×100 mm, 5 micron, flow rate 40 mL/min, A: H₂O/MeOH (9:1), B: H₂O/MeOH (1:9), 0.1% TFA, 40 to 80% B, 10 min gradient to yield a mixture of diastereomers. The diastereomers were separated by WELKO column (75% EtOH/MeOH/25% Heptane) to yield diastereomer 1 (21 mg, 0.038 mmol, 13% yield) and Example 21 (21 mg, 0.038 mmol, 13% yield) as white solids. Characterization for Example 21: MS (ESI) m/z 555.5 (M+H)+. 1H NMR (400 MHz, Acetonitrile-d$_3$) δ ppm 1.23 (d, J=6.60 Hz, 3H) 3.18 (s, 3H) 3.29 (s, 3H) 3.32-3.44 (m, 1H) 3.78-3.97 (m, 2H) 4.29-4.45 (m, 2H) 4.58 (t, J=10.99 Hz, 1H) 5.38 (d, J=17.04 Hz, 1H) 5.62 (s, 1H) 5.92 (s, 1H) 6.35 (d, J=7.15 Hz, 1H) 6.61-6.70 (m, 1H) 6.81 (d; J=7.15 Hz, 1H) 7.10 (s, 1H) 7.12-7.21 (m, 2H) 7.27-7.41 (m, 3H) 7.45 (d, J=2.20 Hz, 1H) 7.60 (d, J=6.05 Hz, 1H) 9.45 (d, 1H). Analytical HPLC (Method A): Col A: 6.67 min, 99%; Col B: 6.79 min, 99%.

Example 22

(2R,15R)-4,15,17-Trimethyl-7-(2-methyl-2H-pyrazol-3-yl)-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

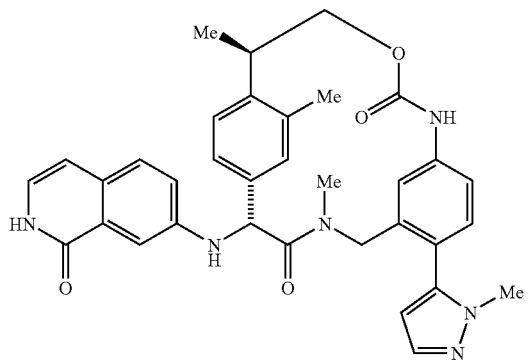 [SMILES: Cc1cc2ccc1[C@@H](C)COC(=O)Nc1ccc(-c3ccnn3C)c(c1)CN(C)C(=O)[C@@H]2Nc1ccc2cc[nH]c(=O)c2c1]

22A

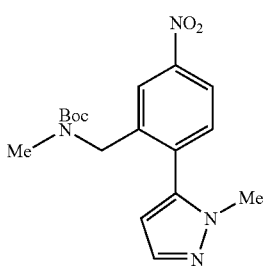 [SMILES: CN(Cc1cc([N+](=O)[O-])ccc1-c1ccnn1C)C(=O)OC(C)(C)C]

A suspension of Intermediate 18 (470 mg, 1.362 mmol), 1-methyl-5-(4,4,5,5-tetramethyl-1,3,2-dioxaborolan-2-yl)-1H-pyrazole (850 mg, 4.08 mmol), and sodium carbonate (1732 mg, 16.34 mmol) in THF (10 mL)/Water (5.00 mL) was degassed with argon. Tetrakis(triphenylphosphine)palladium (0) (79 mg, 0.068 mmol) was added and the reaction vessel was sealed, sparged with argon, and stirred for 15 h at 80° C. The reaction mixture was partitioned between EtOAc (100 mL) and water (50 mL). The organic layer was separated, washed with brine, dried over Na$_2$SO$_4$ and concentrated. The crude product was purified by column chromatography (0 to 60% EtOAc in hexanes) to yield 22A (395 mg, 1.140 mmol, 84% yield) as a yellow solid contaminated with 2,3-dimethylbutane-2,3-diol. MS (ESI) m/z 347.36 (M+H)+. 1H NMR (400 MHz, CDCl$_3$) δ ppm 1.36-1.55 (m, 9H) 2.76 (s, 3H) 3.67 (s, 3H) 4.25-4.37 (m, 2H) 6.26 (d, J=2.20 Hz, 1H) 7.42 (d, J=8.25 Hz, 1H) 7.57 (s, 1H) 8.10-8.30 (m, 2H).

22B

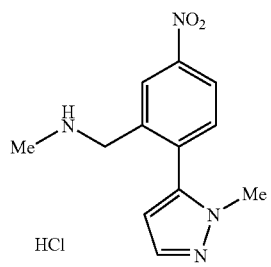 [SMILES: CNCc1cc([N+](=O)[O-])ccc1-c1ccnn1C ; Cl]

A (450 mg, 1.299 mmol) was dissolved in dioxane (5 mL). HCl in dioxane (4.0 M, 5 mL) was added and the reaction mixture was stirred for 8 h at rt The reaction was concentrated to yield 22B (350 mg, 1.238 mmol, 95% yield) as a yellow powder. MS (ESI) m/z 247.3 (M+H)+. 1H NMR (400 MHz, DMSO-d$_6$) δ ppm 2.62 (t, J=5.31 Hz, 3H) 3.92 (s, 3H) 4.31-4.42 (m, 2H) 7.71 (d, J=8.84 Hz, 1H) 7.83 (s, 1H) 8.20 (s, 1H) 8.24 (dd, J=8.59, 2.53 Hz, 1H) 8.59 (d, J=2.27 Hz, 1H) 9.38 (s, 2H).

22C

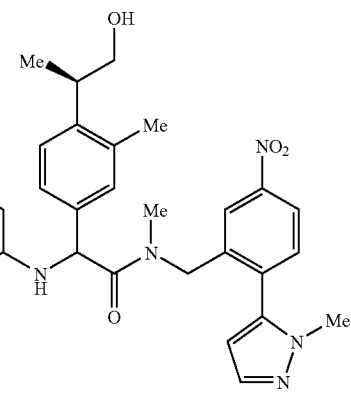

A solution of 22B (231 mg, 0.819 mmol) and DIEA (0.298 mL, 1.706 mmol) in DMF (3 mL) was added to a solution of 21I in DMF (3 mL). BOP (302 mg, 0.682 mmol) was added and the reaction mixture was stirred for 15 h at rt. The reaction mixture was partitioned between EtOAc (100 mL) and H$_2$O (50 mL). The phases were separated and the organics were washed with brine, dried over Na$_2$SO$_4$ and concentrated. The crude solid was purified by column chromatography (0 to 20% MeOH in CH$_2$Cl$_2$) to yield 22C (271 mg, 0.456 mmol, 66.8% yield) as a yellow solid. MS (ESI) m/z 595.4 (M+H)+.

129

22D

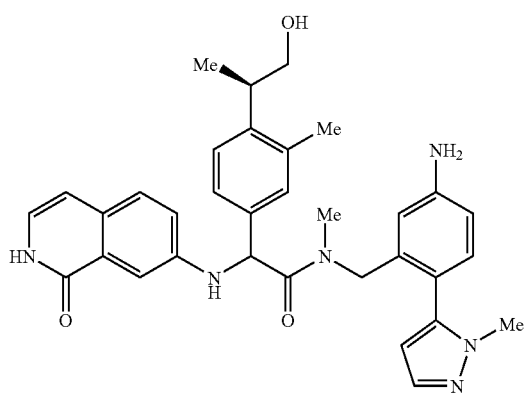 [SMILES: Cc1cc(C(Nc2ccc3cc[nH]c(=O)c3c2)C(=O)N(C)Cc2cc(N)ccc2-c2ccnn2C)ccc1[C@@H](C)CO]

A solution of 22C (271 mg, 0.456 mmol) in MeOH (5 mL) with Pd/C (25 mg) was stirred under $H_2$ (20 psi) for 16 h. The reaction was filtered and concentrated. The crude product was purified by ISCO (0 to 20% MeOH in $CH_2Cl_2$) to yield 22D (185 mg, 0.328 mmol, 71.9% yield) as a yellow glass. MS (ESI) m/z 565.6 (M+H)+.

Example 22

Using a procedure analogous to that used to prepare 7H, 22D (185 mg, 0.328 mmol) was reacted with Phosgene and triethylamine and purified by prep HPLC (Phenom. Luna Axia, 30×100 mm, 5 micron, flow rate 40 mL/min, A: $H_2O$/MeOH (9:1), B: $H_2O$/MeOH (1:9), 0.1% TFA, 40 to 80% B, 10 min gradient to yield a mixture of diasteromers. The mixture was separated into diastereomer 1 (17 mg, 0.029 mmol, 8.78% yield) and Example 22 (15 mg, 0.025 mmol, 7.75% yield) using a R,R-Welko-O 1 column (21.1 mm×250 mm, 10 micron, Regis Technologies, Inc.), 80% MeOH/EtOH (1:1)/20% Heptane, 20 mL/min flow rate, and uv detection at 220 nm. Characterization for Example 22: MS (ESI) m/z 591.6 (M+H)+. $^1$H NMR (400 MHz, $CD_3OD$); ppm 1.29 (d, J=6.60 Hz, 3H) 2.25-2.26 (m, 3H) 3.39-3.53 (m, 1H) 3.55-3.64 (m, 2H) 3.65 (s, 3H) 3.95 (dd, J=10.99, 4.40 Hz, 1H) 4.64 (t, J=10.99 Hz, 1H) 5.04 (d, J=16.49 Hz, 1H) 5.59 (s, 1H) 6.17 (s, 1H) 6.27 (s, 1H) 6.51 (d, J=7.15 Hz, 1H) 6.74-6.83 (m, 1H) 6.88 (d, J=7.15 Hz, 1H) 7.10 (d, J=7.70 Hz, 1H) 7.18-7.24 (m, 2H) 7.32-7.46 (m, 3H) 7.51 (d, J=2.20 Hz, 1H) 7.62 (d, J=7.70 Hz, 1H) 9.10 (s, 1H). Analytical HPLC (Method A): Col A: 6.38 min, 98%; Col B: 6.38 min, 98%.

Example 23

(2R,15R)-4,15,17-Trimethyl-7-(1-methyl-1H-pyrazol-4-yl)-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

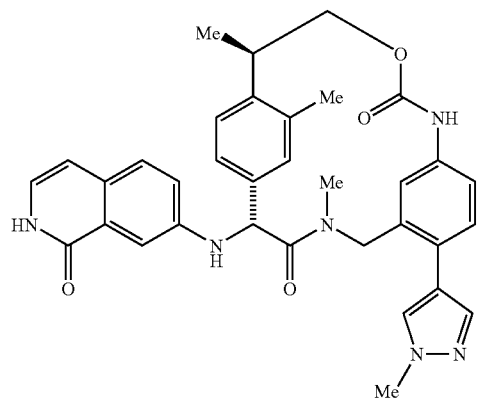 [SMILES: Cc1cc2ccc1[C@@H](C)COC(=O)Nc1ccc(-c3cnn(C)c3)c(c1)CN(C)C(=O)[C@@H]2Nc1ccc2cc[nH]c(=O)c2c1]

130

23A

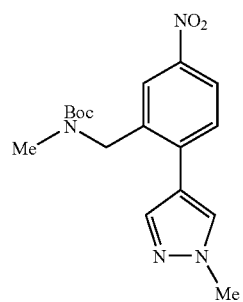

Using a procedure analogous to that used to prepare 22A, Intermediate 18 (500 mg, 1.448 mmol) was reacted with 1-methyl-4-(4,4,5,5-tetramethyl-1,3,2-dioxaborolan-2-yl)-1H-pyrazole, sodium carbonate and Tetrakis(triphenylphosphine)palladium(0). The crude product was purified by column chromatography (0 to 100% EtOAc in hexanes) to yield 23A (450 mg, 1.299 mmol, 90% yield). $^1$H NMR (400 MHz, $CDCl_3$) δ ppm 2.82 (s, 3H) 3.98 (s, 3H) 4.59 (s, 2H) 7.47 (d, J=8.79 Hz, 1H) 7.53 (s, 1H) 7.61 (s, 1H) 8.06 (s, 1H) 8.11 (d, J=10.44 Hz, 1H).

23B

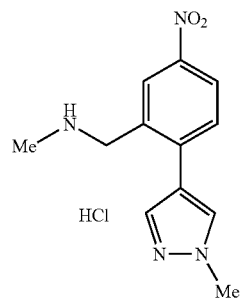 [SMILES: CNCc1cc([N+](=O)[O-])ccc1-c1cnn(C)c1 ; Cl]

23A (450 mg, 1.299 mmol) was dissolved in dioxane (5 mL). HCl in dioxane (4.0 M, 5 mL) was added and the reaction mixture was stirred for 8 h at rt. The reaction was concentrated to yield 23B (350 mg, 1.238 mmol, 95% yield) as a yellow powder. MS (ESI) m/z 247.3 (M+H)+. $^1$H NMR (400 MHz, DMSO-$d_6$) δ ppm 2.62 (t, J=5.31 Hz, 3H) 3.92 (s, 3H) 4.31-4.42 (m, 2H) 7.71 (d, J=8.84 Hz, 1H) 7.83 (s, 1H) 8.20 (s, 1H) 8.24 (dd, J=8.59, 2.53 Hz, 1H) 8.59 (d, J=2.27 Hz, 1H) 9.38 (s, 2H).

23C

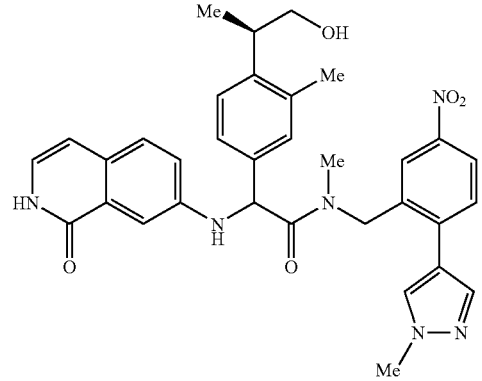 [SMILES: Cc1cc(C(Nc2ccc3cc[nH]c(=O)c3c2)C(=O)N(C)Cc2cc([N+](=O)[O-])ccc2-c2cnn(C)c2)ccc1[C@@H](C)CO]

Intermediate 10 (375 mg, 1.216 mmol), intermediate 3 (195 mg, 1.216 mmol), and glyoxylic acid monohydrate (112 mg, 1.216 mmol) were dissolved in acetonitrile (2.4 mL)/DMF (2.4 mL) and heated at 100° C. in the microwave for 10 min. A solution of 23B (344 mg, 1.216 mmol) and TEA (424 μL, 3.04 mmol) in DMF (6 mL) was added followed by BOP (538 mg, 1.216 mmol) as a solid. The reaction mixture was stirred at RT for 3 h. The reaction mixture was diluted with EtOAc, washed with water and brine, dried over $Na_2SO_4$ and concentrated. The crude material was purified by column chromarography (0 to 20% MeOH in $CH_2Cl_2$) to yield 23C (700 mg, 1.177 mmol, 97% yield). MS (ESI) m/z 593.5 (M–H)⁻.

23D

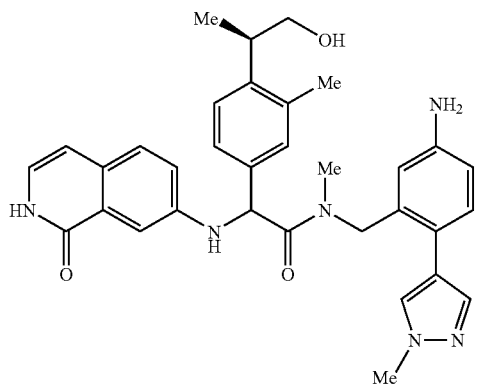 [SMILES: Cc1cc(C(Nc2ccc3cc[nH]c(=O)c3c2)C(=O)N(C)Cc2cc(N)ccc2-c2cnn(C)c2)ccc1[C@@H](C)CO]

Ammonium chloride (252 mg, 4.71 mmol), zinc (308 mg, 4.71 mmol) and 23C (700 mg, 1.177 mmol) were added to EtOH (15 mL). The grey suspension was heated to 60° C. and stirred for 2 h. $Na_2CO_3$ (50 mL, sat'd) was added and the mixture was stirred for 2 h. The mixture was extracted with EtOAc (3×80 mL). The organics were combined, dried over $Na_2SO_4$ and concentrated. The crude product was purified by column chromatography (0 to 20% MeOH in $CH_2Cl_2$) to yield 23D (300 mg, 0.531 mmol, 45.1% yield) as an off-white solid. MS (ESI) m/z 565.4 (M+H)⁺.

Example 23

Using a procedure analogous to that used to prepare 7H, 23D (280 mg, 0.496 mmol) was reacted with Phosegene and $Et_3N$. The crude product was purified by prep HPLC (Phenom. Luna Axia, 30×100 mm, 5 micron, flow rate 40 mL/min, A: $H_2O$/MeOH (9:1), B: $H_2O$/MeOH (1:9), 0.1% TFA, 40 to 80% B, 10 min gradient to yield a mixture of diasteromers. The mixture was separated into diasteromer 1 (25 mg, 0.042 mmol, 8.54% yield) and Example 23 (25 mg, 0.042 mmol, 8.54% yield) using a R,R-Welko-O 1 column (21.1 mm×250 mm, 10 micron, Regis Technologies, Inc.), 80% MeOH/EtOH (1:1)/20% Heptane, 20 mL/min flow rate, and uv detection at 220 nm. Characterization for Example 23: MS (ESI) m/z 589.5 (M+H)⁺. ¹H NMR (400 MHz, $CD_3OD$) δ ppm 1.30 (d, J=6.60 Hz, 3H) 2.33 (s, 3H) 3.38-3.57 (m, 1H) 3.91 (s, 3H) 3.92-4.00 (m, 2H) 4.62 (t, J=10.99 Hz, 1H) 5.40 (d, J=16.49 Hz, 1H) 5.62 (s, 1H) 6.03-6.08 (m, 1H) 6.53 (d, J=7.15 Hz, 1H) 6.72 (dd, J=7.70, 2.20 Hz, 1H) 6.90 (d, J=6.60 Hz, 1H) 7.16-7.28 (m, 3H) 7.36-7.44 (m, 3H) 7.58 (s, 1H) 7.62 (dd, J=7.97, 1.92 Hz, 1H) 7.72 (s, 1H) 8.90 (s, 1H). Analytical HPLC (Method A): Col A: 6.34 min, 98%; Col B: 6.32 min, 97%.

Example 24

(2R,15R)-7-(3,5-Dimethyl-isoxazol-4-yl)-4,15,17-trimethyl-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaene-3,12-dione

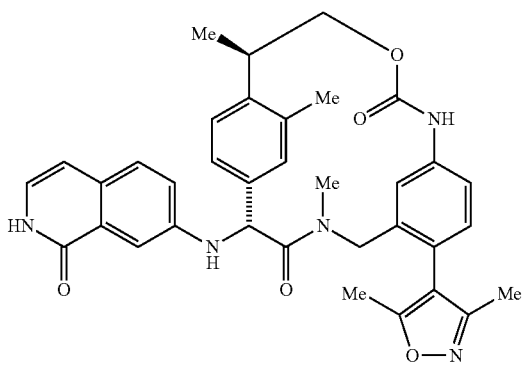 [SMILES: Cc1cc2ccc1[C@@H](C)COC(=O)Nc1ccc(-c3c(C)noc3C)c(c1)CN(C)C(=O)[C@@H]2Nc1ccc2cc[nH]c(=O)c2c1]

24A

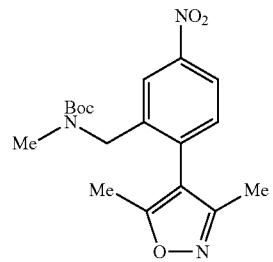 [SMILES: Cc1noc(C)c1-c1ccc([N+](=O)[O-])cc1CN(C)C(=O)OC(C)(C)C]

Using a procedure analogous to that used to prepare 22A, Intermediate 18 (500 mg, 1.448 mmol) was reacted with 3,5-dimethyl-4-(4,4,5,5-tetramethyl-1,3,2-dioxaborolan-2-yl)isoxazole (969 mg, 4.35 mmol), sodium carbonate and Tetrakis(triphenylphosphine)palladium(0). The crude product was purified by column chromatography (0 to 40% EtOAc in hexanes) to yield 24A (480 mg, 1.328 mmol, 92% yield) as a pale yellow solid. ¹H NMR (400 MHz, CHLOROFORM-d) δ ppm 1.46 (s, 9H) 2.09 (s, 3H) 2.25 (s, 3H) 2.74 (s, 3H) 4.27 (d, 2H) 7.30 (d, J=8.59 Hz, 1H) 8.17 (d, J=8.08 Hz, 2H).

24B

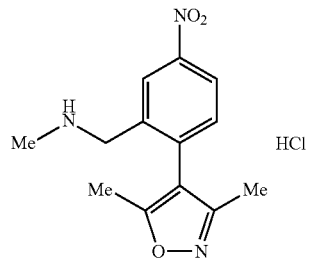 [SMILES: CNCc1cc([N+](=O)[O-])ccc1-c1c(C)noc1C ; Cl]

24A (480 mg, 1.332 mmol) was dissolved in dioxane (5 mL). HCl in dioxane (4.0 M, 5 mL) was added and the reaction mixture was stirred for 8 h at rt. The reaction was concentrated to yield 24B (390 mg, 1.310 mmol, 98% yield) as a yellow powder. MS (ESI) m/z 262.3 (M+H)+. $^1$H NMR (400 MHz, DMSO-$d_6$) δ ppm 2.08 (s, 3H) 2.26 (s, 3H) 2.52 (s, 3H) 3.56 (s, 3H) 4.06 (s, 2H) 7.62 (d, J=8.59 Hz, 1H) 8.30 (dd, J=8.46, 2.40 Hz, 1H) 8.75 (d, J=2.02 Hz, 1H) 9.32 (s, 2H).

24C

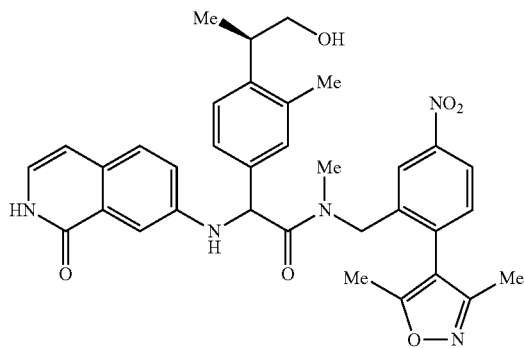 [SMILES: Cc1cc(C(Nc2ccc3cc[nH]c(=O)c3c2)C(=O)N(C)Cc2cc([N+](=O)[O-])ccc2-c2c(C)noc2C)ccc1[C@@H](C)CO]

Intermediate 10 (150 mg, 0.487 mmol), Intermediate 3 (78 mg, 0.487 mmol), and glyoxylic acid monohydrate (44.8 mg, 0.487 mmol) were dissolved in acetonitrile (1 mL)/DMF (1 mL) and heated at 100° C. in the microwave for 10 min. A solution of 24B (145 mg, 0.487 mmol) and TEA (170 μL, 1.216 mmol) in DMF (3 mL) was added followed by BOP (215 mg, 0.487 mmol) as a solid. The reaction mixture was stirred at rt for 3 h. The reaction mixture was diluted with EtOAc, washed with water and brine, dried over Na$_2$SO$_4$ and concentrated. The crude material was combined with another batch (256 mg of Intermediate 10, similar procedure) and purified by column chromatography (0 to 20% MeOH in CH$_2$Cl$_2$) to yield 24C (700 mg, 90% yield). MS (ESI) m/z 610.6 (M+H)+.

24D

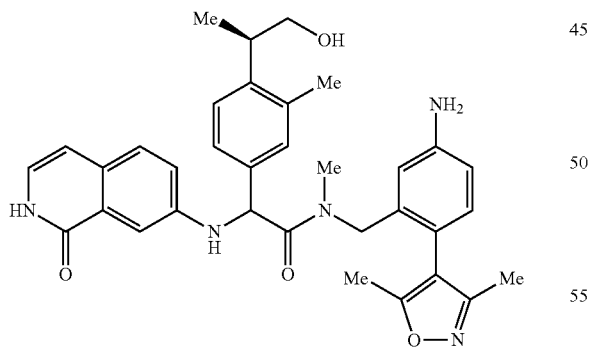

C (700 mg, 1.148 mmol), ammonium chloride (246 mg, 4.59 mmol) and zinc (300 mg, 4.59 mmol) were added to EtOH (20 mL). The grey suspension was heated to 60° C. and stirred for 2 h. Na$_2$CO$_3$ (50 mL, sat'd) was added and the mixture was stirred for 2 h. The mixture was extracted with EtOAc (3×80 mL). The organics were combined, dried over Na$_2$SO$_4$ and concentrated. The crude product was purified by column chromatography (0 to 20% MeOH in CH$_2$Cl$_2$) to yield 24D (480 mg, 0.828 mmol, 72.1% yield) as an off-white solid. MS (ESI) m/z 580.5 (M+H)+.

Example 24

Using a procedure analogous to that used to prepare 7H, 24D (460 mg, 0.794 mmol) was reacted with Phosegene and Et$_3$N and purified by prep HPLC (Phenom. Luna Axia, 30×100 mm, 5 micron, flow rate 40 mL/min, A: H$_2$O/MeOH (9:1), B: H$_2$O/MeOH (1:9), 0.1% TFA, 40 to 80% B, 10 min gradient to yield a mixture of diasteromers. The mixture was separated into diastereomer 1 (55 mg, 0.091 mmol, 11.44% yield) and Example 24 (65 mg, 0.107 mmol, 13.52% yield.) using a R,R-Welko-O 1 column (21.1 mm×250 mm, 10 micron, Regis Technologies, Inc.), 40% MeOH/EtOH (1:1)/60% Heptane, 20 mL/min flow rate, and uv detection at 220 nm. Characterization for Example 24: MS (ESI) m/z 604.4 (M+H)+. $^1$H NMR (400 MHz, CD$_3$OD) 86 ppm 1.30 (d, J=7.15 Hz, 3H) 2.03 (s, 1.5H) 2.12 (s, 1.5H) 2.20 (s, 1.5H) 2.27 (s, 1.5H) 2.32 (s, 3H) 3.43-3.63 (m, 2H) 3.96 (dd, J=10.72, 4.12 Hz, 1H) 4.60-4.72 (m, 1H) 5.05 (dd, J=33.53, 16.49 Hz, 1H) 5.61 (d, J=1.65 Hz, 1H) 6.13 (d, J=6.60 Hz, 1H) 6.52 (d, J=6.60 Hz, 1H) 6.72-6.80 (m, J=7.15, 3.30 Hz, 1H) 6.89 (d, J=7.70 Hz, 1H) 7.00 (dd, J=7.97, 3.02 Hz, 1H) 7.18-7.25 (m, J=8.79, 2.20 Hz, 2H) 7.34-7.40 (m, 2H) 7.42 (d, J=8.25 Hz, 1H) 7.62 (d, J=8.24 Hz, 1H) 9.04 (d, J=4.95 Hz, 1H). Analytical HPLC (Method A): Col A: 7.09 min, 93%; Col B: 7.16 min, 93%.

Example 25

(2R,15R)-7-(2-Ethyl-2H-pyrazol-3-yl)-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

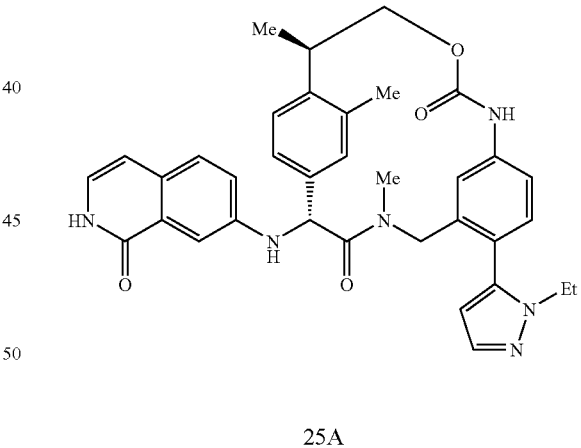

25A

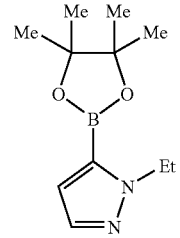 [SMILES: CCn1nccc1B1OC(C)(C)C(C)(C)O1]

BuLi (4.09 mL, 11.44 mmol) was added to a solution of 1-ethyl-1H-pyrazole (1 g, 10.40 mmol) in THF (50 mL) at −78° C. The reaction mixture was stirred for 30 min at −78° C. and then 2-isopropoxy-4,4,5,5-tetramethyl-1,3,2-dioxaborolane (3.18 mL, 15.60 mmol) was added. The cooling bath was removed and the mixture was stirred overnight. The reaction was partioned between Et$_2$O (100 mL) and H$_2$O (100 mL). The phases were separated and the aq was washed with Et$_2$O (2×50 mL). The organics were combined, washed with brine, dried over Na$_2$SO$_4$ and concentrated. The crude solid was purified by column chromatography (0 to 50% EtOAC in hexanes) to yield 25A (620 mg, 2.79 mmol, 26.8% yield) as a clear solid. MS (ESI) m/z 223.3 (M−H)$^−$. $^1$H NMR (400 MHz, CHLOROFORM-d) δ ppm 1.33 (s, 12H) 1.41 (t, J=7.20 Hz, 3H) 4.44 (q, J=7.33 Hz, 2H) 6.70 (d, J=1.77 Hz, 1H) 7.49 (d, J=1.77 Hz, 1H).

25B

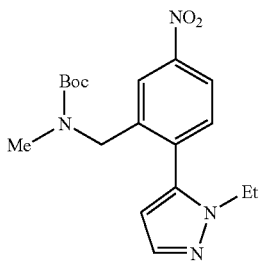 [SMILES: CCn1nccc1-c1ccc([N+](=O)[O-])cc1CN(C)C(=O)OC(C)(C)C]

Using a procedure analogous to that used to prepare 22A, Intermediate 18 (500 mg, 1.448 mmol) was reacted with 25A, sodium carbonate and Tetrakis(triphenylphosphine)palladium(0). The crude product was purified by column chromatography (0 to 60% EtOAc in hexanes) to yield 25B (500 mg, 1.387 mmol, 102% yield) as a yellow oil contaminated with 2,3-dimethylbutane-2,3-diol. MS (ESI) m/z 361.37 (M+H)$^+$. $^1$H NMR (400 MHz, CDCl$_3$) δ ppm 1.32 (t, J=7.15 Hz, 3H) 1.38-1.54 (m, 9H) 2.77 (s, 3H) 3.85-4.01 (m, J=6.60 Hz, 2H) 4.30 (s, 2H) 6.23 (d, J=2.20 Hz, 1H) 7.42 (d, J=8.79 Hz, 1H) 7.60 (s, 1H) 8.10-8.25 (m, 2H).

25C

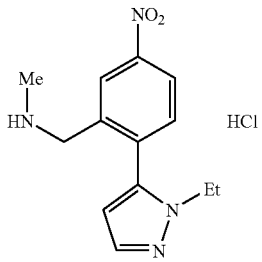 [SMILES: CCn1nccc1-c1ccc([N+](=O)[O-])cc1CNC ; Cl]

25B was dissolved in dioxane (5 mL). HCl in dioxane (4.0 M, 5 mL) was added and the reaction mixture was stirred for 8 h at rt. The reaction was concentrated to yield 25C (411 mg, 1.385 mmol, 100% yield) as a yellow powder. MS (ESI) m/z 261.3 (M+H)$^+$. $^1$H NMR (400 MHz, DMSO-d$_6$) δ ppm 1.24 (dd, J=7.15 Hz, 3H) 3.90 (q, J=7.15 Hz, 2H) 4.06 (t, J=6.32 Hz, 2H) 6.58 (d, J=2.20 Hz, 1H) 7.62 (s, 1H) 7.70 (d, J=8.79 Hz, 1H) 8.33 (dd, J=8.52, 2.47 Hz, 1H) 8.79 (d, J=2.20 Hz, 1H) 9.66 (s, 2H).

25D

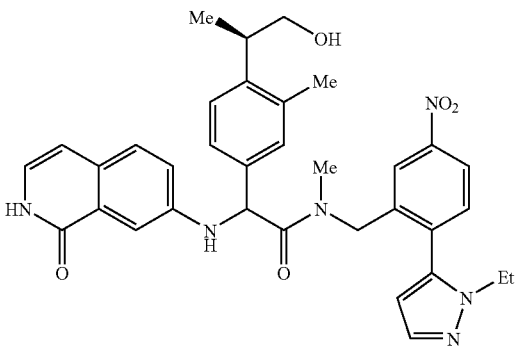 [SMILES: CCn1nccc1-c1ccc([N+](=O)[O-])cc1CN(C)C(=O)C(Nc1ccc2cc[nH]c(=O)c2c1)c1ccc([C@@H](C)CO)c(C)c1]

Intermediate 10 (375 mg, 1.216 mmol), Intermediate 3 (195 mg, 1.216 mmol), and glyoxylic acid monohydrate (112 mg, 1.216 mmol) were dissolved in acetonitrile (2.4 mL)/DMF (2.4 mL) and heated at 100° C. in the microwave for 10 min. A solution of 25C (361 mg, 1.216 mmol) and TEA (509 µL, 3.65 mmol) in DMF (6 mL) was added followed by BOP (538 mg, 1.216 mmol) as a solid. The reaction mixture was stirred at rt for 3 h. The reaction mixture was diluted with EtOAc, washed with water and brine, dried over Na$_2$SO$_4$ and concentrated. The crude material was purified by column chromatography (0 to 20% MeOH in CH$_2$Cl$_2$) to yield 25D (420 mg, 0.690 mmol, 56.7% yield). MS (ESI) m/z 609.5 (M+H)$^+$.

25E

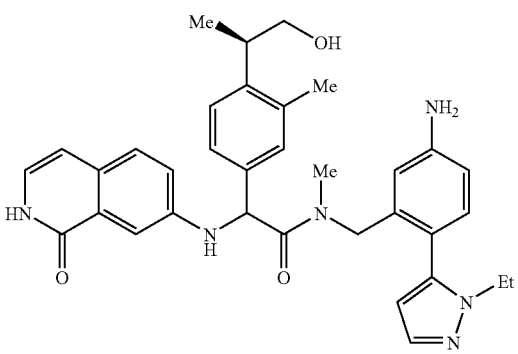

A solution of 25D (420 mg, 0.690 mmol) in MeOH (8 mL) was stirred with Pd/C (20 mg, 0.019 mmol) under H$_2$ (20 psi) for 14 h. The reaction mixture was filtered and concentrated. The crude product was purified by flash chromatography (0% to 20% methanol in dichloromethane over 15 min using a 40 g silica gel cartridge) to yield 25E (290 mg, 0.501 mmol). MS (ESI) m/z 579.4 (M+H)$^+$.

Example 25

Using a procedure analogous to that used to prepare 7H, 25E (290 mg, 0.501 mmol) was reacted with Phosegene and Et₃N and purified by prep HPLC: Luna Axia C18 column, 30×100 mm, 5 micron, flow rate 40 mL/min, A: H₂O/MeOH (9:1), B: H₂O/MeOH (1:9), 0.1% TFA, 60 to 100% B, 10 min gradient. The mixture of diastereomers was separated into diastereomer 1 (32 mg, 0.053 mmol, 10.56% yield) and Example 25 (32 mg, 0.053 mmol, 10.56% yield) using a R,R-Welko-O 1 column (21.1 mm×250 mm, 10 micron, Regis Technologies, Inc.), 40% MeOH/EtOH (1:1)/60% Heptane, 20 mL/min flow rate, and uv detection at 254 nm. MS (ESI) m/z 605.4 (M+H)⁺. ¹H NMR (400 MHz, CD₃OD) b ppm 1.27 (t, J=7.15 Hz, 3H) 1.31 (d, J=7.15 Hz, 3H) 2.33 (s, 3H) 3.43-3.55 (m, 1H) 3.61 (d, J=17.59 Hz, 1H) 3.89-4.05 (m, 3H) 4.65 (t, J=10.99 Hz, 1H) 5.05 (d, J=17.04 Hz, 1H) 5.60 (s, 1H) 6.17 (d, J=1.65 Hz, 1H) 6.26 (d, J=1.65 Hz, 1H) 6.52 (d, J=7.15 Hz, 1H) 6.79 (dd, J=7.70, 2.20 Hz, 1H) 6.89 (d, J=6.60 Hz, 1H) 7.10 (d, J=7.70 Hz, 1H) 7.17-7.27 (m, 2H) 7.34-7.41 (m, 2H) 7.43 (d, J=8.24 Hz, 1H) 7.54 (d, J=2.20 Hz, 1H) 7.63 (dd, J=7.70, 1.65 Hz, 1H). Analytical HPLC (Method A): Col A: 6.77 min, 95%; Col B: 6.79 min, 97%.

Example 26

(2R,15R)-7-(2,3-Dimethyl-3H-imidazol-4-yl)-4,15,17-trimethyl-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaene-3,12-dione

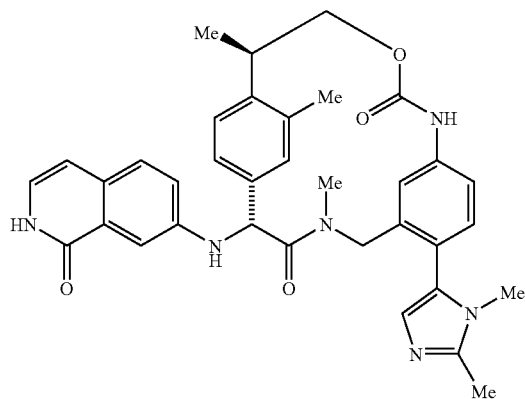 [SMILES: Cc1cc2ccc1[C@@H](C)COC(=O)Nc1ccc(-c3cnc(C)n3C)c(c1)CN(C)C(=O)[C@@H]2Nc1ccc2cc[nH]c(=O)c2c1]

26A

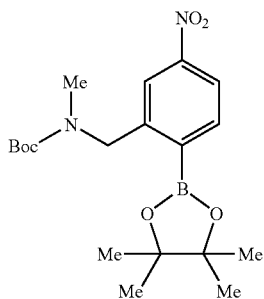 [SMILES: CN(Cc1cc([N+](=O)[O-])ccc1B1OC(C)(C)C(C)(C)O1)C(=O)OC(C)(C)C]

A mixture of Intermediate 18 (1.1 g, 3.2 mmol), (1,1'-bis(diphenylphosphino)ferrocene)-dichloropalladium(II) (0.131 g, 0.159 mmol), potassium acetate (0.938 g, 9.56 mmol) and Bis(pinacolato)diboron (1.214 g, 4.78 mmol) in DMSO (8 mL) was degassed and stirred overnight at 80° C. in a sealed tube. The reaction mixture was diluted with EtOAc (200 mL), washed with H₂O (1×100 mL), and brine (1×100 mL), dried over Na₂SO₄ and concentrated. The crude product was purified by column chromatography (0 to 50% EtOAc in Hexanes) to yield 26A (1.24 g, 3.16 mmol, 99% yield) as a yellow solid. ¹H NMR (400 MHz, CHLOROFORM-d) δ ppm 1.35 (s, 12H) 1.48 (d, J=26.02 Hz, 9H) 2.89 (s, 3H) 4.79 (d, J=13.39 Hz, 2H) 7.90-8.23 (m, 3H).

26B

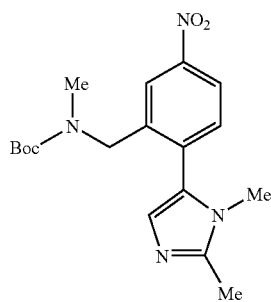 [SMILES: Cc1ncc(-c2ccc([N+](=O)[O-])cc2CN(C)C(=O)OC(C)(C)C)n1C]

A microwave tube was charged with 26A (500 mg, 1.275 mmol), 5-bromo-1,2-dimethyl-1H-imidazole (446 mg, 2.55 mmol), sodium carbonate (540 mg, 5.10 mmol), and Tetrakis(triphenylphosphine)palladium(0) (73.6 mg, 0.064 mmol) then DME (10 mL) and Water (3.33 mL), degassed and stirred for 16 h at 80° C. The reaction was diluted with EtOAc (80 mL) and water (40 mL). The phases were separated. The organics were washed with brine, dried over Na₂SO₄ and concentrated. The crude material was purified by flash chromatography (0 to 100% EtOAc in hexanes then eluted with 10% MeOH/90% EtOAc) to yield 26B (285 mg, 0.791 mmol, 62.0% yield) as a yellow oil. ¹H NMR (400 MHz, MeOD) δ ppm 1.43 (d, J=34.08 Hz, 9H) 2.44 (s, 3H) 2.72-2.83 (m, 3H) 3.38 (s, 3H) 4.42 (s, 2H) 6.90 (s, 1H) 7.53 (d, J=8.79 Hz, 1H) 8.11-8.19 (m, J=4.95 Hz, 1H) 8.23 (d, J=8.25 Hz, 1H).

26C

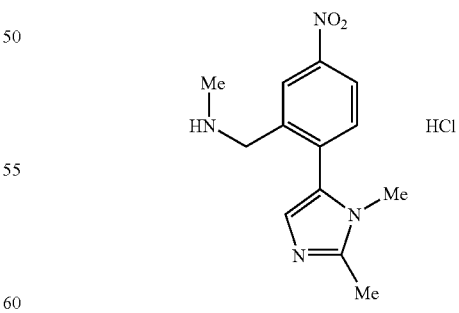

26B was dissolved in dioxane (5 mL). HCl in dioxane (4.0 M, 5 mL) was added and the reaction mixture was stirred for 8 h at rt. The reaction was concentrated to yield 26C (225 mg, 0.758 mmol, 98% yield) as a yellow powder. ¹H NMR (400 MHz, DMSO-d₆) δ ppm 2.51-2.56 (m, 3H) 2.67 (s, 3H) 3.46 (s, 3H) 4.14-4.28 (m, 2H) 7.77 (d, J=8.25 Hz, 1H) 7.94 (s, 1H)

8.41 (dd, J=8.52, 2.47 Hz, 1H) 8.85 (d, J=2.75 Hz, 1H) 9.72-9.83 (m, J=3.85 Hz, 2H).

26D

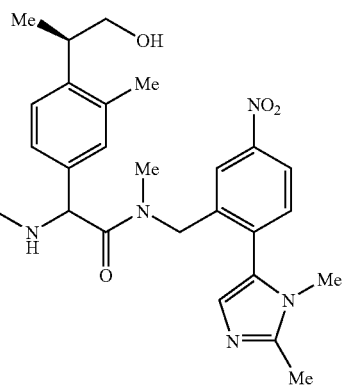

Intermediate 10 (175 mg, 0.568 mmol), Intermediate 3 (91 mg, 0.568 mmol), and glyoxylic acid monohydrate (52.3 mg, 0.568 mmol) were dissolved in acetonitrile (1135 µL)/DMF (1135 µL) and heated at 100° C. in the microwave for min. A solution of 26C (168 mg, 0.568 mmol) and TEA (237 µL, 1.703 mmol) in DMF (6 mL) was added followed by BOP (251 mg, 0.568 mmol) as a solid. The reaction mixture was stirred at rt for 3 h. The reaction mixture was diluted with EtOAc, washed with water and brine, dried over Na$_2$SO$_4$ and concentrated. The crude material was purified by column chromarography (0 to 20% MeOH in CH$_2$Cl$_2$) to yield 26D (190 mg, 0.312 mmol, 55.0% yield). MS (ESI) m/z 609.5 (M+H)$^+$.

26E

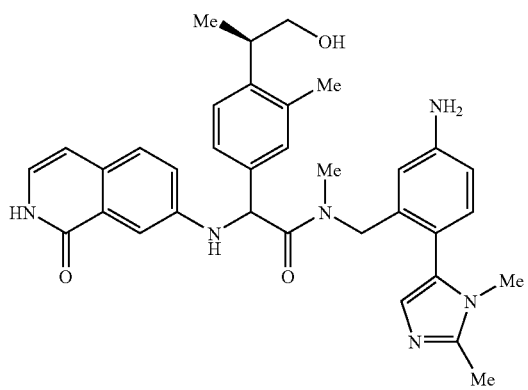 [SMILES: Cc1cc(C(Nc2ccc3cc[nH]c(=O)c3c2)C(=O)N(C)Cc2cc(N)ccc2-c2cnc(C)n2C)ccc1[C@@H](C)CO]

A solution of 26D (190 mg, 0.312 mmol) in MeOH (5 mL) was stirred with Pd/C (10 mg, 9.40 mmol) under H$_2$ (20 psi) for 14 h. The reaction mixture was filtered and concentrated. The crude product was purified by flash chromatography (0% to 20% methanol in dichloromethane) to yield 26E (115 mg, 0.199 mmol, 63.7% yield) as a yellow solid. MS (ESI) m/z 579.4 (M+H)$^+$.

Example 26

Using a procedure analogous to that used to prepare 711, 26E (110 mg mg, 0.19 mmol) was reacted with Phosegene and Et$_3$N and purified by prep HPLC: Luna Axia C18 column, 30×100 mm, 5 micron, flow rate 40 mL/min, A: H$_2$O/MeOH (9:1), B: H$_2$O/MeOH (1:9), 0.1% TFA, 60 to 100% B, 10 min gradient. The mixture of diastereomers was separated into Example 26 (3 mg) and its diasteromer (3 mg) using a OD column (21.1 mm×250 mm, 10 micron), 75% MeOH/EtOH (1:1)/25% Heptane, 20 mL/min flow rate, and uv detection at 254 nm. MS (ESI) m/z 605.6 (M+H)$^+$. $^1$H NMR (400 MHz, MeOD) δ ppm 1.32 (d, J=7.07 Hz, 3H) 2.34 (s, 3H) 2.46 (s, 3H) 3.68 (d, J=16.67 Hz, 1H) 3.98 (dd, J=10.86, 4.04 Hz, 1H) 4.65 (t, J=11.12 Hz, 1H) 5.04 (d, J=16.67 Hz, 1H) 5.60 (s, 1H) 6.21 (s, 1H) 6.54 (d, J=7.07 Hz, 1H) 6.79 (dd, J=7.96, 2.15 Hz, 1H) 6.90 (d, J=7.07 Hz, 1H) 6.95 (s, 1H) 7.11 (d, J=8.08 Hz, 1H) 7.16-7.29 (m, 2H) 7.31-7.48 (m, 3H) 7.62 (d, J=7.83 Hz, 1H). Analytical HPLC (Method A): Col A: 5.66 min, 87%; Col B: 4.85 min, 80%.

Example 27

(2R,15R)-15,17-Dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

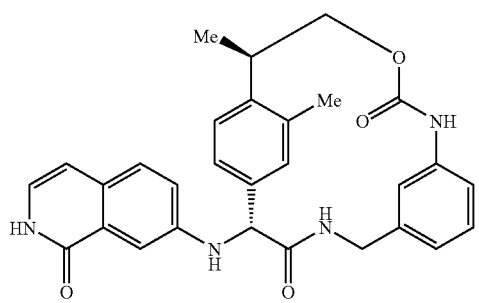 [SMILES: Cc1cc2ccc1[C@@H](C)COC(=O)Nc1cccc(c1)CNC(=O)[C@@H]2Nc1ccc2cc[nH]c(=O)c2c1]

27A

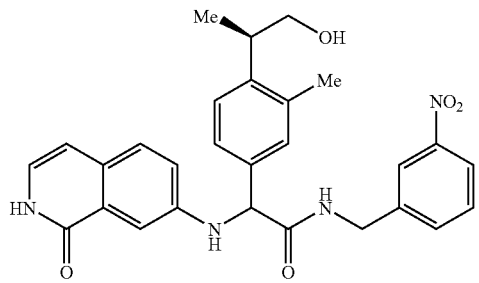 [SMILES: Cc1cc(C(Nc2ccc3cc[nH]c(=O)c3c2)C(=O)NCc2cccc([N+](=O)[O-])c2)ccc1[C@@H](C)CO]

Intermediate 10 (265 mg, 0.860 mmol), Intermediate 3 (138 mg, 0.860 mmol), and glyoxylic acid monohydrate (79 mg, 0.860 mmol) were dissolved in acetonitrile (1.7 mL)/DMF (1.7 mL) and heated at 100° C. in the microwave for 10 min. A solution of (3-nitrophenyl)methanamine hydrochloride (162 mg, 0.860 mmol) and TEA (359 µL, 2.58 mmol) in DMF (4 mL) were added followed by BOP (380 mg, 0.860 mmol) as a solid. The reaction mixture was stirred at rt for 3 h. The reaction mixture was diluted with EtOAc, washed with water and brine, dried over Na$_2$SO$_4$ and concentrated. The crude material was purified by column chromarography (0 to 20% MeOH in CH$_2$Cl$_2$) to yield 27A (390 mg, 0.779 mmol, 91% yield). MS (ESI) m/z 501.5 (M+H)$^+$.

27B

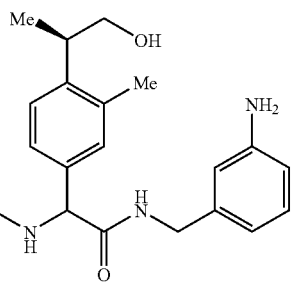

27A (385 mg, 0.769 mmol) in MeOH (25 mL) with Pd/C (35 mg, 0.033 mmol) was stirred under H$_2$ (20 psi) for 14 h. The reaction was filtered and concentrated. The crude product was purified by flash chromatography (loading in dichloromethane, 0% to 20% methanol in dichloromethane over 15 min using a 40 g silica gel cartridge) to yield 27B (235 mg, 0.499 mmol, 64.9% yield) as an off white solid. MS (ESI) m/z 471.6 (M+H)$^+$.

Example 27

Using a procedure analogous to that used to prepare 7H, 27B (235 mg, 0.50 mmol) was reacted with Phosegene and Et$_3$N and purified by prep HPLC: Luna Axia C18 column, 30×100 mm, 5 micron, flow rate 40 mL/min, A: H$_2$O/MeOH (9:1), B: H$_2$O/MeOH (1:9), 0.1% TFA, 60 to 100% B, 10 min gradient. The mixture of diastereomers was separated into diastereomer 1 (3 mg, 0.008 mmol, 3% yield) and Example 27 (3 mg, 0.008 mmol, 3% yield) using a R,R-Welko-O 1 column (21.1 mm×250 mm, 10 micron, Regis Technologies, Inc.), 50% MeOH/EtOH (1:1)/50% Heptane, 20 mL/min flow rate, and uv detection at 254 nm. MS (ESI) m/z 497.4 (M+H)$^+$. $^1$H NMR (400 MHz, CD$_3$OD) δ ppm 1.31 (d, J=7.15 Hz, 3H) 2.34 (s, 3H) 4.07 (d, J=15.94 Hz, 1H) 4.18 (dd, J=10.72, 4.12 Hz, 1H) 4.49-4.62 (m, 1H) 4.72 (d, J=15.94 Hz, 1H) 5.09 (s, 1H) 6.12 (s, 1H) 6.54 (d, J=7.15 Hz, 1H) 6.65 (d, J=7.70 Hz, 1H) 6.84-6.93 (m, 1H) 7.12 (t, J=7.70 Hz, 1H) 7.18-7.29 (m, 1H) 7.35-7.45 (m, 2H) 7.51 (d, J=8.25 Hz, 1H). Analytical HPLC (Method A): Col A: 6.40 min, 87%; Col B: 6.49 min, 88%.

Example 29

7-Cyclopropanesulfonyl-4-methyl-2-(4-oxo-3,4-dihydro-quinazolin-6-ylamino)-13-oxa-4,11-diazatricyclo[14.2.2.1 6,10]henicosa-1(19),6,8,10(21),16(20),17-hexaene-3,12-dione

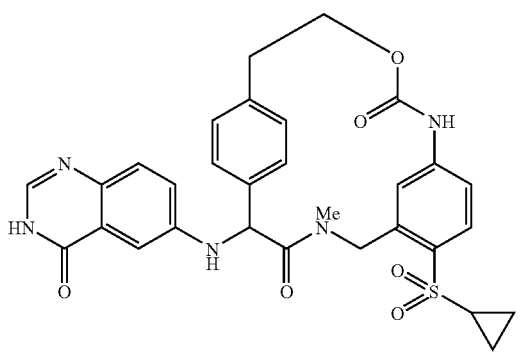 [SMILES: CN1Cc2cc(ccc2S(=O)(=O)C2CC2)NC(=O)OCCc2ccc(cc2)C(Nc2ccc3nc[nH]c(=O)c3c2)C1=O]

29A

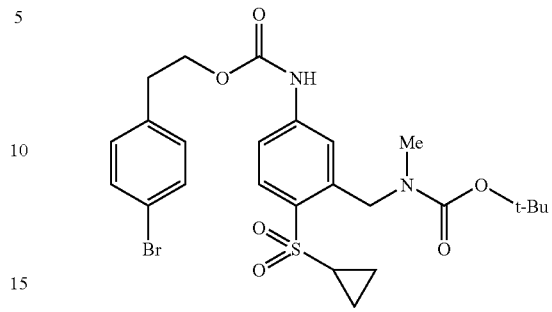

To Intermediate 11 (800 mg, 2.350 mmol), sodium bicarbonate (987 mg, 11.75 mmol) in CH$_2$Cl$_2$ (25 ml) at 0° C. was added phosgene (20% in toluene, 3.73 ml, 7.05 mmol). The mixture was stirred for 15 min. The crude was filtered to a second flask and the solvent and excess of phosgene was removed under vaccuo. The crude was redissolved in CH$_2$Cl$_2$ (25 ml), and 2-(4-bromophenyl)ethanol (567 mg, 2.82 mmol), TEA (1.638 ml, 11.75 mmol) was added in that order. The mixture was stirred at 0° C. for 15 min and then at rt for 15 min. Solvent was removed. The crude was suspended in EtOAc/H$_2$O and extracted with EtOAc, washed with 0.5 M HCl, sat. NaHCO$_3$ and brine and dried over Na$_2$SO$_4$. After removal of the solvent, the crude product was added to a silica gel column (80 g) and was eluted with EtOAc/hexanes from 0-50% to give 29A (1.2 g, 90% yield) as a white solid. $^1$H NMR (400 MHz, CDCl$_3$) δ ppm 0.98-1.08 (m, 2H) 1.27-1.51 (m, 11H) 2.52 (br s, t H) 2.95 (t, J=6.59 Hz, 5H) 4.38 (q, J=7.03 Hz, 2H) 4.92 (s, 2H) 7.11 (t, J=7.69 Hz, 3H) 7.41-7.47 (m, 2H) 7.5-7.7 (br s, 1H) 7.87 (d, J=8.79 Hz, 1H), LC-MS 567 and 569.

29B

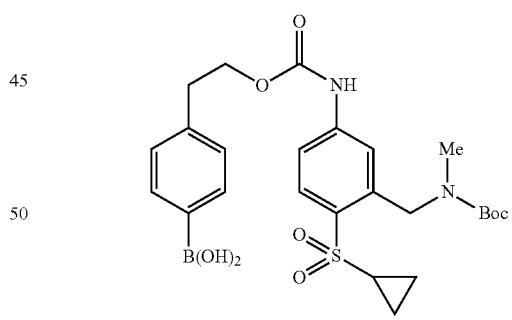

In a pressure flask were added 29A (1.2 g, 2.115 mmol), bis(neopentyl glycolato)diboron (0.525 g, 2.326 mmol), and potassium acetate (0.519 g, 5.29 mmol). DMSO (12 mL) was added, then the suspension was degassed by flushing with argon for 10 min. (1,1'-bis(diphenylphosphino)ferrocene)-dichloropalladium(II) (0.087 g, 0.106 mmol) was added, the reaction flask was lowered into an 80° C. oil bath and stirred for 3.25 h. The reaction mixture was diluted with EtOAc, washed with H$_2$O (2×) and brine, dried (Na$_2$SO$_4$) to give a dark brown oil as crude. The crude product was added to a silica gel column (40 g) and was eluted with EtOAc/hexanes from 25% to 100% in 12 min to give a slightly yellow solid that was hydrolyzed to boronic acid under prep HPLC purification (CH₃CN/H₂O, 0.1% TFA). 29B (710 mg, 1.334 mmol, 63.1% yield) was obtained as a off-white solid after lyophilization: ¹H NMR (400 MHz, CD₃CN) δ ppm 0.94-1.03 (m, 2H) 1.08-1.16 (m, 2H) 1.31 (br s, 5H) 1.45 (br s, 4H) 2.64 (s, 1H) 2.90 (s, 3H) 2.92-2.99 (m, 2H) 4.30-4.41 (m, 2H) 4.82 (s, 2H) 7.28 (d, J=7.91 Hz, 2H) 7.42 (d, J=7.91 Hz, 1H) 7.64-7.68 (d, J=7.91 Hz, 2H) 7.77 (d, J=8.79 Hz, 1H) 8.12 (d, J=7.91 Hz, 1H). MS (ESI) m/z 533 (M+H)⁺.

29C

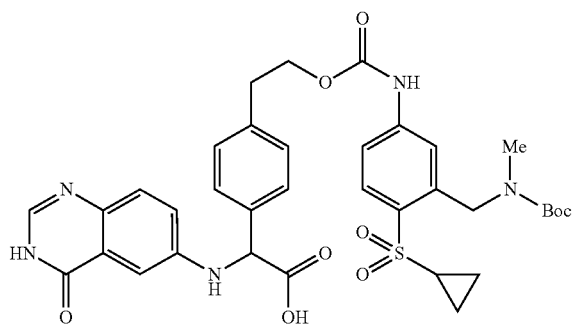

To a mixture of 29B (310 mg, 0.582 mmol), Intermediate 4 (108 mg, 0.670 mmol) and glyoxylic acid monohydrate (59.0 mg, 0.640 mmol) was added acetonitrile (3.0 mL), and DMF (3.0 mL). The mixture was stirred at 70° C. overnight. TLC and LC-MS indicated ca 40% of boronic acid still remaining. Solvent was completely removed and the crude was added to a silica gel column (40 g) and was eluted with CH₂Cl₂/MeOH (2% to 25%) in 15 min to give 29C (124 mg, 30%) as a brown solid. ¹H NMR (400 MHz, methanol-d₄) δ ppm 0.95-1.04 (m, 2H) 1.11-1.18 (m, 2H) 1.32 (s, 5H) 1.46 (s, 4H) 2.71 (m, 1H) 2.85-2.93 (m, 5H) 4.28 (t, J=6.59 Hz, 2H) 4.86 (s, 2H) 5.14 (s, 1H) 7.13 (d, J=2.64 Hz, 1H) 7.18-7.25 (m, 3H) 7.39 (d, J=8.79 Hz, 1H) 7.46 (d, J=8.35 Hz, 4H) 7.73 (d, J=8.35 Hz, 1H) 7.79-7.85 (m, 1H); LC-MS 706 (M+H)⁺.

29D

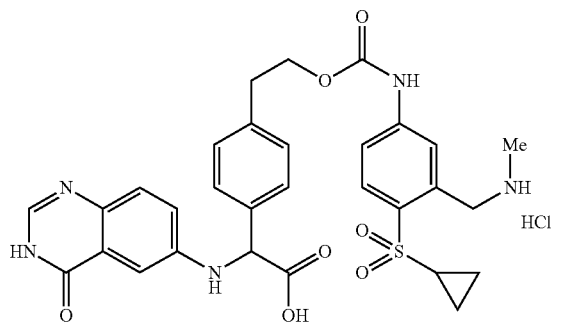 [SMILES: CNCc1cc(NC(=O)OCCc2ccc(C(Nc3ccc4nc[nH]c(=O)c4c3)C(=O)O)cc2)ccc1S(=O)(=O)C1CC1 ; Cl]

To 29C (124 mg, 0.176 mmol) was added 4.0 N HCl in dioxane (3.6 mL, 14.40 mmol). The mixture was stirred at rt for 1.5 h. LC-MS indicated a clean reaction. Solvent was removed and chased twice with EtOAc to give 29D (112 mg, 99% yield) as a white solid. ¹H NMR (400 MHz, DMSO-d₆) δ ppm 1.02-1.09 (m, 2H) 1.10-1.15 (m, 2H) 2.61 (t, J=5.22 Hz, 3H) 2.96 (t, J=6.60 Hz, 2H) 3.03-3.12 (m, 1H) 4.32-4.42 (m, 4H) 5.24 (s, 1H) 7.12 (d, J=2.20 Hz, 1H) 7.32 (d, J=8.25 Hz, 2H) 7.42-7.50 (m, 3H) 7.55 (d, J=9.34 Hz, 1H) 7.66 (dd, J=8.79, 2.20 Hz, 1H) 7.83-7.89 (m, 2H) 8.58 (s, 1H) 8.92 (d, J=4.95 Hz, 2H); LC-MS 606 (M+H)⁺.

Example 29

To a solution of BOP (152 mg, 0.343 mmol) and DMAP (84 mg, 0.685 mmol) in CH₂Cl₂ (20 ml) and DMF (1.0 ml) at 40° C. was added a solution of 29D (110 mg, 0.171 mmol) and DIEA (0.060 ml, 0.343 mmol) in DMF (3.0 mL) via a syringe pump over 3.0 h. Solvent was completely removed, the residue was redissolved in CHC₃ (60 mL), to this solution was added water (20 mL) and brine (20 mL). Organic layer was collected, aqueous was extracted with one more CHCl₃ (20 mL). Organic layers were dried over Na₂SO₄. After evaporation of solvent, it was dissolved in MeOH/DMSO (4.0 mL, 1:1) and purified (2 injections) by preparative HPLC equipped with a C18 Phenomenex Luna AXIA column (30 mm×100 cm, 5 m) with the UV detector set at 254 nm. The separations were performed using a gradient method: 10-80% B in 10 mins; then 80% B in 2 mins with a flow rate of 40 mL/min. Solvent B is 90% acetonitrile-10% water-0.1% TFA and solvent A is 10% acetonitrile-90% water-0.1% TFA. Example 29 (22 mg) was obtained as a white solid after lyophilazation. ¹H NMR (400 MHz, methanol-d₄) δ ppm 1.01-1.24 (br s, 3H) 1.24 (br s, 1H) 2.82-2.94 (m, 2H) 2.96-3.01 (m, 1H) 3.36 (s, 3H) 4.11 (dd, J=11.21, 2.86 Hz, 1H) 4.22 (d, J=17.14 Hz, 1H) 4.84-4.93 (m, 1H) 5.70 (s, 1H) 5.80 (d, J=17.14 Hz, 1H) 6.51 (s, 1H) 6.87 (dd, J=8.35, 2.20 Hz, 1H) 7.08-7.15 (m, 1H) 7.15-7.21 (m, 1H) 7.34-7.44 (m, 2H) 7.49 (d, J=7.47 Hz, 2H) 7.72 (d, J=8.35 Hz, 1H) 7.81 (d, J=7.47 Hz, 1H) 8.73 (s, 1H). MS (ESI) m/z 588 (M+H)⁺. Analytical HPLC (Method A): Col A: 8.53 min, 93%; Col B: 9.18 min, 91%.

Example 30

7-Cyclopropanesulfonyl-4-methyl-2-(1-oxo-1,2-dihydro-isoquinolin-7-ylamino)-13-oxa-4,11-diaza-tricyclo[14.2.2.16,10]henicosa-1(19),6,8,10(21),16(20),17-hexaene-3,12-dione

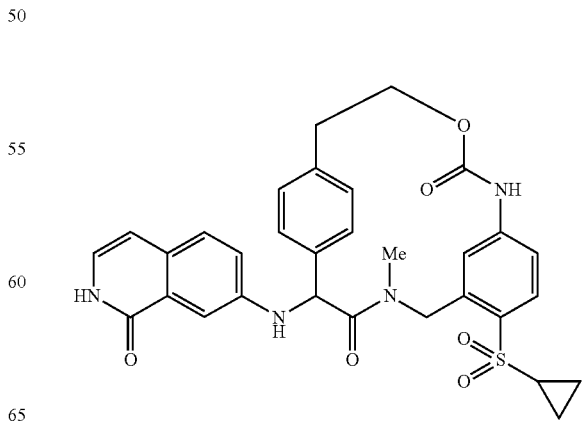

145

30A

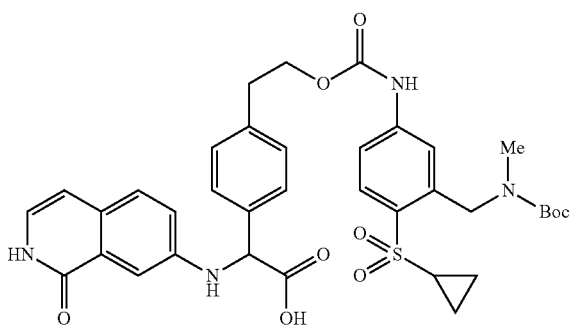 [SMILES: CN(Cc1cc(NC(=O)OCCc2ccc(C(Nc3ccc4cc[nH]c(=O)c4c3)C(=O)O)cc2)ccc1S(=O)(=O)C1CC1)C(=O)OC(C)(C)C]

Using a procedure analogous to that used to prepare 29C, 29B (310 mg, 0.582 mmol), Intermediate 3, and glyoxylic acid monohydrate were reacted and purified by flash chromatography (2% to 25% MeOH in CH$_2$Cl$_2$) to give 30A (96 mg, 24% yield). $^1$H NMR (400 MHz, methanol-d$_4$) δ ppm 1.01 (td, J=7.58, 5.05 Hz, 2H) 1.11-1.19 (m, 2H) 1.34 (s, 5H) 1.48 (s, 4H) 2.67-2.78 (m, 1H) 2.87-2.95 (m, 5H) 4.30 (t, J=6.59 Hz, 2H) 4.87 (s, 2H) 5.16 (s, 1H) 6.47 (d, J=7.03 Hz, 1H) 6.86 (t, J=6.37 Hz, 1H) 7.15-7.25 (m, 3H) 7.27-7.38 (m, 2H) 7.43-7.54 (m, 4H) 7.76 (d, J=8.35 Hz, 1H); LC-MS 705 (M+H)$^+$.

30B

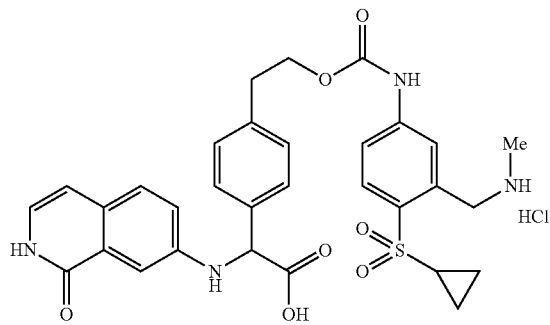 [SMILES: CNCc1cc(NC(=O)OCCc2ccc(C(Nc3ccc4cc[nH]c(=O)c4c3)C(=O)O)cc2)ccc1S(=O)(=O)C1CC1 ; Cl]

To 30A (96 mg, 0.136 mmol) was added 4.0 N HCl in dioxane (2.8 mL, 11.20 mmol). The mixture was stirred at rt for 1.5 h. Solvent was removed and chased twice with EtOAc to give 30B (87 mg, 100 yield) as a brown solid. $^1$H NMR (400 MHz, DMSO-d$_6$) δ ppm 1.02-1.09 (m, 2H) 1.11 (d, J=3.30 Hz, 2H) 2.61 (t, J=5.22 Hz, 3H) 2.95 (t, J=6.60 Hz, 2H) 3.02-3.10 (m, 1H) 4.33-4.43 (m, 4H) 5.15 (s, 1H) 6.35 (d, J=7.15 Hz, 1H) 6.79-6.87 (m, 1H) 7.18 (d, J=2.20 Hz, 1H) 7.24-7.34 (m, 3H) 7.37 (d, J=8.79 Hz, 1H) 7.48 (d, J=8.25 Hz, 2H) 7.64 (dd, J=8.79, 2.20 Hz, 1H) 7.82-7.89 (m, 2H) 8.87 (d, J=4.40 Hz, 2H); LC-MS 605 (M+H).

Example 30

To a solution of BOP (120 mg, 0.271 mmol) and DMAP (83 mg, 0.678 mmol) in CH$_2$Cl$_2$ (18 ml) and DMF (1.0 ml) at 40° C. was added a solution of 30B (87 mg, 0.136 mmol) and DIEA (0.047 ml, 0.271 mmol) in DMF (3.0 mL) via a syringe pump over 3.0 h. Solvent was completely removed, the residue was redissolved in CHCl$_3$ (60 mL), to this solution was added water (20 mL) and brine (20 mL). The organic layer was collected, aqueous was extracted with one more CHCl$_3$ (20 mL). Organic layers were dried over Na$_2$SO$_4$. After evaporation of solvent, it was dissolved in MeOH/DMSO (4.0 mL, 1:1) and purified (2 injections) by preparative HPLC equipped with a C18 Phenomenex Luna AXIA column (30 mm×100 cm, 5 g) with the UV detector set at 254 nm. The separations were performed using a gradient method: 10-80% B in 10 mins; then 80% B in 2 mins with a flow rate of 40 mL/min. Solvent B is 90% acetonitrile-10% water-0.1% TFA and solvent A is 10% acetonitrile-90% water-0.1% TFA. Example 30 (14 mg) was obtained as a white solid after lyophilazation. $^1$H NMR (400 MHz, methanol-d$_4$) δ ppm 0.94-1.07 (m, 3H) 1.20-1.31 (m, 1H) 2.82-2.93 (m, 3H) 3.36 (s, 3H) 4.02-4.10 (m, 1H) 4.25 (d, J=17.58 Hz, 1H) 4.79-4.88 (m, 1H) 5.67 (s, 1H) 5.75 (d, J=17.58 Hz, 1H) 6.51 (s, 1H) 6.55 (d, J=8.35, 2.20 Hz, 1H) 6.83 (dd, J=8.35, 2.20 Hz, 1H) 6.93 (d, J=7.03 Hz, 1H) 7.09 (d, J=7.91 Hz, 1H) 7.16-7.25 (m, 2H) 7.40-7.44 (m, 2H) 7.46 (s, 1H) 7.70 (d, J=8.35 Hz, 1H) 7.74 (dd, J=7.91, 1.76 Hz, 1H). MS (ESI) m/z 587 (M+H)$^+$.

Analytical HPLC (Method A): Col A: 7.01 min, 98%; Col B: 7.15 min, 98%.

Example 31

7-Cyclopropanesulfonyl-4,17,20-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

31A

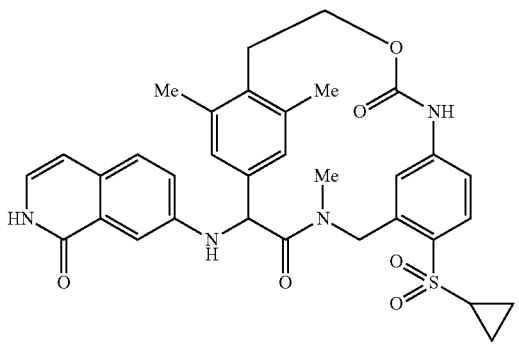 [SMILES: Cc1cc2cc(C)c1CCOC(=O)Nc1ccc(S(=O)(=O)C3CC3)c(c1)CN(C)C(=O)C2Nc1ccc2cc[nH]c(=O)c2c1]

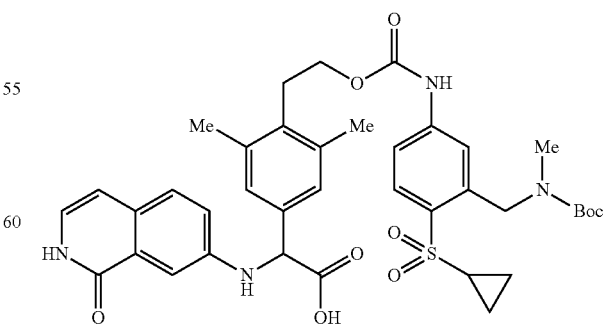

Using a procedure analogous to that used to prepare 29C, 59B (150 mg, 0.268 mmol), Intermediate 3, and glyoxylic acid monohydrate were reacted and purified by flash chromatography (2% to 25% MeOH in CH$_2$Cl$_2$) to give 31A (140 mg, 0.191 mmol, 71.4% yield) as a solid. $^1$H NMR (500 MHz, DMSO-d$_6$) δ ppm 0.99-1.07 (m, 4H) 1.30 (s, 4H) 1.45 (s, 5H) 2.32 (s, 6H) 2.96 (t, J=7.70 Hz, 2H) 3.16 (d, J=3.85 Hz, 1H) 3.32 (s, 3H) 4.19 (t, J=7.42 Hz, 2H) 4.80 (s, 2H) 5.00 (s, 1H) 6.35 (d, J=7.15 Hz, 1H) 6.81-6.85 (m, 1H) 7.18 (s, 3H) 7.23 (dd, J=8.52, 2.47 Hz, 1H) 7.37 (d, J=8.80 Hz, 1H) 7.52 (s, 1H) 7.76 (d, J=8.80 Hz, 1H) 10.24 (s, 1H) 10.91 (d, J=5.50 Hz, 1H). MS (ESI) m/z 733 (M+H)$^+$.

Example 31

To a solution of BOP (142 mg, 0.321 mmol) and DMAP (23.73 mg, 0.194 mmol) in CH$_2$Cl$_2$ (25 ml) and DMF (1.0 ml) at 38° C. was added a solution of 31A (130 mg, 0.194 mmol) and DIEA (0.170 ml, 0.971 mmol) in DMF (3.5 mL) via a syringe pump over 3.5 h. Right after addition of 31A, solvent was completely removed. The crude residue was dissolved in MeOH/DMSO (2 mL/2 mL) and purified (2 injections) using a preparative HPLC equipped with a C18 Phenomenex Luna AXIA column (30 mm×75 cm, 5µ) with the UV detector set at 254 nm. The separations were performed using a gradient method: 10-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions (25 mg) were combined and purified again with the same prep condition to give Example 31 (18 mg, 0.029 mmol, 15.07% yield). $^1$H NMR (400 MHz, methanol-d$_4$) δ ppm 0.98-1.10 (m, 3H) 1.19-1.26 (m, 1H) 2.28 (s, 3H) 2.45 (s, 3H) 2.80-2.89 (m, 2H) 3.17 (td, J=13.60, 4.67 Hz, 1H) 3.34 (s, 3H) 4.07 (d, J=7.70 Hz, 1H) 4.27 (d, J=17.59 Hz, 1H) 4.92-5.03 (m, 1H) 5.58 (s, 1H) 5.74 (d, J=17.04 Hz, 1H) 6.45 (s, 1H) 6.53 (d, J=6.60 Hz, 1H) 6.79-6.85 (m, 1H) 6.93 (d, J=6.60 Hz, 1H) 6.99 (s, 1H) 7.25 (dd, J=8.79, 2.20 Hz, 1H) 7.38-7.44 (m, 2H) 7.50 (s, 1H) 7.70 (d, J=8.24 Hz, 1H) MS (ESI) m/z 615 (M+H)$^+$. Analytical HPLC (Method A): Col A: 7.61 min, 88%; Col B: 7.64 min, 92%.

Example 32

(2R,15R)-7-Cyclopropanesulfonyl-4,15-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

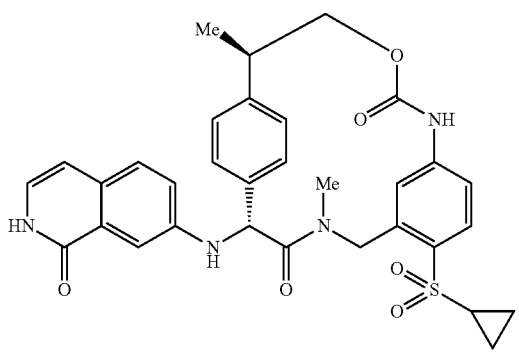 [SMILES: C[C@H]1COC(=O)Nc2ccc(S(=O)(=O)C3CC3)c(c2)CN(C)C(=O)[C@H](Nc2ccc3cc[nH]c(=O)c3c2)c2ccc1cc2]

32A

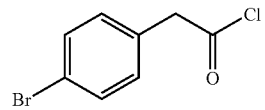 [SMILES: O=C(Cl)Cc1ccc(Br)cc1]

A solution of 2-(4-bromophenyl)acetic acid (15.4 g, 71.6 mmol) in sulfurous dichloride (46 mL, 630 mmol) was stirred at rt over night. A small aliqua was drawn and quenched with MeOH, LC-MS indicated a clean formation of methylester, suggesting complete conversion to acyl chloride. Thionyl chloride was removed under vacuum and chased twice with CH$_2$Cl$_2$. After drying under vacuum, 32A (16.7 g, 71.5 mmol, 100% yield) was obtained as an oil. $^1$H NMR (400 MHz, CDCl$_3$) δ ppm 4.08 (s, 2H) 7.13 (d, J=8.25 Hz, 2H) 7.49 (d, J=8.25 Hz, 2H).

32B: Br

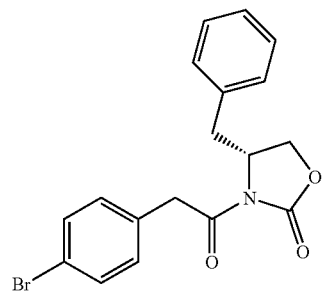 [SMILES: O=C(Cc1ccc(Br)cc1)N1C(=O)OC[C@H]1Cc1ccccc1]

Using a procedure analogous to that used to prepare 17E, 32A (16.7 g, 71.5 mmol) was reacted with (R)-4-benzyloxazolidin-2-one to yield 32B (17 g, 64% yield) as a white solid. $^1$H NMR (400 MHz, CDCl$_3$) δ ppm 2.75 (dd, J=13.19, 9.34 Hz, 1H) 3.25 (dd, J=13.74, 3.30 Hz, 1H) 4.18-4.24 (m, 4H) 4.67 (ddd, J=13.05, 7.28, 3.30 Hz, 1H) 7.12 (s, 1H) 7.14 (d, J=2.20 Hz, 1H) 7.20-7.24 (m, 2H) 7.25-7.32 (m, 3H) 7.47 (d, J=8.79 Hz, 2H). MS (ESI) m/z 374, 376 (M+H)$^+$.

32C

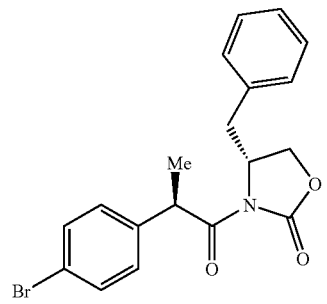 [SMILES: C[C@@H](C(=O)N1C(=O)OC[C@H]1Cc1ccccc1)c1ccc(Br)cc1]

Using a procedure analogous to that used to prepare 17F, 32B (3.57 g, 9.54 mmol) was reacted with NaHMDS and iodomethane and purified by column chromatography (EtOAc/hexanes 0-25%) to give 32C (2.52 g, 6.49 mmol, 68.0% yield) as a semi-solid. $^1$H NMR (400 MHz, CDCl$_3$) δ ppm 1.52 (d, J=7.15 Hz, 3H) 2.80 (dd, J=13.19, 9.34 Hz, 1H) 3.33 (dd, J=13.19, 3.30 Hz, 1H) 4.05-4.15 (m, 2H) 4.59 (ddd, J=12.64, 7.42, 3.02 Hz, 1H) 5.08 (q, J=6.96 Hz, 1H) 7.20-7.30 (m, 5H) 7.34 (t, J=7.15 Hz, 2H) 7.41-7.45 (m, 2H). MS (ESI) m/z 388, 390 (M+H)+.

32D

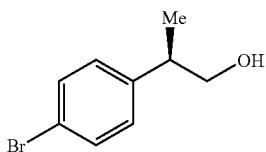

To 32C (2.5 g, 6.44 mmol) in THF (8 mL) at 0° C. was added 2.0 M LiBH₄ in THF (8.0 mL, 16.00 mmol) slowly. The mixture was stirred for 2 h. It was quenched with 5.0 mL 1.0 N NaOH at 0° C. and stirred for 1.0 h. The crude was filtered through a pad of wet celite, extracted with EtOAc and washed with brine, dried over Na₂SO₄. The crude product in small amount of CHCl₃ was charged to a 80 g silica gel column, eluted with hexanes for 8 min and then ethyl acetate in hexanes from 0-35% in 18 min gradient time to give 32D (0.89 g, 4.14 mmol, 64.3% yield) as a white solid. ¹H NMR (400 MHz, CDCl₃) δ ppm 1.26 (d, J=7.15 Hz, 3H) 1.33 (t, J=5.50 Hz, 1H) 2.87-2.96 (m, 1H) 3.64-3.73 (m, 2H) 7.12 (d, J=8.24 Hz, 2H) 7.45 (d, J=8.25 Hz, 2H). MS (ESI) m/z 197, 199 (M+H)*.

32E

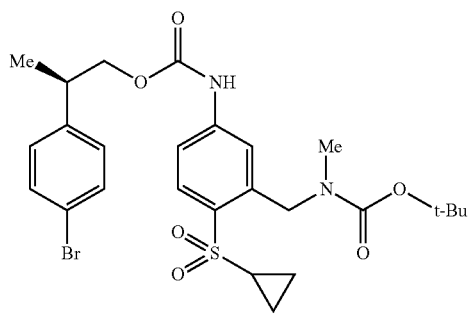 [SMILES: C[C@@H](COC(=O)Nc1ccc(S(=O)(=O)C2CC2)c(CN(C)C(=O)OC(C)(C)C)c1)c1ccc(Br)cc1]

Using a procedure analogous to that used to prepare 29A, Intermediate 11 was reacted with sodium bicarbonate and phosgene followed by 32D and TEA. The crude product was added to a silica gel column (40 g) and was eluted with EtOAc/hexanes (2-40% in 15 min) to give 32E (1.27 g, 2.184 mmol, 94% yield) as a white solid. ¹H NMR (400 MHz, CDCl₃) δ ppm 0.96-1.04 (m, 2H) 1.27-1.32 (m, 2H) 1.27 (d, J=7.80 Hz, 3H) 1.38-1.49 (br s, 9H) 2.50 (s, 1H) 2.92 (s, 3H) 3.06-3.15 (m, 1H) 4.20-4.28 (m, 2H) 4.90 (s, 2H) 6.8-7.0 (br, 1H) 7.11 (d, J=8.25 Hz, 2H) 7.44 (d, J=8.25 Hz, 2H) 7.5-7.6 (br, 1H) 7.85 (d, J=8.79 Hz, 1H). MS (ESI) m/z 581, 583 (M+H)+.

32F

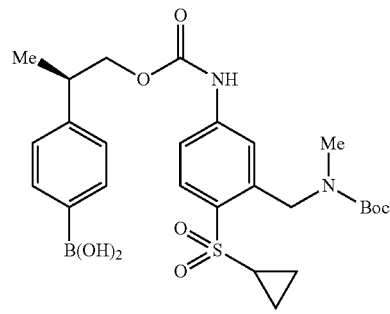 [SMILES: C[C@@H](COC(=O)Nc1ccc(S(=O)(=O)C2CC2)c(CN(C)C(=O)OC(C)(C)C)c1)c1ccc(B(O)O)cc1]

Using a procedure analogous to that used to prepare 29B, 32E was reacted with bis(neopentyl glycolato)diboron), potassium acetate and. (1,1'-bis(diphenylphosphino)ferrocene)-dichloropalladium(II). The crude was purified by flash chromatography (EtOAc/hexanes 2% to 65% and preparative HPLC (CH₃CN/H₂O, 0.1% TFA) to yield 32F (1.0 g, 1.830 mmol, 84% yield) as a white solid. ¹H NMR (400 MHz, methanol-d₄) δ ppm 1.02-1.09 (m, 2H) 1.15-1.20 (m, 2H) 1.33 (d, J=7.15 Hz, 3H) 1.38 (brs, 4H) 1.51 (brs, 45H) 2.76 (br s, 1H) 2.94 (s, 3H) 3.10-3.20 (m, 1H) 4.21-4.31 (m, 2H) 4.89 (s, 2H) 7.29 (d, J=8.25 Hz, 2H) 7.40-7.50 (br, 1H) 7.56 (d, J=7.70 Hz, 2H) 7.78 (d, J=8.79 Hz, 1H); MS (ESI) m/z 547 (M+H)+.

32G

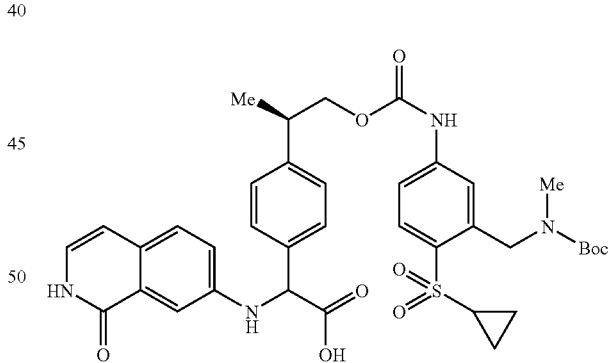

Using a procedure analogous to that used to prepare 1E, 32F (200 mg, 0.366 mmol), Intermediate 3, and glyoxylic acid monohydrate were reacted and purified by flash chromatography (2% to 25% MeOH in CH₂Cl₂) to give 32G (230 mg, 0.320 mmol, 87% yield) as a solid. ¹H NMR (400 MHz, methanol-D₄) δ ppm 1.01-1.09 (m, 2H) 1.15-1.20 (m, 2H) 1.31 (d, J=2.20 Hz, 2H) 1.37 (brs, 4H) 1.49 (brs, 5H) 2.75 (d, J=6.05 Hz, 1H) 2.93 (s, 3H) 3.09-3.19 (m, 1H) 4.24 (d, J=6.60 Hz, 2H) 4.88 (s, 2H) 5.16 (s, 1H) 5.48 (s, 1H) 6.52 (d, J=7.15 Hz, 1H) 6.89 (d, J=7.15 Hz, 1H) 7.19 (dd, J=8.52, 2.47 Hz, 1H) 7.26-7.34 (m, 3H) 7.40 (d, J=8.79 Hz, 1H) 7.46-7.57 (m, 4H) 7.77 (d, J=8.79 Hz, 1H). MS (ESI) m/z 719 (M+H)+.

32H

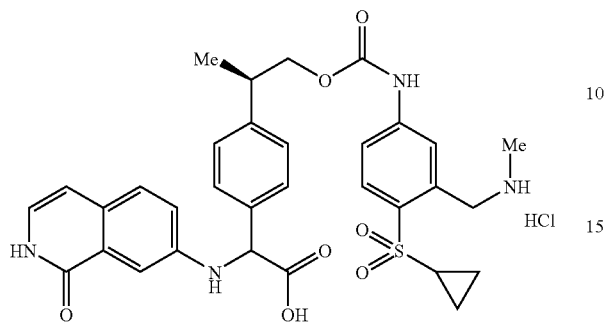

To 32G (217 mg, 0.302 mmol) was added 4.0 N HCl/dioxane (5.2 mL, 20.80 mmol). The mixture was stirred at rt for 1.0 h. LC-MS indicated a clean reaction. Solvent was removed under vacuum, chased once with EtOAc and dried under high vacuum over night to give 32H (210 mg, 0.321 mmol, 106% yield) as a slightly yellow solid. $^1$H NMR (400 MHz, methanol-$d_4$) δ ppm 0.98-1.04 (m, 2H) 1.16 (dd, J=7.42, 3.02 Hz, 2H) 1.23 (d, J=7.15 Hz, 3H) 2.69 (s, 3H) 2.75-2.80 (m, 1H) 3.09 (m, 1H) 4.16-4.24 (m, 2H) 4.38 (s, 2H) 5.20 (d, J=2.20 Hz, 1H) 5.40 (s, 1H) 6.53 (d, J=7.15 Hz, 1H) 6.94 (d, J=7.15 Hz, 1H) 7.22-7.30 (m, 3H) 7.37-7.46 (m, 4H) 7.51-7.56 (m, 1H) 7.76-7.85 (m, 2H). MS (ESI) m/z 619 (M+H)+.

Example 32

To a solution of BOP (284 mg, 0.641 mmol) and DMAP (157 mg, 1.282 mmol) in CH$_2$Cl$_2$ (35 ml) and DMF (4.0 ml) at 40° C. was added a solution of 32I1 (210 mg, 0.321 mmol) and DIEA (0.112 mL, 0.641 mmol) in DMF (4.0 mL) via a syringe pump over 4.0 h. To the reaction mixture was added 0.5 N HCl (30 mL). Layer separated, aqueous was extracted with one more CH$_2$Cl$_2$ (30 mL). The organic layers were washed with sat. NaHCO$_3$/brine and dried over Na$_2$SO$_4$. After evaporation of solvent, it was dissolved in MeOH/DMSO (4.0 mL, 1:1) and purified (2 injections) by preparative HPLC equipped with a C18 Phenomenex Luna AXIA column (30 mm×75 cm, 5µ) with the UV detector set at 254 nm. The separations were performed using a gradient method: 10-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The mixture of diatereomers (80 mg) was dissolved in 7.0 mL of 50/50 Methanol-Ethanol and 2.0 mL of Heptane and separated by a Chiral Regis Whelk-01 (R,R), 250×20 mm column eluting with 60% (50/50 Methanol-Ethanol): 40% Heptane at 20 mL/min to obtain the first peak (RT=9 min, 35 mg) and the second peak (RT=15 min, 22 mg). The second peak was confirmed to be Example 32: $^1$H NMR (500 MHz, methanol-$d_4$) δ ppm 0.97 (m, 1H) 1.01-1.08 (m, 2H) 1.23 (m, 1H) 1.36 (d, J=7.15 Hz, 3H) 2.83-2.89 (m, 1H) 3.02 (ddd, J=11.13, 7.01, 4.40 Hz, 1H) 3.39 (s, 3H) 3.89 (dd, J=10.72, 4.12 Hz, 1H) 4.26 (d, J=17.60 Hz, 1H) 4.54 (t, J=11.00 Hz, 1H) 5.67 (s, 1H) 5.75 (d, J=17.05 Hz, 1H) 6.48 (s, 1H) 6.54 (d, J=7.15 Hz, 1H) 6.81-6.85 (m, 1H) 6.91 (d, J=7.15 Hz, 1H) 7.07 (d, J=7.70 Hz, 1H) 7.17 (d, J=7.70 Hz, 1H) 7.21 (dd, J=8.52, 2.47 Hz, 1H) 7.41 (d, J=8.80 Hz, 2H) 7.50 (d, J=8.25 Hz, 1H) 7.70 (d, J=8.25 Hz, 1H) 7.82 (d, J=6.05 Hz, 1H); MS (ESI) m/z 601 (M+H)+; Analytical HPLC (Method A): Col A: 7.50 min., 98%; Col B: 7.51 min, 98%.

Example 33

(2R,15R)-7-Cyclopropanesulfonyl-15-ethyl-4-methyl-2-(1-oxo-1,2-dihydro-isoquinolin-7-ylamino)-13-oxa-4,11-diaza-tricyclo[14.2.2.16,10]henicosa-1(19),6,8,10(21),16(20),17-hexaene-3,12-dione

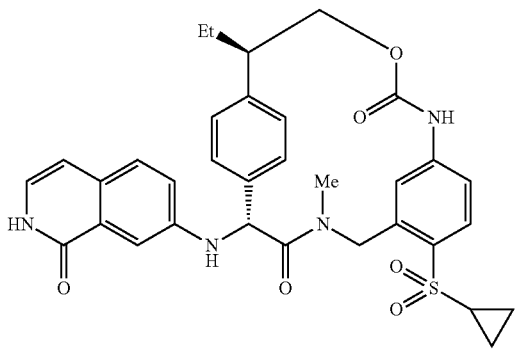 [SMILES: CC[C@H]1COC(=O)Nc2ccc(S(=O)(=O)C3CC3)c(c2)CN(C)C(=O)[C@H](Nc2ccc3cc[nH]c(=O)c3c2)c2ccc1cc2]

33A

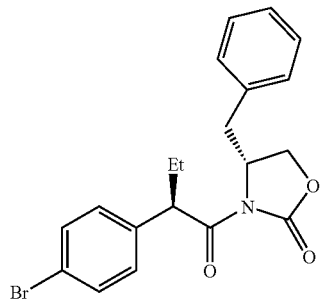 [SMILES: CC[C@@H](C(=O)N1C(=O)OC[C@H]1Cc1ccccc1)c1ccc(Br)cc1]

Using a procedure analogous to that used to prepare 17F, 32B (4.0 g, 10.69 mmol) was reacted with NaHMDS and iodoethane and purified by column chromatography (EtOAc/hexanes 0-28%) to give 33A (2.18 g, 5.42 mmol, 50.7% yield) as a semi-solid. $^1$H NMR (400 MHz, CDCl$_3$) δ ppm 0.81 (t, J=7.15 Hz, 3H) 1.67-1.78 (m, 1H) 2.05 (ddd, J=13.88, 7.15, 7.01 Hz, 1H) 2.68 (dd, J=13.47, 9.62 Hz, 1H) 3.25 (dd, J=13.74, 3.30 Hz, 1H) 3.95-4.03 (m, 2H) 4.46-4.52 (m, 1H) 4.79 (t, J=7.42 Hz, 1H) 7.10-7.20 (m, 5H) 7.23 (t, J=7.15 Hz, 2H) 7.33 (d, J=8.25 Hz, 2H); MS (ESI) m/z 402, 404 (M+H)+.

33B

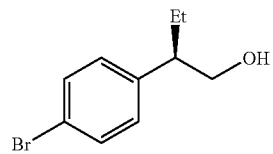 [SMILES: CC[C@@H](CO)c1ccc(Br)cc1]

Using a procedure analogous to that used to prepare 32D, 32A (3.57 g, 9.54 mmol) was reacted with LiBH$_4$ and purified by column chromatography (EtOAc/hexanes 0-35%) to give 33B (810 mg, 3.54 mmol, 65.2% yield) as a colorless oil. $^1$H NMR (400 MHz, CDCl$_3$) δ ppm 0.83 (t, J=7.15 Hz, 3H) 1.23-1.34 (m, 1H) 1.53 (ddd, J=9.07, 7.15, 6.87 Hz, 1H) 1.58 (s, 1H) 1.70-1.81 (m, 1H) 2.62-2.70 (m, 1H) 3.67-3.79 (m, 2H) 7.09 (d, J=8.79 Hz, 2H) 7.46 (d, J=8.24 Hz, 2H).

33C

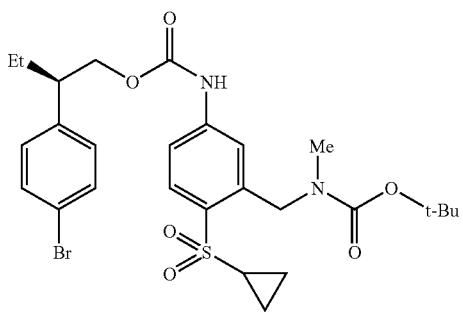 [SMILES: CC[C@@H](COC(=O)Nc1ccc(S(=O)(=O)C2CC2)c(CN(C)C(=O)OC(C)(C)C)c1)c1ccc(Br)cc1]

Using a procedure analogous to that used to prepare 29A, Intermediate 11 was reacted with sodium bicarbonate and phosgene followed by 33B and TEA. The crude product was added to a silica gel column (40 g) and was eluted with EtOAc/hexanes (2-40% in 15 min) to give to give 33C (742 mg, 1.246 mmol, 81% yield) as a white solid. $^1$H NMR (400 MHz, CDCl$_3$) δ ppm 0.82 (t, J=7.15 Hz, 3H) 0.99 (q, J=6.78 Hz, 2H) 1.28-1.62 (m, 13H) 1.77 (ddd, J=13.33, 6.87, 6.73 Hz, 1H) 2.50 (s, 1H) 2.80-2.88 (m, 1H) 2.91 (s, 3H) 4.18-4.27 (m, 1H) 4.29-4.38 (m, 1H) 4.90 (s, 2H) 6.70-6.80 (m, 1H) 7.07 (d, J=7.70 Hz, 2H) 7.44 (d, J=7.70 Hz, 2H) 7.45-7.70 (m, 1H) 7.84 (d, J=8.79 Hz, 1H). MS (ESI) m/z 595, 597 (M+H)$^+$.

33D

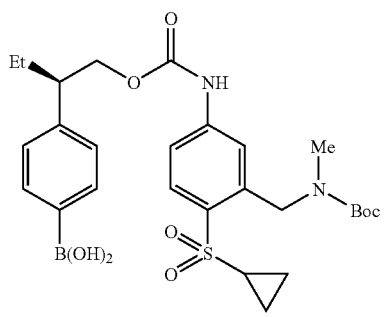 [SMILES: CC[C@@H](COC(=O)Nc1ccc(S(=O)(=O)C2CC2)c(CN(C)C(=O)OC(C)(C)C)c1)c1ccc(B(O)O)cc1]

Using a procedure analogous to that used to prepare 29B, 33C (742 mg, 1.246 mmol) was reacted with bis(neopentyl glycolato)diboron, potassium acetate and. (1,1'-bis(diphenylphosphino)ferrocene)-dichloropalladium(II). The crude was purified by flash chromatography (EtOAc/hexanes 2% to 65% and preparative HPLC (CH$_3$CN/H$_2$O, 0.1% TFA) to yield 33D (530 mg, 0.946 mmol, 76% yield) was obtained as a white solid. $^1$H NMR (400 MHz, methanol-d$_4$) δ ppm 0.84 (t, J=7.42 Hz, 3H) 1.02-1.10 (m, 2H) 1.16-1.21 (m, 2H) 1.38 (brs, 4H) 1.51 (brs, 5H) 1.60-1.72 (m, 1H) 1.80-1.91 (m, 1H) 2.75 (s, 1H) 2.86-2.93 (m, 1H) 2.94 (s, 3H) 4.26-4.37 (m, 2H) 4.89 (s, 2H) 7.26 (d, J=7.70 Hz, 2H) 7.3-7.4 (br, 2H) 7.57 (d, J=7.70 Hz, 2H) 7.77 (d, J=8.79 Hz, 1H); MS (ESI) m/z 561 (M+H)$^+$.

33E

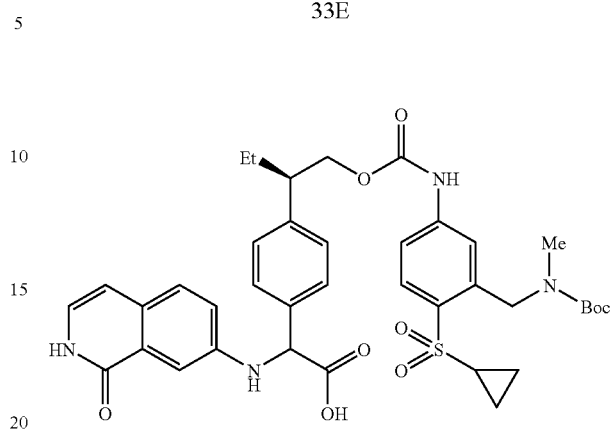

Using a procedure analogous to that used to prepare 1E, 33D (200 mg, 0.357 mmol), Intermediate 3, and glyoxylic acid monohydrate were reacted and purified by flash chromatography (1% to 18% MeOH in CH$_2$Cl$_2$) to give 33E (200 mg, 0.273 mmol, 76% yield) as a slightly yellow solid. $^1$H NMR (400 MHz, CDCl$_3$) δ ppm 0.83 (t, J=6.87 Hz, 3H) 1.01-1.08 (m, 2H) 1.15-1.20 (m, 2H) 1.37 (brs, 5H) 1.49 (brs, 4H) 1.58-1.69 (m, 1H) 1.77-1.87 (m, 1H) 2.76 (d, J=5.50 Hz, 1H) 2.88 (d, J=6.60 Hz, 1H) 2.93 (s, 3H) 4.22-4.29 (m, 1H) 4.29-4.37 (m, 1H) 4.88 (s, 2H) 5.17 (s, 1H) 6.53 (d, J=6.60 Hz, 1H) 6.89 (d, J=7.15 Hz, 1H) 7.20 (dd, J=8.52, 2.47 Hz, 1H) 7.27 (d, J=7.70 Hz, 2H) 7.30-7.34 (m, 1H) 7.40 (d, J=8.79 Hz, 1H) 7.45-7.57 (m, 4H) 7.76 (d, J=8.79 Hz, 1H). MS (ESI) m/z 733 (M+H)$^+$.

33F

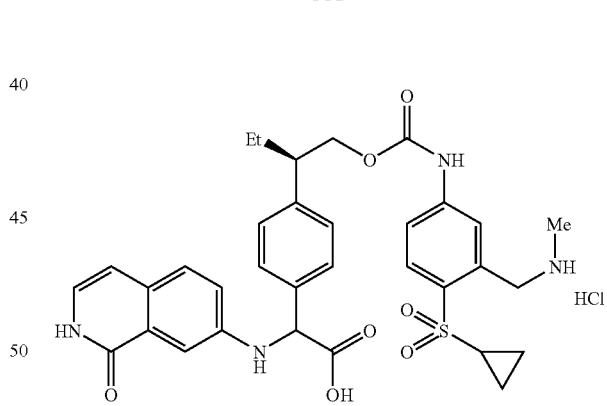

To 33E (200 mg, 0.273 mmol) was added 4.0 N HCl/dioxane (5.0 mL, 20.00 mmol). The mixture was stirred at rt for 1.0 h. LC-MS indicated a clean reaction. Solvent was removed under vacuum, chased once with EtOAc and dried under high vacuum over night to give 33F (190 mg, 0.284 mmol, 104% yield) as a slightly yellow solid. $^1$H NMR (400 MHz, methanol-d$_4$) δ ppm 0.70-0.77 (t, J=7.8 Hz, 3H) 0.98-1.04 (m, 2H) 1.12-1.19 (m, 2H) 1.49-1.61 (m, 1H) 1.69-1.79 (m, 1H) 2.69 (s, 3H) 2.77 (ddd, J=12.64, 7.97, 4.67 Hz, 1H) 2.83 (br s, 1H) 4.20 (ddd, J=10.99, 7.70, 3.85 Hz, 1H) 4.25-4.33 (m, 1H) 4.37 (s, 2H) 5.18 (d, J=2.75 Hz, 1H) 6.51 (d, J=7.15 Hz, 1H) 6.91 (d, J=6.05 Hz, 1H) 7.17-7.25 (m, 3H) 7.37-7.44 (m, 4H) 7.52 (d, J=8.79 Hz, 1H) 7.77-7.84 (m, 2H). MS (ESI) m/z 633 (M+H)$^+$.

Example 33

To a solution of BOP (251 mg, 0.568 mmol) and DMAP (139 mg, 1.136 mmol) in CH$_2$Cl$_2$ (40 ml) and DMF (6.0 ml) at 40° C. was added a solution of 33F (190 mg, 0.284 mmol) and DIEA (0.099 ml, 0.568 mmol) in DMF (4.0 mL) via a syringe pump over 4.0 h. To the reaction mixture was added 0.5 N HCl (30 mL). Layers were separated, aqueous was extracted with CH$_2$Cl$_2$ (30 mL) one more time. The organic layers were washed with sat. NaHCO$_3$/brine and dried over Na$_2$SO$_4$. After evaporation of solvent, it was dissolved in MeOH/DMSO (4.0 mL, 1:1) and purified (2 injections) by preparative HPLC equipped with a C18 Phenomenex Luna AXIA column (30 mm×75 cm, 5μ) with the UV detector set at 254 nm. The separations were performed using a gradient method: 5-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. A total of 78 mg (45% yield) as a mixture of 2 diastereoisomers was obtained. The mixture (70 mg) was dissolved in 8.0 mL of 50/50 Methanol-Ethanol and 2.0 mL of acetonitrile and separated by a Chiral Regis Whelk-01 (R,R), 250×20 mm column eluting with 60% (50/50 Methanol-Ethanol): 40% Heptane at 20 mL/min to obtain the first peak (RT=8.5 min, 38 mg) and the second peak (RT=14.5 min., 22 mg). The second peak was confirmed to be Example 33: $^1$H NMR (500 MHz, methanol-d$_4$) δ ppm 0.82 (m, 1H) 0.91 (t, J=7.42 Hz, 3H) 0.91 (m, 1H) 0.93-1.00 (m, 1H) 1.15-1.21 (m, 1H) 1.69-1.77 (m, 1H) 1.83 (ddd, J=13.88, 9.76, 7.15 Hz, 1H) 2.71-2.80 (m, 2H) 3.38 (s, 3H) 3.92 (dd, J=11.00, 3.85 Hz, 1H) 4.26 (d, J=17.60 Hz, 1H) 4.57 (t, J=11.00 Hz, 1H) 5.67 (s, 1H) 5.73 (d, J=17.05 Hz, 1H) 6.47 (s, 1H) 6.53 (d, J=6.60 Hz, 1H) 6.83 (dd, J=8.80, 2.20 Hz, 1H) 6.91 (d, J=7.15 Hz, 1H) 6.97 (d, J=8.25 Hz, 1H) 7.19 (d, J=8.80 Hz, 2H) 7.38 (d, J=8.25 Hz, 1H) 7.41-7.46 (m, 2H) 7.68 (d, J=8.80 Hz, 1H) 7.81 (d, J=6.60 Hz, 1H). MS (ESI) m/z 615 (M+H)$^+$ Analytical HPLC (Method A): Col A: 7.90 min, 99%; Col B: 7.86 min, 99%.

Example 36

[(2R,15R)-7-Cyclopropanesulfonyl-4-methyl-3,12-dioxo-2-(1-oxo-1,2-dihydro-isoquinolin-7-ylamino)-13-oxa-4,11-diaza-tricyclo[14.2.2.16,10]henicosa-1(19),6,8,10(21),16(20),17-hexaen-15-yl]-carbamic acid benzyl ester

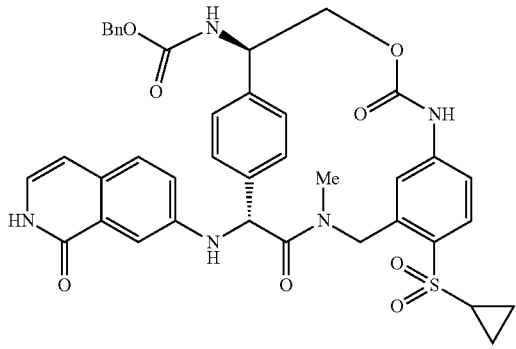 [SMILES: CN1Cc2cc(ccc2S(=O)(=O)C2CC2)NC(=O)OC[C@H](NC(=O)OCc2ccccc2)c2ccc(cc2)[C@@H](Nc2ccc3cc[nH]c(=O)c3c2)C1=O]

36A

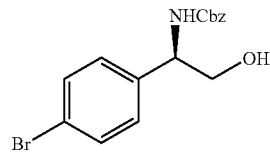 [SMILES: O=C(N[C@@H](CO)c1ccc(Br)cc1)OCc1ccccc1]

A 100 mL round-bottom flask was charged with benzyl carbamate (937 mg, 6.2 mmol) and n-PrOH (8.0 ml). To this stirred solution was added a freshly prepared aqueous solution of sodium hydroxide (244 mg, 6.1 mmol) dissolved in Water (15 mL), followed by freshly prepared tert-butyl hypochlorite (0.701 mL, 6.1 mmol). After 5 min a solution of (DHQD)$_2$PHAL (78 mg, 0.100 mmol) in n-PrOH (7.0 mL) was added; the reaction mixture should be homogeneous at this point. 1-bromo-4-vinylbenzene (0.261 mL, 2.0 mmol) dissolved in 10 mL of n-PrOH was then added, and followed by potassium osmate dihydrate (29.5 mg, 0.080 mmol). The light green solution was stirred at rt and became light yellow after 1.0 h, indicating completion of reaction. The reaction mixture was then cooled to ice-bath and quenched by saturated sodium sulfite (20 mL). The two phases were separated and aqueous phase was extracted with EtOAc, and dried over Na$_2$SO$_4$. After evaporation of solvent, a brown solid was obtained. The crude product was purified using a preparative HPLC equipped with a C18 Phenomenex Luna AXIA column (30 mm×75 cm, 5μ) with the UV detector set at 254 nm. The separations were performed using a gradient method: 25-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected to give 36A (300 mg, 43% yield). [$^a$]$_{25}$D=−31.3 (lit of the enantiomer+33.6) (c=0.5, 95% EtOH).

36B

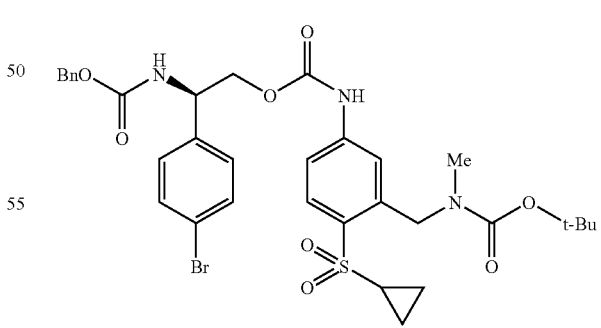

Using a procedure analogous to that used to prepare 29A, Intermediate 11 was reacted with sodium bicarbonate and phosgene followed by 36A (486 mg, 1.388 mmol) and TEA. The crude product was added to a silica gel column (40 g) and was eluted with EtOAc/hexanes (2-60% in 15 min) to give 36B (1.21 g) as a white solid. MS (ESI) m/z 716, 718 (M+H)$^+$.

36C

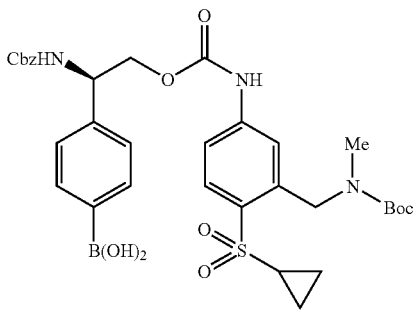 [SMILES: CN(Cc1cc(NC(=O)OC[C@H](NC(=O)OCc2ccccc2)c2ccc(B(O)O)cc2)ccc1S(=O)(=O)C1CC1)C(=O)OC(C)(C)C]

Using a procedure analogous to that used to prepare 29B, 36B (1200 mg, 1.674 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 2% to 65% and preparative HPLC (CH$_3$CN/H$_2$O, 0.1% TFA) to yield 36C (800 mg, 1.174 mmol, 70.1% yield) as a white solid. MS (ESI) m/z 683 (M+H)$^+$.

36D

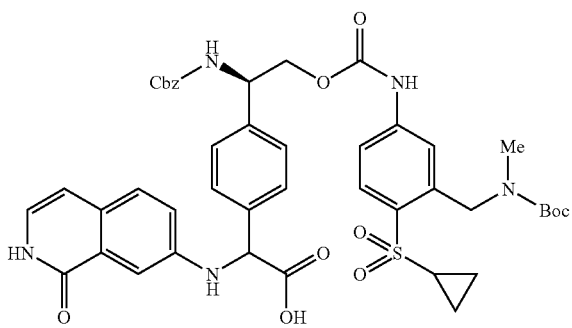 [SMILES: CN(Cc1cc(NC(=O)OC[C@H](NC(=O)OCc2ccccc2)c2ccc(C(Nc3ccc4cc[nH]c(=O)c4c3)C(=O)O)cc2)ccc1S(=O)(=O)C1CC1)C(=O)OC(C)(C)C]

Using a procedure analogous to that used to prepare 1E, 36C (681 mg, 0.999 mmol), Intermediate 3, and glyoxylic acid monohydrate were reacted and purified by flash chromatography (2% to 25% MeOH in CH$_2$Cl$_2$) to give a crude product which was further purified by prep HPLC to give 36D (260 mg, 0.304 mmol, 30.5% yield). MS (ESI) m/z 854 (M+H)$^+$.

36E

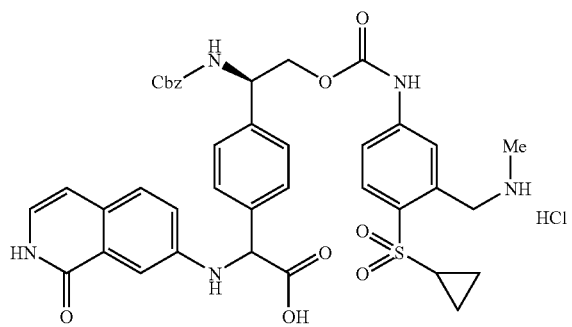 [SMILES: CNCc1cc(NC(=O)OC[C@H](NC(=O)OCc2ccccc2)c2ccc(C(Nc3ccc4cc[nH]c(=O)c4c3)C(=O)O)cc2)ccc1S(=O)(=O)C1CC1 ; Cl]

To 36D (0.26 g, 0.304 mmol) was added 4.0 N HCl/dioxane (3.81 mL, 15.22 mmol). The mixture was stirred at rt for 1.0 h. Solvent was removed under vacuum, chased once with EtOAc and dried under high vacuum over night to give 36E (100 mg, 0.127 mmol, 41.6% yield) as a slightly yellow solid. MS (ESI) m/z 754 (M+H)$^+$.

36F

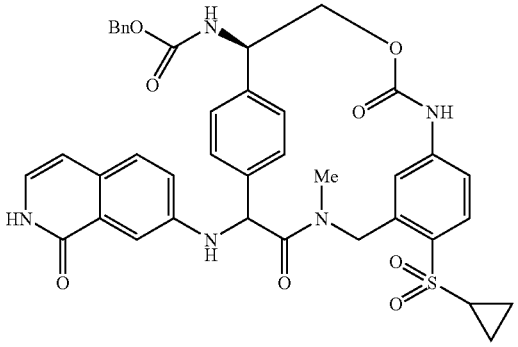 [SMILES: CN1Cc2cc(ccc2S(=O)(=O)C2CC2)NC(=O)OC[C@H](NC(=O)OCc2ccccc2)c2ccc(cc2)C(Nc2ccc3cc[nH]c(=O)c3c2)C1=O]

To a solution of BOP (112 mg, 0.253 mmol) and DMAP (61.8 mg, 0.506 mmol) in CH$_2$Cl$_2$ (20 mL) and DMF (5.0 ml) at 37° C. was added a solution of 36E (100 mg, 0.127 mmol) and DIEA (0.044 mL, 0.253 mmol) in DMF (4.0 mL) via a syringe pump over 4.0 h. The reaction was left stirring over night at rt. After evaporation of solvent, it was partitioned in MeOH, the insolubale material was filtered. The filtrate was concentrated and dissolved in MeOH/DMSO (4.0 mL, 1:1) and purified (2 injections) by preparative HPLC equipped with a C18 Phenomenex Luna AXIA column (30 mm×75 cm, 5 g) with the UV detector set at 254 nm. The separations were performed using a gradient method: 0-100% B in 10 mins; then 100% B in 2 min with a flow rate of 40 mL/min. Solvent B is 90% acetonitrile-10% water-0.1% TFA and solvent A is 10% acetonitrile-90% water-0.1% TFA to give the diastereoisomeric mixture 36F (12 mg, 13% yield). MS (ESI) m/z 735 (M+H)$^+$.

Example 36

36F (12 mg) was dissolved in 3.0 mL of 50/50 Methanol-Ethanol and 2.0 mL of Heptane and separated by a Chiral Regis Whelk-01 (R,R), 250×20 mm column eluting with 60% (50/50 Methanol-Ethanol): 40% Heptane at 20 mL/min to obtain the first peak (RT=14 min, 4.4 mg) and then the second peak (RT=22 min., 3.3 mg). The second peak was confirmed to be Example 36: $^1$H NMR (500 MHz, methanol-d$_4$) δ ppm 0.71-1.25 (m, 4H) 2.72 (m, 1H) 3.37 (s, 3H) 4.00 (dd, J=9.90, 4.40 Hz, 1H) 4.25 (d, J=17.60 Hz, 1H) 4.59-4.74 (m, 4H) 5.06 (s, 2H) 5.69 and 5.75 (s, 2H) 6.44 (s, 1H) 6.54 (d, J=7.15 Hz, 1H) 6.86 (d, J=8.25 Hz, 1H) 6.91 (d, J=6.60 Hz, 1H) 6.99 (d, J=8.25 Hz, 1H) 7.20 (d, J=8.25 Hz, 2H) 7.24-7.33 (m, 4H) 7.36-7.44 (m, 2H) 7.57 (d, J=7.70 Hz, 1H) 7.73 (d, J=8.80 Hz, 1H) 7.87 (d, J=8.25 Hz, 1H); MS (ESI) m/z 736 (M+H)$^+$ Analytical HPLC (Method A): Col A: 7.94 min, 99%; Col B: 7.96 min, 98%.

Example 37

(R)-7-Cyclopropanesulfonyl-15-fluoro-20-methoxy-4-methyl-2-(1-oxo-1,2-dihydro-isoquinolin-7-ylamino)-13-oxa-4,11-diaza-tricyclo[14.2.2.1.6,10]henicosa-1(19),6,8,10(21),16(20),17-hexaene-3,12-dione

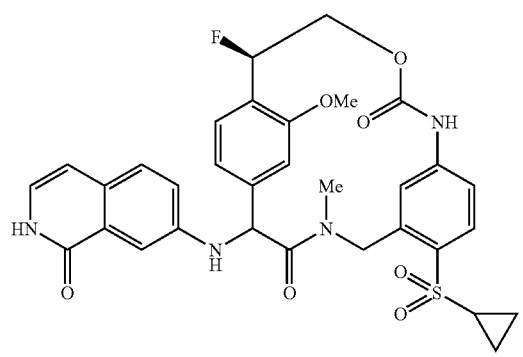 [SMILES: COc1cc2ccc1[C@@H](F)COC(=O)Nc1ccc(S(=O)(=O)C3CC3)c(c1)CN(C)C(=O)C2Nc1ccc2cc[nH]c(=O)c2c1]

37A

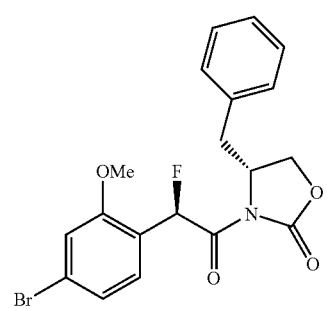 [SMILES: COc1cc(Br)ccc1[C@@H](F)C(=O)N1C(=O)OC[C@H]1Cc1ccccc1]

To (R)-4-benzyl-3-(2-(4-bromo-2-methoxyphenyl)acetyl)oxazolidin-2-one (2.0 g, 4.95 mmol) in THF (15 ml) at −78° C. was added 1.0 M NaHMDS in THF (5.94 ml, 5.94 mmol) dropwise. The mixture was stirred for 40 min before it was cannulated into a solution of N-fluoro-N-(phenylsulfonyl)benzenesulfonamide (2.028 g, 6.43 mmol) in THF (10.0 mL) at −78° C. The mixture was stirred for 60 min at −78° C. and then allowed to warm to rt and stirred for additional 1.5 h. It was quenched with sat. NH$_4$Cl, extracted with EtOAc, washed with sat. NaHCO$_3$, brine and dried over Na$_2$SO$_4$. After removal of solvent, the crude was treated with CHCl$_3$, the precipitate formed was filtered. The filtrate was concentrated and charged to a 40 g silica gel column, eluted with hexanes for 6 min and then with ethyl acetate in hexanes from 0-30% in 15 min gradient time to give 37A (2.2 g, 4.69 mmol, 95% yield) as a white solid. $^1$H NMR (400 MHz, CDCl$_3$) δ ppm 2.82 (dd, J=13.47, 9.62 Hz, 1H) 3.35 (dd, J=13.19, 3.30 Hz, 1H) 3.81-3.83 (m, 3H) 4.09-4.18 (m, 2H) 4.59-4.66 (m, 1H) 6.96-7.30 (m, 9H); $^{19}$F NMR −178.04; MS (ESI) m/z 402, 404 (M-F).

37B

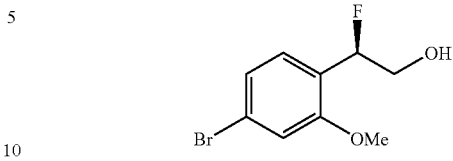

Using a procedure analogous to that used to prepare 32D, 37A (3.57 g, 9.54 mmol) was reacted with LiBH$_4$ and purified by column chromatography (EtOAc/hexanes 0-60%) to give 37B (980 mg, 3.93 mmol, 76% yield) as a clear oil. $^1$H NMR (400 MHz, CDCl$_3$) δ ppm 1.90 (s, 1H) 3.75-3.85 (m, 5H) 5.84 (ddd, $^2$J$_{HF}$=47.82, J=7.15, 2.75 Hz, 1H) 7.00 (s, 1H) 7.13 (d, J=8.24 Hz, 1H) 7.26 (d, J=4.40 Hz, 1H); $^{19}$F NMR −195.09; MS (ESI) m/z 229, 231 (M-F).

37C

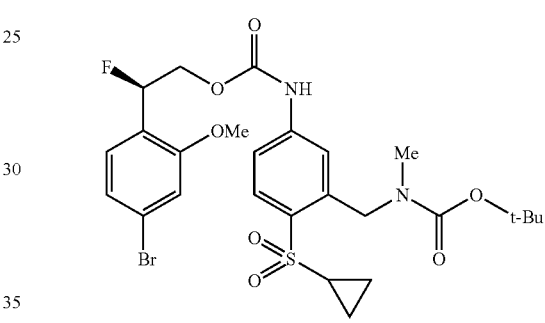

Using a procedure analogous to that used to prepare 29A, Intermediate 11 was reacted with sodium bicarbonate and phosgene followed by 37B (490 mg, 1.967 mmol) and TEA. The crude product was added to a silica gel column (40 g) and was eluted with EtOAc/hexanes (2-60% in 15 min) to give 37C (907 mg, 1.474 mmol, 82% yield) as a white solid. $^1$H NMR (400 MHz, CDCl$_3$) δ ppm 0.98-1.05 (m, 2H) 1.29 (d, J=2.75 Hz, 2H) 1.38 (brs, 5H) 1.50 (brs, 4H) 2.52 (s, 1H) 2.93 (s, 3H) 3.84 (s, 3H) 4.31-4.52 (m, 2H) 4.92 (brs, 2H) 6.90 (br 1H) 7.02 (s, 1H) 7.15 (d, J=8.25 Hz, 1H) 7.26-7.32 (m, 1H) 7.6 (br, 1H) 7.87 (d, J=8.79 Hz, 1H); $^{19}$F NMR −192.67; MS (ESI) m/z 615, 617 (M+H)$^+$.

37D

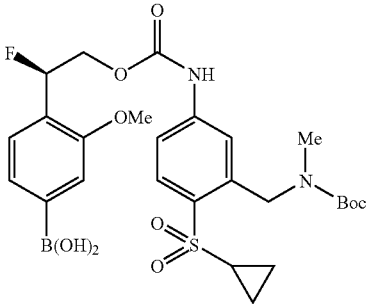 [SMILES: COc1cc(B(O)O)ccc1[C@@H](F)COC(=O)Nc1ccc(S(=O)(=O)C2CC2)c(CN(C)C(=O)OC(C)(C)C)c1]

Using a procedure analogous to that used to prepare 29B, 37C (905 mg, 1.470 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 2% to 65% and preparative HPLC (CH$_3$CN/H$_2$O, 0.1% TFA) to give 37D (552 mg, 0.951 mmol, 64.7% yield) as a white solid after lyophilization. $^1$H NMR (400 MHz, methanol-D$_4$) δ pp 1.03-1.10 (m, 2H) 1.19 (ddd, J=7.01, 4.53, 4.40 Hz, 2H) 1.39 (brs, 5H) 1.50 (br s, 4H) 2.79 (m, 1H) 2.95 (s, 3H) 3.87 (s, 3H) 4.41-4.49 (m, 2H) 4.90 (s, 2H) 7.18-7.59 (m, 5H) 7.80 (d, J=8.79 Hz, 1H). $^{19}$F NMR −193.56; MS (ESI) m/z 581 (M+H)$^+$.

37E

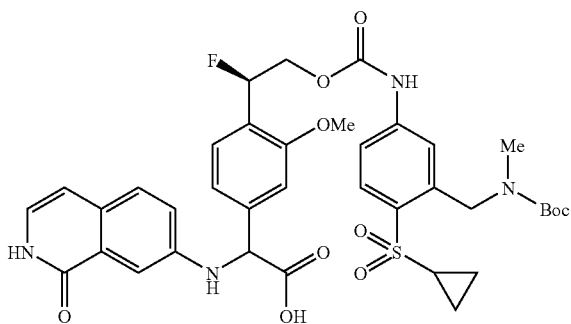 [SMILES: COc1cc(C(Nc2ccc3cc[nH]c(=O)c3c2)C(=O)O)ccc1[C@@H](F)COC(=O)Nc1ccc(S(=O)(=O)C2CC2)c(CN(C)C(=O)OC(C)(C)C)c1]

Using a procedure analogous to that used to prepare 1E, 37D (200 mg, 0.345 mmol), Intermediate 3, and glyoxylic acid monohydrate were reacted for 30 min and purified by flash chromatography (2% to 25% MeOH in CH$_2$Cl$_2$) to give 37E (180 mg, 45% yield, ca 70% purity). MS (ESI) min/z 753 (M+H)$^+$.

37F

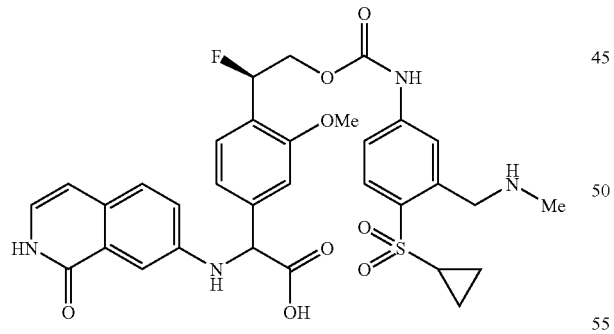

To 37E (180 mg, 0.239 mmol) was added 4.0 N HCl in dioxane (4184 μL, 16.74 mmol) and DMF (0.5 mL). The mixture was stirred at rt for 1.0 h. Solvent was removed. The crude residue was purified using a preparative HPLC to yield 37F (99 mg, 0.106 mmol, 44.4% yield) was obtained as a solid after lyophilization. $^1$H NMR (400 MHz, acetonitrile-d$_3$) δ ppm 0.99-1.10 (m, 2H) 1.17 (d, J=3.85 Hz, 2H) 2.65-2.76 (m, 4H) 3.68 and 3.77 (s, 3H) 4.34 (m, 4H) 5.23 (s, 1H) 5.84-5.95 (m, 1H) 6.52 (d, J=5.50 Hz, 1H) 6.89 (d, J=6.60 Hz, 1H) 7.14-8.74 (m, 9H); $^{19}$F NMR −189.93; MS (ESI) m/z 653 (M+H)$^+$.

Example 37

To a solution of BOP (131 mg, 0.297 mmol) and DMAP (72.6 mg, 0.594 mmol) in CH$_2$Cl$_2$ (30 ml) and DMF (4.0 ml) at 32° C. was added a solution of 37F (97 mg, 0.149 mmol) and DIEA (0.078 ml, 0.446 mmol) in DMF (5.0 mL) via a syringe pump over 8 h. The reaction was left stirring over night at rt. After evaporation of solvent, it was partitioned in MeOH, the insolubale material was filtered. The filtrate was concentrated and dissolved in MeOH/DMSO (4.0 mL, 1:1) and purified (2 injections) by preparative HPLC equipped with a C18 Phenomenex Luna AXIA column (30 mm×75 cm, 5μ) with the UV detector set at 254 nm. The separations were performed using a gradient method: 10-85% B in 10 mins; then 85% B in 2 mins with a flow rate of 40 mL/min. Solvent B is 90% acetonitrile-10% water-0.1% TFA and solvent A is 10% acetonitrile-90% water-0.1% TFA. The desired fractions were collected to give Example 37 (17 mg). $^{19}$F NMR −197.3; MS (ESI) m/z 635 (M+H)$^+$. $^1$H NMR is complicated due to a mixture of two diastereoisomers: $^1$H NMR (400 MHz, acetonitrile-d$_3$) δ ppm 0.94-1.25 (m, 4H) 2.63-2.73 (m, 2H) 3.15 and 3.31 (s, 3H) 3.63 and 3.98 (s, 3H) 4.13-5.00 (m, 5H) 5.61-7.91 (m, 12H)

Example 38

(2R,15R)-7-Cyclopropanesulfonyl-15-fluoro-4-methyl-2-(1-oxo-1,2-dihydro-isoquinolin-7-ylamino)-13-oxa-4,11-diaza-tricyclo[14.2.2.16,10]henicosa-1 (19),6,8,10(21),16(20),17-hexaene-3,12-dione

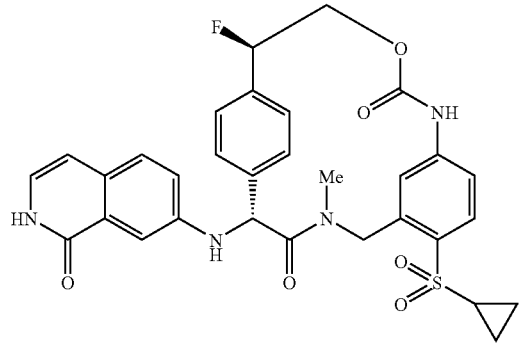 [SMILES: CN1Cc2cc(ccc2S(=O)(=O)C2CC2)NC(=O)OC[C@H](F)c2ccc(cc2)[C@@H](Nc2ccc3cc[nH]c(=O)c3c2)C1=O]

38A

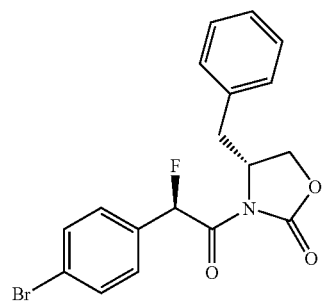 [SMILES: O=C1OC[C@@H](Cc2ccccc2)N1C(=O)[C@H](F)c1ccc(Br)cc1]

Using a procedure analogous to that used to prepare 37A, 32B (1.0 g, 2.67 mmol) was reacted with NaHMDS and N-fluoro-N-(phenylsulfonyl)benzenesulfonamide and purified by column chromatography (EtOAc/hexanes 0-25%) to give 38A (800 mg, 2.040 mmol, 76% yield) as a white semi-solid. $^1$H NMR (400 MHz, CDCl$_3$) δ ppm 2.87 (dd, J=13.47, 9.62 Hz, 1H) 3.42 (dd, J=13.19, 3.30 Hz, 1H) 4.16 (d, J=9.89 Hz, 1H) 4.19-4.23 (m, 1H) 4.57-4.63 (m, 1H) 6.90 (d, $^2J_{HF}$=48 Hz, 1H) 7.23 (d, J=6.60 Hz, 2H) 7.28-7.33 (m, 1H) 7.33-7.38 (m, 2H) 7.44-7.48 (m, 2H) 7.52-7.56 (m, 2H). $^{19}$F NMR (376 MHz, CDCl$_3$) δ ppm −173.40 (d, $^2J_{HF}$=48 Hz). MS (ESI) m/z 392, 394 (M+H)$^+$.

38B

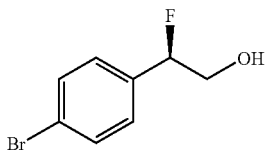

Using a procedure analogous to that used to prepare 32D, 38A (1.6 g, 4.08 mmol) was reacted with LiBH$_4$ and purified by column chromatography (EtOAc/hexanes 0-35%) to give 38B (600 mg, 2.74 mmol, 67.1% yield) as a white solid. $^1$H NMR (500 MHz, CDCl$_3$) δ ppm 3.77-3.93 (m, 2H) 5.55 (ddd, 2J$_H$=47.8, J=7.70, 3.30 Hz, 1H) 7.23 (d, J=8.25 Hz, 2H) 7.54 (d, J=8.25 Hz, 2H); $^{19}$F NMR (376 MHz, CDCl$_3$) δ ppm −187.6; MS (ESI) rz/z 219, 211 (M-F).

38C

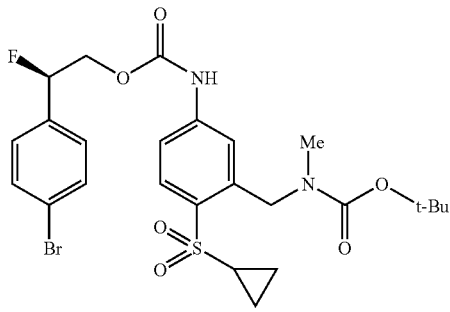 [SMILES: CN(Cc1cc(NC(=O)OC[C@H](F)c2ccc(Br)cc2)ccc1S(=O)(=O)C1CC1)C(=O)OC(C)(C)C]

Using a procedure analogous to that used to prepare 29A, Intermediate 11 was reacted with sodium bicarbonate and phosgene followed by 38B (450 mg, 2.054 mmol) and TEA. The crude product was added to a silica gel column (40 g) and was eluted with EtOAc/hexanes (2-40% in 15 min) to give 38C (782 mg, 1.336 mmol, 78% yield) as a slightly yellow solid. $^1$H NMR (400 MHz, CDCl$_3$) δ ppm 0.98-1.04 (m, 2H) 1.29 (d, J=2.20 Hz, 2H) 1.39 (brs, 5H) 1.50 (brs, 4H) 2.51 (brs, 1H) 2.93 (s, 3H) 4.32-4.44 (m, 2H) 4.92 (s, 2H) 5.65 (ddd, $^2J_{HF}$=48.4 Hz, J=7.7, 2.8 Hz, 1H) 7.23-7.30 (m, 4H) 7.54 (d, J=8.24 Hz, 2H) 7.87 (d, J=8.79 Hz, 1H). $^{19}$F NMR (376 MHz, Solvent) δ ppm −185.44 ppm; MS (ESI) m/z 585, 587 (M+H)$^+$.

38D

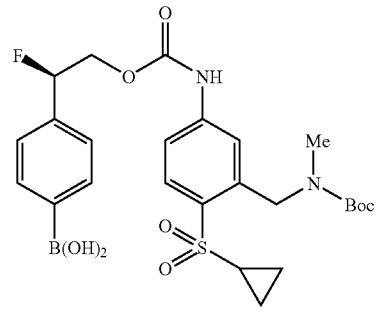 [SMILES: CN(Cc1cc(NC(=O)OC[C@H](F)c2ccc(B(O)O)cc2)ccc1S(=O)(=O)C1CC1)C(=O)OC(C)(C)C]

Using a procedure analogous to that used to prepare 29B, 38C (780 mg, 1.332 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 2% to 65% and preparative HPLC (CH$_3$CN/H$_2$O, 0.1% TFA) to yield 38D (515 mg, 0.936 mmol, 70.2% yield) was obtained as a white solid after lyophilization. $^1$H NMR (400 MHz, methanol-d$_4$) δ ppm 1.06 (td, J=7.25, 4.39 Hz, 2H) 1.17-1.21 (m, 2H) 1.39 (brs, 5H) 1.51 (brs, 4H) 2.71-2.82 (m, 1H) 2.95 (s, 3H) 4.40-4.50 (m, 2H) 5.80 (ddd, $^2J_{HF}$=48.78 Hz, J=6.15, 3.96 Hz, 1H) 7.37-7.84 (7 aromatic H); $^{19}$F NMR (376 MHz, Solvent) δ ppm −187.05; MS (ESI) m/z 565 (M+H)$^+$.

38E

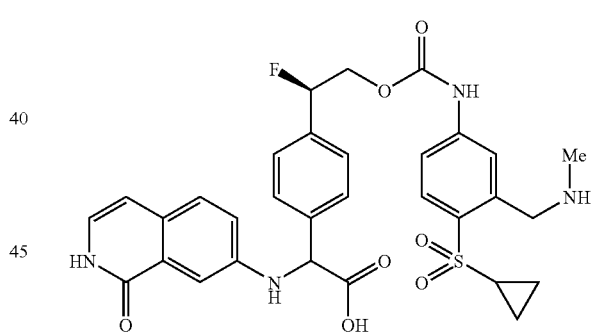

To a mixture of 38D (100 mg, 0.182 mmol), Intermediate 3 (37.8 mg, 0.236 mmol) and Glyoxylic acid monohydrate (18.40 mg, 0.200 mmol) was added Acetonitrile (2.0 mL) and DMF (0.5 mL). The mixture was placed in a microwave reactor at 100° C. for 25 min. The crude was partitioned between CHCl$_3$ and brine. The organic phase was dried over Na$_2$SO$_4$. Solvent was completely removed and the crude was treated with 4.0N HCl (1.8 mL) in EtOAC (1.5 mL) for 1.0 h. Solvent was removed and the crude was purified using a preparative HPLC to give 38E (50 mg, 30%) as a slightly yellow solid after lyophilization. $^1$H NMR (400 MHz, acetonitrile-d$_3$) d ppm 1.00-1.10 (m, 2H) 1.14-1.25 (m, 2H) 2.65-2.74 (m, 4H) 4.32-4.42 (m, 4H) 5.23 (s, 1H) 5.59-5.70 (m, 1H) 6.48 (d, J=5.50 Hz, 1H) 6.85 (d, J=6.60 Hz, 1H) 7.13-7.21 (m, 2H) 7.35 (d, J=7.70 Hz, 2H) 7.51-7.62 (m, 2H) 7.75-7.86 (m, 2H) 7.89-8.01 (m, 2H) 8.65-8.74 (m, 1H); $^{19}$F NMR −184.13; MS (ESI) m/z 623 (M+H)$^+$.

38F

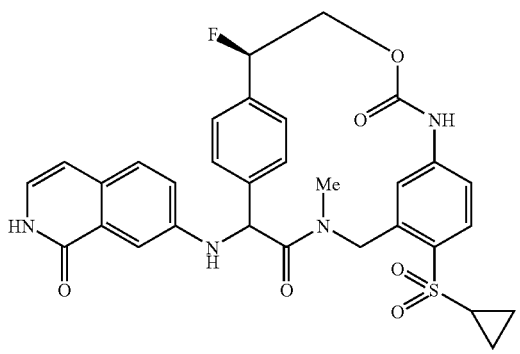 [SMILES: CN1Cc2cc(ccc2S(=O)(=O)C2CC2)NC(=O)OC[C@H](F)c2ccc(cc2)C(Nc2ccc3cc[nH]c(=O)c3c2)C1=O]

To a solution of BOP (121 mg, 0.273 mmol) and DMAP (66.7 mg, 0.546 mmol) in $CH_2Cl_2$ (30 ml) and DMF (4.0 ml) at 32° C. was added a solution of 38E (85 mg, 0.137 mmol) and DIEA (0.072 ml, 0.410 mmol) in DMF (5.0 mL) via a syringe pump over 8 h. The reaction was left stirring over night at rt. After evaporation of solvent, it was partitioned in MeOH, the insolubale material was filtered off. The filtrate was concentrated and dissolved in MeOH/DMSO (4.0 mL, 1:1) and purified (2 injections) by preparative HPLC equipped with a C18 Phenomenex Luna AXIA column (30 mm×75 cm, 5μ) with the UV detector set at 254 nm. The separations were performed using a gradient method: 0-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected to give 38F (14 mg, 17% yield).

Example 38

38F (14 mg) was dissolved in 3.0 mL of 50/50 methanol-ethanol and 2.0 mL of heptane and separated by a Chiral Regis Whelk-01 (R,R), 250×20 mm column eluting with 55% (50/50 methanol-ethanol): 45% Heptane at 20 mL/min to obtain the first peak (RT=12.5 min, 6 mg) and then the second peak (RT=16 min., 4 mg). The second peak was confirmed to be Example 38: $^1$H NMR (500 MHz, acetonitrile-$d_3$) δ ppm 0.96-1.04 (m, 2H) 1.05-1.12 (m, 1H) 1.16-1.22 (m, 1H) 2.70 (m, 1H) 4.26 (d, J=17.05 Hz, 1H) 4.33 (brs, 1H) 4.57-4.65 (m, 1H) 5.66 (d, J=17.05 Hz, 1H) 5.74 (s, 1H) 6.28 (d, J=2.20 Hz, 1H) 6.33 (d, J=7.15 Hz, 1H) 6.77-6.82 (m, 1H) 6.88 (dd, J=8.80, 2.20 Hz, 1H) 7.11 (d, J=8.25 Hz, 1H) 7.16 (dd, J=8.52, 2.47 Hz, 1H) 7.23 (d, J=8.25 Hz, 1H) 7.34 (d, J=8.80 Hz, 1H) 7.41 (d, J=2.20 Hz, 1H) 7.60 (d, J=6.60 Hz, 1H) 7.74 (d, J=8.80 Hz, 1H) 7.81-7.89 (m, 2H) 9.06 (s, 1H); $^{19}$F NMR (376 MHz, Solvent) δ ppm -192.1; MS (ESI) m/z 605 (M+H)P Analytical HPLC (Method A): Col A: 6.76 min, 99%; Col B: 6.74 min, 99%.

Example 39

(2R,15R)-7-Cyclopropanesulfonyl-15-methoxymethoxy-4-methyl-2-(1-oxo-1,2-dihydro-isoquinolin-7-ylamino)-13-oxa-4,11-diaza-tricyclo [14.2.2.16,10]henicosa-1(19),6,8,10(21),16(20),17-hexaene-3,12-dione

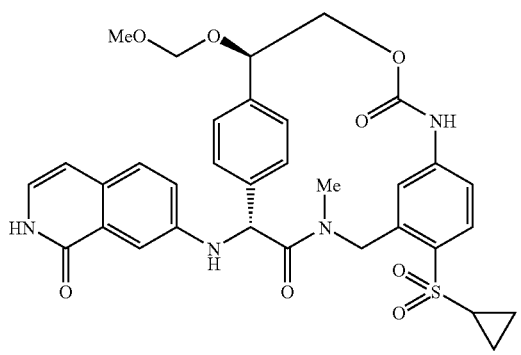 [SMILES: COCO[C@H]1COC(=O)Nc2ccc(S(=O)(=O)C3CC3)c(c2)CN(C)C(=O)[C@H](Nc2ccc3cc[nH]c(=O)c3c2)c2ccc1cc2]

39A

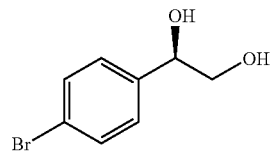

To t-BuOH (40.0 mL) and Water (40 mL) was added AD-MIX-BETA (11.2 g, 8.00 mmol). The mixture was stirred at rt until both phases are clear, and then cooled to 5° C. with an ice bath. 1-Bromo-4-vinylbenzene (1.046 ml, 8.0 mmol) was added, and the slurry was stirred vigorously for 1.0 h at 5° C. and 30 min at rt. The reaction was cooled with an ice/bath and quenched with 6.0 g sodium sulfite and then warm up to rt and stirred for 10 min. t-BuOH was removed under vacuum and the mixture was extracted with EtOAc, washed with brine and dried over $Na_2SO_4$. After removal of solvent, 39A (1.7 g, 98% yield) was obtained as a white solid. $^1$H NMR (400 MHz, methanol-$d_4$) δ ppm 2.06 (br s, 1H) 2.63 (s, 1H) 3.62 (dd, J=11.27, 7.97 Hz, 1H) 3.75 (dd, J=11.27, 3.57 Hz, 1H) 4.79 (dd, J=7.97, 3.57 Hz, 1H) 7.24-7.27 (d, J=8.25 Hz, 2H) 7.49 (d, J=8.25 Hz, 2H).

39B

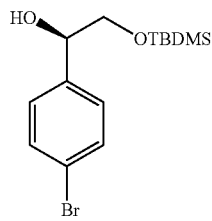 [SMILES: CC(C)(C)[Si](C)(C)OC[C@H](O)c1ccc(Br)cc1]

To 39A (1.7 g, 7.83 mmol) in CH$_2$Cl$_2$ (40 mL) was added DMAP (0.096 g, 0.783 mmol), followed by TEA (1.856 mL, 13.31 mmol). Then a solution of TBDMS-Cl (2.007 g, 13.31 mmol) in CH$_2$Cl$_2$ (4.0 mL) was added dropwise. The mixture was stirred at rt overnight. It was quenched with 0.5 N HCl, extracted with CH$_2$Cl$_2$ and washed with sat NaHCO$_3$, brine and dried over Na$_2$SO$_4$. The crude product in small amount of CHCl$_3$ was charged to a 40 g silica gel column, eluted with hexanes for 6 min., then ethyl acetate in hexanes from 0-18% in 15 min. gradient time to give 39B (1.9 g, 73% yield). $^1$H NMR (400 MHz, CDCl$_3$) δ ppm 0.00 (d, J=2.75 Hz, 6H) 0.85 (s, 9H) 2.90 (d, J=2.20 Hz, 1H) 3.41-3.47 (m, 1H) 3.68 (dd, J=9.89, 3.30 Hz, 1H) 4.63-4.67 (m, 1H) 7.19 (d, J=9.34 Hz, 2H) 7.41 (d, J=8.24 Hz, 2H). MS (ESI) m/z 329, 331 (M—OH)$^+$.

39C

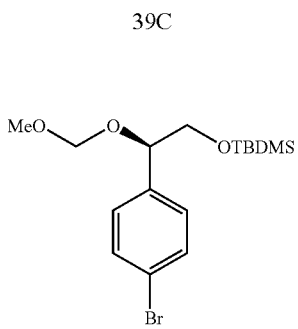

To 39B (2.3 g, 6.94 mmol) in dichloromethane (20 mL) was added DMAP (0.085 g, 0.694 mmol) and DIEA (6.06 mL, 34.7 mmol), followed by chloro(methoxy)methane (1.582 mL, 20.83 mmol). The mixture was heated at 65° C. for 4.0 h. TLC indicated a complete reaction. After it cooled to rt, the reaction mixture was washed with 0.5 N HCl, the organic layers were washed with sat. NaHCO$_3$, brine and dried over Na$_2$SO$_4$. The crude product in small amount of CHCl$_3$ was charged to a 120 g silica gel column, eluted with hexanes for 10 min and then ethyl acetate in hexanes from 0-15% in 15 min gradient time to give 39C (2.5 g, 6.66 mmol, 96% yield) as a clear liquid. $^1$H NMR (400 MHz, CDCl$_3$) δ ppm −0.01 (s, 3H) 0.03 (s, 3H) 0.87-0.90 (s, 9H) 3.38 (s, 3H) 3.68 (dd, J=10.77, 4.61 Hz, 1H) 3.82 (dd, J=10.77, 7.25 Hz, 1H) 4.61 (d, J=6.59 Hz, 1H) 4.65-4.70 (m, 2H) 7.25 (d, J=8.35 Hz, 2H) 7.49 (d, J=8.35 Hz, 2H); MS (ESI) m/z 314, 316 (M-MOM).

39D

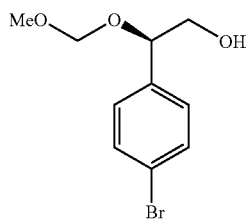

To 39C (2.5 g, 6.66 mmol) in THF (2.0 mL) at 0° C. was added 1.0 N TBAF in THF (9.99 mL, 9.99 mmol). The mixture was stirred at rt for 1.0 h. It was diluted with EtOAc and quenched with sat. NH$_4$Cl. The organic layers were washed with brine and dried over Na$_2$SO$_4$. The crude product in small amount of CHCl$_3$ was charged to a 40 g silica gel column, eluted with 2% EtOAc for 6 min and then with ethyl acetate in hexanes from 2-55% in 14 min gradient time to give 39D (1.67 g, 6.40 mmol, 96% yield) as a viscous oil. $^1$H NMR (400 MHz, CDCl$_3$) δ ppm 2.48 (brs, 1H) 3.38 (s, 3H) 3.62-3.73 (m, 2H) 4.61-4.68 (m, 3H) 7.21 (d, J=8.35 Hz, 2H) 7.47 (d, J=8.35 Hz, 2H); MS (ESI) m/z 283, 285 (M+Na).

39E

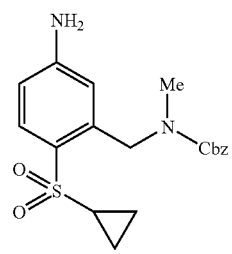 [SMILES: CN(Cc1cc(N)ccc1S(=O)(=O)C1CC1)C(=O)OCc1ccccc1]

To Intermediate 11 in EtOAc (6 mL) was added 4.0N HCl in dioxane (7866 mL, 31.5 mmol). The mixture was stirred at rt for 40 min. LC-MS indicated completion of reaction. Solvent was removed under vaccuo to give the HCl salt as a white solid: $^1$H NMR (400 MHz, DMSO-d$_6$) δ ppm 0.95-1.05 (m, 4H) 2.57 (t, J=5.27 Hz, 3H) 2.89-2.96 (m, 1H) 3.55 (s, 3H) 4.24 (t, J=5.93 Hz, 2H) 6.68 (dd, J=8.35, 2.20 Hz, 1H) 6.74 (d, J=2.20 Hz, 1H) 7.48-7.54 (m, 1H) 8.92 (s, 2H). To the above diamine salt was added THF (14.0 mL) and sodium carbonate (770 mg, 7.26 mmol) dissolved in H$_2$O (12 mL). The mixture was stirred and cooled to 0° C. To this solution was added benzyl chloroformate (380 μL, 2.66 mmol) in THF (3.0 mL) slowly. After 20 min stirring at 0° C., TLC indicated a completion of reaction. The mixture was diluted with EtOAc/H$_2$O, the organic layer was separated and washed with brine and dried over Na$_2$SO$_4$. The crude product in small amount of CHCl$_3$ was charged to a 40 g silica gel column, eluted with 2% EtOAc in hexanes for 6 mim and then ethyl acetate in hexanes from 2-60% in 14 min gradient time to give 39E (770 mg, 2.056 mmol, 85% yield) as a solid. $^1$H NMR (400 MHz, CDCl$_3$) δ ppm 0.77 (br s, 2H) 0.97 (br s, 2H) 1.17 (s, 2H) 1.24 (br s, 2H) 2.27 and 2.49 (br s, 1H) 2.97 and 3.00 (br s, 3H) 4.88 and 4.94 (br s, 2H) 5.10 and 5.18 (br s, 2H) 6.47 and 6.53 (br s, 1H) 6.60 (d, J=8.79 Hz, 1H) 7.17-7.38 (m, 5H) 7.68 (br s, 1H). MS (ESI) m/z 375 (M+H)$^+$.

39F

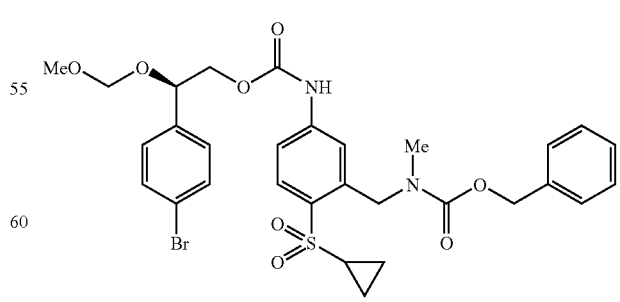

Using a procedure analogous to that used to prepare 29A, 39E (600 mg, 1.602 mmol) was reacted with sodium bicarbonate and phosgene followed by 39D (460 mg, 1.762 mmol)

and TEA. The crude product was added to a silica gel column (40 g) and was eluted with EtOAc/hexanes (2-40% in 15 min) to give 39F (940 mg, 1.421 mmol, 89% yield) as a white solid. ¹H NMR (400 MHz, CDCl₃) δ ppm 0.78-1.01 (m, 2H) 1.24 (m, 2H) 3.02 (s, 3H) 3.32 (s, 3H) 4.26-4.37 (m, 2H) 4.55-4.60 (m, 1H) 4.61-4.66 (m, 1H) 4.86 (dd, J=7.03, 4.39 Hz, 1H) 4.93 and 4.98 (brs, 2H) 5.07 and 5.21 (brs, 2H) 6.82-7.85 (m, 12H). MS (ESI) m/z 661, 663 (M+H)⁺.

39G

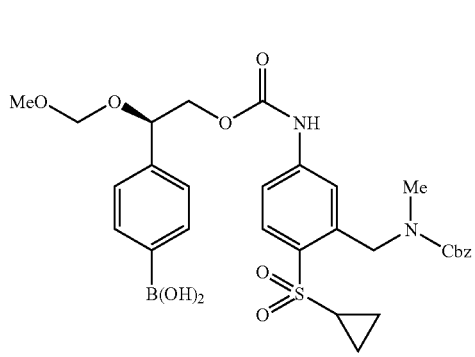 [SMILES: COCO[C@@H](COC(=O)Nc1ccc(S(=O)(=O)C2CC2)c(CN(C)C(=O)OCc2ccccc2)c1)c1ccc(B(O)O)cc1]

Using a procedure analogous to that used to prepare 29B, 39F (938 mg, 1.418 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 2% to 65% and preparative HPLC (CH₃CN/H₂O, 0.1% TFA) to give 39G (611 mg, 0.975 mmol, 68.8% yield) as a white solid after lyophilization. ¹H NMR (400 MHz, DMSO-d₆) δ ppm 0.89 (brs, 1H) 1.02 (br s, 3H) 2.98 (s, 3H) 3.22 and 3.26 (s, 3H) 4.21-4.29 (m, 1H) 4.30-4.37 (m, 1H) 4.51 (t, J=5.93 Hz, 1H) 4.63 (d, J=6.59 Hz, 1H) 4.83-4.91 (m, 3H) 5.05 (s, 1H) 5.15 (s, 1H) 7.15-8.07 (m, 12H); MS (ESI) m/z 627 (M+H)⁺.

39H

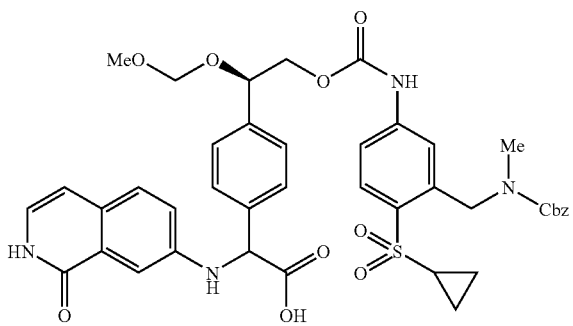 [SMILES: COCO[C@@H](COC(=O)Nc1ccc(S(=O)(=O)C2CC2)c(CN(C)C(=O)OCc2ccccc2)c1)c1ccc(C(Nc2ccc3cc[nH]c(=O)c3c2)C(=O)O)cc1]

To a mixture of 39G (200 mg, 0.319 mmol), Intermediate 3 (51.1 mg, 0.319 mmol) and Glyoxylic acid monohydrate (29.4 mg, 0.319 mmol) was added Acetonitrile (3.0 mL) and DMF (0.8 mL). The mixture was directly loaded onto a 12 g silica gel column, eluted with first with CH₂Cl₂ for 5 min then MeOH in CH₂Cl₂ from 0-25% in 12 min gradient time to give crude product that was further purified by column chromatography: 12 g silica gel column, eluted with ethyl acetate for 5 min then MeOH in EtOAc from 0-20% in 12 min to give 39H (204 mg, 0.255 mmol, 80% yield) as a solid after lyophilization. ¹H NMR (400 MHz, DMSO-d₆) δ ppm 0.89 (br s, 1H) 1.03 (br s, 3H) 2.98 (s, 3H) 3.21 (s, 3H) 4.24-4.29 (m, 1H) 4.34 (m, 1H) 4.50 (dd, J=6.60, 2.20 Hz, 1H) 4.63 (dd, J=6.60, 2.20 Hz, 1H) 4.83-4.91 (m, 3H) 5.05 (s, 1H) 5.13 (br s, 2H) 6.35 (d, J=7.15 Hz, 1H) 6.80-7.81 (m, 17H) 10.25 (s, 1H) 10.92 (d, J=5.50 Hz, 1H). MS (ESI) m/z 799 (M+H)⁺.

39I

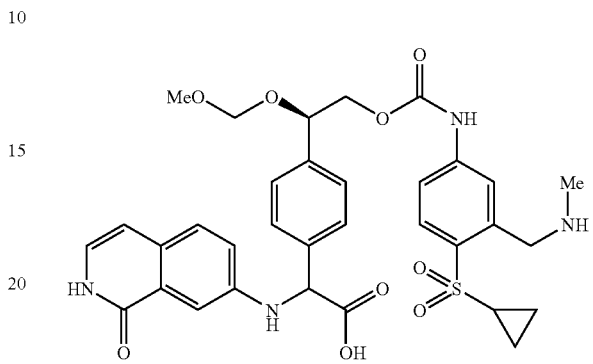

39H (180 mg, 0.225 mmol) and 10% Pd on carbon (120 mg, 0.225 mmol) in MeOH (30 mL) and DMF (8.0 mL) was hydrogenated with a hydrogen balloon for 1.0 h. HPLC indicated a clean reaction. Pd/C was filtered off and washed with a mixture of MeOH/DMF (1:1, 20 mL), and the filtrate was condensed and lyophilized. The crude was further purified using a preparative HPLC 39I (110 mg, 0.165 mmol, 73.4% yield) was obtained as a solid after lyophilization. ¹H NMR (400 MHz, DMSO-d₆) δ ppm 0.77-1.11 (m, 4H) 2.49 (s, 3H) 2.99 (m, 1H) 3.20 and 3.21 (s, 3H) 4.00-4.17 (m, 3H) 4.47-4.79 (m, 4H) 5.19 (s, 1 h) 6.34 (d, J=7.26 Hz, 1H) 6.84 (t, J=7.12 Hz, 1H) 7.25-7.67 (m, 10H). MS (ESI) m/z 665 (M+H)⁺.

Example 39

To a solution of BOP (314 mg, 0.709 mmol) and DMAP (173 mg, 1.418 mmol) in CH₂Cl₂ (70 ml) and DMF (8.0 ml) at 25° C. was added a solution of 39I (270 mg, 0.354 mmol) and DIEA (0.186 ml, 1.063 mmol) in DMF (6.0 mL) via a syringe pump over 10 h. To the reaction mixture was added water and 0.2 N HCl, stirred for 10 min. The organic layer was collected and aqueous was extracted with CH₂Cl₂. The organic layers were dried over Na₂SO₄. After evaporation of solvent, it was dissolved in MeOH/DMSO (6.0 mL, 1:1) and purified (3 injections) by preparative HPLC equipped with a C18 Phenomenex Luna AXIA column (30 mm x75 cm, 5μ) with the UV detector set at 254 nm. The separations were performed using a gradient method: 10-80% B in 10 mins; then 85% B in 2 nm ins with a flow rate of 40 mL/min. Solvent B is 90% acetonitrile-10% water-0.1% TFA and solvent A is 10% acetonitrile-90% water-0.1% TFA. Two peaks were collected. The second peak (33 mg) was confirmed to be Example 39: ¹H NMR (500 MHz, methanol-d₄) δ ppm 0.79 (d, J=4.40 Hz, 1H) 0.84-0.88 (m, 1H) 0.89-0.94 (m, 1H) 1.08-1.16 (m, 1H) 2.67-2.74 (m, 1H) 3.27 (s, 3H) 3.28 (s, 3H) 3.99 (dd, J=9.90, 3.85 Hz, 1H) 4.18 (d, J=17.60 Hz, 1H) 4.52-4.61 (m, 4H) 5.61-5.68 (m, 2H) 6.36 (s, 1H) 6.45 (d, J=7.15 Hz, 1H) 6.73-6.77 (m, 1H) 6.83 (d, J=7.15 Hz, 1H) 6.96 (d, J=6.05 Hz, 1H) 7.11-7.17 (m, 2H) 7.32 (d, J=8.25 Hz, 1H) 7.36 (d, J=2.75 Hz, 1H) 7.57 (d, J=7.70 Hz, 1H) 7.61 (d, J=8.80 Hz, 1H) 7.78 (d, J=7.70 Hz, 1H); MS (ESI) m/z 647 (M+H)⁺; Analytical HPLC (Method A): Col A: 6.39 min, 88%; Col B: 6.41 min, 89%.

Example 40

(2R,15R)-7-Cyclopropanesulfonyl-15-ethoxy-4,20-dimethyl-2-(1-oxo-1,2-dihydro-isoquinolin-7-ylamino)-13-oxa-4,11-diaza-tricyclo[14.2.2.16,10]henicosa-1(19),6,8,10(21),16(20),17-hexaene-3,12-dione

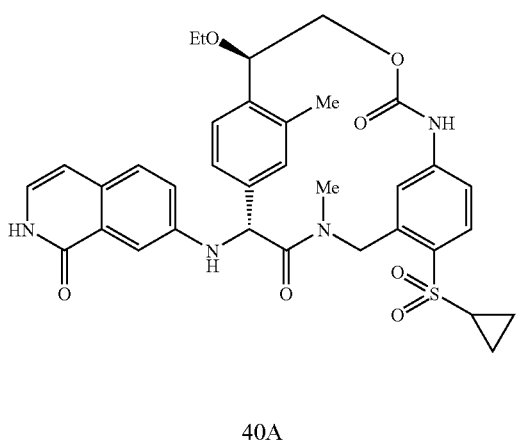

40A

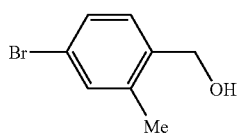

To a suspension of 4-bromo-2-methylbenzoic acid (5.59 g, 26.0 mmol) in THF (10 mL) at 0° C. was slowly added 1.0M BH$_3$:THF in THF (36.4 mL, 36.4 mmol) in 10 min. The mixture was stirred from 0° C. to rt overnight. The reaction was quenched at 0° C. by addition of 5.0 mL of H$_2$O, diluted with EtOAc, washed with 10% Na$_2$CO$_3$. The aqueous was extracted with EtOAc. The combined organic was washed with 10% Na$_2$CO$_3$, brine and dried over Na$_2$SO$_4$. After evaporation of solvent, 40A (5.1 g, 25.4 mmol, 98% yield) was obtained as a slightly yellow liquid. $^1$H NMR (400 MHz, CDCl$_3$) δ ppm 2.32 (s, 3H) 4.64 (s, 2H) 7.21-7.25 (m, 1H) 7.30-7.34 (m, 2H).

40B

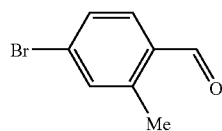

To pyridinium chlorochromate (10.94 g, 50.7 mmol) in Dichloromethane (200 mL) was added a solution of 40A (5.1 g, 25.4 mmol) in dichloromethane (60 mL) in 10 min. The mixture was stirred for 3.0 h. TLC indicated a clean reaction. Solvent was removed and the residue was triturated with diethyl ether, filtered through a pad of Celite®, washed with water, brine and the organic layers were dried over Na$_2$SO$_4$. The crude product in small amount of CHCl$_3$ was charged to a 40 g silica gel column, eluted first with hexanes for 6 min and then with ethyl acetate in hexanes from 0-20% in 10 min gradient time to give 40B (4.0 g, 20.10 mmol, 79% yield) as a clear oil. $^1$H NMR (400 MHz, CDCl$_3$) δ ppm 2.63 (s, 3H) 7.42 (s, 1H) 7.48 (d, J=8.35 Hz, 1H) 7.63 (d, J=8.35 Hz, 1H) 10.19 (s, 1H).

40C

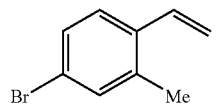

A suspension of methyltriphenylphosphonium bromide (8.02 g, 22.44 mmol) in THF (80 mL) was treated at rt with 2.5M n-BuLi in hexanes (9.79 mL, 24.48 mmol). The orange solution was stirred at rt for 1.0 h. A solution of 40B (4.06 g, 20.40 mmol) in THF (10 mL) was added dropwise at rt and stirred for 1.0 h. TLC indicated completion of reaction. Hexanes was added and stirred to precipitate triphenylphosphine oxide. The precipitate was removed by filtration. The filtrate was concentrated and charged to a 120 g silica gel column, eluted with hexanes for 10 min. and then ethyl acetate in hexanes from 0-12% in 14 min gradient time to give first 40C (2.9 g, 14.72 mmol, 72.1% yield) followed by retrieved starting material 40B (700 mg). $^1$H NMR (400 MHz, CDCl$_3$) δ ppm 2.30 (s, 3H) 5.30 (d, J=10.99 Hz, 1H) 5.61 (d, J=17.58 Hz, 1H) 6.83 (dd, J=17.14, 10.99 Hz, 1H) 7.26-7.32 (m, 3H).

40D

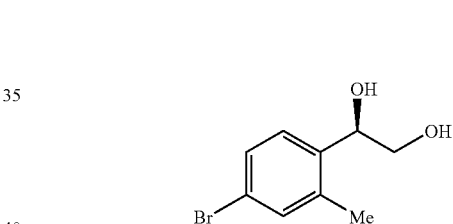

To t-BuOH (90 mL) and water (90 mL) was added AD-mix-beta (22.4 g, 14.72 mmol). The mixture was stirred at rt until both phases are clear, and then cooled to 5° C. with an ice bath. 40C (2.9 g, 14.72 mmol) was added, and the slurry was stirred vigorously for 1.0 h at 5° C. The reaction was quenched with 15 g sodium sulfite and then warm up to rt and stirred for 10 min. The mixture was extracted with EtOAc, washed with brine and dried over Na$_2$SO$_4$. 40D (3.3 g, 97% yield) was obtained after removal of solvent. It was used for next step without further purification. $^1$H NMR (400 MHz, CDCl$_3$) δ ppm 2.28 (s, 3H) 2.34 (s, 1H) 2.72 (s, 1H) 3.52 (dd, J=11.21, 8.57 Hz, 1H) 3.67 (d, J=9.23 Hz, 1H) 4.96 (dd, J=8.35, 3.08 Hz, 1H) 7.27 (s, 1H) 7.30-7.36 (m, 2H).

40E

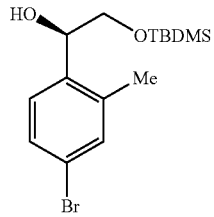 [SMILES: Cc1cc(Br)ccc1[C@@H](O)CO[Si](C)(C)C(C)(C)C]

To 40D (3.35 g, 14.50 mmol) and imidazole (1.382 g, 20.30 mmol) in DMF (20 mL) at 0° C. was added TBDMS-Cl (2.403 g, 15.95 mmol). The mixture was stirred from 0° C. for 20 min and then at rt for 2.5 h. It was quenched with H₂O (40 mL), extracted with diethyl ether and washed with sat NaHCO₃, brine, and dried over Na₂SO₄. The crude product in small amount of CHCl₃ was charged to a 120 g silica gel column, eluted with hexanes for 10 min, then ethyl acetate in hexanes from 0-14% in 12 min gradient time. The fraction containing the product was collected and purified once again by flash column chromatography to give 40E (4.3 g, 12.45 mmol, 86% yield). ¹H NMR (400 MHz, CDCl₃) δ ppm −0.01 (s, 6H) 0.84 (s, 9H) 2.23 (s, 3H) 2.87 (s, 1H) 3.34-3.40 (m, 1H) 3.64 (dd, J=10.11, 3.52 Hz, 1H) 4.84 (d, J=7.47 Hz, 1H) 7.21 (s, 1H) 7.25-7.29 (m, 1H) 7.30-7.34 (m, 1H).

40F

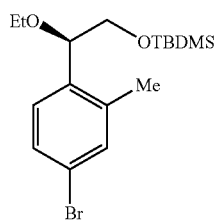 [SMILES: CCO[C@@H](CO[Si](C)(C)C(C)(C)C)c1ccc(Br)cc1C]

To 40E (2.0 g, 5.79 mmol) and EtI (3.61 g, 23.17 mmol) in acetonitrile (50 mL) was added potassium tert-butoxide (0.715 g, 6.37 mmol). The mixture was stirred at room temperature for 20 h. The reaction was quenched by saturated NH₄Cl (10 mL), acetonitrile was removed under vaccuo and the mixture was extracted with EtOAc. The combined organic layers were dried over Na₂SO₄ and concentrated to an oil. The residue was dissolved in small amount of CHCl₃ and added to a 40 g silica gel column and was first eluted with hexanes for 8 min and then with 0-14% EtOAc/Hexanes in 12 min to give 40F (1.1 g, 2.95 mmol, 50.9% yield) as clear oil. ¹H NMR (400 MHz, CDCl₃) δ ppm 0.01 (s, 3H) 0.02 (s, 3H) 0.87-0.90 (s, 9H) 1.21 (t, J=7.03, 3H) 2.36 (s, 3H) 3.43 (q, J=7.03 Hz, 2H) 3.61 (dd, J=10.77, 5.05 Hz, 1H) 3.80 (dd, J=10.99, 7.03 Hz, 1H) 4.60 (dd, J=6.81, 5.05 Hz, 1H) 7.30-7.38 (m, 3H). MS (ESI) m/z 327, 329 (M-OEt).

40G

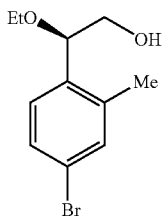

To 40F (1.1 g, 2.95 mmol) in THF (2.0 mL) at 0° C. was added 1.0N TBAF in THF (4.42 mL, 4.42 mmol). The mixture was stirred at rt for 1.0 h. TLC indicated completion of reaction. It was diluted with EtOAc and quenched with sat. NH₄Cl. The organic layers were washed with brine and dried over Na₂SO₄. The crude product in small amount of CHCl₃ was charged to a 40 g silica gel column, eluted with 2% EtOAc for 6 min and then with ethyl acetate in hexanes from 2-55% in 14 min gradient time to give 40G (510 mg, 1.968 mmol, 66.8% yield) as a viscous oil. ¹H NMR (400 MHz, CDCl₃) δ ppm 1.21 (t, J=7.03 Hz, 3H) 2.31 (s, 3H) 3.34-3.39 (m, 1H) 3.40-3.47 (m, 1H) 3.54 (d, J=6.15 Hz, 2H) 4.61 (t, J=5.93 Hz, 1H) 7.25-7.36 (m, 3H).

40H

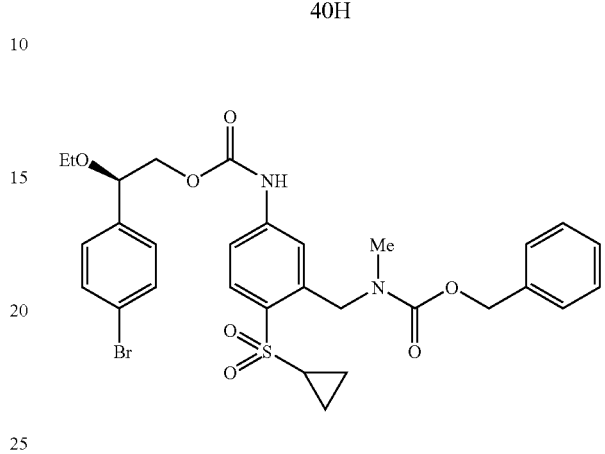

Using a procedure analogous to that used to prepare 29A, 39E (657 mg, 1.754 mmol), was reacted with sodium bicarbonate and phosgene followed by 40G (500 mg, 1.929 mmol) and TEA. The crude product was added to a silica gel column (40 g) and was eluted with EtOAc/hexanes (2-66% in 15 min) to give 40H (1.1 g, 1.668 mmol, 95% yield) as a white solid. ¹H NMR (400 MHz, CDCl₃) δ ppm 0.82 (br s, 1H) 1.01 (br s, 1H) 1.22 (t, J=7.03 Hz, 3H) 1.24 (br s, 2H) 2.35 (s, 3H) 2.51 and 2.30 (br s, 1H) 3.02 (s, 3H) 3.36-3.45 (m, 2H) 4.09-4.13 (m, 1H) 4.28 (dd, J=11.86, 3.08 Hz, 1H) 4.77 (dd, J=8.13, 3.30 Hz, 1H) 4.92 (s, 1H) 4.98 (s, 1H) 5.10 (s, 1H) 5.19 (s, 1H) 6.83 (s, 1H) 7.29-7.38 (m, 7H) 7.40 (s, 1H) 7.65 (s, 1H) 7.85 (s, 1H); MS (ESI) m/z 659, 661 (M+H)⁺.

40I

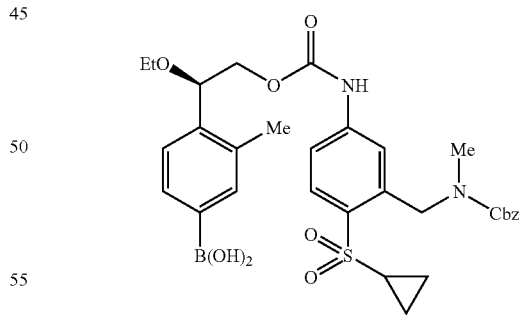

Using a procedure analogous to that used to prepare 29B, 40H (1.1 g, 1.668 mmol) was reacted with bis(neopentyl glycolato)diboron, potassium acetate and (1,1'-bis(diphenylphosphino)ferrocene)-dichloropalladium(II). The crude was purified by flash chromatography (EtOAc/hexanes 2% to 65% and preparative HPLC (CH₃CN/H₂O, 0.1% TFA) to give 40I (836 mg, 1.339 mmol, 80% yield) as a white solid after lyophilization. ¹H NMR (400 MHz, methanol-d₄) δ ppm 0.82-1.21 (m, 7H) 2.40 (s, 3H) 3.06 (s, 3H) 3.38-3.46 (m, 2H)

4.17-4.26 (m, 2H) 4.92-5.00 (m, 2H) 5.08 (s, 1H) 5.19 (s, 1H) 7.13-7.79 (m, 11H); MS (ESI) m/z 625 (M+H)⁺.

40J

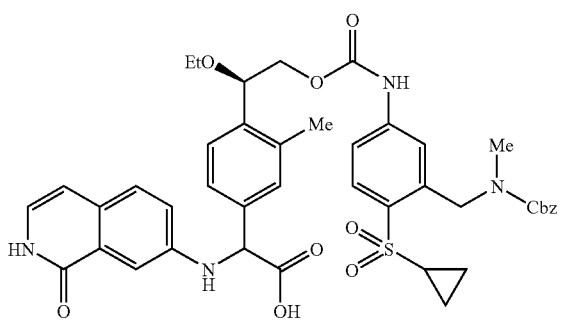 [SMILES: CCO[C@@H](COC(=O)Nc1ccc(S(=O)(=O)C2CC2)c(CN(C)C(=O)OCc2ccccc2)c1)c1ccc(C(Nc2ccc3cc[nH]c(=O)c3c2)C(=O)O)cc1C]

Using a procedure analogous to that used to prepare 1E, 40I (300 mg, 0.480 mmol), Intermediate 3, and glyoxylic acid monohydrate were reacted and purified by flash chromatography (0% to 20% MeOH in CH₂Cl₂) to give 40J (380 mg, 0.429 mmol, 89% yield). ¹H NMR (400 MHz, DMSO-d₆) δ ppm 0.88-1.11 (m, 7H) 2.36 (s, 3H) 2.98 (s, 3H) 4.09-4.21 (m, 2H) 4.80 (dd, J=7.47, 3.08 Hz, 1H) 4.88 (s, 2H) 5.05 (m, 1H) 5.11 (s, 1H) 5.14 (s, 1H) 6.35 (d, J=7.03 Hz, 1H) 6.79-6.86 (m, 1H) 7:16-7.75 (m, 14H). MS (ESI) m/z 797 (M+H)⁺.

40K

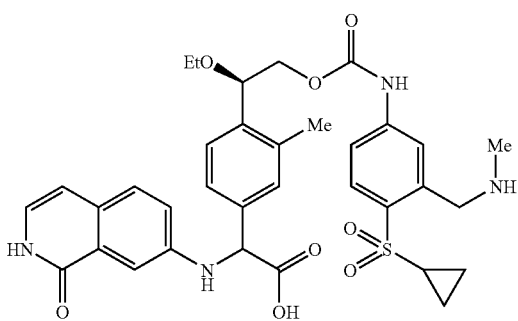 [SMILES: CCO[C@@H](COC(=O)Nc1ccc(S(=O)(=O)C2CC2)c(CNC)c1)c1ccc(C(Nc2ccc3cc[nH]c(=O)c3c2)C(=O)O)cc1C]

40J (380 mg, 0.477 mmol) and 10% Pd on carbon (220 mg, 0.477 mmol) in MeOH (30 mL) and DMF (7.0 mL) was hydrogenated with a hydrogen balloon for 1.0 h. HPLC indicated a clean reaction. Pd/C was filtered off and washed with mixture of MeOH/DMF (1:1, 20 mL), and the filtrate was condensed and lyophilized to give 40K (245 mg, 0.370 mmol, 78% yield.) as a slightly yellow solid. ¹H NMR (500 MHz, DMSO-d₆) δ ppm 0.90-1.08 (m, 7H) 2.49 and 2.50 (s, 3H) 2.66 and 2.82 (s, 3H) 2.97 (m, 1H) 4.00-4.13 (m, 4H) 4.62 (br s, 1H) 6.70 (m, 1H) 6.26-7.88 (m, 11H). MS (ESI) m/z 663 (M+H)⁺.

Example 40

To a solution of BOP (320 mg, 0.724 mmol) and DMAP (177 mg, 1.449 mmol) in CH₂Cl₂ (60 ml) and DMF (6 mL) at 32° C. was added a solution of 40K (240 mg, 0.362 mmol) and DIEA (0.190 mL, 1.086 mmol) in DMF (6.0 mL) via a syringe pump over 6 h. To the reaction mixture was added water and 0.5 N HCl, stirred for 10 min. The organic layer was collected and aqueous was extracted with CH₂Cl₂. The organic layers were dried over Na₂SO₄. After evaporation of solvent, it was dissolved in MeOH/DMSO (6.0 mL, 1:1) and purified (3 injections) by preparative HPLC equipped with a C18 Phenomenex Luna AXIA column (30 mm×75 cm, 5 g) with the UV detector set at 254 nm. The separations were performed using a gradient method: 10-80% B in 10 mins; then 80% B in 2 mins with a flow rate of 40 mL/min (Solvent B is 90% acetonitrile-10% water-0.1% TFA and solvent A is 10% acetonitrile-90% water-0.1% TFA) to give the first fraction (40 mg) and the second fraction (40 mg). The second fraction (40 mg) obtained above was dissolved in 5.0 mL of 50/50 methanol-ethanol and 2.0 mL of Heptane and separated by a Chiral Regis Whelk-01 (R,R), 250×20 mm column eluting with 60% (50/50 methanol-ethanol): 40% heptane at 20 mL/min to obtain the second peak (20 mg, RT=14.6 min) as Example 40: ¹H NMR (500 MHz, methanol-d₄) δ ppm 0.92-1.04 (m, 3H) 1.15-1.19 (m, 3H) 1.19-1.27 (m, 1H) 2.20 (s, 3H) 2.78-2.85 (m, 1H) 3.36 (s, 3H) 3.38-3.47 (m, 2H) 4.10 (d, J=5.50 Hz, 1H) 4.28 (d, J=17.60 Hz, 1H) 4.61 (t, J=10.17 Hz, 1H) 4.81 (dd, J=10.45, 4.95 Hz, 1H) 5.65 (s, 1H) 5.73 (d, J=17.05 Hz, 1H) 6.39 (d, J=2.20 Hz, 1H) 6.51 (d, J=7.15 Hz, 1H) 6.79-6.83 (m, 1H) 6.89 (d, J=7.15 Hz, 1H) 7.15 (s, 1H) 7.21 (dd, J=8.52, 2.47 Hz, 1H) 7.35 (d, J=8.80 Hz, 1H) 7.43 (d, J=2.20 Hz, 1H) 7.58 (d, J=7.70 Hz, 1H) 7.68-7.73 (m, 2H) 9.52 (s, 1H); MS (ESI) m/z 645 (M+H)⁺ Analytical HPLC (Method A): Col A: 6.81 min, 92%; Col B: 6.87 min, 91%.

Example 41

(2R,15S)-7-(3,5-Dimethyl-isoxazol-4-yl)-4,15,20-trimethyl-2-(1-oxo-1,2-dihydro-isoquinolin-7-ylamino)-4,11-diaza-tricyclo[14.2.2.16,10]henicosa-1(19),6,8,10(21),16(20),17-hexaene-3,12-dione

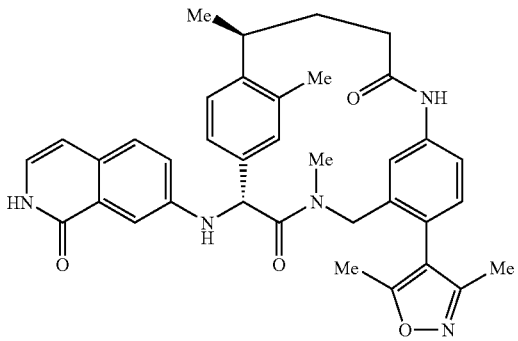 [SMILES: Cc1cc2ccc1[C@@H](C)CCC(=O)Nc1ccc(-c3c(C)noc3C)c(c1)CN(C)C(=O)[C@@H]2Nc1ccc2cc[nH]c(=O)c2c1]

41A

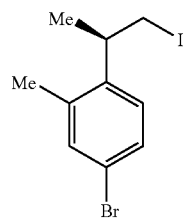 [SMILES: Cc1cc(Br)ccc1[C@@H](C)CI]

To triphenylphosphine (6.87 g, 26.2 mmol) and imidazole (1.783 g, 26.2 mmol) in diethyl ether (30 mL) and acetonitrile (12 mL) was added iodine (4.43 g, 17.46 mmol) portionwise and stirred at rt for 1 h. To the resulting suspension was added Intermediate 8 (2.0 g, 8.73 mmol) in $Et_2O$ (12 mL). The mixture was stirred at rt for 1 h. Saturated sodium sulfite was added until solution was colorless. The reaction was then extracted with ethyl acetate. The extracts were combined and washed with saturated sodium bicarbonate, water and brine and dried over sodium sulfate. The solvent was removed and residue was triturated with 20% ethyl acetate/hexanes. The white solid was then filtered off and washed with 20% ethyl acetate/hexanes. The solvent was removed and residue was redissolved in acetone (30 mL) and iodomethane (1.637 mL, 26.2 mmol) was added. The reaction was stirred at rt for 1 h. The solvent was removed and the residue was triturated with 20% ethylacetate/hexanes. The white solid was filtered off and washed with 20% ethylacetate/hexanes through 1" of silica plug. The filtrate was evaporated to give 41A (2.45 g, 83% yield) as a colorless oil. $^1H$ NMR (400 MHz, $CDCl_3$) δ ppm 1.35 (d, J=6.32 Hz, 3H) 2.30 (s, 3H) 3.18-3.35 (m, 3H) 6.98-7.06 (min, 1H) 7.28-7.35 (m, 2H).

41B

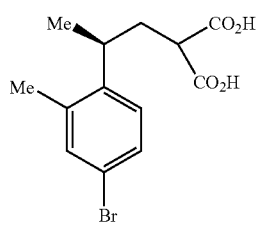 [SMILES: Cc1cc(Br)ccc1[C@@H](C)CC(C(=O)O)C(=O)O]

To a solution of dimethyl malonate (0.591 mL, 5.16 mmol) in DMPU (4.0 mL) was added 90% sodium hydride (118 mg, 4.42 mmol) at rt. The reaction mixture was stirred for 10 min at rt and then heated to 85° C. A solution of 41A (500 mg, 1.475 mmol) in DMPU (2.0 mL) was added to the mixture slowly and heated at 85° C. for 3.5 h. It was cooled to rt, diluted with EtOAc, quenched with 8.0 mL sat. $NH_4Cl$, extracted with diethyl ether, washed with brine and dried over $Na_2SO_4$. The crude product in small amount of $CHCl_3$ was charged to a 40 g silica gel column, eluted with hexanes for 8 min and then ethyl acetate in hexanes from 0-15% in 14 min gradient time to give 41B (410 mg, 1.195 mmol, 81% yield) as a viscous oil. $^1H$ NMR (400 MHz, $CDCl_3$) δ ppm 1.18 (d, J=6.59 Hz, 3H) 2.14-2.20 (m, 2H) 2.22 (s, 3H) 2.91-3.00 (m, 1H) 3.19-3.24 (m, 1H) 3.64 (s, 3H) 3.70 (s, 3H) 7.03 (d, J=7.91 Hz, 1H) 7.25-7.29 (m, 2H); MS (ESI) m/z 615 $(M+H)^+(M-OMe)$.

41C

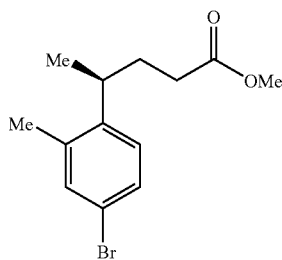 [SMILES: COC(=O)CC[C@H](C)c1ccc(Br)cc1C]

To a solution of 41B (1.38 g, 4.02 mmol) in DMSO (6.0 mL) was added lithium chloride (0.511 g, 12.06 mmol) and water (0.072 mL, 4.02 mmol). The mixture was heated at 150° C. in a microwave reactor for 1.0 h. The mixture was diluted with EtOAc, extracted with diethyl ether, washed with brine. The organic layer was dried over $Na_2SO_4$. After evaporation of solvent, 41C (1.14 g, 4.00 mmol, 99% yield) was obtained as a slightly yellow oil. It was used for next step without purification. $^1H$ NMR (400 MHz, $CDCl_3$) δ ppm 1.17 (d, J=7.03 Hz, 3H) 1.87 (q, J=7.62 Hz, 2H) 2.18-2.21 (s, 2H) 2.27 (s, 3H) 2.90-2.99 (m, 1H) 3.60-3.62 (s, 3H) 7.02 (d, J=7.91 Hz, 1H) 7.24-7.29 (m, 2H). MS (ESI) m/z 255, 257 $(M+H)^+(M-OMe)$.

41D

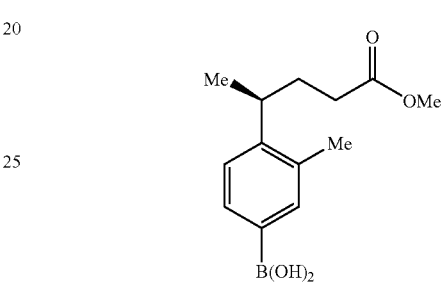

Using a procedure analogous to that used to prepare 29B, 41C (300 mg, 1.052 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes, 0% to 30%) and preparative HPLC ($CH_3CN/H_2O$, 0.1% TFA) to give 41D (160 mg, 0.640 mmol, 60.8H)3. % viscous oil after lyophilization. $^1H$ NMR (400 MHz, methanol-$d_4$) δ ppm 1.18-1.21 (m, 3H) 1.86-1.94 (m, 2H) 2.20-2.23 (m, 2H) 2.28 (m, 3H) 3.00-3.08 (m, 1H) 3.59 (s, 3H) 7.13-7.20 (m, 1H) 7.36-7.55 (m, 2H).

41E

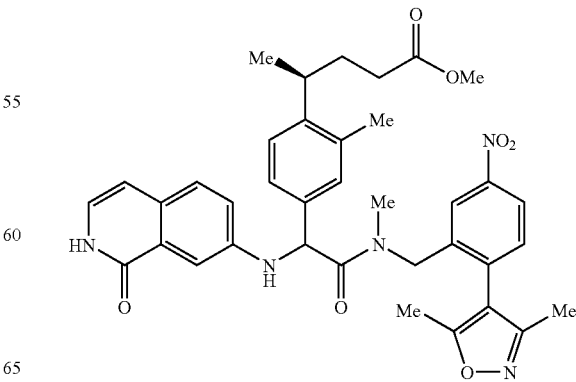

A mixture of 41D (150 mg, 0.600 mmol), Intermediate 3 (96 mg, 0.600 mmol) and 2-oxoacetic acid hydrate (55.2 mg, 0.600 mmol) in DMF (1.0 mL)/acetonitrile (2.5 mL) was heated at 105° C. for 15 min in a microwave reactor. Then a solution of 24B (179 mg, 0.600 mmol) in DMF (1.5 mL) and DIEA (0.262 mL, 1.499 mmol) was added to the above mixture followed by BOP (265 mg, 0.600 mmol) as a solid. The mixture was stirred at rt over night. LC-MS indicated a clean reaction. It was diluted with $CH_2Cl_2$ and 0.5 N HCl, filtered through a pad of wet celite, extracted with $CH_2Cl_2$. The organic layer was dried over $Na_2SO_4$. The crude material in small amount of $CHCl_3$ was charged to a 12 g silica gel column, eluted with $CH_2Cl_2$ for 6 min and then MeOH in $CH_2Cl_2$ from 0-5% in 14 min gradient time to give crude product (400 mg) as a brown solid. The crude residue was further purified using a preparative HPLC equipped with a C18 Phenomenex Luna AXIA column (30 mm×75 cm, 5μ) with the UV detector set at 220 mm. The separations were performed using a gradient method: 25-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected to give 41E (302 mg, 0.454 mmol, 76% yield) as a yellow solid. $^1$H NMR (400 MHz, $CDCl_3$) b ppm 1.14 (dd, J=6.81, 2.42 Hz, 3H) 1.78-1.89 (m, 2H) 2.00 and 2.09 (s, 3H) 2.12-2.23 (m, 8H) 2.84-2.92 (m, 1H) 2.94 and 2.941 (s, 3H) 3.55 and 3.556 (s, 3H) 4.32-4.41 (m, 1H) 4.44-4.55 (m, 1H) 5.32 (d, J=5.27 Hz, 1H) 6.87 (d, J=6.59 Hz, 1H) 7.04-7.10 (m, 1H) 7.15-7.22 (m, 5H) 7.26 (d, J=10.99 Hz, 2H) 7.45-7.49 (m, 1H) 7.79 (ddd, J=5.49, 2.64, 2.42 Hz, 1H) 8.08 (d, J=8.35 Hz, 1H). MS (ESI) m/z 666 (M+H)$^+$.

41F

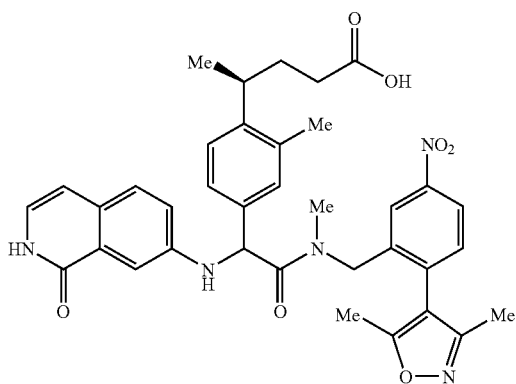

To a solution of 41E (302 mg, 0.454 mmol) in THF (2.0 mL) and MeOH (1.0 mL) was added 1.0 N NaOH (1.247 mL, 1.247 mmol). The mixture was stirred at rt for 20 min, TLC indicated ca 40-50% conversion, another portion of 1.0 N NaOH (1.247 mL, 1.247 mmol) was added and stirred at rt for 30 min, a third portion of 1.0 N NaOH (1.247 mL, 1.247 mmol) was added and stirred for 15 min. HPLC indicated a complete conversion of ester to acid. It was acidified with 6.0 mL 1.0 N HC (pH ca 3.0), extracted with EtOAc and washed with brine, dried over $Na_2SO_4$. After removal of solvent, 41F (290 mg, 98% yield) was obtained as a solid, NMR is complicated by the presence of two diastereoisomers. MS (ESI) m/z 652 (M+H)$^+$.

41G

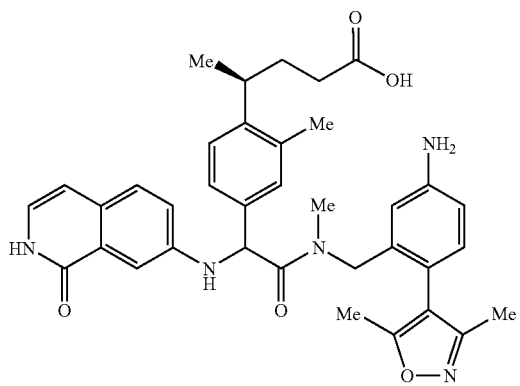 [SMILES: Cc1cc(C(Nc2ccc3cc[nH]c(=O)c3c2)C(=O)N(C)Cc2cc([N+](=O)[O-])ccc2-c2c(C)noc2C)ccc1[C@@H](C)CCC(=O)O]

41F (300 mg, 0.460 mmol) and 10% Pd/C (90 mg, 0.460 mmol) in MeOH (10 mL) was hydrogenated with a hydrogen balloon for 1.5 h. LC-MS indicated completion of reaction. Pd/C was removed by filtration and the filtrate was concentrated to give 41G (290 mg, 0.303 mmol, 65.9% yield) as a yellow solid. MS (ESI) m/z 622 (M+H)$^+$.

Example 41

To a solution of BOP (413 mg, 0.933 mmol) and DMAP (228 mg, 1.866 mmol) in $CH_2Cl_2$ (60 ml) and DMF (6 ml) at rt was added a solution of 41G (290 mg, 0.466 mmol) and DIEA (0.244 ml, 1.399 mmol) in DMF (7.0 mL) via a syringe pump over 8 h. To the reaction mixture was added 0.5 N HCl (30 mL), stirred for 10 min. The organic layer was collected and aqueous was extracted with $CH_2Cl_2$. The organic layers were dried over $Na_2SO_4$. After evaporation of solvent, it was dissolved in MeOH/DMSO (5.0 mL, 2:1) and purified (3 injections) by preparative HPLC equipped with a C18 Phenomenex Luna AXIA column (30 mm×75 cm, 5μ) with the UV detector set at 254 nm. The separations were performed using a gradient method: 20-75% B in 10 mins; then 75% B in 2 mins with a flow rate of 40 mL/min. Solvent B is 90% acetonitrile-10% water-0.1% TFA and solvent A is 10% acetonitrile-90% water-0.1% TFA. The desired fractions were collected to give a mixture of two diastereoisomers (100 mg). The mixture of two diastereoisomers (100 mg) was dissolved in 4.0 mL of 50/50 methanol-ethanol and 6.0 mL of heptane and separated by a Chiral Regis Whelk-01 (R,R), 250×20 mm column eluting with 30% (50/50 methanol-ethanol): 300% heptane at 20 mL/min. The second peak (34 mg, RT=14 min) was confirmed to be Example 41: $^1$H NMR (500 MHz, methanol-$d_4$) δ ppm 1.19 (d, J=7.15 Hz, 3H) 1.82-1.89 (m, 1H) 2.00, 2.10, 2.19 and 2.25 (s, 9H) 2.32-2.41 (m, 3H) 2.95-3.03 (m, 1H) 3.37 and 3.38 (s, 3H) 3.51 (dd, J=16.77, 9.07 Hz, 1H) 4.96 and 5.01 (d, J=16.77 Hz, 1H) 5.59 (d, J=4.40 Hz, 1H) 6.05-6.10 (m, 1H) 6.46 (d, J=7.15 Hz, 1H) 6.77 (d, J=8.25 Hz, 1H) 6.84 (d, J=7.15 Hz, 1H) 7.00 (d, J=7.70 Hz, 1H) 7.08 (d, J=13.20 Hz, 1H) 7.16 (dt, J=8.80, 2.75 Hz, 1H) 7.27 (d, J=8.80 Hz, 1H) 7.37 (d, J=8.25 Hz, 2H) 7.58 (d, J=8.25 Hz, 1H). MS (ESI) m/z 604 (M+H)$^+$. Analytical HPLC (Method A): Col A: 6.72 min, 99%; Col B: 6.80 min, 98%.

Example 42

(2R,15S)-2-(4-Fluoro-1-oxo-1,2-dihydro-isoquinolin-7-ylamino)-4,15,20-trimethyl-7-trifluoromethoxy-4,11-diaza-tricyclo[14.2.2.16,10]henicosa-1(19),6,8,10(21),16(20),17-hexaene-3,12-dione

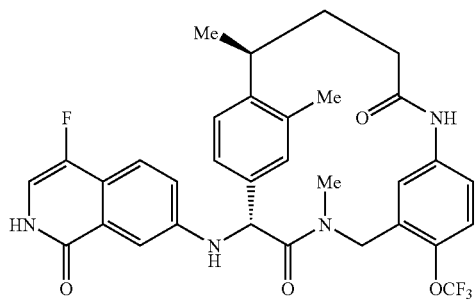

42A

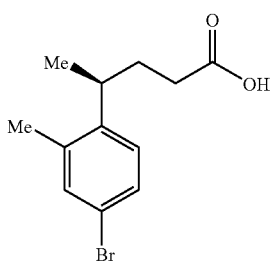 [SMILES: Cc1cc(Br)ccc1[C@@H](C)CCC(=O)O]

To 41C (1.14 g, 4.00 mmol) in THF (8.0 mL) and MeOH (2.0 mL) was added 1.0 N NaOH (8.00 mL, 8.00 mmol) and the mixture was stirred at rt for 40 min. TLC and LC-MS indicated a clean conversion of ester to acid. It was acidified with 10.0 mL 1.0 N HCl, extracted with EtOAc and washed with brine, and dried over Na$_2$SO$_4$. After removal of solvent, 42A (1.07 g, 99% yield) was obtained. $^1$H NMR (400 MHz, CDCl$_3$) δ ppm 1.18 (d, J=6.59 Hz, 3H) 1.89 (q, J=7.47 Hz, 2H) 2.23 (d, J=7.91 Hz, 2H) 2.26 (s, 3H) 2.92-3.02 (m, 1H) 7.02 (d, J=7.91 Hz, 1H) 7.24-7.28 (m, 2H); MS (ESI) m/z 269, 271 (M–H)$^-$.

42B

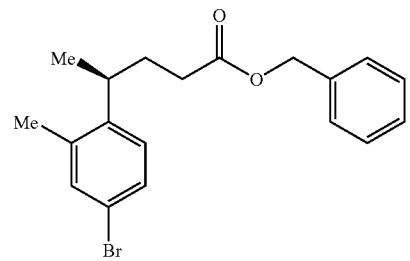 [SMILES: Cc1cc(Br)ccc1[C@@H](C)CCC(=O)OCc1ccccc1]

A mixture of 42A (1.00 g, 3.69 mmol) and sodium bicarbonate (1.2 g, 14.28 mmol) in DMF (10 mL) was stirred at rt for 10 min. Then benzyl bromide (1.535 mL, 12.91 mmol) was added and the reaction was stirred at 65° C. for 15 h. TLC indicated a clean reaction. It was diluted with diethyl ether, washed with water, brine and dried over Na$_2$SO$_4$. After evaporation of solvent, the crude material in small amount of CHCl$_3$/hexanes was charged to a 40 g silica gel column, eluted with hexanes for 8 min and then with ethyl acetate in hexanes from 0-13% in 13 min gradient time to give 42B (1.4 g, 3.88 mmol, 105% yield) as a clear oil. $^1$H NMR (400 MHz, CDCl$_3$) δ ppm 1.19 (d, J=6.59 Hz, 3H) 1.92 (q, J=7.62 Hz, 2H) 2.22-2.30 (m, 5H) 2.92-3.01 (m, 1H) 5.07 (s, 2H) 7.04 (d, J=8.35 Hz, 1H) 7.29-7.40 (m, 8H).

42C

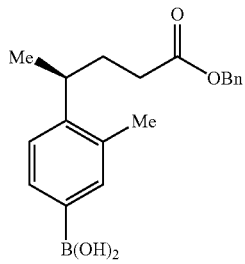

Using a procedure analogous to that used to prepare 29B, 42B (1.4 g, 3.88 mmol) (1200 mg, 1.674 mmol) was reacted with bis(neopentyl glycolato)diboron), potassium acetate and (1,1'-bis(diphenylphosphino)ferrocene)-dichloropalladium (II). The crude was purified by flash chromatography (EtOAc/hexanes 0% to 20% and preparative HPLC (CH$_3$CN/H$_2$O, 0.1% TFA) to give 42C (810 mg, 2.483 mmol, 64.1% yield) as viscous oil after lyophilization. $^1$H NMR (400 MHz, methanol-d$_4$) δ ppm 1.18 (d, J=7.03 Hz, 3H) 1.91 (q, J=7.18 Hz, 2H) 2.19-2.27 (m, 5H) 2.97-3.06 (m, 1H) 5.04 (s, 2H) 7.11-7.55 (m, 8H). MS (ESI) m/z 344 (M+NH$_4$)$_t$.

42D

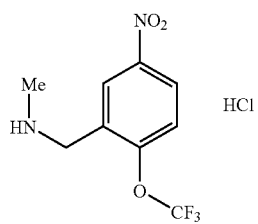 [SMILES: CNCc1cc([N+](=O)[O-])ccc1OC(F)(F)F ; Cl]

To Intermediate 14 (0.94 g, 2.68 mmol) was added 4.0N HCl in dioxane (10.06 mL, 40.3 mmol). The mixture was stirred at rt for 15.0 h. LC-MS indicated a clean reaction. Solvent was removed to give 42D (760 mg, 2.65 mmol, 99% yield) as a white solid. $^1$H NMR (400 MHz, methanol-d$_4$) δ ppm 2.81 (s, 3H) 4.42 (s, 2H) 7.72 (dd, J=9.01, 1.98 Hz, 1H) 8.48 (dd, J=9.23, 2.64 Hz, 1H) 8.61 (d, J=2.64 Hz, 1H); $^{19}$F NMR (376 MHz, Solvent) δ ppm −58.71 ppm. MS (ESI) m/z 251 (M+H)$^+$.

42E

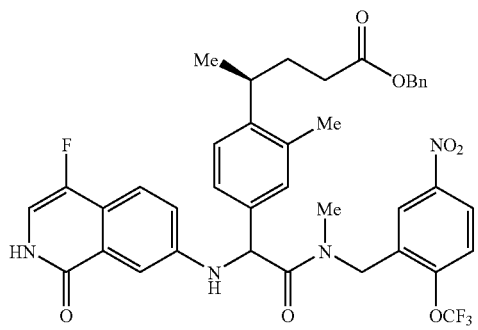 [SMILES: Cc1cc(C(Nc2ccc3c(F)c[nH]c(=O)c3c2)C(=O)N(C)Cc2cc([N+](=O)[O-])ccc2OC(F)(F)F)ccc1[C@@H](C)CCC(=O)OCc1ccccc1]

Using a procedure analogous to that used to prepare 41E, a mixture of 42C (112 mg, 0.342 mmol), Intermediate 6 (100 mg, 0.342 mmol) and 2-oxoacetic acid hydrate were reacted. The resulting solution was reacted with 42D (98 mg, 0.342 mmol) using BOP and DIEA. The crude product was purified by prep HPLC to give 42E (185 mg, 0.247 mmol, 72.2% yield) as a yellow solid. MS (ESI) m/z 749 (M+H)$^+$.

42F

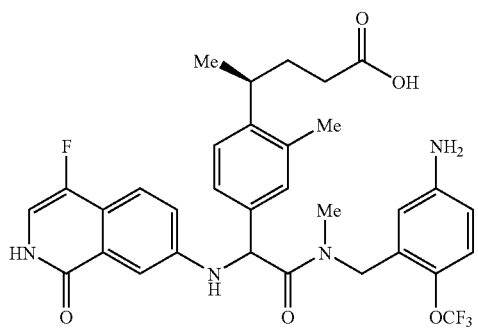 [SMILES: Cc1cc(C(Nc2ccc3c(F)c[nH]c(=O)c3c2)C(=O)N(C)Cc2cc(N)ccc2OC(F)(F)F)ccc1[C@@H](C)CCC(=O)O]

A solution of 42E (185 mg, 0.247 mmol) and 10% Pd/C (120 mg, 0.247 mmol) in MeOH (10 mL) and a few drops of water were hydrogenated with a hydrogen balloon for 3.0 h. TLC indicated completion of reaction. Pd/C was removed by filtration. The filtrate was concentrated to give 42F (140 mg, 0.223 mmol, 90% yield) as a yellow solid (>90% purity). It was used for next step without further purification. MS (ESI) m/z 629 (M+H)$^+$.

Example 42

To a solution of BOP (191 mg, 0.433 mmol) and DMAP (106 mg, 0.865 mmol) in CH$_2$Cl$_2$ (33 ml) and DMF (3 mL) at rt was added a solution of 42F (136 mg, 0.216 mmol) and DIEA (0.113 mL, 0.649 mmol) in DMF (8.0 mL) via a syringe pump over 8 h. To the reaction mixture was added 0.5 N HCl (30 mL), stirred for 10 min. The organic layer was collected and aqueous was extracted with CH$_2$Cl$_2$. The organic layers were dried over Na$_2$SO$_4$. After evaporation of solvent, it was dissolved in MeOH/DMSO (5.0 mL, 10:1) and purified (3 injections) by preparative HPLC equipped with a C18 Phenomenex Luna AXIA column (30 mm×75 cm, 5μ) with the UV detector set at 254 nm. The separations were performed using a gradient method: 10-100% B in 10 min; then 100% B in 2 min with a flow rate of 40 mL/min. Solvent B is 90% acetonitrile-10% water-0.1% TFA and solvent A is 10% acetonitrile-90% water-0.1% TFA. The desired fractions were collected to give a mixture of diastereoisomers (88 mg). The mixture of diastereoisomers (88 mg) was dissolved in 6.0 mL of 50/50 methanol-ethanol and 4.0 mL of heptane and separated by a Chiral Regis Whelk-01 (R,R), 250×20 mm column eluting with 40% (50/50 methanol-ethanol): 60% Heptane at 20 mL/min to obtain the first peak (RT=5.9 min, 31 mg) and then second peak (31 mg, RT=13 min). The second peak was confirmed to be Example 42: $^1$H NMR (500 MHz, methanol-d$_4$) δ ppm 1.14 (d, J=7.15 Hz, 3H) 1.77-1.84 (m, 1H) 2.14 (s, 3H) 2.24-2.34 (m, 3H) 2.91-2.99 (m, 1H) 3.32 (s, 3H) 3.79 (d, J=17.05 Hz, 1H) 5.34 (d, J=17.05 Hz, 1H) 5.56 (s, 1H) 5.90 (d, J=2.20 Hz, 1H) 6.69 (dd, J=8.80, 2.75 Hz, 1H) 6.79 (d, J=5.50 Hz, 1H) 7.00 (s, 1H) 7.07 (d, J=7.15 Hz, 1H) 7.22 (dd, J=8.80, 2.20 Hz, 1H) 7.28-7.33 (m, 2H) 7.46 (d, J=8.80 Hz, 1H) 7.50-7.53 (m, 1H). $^{19}$F NMR (471 MHz, Methanol-d$_4$) δ ppm −160.12 (s, 1F)-59.04 (s, 3F). MS (ESI) m/z 611 (M+H)$^+$. Analytical HPLC (Method A): Col A: 7.56 min, 99%; Col B: 7.97 min, 99%.

Example 43

(2R,15S)-2-(4-Fluoro-1-oxo-1,2-dihydro-isoquinolin-7-ylamino)-17-methoxy-4,15-dimethyl-4,11-diaza-tricyclo[14.2.2.16,10]henicosa-1(19),6,8,10(21),16(20),17-hexaene-3,12-dione

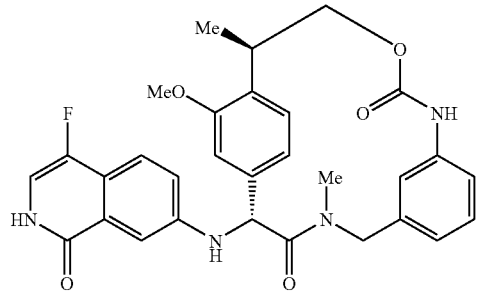 [SMILES: COc1cc2ccc1[C@@H](C)COC(=O)Nc1cccc(c1)CN(C)C(=O)[C@@H]2Nc1ccc2c(F)c[nH]c(=O)c2c1]

43A

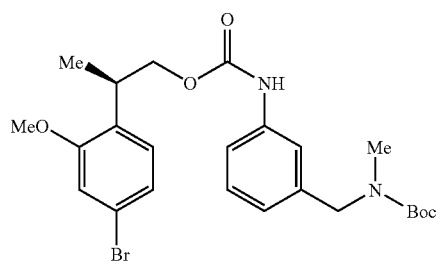

Using a procedure analogous to that used to prepare 29A, 171 (1.473 g, 6.23 mmol) was reacted with sodium bicarbonate and phosgene followed by Intermediate 9 (1.175 g, 4.79 mmol) and TEA. The crude product was added to a silica gel column (120 g) and was eluted with EtOAc/hexanes (0-50% in 50 min) to give 43A 1.56 g (64%) white solid material. $^1$H NMR (400 MHz, DMSO-d$_6$) δ ppm 1.15-1.21 (m, 3H) 1.40

(d, J=10.86 Hz, 9H) 2.72 (s, 3H) 3.79 (s, 3H) 4.16 (d, J=6.82 Hz, 2H) 4.30 (s, 2H) 6.81 (d, J=7.07 Hz, 1H) 7.07-7.16 (m, 2H) 7.17-7.25 (m, 2H) 7.26-7.44 (m, 2H).

43B

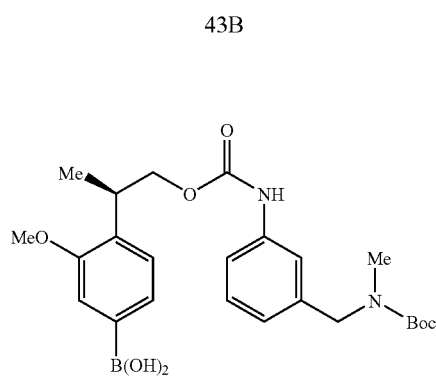

Using a procedure analogous to that used to prepare 29B, 43A (1.0 g, 1.971 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 60% and preparative HPLC (CH$_3$CN/H$_2$O, 0.1% TFA) to give 43B (0.67 g, 73% yield) as a white solid. $^1$H NMR (400 MHz, DMSO-d$_6$) δ ppm 1.21 (d, J=7.07 Hz, 3H) 1.41 (d, J=11.62 Hz, 9H) 2.72 (s, 3H) 3.69-3.86 (m, 3H) 4.09-4.25 (m, 2H) 4.30 (s, 2H) 6.81 (d, J=7.33 Hz, 1H) 7.15-7.26 (m, 2H) 7.26-7.46 (m, 4H) 9.56 (s, 1H); $^{19}$F NMR (376 MHz, DMSO-d$_6$) δ ppm −75.23 (s, 1F); MS (ESI) m/z 413.4 (M-tBu)$^+$.

43C

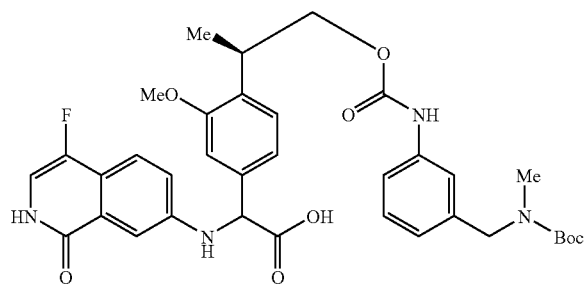 [SMILES: COc1cc(C(Nc2ccc3c(F)c[nH]c(=O)c3c2)C(=O)O)ccc1[C@@H](C)COC(=O)Nc1cccc(CN(C)C(=O)OC(C)(C)C)c1]

Using a procedure analogous to that used to prepare 1E, 43B (0.1 g, 0.212 mmol) Intermediate 6, and glyoxylic acid monohydrate were reacted and purified by flash chromatography (0% to 10% MeOH in CH$_2$Cl$_2$) to give 43C (0.091 g, 68% yield) as an orange sticky solid. $^1$H NMR (400 MHz, DMSO-d$_6$) δ ppm 1.15-1.22 (m, 3H) 1.32-1.48 (m, 9H) 2.69-2.75 (m, 3H) 3.42-3.53 (m, 1H) 3.78 (d, J=1.77 Hz, 3H) 4.17 (d, J=6.57 Hz, 2H) 4.29 (s, 2H) 5.18 (s, 1H) 6.80 (d, J=6.82 Hz, 1H) 6.93-7.02 (m, 2H) 7.04-7.13 (m, J=13.64 Hz, 1H) 7.15-7.24 (m, 2H) 7.23-7.43 (m, 4H) 7.49 (d, J=8.84 Hz, 1H) 9.58 (s, 1H) 10.80 (d, J=6.32 Hz, 1H); MS (ESI) m/z 663.2 (M+H)$^+$.

43D

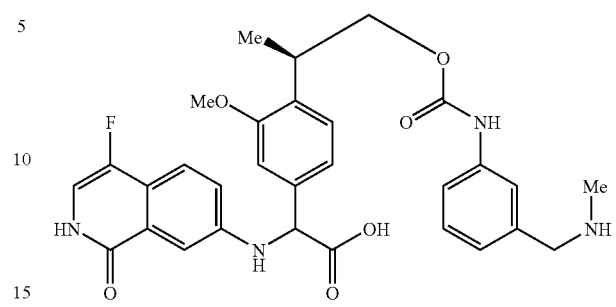

To 43C (0.185 g, 0.279 mmol) was added 4M HCl in dioxane (4.89 mL, 19.54 mmol). The mixture was stirred at rt for 1 h. The solvent was removed and residue was dried under high vacuum to give 43D in quantitative yield. The product was taken to the next step without further purification. $^1$H NMR (400 MHz, DMSO-d$_6$) δ ppm m 1.14-1.24 (m, 3H) 2.61-2.68 (m, J=2.02 Hz, 1H) 2.72 (s, 3H) 3.78 (d, J=1.52 Hz, 3H) 3.96-4.09 (m, 2H) 4.14-4.25 (m, 2H) 5.19 (s, 1H) 7.00 (s, 1H) 7.10 (d, J=7.83 Hz, 2H) 7.19 (d, J=5.31 Hz, 1H) 7.23-7.43 (m, 5H) 7.50 (d, J=8.84 Hz, 1H) 7.64 (s, 1H) 8.75-8.91 (m, 1H) 9.73 (s, 1H) 10.80 (d, J=5.81 Hz, 1H). MS (ESI) m/z 563.5 (M+H)$^+$. LCMS at 1.347 min showed MS (ESI) (m/z) 563.5 [M+H]$^+$.

Example 43

To a solution of BOP (0.314 g, 0.711 mmol) and DMAP (0.174 g, 1.422 mol) in dichloromethane (40 mL) and DMF (5 mL) at rt was added a solution of 43D (0.2 g, 0.355 mmol) and DIEA (0.124 mL, 0.711 mmol) in DMF (5 mL) via a syringe pump over 10 h. The reaction was diluted with dichloromethane, washed with 0.5N HCl, brine and water and dried over sodium sulfate. The layers were separated and the organic layer was dried over sodium sulfate. The solvent was removed and residue was redissolved in solvent B (90% acetonitrile-10% water-0.1% TFA). The sample was purified using a preparative HPLC equipped with a C18 Phenomenex AXIA Luna column (30 mm×100 mm, 5μ). The UV detector was set at 254 nm. The separations were performed using a gradient method: 30-80% B in 15 mins; then 100% B in 2 mins with a flow rate of 40 mL/min. Solvent B is 90% acetonitrile-10% water-0.1% TFA and solvent A is 10% acetonitrile-90% water-0.1% TFA. The fractions were collected-two peaks of same MW corresponding diastereomers. The isomers were further purified and separated using a preparative HPLC equipped with a Whelko-01 column. The separations were performed using an isocratic method of 30% 1:1 ethanol/methanol: heptane for 40 min with a flow rate of mL/min. The fractions of the second peak were combined to give Example 43 (0.008 g, 8% yield): Chiral HPLC-14.05 min retention time-Anal Chiral HPLC, Whelko-01 column (4.6× 250 mm, 10μ); $^1$H NMR (400 MHz, methanol-d$_4$) δ ppm 1.26 (t, J=7.20 Hz, 3H) 3.27 (s, 3H) 3.66 (s, 3H) 3.84 (none, 2H) 4.19 (d, J=9.60 Hz, 1H) 4.37 (t, J=10.11 Hz, 1H) 5.42-5.51 (m, 1H) 5.70 (s, 1H) 6.05 (s, 1H) 6.69 (d, J=7.83 Hz, 1H) 6.89 (t, J=5.94 Hz, 2H) 7.03 (s, 1H) 7.16 (t, J=7.83 Hz, 1H) 7.30-7.37 (m, 3H) 7.41-7.46 (m, 1H) 7.57 (d, J=8.84 Hz, 1H); $^{19}$F NMR (376 MHz, methanol-d$_4$) δ ppm −160.74 (s, 1F); MS (ESI) m/z 545.7 (M+H)$^+$ Analytical HPLC (Method B): Col A: 13.26 min, 98%; Col B: 13.36 min, 86%.

Example 44

(2R,15S)-2-(4-Chloro-1-oxo-1,2-dihydro-isoquinolin-7-ylamino)-17-methoxy-4,15-dimethyl-4,11-diaza-tricyclo[14.2.2.16,10]henicosa-1(19),6,8,10(21),16(20),17-hexaene-3,12-dione

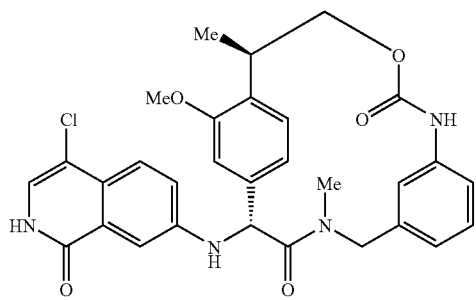

44A

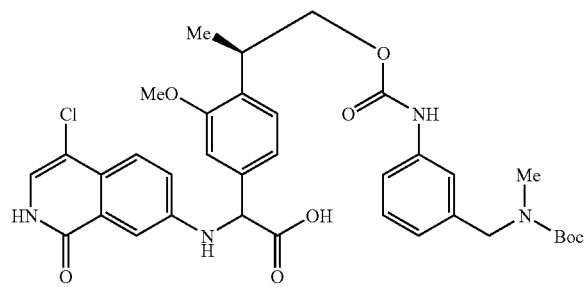

Using a procedure analogous to that used to prepare 1E, 43B (0.2 g, 0.423 mmol), Intermediate 5, and glyoxylic acid monohydrate were reacted and purified by flash chromatography (0% to 10% MeOH in CH$_2$Cl$_2$) to give 44A as an orange sticky solid in quantitative yield. MS (ESI) m/z 679.6 (M+H)$^+$.

44B

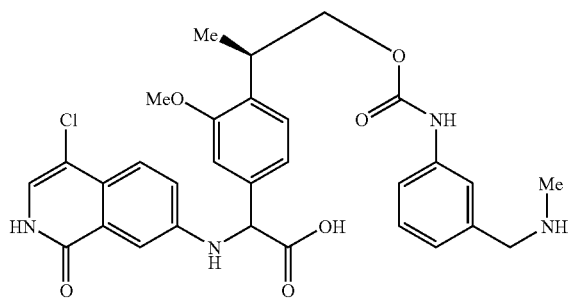 [SMILES: CNCc1cccc(NC(=O)OC[C@H](C)c2ccc(C(Nc3ccc4c(Cl)c[nH]c(=O)c4c3)C(=O)O)cc2OC)c1]

To 44A (0.32 g, 0.471 mmol) was added 4M HCl in dioxane (8.25 mL, 33.0 mmol). The mixture was stirred at rt for 1 h. The solvent was removed and residue was dried under high vacuum to give 44B (0.27 g, 99% yield) as an orange sticky solid. The product was taken to the next step without further purification. MS (ESI) m/z 579.4 (M+H)$^+$.

Example 44

To a solution of BOP (0.412 g, 0.933 mmol) and DMAP (0.228 g, 1.865 mmol) in dichloromethane (40 mL) and DMF (5 mL) at rt was added a solution of 44B (0.27 g, 0.466 mmol) and DIEA (0.2 mL, 1.145 mmol) in DMF (5 mL) via a syringe pump over 10 hrs. The reaction was diluted with dichloromethane, washed with 0.5N HCl, brine and water and dried over sodium sulfate. The layers were separated and the org layer was dried over sodium sulfate. The solvent was removed and residue was purified using a preparative HPLC equipped with a C18 Phenomenex AXIALuna column (30 mm×100 mm, 5µ). The UV detector was set at 254 nm. The separations were performed using a gradient method: 30-80% B in 15 mins; then 100% B in 2 mins with a flow rate of 40 mL/min. Solvent B is 90% acetonitrile-10% water-0.1% TFA and solvent A is 10% acetonitrile-90% water-0.1% TFA. The fractions were collected to give a mixture of two diastereomers. The isomers were further purified and separated using a preparative HPLC equipped with a Whelko-01 column. The separations were performed using an isocratic method of 30% 1:1 ethanol/methanol: heptane for 40 min with a flow rate of 20 mL/min. The second peak (6.0 mg, 5% yield.) was conformed to be Example 44: Chiral HPLC: 14.74 min retention time-Anal Chiral HPLC, Whelko-01 column (4.6×250 mm, 10µ); $^1$H NMR (400 MHz, methanol-d$_4$) δ ppm 1.21 (t, J=6.95 Hz, 3H) 3.18-3.24 (m, 3H) 3.61 (s, 3H) 3.79 (d, J=16.42 Hz, 1H) 4.08-4.20 (m, 1H) 4.25-4.37 (m, 1H) 4.83 (s, 1H) 5.40 (d, J=16.17 Hz, 1H) 5.63 (s, 1H) 5.98 (s, 1H) 6.62 (d, J=7.33 Hz, 1H) 6.83 (d, J=7.58 Hz, 1H) 6.97 (s, 2H) 7.10 (t, J=7.71 Hz, 1H) 7.23-7.34 (m, 3H) 7.40 (d, J=2.53 Hz, 1H) 7.61 (d, J=8.84 Hz, 1H); MS (ESI) m/z 561.6 (M+H)$^+$ Analytical HPLC (Method B): Col A: 13.92 min, 98%; Col B: 14.15 min, 92%.

Example 45

(2R,15R)-2-(6-Fluoro-3-oxo-2,3-dihydro-1H-isoindol-5-ylamino)-17-methoxy-4,15-dimethyl-13-oxa-4,11-diaza-tricyclo[14.2.2.16,10]henicosa-1(19),6,8,10(21),16(20),17-hexaene-3,12-dione

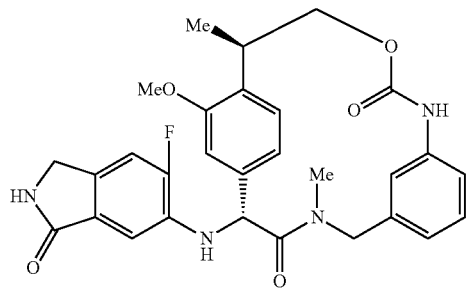 [SMILES: COc1cc2ccc1[C@@H](C)COC(=O)Nc1cccc(c1)CN(C)C(=O)[C@@H]2Nc1cc2c(cc1F)CNC2=O]

45A

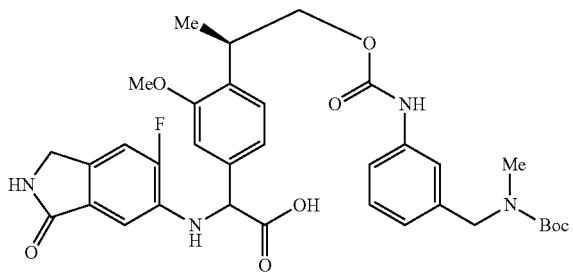 [SMILES: COc1cc(C(Nc2cc3c(cc2F)CNC3=O)C(=O)O)ccc1[C@@H](C)COC(=O)Nc1cccc(CN(C)C(=O)OC(C)(C)C)c1]

Using a procedure analogous to that used to prepare 1E, 43B (0.1 g, 0.212 mmol), Intermediate 7, and glyoxylic acid monohydrate were reacted and purified by flash chromatography (0% to 10% MeOH in $CH_2Cl_2$) to give 45A (0.049 g, 67% yield) as a white solid. $^1$H NMR (400 MHz, DMSO-$d_6$) δ ppm 1.18 (d, J=7.33 Hz, 3H) 1.40 (d, J=11.87 Hz, 9H) 2.72 (s, 3H) 3.76 (d, J=4.55 Hz, 2H) 4.11-4.21 (m, 5H) 4.29 (s, 1H) 5.19-5.36 (m, 2H) 5.67-5.79 (m, 1H) 6.74-6.88 (m, 2H) 7.01 (d, J=8.34 Hz, 1H) 7.04-7.13 (m, 1H) 7.15-7.27 (m, 3H) 7.28-7.36 (m, 2H) 8.32 (s, 1H) 8.38 (s, 1H) 9.58 (s, 1H); $^{19}$F NMR (376 MHz, DMSO-$d_6$) δ ppm −130.00 (s, 1F); MS (ESI) m/z 651.7 (M+H)$_j$.

45B

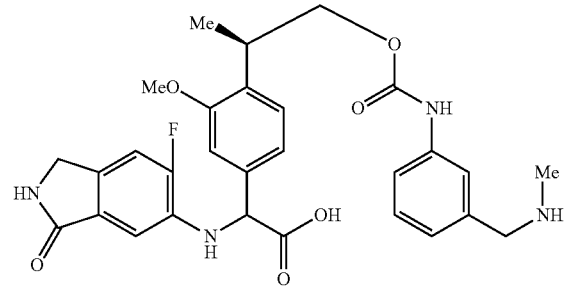 [SMILES: CNCc1cccc(NC(=O)OC[C@H](C)c2ccc(C(Nc3cc4c(cc3F)CNC4=O)C(=O)O)cc2OC)c1]

To 45A (0.15 g, 0.231 mmol) was added 4M HCl in dioxane (4.03 mL, 16.14 mmol). The mixture was stirred at rt for 1 h. The solvent was removed and residue was dried under high vacuum overnight to give 45B (0.12 g) in quantitative yield. The prod was taken to the next step without further purification. MS (ESI) m/z 551.3 (M+H)$^+$.

Example 45

To a solution of BOP (0.204 g, 0.461 mmol) and DMAP (0.113 g, 0.923 mmol) in dichloromethane (40 mL) and DMF (5 mL) at rt was added a solution of 45B (0.127 g, 0.231 mmol) and DIEA (0.081 mL, 0.461 mmol) in DMF (5 mL) via a syringe pump over 10 h. The reaction was diluted with dichloromethane, washed with 0.5N HCl, brine and water and dried over sodium sulfate. The layers were separated and the organic layer was dried over sodium sulfate. The crude was purified using a preparative HPLC equipped with a C18 Phenomenex AXIALuna column (30 mm×100 mm, 5µ). The UV detector was set at 254 nm. The separations were performed using a gradient method: 30-80% B in 15 mins; then 100% B in 2 mins with a flow rate of 40 mL/min. Solvent B is 90% acetonitrile-10% water-0.1% TFA and solvent A is 10% acetonitrile-90% water-0.1% TFA. The fractions were collected to give a mixture of two diastereoisomers. The isomers were further purified and separated using a preparative HPLC equipped with a Whelko-01 column. The separations were performed using an isocratic method of 30% 1:1 ethanol/methanol: heptane for 40 min with a flow rate of 20 mL/min. The second peak (5.0 mg, 8% yield) was confirmed to be Example 45: Chiral HPLC: 19.83 min retention time-Anal Chiral HPLC, Whelko-01 column (4.6×250 mm, 10µ). $^1$H NMR (400 MHz, methanol-$d_4$) δ ppm 1.20 (d, J=7.33 Hz, 3H) 3.19 (s, 3H) 3.59 (s, 3H) 3.80 (d, J=16.42 Hz, 1H) 4.09-4.17 (m, J=18.95 Hz, 1H) 4.21 (d, J=2.27 Hz, 2H) 4.26-4.38 (m, 1H) 5.40 (d, J=16.17 Hz, 1H) 5.61-5.69 (m, 1H) 5.96 (s, 1H) 6.58-6.65 (m, 1H) 6.80-6.87 (m, 2H) 7.03-7.19 (m, 4H) 7.27 (s, 2H); $^{19}$F NMR (376 MHz, methanol-$d_4$) δ ppm −131.58 (none, 253F); MS (ESI) m/z 533.3 (M+H)$^+$ Analytical HPLC (Method B): Col A: 12.85 min, 98%; Col B: 12.65 min, 96%.

Example 46

(2R,15R)-7-Cyclopropanesulfonyl-15-methoxy-4,20-dimethyl-2-(1-oxo-1,2-dihydro-isoquinolin-7-ylamino)-13-oxa-4,11-diaza-tricyclo[14.2.2.16,10]henicosa-1(19),6,8,10(21),16(20),17-hexaene-3,12-dione

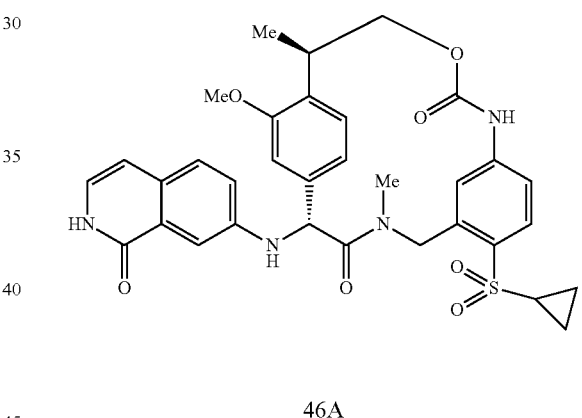

46A

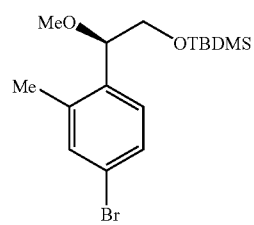 [SMILES: CO[C@@H](CO[Si](C)(C)C(C)(C)C)c1ccc(Br)cc1C]

To 40E (2.2 g, 6.37 mmol) and iodomethane (1.190 mL, 19.11 mmol) in acetonitrile (50 mL) was added potassium tert-butoxide (0.911 g, 8.12 mmol). The mixture was stirred at room temperature overnight. The reaction was quenched by saturated NH$_4$Cl 100 mL, extracted with EtOAc (2×100 mL) and the combined organic layers were dried over sodium sulfate and concentrated to an oil. The residue was dissolved in small amount of chloroform and added to a 40 g ISCO column and was first eluted with hexanes for 8 min and then eluted with 0-14% EtOAc/Hex in 12 min to give 46A (1.4 g, 3.90 mmol, 61.2% yield) as clear oil. $^1$H NMR (400 MHz, CDCl$_3$) δ ppm −0.00 (s, 3H) 0.03 (s, 3H) 0.88-0.90 (s, 9H) 2.36 (s, 3H) 3.30 (s, 3H) 3.63 (dd., J=10.99, 4.39 Hz, 1H) 3.79 (dd, J=10.99, 7.03 Hz, 1H) 4.50 (dd, J=7.03, 4.39 Hz, 1H) 7.29-7.40 (m, 3H).

46B

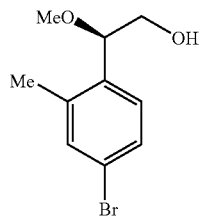 [SMILES: CO[C@@H](CO)c1ccc(Br)cc1C]

To 46A (1.4 g, 3.90 mmol) in THF (3 mL) at 0° C. was added TBAF (5.84 mL, 5.84 mmol). The reaction was stirred at rt for 1 h. The reaction was quenched with saturated ammonium chloride and extracted with ethyl acetate. The organic layer was then washed with brine and dried over sodium sulfate. The solvent was removed and the residue was dissolved in a small amount of dichloromethane and charged to a 120 g silica gel cartridge which was eluted with 0-50% ethyl acetate/hexanes over a period of 50 min to give 46B (0.69 g, 72.3% yield). $^1$H NMR (400 MHz, DMSO-d$_6$) δ ppm 2.29 (s, 3H) 3.15 (s, 3H) 3.32-3.50 (m, 2H) 4.40 (dd, J=7.07, 4.29 Hz, 1H) 4.86 (t, J=5.94 Hz, 1H) 7.16-7.22 (m, 1H) 7.32-7.42 (m, 2H); MS (ESI) m/z 247.3 (M+H)$^+$.

46C

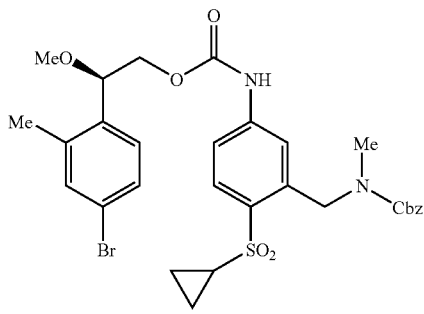 [SMILES: CO[C@@H](COC(=O)Nc1ccc(S(=O)(=O)C2CC2)c(CN(C)C(=O)OCc2ccccc2)c1)c1ccc(Br)cc1C]

Using a procedure analogous to that used to prepare 29A, 39E (0.958 g, 2.56 mmol) was reacted with sodium bicarbonate and phosgene followed by 46B (0.690 g, 2.81 mmol) and TEA. The crude product was added to a silica gel column (80 g) and was eluted with EtOAc/hexanes (0-80% in 15 min) to give 46C (1.45 g, 88% yield) as a white solid material. $^1$H NMR (400 MHz, DMSO-d$_6$) δ ppm 0.86-0.93 (m, 1H) 1.03 (d, J=8.84 Hz, 3H) 2.35 (s, 3H) 2.98 (s, 3H) 3.18 (s, 3H) 4.07-4.25 (m, 2H) 4.70 (dd, J=7.71, 3.41 Hz, 1H) 4.88 (s, 2H) 5.10 (d, J=37.64 Hz, 2H) 7.11-7.20 (m, 1H) 7.20-7.47 (m, 7H) 7.47-7.54 (m, 1H) 7.59-7.71 (m, 1H) 7.71-7.81 (m, 1H) 10.29 (s, 1H). MS (ESI) m/z 647.4 (M+H)$^+$.

46D

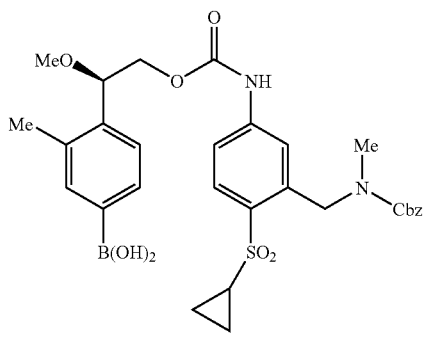 [SMILES: CO[C@@H](COC(=O)Nc1ccc(S(=O)(=O)C2CC2)c(CN(C)C(=O)OCc2ccccc2)c1)c1ccc(B(O)O)cc1C]

Using a procedure analogous to that used to prepare 29B, 46C (1.4 g, 2.169 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 2% to 70% and preparative HPLC (CH$_3$CN/H$_2$O, 0.1% TFA) to yield 46D (1.02 g, 1.671 mmol, 77% yield) as a white solid after lyophilization. $^1$H NMR (400 MHz, methanol-d$_4$) δ ppm 0.76-1.09 (m, 4H) 2.30 (s, 3H) 2.47 and 2.71 (br s, 1H) 2.97 (s, 3H) 3.16 (s, 3H) 4.08-4.16 (m, 2H) 4.72 (t, J=5.49 Hz, 1H) 4.85 (s, 2H) 4.99 (br s, 1H) 5.10 (br s, 1H) 7.04-7.69 (m, 11H); MS (ESI) m/z 611 (M+H)$^+$.

46E

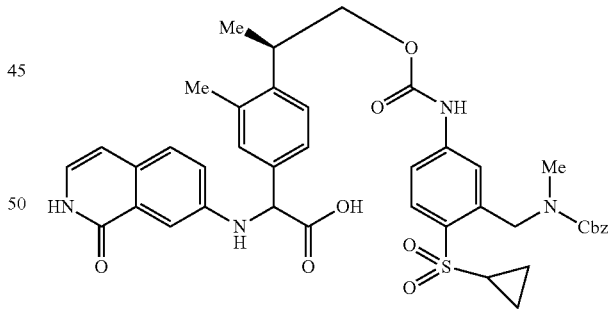

Using a procedure analogous to that used to prepare 1E, 46D (0.03 g, 0.491 mmol), Intermediate 3, and glyoxylic acid monohydrate were reacted and purified by flash chromatography (0% to 20% MeOH in CH$_2$Cl$_2$) to yield 46E (0.27 g, 70% yield). $^1$H NMR (400 MHz, DMSO-d$_6$) δ ppm 0.80-1.09 (m, 4H) 2.28-2.40 (m, 3H) 2.98 (s, 3H) 3.11-3.20 (m, 4H) 4.16 (d, J=22.99 Hz, 2H) 4.71 (s, 1H) 4.88 (s, 2H) 4.99-5.17 (m, 3H) 6.31-6.41 (m, 1H) 6.77-6.90 (m, 1H) 7.08-7.45 (m, 11H) 7.51 (d, J=12.38 Hz, 1H) 7.60-7.89 (m, 2H) 10.31 (s, 1H) 10.91 (s, 1H); MS (ESI) m/z 783.5 (M+H)⁺.

46F

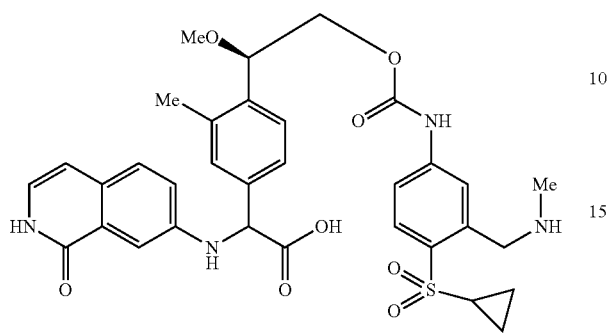

46E (0.27 g, 0.345 mmol) and 10% Pd on carbon (0.16 g, 0.345 mmol) in MeOH (20 mL) and DMF (3.0 mL) was hydrogenated with a hydrogen balloon for 1.0 h. HPLC indicated a clean reaction. Pd/C was filtered off and washed with mixture of MeOH/DMF (3:1) and the filtrate was combined, evaporated and dried to give 46F (0.277 g) as a yellow solid in quantitative yield. ¹H NMR (400 MHz, DMSO-d₆) δ ppm 0.96-1.13 (m, 4H) 2.25-2.39 (m, 4H) 3.10 (d, J=28.30 Hz, 2H) 3.12-3.26 (m, 3H) 4.20 (d, J=7.33 Hz, 2H) 4.39 (s, 1H) 4.52-4.76 (m, 2H) 6.26-6.50 (m, 2H) 6.78 (s, 1H) 6.91-7.05 (m, 1H) 7.07-7.40 (m, 6H) 7.48 (s, 1H) 7.74 (dd, J=8.59, 2.27 Hz, 1H) 10.11 (d, J=13.14 Hz, 1H) 10.85 (s, 1H); MS (ESI) m/z 649.3 (M+H)⁺.

Example 46

To a solution of BOP (0.3 g, 0.678 mmol) and DMAP (0.17 g, 1.357 mmol) in dichloromethane (60 mL) and DMF (6 mL) was added a solution of 46F (220 mg, 0.339 mmol) and DIEA (0.178 ml, 1.017 mmol) in DMF (6.0 mL) via a syringe pump over 10 h. To the reaction mixture was added water and 0.5 N HCl, stirred for 10 min. The organic layer was collected and aqueous was extracted with dichloromethane. The organic layers were dried over sodium sulfate. The solvent was removed and the sample was purified using a preparative HPLC equipped with a C18 Phenomenex Luna column (30 mm×100 mm, 5 g). The UV detector was set at 220 nm. The separations were performed using a gradient method: 10-50% B in 12 mins; then 50% B in 3 min with a flow rate of 40 mL/min. Solvent B is 90% acetonitrile-10% water-0.1% TFA and solvent A is 10% acetonitrile-90% water-0.1% TFA. The fractions were collected to give a mixture of two diastereoisomers. The isomers were further purified and separated using a preparative HPLC equipped with a Whelko-01 column. The separations were performed using an isocratic method of 50% 1:1 ethanol/methanol: heptane for 40 min with a flow rate of 20 mL/min. The second peak (12.0 mg, 12% yield) was confirmed to be Example 46:

Chiral HPLC: 15.16 min retention time-Anal Chiral HPLC, Whelko-01 column (4.6×250 mm, 10μ). ¹H NMR (400 MHz, methanol-d₄) δ ppm 0.91-1.27 (m, 4H) 2.25 (s, 3H) 2.73-2.88 (m, 1H) 3.25-3.40 (m, 6H) 4.01-4.33 (m, 2H) 4.49-4.75 (m, 2H) 5.60 (s, 1H) 5.68 (d, J=17.68 Hz, 1H) 6.35 (s, 1H) 6.49 (d, J=6.82 Hz, 1H) 6.76 (d, J=8.34 Hz, 1H) 6.85 (d, J=6.82 Hz, 1H) 7.11 (s, 1H) 7.15-7.24 (m, 1H) 7.31-7.41 (m, 2H) 7.51 (d, J=7.58 Hz, 1H) 7.65 (d, J=8.59 Hz, 2H); MS (ESI) m/z 631.3 (M+H)⁺ Analytical HPLC (Method B): Col A: 11.71 min, 99%; Col B: 11.13 min, 98%.

Example 47

(2R,15S)-17-Methoxy-4,15-dimethyl-2-(1-oxo-1,2-dihydro-isoquinolin-7-ylamino)-4,11-diaza-tricyclo[14.2.2.1⁶,¹⁰]henicosa-1(19),6,8,10(21),16(20),17-hexaene-3,12-dione

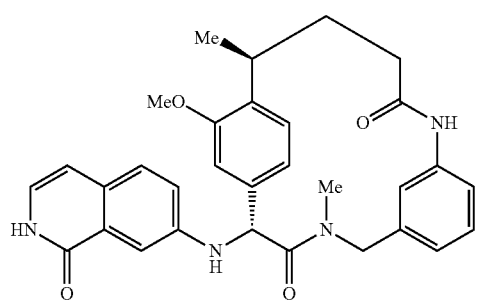 [SMILES: COc1cc2ccc1[C@@H](C)CCC(=O)Nc1cccc(c1)CN(C)C(=O)[C@@H]2Nc1ccc2cc[nH]c(=O)c2c1]

47A

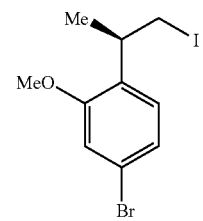 [SMILES: COc1cc(Br)ccc1[C@@H](C)CI]

Using a procedure analogous to that used to prepare 41A, Intermediate 9 (1.5 g, 6.12 mmol) was reacted with triphenylphosphine, imidazole, and iodine and purified by column chromatography (EtOAc/hexanes 0-25%) to give 47A (0.84 g, 97%) as a colorless oil. ¹H NMR (400 MHz, methanol-d₄) δ ppm 1.13-1.41 (m, 3H) 3.32-3.41 (m, 2H) 3.40-3.53 (m, 1H) 3.77-3.90 (m, 3H) 6.94-7.16 (m, 3H).

47B

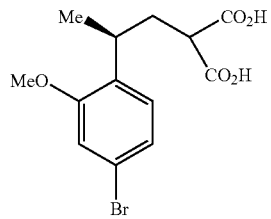 [SMILES: COc1cc(Br)ccc1[C@@H](C)CC(C(=O)O)C(=O)O]

Using a procedure analogous to that used to prepare 41B, 47A (1.23 g, 3.46 mmol) was reacted with dimethyl malonate and NaH and purified by column chromatography (EtOAc/hexanes 0-22%) to give 47B (1.24 g, 3.45 mmol, 100% yield) as a viscous oil. ¹H NMR (400 MHz, CDCl₃) δ ppm 1.19 (d, J=6.59 Hz, 3H) 2.05-2.13 (m, 1H) 2.20 (ddd, J=14.06, 8.79, 5.71 Hz, 1H) 3.11-3.20 (m, 2H) 3.61 (s, 3H) 3.69 (s, 3H) 3.73 (s, 3H) 3.75 (s, 3H) 6.93 (s, 1H) 6.96-7.05 (m, 2H). MS (ESI) m/z 359, 361 (M+H)$^+$.

47C

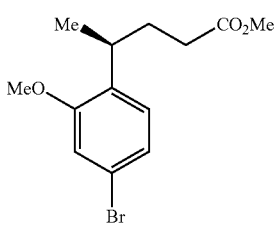 [SMILES: COC(=O)CC[C@H](C)c1ccc(Br)cc1OC]

Using a procedure analogous to that used to prepare 41C, 47B (1.05 g, 2.92 mmol) was reacted with LiCl in DMSO and purified by column chromatography (EtOAc/hexanes 0-22%) to give 47C (0.82 g, 2.72 mmol, 93% yield) as a slightly yellow oil. $^1$H NMR (400 MHz, CDCl$_3$) δ ppm 1.17 (d, J=7.24 Hz, 3H) 1.85 (m, 2H) 2.13-2.24 (m, 2H) 3.09-3.18 (m, 1H) 3.60 (s, 3H) 3.76 (s, 3H) 6.93 (d, J=1.76 Hz, 1H) 6.97-7.04 (m, 2H). MS (ESI) m/z 285, 287 (M+H)$^+$.

47D

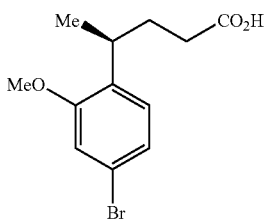 [SMILES: COc1cc(Br)ccc1[C@@H](C)CCC(=O)O]

To 47C (0.33 g, 1.096 mmol) in THF (1 mL) and MeOH (0.5 mL was added LiOH (4 mL, 4.00 mmol). The reaction was stirred overnight at rt. The organic solvent was removed and the aqueous layer was acidified to pH 4 using 6 N HCl. The prod was extracted with ethyl acetate and the organic layer was washed with water and brine and dried over sodium sulfate. The solvent was removed to give 47D (0.297 g, 92% yield) as colorless oil. $^1$H NMR (400 MHz, DMSO-d$_6$) δ ppm 1.11 (d, J=7.07 Hz, 3H) 1.68-1.79 (m, 2H) 2.00-2.08 (m, 2H) 3.02-3.10 (m, 1H) 3.67-3.84 (m, 3H) 6.96-7.21 (m, 3H) 11.94 (s, 1H); MS (ESI) m/z 287.4 (M+H)$^+$.

47E

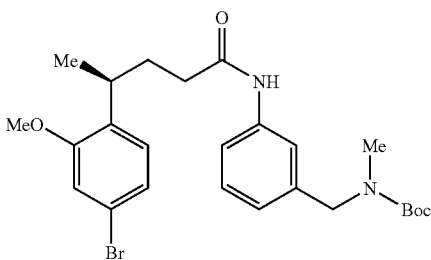

To 47D (0.28 g, 0.975 mmol), HOAt (0.133 g, 0.975 mmol) and 17I (0.253 g, 1.073 mmol) in dichloromethane (5 ml) was added N-methylmorpholine (0.322 mL, 2.93 mmol) and then EDC (0.374 g, 1.950 mmol) was added last. The reaction was stirred at room temperature overnight. The reaction was quenched with water, extracted with EtOAc (3×30 mL). The combined organic layer was washed with 1N HCl. sat. NaHCO$_3$, brine and dried over sodium sulfate. The crude product was purified by flash column chromatography to give 47E (0.33 g, 66% yield). $^1$H NMR (400 MHz, DMSO-d$_6$) δ ppm 1.13 (d, J=7.07 Hz, 3H) 1.40 (d, J=9.60 Hz, 9H) 1.73-1.92 (m, 2H) 2.05-2.23 (m, 2H) 2.72 (s, 3H) 3.02-3.17 (m, J=7.33 Hz, 1H) 3.75 (s, 3H) 4.31 (s, 2H) 6.84 (d, J=7.58 Hz, 1H) 7.05-7.16 (m, 3H) 7.22 (t, J=7.96 Hz, 1H) 7.35-7.56 (m, 2H) 9.76 (s, 1H); MS (ESI) m/z 451.2 (M-tBu)$^+$.

47F

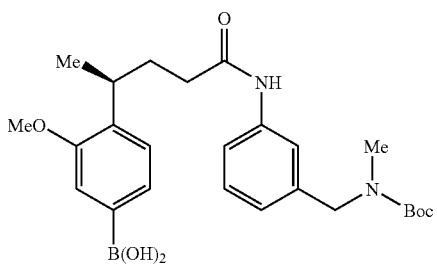

Using a procedure analogous to that used to prepare 29B, 47E (0.32 g, 0.633 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 50% and preparative HPLC (CH$_3$CN/H$_2$O, 0.1% TFA) to give 47F (0.21 g, 71%) white solid. $^1$H NMR (400 MHz, DMSO-d$_6$) δ ppm 1.15 (d, J=6.82 Hz, 3H) 1.38 (s, 9H) 1.75-1.90 (m, 2H) 2.04-2.25 (m, 2H) 2.72 (s, 3H) 3.10-3.21 (m, 1H) 3.74 (s, 3H) 4.30 (s, 2H) 6.84 (d, J=7.83 Hz, 1H) 7.14 (d, J=7.83 Hz, 1H) 7.22 (t, J=7.83 Hz, 1H) 7.33-7.39 (m, 2H) 7.39-7.55 (m, 2H) 9.77 (s, 1H); MS (ESI) m/z 411 (M-tBu)$^+$.

47G

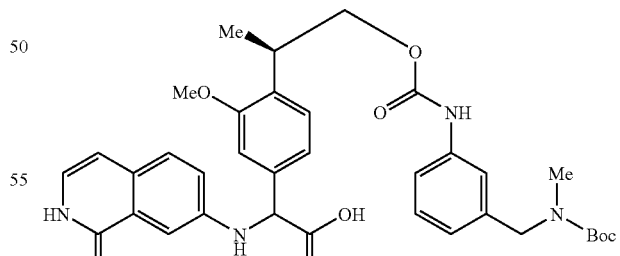

Using a procedure analogous to that used to prepare 1E, 47F (0.3 g, 0.638 mmol, Intermediate 3, and glyoxylic acid monohydrate were reacted and purified by flash chromatography to give 47G (0.36 g, 88% yield) as a brown solid. $^1$H NMR (400 MHz, DMSO-d$_6$) δ ppm 1.14 (d, J=5.05 Hz, 3H) 1.32-1.47 (m, 9H) 1.76-1.90 (m, 2H) 2.08-2.24 (m, 2H) 2.68-2.76 (m, 3H) 3.37-3.49 (m, 1H) 3.76 (d, J=4.04 Hz, 3H)

4.27-4.33 (m, 2H) 5.09 (s, 1H) 6.35 (d, J=6.82 Hz, 1H) 6.79-6.89 (m, 2H) 7.04-7.12 (m, 1H) 7.15 (dd, J=5.81, 1.26 Hz, 1H) 7.17-7.29 (m, 4H) 7.33-7.40 (m, 1H) 7.40-7.56 (m, 2H) 9.80 (s, 1H) 10.91 (d, J=5.56 Hz, 1H) 12.92 (s, 1H); MS (ESI) m/z 643.6 (M+H)+.

47H

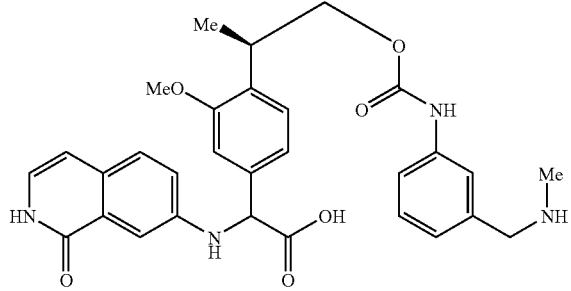 [SMILES: CNCc1cccc(NC(=O)OC[C@H](C)c2ccc(C(Nc3ccc4cc[nH]c(=O)c4c3)C(=O)O)cc2OC)c1]

To 47G (0.38 g, 0.591 mmol) was added 4M in HCl (10.35 mL, 41.4 mmol) and the reaction was stirred at rm temp for 1 h. The solvent was removed and the residue was dried overnight at high vacuum to give 47H (0.32 g) as a yellow solid in quantitative yield. $^1$H NMR (400 MHz, DMSO-d$_6$) δ ppm 1.07-1.15 (m, 3H) 1.55 (s, 3H) 1.76-1.86 (m, 2H) 2.10-2.23 (m, 2H) 3.04-3.16 (m, 1H) 3.73 (d, J=3.54 Hz, 3H) 3.96-4.06 (m, 2H) 5.09 (d, J=1.26 Hz, 1H) 6.33 (d, J=7.07 Hz, 1H) 6.82 (dd, J=6.95, 5.68 Hz, 1H) 7.03-7.10 (m, 1H) 7.10-7.19 (m, 3H) 7.19-7.24 (m, 2H) 7.29 (t, J=7.83 Hz, 1H) 7.35 (d, J=9.35 Hz, 1H) 7.42 (d, J=7.83 Hz, 1H) 7.78 (d, J=1.26 Hz, 1H) 8.93 (s, 1H) 9.93 (s, 1H) 10.90 (s, 1H); MS (ESI) m/z 543.5 (M+H)+.

Example 47

To a solution of BOP (0.522 g, 1.179 mmol) and DMAP (0.288 g, 2.359 mmol) in dichloromethane (60 mL) and DMF (6 mL) was added a solution of 47H (0.32 g, 0.590 mmol) and DIEA (0.309 mL, 1.769 mmol) in DMF (6.0 mL) via a syringe pump over 6 h. To the reaction mixture was added water and 0.5 N HCl, stirred for 10 min. The organic layer was collected and aqueous was extracted with dichloromethane. The organic layers were dried over sodium sulfate. The solvent was removed and residue was purified using a preparative HPLC equipped with a C18 Phenomenex Luna column (30 mm×100 mm, 5µ). The UV detector was set at 220 nm. The separations were performed using a gradient method: 0-100% B in 12 min; then 100% B in 2 min with a flow rate of 40 mL/min. Solvent B is 90% acetonitrile-10% water-0.1% TFA and solvent A is 10% acetonitrile-90% water-0.1% TFA. The fractions were collected to give a mixture of diastereoisomers that were further separated using a preparative HPLC equipped with a Whelko-01 column. The residue was dissolved in 1:1 DMSO:(MeOH/EtOH). The separations were performed using an isocratic method of 40% 1:1 ethanol/methanol: heptane for 40 min with a flow rate of 20 mL/min. The second peak (23.0 mg, 15% yield) was confirmed to be Example 47: Chiral HPLC: 12.45 min retention time-Anal Chiral HPLC, Whelko-01 column (4.6×250 mm, 10µ); $^1$H NMR (400 MHz, DMSO-d$_6$) δ ppm 1.15 (d, J=7.07 Hz, 3H) 1.70-1.84 (m, 1H) 2.05 (q, J=10.69 Hz, 1H) 2.16-2.29 (m, 2H) 3.23-3.27 (m, 3H) 3.28-3.34 (m, 1H) 3.41-3.47 (m, 3H) 3.86 (d, J=16.17 Hz, 1H) 5.17 (d, J=16.17 Hz, 1H) 5.66 (d, J=8.08 Hz, 1H) 6.04 (s, 1H) 6.33 (d, J=7.07 Hz, 1H) 6.46 (d, J=8.08 Hz, 1H) 6.62 (d, J=7.33 Hz, 1H) 6.69 (s, 1H) 6.77-6.88 (m, 2H) 7.13 (t, J=7.71 Hz, 1H) 7.19-7.30 (m, 3H) 7.31-7.37 (m, 2H) 9.39 (s, 1H) 10.87 (d, J=5.31 Hz, 1H); MS (ESI) m/z 525.5 (M+H)+ Analytical HPLC (Method B): Col A: 11.23 min, 98%; Col B: 11.26 min, 99%.

Example 48

(2R,15S)-4,15,20-Trimethyl-7-(2-methyl-2H-pyrazol-3-yl)-2-(1-oxo-1,2-dihydro-isoquinolin-7-ylamino)-4,11-diaza-tricyclo[14.2.2.16,10]henicosa-1(19),6,8,10(21),16(20),17-hexaene-3,12-dione

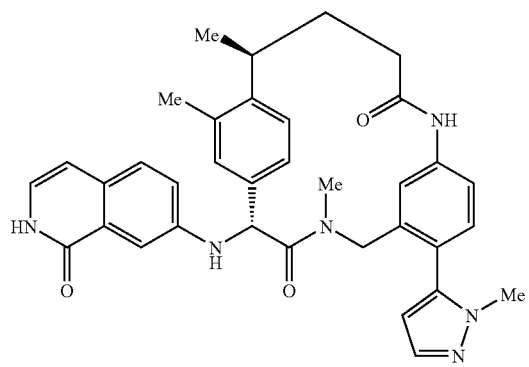 [SMILES: Cc1cc2ccc1[C@@H](C)CCC(=O)Nc1ccc(-c3ccnn3C)c(c1)CN(C)C(=O)[C@@H]2Nc1ccc2cc[nH]c(=O)c2c1]

48A

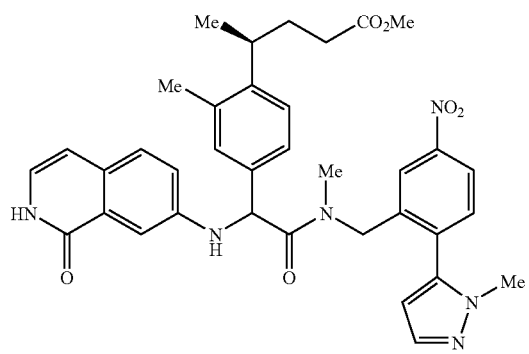 [SMILES: COC(=O)CC[C@H](C)c1ccc(C(Nc2ccc3cc[nH]c(=O)c3c2)C(=O)N(C)Cc2cc([N+](=O)[O-])ccc2-c2ccnn2C)cc1C]

Using a procedure analogous to that used to prepare 41E, 41D (0.2 g, 0.800 mmol), Intermediate 3 and 2-oxoacetic acid hydrate were reacted. The resulting solution was reacted with 22B (0.249 g, 0.880 mmol) using BOP and DIEA. The crude product was purified by column chromatography (0-10% dichloromethane/methanol) to yield 48A (0.5 g, 96% yield) as brown semi solid. MS (ESI) m/z 651.7 (M+H)+.

48B

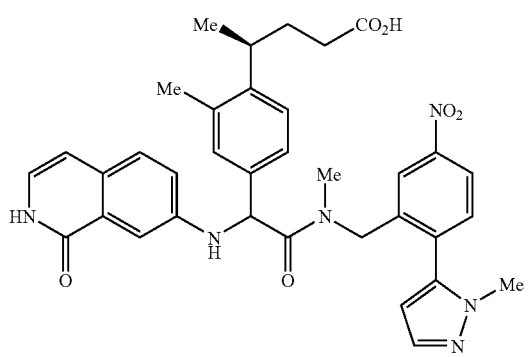 [SMILES: Cc1cc(C(Nc2ccc3cc[nH]c(=O)c3c2)C(=O)N(C)Cc2cc([N+](=O)[O-])ccc2-c2ccnn2C)ccc1[C@@H](C)CCC(=O)O]

To 48A (0.63 g, 0.968 mmol) in MeOH (1 mL) and THF (1 mL) was added LiOH (4.84 mL, 4.84 mmol). The reaction was stirred for 2 h at rt. Solvent was removed and residue was acidified with 1N HCl and extracted with ethyl acetate. The organic extracts were combined and washed with brine and dried over sodium sulfate. The crude product was dissolved in a small amount of chloroform with few drops of methanol and charged to a 12 g silica gel cartridge which was eluted with 0-10% dichloromethane/methanol over a period of 40 mins. After evaporation of solvent, 48B (0.3 g, 96% yield) was obtained as yellow solid. $^1$H NMR—showed rotamers and diastereomeric mixture; MS (ESI) m/z 637.7 (M+H)$^+$.

48C

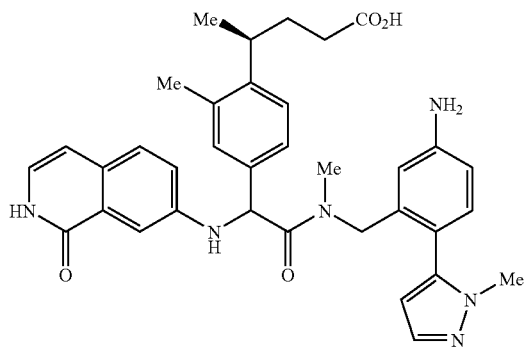 [SMILES: Cc1cc(C(Nc2ccc3cc[nH]c(=O)c3c2)C(=O)N(C)Cc2cc(N)ccc2-c2ccnn2C)ccc1[C@@H](C)CCC(=O)O]

To 48B (0.3 g, 0.471 mmol) in MeOH (5 mL) under nitrogen was added Pd/C (0.100 g, 0.094 mmol). The flask was purged with N$_2$ and degassed (3×). Then H$_2$ balloon was introduced and the system was purged and degassed (3×). The reaction was stirred at room temp under 1 atm of hydrogen gas for 2 h. LCMS shows reaction half way done (NH—OH observed). Added a drop of 6N HCl and reaction was stirred at rt overnight. The catalyst was filtered over celite and washed with methanol. The filtrates were combined and evaporated to give 48C (0.25 g, 87% yield) yellow solid. MS (ESI) m/z 607.7 (M+H)$^+$.

Example 48

To a solution of BOP (0.364 g, 0.824 mmol) and DMAP (0.201 g, 1.648 mmol) in dichloromethane (60 mL) and DMF (6 mL) at rt was added a solution of 48C (0.25 g, 0.412 mmol) and DIEA (0.216 mL, 1.236 mmol) in DMF (7.0 mL) via a syringe pump over 8 h. To the reaction mixture was added 0.5 N HCl, stirred for 10 min. The organic layer was collected and aqueous was extracted with dichloromethane. The organic layers was washed with brine and dried over Na$_2$SO$_4$. After evaporation of solvent, the crude residue was dissolved in MeOH with 0.2% TFA and purified (5 injections) by preparative HPLC equipped with a C18 Phenomenex Luna AXIA column (30 mm×100 cm, 5 m) with the UV detector set at 254 nm. The separations were performed using a gradient method: 10-80% B in 10 mins; then 80% B in 2 min with a flow rate of 40 mL/min. Solvent B is 90% acetonitrile-10% water-0.1% TFA and solvent A is 10% acetonitrile-90% water-0.1% TFA. The fractions were collected and isomers were further purified using a preparative HPLC equipped with a Whelko-01 column. The residue was dissolved in 1:1 DMSO:(MeOH/EtOH). The separations were performed using an isocratic method of 30% 1:1 ethanol/methanol: heptane for 40 min with a flow rate of 20 mL/min. The second peak (29.0 mg, 24% yield) was confirmed to be Example 48: Chiral HPLC: 8.76 min retention time-Anal Chiral HPLC, Whelko-01 column (4.6×250 mm, 10µ), 50% 1:1 ethanol/methanol: heptane column. $^1$H NMR (400 MHz, methanol-d$_4$) δ ppm 1.25 (d, J=6.82 Hz, 3H) 1.85-1.98 (m, 1H) 2.27 (s, 3H) 2.31-2.50 (m, 3H) 3.01-3.17 (m, 1H) 3.42 (s, 3H) 3.65 (d, J=17.18 Hz, 1H) 3.68 (s, 3H) 5.00 (d, J=16.67 Hz, 1H) 5.59 (s, 1H) 6.18 (s, 1H) 6.29 (d, J=1.77 Hz, 1H) 6.53 (d, J=7.07 Hz, 1H) 6.81 (dd, J=8.08, 1.77 Hz, 1H) 6.89 (d, J=6.82 Hz, 1H) 7.07 (s, 1H) 7.13 (d, J=8.08 Hz, 1H) 7.21 (dd, J=8.59, 2.53 Hz, 1H) 7.33-7.43 (m, 3H) 7.51 (d, J=1.77 Hz, 1H) 7.59 (dd, J=7.96, 1.39 Hz, 1H); MS (ESI) m/z 589.7 (M+H)$^+$ Analytical HPLC (Method B): Col A: 11.41 min, 98%; Col B: 11.20 min, 99%.

Example 49

(2R,15S)-4,15,20-Trimethyl-2-(1-oxo-1,2-dihydro-isoquinolin-7-ylamino)-7-trifluoromethoxy-4,11-diaza-tricyclo[14.2.2.16,10]henicosa-1(19),6,8,10 (21),16(20),17-hexaene-3,12-dione

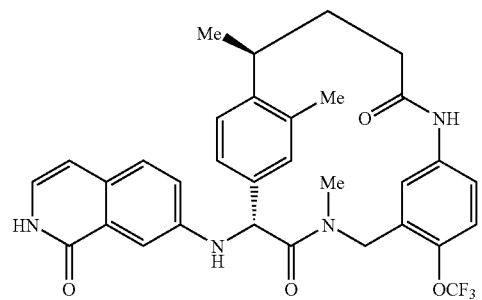

49A

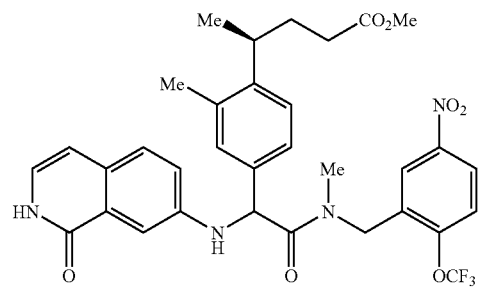 [SMILES: COC(=O)CC[C@H](C)c1ccc(C(Nc2ccc3cc[nH]c(=O)c3c2)C(=O)N(C)Cc2cc([N+](=O)[O-])ccc2OC(F)(F)F)cc1C]

Using a procedure analogous to that used to prepare 41E, a mixture of 41D (0.16 g, 0.640 mmol), Intermediate 3 and 2-oxoacetic acid hydrate were reacted. The resulting solution was reacted with 42D (98 mg, 0.342 mmol) using BOP and DIEA. The crude product was purified by column chromarography (0-10% dichloromethane/methanol) to yield 49A was obtained in quantitative yield as a brown solid. $^1$H NMR— shows rotamers and diastereomeric mixture. MS (ESI) m/z 655.6 (M+H)$^+$.

49B

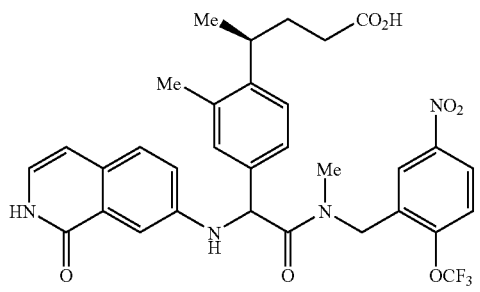 [SMILES: Cc1cc(C(Nc2ccc3cc[nH]c(=O)c3c2)C(=O)N(C)Cc2cc([N+](=O)[O-])ccc2OC(F)(F)F)ccc1[C@@H](C)CCC(=O)O]

To 49A (0.49 g, 0.749 mmol) in MeOH (1 mL) and THF (1.000 mL) was added LiOH (4 mL, 1N, 4.00 mmol). The reaction was stirred for 2 hr rt. Solvent was removed and residue was acidified with 1N HCl and extracted with ethyl acetate, The organic extracts were combined and washed with brine and dried over sodium sulfate. The crude product was dissolved in a small amount of chloroform with few drops of methanol and charged to a 12 g silica gel cartridge which was eluted with 0-10% dichloromethane/methanol over a period of 40 mins. After evaporation of solvent 49B (0.31 g, 65% yield) as a yellow solid. $^1$H NMR shows rotamers and diastereomeric mixture; MS (ESI) m/z 641.6 (M+H)$^+$.

49C

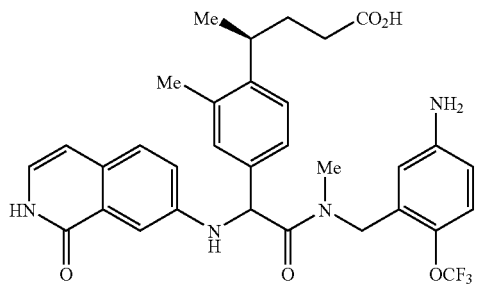

To 49B (0.31 g, 0.484 mmol) in MeOH (5 mL) under nitrogen was added Pd/C (0.1 g, 0.094 mmol). The flask was purged with N$_2$ and degassed (3×). Then H$_2$ balloon was introduced and the system was purged and degassed (3×). Added a drop of 6N HCl and reaction was stirred at rm temp for 5 h. The catalyst was filtered over celite and washed with methanol. The filtrates were combined and evaporated to give 49C (0.26 g, 88% yield) as a white solid. MS (ESI) m/z 611.6 (M+H)$^+$.

Example 49

To a solution of BOP (0.377 g, 0.852 mmol) and DMAP (0.208 g, 1.703 mmol) in dichloromethane (60 ml) and DMF (6 mL) at rt was added a solution of 49C (0.26 g, 0.426 mmol) and DIEA (0.223 ml, 1.277 mmol) in DMF (7.0 mL) via a syringe pump over 9 h. To the reaction mixture was added 0.5 N HCl (30 mL), stirred for 10 min. The organic layer was collected and aqueous was extracted with dichloromethane. The organic layers was washed with brine and dried over sodium sulfate. After evaporation of solvent, the crude residue was dissolved in MeOH with 0.2% TFA and purified (3 injections) by preparative HPLC equipped with a C18 Phenomenex Luna AXIA column (30 mm×100 mm, 5μ) with the UV detector set at 254 nm. The separations were performed using a gradient method: 10-90% B in 10 mins; then 90% B in 2 mins with a flow rate of 40 mL/min. Solvent B is 90% acetonitrile-10% water-0.1% TFA and solvent A is 10% acetonitrile-90% water-0.1% TFA. The fractions were collected and isomers were further purified using a preparative HPLC equipped with a Whelko-01 column. The residue was dissolved in 1:14 DMSO: (MeOH/EtOH). The separations were performed using an isocratic method of 60% 1:1 ethanol/methanol: heptane for 40 min with a flow rate of 20 mL/min. The second peak (48 mg, 38% yield) was confirmed to be Example 49: Chiral HPLC: 8.86 min retention time-Anal Chiral HPLC, Whelko-01 column (4.6×250 mm, 10 μl), 60% 1:1 ethanol/methanol: heptane column. $^1$H NMR (400 MHz, methanol-d$_4$) δ ppm 1.23 (d, J=7.07 Hz, 3H) 1.83-1.95 (m, 1H) 2.26 (s, 3H) 2.30-2.48 (m, 3H) 3.00-3.11 (m, 1H) 3.41 (s, 3H) 3.87 (d, J=16.93 Hz, 1H) 5.43 (d, J=16.93 Hz, 1H) 5.64 (s, 1H) 5.99 (d, J=2.53 Hz, 1H) 6.54 (d, J=7.07 Hz, 1H) 6.78 (dd, J=8.59, 2.53 Hz, 1H) 6.90 (d, J=7.07 Hz, 1H) 7.09 (d, J=1.52 Hz, 1H) 7.15 (dd, J=8.72, 1.64 Hz, 1H) 7.22 (dd, J=8.59, 2.53 Hz, 1H) 7.35-7.43 (m, 3H) 7.59 (dd, J=7.96, 1.89 Hz, 1H); MS (ESI) m/z 593.6 (M+H)$^+$ Analytical HPLC (Method A):

Col A: 11.96 min, 99%; Col B: 12.17 min, 99%.

Example 50

(2R,15S)-7-Difluoromethoxy-4,15,20-trimethyl-2-(1-oxo-1,2-dihydro-isoquinolin-7-ylamino)-4,11-diaza-tricyclo[14.2.2.16,10]henicosa-1(19),6,8,10 (21),16(20),17-hexaene-3,12-dione

50A

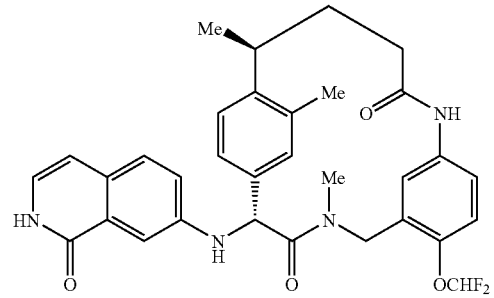 [SMILES: Cc1cc2ccc1[C@@H](C)CCC(=O)Nc1ccc(OC(F)F)c(c1)CN(C)C(=O)[C@@H]2Nc1ccc2cc[nH]c(=O)c2c1]

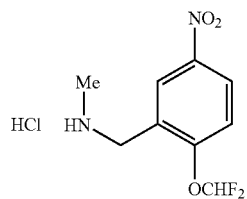 [SMILES: Cl ; CNCc1cc([N+](=O)[O-])ccc1OC(F)F]

To Intermediate 15 (0.77 g, 2.317 mmol) was added 4.0N HCl in dioxane (8.69 mL, 34.8 mmol). The mixture was stirred at rt for 15.0 h. LC-MS indicated a clean reaction. Solvent was concentrated to give 50A (600 mg, 2.233 mmol, 96% yield) as a white solid. $^1$H NMR (400 MHz, methanol-$d_4$) δ ppm 2.79 (s, 3H) 4.37 (s, 2H) 7.22 (t, $J_{HF}$=72 Hz, 1H) 7.40 (s, 1H) 7.54 (d, J=9.23 Hz, 1H) 8.43 (dd, J=9.23, 3.08 Hz, 1H) 8.53 (d, J=3.08 Hz, 1H). $^{19}$F NMR: −85.50 ppm; MS (ESI) m/z 233 (M+H)$^+$.

50B

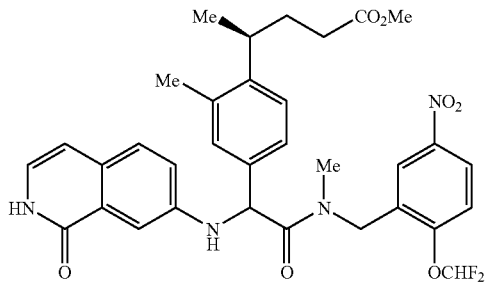

Using a procedure analogous to that used to prepare 41E, a mixture of 41D (0.16 g, 0.640 mmol), Intermediate 3 (100 mg, 0.342 mmol) and 2-oxoacetic acid hydrate were reacted. The resulting solution was reacted with of 50A (0.189 g, 0.704 mmol) using BOP and DIEA. The crude product was purified by column chromatography (0-10% dichloromethane/methanol) to yield 50B (0.34 g, 83% yield) as a yellow solid. $^1$H NMR shows rotamers and diastereomeric mixture; MS (ESI) m/z 637.6 (M+H)$^+$.

50C

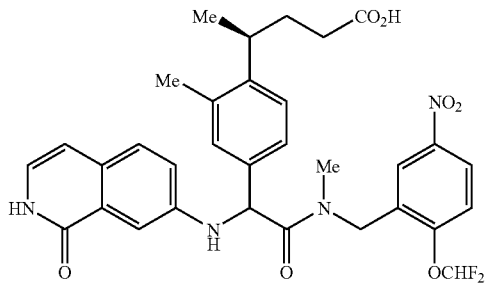

To 50B (0.34 g, 0.534 mmol) in MeOH (1 mL) and THF (1.000 mL) was added LiOH (4 mL, 4.00 mmol). The reaction was stirred for 2 h at rt. Solvent was removed and residue was acidified with 1N HCl and extracted with ethyl acetate. The organic extracts were combined and washed with brine and dried over sodium sulfate. The crude product was dissolved in a small amount of chloroform with few drops of methanol and charged to a 12 g silica gel cartridge which was eluted with 0-10% dichloromethane/methanol over a period of 40 min. 50C (0.25 g, 75% yield) was obtained as a yellow solid after evaporation of solvent. $^1$H NMR shows rotamers and diastereomeric mixture. MS (ESI) m/z 623.6 (M+H)$^+$.

50D

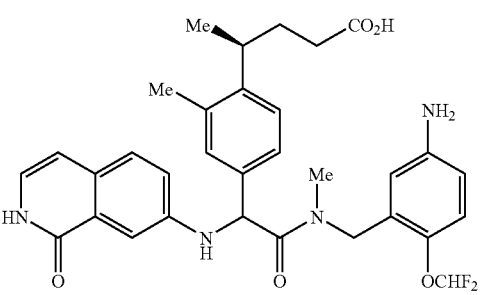 [SMILES: Cc1cc(C(Nc2ccc3cc[nH]c(=O)c3c2)C(=O)N(C)Cc2cc([N+](=O)[O-])ccc2OC(F)F)ccc1[C@@H](C)CCC(=O)O]

To 5° C. (0.25 g, 0.402 mmol) in MeOH (5 mL) under nitrogen was added Pd/C (0.1 g, 0.094 mmol). The flask was purged with $N_2$ and degassed (3×). Then $H_2$ balloon was introduced and the system was purged and degassed (3×). Added a drop of 6N HCl and reaction was stirred at rt for 5 hr. The catalyst was filtered over celite and washed with methanol. The filtrates were combined and evaporated to give 50D (0.22 g, 92% yield) as an off white solid. MS (ESI) m/z 593.6 (M+H)$^+$.

Example 50

To a solution of BOP (0.328 g, 0.742 mmol) and DMAP (0.181 g, 1.485 mmol) in dichloromethane (60 mL) and DMF (6 mL) at rt was added a solution of 50D (0.22 g, 0.371 mmol) and DIEA (0.195 ml, 1.114 mmol) in DMF (7.0 mL) via a syringe pump over 5 h. To the reaction mixture was added 0.5 N HCl (30 mL), stirred for 10 min. The organic layer was collected and aqueous was extracted with dichloromethane. The organic layers was washed with brine and dried over sodium sulfate. After evaporation of solvent, the crude residue was dissolved in MeOH with 0.2% TFA and purified (4 injections) by preparative HPLC equipped with a C18 Phenomenex Luna AXIA column (30 mm×100 mm, 5 g) with the UV detector set at 254 nm. The separations were performed using a gradient method: 10-90% B in 10 mins; then 90% B in 2 mins with a flow rate of 40 mL/min. Solvent B is 90% acetonitrile-10% water-0.1% TFA and solvent A is 10% acetonitrile-90% water-0.1% TFA. The fractions were collected and isomers were further purified using a preparative HPLC equipped with a Whelko-01 column. The residue was dissolved in 1:14 DMSO: (MeOH/EtOH). The separations were performed using an isocratic method of 60% 1:1 ethanol/methanol: heptane for 40 min with a flow rate of 20 mL/min. The second peak (64.0 mg, 60% yield) was confirmed to be Example 50: Chiral HPLC: 10.11 min retention time-Anal Chiral HPLC, Whelko-01 column (4.6×250 mm, 10.), 60% 1:1 ethanol/methanol: heptane column. $^1$H NMR (400 MHz, methanol-$d_4$) δ ppm 1.22 (d, J=6.82 Hz, 3H) 1.81-1.95 (m, 1H) 2.25 (s, 3H) 2.28-2.45 (m, 3H) 3.06 (d, J=6.82 Hz, 1H) 3.40 (s, 3H) 3.86 (d, J=17.18 Hz, 2H) 5.38 (d, J=16.93 Hz, 1H) 5.64 (s, 1H) 5.89 (d, J=2.27 Hz, 1H) 6.53 (d, J=7.07 Hz, 1H) 6.70-6.79 (m, 2H) 6.90 (d, J=7.07 Hz, 1H) 7.02 (d, J=8.59 Hz, 1H) 7.10 (d, J=1.26 Hz, 1H) 7.22 (dd, J=8.72, 2.40 Hz, 1H) 7.34-7.43 (m, 3H) 7.59 (dd, J=7.96, 1.64 Hz, 1H); MS (ESI) m/z 575.6 (M+H)$^+$ Analytical HPLC (Method B): Col A: 11.48 min, 99%; Col B: 11.45 min, 97%.

Example 51

(2R,15S)-2-(6-Fluoro-3-oxo-2,3-dihydro-1H-isoindol-5-ylamino)-4,15,20-trimethyl-7-trifluoromethoxy-4,11-diaza-tricyclo[14.2.2.16,10]henicosa-1(19),6,8,10(21),16(20),17-hexaene-3,12-dione

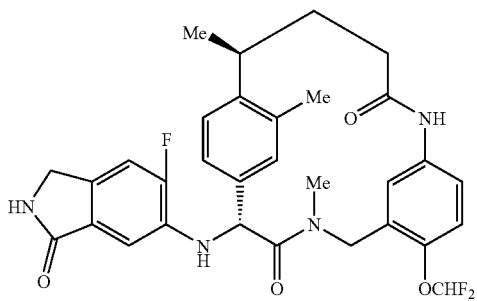 [SMILES: Cc1cc2ccc1[C@@H](C)CCCCC(=O)Nc1ccc(OC(F)F)c(c1)CN(C)C(=O)[C@@H]2Nc1cc2c(cc1F)CNC2=O]

51A

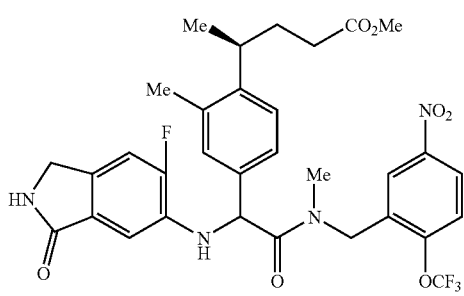 [SMILES: COC(=O)CC[C@H](C)c1ccc(C(Nc2cc3c(cc2F)CNC3=O)C(=O)N(C)Cc2cc([N+](=O)[O-])ccc2OC(F)(F)F)cc1C]

Using a procedure analogous to that used to prepare 41E, a mixture of 41D (0.16 g, 0.640 mmol), Intermediate 7 and 2-oxoacetic acid hydrate were reacted. The resulting solution was reacted with 42D using BOP and DIEA. The crude product was purified by column chromatography (0-10% dichloromethane/methanol) to afford 51A inquantitative yield as a brown solid. ¹H NMR shows rotamers and diastereomeric mixture. MS (ESI) m/z 661.6 (M+H)⁺.

51B

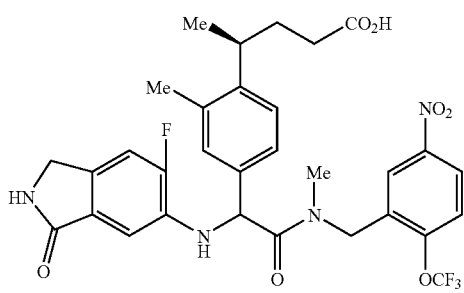

To 51A (0.5 g, 0.757 mmol) in MeOH (1 mL) and THF (2 mL) was added LiOH (5 mL, 5.00 mmol), The reaction was stirred for 2 h at rt. Solvent was removed and residue was acidified with 1N HCl and extracted with ethyl acetate. The organic extracts were combined and washed with brine and dried over sodium sulfate. The crude product was dissolved in a small amount of chloroform with few drops of methanol and charged to a 12 g silica gel cartridge which was eluted with 0-10% dichloromethane/methanol over a period of 40 mins. After evaporation of solvent, 51B (0.34 g, 70% yield) was obtained as a yellow solid. ¹H NMR shows rotamers and diastereomeric mixture. MS (ESI) m/z 647.6 (M+H)⁺.

51C

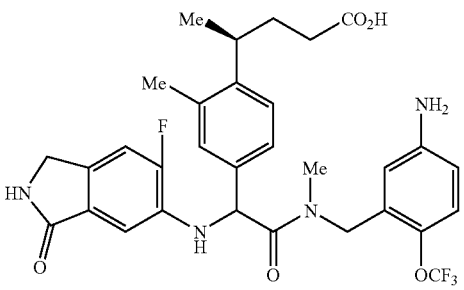 [SMILES: Cc1cc(C(Nc2cc3c(cc2F)CNC3=O)C(=O)N(C)Cc2cc([N+](=O)[O-])ccc2OC(F)(F)F)ccc1[C@@H](C)CCC(=O)O]

To 51B (0.34 g, 0.526 mmol) in MeOH (5 mL) under nitrogen was added Pd/C (0.1 g, 0.094 mmol). The flask was purged with N₂ and degassed (3×). Then H₂ balloon was introduced and the system was purged and degassed (3×). Added a drop of 6N HCl and reaction was stirred at rm temp for 5 h. The catalyst was filtered over Celite® and washed with methanol. The filtrates were combined and evaporated to give 51C (0.19 g, 59% yield) as a white solid. MS (ESI) m/z 617.6 (M+H)⁺.

Example 51

To a solution of BOP (0.273 g, 0.616 mmol) and DMAP (0.151 g, 1.233 mmol) in dichloromethane (60 mL) and DMF (6 mL) at rt was added a solution of 51C (0.19 g, 0.308 mmol) and DIEA (0.161 mL, 0.924 mmol) in DMF (5.0 mL) via a syringe pump over 5.5 h. To the reaction mixture was added 0.5 N HCl (30 mL), stirred for 10 min. The organic layer was collected and aqueous was extracted with dichloromethane. The organic layers was washed with brine and dried over sodium sulfate. After evaporation of solvent, the crude residue was dissolved in 90% acetonitrile-10% water-0.1% TFA and purified (3 injections) by preparative HPLC equipped with a C18 Phenomenex Luna column (30 mm×100 mm, 5 g) with the UV detector set at 254 nm. The separations was performed using a gradient method: 20-80% B in 10 min; then 80% B in 2 min with a flow rate of 40 mL/min. Solvent B is 90% acetonitrile-10% water-0.1% TFA and solvent A is 10% acetonitrile-90% water-0.1% TFA. The fractions were collected and isomers were further purified using a preparative HPLC equipped with a Whelko-01 column. The residue was dissolved in MeOH/EtOH. The separations were performed using an isocratic method of 60% 1:1 ethanol/methanol: heptane for 40 min with a flow rate of 20 mL/min. The second peak (47 mg, 51% yield) was confirmed to be Example 51: Chiral HPLC: 10.45 min retention time-Anal Chiral HPLC, Whelko-01 column (4.6×250 mm, 10.), 60% 1:1 ethanol/methanol: heptane column. ¹H NMR (400 MHz, methanol-d₄) δ ppm 1.22 (d, J=6.82 Hz, 3H) 1.81-1.96 (m, 1H) 2.23 (s, 3H) 2.27-2.48 (m, 3H) 2.96-3.11 (m, 1H) 3.87 (d, J=16.93 Hz, 1H) 4.15-4.33 (m, 2H) 5.42 (d, J=17.18 Hz, 1H) 5.66 (s, 1H) 5.96 (d, J=2.53 Hz, 1H) 6.77 (dd, J=8.72, 2.40 Hz, 1H) 6.98 (s, 1H) 7.06-7.21 (m, 3H) 7.38 (d, J=7.83 Hz, 1H) 7.60 (dd, J=7.96, 1.64 Hz, 1H) 9.69 (s, 1H); ¹⁹F NMR (376 MHz, Solvent) δ ppm −129.94 (none, 1F)-59.61 (s, 3F); MS (ESI) m/z 599.6 (M+H)⁺ Analytical HPLC (Method B): Col A: 12.15 min, 99%; Col B: 12.20 min, 99%.

Example 52

(2R,15S)-7-Difluoromethoxy-2-(6-fluoro-3-oxo-2,3-dihydro-1H-isoindol-5-ylamino)-4,15,20-trimethyl-4,11-diaza-tricyclo[14.2.2.16,10]henicosa-1(19),6,8,10(21),16(20),17-hexaene-3,12-dione

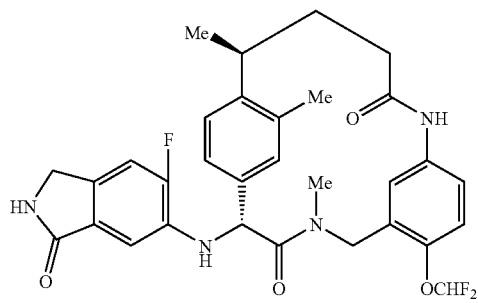 [SMILES: Cc1cc2ccc1[C@@H](C)CCCCC(=O)Nc1ccc(OC(F)F)c(c1)CN(C)C(=O)[C@@H]2Nc1cc2c(cc1F)CNC2=O]

52A

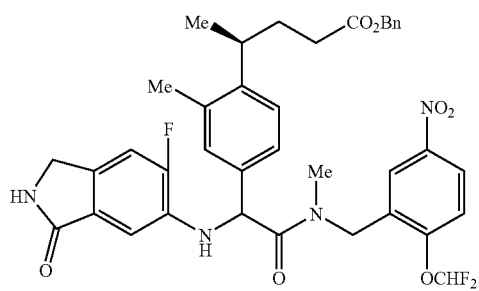 [SMILES: Cc1cc(C(Nc2cc3c(cc2F)CNC3=O)C(=O)N(C)Cc2cc([N+](=O)[O-])ccc2OC(F)F)ccc1[C@@H](C)CCC(=O)OCc1ccccc1]

Using a procedure analogous to that used to prepare 41E, a mixture of 42C (130 mg, 0.399 mmol), Intermediate 7 and 2-oxoacetic acid hydrate were reacted. The resulting solution was reacted with 50A using BOP and DIEA. The crude product was purified by column chromatography (0-10% dichloromethane/methanol) to yield 52A in quantitative yield a brown solid. MS (ESI) rz/z 719 (M+H)$^+$.

52B

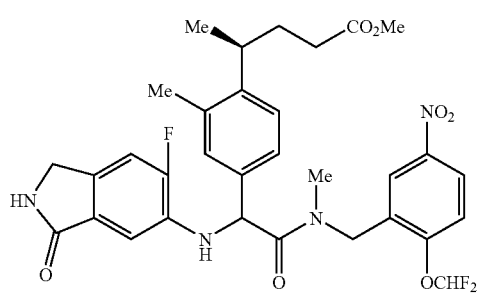

To 52A (0.26 g, 0.362 mmol) in MeOH (5 mL) under nitrogen was added Pd/C (0.1 g, 0.094 mmol). The flask was purged with $N_2$ and degassed (3×). Then $H_2$ balloon was introduced and the system was purged and degassed (3×). Added a drop of 6N HCl and reaction was stirred at rt overnight. LCMS shows methyl ester derivative as product. The catalyst was filtered over Celite® and washed with methanol. The filtrates were combined and evaporated to give 52B (0.19 g, 86% yield) as a white solid. MS (ESI) m/z 613.6 (M+H)$^+$.

52C

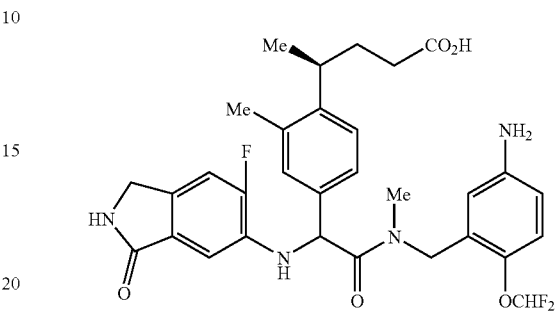

To 52B (0.19 g, 0.310 mmol) in MeOH (1.5 mL) and THF (2.5 mL) was added LiOH (5 mL, 5.00 mmol). The reaction was stirred for 2 hr at rt. Solvent was removed and residue was acidified with 1N HCl and extracted with ethyl acetate. The organic extracts were combined and washed with brine and dried over sodium sulfate. The solution was filtered and dried to give 52C (0.17 g, 92% yield) as a yellow solid. MS (ESI) m/z 599.6 (M+H)$^+$.

Example 52

To a solution of BOP (0.251 g, 0.568 mmol) and DMAP (0.139 g, 1.136 mmol) in dichloromethane (60 ml) and DMF (6 mL) at rt was added a solution of 52C (0.17 g, 0.284 mmol) and DIEA (0.149 mL, 0.852 mmol) in DMF (4.0 mL) via a syringe pump over 10 h. To the reaction mixture was added 0.5 N HCl (30 mL), stirred for 10 min. The organic layer was collected and aqueous was extracted with dichloromethane. The organic layers was washed with brine and dried over sodium sulfate. After evaporation of solvent, the crude residue was dissolved in MeOH with 0.2% TFA and purified (3 injections) by preparative HPLC equipped with a C18 Phenomenex Luna AXIA column (30 mm×100 mm, 5 g) with the UV detector set at 254 nm. The separations were performed using a gradient method: 20-80% B in 10 mins; then 80% B in 2 min with a flow rate of 40 mL/min. Solvent B is 90% acetonitrile-10% water-0.1% TFA and solvent A is 10% acetonitrile-90% water-0.1% TFA. The fractions were collected and isomers were further purified and separated using a preparative HPLC equipped with a Whelko-01 column. The residue was dissolved in 1:2 DMSO: (MeOH/EtOH). The separations were performed using an isocratic method of 60% 1:1 ethanol/methanol: heptane for 40 min with a flow rate of 20 mL/min. The second peak (29.0 mg, 35% yield) was confirmed to be Example 52: Chiral HPLC: 12.53 min retention time-Anal Chiral HPLC, Whelko-Oi column (4.6×250 mm, 10μ), 60% 1:1 ethanol/methanol: heptane column. $^1$H NMR (400 MHz, methanol-d$_4$) δ ppm 1.16 (d, J=7.07 Hz, 3H) 1.81 (dd, J=14.65, 7.07 Hz, 1H) 2.17 (s, 3H) 2.20-2.40 (m, 3H) 2.90-3.04 (m, 1H) 3.31 (s, 3H) 3.80 (d, J=16.93 Hz, 1H) 4.20 (d, J=3.54 Hz, 2H) 5.32 (d, J=17.18 Hz, 1H) 5.61 (s, 1H) 5.76-5.83 (m, 1H) 6.49-6.74 (m, 2H) 6.86-7.00 (m, 2H) 7.01-7.16 (m, 2H) 7.32 (d, J=8.08 Hz, 1H) 7.53 (dd, J=7.83, 1.77 Hz, 1H); $^{19}$F NMR (376 MHz, methanol-d$_4$) δ ppm −131.19

(1F)-83.56 (2F); MS (ESI) i/z 581.5 (M+H)+ Analytical HPLC (Method B): Col A: 11.62 min, 98%; Col B: 11.48 min, 98%.

Example 53

(2R,15S)-7-Bromo-4,15,20-trimethyl-2-(1-oxo-1,2-dihydro-isoquinolin-7-ylamino)-4,11-diaza-tricyclo[14.2.2.16,10]henicosa-1(19),6,8,10(21),16(20),17-hexaene-3,12-dione

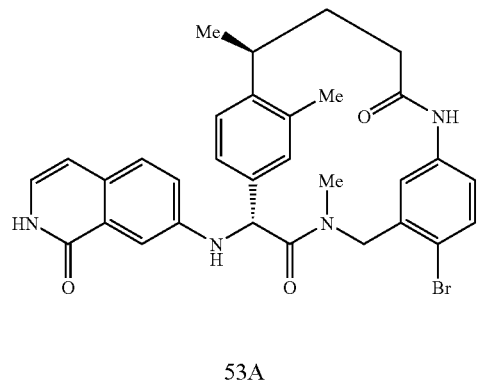

53A

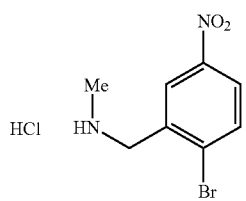

To intermediate 18 (0.34 g, 0.985 mmol) was added HCl, 4 M in dioxane (2.5 mL, 10.00 mmol). The reaction was stirred at rt overnight. The solvent was removed and the residue dried under vacuo to give 53A (0.26 g, 94% yield) as a white solid. $^1$H NMR (400 MHz, methanol-$d_4$) δ ppm 2.85 (s, 3H) 4.50 (s, 2H) 8.02 (d, J=8.84 Hz, 1H) 8.23 (dd, J=8.84, 2.78 Hz, 1H) 8.52 (d, J=2.53 Hz, 1H); MS (ESI) m/z 245.3, 247.2 (M+H)+.

53B

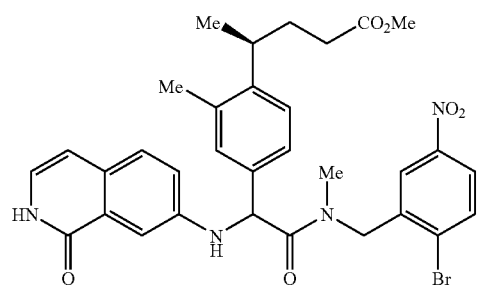 [SMILES: COC(=O)CC[C@H](C)c1ccc(C(Nc2ccc3cc[nH]c(=O)c3c2)C(=O)N(C)Cc2cc([N+](=O)[O-])ccc2Br)cc1C]

Using a procedure analogous to that used to prepare 41E, a mixture of 41D (0.17 g, 0.680 mmol), Intermediate 3 and 2-oxoacetic acid hydrate were reacted. The resulting solution was reacted with 53A (0.191 g, 0.680 mmol) using BOP and DIEA. The crude product was purified by prep HPLC to give 53B in quantitative yield as a brown solid. $^1$H NMR (400 MHz, methanol-$d_4$) δ ppm 0.93-1.27 (m, 3H) 1.56-1.73 (m, 1H) 1.84-2.00 (m, 1H) 2.01-2.15 (m, J=21.22 Hz, 2H) 2.16-2.27 (m, 1H) 2.31 (d, J=2.53 Hz, 2H) 2.68-2.84 (m, 1H) 3.03-3.24 (m, 3H) 3.53-3.61 (m, 3H) 4.47-4.72 (m, 1H) 4.97-5.28 (m, 1H) 5.62 (d, J=26.53 Hz, 1H) 6.48-6.63 (m, 1H) 6.88-7.00 (m, 1H) 7.09-7.32 (m, 3H) 7.33-7.50 (m, 3H) 7.64-7.90 (m, 2H) 7.99 (dd, J=8.46, 2.65 Hz, 1H); MS (ESI) m/z 649.6, 651.6 (M+H)+.

53C

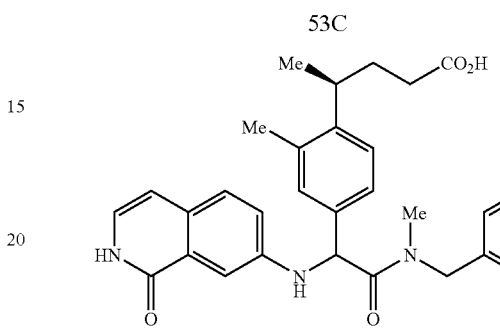

To 53B (0.5 g, 0.770 mmol) in MeOH (3 mL) and THF (4 mL) was added LiOH (5 mL, 5.00 mmol). The reaction was stirred for 2 hr at rt. Solvent was removed and residue was acidified with 1N HCl and extracted with ethyl acetate. The organic extracts were combined and washed with brine and dried over sodium sulfate. The crude product was dissolved in a small amount of chloroform with a few drops of methanol and charged to a 12 g silica gel cartridge which was eluted with 0-10% dichloromethane/methanol over a period of 40 mins. After evaporation of solvent, 53C (0.3 g, 61% yield) was obtained as a yellow solid. MS (ESI) m/z 635.5, 637.5 (M+H)+.

53D

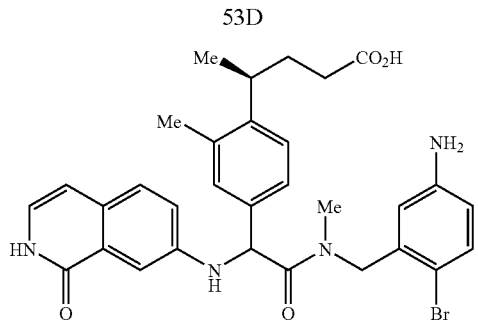

To a solution of 53C (0.3 g, 0.472 mmol) in methanol (3 mL) and EtOH (7 mL) in a scintillation vial was added zinc (dust) (0.617 g, 9.44 mmol) and ammonium chloride (0.505 g, 9.44 mmol). The resulting mixture was stirred vigorously overnight at rt. The solvent was removed. Ethyl acetate and water was added and 1N HCl was added to adjust pH to 3. The organic layer was separated and washed with brine and dried over sodium sulfate. The solvent was removed to give 53D (0.22 g, 77% yield) as a yellow solid.

Example 53

To a solution of BOP (0.321 g, 0.727 mmol) and DMAP (0.178 g, 1.453 mmol) in dichloromethane (60 ml) and DMF (6 mL) at rt was added a solution of 53D (0.22 g, 0.363 mmol) and DIEA (0.190 mL, 1.090 mmol) in DMF (5.0 mL) via a syringe pump over 9 h. To the reaction mixture was added 0.5 N HCl (30 mL), stirred for 10 min. The organic layer was collected and aqueous was extracted with dichloromethane.

The organic layers was washed with brine and dried over sodium sulfate. After evaporation of solvent, the crude residue was dissolved in 90% acetonitrile-10% water-0.1% TFA and purified (3 injections) by preparative HPLC equipped with a C18 Phenomenex Luna column (30 mm×100 mm, 5) with the UV detector set at 254 nm. The separations were performed using a gradient method: 10-90% B in 10 min; then 90% B in 2 mins with a flow rate of 40 mL/min. Solvent B is 90% acetonitrile-10% water-0.1% TFA and solvent A is 10% acetonitrile-90% water-0.1% TFA. The fractions were collected and isomers were further purified using a preparative HPLC equipped with a Whelko-01 column. The residue was dissolved in MeOH/EtOH. The separations were performed using an isocratic method of 80% 1:1 ethanol/methanol: heptane for 40 min with a flow rate of 20 mL/min. The second peak (46.0 mg, 43% yield) was confirmed to be Example 53: Chiral HPLC: 12.82 min retention time-Anal Chiral HPLC, Whelko-01 column (4.6×250 mm, 10 g), 80% 1:1 ethanol/methanol: heptane column. $^1$H NMR (400 MHz, methanol-d$_4$) δ ppm 1.17 (d, J=6.82 Hz, 3H) 1.75-1.87 (m, 1H) 2.18 (s, 3H) 2.21-2.41 (m, 3H) 2.92-3.03 (m, 1H) 3.30-3.38 (m, 3H) 3.75 (d, J=16.93 Hz, 1H) 5.29 (d, J=16.93 Hz, 1H) 5.57 (s, 1H) 5.84 (d, J=2.53 Hz, 1H) 6.47 (d, J=7.07 Hz, 1H) 6.56 (dd, J=8.34, 2.27 Hz, 1H) 6.83 (d, J=6.82 Hz, 1H) 7.03 (s, 1H) 7.16 (dd, J=8.59, 2.53 Hz, 1H) 7.28-7.41 (m, 4H) 7.49-7.58 (m, 1H) 9.56 (s, 1H); MS (ESI) m/z 587.5, 589.5 (M+H)$^+$ Analytical HPLC (Method B): Col A: 11.95 min, 99%; Col B: 11.86 min, 98%.

Example 54

(2R,5R,15S)-5,15,20-Trimethyl-2-(1-oxo-1,2-dihydro-isoquinolin-7-ylamino)-4,11-diaza-tricyclo [14.2.2.16,10]henicosa-1(19),6,8,10(21),16(20),17-hexaene-3,12-dione

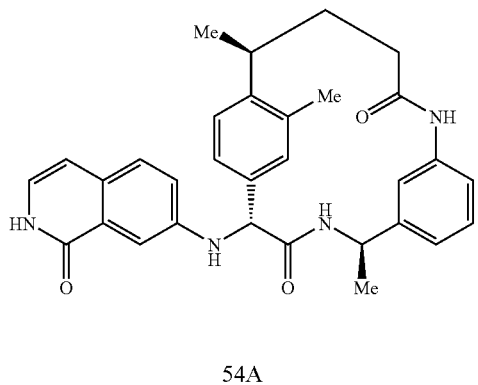

54A

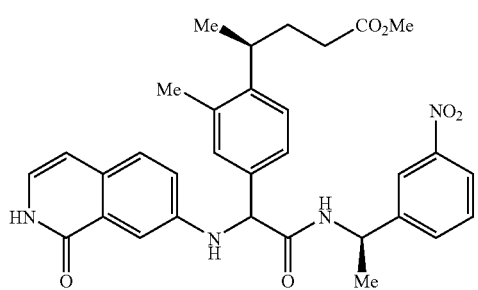 [SMILES: COC(=O)CC[C@H](C)c1ccc(C(Nc2ccc3cc[nH]c(=O)c3c2)C(=O)N[C@H](C)c2cccc([N+](=O)[O-])c2)cc1C]

Using a procedure analogous to that used to prepare 41E, a mixture of 41D (0.16 g, 0.640 mmol), Intermediate 3 (100 mg, 0.342 mmol) and 2-oxoacetic acid hydrate were reacted. The resulting solution was reacted with (R)-1-(3-nitrophenyl) ethanamine hydrochloride using BOP and DIEA. The crude product was purified by column chromatography (0-10% dichloromethane/methanol) to obtain 54A in quantitative yield as a brown solid. $^1$H NMR showed rotamers and diastereomeric mixture; MS (ESI) m/z 571.6 (M+H)$^+$.

54B

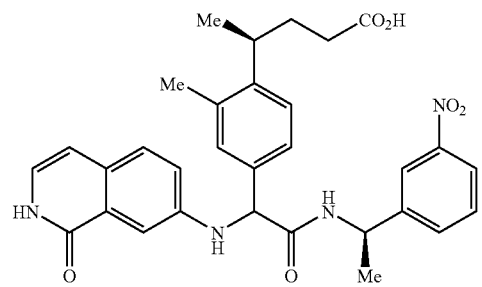 [SMILES: Cc1cc(C(Nc2ccc3cc[nH]c(=O)c3c2)C(=O)N[C@H](C)c2cccc([N+](=O)[O-])c2)ccc1[C@@H](C)CCC(=O)O]

To 54A (0.45 g, 0.789 mmol) in MeOH (1 mL) and THF (2.000 mL) was added LiOH (5 mL, 5.00 mmol). The reaction was stirred for 2 h at rt. The solvent was removed and residue was acidified with 1N HCl and extracted with ethyl acetate. The org extracts were combined and washed with brine and dried over sodium sulfate. The crude product was dissolved in a small amount of chloroform with few drops of methanol and charged to a 12 g silica gel cartridge which was eluted with 0-10% dichloromethane/methanol over a period of 40 mins. After evaporation of solvent, 54B (0.35 g, 85% yield) as a yellow solid. $^1$H NMR showed rotamers and diastereomeric mixture. MS (ESI) m/z 557.6 (M+H)$^+$.

54C

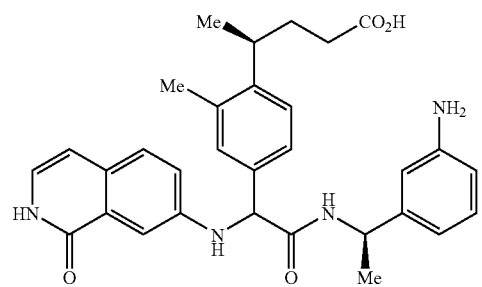 [SMILES: Cc1cc(C(Nc2ccc3cc[nH]c(=O)c3c2)C(=O)N[C@H](C)c2cccc(N)c2)ccc1[C@@H](C)CCC(=O)O]

To 54B (0.35 g, 0.629 mmol) in MeOH (5 mL) under nitrogen was added Pd/C (0.1 g, 0.094 mmol). The flask was purged with N$_2$ and degassed (3×). Then H$_2$ balloon was introduced and the system was purged and degassed (3×). A drop of 6N HCl was added and the reaction was stirred at rt for 5 h. The catalyst was filtered over celite and washed with methanol. The filtrates were combined and evaporated to give 54C (0.26 g, 78% yield) as a light brown solid. MS (ESI) m/z 527.6 (M+H)$^+$.

Example 54

To a solution of BOP (0.432 g, 0.976 mmol) and DMAP (0.238 g, 1.952 mmol) in dichloromethane (60 ml) and DMF (6 mL) at rt was added a solution of 54C (0.257 g, 0.488 mmol) and DIEA (0.256 ml, 1.464 mmol) in DMF (5.0 mL) via a syringe pump over 9 h. To the reaction mixture was added 0.5 N HCl (30 mL), stirred for 10 min. The organic layer was collected and aquous was extracted with dichloromethane. The organic layers was washed with brine and dried over sodium sulfate. After evaporation of solvent, the crude residue was dissolved in 90% acetonitrile-10% water-0.1% TFA and purified (4 injections) by preparative HPLC equipped with a C18 Phenomenex Luna column (30 mm×100 mm, 5μ) with the UV detector set at 254 nm. The separations were performed using a gradient method: 10-90% B in 10 mins; then 90% B in 2 mins with a flow rate of 40 mL/min. Solvent B is 90% acetonitrile-10% water-0.1% TFA and solvent A is 10% acetonitrile-90% water-0.1% TFA. The fractions were collected and isomers were further purified and separated using a preparative HPLC equipped with a Chiralpak AD column. The residue was dissolved in ethanol. The separations were performed using an isocratic method of 60% EtOH/Heptane with 0.1% DEA for 40 min with a flow rate of 20 mL/min. The second peak (51 mg, 41% yield) was confirmed to be Example 54: Chiral HPLC: 13.06 min retention time-Anal Chiral HPLC, Chirakpak AD (4.6×250 mm, 10 g) column, 60% ethanol:heptane 0.1% DEA. $^1$H NMR (400 MHz, methanol-$d_4$) δ ppm 1.12 (d, J=7.07 Hz, 3H) 1.37 (d, J=7.07 Hz, 3H) 1.78-1.89 (m, 1H) 2.16 (s, 3H) 2.19-2.26 (m, 1H) 2.28-2.47 (m, 2H) 2.93-3.05 (m, 1H) 4.82 (d, J=6.57 Hz, 1H) 5.03 (s, 1H) 6.07-6.12 (m, 1H) 6.46 (d, J=7.07 Hz, 1H) 6.55-6.61 (m, 1H) 6.82 (d, J=7.07 Hz, 1H) 6.86 (d, J=7.58 Hz, 1H) 6.92 (s, 1H) 7.06 (t, J=7.71 Hz, 1H) 7.12 (dd, J=8.59, 2.53 Hz, 1H) 7.27-7.36 (m, 3H) 7.47-7.52 (m, 2H) 8.49 (d, J=6.82 Hz, 1H) 9.41 (s, 1H); MS (ESI) m/z 509.5 (M+H)$^+$. Analytical HPLC (Method B): Col A: 10.83 min, 99%; Col B: 11.15 min, 99%.

Example 55

(2R,15S)-4,15,20-Trimethyl-2-(1-oxo-1,2-dihydro-isoquinolin-7-ylamino)-4,11-diaza-tricyclo[14.2.2.16,10]henicosa-1(19),6,8,10(21),16(20),17-hexaene-3,12-dione

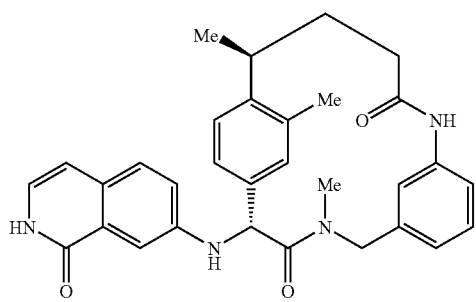

To Example 53 (0.028 g, 0.048 mmol) and Pd/C (0.0051 g, 4.79 μmol) was added MeOH (5 mL). The reaction vessel was flushed with $N_2$ and degassed (3×). Hydrogen balloon was introduced. The reaction was stirred rt for 4 h. The catalyst was filtered over celite and washed with methanol. The filtrates were combined and evaporated. The crude residue was purified using a preparative HPLC equipped with a C18 Phenomenex Luna column (30 mm×100 mm, 5μ). The UV detector was set at 254 nm. The separations were performed using a gradient method: 10-60% B in 10 mins; then 60% B in 2 mins with a flow rate of 40 mL/min. Solvent B is 90% acetonitrile-10% water-0.1% TFA and solvent A is 10% acetonitrile-90% water-0.1% TFA. The sample was lyophilized to give Example 55 (16.5 mg, 66% yield) as a yellow amorphous solid. $^1$H NMR (400 MHz, methanol-$d_4$) δ ppm 1.15 (d, J=7.07 Hz, 3H) 1.78-1.88 (m, 1H) 2.20 (s, 3H) 2.23-2.39 (m, 3H) 2.95-3.04 (m, 1H) 3.29 (s, 3H) 3.82 (d, J=16.42 Hz, 1H) 5.30 (d, J=16.17 Hz, 1H) 5.59 (s, 1H) 5.81 (s, 1H) 6.48 (d, J=7.07 Hz, 1H) 6.59-6.66 (m, 1H) 6.82-6.89 (min, 2H) 7.07 (d, J=1.52 Hz, 1H) 7.11 (t, J=7.71 Hz, 1H) 7.20 (dd, J=8.72, 2.65 Hz, 1H) 7.30 (d, J=8.08 Hz, 1H) 7.37 (d, J=8.59 Hz, 1H) 7.43 (d, J=2.53 Hz, 1H) 7.46 (dd, J=7.83, 1.77 Hz, 1H); MS (ESI) m/z 509.5 (M+H)$^+$ Analytical HPLC (Method B): Col A: 10.01 min, 99%; Col B: 10.93 min, 98%.

Example 56

4-Methyl-2-(1-oxo-1,2-dihydro-isoquinolin-7-ylamino)-7-(propane-2-sulfonyl)-13-oxa-4,11-diaza-tricyclo[14.2.2.16,10]henicosa-1(19),6,8,10(21),16(20),17-hexaene-3,12-dione

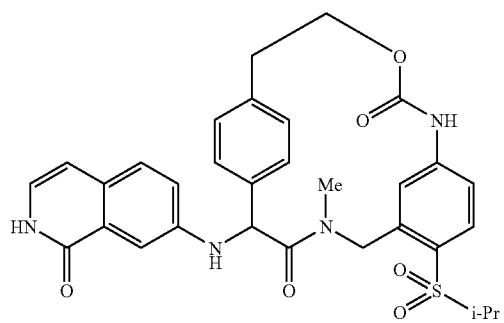 [SMILES: CC(C)S(=O)(=O)c1ccc2cc1CN(C)C(=O)C(Nc1ccc3cc[nH]c(=O)c3c1)c1ccc(cc1)CCOC(=O)N2]

56A

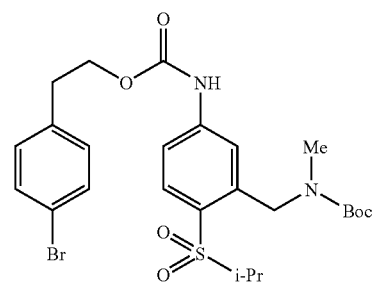 [SMILES: CC(C)S(=O)(=O)c1ccc(NC(=O)OCCc2ccc(Br)cc2)cc1CN(C)C(=O)OC(C)(C)C]

Using a procedure analogous to that used to prepare 29A, Intermediate 11 was reacted with sodium bicarbonate and phosgene followed by 4-bromophenethyl alcohol (0.445 ml, 3.18 mmol) and TEA. The crude product was added to a silica gel column (40 g) and was eluted with EtOAc/hexanes (0-100% in 40 min) to give 56A (1.5 g, 99%) as a colorless oil. LCMS 469, 471 [M+H-Boc].

56B

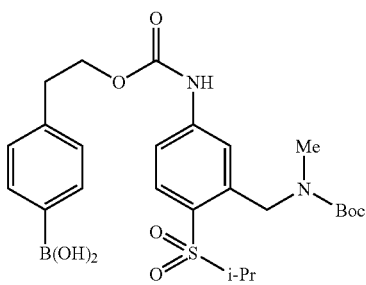 [SMILES: CC(C)S(=O)(=O)c1ccc(NC(=O)OCCc2ccc(B(O)O)cc2)cc1CN(C)C(=O)OC(C)(C)C]

Using a procedure analogous to that used to prepare 29B, 56A (1.75 g, 3.07 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 100% and preparative HPLC (CH$_3$CN/H$_2$O, 0.1% TFA) to give 56B (1 g, 61%) was obtained as a white solid.

56C

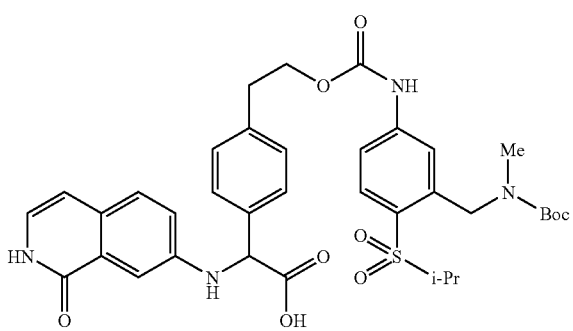

Using a procedure analogous to that used to prepare 1E, 56B (320 mg, 0.599 mmol), Intermediate 3, and glyoxylic acid monohydrate were reacted and purified by flash chromatography (0% to 20% MeOH in CH$_2$Cl$_2$) to yield 56C (240 mg, 57%) as a yellow solid. LCM 706 [M+H]

56D

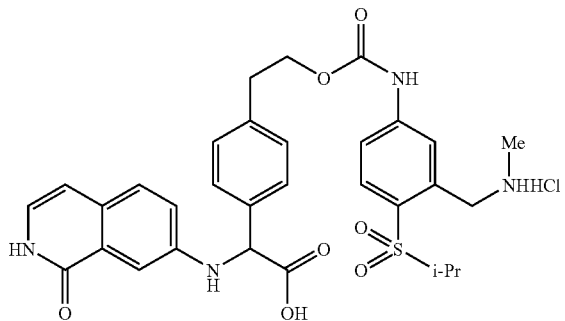

In a 100 mL flask was added 56C (240 mg, 0.340 mmol) in ethyl acetate (8.5 mL) to give a yellow solution. 4N HCl in dioxane (8.49 mL, 34.0 mmol) was added and the mixture was stirred at rt for 2 h. LCMS indicated the completion of the reaction but contained ~10% impurity. Solvent was removed to give 56D (218 mg, 100%) as a yellow solid. LCMS 607 [M+H].

Example 56

To a solution of BOP (300 mg, 0.678 mmol) and DMAP (166 mg, 1.356 mmol) in CH$_2$Cl$_2$ (40 mL) at 40° C. was added a solution of 56D (218 mg, 0.339 mmol) and DIEA (0.118 mL, 0.678 mmol) in DMF (3.0 mL) via a syringe pump over 3.0 h. Solvent was removed, the residue was diluted by CHCl$_3$ (60 mL), to this solution was added water (20 mL) and brine (20 mL). Layers were separated, the aqueous layer was extracted with CHCl$_3$ (20 mL) one more time. The organic layer was dried over Na$_2$SO$_4$. After evaporation of solvent, it was dissolved in MeOH/DMF (10.0 mL, 1:1) and purified by prep HPLC using AXIA column (5 injections) eluting with 80% water to 10% water in acetonitrile with 0.1% TFA in 12 min. Example 56 (17 mg, 8.52% yield) was obtained as a racemic mixture. $^1$H NMR (400 MHz, methanol-d$_4$) δ ppm 1.20 (d, J=6.59 Hz, 3H) 1.31 (d, J=6.59 Hz, 3H) 2.81-3.00 (m, 1H) 3.09-3.25 (m, 1H) 3.35 (s, 3H) 3.43-3.57 (m, 1H) 4.02-4.10 (m, 1H) 4.17 (d, J=17.58 Hz, 1H) 4.78-4.87 (m, 1H) 5.61 (d, J=17.14 Hz, 1H) 5.65 (s, 1H) 6.54-6.58 (m, 2H) 6.85 (dd, J=8.35, 2.20 Hz, 1H) 6.93 (d, J=7.03 Hz, 1H) 7.10-7.19 (m, 2H) 7.23 (dd, J=8.57, 2.42 Hz, 1H) 7.43 (d, J=8.79 Hz, 3H) 7.71-7.77 (m, 2H). MS (ESI) m/z 589 (M+H)$^+$ Analytical HPLC (Method A): Col A: 7.19 min, 90%; Col B: 7.21 min, 91%.

Example 57

4,17,20-Trimethyl-2-(4-oxo-3,4-dihydro-quinazolin-6-ylamino)-7-(propane-2-sulfonyl)-13-oxa-4,11-diaza-tricyclo[14.2.2.2.1$^{6,10}$]henicosa-1(19),6,8,10 (21),16(20),17-hexaene-3,12-dione

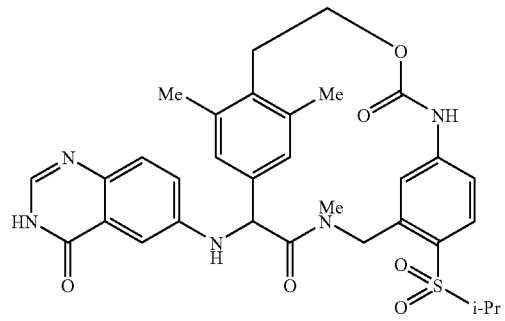 [SMILES: Cc1cc2cc(C)c1CCOC(=O)Nc1ccc(S(=O)(=O)C(C)C)c(c1)CN(C)C(=O)C2Nc1ccc2nc[nH]c(=O)c2c1]

57A

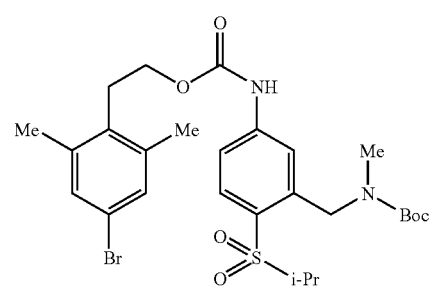 [SMILES: Cc1cc(Br)cc(C)c1CCOC(=O)Nc1ccc(S(=O)(=O)C(C)C)c(CN(C)C(=O)OC(C)(C)C)c1]

Using a procedure analogous to that used to prepare 29A, 3E was reacted with sodium bicarbonate and phosgene followed by 7C (803 mg, 3.50 mmol) and TEA. The crude product was added to a silica gel column (40 g) and was eluted with EtOAc/hexanes (0-100% in 40 min) to give 57A (1.7 g, 99%) as a white foam solid. $^1$H NMR (400 MHz, methanol-$d_4$) δ ppm 1.26 (d, J=6.59 Hz, 6H) 1.45 (d, J=43.06 Hz, 9H) 2.36 (s, 6H) 2.95 (s, 3H) 3.03 (t, J=7.69 Hz, 2H) 3.27-3.37 (m, 1H) 4.24 (t, J=7.69 Hz, 2H) 4.82 (s, 2H) 7.17 (s, 2H) 7.44-7.73 (m, 2H) 7.82 (d, J=8.79 Hz, 1H). LCMS 597, 599 [M+H].

57B

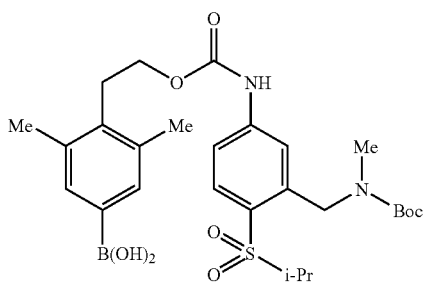 [SMILES: Cc1cc(B(O)O)cc(C)c1CCOC(=O)Nc1ccc(S(=O)(=O)C(C)C)c(CN(C)C(=O)OC(C)(C)C)c1]

Using a procedure analogous to that used to prepare 29B, 57A (1.7 g, 2.84 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 100% and preparative HPLC (CH$_3$CN/H$_2$O, 0.1% TFA) to give 57B (0.92 g, 57.5%) as a white solid. $^1$H NMR (400 MHz, methanol-$d_4$) δ ppm 1.21-1.31 (m, 6H) 1.35-1.60 (m, 9H) 2.39 (d, J=8.79 Hz, 6H) 2.93-2.98 (m, 3H) 3.04-3.15 (m, 2H) 3.28-3.39 (m, 1H) 4.21-4.31 (m, 2H) 4.80-4.86 (m, 2H) 7.20-7.44 (m, 2H) 7.45-7.75 (m, 2H) 7.83 (t, J=9.23 Hz, 1H).

57C

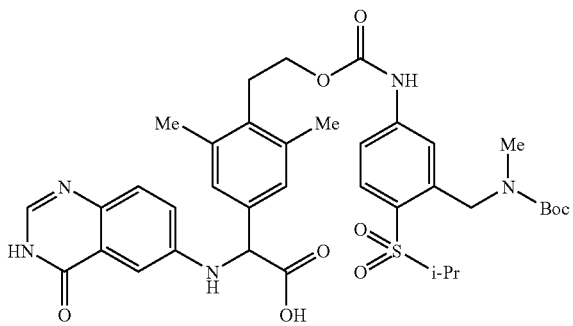

Using a procedure analogous to that used to prepare 1E, 57B (150 mg, 0.267 mmol), Intermediate 4, and glyoxylic acid monohydrate were reacted and purified by flash chromatography (0% to 20% MeOH in CH$_2$Cl$_2$) to yield 57C (180 mg, 92%) as a yellow solid. $^1$H NMR (400 MHz, methanol-$d_4$) δ ppm 1.13 (d, J=7.03 Hz, 6H) 1.33 (d, J=42.18 Hz, 9H) 2.27 (s, 6H) 2.82 (s, 3H) 2.94 (t, J=7.69 Hz, 2H) 4.11 (t, J=7.69 Hz, 2H) 4.70 (s, 2H) 4.94 (s, 1H) 7.06 (d, J=3.08 Hz, 1H) 7.09 (s, 2H) 7.19 (dd, J=9.01, 2.86 Hz, 1H) 7.35 (d, J=8.79 Hz, 1H) 7.39-7.62 (m, 2H) 7.69 (d, J=8.79 Hz, 1H) 7.91 (s, 1H). LCMS 736 [M+H].

57D

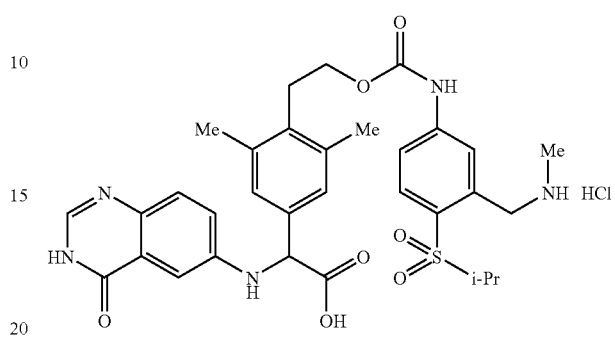

In a 100 mL pear flask was added 57C (180 mg, 0.245 mmol) in ethyl acetate (5 mL) to give a yellow solution, 4N HCl in dioxane (4892 μL, 19.57 mmol) was added to give a yellow suspension. The mixture was stirred at room temperature for 2 h. Solvent was removed and dried under vacuum overnight to give 57D (170 mg, 97%) as a yellow solid. $^1$H NMR (400 MHz, methanol-$d_4$) δ ppm 1.16 (d, J=6.59 Hz, 6H) 2.27 (s, 6H) 2.65 (s, 3H) 2.96 (t, J=7.91 Hz, 2H) 3.23-3.33 (m, J=7.03 Hz, 1H) 4.13 (t, J=7.91 Hz, 2H) 4.28 (s, 2H) 4.99 (s, 1H) 7.09 (s, 2H) 7.13 (d, J=2.64 Hz, 1H) 7.27-7.32 (m, 1H) 7.37-7.41 (m, 1H) 7.57 (d, J=8.79 Hz, 1H) 7.81 (d, J=8.79 Hz, 1H) 7.85 (s, 1H) 8.84 (s, 1H). MS (ESI) m/z 636 (M+H)$^+$.

Example 57

To a solution of BOP (224 mg, 0.506 mmol) and DMAP (124 mg, 1.012 mmol) in CH$_2$Cl$_2$ (25 ml) and DMF (2 mL) at 40° C. was added a solution of 57D (170 mg, 0.253 mmol) and DIEA (0.088 mL, 0.506 mmol) in DMF (3.0 mL) via a syringe pump over 3.0 h. Right after addition of 57D, Solvent was removed, the residue was diluted by CHCl$_3$ (60 mL), to this solution was added water (20 mL) and brine (20 mL). The layers were separated, the aqueous layer was extracted with CHCl$_3$ (20 mL) one more time. The organic layer was dried over Na$_2$SO$_4$. After evaporation of solvent, it was dissolved in MeOH/DMF (10.0 mL, 1:1) and purified by prep HPLC using AXIA column (3 injections) eluting with 90% water to 10% water in acetonitrile with 0.1% TFA in 12 min. Example 57 (19 mg, 12% yield) was obtained as racemic mixture. $^1$H NMR (400 MHz, methanol-$d_4$) δ ppm 1.13 (d, J=6.60 Hz, 3H) 1.21 (d, J=6.60 Hz, 3H) 2.19 (s, 3H) 2.40 (s, 3H) 2.78 (d, J=10.45 Hz, 2H) 2.84 (d, J=14.85 Hz, 1H) 3.06-3.15 (m, 1H) 3.28 (s, 3H) 3.30-3.39 (m, 11H) 4.00 (d, 1H) 4.12 (d, J=17.05 Hz, 1H) 4.92 (s, 1H) 5.48 (s, 1H) 5.52 (d, J=17.60 Hz, 1H) 6.38 (s, 1H) 6.71-6.77 (m, 1H) 6.83 (s, 1H) 7.22 (d, J=2.75 Hz, 1H) 7.26 (dd, J=8.52, 2.47 Hz, 1H) 7.37 (s, 2H) 7.64 (d, J=8.25 Hz, 1H) 9.42 (S, 1H). MS (ESI) m/z 617 (M+H)$^+$ Analytical HPLC (Method A): Col A: 6.22 min, 91%; Col B: 6.76 min, 97%.

Example 58

4-Methyl-2-(4-oxo-3,4-dihydro-quinazolin-6-ylamino)-7-(propane-2-sulfonyl)-13-oxa-4,11-diaza-tricyclo[14.2.2.1$^{6,10}$]henicosa-1(19),6,8,10(21),16(20),17-hexaene-3,12-dione

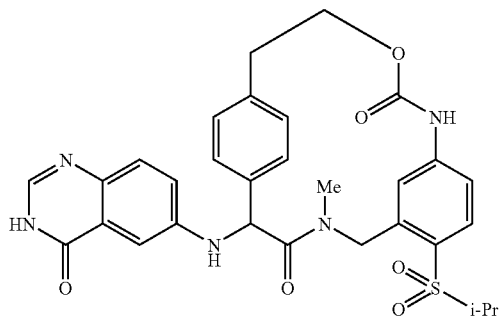 [SMILES: CC(C)S(=O)(=O)c1ccc2cc1CN(C)C(=O)C(Nc1ccc3nc[nH]c(=O)c3c1)c1ccc(cc1)CCOC(=O)N2]

58A

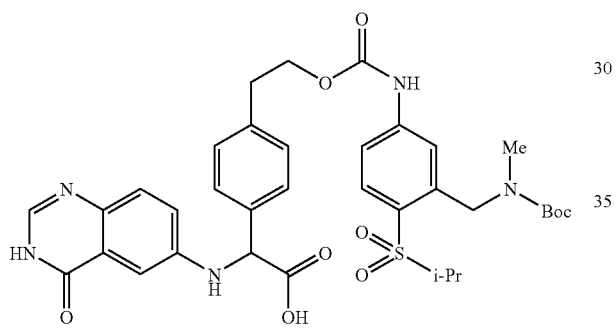

Using a procedure analogous to that used to prepare 29C, 56B, Intermediate 4, and glyoxylic acid monohydrate were reacted and purified by flash chromatography (0% to 20% MeOH in CH$_2$Cl$_2$) to give 58A (280 mg, 66% yield) as a yellow foam. MS (ESI) min/z 708 (M+H)$^+$.

58B

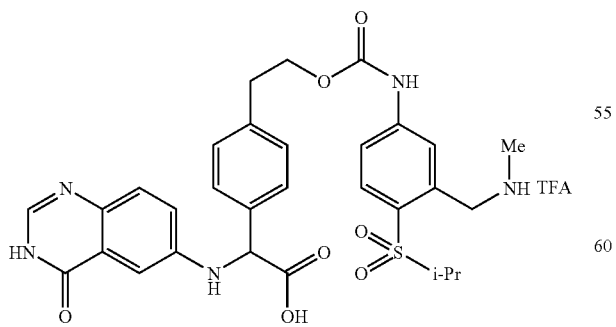

58B was obtained from 58A using the same procedures as used for the preparation of 56D. The crude product was purified by prep HPLC using Luna column (3 injections) eluting with 90% water to 10% water in acetonitrile with 0.1% TFA in 12 min. MS (ESI) m/z 607 (M+H)$^+$.

Example 58

To a solution of BOP (95 mg, 0.214 mmol) and DMAP (52.3 mg, 0.428 mmol) in CH$_2$Cl$_2$ (20 mL) and DMF (3 mL) at 40° C. was added a solution of 58B (69 mg, 0.107 mmol) and DIEA (0.037 mL, 0.214 mmol) in DMF (3.0 mL) via a syringe pump over 3.0 h. Solvent was removed, the residue was diluted by CHCl$_3$ (60 mL), to this solution was added water (20 mL) and brine (20 mL). The layers were separated, the aqueous was extracted with CHCl$_3$ (20 mL) one more time. The organic layer was dried over Na$_2$SO$_4$. After evaporation of solvent, it was dissolved in MeOH/DMF (10.0 mL, 1:1) and purified by prep HPLC using AXIA column eluting with 90% water to 10% water in acetonitrile with 0.1% TFA in 12 min. Example 58 (7.0 mg, 11% yield) was obtained as a racemic mixture. $^1$H NMR (500 MHz, methanol-d$_4$) δ ppm 1.13 (d, J=6.60 Hz, 3H) 1.23 (d, J=6.60 Hz, 3H) 2.74-2.83 (m, 1H) 2.84-2.90 (m, 1H) 3.27 (s, 3H) 3.37-3.45 (m, 1H) 3.99 (dd, J=11.27, 2.47 Hz, 1H) 4.09 (d, J=17.60 Hz, 1H) 4.72-4.77 (m, 1H) 5.53 (d, J=17.05 Hz, 1H) 5.58 (s, 1H) 6.46 (d, J=2.75 Hz, 1H) 6.77 (dd, J=8.25, 2.20 Hz, 1H) 7.04 (s, 2H) 7.23 (d, J=2.75 Hz, 1H) 7.24-7.29 (m, 1H) 7.37 (t, J=9.35 Hz, 2H) 7.65 (d, J=8.25 Hz, 1H) 7.68 (d, J=7.70 Hz, 1H) 8.17 (s, 1H). LCMS 589 [M+H]. Analytical HPLC (Method A): Col A: 5.83 min, 99%; Col B: 6.33 min, 99%.

Example 59

(R)-7-Cyclopropanesulfonyl-4,17,20-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

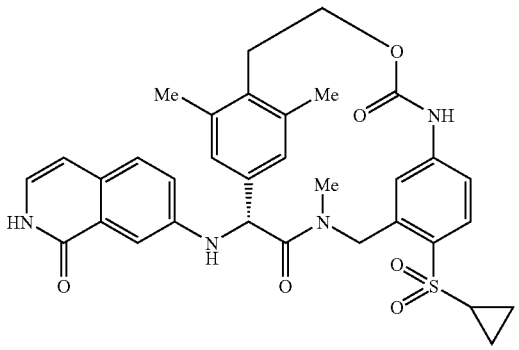 [SMILES: Cc1cc2cc(C)c1CCOC(=O)Nc1ccc(S(=O)(=O)C3CC3)c(c1)CN(C)C(=O)[C@@H]2Nc1ccc2cc[nH]c(=O)c2c1]

59A

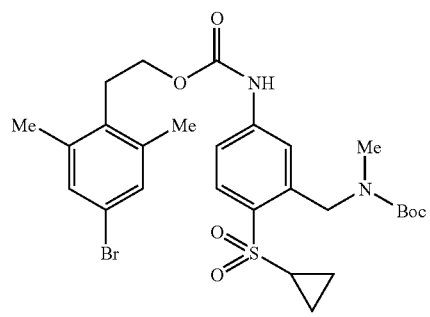 [SMILES: Cc1cc(Br)cc(C)c1CCOC(=O)Nc1ccc(S(=O)(=O)C2CC2)c(CN(C)C(=O)OC(C)(C)C)c1]

Using a procedure analogous to that used to prepare 29A, Intermediate 11 was reacted with sodium bicarbonate and phosgene followed by 7C (1.375 g, 6.00 mmol) and TEA. The crude product was added to a silica gel column (40 g) and was eluted with EtOAc/hexanes (0-100% in 40 min) to give 59A (2.59 g, 87%) as an white foam solid. $^1$H NMR (400 MHz, methanol-d$_4$) δ ppm 1.02-1.10 (m, 2H) 1.16-1.21 (m, 2H) 1.46 (d, J=50.09 Hz, 9H) 2.36 (s, 6H) 2.69-2.83 (m, 1H) 2.87 (t, J=7.69 Hz, 1H) 2.96 (s, 3H) 3.04 (t, J=7.69 Hz, 2H) 3.59 (t, J=7.69 Hz, 1H) 4.24 (t, J=7.69 Hz, 2H) 7.14 (s, 1H) 7.18 (s, 2H) 7.61 (broad, 1H) 7.81 (d, J=8.35 Hz, 1H). MS (ESI) m/z 595, 597 (M+H)$^+$.

59B

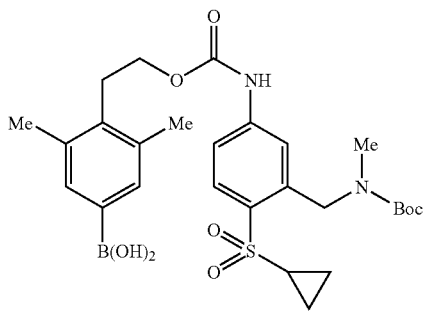 [SMILES: Cc1cc(B(O)O)cc(C)c1CCOC(=O)Nc1ccc(S(=O)(=O)C2CC2)c(CN(C)C(=O)OC(C)(C)C)c1]

Using a procedure analogous to that used to prepare 29B, 59A (2.5 g, 4.20 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 50% and preparative HPLC (CH$_3$CN/H$_2$O, 0.1% TFA) to give 59B (1.3 g, 55%) was obtained as a white solid. $^1$H NMR (400 MHz, methanol-d$_4$) δ ppm 1.03-1.10 (m, 2H) 1.16-1.23 (m, 2H) 1.46 (d, J=49.65 Hz, 9H) 2.39 (s, 6H) 2.72-2.84 (m, 1H) 2.96 (s, 3H) 3.09 (t, J=7.69 Hz, 2H) 4.25 (t, J=7.69 Hz, 2H) 4.90 (s, 2H) 7.22-7.42 (m, 2H) 7.43-7.74 (m, 2H) 7.81 (d, J=8.79 Hz, 1H).

59C

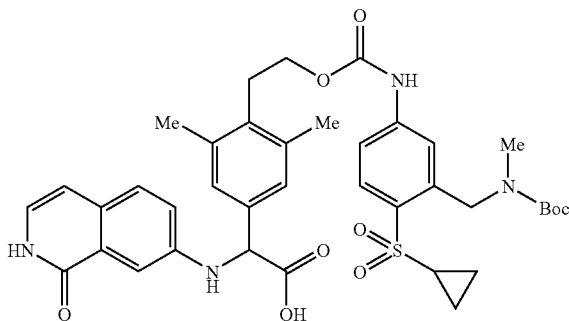 [SMILES: Cc1cc(C(Nc2ccc3cc[nH]c(=O)c3c2)C(=O)O)cc(C)c1CCOC(=O)Nc1ccc(S(=O)(=O)C2CC2)c(CN(C)C(=O)OC(C)(C)C)c1]

Using a procedure analogous to that used to prepare 1E, 59B (200 mg, 0.357 mmol), Intermediate 3, and glyoxylic acid monohydrate were reacted and purified by flash chromatography (0% to 20% MeOH in CH$_2$Cl$_2$) to yield 59C (230 mg, 88%) as a yellow solid. $^1$H NMR (400 MHz, methanol-d$_4$) δ ppm 1.03-1.09 (m, 2H) 1.16-1.21 (m, 2H) 1.45 (d, J=61.59 Hz, 9H) 2.38 (s, 6H) 2.76 (broad, 1H) 2.94 (s, 3H) 3.04-3.08 (m, 2H) 4.23 (t, J=7.70 Hz, 2H) 4.90 (s, 2H) 5.07 (s, 1H) 6.54 (d, J=6.60 Hz, 1H) 6.89 (d, J=6.60 Hz, 1H) 7.19-7.23 (m, 3H) 7.31 (d, J=2.75 Hz, 1H) 7.41 (d, J=8.80 Hz, 1H) 7.44-7.72 (broad, m, 2H) 7.80 (d, J=8.80 Hz, 1H), MS (ESI) m/z 733 (M+H)$^+$.

59D

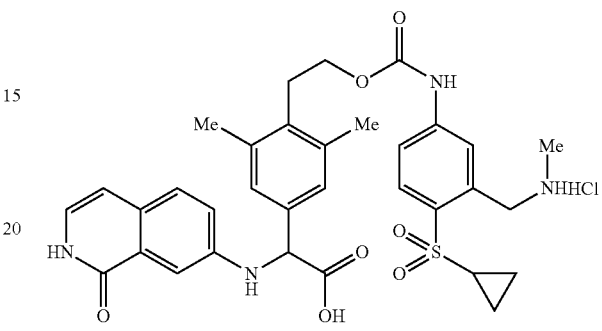

In a 150 mL round-bottomed flask was added 59C (230 mg, 0.314 mmol) in 6 ml of EtOAc, 4N HCl in dioxane (6277 μL, 25.1 mmol) was added. The mixture was stirred at rt for 1 h. Solvent was removed and dried under vacuum overnight to give 59D (210 mg, 100%) as a yellow solid. $^1$H NMR (400 MHz, DMSO-d$_6$) δ ppm 1.03-1.08 (m, 2H) 1.09-1.16 (m, 2H) 2.33 (s, 6H) 2.62 (t, J=5.22 Hz, 3H) 2.98 (t, J=7.42 Hz, 2H) 3.02-3.09 (m, 1H) 4.23 (t, J=7.70 Hz, 2H) 4.37-4.45 (m, 2H) 5.03 (s, 1H) 6.35 (d, J=7.15 Hz, 1H) 6.82-6.86 (m, 1H) 7.16-7.18 (m, 1H) 7.20 (s, 2H) 7.22-7.26 (m, 2H) 7.37 (d, J=8.80 Hz, 1H) 7.65 (dd, J=8.80, 2.20 Hz, 1H) 7.86 (d, J=8.80 Hz, 1H) 7.91 (s, 1H) 8.81 (s, 2H) 10.42 (s, 1H). MS (ESI) m/z 733 (M+H)$^+$.

Example 59

To a solution of BOP (278 mg, 0.628 mmol) and DMAP (153 mg, 1.256 mmol) in CH$_2$Cl$_2$ (45 ml) at 40° C. was added a solution of 59D (210 mg, 0.314 mmol) and DIEA (0.110 ml, 0.628 mmol) in DMF (3.0 mL) via a syringe pump over 3.0 h. Right after addition of 59D, LC-MS indicated the reaction was completed. The solvent was removed, the residue was dissolved in CH$_3$CN/H$_2$O (9:1) and purified by prep HPLC using AXIA column (3 injection) eluting with 80% water to 10% water in acetonitrile with 0.1% TFA in 12 min to obtain the macrocycle (29 mg) as a racemic mixture. The crude cycle with material from another synthesis (35 mg) was dissolved in 18 ml of 60% MeOH/EtOH (1:1)/20% Heptane and was purified using a preparative HPLC equipped with a Whelko-01 column. The separations were performed using an isocratic method of 60% 1:1 ethanol/methanol: heptane for 40 min with a flow rate of 20 mL/min. The fractions of the second peak were combined to give Example 59 (RT=12.5 min, 12 mg, 40% yield): $^1$H NMR (500 MHz, methanol-d$_4$) δ ppm 0.98-1.13 (m, 3H) 1.22-1.32 (m, 1H) 2.29 (s, 3H) 2.49 (s, 3H) 2.82-2.90 (m, 1H) 2.93 (d, J=14.85 Hz, 1H) 3.15-3.25 (m, 1H) 3.39 (s, 3H) 4.08 (s, 1H) 4.28 (d, J=17.60 Hz, 1H) 5.01 (s, 1H) 5.56 (s, 1H) 5.74 (d, J=17.60 Hz, 1H) 6.46 (s, 1H) 6.54 (d, J=6.60 Hz, 1H) 6.80-6.85 (m, 1H) 6.91 (d, J=7.15 Hz, 1H) 6.97 (s, 1H) 7.22 (dd, J=8.52, 2.47 Hz, 1H) 7.37-7.42 (m, 2H) 7.46 (s, 1H) 7.71 (d, J=8.25 Hz, 1H). Chiral analytic HPLC: Column: Regis Whelk-01 (R,R), 250×4.6 mm ID; 10 μm, Mobile Phase: 60% (50/50 Methanol-Ethanol): 40% Heptane, UV Detection: 254 and 256 nm, Retention Time (min): 11.0 min. Analytical HPLC (Method A): Col A: 7.74 min, 99%; Col B: 7.75 min, 99%.

Example 60

(R)-7-Cyclopropanesulfonyl-4,17,20-trimethyl-2-(4-oxo-3,4-dihydro-quinazolin-6-ylamino)-13-oxa-4,11-diaza-tricyclo[14.2.2.1$^{6,10}$]henicosa-1(19),6,8,10(21),16(20),17-hexaene-3,12-dione

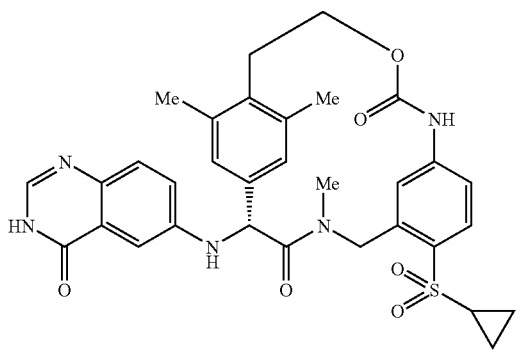 [SMILES: Cc1cc2cc(C)c1CCOC(=O)Nc1ccc(S(=O)(=O)C3CC3)c(c1)CN(C)C(=O)[C@@H]2Nc1ccc2nc[nH]c(=O)c2c1]

60A

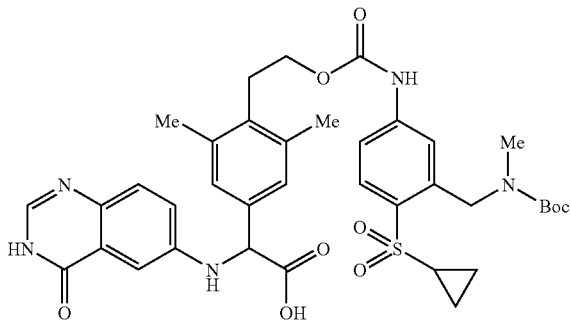 [SMILES: Cc1cc(C(Nc2ccc3nc[nH]c(=O)c3c2)C(=O)O)cc(C)c1CCOC(=O)Nc1ccc(S(=O)(=O)C2CC2)c(CN(C)C(=O)OC(C)(C)C)c1]

Using a procedure analogous to that used to prepare 1E, 59B (265 mg, 0.473 mmol), Intermediate 4, and glyoxylic acid monohydrate were reacted and purified by flash chromatography (0% to 20% MeOH in CH$_2$Cl$_2$) to yield 60A (323 mg, 93%) as a yellow solid. $^1$H NMR (500 MHz, methanol-d$_4$) δ ppm 1.03-1.10 (m, 2H) 1.17-1.21 (m, 2H) 1.46 (d, J=62.13 Hz, 9H) 2.39 (s, 6H) 2.71-2.84 (m, 1H) 2.95 (s, 3H) 3.07 (t, J=7.70 Hz, 2H) 4.24 (t, J=7.70 Hz, 2H) 4.91 (s, 2H) 5.06 (s, 1H) 7.16-7.23 (m, 3H) 7.29 (d, J=7.70 Hz, 1H) 7.47 (d, J=8.25 Hz, 1H) 7.50-7.71 (m, 2H) 7.80 (d, J=8.80 Hz, 1H) 7.83-7.89 (m, 1H). MS (ESI) m/z 734 (M+H)$^+$.

60B

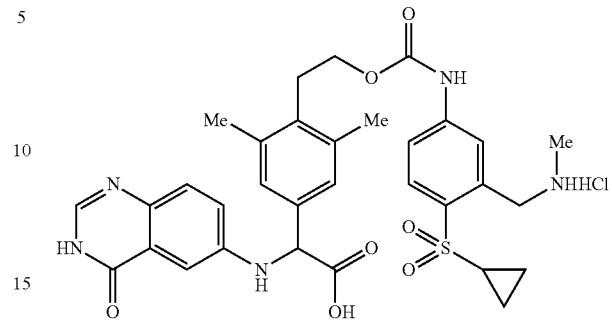

In a 150 mL round-bottomed flask was added 60A (320 mg, 0.436 mmol) in 9 ml of EtOAc, 4N HCl in dioxane (8721 μL, 34.9 mmol) was added. The mixture was stirred at rt for 1 h. Solvent was removed and dried under vacuum overnight to a yellow solid of 60B (278 mg, 95%). $^1$H NMR (400 MHz, DMSO-d$_6$) δ ppm 1.01-1.09 (m, 2H) 1.09-1.15 (m, 2H) 2.34 (s, 6H) 2.61 (t, J=5.22 Hz, 3H) 2.98 (t, J=7.42 Hz, 2H) 3.04-3.11 (m, 1H) 4.22 (t, J=7.70 Hz, 2H) 4.40 (t, J=5.77 Hz, 2H) 5.10 (s, 1H) 7.12 (s, 1H) 7.19 (s, 2H) 7.43 (dd, J=9.07, 2.47 Hz, 1H) 7.57 (d, J=9.35 Hz, 1H) 7.68 (dd, J=8.80, 2.20 Hz, 1H) 7.86 (d, J=8.80 Hz, 1H) 8.56-8.68 (m, 1H) 8.95 (s, 2H) 10.44 (s, 1H). MS (ESI) m/z 634 (M+H)$^+$.

Example 60

To a solution of BOP (0.367 g, 0.830 mmol) and DMAP (0.203 g, 1.659 mmol) in CH$_2$Cl$_2$ (60 mL) at 40° C. was added a solution of 60B (0.278 g, 0.415 mmol) and DIEA (0.145 mL, 0.830 mmol) in DMF (3.0 mL) via a syringe pump over 3.0 h. Solvent was removed, the residue was dissolved in CH$_3$CN/H$_2$O (9:1) and purified by prep HPLC using AXIA column (3 injection) eluting with 80% water to 10% water in acetonitrile with 0.1% TFA in 12 min. The crude cycle (35 mg, 14% yield) was obtained as a racemic mixture. The racemate (32 mg) was dissolved in 22 mL of 60% MeOH/EtOH (1:1)/20% heptane and was separated using a preparative HPLC equipped with a Whelko-01 column. The separations were performed using an isocratic method of 60% 1:1 ethanol/methanol: heptane for 40 min with a flow rate of mL/min. The fractions of the second peak (RT=14.5 min, 11 mg, 40% yield) were combined to give Example 60: $^1$H NMR (400 MHz, methanol-d$_4$) δ ppm 1.00-1.14 (m, 3H) 1.22-1.32 (m, 1H) 2.30 (s, 3H) 2.49 (s, 3H) 2.83-2.90 (m, 1H) 2.94 (d, J=14.29 Hz, 1H) 3.15-3.26 (m, 1H) 3.39 (s, 3H) 4.09 (s, 1H) 4.29 (d, J=17.04 Hz, 1H) 4.97-5.09 (m, 1H) 5.56 (s, 1H) 5.75 (d, J=17.59 Hz, 1H) 6.46 (s, 1H) 6.79-6.86 (m, 1H) 6.96 (s, 1H) 7.27-7.34 (m, 2H) 7.45 (d, J=4.40 Hz, 2H) 7.72 (d, J=8.79 Hz, 1H) 7.84 (s, 1H). Chiral analytic HPLC: Column: Regis Whelk-01 (R,R), 250×4.6 mm ID; 10 μm, Mobile Phase: 60% (50/50 Methanol-Ethanol): 40% Heptane, UV Detection: 254 and 256 nm, Retention Time (min): 12.34 min. Analytical HPLC (Method A): Col A: 6.19 min, 99%; Col B: 6.74 min, 99%.

Example 61

7-Cyclopropanesulfonyl-2-(7-fluoro-4-oxo-3,4-dihydro-quinazolin-6-ylamino)-4,17,20-trimethyl-13-oxa-4,11-diaza-tricyclo[14.2.2.1$^{6,10}$]henicosa-1(19),6,8,10(21),16(20),17-hexaene-3,12-dione

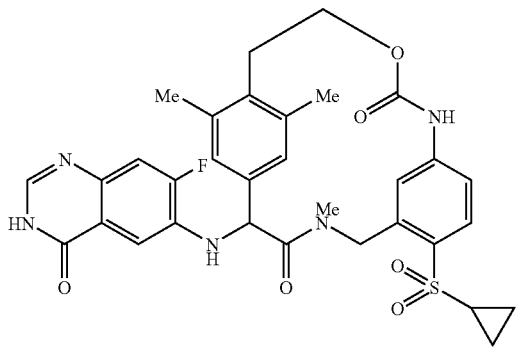 [SMILES: Cc1cc2cc(C)c1CCOC(=O)Nc1ccc(S(=O)(=O)C3CC3)c(c1)CN(C)C(=O)C2Nc1cc2c(=O)[nH]cnc2cc1F]

61A

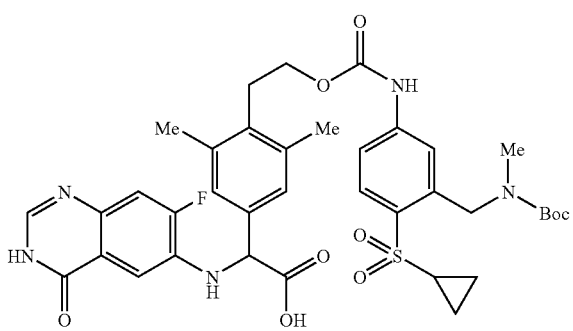 [SMILES: Cc1cc(C(Nc2cc3c(=O)[nH]cnc3cc2F)C(=O)O)cc(C)c1CCOC(=O)Nc1ccc(S(=O)(=O)C2CC2)c(CN(C)C(=O)OC(C)(C)C)c1]

Using a procedure analogous to that used to prepare 1E, 59B (120 mg, 0.214 mmol), Intermediate 12, and glyoxylic acid monohydrate were reacted and purified by flash chromatography (0% to 20% MeOH in CH$_2$Cl$_2$) to yield 61A (146 mg, 91%) as a yellow solid. MS (ESI) m/z 752 (M+H)$^+$.

61B

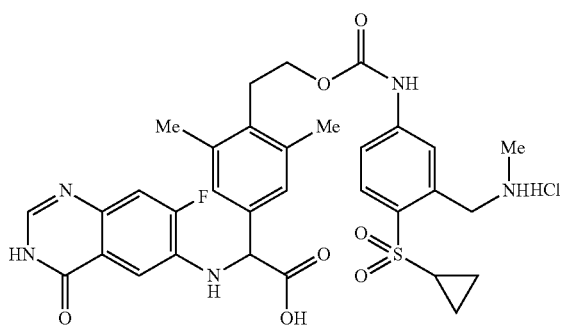

In a 150 mL round-bottomed flask was added 61A (146 mg, 0.194 mmol) in 4 ml of EtOAc, 4N HCl in dioxane (3880 μL, 15.52 mmol) was added. The mixture was stirred at room temperature for 1 h. Solvent was removed and dried under vacuum overnight to give 61B (110 mg, 82%) as a yellow solid. $^1$H NMR (400 MHz, DMF-d$_7$) δ ppm 1.13 (d, J=4.95 Hz, 2H) 1.20 (d, J=3.85 Hz, 2H) 2.40 (s, 6H) 2.82 (s, 3H) 3.05 (t, J=7.15 Hz, 2H) 3.24 (d, J=4.40 Hz, 1H) 4.26 (t, J=7.42 Hz, 2H) 4.65 (s, 2H) 5.40 (s, 1H) 7.31 (d, J=8.79 Hz, 1H) 7.36 (s, 2H) 7.82-7.96 (m, 3H) 8.05 (s, 1H) 9.00 (s, 1H) 9.79 (s, 2H) 10.46 (s, 1H). MS (ESI) m/z 650 (M−H)$^−$.

Example 61

To a solution of BOP (0.141 g, 0.320 mmol) and DMAP (0.078 g, 0.639 mmol) in CH$_2$Cl$_2$ (30 mL) at 40° C. was added a solution of 61B (0.110 g, 0.160 mmol) and DIEA (0.056 mL, 0.320 mmol) in DMF (3.0 mL) via a syringe pump over 3.0 hrs and the reaction mixture was continued at 40° C. for 30 min. Solvent was removed, the residue was dissolved in CH$_3$CN/H$_2$O (9:1) and purified by prep HPLC using AXIA column (2 injection) eluting with 90% water to 20% water in acetonitrile with 0.1% TFA in 12 min. Example 61 (12 mg, 12% yield) was obtained as a racemic mixture. $^1$H NMR (400 MHz, methanol-d$_4$) δ ppm 1.03-1.17 (m, 3H) 1.23-1.32 (m, 1H) 2.27 (s, 3H) 2.51 (s, 3H) 2.85-2.96 (m, 2H) 3.13-3.23 (m, 1H) 3.37 (s, 3H) 4.11 (s. 1H) 4.28 (d, J=17.59 Hz, 1H) 4.96-5.08 (m, 1H) 5.66 (s, 1H) 5.76 (d, J=17.59 Hz, 1H) 6.83 (d, J=8.24 Hz, 1H) 6.86 (s, 1H) 7.32 (d, J=12.09 Hz, 1H) 7.47 (d, J=8.79 Hz, 1H) 7.55 (s, 1H) 7.72 (d, J=8.79 Hz, 1H) 8.33 (s, 1H) 9.49 (s, 1H). LCMS 634 [M+H].

Example 64

(2R,15R)-7-Cyclopropanesulfonyl-4,15-dimethyl-2-(4-oxo-3,4-dihydro-quinazolin-6-ylamino)-13-oxa-4,11-diaza-tricyclo[14.2.2.1$^{6,10}$]henicosa-1(19),6,8,10(21),16(20), 17-hexaene-3,12-dione

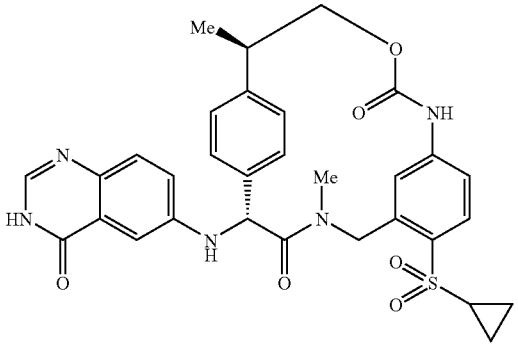

64A

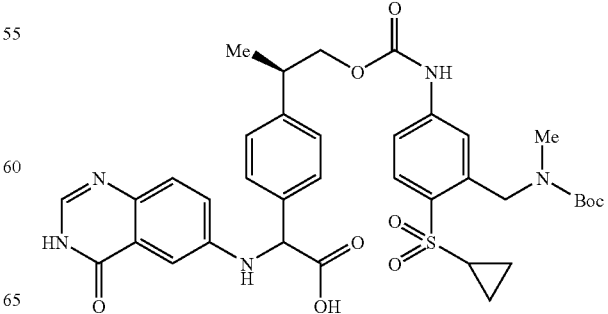

Using a procedure analogous to that used to prepare 1E, 32F (200 mg, 0.366 mmol), Intermediate 4, and glyoxylic acid monohydrate were reacted and purified by flash chromatography (0% to 20% MeOH in CH$_2$Cl$_2$) to yield 64A (230 mg, 0.320 mmol, 87% yield) as a yellow solid. $^1$H NMR (400 MHz, methanol-d$_4$) δ ppm 1.02-1.09 (m, 2H) 1.15-1.21 (m, 2H) 1.31 (d, J=7.15 Hz, 3H) 1.44 (d, J=67.63 Hz, 9H) 2.64-2.85 (m, J=3.85 Hz, 1H) 2.94 (s, 3H) 3.16 (q, J=6.96 Hz, 1H) 4.25 (d, J=7.15 Hz, 2H) 4.85-4.93 (m, 2H) 5.16 (s, 1H) 7.17 (dd, J=4.95, 2.75 Hz, 1H) 7.26-7.33 (m, 3H) 7.41-7.64 (m, J=29.69, 8.25 Hz, 2H) 7.46 (d, J=8.80 Hz, 1H) 7.52 (d, J=7.70 Hz, 2H) 7.77 (d, J=8.80 Hz, 1H) 7.82-7.86 (m, 1H). LCMS 720 [M+H].

64B

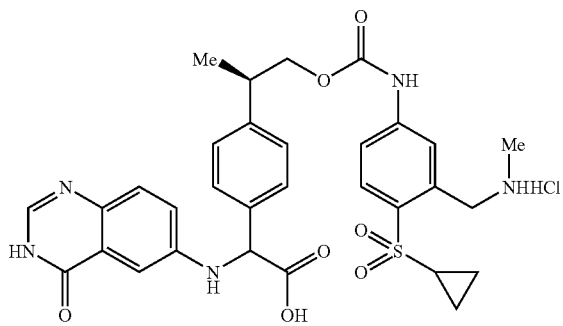

In a 100 mL round-bottomed flask was added 64A (230 mg, 0.32 mmol) in 6 mL of EtOAc, 4N HCl in dioxane (6.4 mL, 25.6 mmol) was added. The mixture was stirred at rt for 1 h. Solvent was removed and dried under vacuum overnight to a yellow solid of 64B (210 mg, 100%). $^1$H NMR (400 MHz, methanol-d$_4$) δ ppm 1.12 (d, J=4.95 Hz, 2H) 1.19 (d, J=4.40 Hz, 2H) 1.31 (d, J=6.60 Hz, 3H) 2.81 (s, 3H) 3.11-3.30 (m, 2H) 4.18-4.37 (m, 2H) 4.63 (s, 2H) 5.44 (s, 1H) 7.36 (d, J=2.75 Hz, 1H) 7.41 (d, J=8.25 Hz, 2H) 7.62-7.68 (m, 2H) 7.88-7.93 (m, 3H) 7.98-8.05 (m, 3H) 8.94 (s, 1H) 9.83 (s, 2H) 10.32-10.59 (m, 1H). LCMS 620 [M+H].

64C

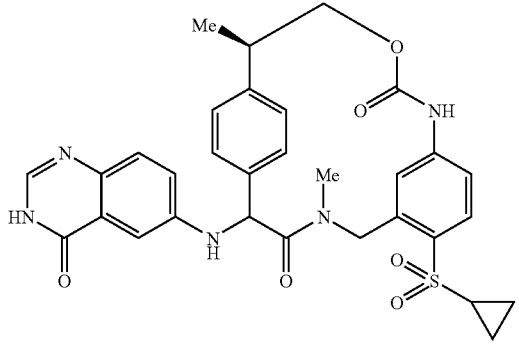

To a solution of BOP (283 mg, 0.640 mmol) and DMAP (156 mg, 1.280 mmol) in CH$_2$Cl$_2$ (60 mL)) at 40° C. was added a solution of 64B (210 mg, 0.32 mmol) and DIEA (0.112 mL, 0.64 mmol) in DMF (4.0 mL) via a syringe pump over 4.5 h. The reaction was continued at 40° C. for 30 min. LC-MS indicated the reaction was completed. Solvent was removed, the residue was diluted by EtOAc 200 ml and washed by H$_2$O and brine, the organic layer was dried by MgSO$_4$ and concentrated. The residue was dissolved in CH$_3$CN/H$_2$O (9:1) and purified by prep HPLC using AXIA column (2 injection) eluting with 90% water to 10% water in Acetonitrile with 0.1% TFA in 12 min. to give 64C (80 mg, 70% pure). LCMS 602 [M+H].

Example 64

64C (80 mg, 70% pure) was dissolved in 22 ml of 60% MeOH/EtOH (1:1)/20% heptane and was purified using a preparative HPLC equipped with a Whelko-01 column. The separations were performed using an isocratic method of 60% 1:1 ethanol/methanol: heptane for 40 min with a flow rate of 20 mL/min. The fractions of the second peak (RT=15.10 min, 6 mg, 6% yield) were combined to give Example 64: $^1$H NMR (400 MHz, methanol-d$_4$) δ ppm 0.98-1.14 (m, 2H) 1.22-1.33 (m, 2H) 1.37 (d, J=7.15 Hz, 3H) 2.85-2.92 (m, 1H) 3.00-3.08 (m, 1H) 3.39 (s, 3H) 3.90 (dd, J=10.99, 4.40 Hz, 1H) 4.27 (d, J=17.59 Hz, 1H) 4.55 (t, J=10.99 Hz, 1H) 5.67 (s, 1H) 5.76 (d, J=17.59 Hz, 1H) 6.47 (s, 1H) 6.83 (dd, J=8.24, 2.20 Hz, 1H) 7.08-7.14 (m, 1H) 7.15-7.20 (m, 1H) 7.27-7.34 (m, 2H) 7.43-7.48 (m, 1H) 7.51 (d, J=8.25 Hz, 1H) 7.71 (d, J=8.79 Hz, 1H) 7.79-7.87 (m, 2H). Chiral analytic HPLC: Column: Regis Whelk-10 (R,R), 250×4.6 mm ID; 10 μm, Mobile Phase: 60% (50/50 Methanol-Ethanol): 40% Heptane, UV Detection: 254 and 256 nm, Retention Time (min): 13.63 min. Analytical HPLC (Method A): Col A: 6.09 min, 99%; Col B: 6.61 min, 99%.

Example 65

(2R,15R)-7-Cyclopropanesulfonyl-15-ethyl-4-methyl-2-(4-oxo-3,4-dihydro-quinazolin-6-ylamino)-13-oxa-4,11-diaza-tricyclo[14.2.2.1$^{6,10}$]henicosa-1(19),6,8,10(21),16(20),17-hexaene-3,12-dione

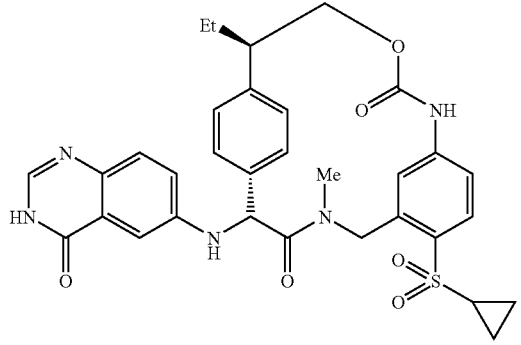 [SMILES: C[C@H]1COC(=O)Nc2ccc(S(=O)(=O)C3CC3)c(c2)CN(C)C(=O)[C@H](Nc2ccc3nc[nH]c(=O)c3c2)c2ccc1cc2]

65A

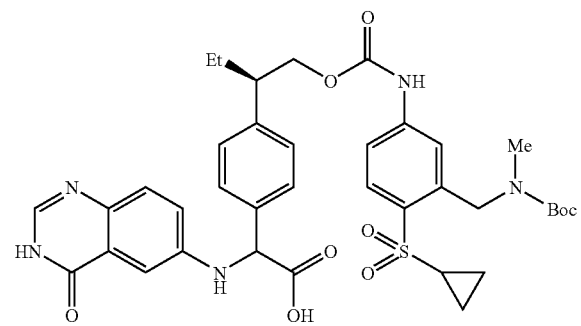

Using a procedure analogous to that used to prepare 1E, 33D (200 mg, 0.357 mmol), Intermediate 4, and glyoxylic acid monohydrate were reacted for 25 min and purified by flash chromatography (0% to 20% MeOH in CH$_2$Cl$_2$) to yield 65A (215 mg, 0.295 mmol, 82% yield) as a yellow solid. $^1$H NMR (400 MHz, methanol-d$_4$) δ ppm 0.83 (t, J=7.15 Hz, 3H) 1.00-1.11 (m, 2H) 1.14-1.21 (m, 2H) 1.44 (d, J=48.37 Hz, 9H) 1.64 (dd, J=7.70, 3.85 Hz, 1H) 1.74-1.92 (m, 1H) 2.76 (m, 1H) 2.87-2.97 (m, 1H) 2.94 (s, 3H) 4.20-4.30 (m, 1H) 4.30-4.40 (m, 1H) 4.89 (s, 2H) 5.15 (s, 1H) 7.18 (dd, J=6.05, 2.75 Hz, 1H) 7.24-7.33 (m, 3H) 7.41-7.61 (m, J=23.91, 8.52 Hz, 2H) 7.46 (d, J=8.79 Hz, 1H) 7.52 (d, J=8.24 Hz, 2H) 7.77 (d, J=8.79 Hz, 1H) 7.83 (s, 1H). LCMS 734 [M+H].

65B

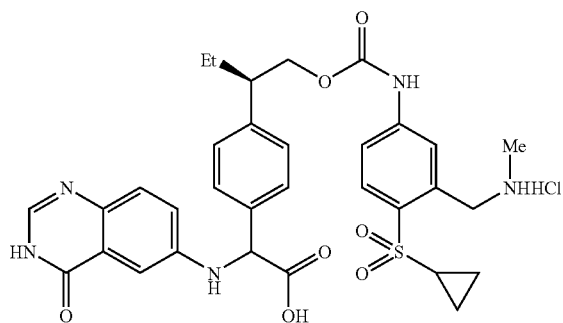

In a 100 mL round-bottomed flask was 65A (215 mg, 0.293 mmol) in 6 mL of EtOAc, 4N HCl in dioxane (5.86 mL, 23.44 mmol) was added. The mixture was stirred at room temperature for 1 h. Solvent was removed and dried under vacuum overnight to a yellow solid of 65B (196 mg, 100%). $^1$H NMR (400 MHz, DMF-d$_7$) δ ppm 0.76-0.84 (m, 3H) 1.12 (d, J=5.50 Hz, 2H) 1.20 (d, J=3.85 Hz, 2H) 1.57-1.75 (m, 1H) 1.75-1.94 (m, 1H) 2.88-3.00 (m, 1H) 3.15-3.27 (m, 1H) 4.27-4.37 (m, J=6.60, 6.60 Hz, 2H) 4.62 (s, 2H) 5.44 (s, 1H) 7.39 (d, J=7.70 Hz, 2H) 7.62-7.68 (m, 2H) 7.89-7.93 (m, 3H) 7.97-8.04 (m, 3H) 8.96 (s, 1H) 9.82 (s, 2H) 10.47 (d, J=10.44 Hz, 1H) LCMS 634 [M+H].

65C

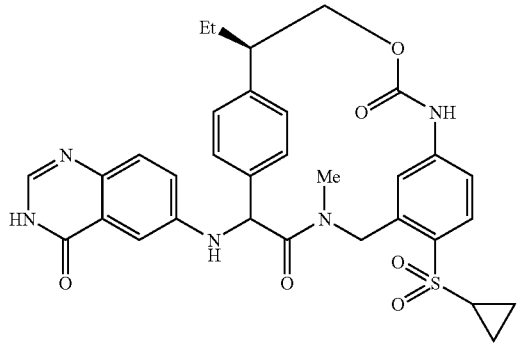

To a solution of BOP (259 mg, 0.586 mmol) and DMAP (143 mg, 1.172 mmol) in CH$_2$Cl$_2$ (50 mL) and DMF (5.0 mL) at 40° C. was added a solution of 65B (196 mg, 0.293 mmol) and DIEA (0.102 mL, 0.586 mmol) in DMF (4.0 mL) via a syringe pump over 5 h, then the reaction mixture was stirred for 30 min. LC-MS indicated the reaction was completed. Solvent was removed, the residue was diluted by EtOAc 200 mL and washed by H$_2$O and brine, the organic layer was dried by MgSO$_4$ and concentrated. The residue was dissolved in CH$_3$CN/H$_2$O (9:1) and purified by prep HPLC using AXIA column (2 injection) eluting with 90% water to 10% water in acetonitrile with 0.1% TFA in 12 min. to give 65C. LCMS 616 [M+H].

Example 65

65C was dissolved in 20 ml of 60% MeOH/EtOH (1:1)/20% Heptane and was purified using a preparative HPLC equipped with a Whelko-01 column. The separations were performed using an isocratic method of 60% 1:1 ethanol/methanol: heptane for 40 min with a flow rate of 20 mL/min. The fractions of the second peak (RT=13.83 min, 9.4 mg, 5.21% yield) were combined to give Example 65: $^1$H NMR (400 MHz, methanol-d$_4$) δ ppm 0.92 (t, J=7.42 Hz, 3H) 0.95-1.11 (m, 3H) 1.20-1.35 (m, 1H) 1.69-1.93 (m, 2H) 2.73-2.90 (m, 2H) 3.39 (s, 3H) 3.94 (dd, J=10.99, 3.85 Hz, 1H) 4.27 (d, J=17.59 Hz, 1H) 4.59 (t, J=10.99 Hz, 1H) 5.67 (s, 1H) 5.75 (d, J=17.59 Hz, 1H) 6.47 (s, 1H) 6.75-6.89 (m, 1H) 7.06 (d, J=7.70 Hz, 1H) 7.15-7.24 (m, 1H) 7.26-7.32 (m, 2H) 7.42-7.52 (m, 2H) 7.71 (d, J=8.25 Hz, 1H) 7.79-7.88 (m, 2H). Chiral analytic HPLC: Column: Regis Whelk-01 (R,R), 250× 4.6 mm ID; 10 μm, Mobile Phase: 60% (50/50 Methanol-Ethanol): 40% Heptane, UV Detection: 254 and 256 nm, Retention Time (min): 12.63 min. Analytical HPLC (Method A): Col A: 6.41 min, 99%; Col B: 6.95 min, 99%.

Example 66

(2R,15R)-7-Cyclopropanesulfonyl-15-methoxy-4-methyl-2-(1-oxo-1,2-dihydro-isoquinolin-7-ylamino)-13-oxa-4,11-diaza-tricyclo[14.2.2.1$^{6,10}$] henicosa-(19),6,8,10(21),16(20),17-hexaene-3,12-dione

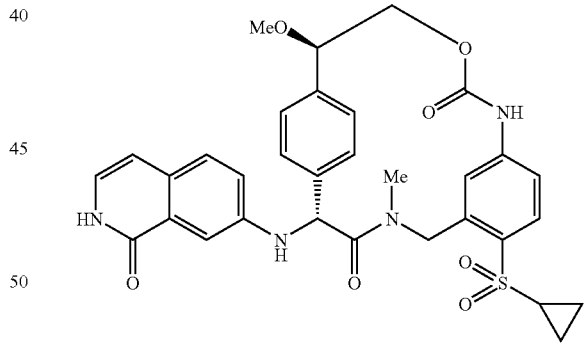

66A

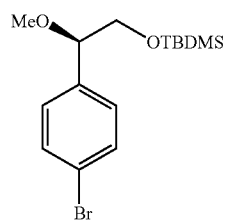

39B (5.1 g, 15.39 mmol) and iodomethane (7.03 mL, 46.2 mmol) were dissolved in acetonitrile (80 mL) and potassium tert-butoxide (1.900 g, 16.93 mmol) was added. The mixture was stirred at rt over the weekend. The reaction was quenched by 200 mL of saturated NH$_4$Cl and extracted by EtOAc (2×200 mL) and the combined organic layers were dried with MgSO$_4$ and concentrated to an oil. The residue was dissolved in small amount of dichloromethane and added to a 120 g ISCO column and was eluted with 0-30% EtOAc/Hexanes for 40 min. 66A (3.4, 64% yield) was obtained as a colorless oil. $^1$H NMR (400 MHz, CDCl$_3$) δ ppm –0.06 (s, 3H)-0.03 (s, 3H) 0.83 (s, 9H) 3.28 (s, 3H) 3.55-3.63 (m, 1H) 3.73-3.80 (m, 1H) 4.14-4.20 (m, 1H) 7.18 (d, J=8.24 Hz, 2H) 7.46 (d, J=8.24 Hz, 2H).

66B

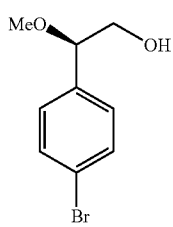 [SMILES: CO[C@@H](CO)c1ccc(Br)cc1]

In a 250 mL pear flask was added 66A (3.2 g, 9.27 mmol) in acetonitrile (30 ml) to give a colorless solution. TBAF (18.53 ml, 18.53 mmol) was added. The mixture was stirred at room temperature for 2 hours. The reaction was quenched by 50 ml of brine and extracted by EtOAc (2×100 ml). The combined organic layer was dried with MgSO$_4$ concentrated. The residue was dissolved in small amount of dichloromethane and added to a 120 g ISCO column and was eluted with 0-70% EtOAc/Hexanes for 40 min. 66B (1.9 g, 89% yield) was obtained as a clear oil. $^1$H NMR (400 MHz, methanol-d$_4$) δ ppm 3.20 (s, 3H) 3.42-3.50 (m, 1H) 3.50-3.58 (m, 1H) 4.16 (dd, J=7.42, 4.12 Hz, 1H) 7.18 (d, J=8.24 Hz, 2H) 7.44 (d, J=8.24 Hz, 2H).

66C

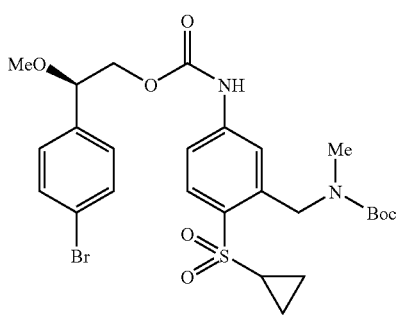 [SMILES: CO[C@@H](COC(=O)Nc1ccc(S(=O)(=O)C2CC2)c(CN(C)C(=O)OC(C)(C)C)c1)c1ccc(Br)cc1]

Using a procedure analogous to that used to prepare 29A, Intermediate 11 was reacted with sodium bicarbonate and phosgene followed by 66B (1 g, 4.33 mmol) and TEA. The crude product was added to a silica gel column (40 g) and was eluted with EtOAc/hexanes (0-100% in 15 min) to give 66C (2.0 g, 93%) was obtained as a foam solid. $^1$H NMR (400 MHz, methanol-d$_4$) δ ppm 1.03-1.10 (m, 2H) 1.16-1.21 (m, 2H) 1.45 (d, J=47.27 Hz, 9H) 2.71-2.82 (m, 1H) 2.96 (s, 3H) 3.29 (s, 3H) 4.17-4.33 (m, 2H) 4.50 (dd, J=7.15, 3.85 Hz, 1H) 4.91 (s, 2H) 7.32 (d, J=8.24 Hz, 2H) 7.44-7.66 (m, 5H) 7.81 (d, J=8.79 Hz, 1H). LCMS 597, 599 [M+H].

66D

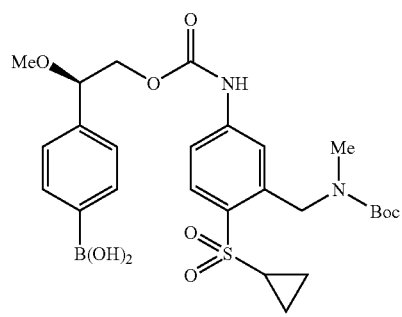 [SMILES: CO[C@@H](COC(=O)Nc1ccc(S(=O)(=O)C2CC2)c(CN(C)C(=O)OC(C)(C)C)c1)c1ccc(B(O)O)cc1]

Using a procedure analogous to that used to prepare 29B, 66C (2.0 g, 3.35 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 50% and preparative HPLC (CH$_3$CN/H$_2$O, 0.1% TFA) to give 66D (1.42 g, 75% yield) as a white solid. $^1$H NMR (400 MHz, methanol-d$_4$) δ ppm 1.04-1.09 (m, 2H) 1.16-1.23 (m, 2H) 1.46 (d, J=53.61 Hz, 9H) 2.78 (s, 1H) 2.96 (s, 3H) 3.29 (s, 3H) 4.19-4.32 (m, 2H) 4.53 (dd, J=7.47, 3.95 Hz, 1H) 7.39 (d, J=7.47 Hz, 2H) 7.46-7.59 (m, 2H) 7.65 (d, J=7.47 Hz, 2H) 7.80 (d, J=8.35 Hz, 1H).

66E

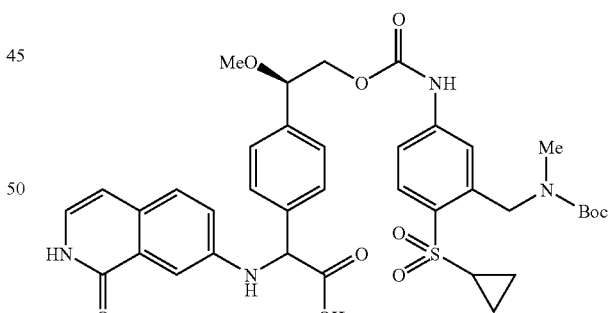

Using a procedure analogous to that used to prepare 1E, 66D (300 mg, 0.533 mmol), Intermediate 3, and glyoxylic acid monohydrate were reacted and purified by flash chromatography (0% to 20% MeOH in CH$_2$Cl$_2$) to yield 66E (120 mg, 31%) as a yellow solid. $^1$H NMR (400 MHz, methanol-d$_4$) δ ppm 1.02-1.10 (m, 2H) 1.16-1.21 (m, 2H) 1.33-1.59 (m, 9H) 2.77 (s, 1H) 2.95 (s, 3H) 3.27 (d, J=3.08 Hz, 3H) 4.17-4.24 (m, 1H) 4.24-4.34 (m, 1H) 4.52 (dd, J=7.25, 4.17 Hz, 1H) 4.90 (s, 2H) 5.23 (s, 1H) 6.54 (d, J=7.03 Hz, 1H) 6.90 (d, J=7.03 Hz, 1H) 7.22 (dd, J=8.57, 2.42 Hz, 1H) 7.31 (t, J=2.64

Hz, 1H) 7.38-7.45 (m, 3H) 7.52-7.65 (m, 2H) 7.62 (d, J=8.35 Hz, 2H) 7.80 (d, J=8.79 Hz, 1H). LCMS 735 [M+H].

66F

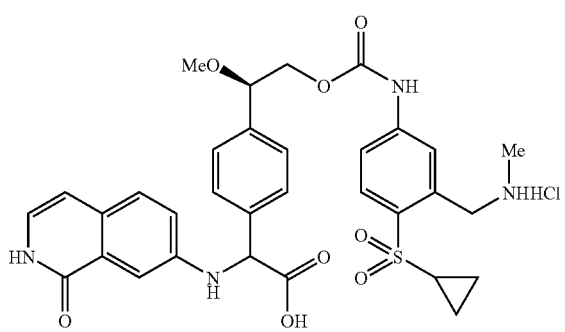

In a 100 mL round-bottomed flask was 66E (120 mg, 0.163 mmol) in mL of EtOAc, 4N HCl in dioxane (11.04 mL, 44.2 mmol) was added. The mixture was stirred at room temperature for 1 h. Solvent was removed and dried under vacuum overnight to a yellow solid of 66F (105 mg, 92%). LCMS 635[M+H].

66G

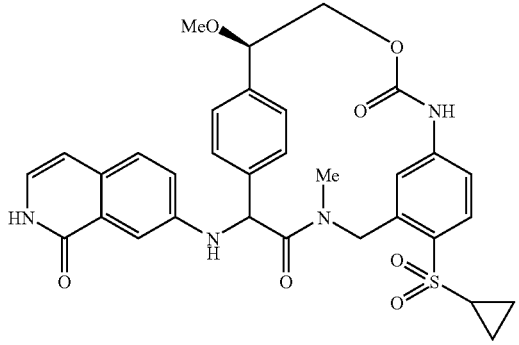

To a solution of BOP (0.145 g, 0.328 mmol) and DMAP (0.080 g, 0.656 mmol) in CH$_2$Cl$_2$ (50 mL) and DMF (3 ml) at 40° C. was added a solution of 66F (0.11 g, 0.164 mmol) and DIEA (0.057 mL, 0.328 mmol) in DMF (5.0 mL) via a syringe pump over 5.0 h and the reaction mixture was continued at 40° C. for 30 min. Solvent was removed, the residue was dissolved in CH$_3$CN/H$_2$O (9:1) and purified by prep HPLC using AXIA column (2 injection) eluting with 90% water to 20% water in acetonitrile with 0.1% TFA in 12 min. 66G was obtained as a mixture of two diastereomers. LCMS 617 [M+H].

Example 66

66G was dissolved in 12 mL of 60% MeOH/EtOH (1:1)/ 20% heptane and was purified using a preparative HPLC equipped with a Whelko-01 column. The separations were performed using an isocratic method of 60% 1:1 ethanol/ methanol: heptane for 40 min with a flow rate of 20 mL/min. The fractions of the second peak (RT=15.67 min, 8.5 mg, 9.4% yield) were combined to give Example 66: $^1$H NMR (400 MHz, methanol-d$_4$) δ ppm 0.90-1.09 (m, 2H) 1.18-1.38 (m, 2H) 2.77-2.94 (m, 1H) 3.34 (s, 3H) 3.39 (s, 3H) 4.06 (dd, J=10.33, 4.61 Hz, 1H) 4.19-4.39 (m, 2H) 4.56 (t, J=10.33 Hz, 1H) 5.62-5.81 (m, 2H) 6.46 (s, 1H) 6.55 (d, J=7.03 Hz, 1H) 6.84 (d, J=7.91 Hz, 1H) 6.92 (d, J=7.03 Hz, 1H) 7.10 (d, J=7.91 Hz, 1H) 7.19-7.28 (m, 2H) 7.38-7.47 (m, 2H) 7.62 (d, J=7.47 Hz, 1H) 7.71 (d, J=8.35 Hz, 1H) 7.90 (d, J=7.47 Hz, 1H). Chiral analytic HPLC: Column: Regis Whelk-01 (R,R), 250×4.6 mm ID; 10 μm, Mobile Phase: 60% (50/50 methanol-ethanol): 40% Heptane, UV Detection: 254 and 256 nm, Retention Time (min): 13.63 min. LCMS 617 [M+H]. Analytical HPLC (Method A): Col A: 7.32 min, 99%; Col B: 7.37 min, 99%.

Example 67

(2R,15R)-7-Cyclopropanesulfonyl-15-ethoxy-4-methyl-2-(1-oxo-1,2-dihydro-isoquinolin-7-ylamino)-13-oxa-4,11-diaza-tricyclo[14.2.2.1$^{6,10}$] henicosa-1(19),6,8,10(21),16(20),17-hexaene-3,12-dione

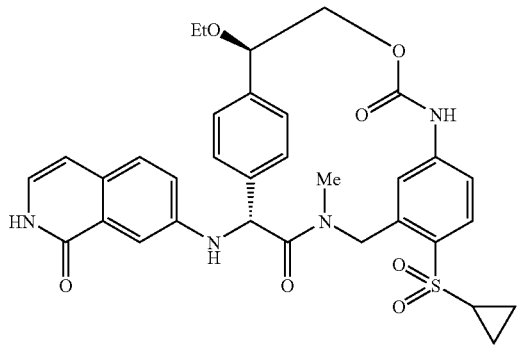

67A

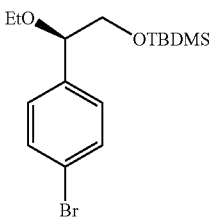 [SMILES: CCO[C@@H](CO[Si](C)(C)C(C)(C)C)c1ccc(Br)cc1]

39B (2.65 g, 8 mmol) and iodoethane (3.74 mL, 24.0 mmol) were dissolved in acetonitrile (40 mL) and potassium tert-butoxide (0.987 g, 8.80 mmol) was added and the mixture was stirred at rt over night. The reaction was quenched by 100 mL of saturated NH$_4$Cl and extracted by EtOAc (2×100 mL). The combined organic layers were dried with MgSO$_4$ and concentrated to an oil. The residue was dissolved in small amount of dichloromethane and added to a 40 g ISCO column and was eluted with 0-30% EtOAc/Hexanes for 40 min. 67A (2.0, 70% yield) was obtained as a colorless oil. $^1$H NMR (400 MHz, CDCl$_3$) δ ppm −0.06 (s, 3H) −0.03 (s, 3H) 0.83 (s, 9H) 1.17 (t, J=6.87 Hz, 3H) 3.38-3.45 (m, 2H) 3.57 (dd, J=10.44, 5.50 Hz, 1H) 3.77 (dd, J=10.72, 6.87 Hz, 1H) 4.25-4.29 (m, 1H) 719 (d, J=8.79 Hz, 2H) 7.44 (d, J=8.24 Hz, 2H).

67B

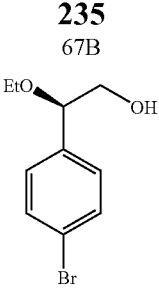

In a 250 mL pear flask was added 67A (2 g, 5.57 mmol) in acetonitrile (20 mL) to give a colorless solution. TBAF (18.53 mL, 18.53 mmol) was added. The mixture was stirred at rt for 2 h. TLC indicated the reaction was completed. The reaction was quenched by 50 mL of brine and extracted by EtOAc (2×100 mL). The combined organic layer was dried with MgSO$_4$ concentrated. The residue was dissolved in small amount of dichloromethane and added to a 40 g ISCO column and was eluted with 0-50% EtOAc/Hexanes for 40 min. 67B (0.95 g, 70% yield) was obtained as a clear oil. $^1$H NMR (400 MHz, methanol-d$_4$) δ ppm 1.18 (t, J=7.15 Hz, 3H) 3.42 (q, J=7.15 Hz, 2H) 3.50-3.56 (m, 1H) 3.58-3.66 (m, 1H) 4.34 (dd, J=7.15, 4.40 Hz, 1H) 7.25 (d, J=8.24 Hz, 2H) 7.50 (d, J=8.25 Hz, 2H).

67C

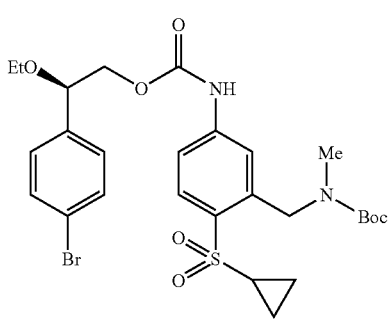 [SMILES: CCO[C@@H](COC(=O)Nc1ccc(S(=O)(=O)C2CC2)c(CN(C)C(=O)OC(C)(C)C)c1)c1ccc(Br)cc1]

Using a procedure analogous to that used to prepare 29A, Intermediate 11 was reacted with sodium bicarbonate and phosgene followed by 67B (0.518 g, 2.115 mmol) and TEA. The crude product was added to a silica gel column (40 g) and was eluted with EtOAc/hexanes (2-40% in 15 min) to give 67C (1.0 g, 93%) was obtained as a foam solid. $^1$H NMR (400 MHz, methanol-d$_4$) δ ppm 1.02-1.10 (m, 2H) 1.18 (t, J=7.03 Hz, 5H) 1.45 (d, J=54.05 Hz, 9H) 2.79 (s, 1H) 2.96 (s, 3H) 3.45 (q, J=6.88 Hz, 2H) 4.14-4.35 (m, 2H) 4.61 (dd, J=7.03, 4.39 Hz, 1H) 7.33 (d, J=8.35 Hz, 2H) 7.44-7.68 (m, 4H) 7.81 (d, J=8.79 Hz, 1H). LCMS 611, 613 [M+H].

67D

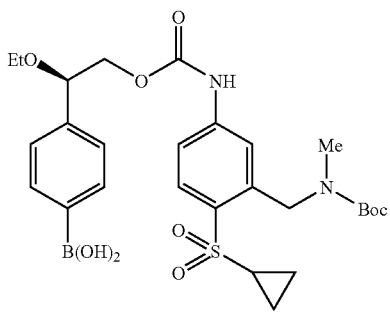 [SMILES: CCO[C@@H](COC(=O)Nc1ccc(S(=O)(=O)C2CC2)c(CN(C)C(=O)OC(C)(C)C)c1)c1ccc(B(O)O)cc1]

Using a procedure analogous to that used to prepare 29B, 67C (1 g, 1.635 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 50% and preparative HPLC (CH$_3$CN/H$_2$O, 0.1% TFA) to give 67D (0.7 g, 74% yield) as a white solid. $^1$H NMR (400 MHz, methanol-d$_4$) δ ppm 0.99-1.13 (m, 2H) 1.19 (q, J=7.15 Hz, 5H) 1.35-1.63 (m, 9H) 2.70-2.83 (m, 1H) 2.96 (s, 3H) 3.11-3.27 (m, 1H) 4.17-4.34 (m, 2H) 4.63 (dd, J=7.42, 4.12 Hz, 1H) 4.91 (s, 1H) 7.40 (d, J=7.70 Hz, 2H) 7.45-7.60 (m, 2H) 7.63 (d, J=7.70 Hz, 2H) 7.80 (d, J=8.79 Hz, 1H).

67E

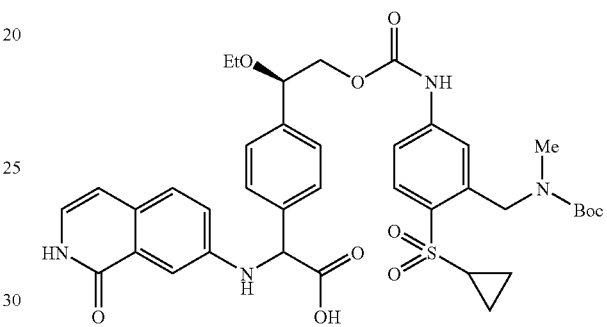

Using a procedure analogous to that used to prepare 1E, 67D (300 mg, 0.520 mmol), Intermediate 3, and glyoxylic acid monohydrate were reacted and purified by flash chromatography (0% to 20% MeOH in CH$_2$Cl$_2$) to yield 67E (200 mg, 51%) as a yellow solid. $^1$H NMR (400 MHz, methanol-d$_4$) δ ppm 1.02-1.10 (m, 2H) 1.13-1.21 (m, 5H) 1.28-1.59 (m, 9H) 2.76 (d, J=7.70 Hz, 1H) 2.95 (s, 3H) 3.40-3.54 (m, 2H) 4.16-4.36 (m, 2H) 4.63 (dd, J=6.60, 4.40 Hz, 1H) 5.22 (s, 1H) 6.54 (d, J=7.15 Hz, 1H) 6.90 (d, J=7.15 Hz, 1H) 7.21 (dd, J=8.79, 2.20 Hz, 1H) 7.32 (d, J=2.75 Hz, 1H) 7.38-7.44 (m, 2H) 7.48-7.66 (m, 2H) 7.60 (d, J=8.25 Hz, 2H) 7.80 (d, J=8.24 Hz, 1H). LCMS 749 [M+H].

67F

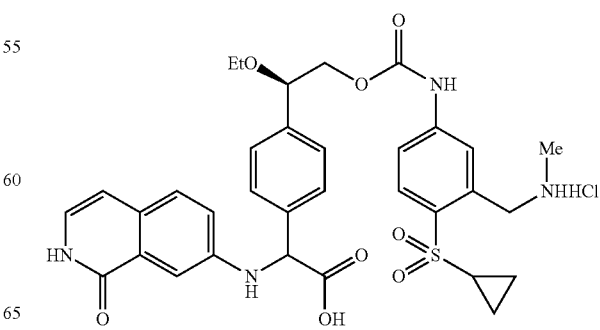

In a 100 mL round-bottomed flask was added 67E (200 mg, 0.267 mmol) in 5 ml of EtOAc, 4N HCl in dioxane (5.340 ml, 21.36 mmol) was added. The mixture was stirred at rt for 1 h. Solvent was removed and dried under vacuum overnight to a yellow solid of 67F (180 mg, 98%). $^1$H NMR (400 MHz, methanol-d$_4$) δ ppm 1.07-1.13 (m, 2H) 1.16 (t, J=6.87 Hz, 3H) 1.23-1.29 (m, 2H) 2.78 (s, 3H) 2.83-2.91 (m, 1H) 3.44 (q, J=6.96 Hz, 1H) 4.19-4.28 (m, 1H) 4.27-4.36 (min, 1H) 4.48 (s, 2H) 4.64 (dd, J=7.15, 3.85 Hz, 1H) 5.29 (s, 1H) 6.60 (d, J=7.15 Hz, 1H) 6.99 (d, J=7.15 Hz, 1H) 7.30-7.35 (m, 1H) 7.39-7.45 (m, 3H) 7.50 (d, J=8.79 Hz, 1H) 7.58 (d, J=8.25 Hz, 2H) 7.64 (d, J=8.79 Hz, 1H) 7.91 (d, J=8.79 Hz, 1H) 7.94 (s, 1H). LCMS 649[M+H].

67G

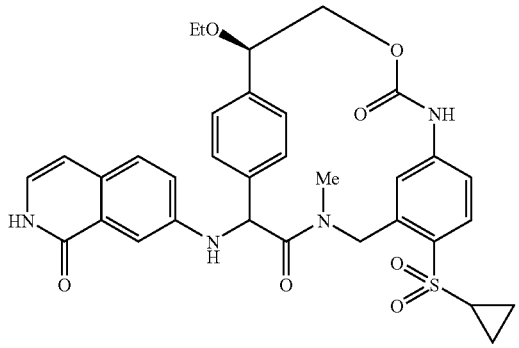

To a solution of BOP (0.232 g, 0.525 mmol) and DMAP (0.128 g, 1.051 mmol) in dichloromethane (50 mL) and DMF (3 mL) at 40° C. was added a solution of 67F (0.18 g, 0.263 mmol) and DIEA (0.092 mL, 0.525 mmol) in DMF (5.0 mL) via a syringe pump over 5.0 h and the reaction mixture was continued at 40° C. for 30 min. Solvent was removed, the residue was dissolved in CH$_3$CN/H$_2$O (9:1) and purified by prep HPLC using AXIA column (2 injection) eluting with 90% water to 20% water in acetonitrile with 0.1% TFA in 12 min to give 67G as a mixture of two diastereoisomrs. LCMS 631 [M+H].

Example 67

67 G was dissolved in 20 mL of 60% MeOH/EtOH (1:1)/ 20% heptane and was purified using a preparative HPLC equipped with a Whelko-01 column. The separations were performed using an isocratic method of 60% 1:1 ethanol/methanol: heptane for 40 min with a flow rate of 20 mL/min. The fractions of the second peak (RT=14.55 min, 6 mg, 7% yield) were combined to give Example 67: $^1$H NMR (400 MHz, methanol-d$_4$) δ ppm 0.87-1.09 (m, 3H) 1.21 (t, J=6.87 Hz, 3H) 1.26-1.39 (m, 1H) 2.80-2.90 (m, 1H) 3.39-3.63 (m, 2H) 4.04 (dd, J=10.17, 4.67 Hz, 1H) 4.27 (d, J=17.59 Hz, 1H) 4.42 (dd, J=10.17, 4.67 Hz, 1H) 4.57 (t, J=10.17 Hz, 1H) 5.70 (s, 1H) 5.75 (d, J=17.59 Hz, 1H) 6.46 (s, 1H) 6.55 (d, J=7.15 Hz, 1H) 6.79-6.89 (m, 1H) 6.92 (d, J=7.15 Hz, 1H) 7.09 (d, J=8.25 Hz, 1H) 7.16-7.30 (m, 2H) 7.35-7.49 (m, 2H) 7.64 (d, J=7.70 Hz, 1H) 7.71 (d, J=8.25 Hz, 1H) 7.89 (d, J=7.70 Hz, 1H) 9.48 (s, 1H). Chiral analytic HPLC: Column: Regis Whelk-011 (R,R), 250×4.6 mm ID; 10 μm, Mobile Phase: 60% (50/50 Methanol-Ethanol): 40% Heptane, UV Detection: 254 and 256 nm, Retention Time (min): 12.57 min.

Example 68

(2R,15R)-17-Methoxy-4,13,15-trimethyl-2-(1-oxo-1, 2-dihydro-isoquinolin-7-ylamino)-4,11,13-triaza-tricyclo[14.2.2.1$^{6,10}$]henicosa-1(19),6,8,10(21),16 (20),17-hexaene-3,12-dione

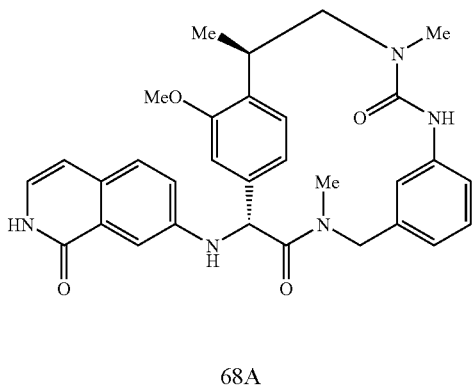

68A

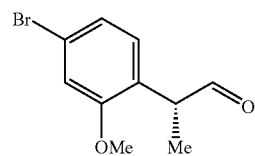 [SMILES: COc1cc(Br)ccc1[C@@H](C)C=O]

In a 25 mL pear flask was added Intermediate 9 (1 g, 4.08 mmol) and dichloromethane (10 mL) to give a colorless solution. Dess-Martin periodinane (1.903 g, 4.49 mmol) was added at rt and the mixture was stirred for 2 h, TLC indicated completion of the reaction. The mixture was filtrated and the filtrate was concentrated. The residue was dissolved in a small amount of dichloromethane and purified by a 40 g silica gel column eluted with 0-100% EtOAc/Hexanes for 40 min. 68A (0.97 g, 98% yield) was obtained as a colorless oil. $^1$H NMR (400 MHz, CDCl$_3$) δ ppm 1.36 (d, J=7.03 Hz, 3H) 3.73-3.87 (m, 4H) 6.96 (d, J=8.35 Hz, 1H) 7.03 (s, 1H) 7.10 (d, J=7.91 Hz, 1H) 9.62 (s, 1H).

68B

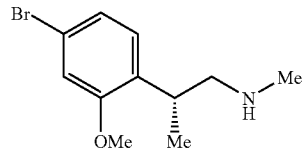 [SMILES: CNC[C@H](C)c1ccc(Br)cc1OC]

In a 25 mL pear flask was added 68A (970 mg, 3.99 mmol) in MeOH (10 mL) to give a colorless solution. 2N methylamine (2.99 mL, 5.99 mmol) was added and the mixture was stirred at rt for 1 h. Sodium borohydride (302 mg, 7.98 mmol) was added at 0° C. and warmed up to rt in 1 h. The reaction was quenched by 50 ml of sat. NaHCO$_3$ then extracted by EtOAc (3×50 mL). The organic layer was dried with MgSO$_4$ and concentrated to give 68B as an oil. $^1$H NMR (400 MHz, CDCl$_3$) δ ppm 1.18 (d, J=7.03 Hz, 3H) 2.37 (s, 3H) 2.62-2.69 (m, 1H) 2.71-2.79 (m, 1H) 3.33-3.40 (m, 1H) 3.46 (s, 3H) 3.79 (s, 3H) 6.96 (d, J=1.76 Hz, 1H) 7.00-7.03 (m, 1H) 7.03-7.07 (m, 1H). LCMS 258, 260 [M+H].

68C

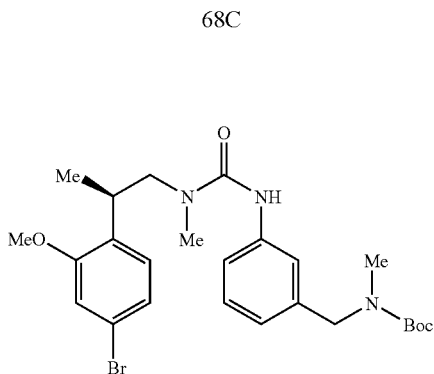

Using a procedure analogous to that used to prepare 29A, tert-butyl 3-aminobenzyl(methyl)carbamate (1.007 g, 4.26 mmol) was reacted with sodium bicarbonate and phosgene followed by 68B (1 g, 3.87 mmol) and TEA. The crude product was added to a silica gel column (120 g) and was eluted with EtOAc/hexanes (0-100% in 40 min) to give 68C (1.5 g, 74%) was obtained as a foam solid. $^1$H NMR (400 MHz, CDCl$_3$) δ ppm 1.32 (d, J=6.15 Hz, 3H) 1.45 (s, 9H) 2.79 (d, J=17.58 Hz, 3H) 2.97 (s, 3H) 3.09-3.31 (m, 1H) 3.44-3.60 (m, 2H) 4.38 (s, 2H) 6.59 (s, 1H) 6.88 (s, 1H) 7.01 (s, 1H) 7.10 (s, 2H) 7.12-7.24 (m, 2H). LCMS 520, 522 [M+H].

68D

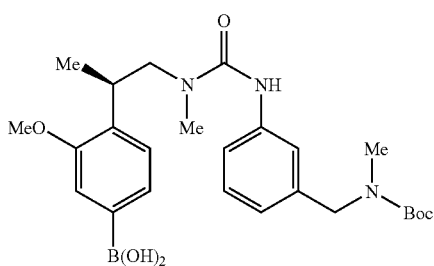 [SMILES: COc1cc(B(O)O)ccc1[C@@H](C)CN(C)C(=O)Nc1cccc(CN(C)C(=O)OC(C)(C)C)c1]

Using a procedure analogous to that used to prepare 29B, 68C (1 g, 1.635 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 50% and preparative HPLC (CH$_3$CN/H$_2$O, 0.1% TFA) to give 68D (1 g, 72% yield) as a white solid. $^1$H NMR (400 MHz, methanol-d$_4$) δ ppm 1.23-1.29 (m, 3H) 1.48 (d, J=9.67 Hz, 9H) 2.82 (s, 3H) 2.86 (s, 3H) 3.40-3.52 (m, 1H) 3.54-3.69 (m, 2H) 3.79-3.87 (m, 3H) 4.39 (s, 2H) 6.88 (d, J=6.59 Hz, 1H) 7.11-7.30 (m, 6H).

68E

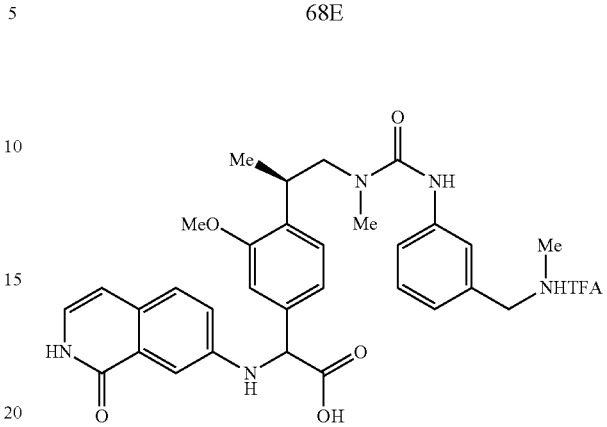

Using a procedure analogous to that used to prepare 1E, 68D (300 mg, 0.515 mmol), Intermediate 3, and glyoxylic acid monohydrate were reacted and purified by prep HPLC to yield 68E (100 mg, 30%) as a yellow solid. $^1$H NMR (400 MHz, methanol-d$_4$) δ ppm 1.24 (d, J=6.59 Hz, 3H) 2.67-2.83 (m, 6H) 3.33-3.53 (m, 1H) 3.55-3.68 (m, 2H) 3.79-3.86 (m, 3H) 4.11 (s, 2H) 5.17 (t, J=4.61 Hz, 1H) 6.50-6.59 (m, 1H) 6.85-6.96 (m, 1H) 7.05-7.21 (m, 3H) 7.20-7.35 (m, 5H) 7.40-7.53 (m, 2H). LCMS 558 [M+H].

68F

[Structure of 68F]

To a solution of BOP (132 mg, 0.298 mmol) and DMAP (72.8 mg, 0.596 mmol) in dichloromethane (50 mL) and DMF (3 mL) at 40° C. was added a solution of 68E (100 mg, 0.149 mmol) and DIEA (0.052 mL, 0.298 mmol) in DMF (5.0 mL) via a syringe pump over 14 h and the reaction mixture was continued at rt for 4 h. Solvent was removed, the residue was dissolved in CH$_3$CN/H$_2$O (9:1) and purified by prep HPLC using AXIA column (2 injections) eluting with 90% water to 30% water in Acetonitrile with 0.1% TFA in 12 min. to give 68F as a mixture of two diastereomers. LCMS 539 [M+H].

Example 68

68F was dissolved in 20 mL of 40% MeOH/EtOH (1:1)/20% heptane and was purified using a preparative HPLC equipped with a Whelko-01 column. The separations were performed using an isocratic method of 40% 1:1 ethanol/methanol: heptane for 40 min with a flow rate of 20 mL/min.

The fractions of the second peak (RT=16.17 min, 13 mg, 16% yield) were combined to give Example 68: $^1$H NMR (400 MHz, methanol-$d_4$) δ ppm 1.24-1.31 (m, 3H) 2.88-3.03 (m, 1H) 3.04 (s, 3H) 3.25 (s, 3H) 3.64-3.76 (m, 4H) 3.79-4.00 (m, 2H) 5.51 (d, J=16.26 Hz, 1H) 5.66 (s, 1H) 6.51-6.59 (m, 1H) 6.76-6.86 (m, 2H) 6.87-6.95 (m, 1H) 7.06 (s, 1H) 7.10-7.20 (m, 1H) 7.22-7.30 (m, 1H) 7.36 (s, 2H) 7.38-7.47 (m, 3H). Chiral analytic HPLC: Column: Regis Whelk-Ol (R,R), 250× 4.6 mm ID; 10 μm, Mobile Phase: 60% (50/50 Methanol-Ethanol): 40% Heptane, UV Detection: 254 and 256 nm, Retention Time (min): 15.36 min. The first peak (RT=10.60 and 13.05 min, 19 mg, 24% yield) is the diastereoisomer of Example 68. Analytical HPLC (Method A): Col A: 6.04 min, 99%; Col B: 6.09 min, 99%.

Example 69

(2R,15R)-7-(3,5-Dimethyl-isoxazol-4-yl)-4,13,15,17-tetramethyl-2-(1-oxo-1,2-dihydro-isoquinolin-7-ylamino)-4,11,13-triaza-tricyclo[14.2.2.1$^{6,10}$]henicosa-1(19),6,8,10(21),16(20),17-hexaene-3,12-dione

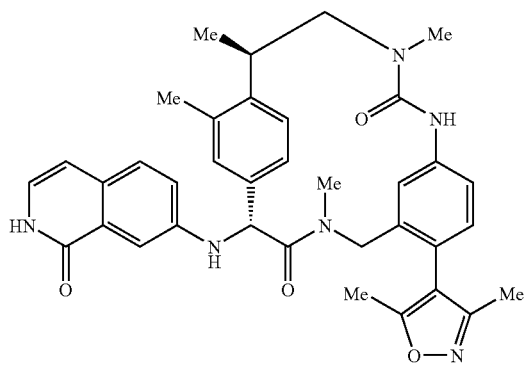 [SMILES: Cc1cc2ccc1[C@@H](C)CN(C)C(=O)Nc1ccc(-c3c(C)noc3C)c(c1)CN(C)C(=O)[C@@H]2Nc1ccc2cc[nH]c(=O)c2c1]

69A

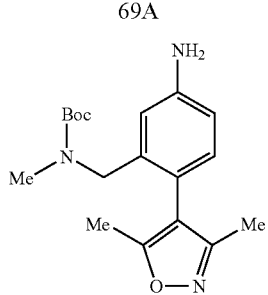

To a solution of 24A (1.2 g, 3.32 mmol) in THF (50 mL) was added 10% Pd/C (0.24 g). The mixture was stirred under H$_2$ balloon overnight. The Pd/C was filtrated and the filtration was concentrated to give 69A (1.1 g, 100% yield) as an oil.

69B

In a 25 mL pear flask was added Intermediate 8 (3.1 g, 13.53 mmol) in dichloromethane (50 mL) to give a colorless solution. Dess-Martin Periodinane (6.31 g, 14.88 mmol) was added at rt and the mixture was stirred for 2 h, TLC indicated the completion of the reaction. The mixture was filtrated and the filtrate was concentrated. The residue was dissolved in a small amount of dichloromethane and purified by a 120 g silica gel column eluted with 0-100% EtOAc/Hexanes for 40 min. 69B (2.9 g, 94% yield) was obtained as a colorless oil.

69C

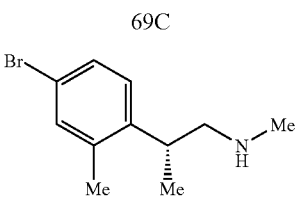

In a 25 mL flask was added 69B (2.9 g, 12.77 mmol) in EtOH (20 mL) to give a colorless solution. 2N methylamine in ethanol (2.385 mL, 19.15 mmol) was added and the mixture was stirred at rt for 1 h. Sodium borohydride (0.966 g, 25.5 mmol) was added at 0° C. and warmed up to rt in one h. The reaction was quenched by 100 mL of sat. NaHCO$_3$ then extracted by EtOAc (3×100 mL). The organic layer was dried by MgSO$_4$ and concentrated to give 69C as an oil. LCMS 242, 244 [M+H].

69D

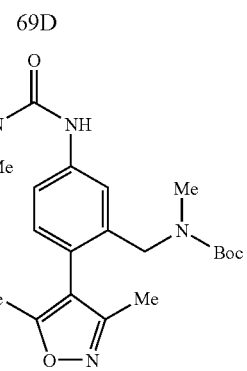

Using a procedure analogous to that used to prepare 29A, 69A (700 mg, 2.112 mmol) was reacted with sodium bicarbonate and phosgene followed by 69C (511 mg, 2.112 mmol) and TEA. The crude product was added to a silica gel column (40 g) and was eluted with EtOAc/hexanes (0-100% in 40 min) to give 69D (1.1 g, 87%) was obtained as a foam. LCMS 599, 601 [M+H].

69E

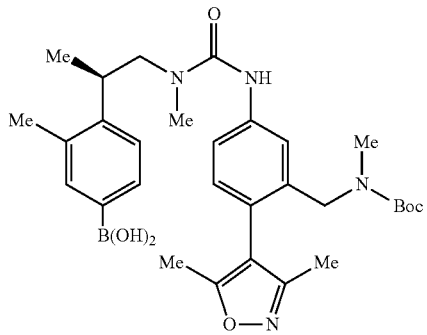 [SMILES: Cc1cc(B(O)O)ccc1[C@@H](C)CN(C)C(=O)Nc1ccc(-c2c(C)noc2C)c(CN(C)C(=O)OC(C)(C)C)c1]

Using a procedure analogous to that used to prepare 29B, 69D (1.1 g, 1.835 mmol) was reacted with bis(neopentyl glycolato)diboron), potassium acetate and (1,1-bis(diphenylphosphino)ferrocene)-dichloropalladium(II). The crude was purified by flash chromatography (EtOAc/hexanes 0% to 50% and preparative HPLC (CH₃CN/H₂O, 0.1% TFA) to give 69E (655 mg, 72% yield) as a white solid.

69F

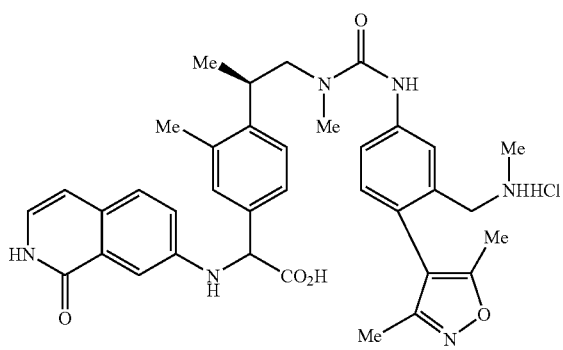

In a 2 mL microwave flask was added 69E (350 mg, 0.516 mmol), Intermediate 3 (91 mg, 0.567 mmol), and glyoxylic acid monohydrate (49.8 mg, 0.541 mmol) in DMF (0.25 mL) and acetonitrile (1 mL) to give a yellow suspension. The mixture was heated at 100° C. in a microwave reactor for 10 min. Solvent was removed and the residue was diluted by EtOAc and washed by H₂O and brine, dried with MgSO₄ and concentrated. The crude product was dissolved in 5 mL of EtOAc and treated with 4N HCl in dioxane (5.16 mL, 20.63 mmol) at rt for 2 h. Solvent was removed under vacuum to give 69F (240 mg, 69%) as a yellow solid. LCMS 637[M+H].

69G

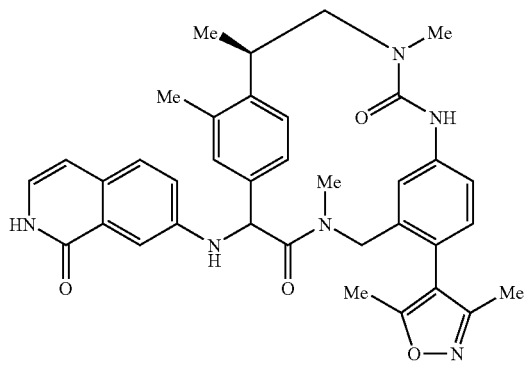 [SMILES: Cc1cc2ccc1[C@@H](C)CN(C)C(=O)Nc1ccc(-c3c(C)noc3C)c(c1)CN(C)C(=O)C2Nc1ccc2cc[nH]c(=O)c2c1]

To a solution of BOP (315 mg, 0.713 mmol) and DMAP (174 mg, 1.426 mmol)) in Dichloromethane (50 ml) and DMF (3 ml) at 40° C. was added a solution of 69F (240 mg, 0.357 mmol) and DIEA (0.125 ml, 0.713 mmol) in DMF (4.0 mL)) via a syringe pump over 10 h and the reaction mixture was continued at room temperature for 4 hours. Solvent was removed, the residue was dissolved in CH₃CN/H₂O (9:1) and purified by prep HPLC using AXIA column (4 injections) eluting with 90% water to 20% water in acetonitrile with 0.1% TFA in 12 min. to give 69G as a mixture of two diastereoisomers. LCMS 619 [M+H].

Example 69

69G was dissolved in 20 mL of 50% MeOH/EtOH (1:1)/20% heptane and was purified and separated using a preparative HPLC equipped with a Whelko-01 column. The separations were performed using an isocratic method of 50% 1:1 ethanol/methanol: heptane for 40 min with a flow rate of 20 mL/min. The fractions of the second peak (RT=13.5 min, 23 mg, 21% yield) were combined to give Example 69: $^1$H NMR (400 MHz, methanol-d₄) δ ppm 1.32 (d, J=7.03 Hz, 3H) 2.04 (s, 3H) 2.10 (s, 3H) 2.21 (s, 3H) 3.05 (s, 3H) 3.24-3.30 (m, 3H) 3.35-3.42 (m, 1H) 3.47 (t, J=16.70 Hz, 2H) 3.86-4.06 (m, 1H) 5.18 (dd, J=25.93, 16.70 Hz, 1H) 5.69 (s, 1H) 6.52 (d, J=7.03 Hz, 1H) 6.88 (d, J=6.59 Hz, 1H) 6.93-7.12 (m, 2H) 7.17-7.25 (m, 1H) 7.25-7.40 (m, 4H) 7.49 (d, J=7.47 Hz, 1H) 7.67 (d, J=6.15 Hz, 1H). Chiral analytic HPLC: Column: Regis Whelk-Ol (R,R), 250×4.6 mm ID; 10 μm, Mobile Phase: 50% (50/50 Methanol-Ethanol): 50% Heptane, UV Detection: 254 and 256 nm, Retention Time (min): 11.62 min. Analytical HPLC (Method A): Col A: 6.88 min, 98%; Col B: 6.91 min, 98%.

Example 70

(2R,15R)-4,13,15,17-Tetramethyl-2-(1-oxo-1,2-dihydro-isoquinolin-7-ylamino)-7-trifluoromethoxy-4,11,13-triaza-tricyclo[14.2.2.1$^{6,10}$]henicosa-1(19),6,8,10(21),16(20),17-hexaene-3,12-dione

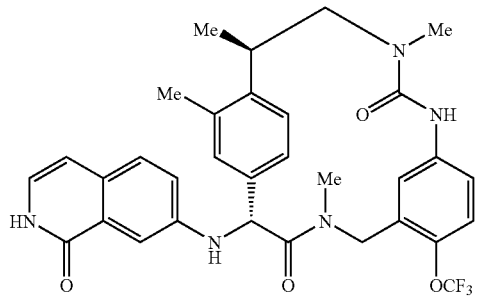 [SMILES: Cc1cc2ccc1[C@@H](C)CN(C)C(=O)Nc1ccc(OC(F)(F)F)c(c1)CN(C)C(=O)[C@@H]2Nc1ccc2cc[nH]c(=O)c2c1]

70A

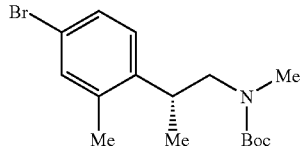 [SMILES: Cc1cc(Br)ccc1[C@@H](C)CN(C)C(=O)OC(C)(C)C]

In a 250 mL round-bottomed flask was added 69C (2.3 g, 9.50 mmol) in THF (30 mL) to give a colorless solution. Boc-anhydride in THF (14.25 mL, 14.25 mmol) and TEA (3.97 mL, 28.5 mmol) were added. The mixture was stirred at rt overnight. The reaction was quenched by H₂O and extracted by EtOAc, the organic layer was washed by brine and dried by MgSO₄ and concentrated. The residue was purified by a 120 g silica gel column eluted with 0-50% EtOAc/hexanes for 40 min. 70A (3.25 g, 100%) was obtained as a colorless oil. $^1$H NMR (400 MHz, CDCl₃) b ppm 1.17 (d, J=6.59 Hz, 3H) 1.39-1.45 (m, 9H) 2.29 (s, 3H) 2.66 (d, J=54.05 Hz, 3H) 2.99-3.65 (m, 3H) 7.04-7.15 (m, 1H) 7.26-7.32 (m, 2H).

70B

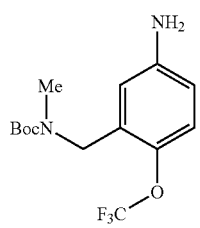

To Intermediate 14 (263 mg, 0.751 mmol) in MeOH (5.0 mL) was added 10% Pd/C (90 mg, 0.751 mmol). The mixture was hydrogenated with a hydrogen balloon for 3.0 h. Pd/C was removed by filtration. The filtrate was concentrated to give 70B (230 mg, 0.718 mmol, 96% yield) as a viscous oil. $^1$H NMR (400 MHz, methanol-$d_4$) δ ppm 1.40 and 1.51 (s, 9H) 2.80 and 2.85 (s, 3H) 4.42 (s, 2H) 6.58 (d, J=6.59 Hz, 1H) 6.65 (dd, J=8.79, 2.20 Hz, 1H) 7.01 (d, J=8.35 Hz, 1H). $^{19}$F NMR (376 MHz, methanol-$d_4$) d ppm −59.29 (s, 3F). LC-MS: (Phenom. Luna C18 30×4.6 mm 5 m; A: 10% MeCN −90% H$_2$O—10 mM NH4Ac; B: 90% MeCN −10% H$_2$O—10 mM NH4Ac; wavelength 220 nm; flow rate 5 mL/min; gradient time 4 min; 0 to 100% B. RT=2.79 min, [M+H]$^+$ =321.

70C

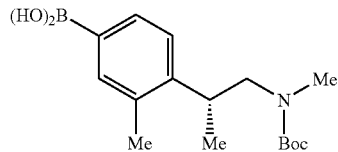 [SMILES: Cc1cc(B(O)O)ccc1[C@@H](C)CN(C)C(=O)OC(C)(C)C]

Using a procedure analogous to that used to prepare 29B, 70A (500 mg, 1.461 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 60% and preparative HPLC (CH$_3$CN/H$_2$O, 0.1% TFA) to give 7° C. (300 mg) as a white solid. $^1$H NMR (400 MHz, acetonitrile-$d_3$) b ppm 1.09-1.28 (m, 3H) 1.33-1.48 (m, 9H) 2.24-2.51 (m, 3H) 2.55-2.84 (m, 3H) 3.45 (dd, J=39.77, 7.69 Hz, 3H) 7.16-8.12 (m, 3H).

70D

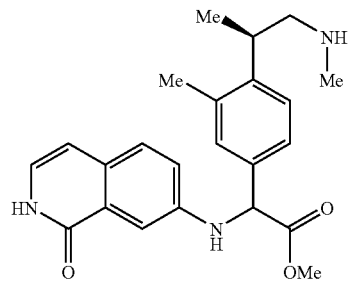 [SMILES: CNC[C@H](C)c1ccc(C(Nc2ccc3cc[nH]c(=O)c3c2)C(=O)OC)cc1C]

In a 2 mL microwave flask was added 70C (300 mg, 0.977 mmol), Intermediate 3 (172 mg, 1.074 mmol), and glyoxylic acid monohydrate (94 mg, 1.025 mmol) in DMF (0.25 mL) and acetonitrile (1 mL) to give a yellow suspension. The mixture was heated at 100° C. in a microwave reactor for 10 min. Then MeOH (1 mL) and trimethylsilyldiazomethane (0.586 mL, 1.172 mmol) were added to the mixture and stirred for 1 h. Solvent was removed and the residue was diluted by EtOAc and was shed by H$_2$O and brine, dried by MgSO$_4$ and concentrated. The crude product was dissolved in a small amount of dichloromethane and was purified by a 40 g silica gel column eluted with 0-100% EtOAc/Hexanes for 40 min. The desired fractions were treated with 4N HCl HCl (5.16 ml, 20.63 mmol) for 2 hours. Solvent was removed to give 70D (227 mg, 51%) as a yellow oil. $^1$H NMR (400 MHz, CDCl$_3$) 86 ppm 0.95 (d, J=7.03 Hz, 3H) 2.05 (d, J=13.18 Hz, 3H) 2.37 (s, 3H) 2.83-3.05 (m, 2H) 3.08-3.22 (m, 1H) 3.46 (s, 3H) 5.19 (s, 1H) 6.52 (d, J=7.03 Hz, 1H) 6.86-7.09 (m, 4H) 7.29-7.38 (m, 2H) 7.38-7.46 (m, 1H). LCMS 395 [M+H].

70E

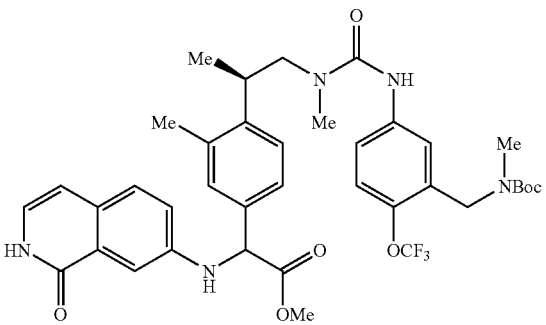

To a mixture of 70B (169 mg, 0.528 mmol) and sodium bicarbonate (222 mg, 2.64 mmol) in Dichloromethane (3 mL) was added phosgene (20% in toluene, 0.838 mL, 1.584 mmol) at 0° C. The mixture was stirred at 0° C. for 15 min, solvent and extra phosgene were removed and under vacuum for 15 min. The residue was resubmitted to dichloromethane (15 mL) and 70D (227 mg, 0.528 mmol) and triethylamine (0.368 mL, 2.64 mmol) was added at 0° C. and stirred for 15 min, then warmed up to rt and stirred for 15 min. LCMS indicated a clean reaction. The reaction mixture was diluted with EtOAc and washed with sat. NaHCO$_3$, and brine. The organic was dried by MgSO$_4$, filtrated and concentrated. The crude product was added to a 40 g silica gel column and was eluted with 0-100% EtOAc/Hexanes for 40 min. 70E (390 mg, 99% yield) was obtained as a foam. LCMS 740 [M+H].

70F

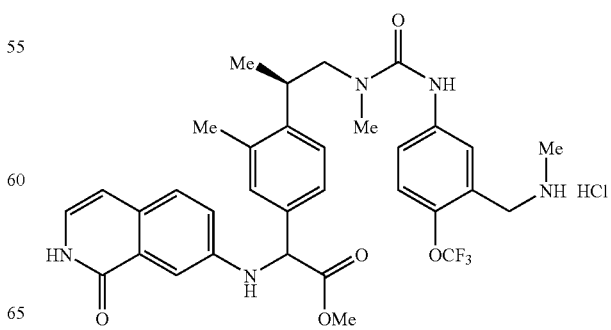

In a 50 mL pear flask was added 70E (390 mg, 0.50 mmol) in MeOH (6 mL) to give a yellow solution. LiOH (1.0 M, 1.5 mL, 1.5 mmol) was added. The mixture was stirred at rt for 1 h. LC MS showed the reaction was complete. The reaction mixture was diluted with EtOAc and quenched by 1N HCl, the aquous layer was extracted by EtOAc. The combined organic layer was washed by brine and dried with $MgSO_4$ and concentrated to a yellow oil. The residue was dissolved in 5 mL of EtOAc and HCl (5.0 mL, 20.00 mmol) was added, the mixture was stirred at rt for 1 h. The mixture was concentrated and dried over weekend under vacuum to give 70F (200 mg, 61%) as a yellow oil. $^1$H NMR (400 MHz, DMF-d) δ ppm 1.20 (d, J=6.59 Hz, 3H) 2.34 (s, 3H) 2.67 (s, 3H) 2.77 (q, J=5.27 Hz, 3H) 3.06-3.94 (m, 3H) 4.31 (d, J=5.27 Hz, 2H) 5.12-5.33 (m, 1H) 6.34-6.50 (m, 1H) 6.86-7.04 (m, 1H) 7.21-7.52 (m, 7H) 7.72-8.15 (m, 2H) 8.60-8.89 (m, 1H) 9.91-10.28 (m, 1H) 10.85-11.38 (m, 1H).

70G

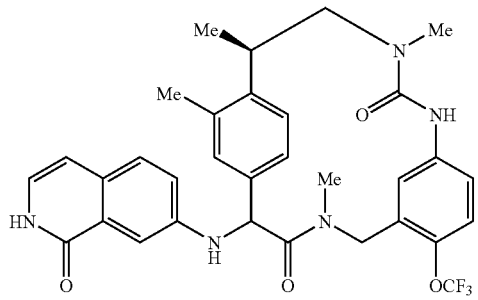

To a solution of BOP (283 mg, 0.639 mmol) and DMAP (156 mg, 1.279 mmol) in dichloromethane (50 mL) and DMF (3 mL) at 40° C. was added a solution of 70F (200 mg, 0.32 mmol) and DIEA (0.112 mL, 0.639 mmol) in DMF (4.0 mL)) via a syringe pump over 10 h and the reaction mixture was continue to stir at rt for 4 h. Solvent was removed, the residue was dissolved in $CH_3CN/H_2O$ (9:1) and purified by prep HPLC using AXIA column (4 injections) eluting with 90% water to 20% water in acetonitrile with 0.1% TFA in 12 min to give 70G as a mixture of two diastereoisomers. LCMS 608 [M+H].

Example 70

70G was dissolved in 20 mL of 50% MeOH/EtOH (1:1)/ 50% heptane and was purified using a preparative HPLC equipped with a Whelko-01 column. The separations were performed using an isocratic method of 50% 1:1 ethanol/methanol: heptane for 40 min with a flow rate of 20 mL/min. The fractions of the second peak (RT=15.0 min, 24 mg, 25% yield) were combined to give Example 70: $^1$H NMR (400 MHz, methanol-$d_4$) δ ppm 1.32 (d, J=7.03 Hz, 3H) 2.19 (s, 3H) 3.07 (s, 3H) 3.34 (s, 3H) 3.83-4.09 (m, J=17.14 Hz, 2H) 4.89 (s, 2H) 5.45 (d, J=17.14 Hz, 1H) 5.70 (s, 1H) 6.54 (d, J=7.03 Hz, 1H) 6.90 (d, J=6.59 Hz, 1H) 7.00 (d, 1H) 7.12 (d, J=8.35 Hz, 1H) 7.25 (d, J=8.35 Hz, 1H) 7.32 (s, 1H) 7.34-7.44 (m, 3H) 7.47 (d, J=7.91 Hz, 1H) 7.65 (d, J=7.03 Hz, 1H). Chiral analytic HPLC: Column: Regis Whelk-01 (R,R), 250× 4.6 mm ID; 10 μm, Mobile Phase: 50% (50/50 Methanol-Ethanol): 50% Heptane, UV Detection: 254 and 256 nm, Retention Time (min): 12.14 min. Analytical HPLC (Method A): Col A: 6.74 min, 99%; Col B: 6.75 min, 99%.

Example 71

(2R,15R)-7-Cyclopropanesulfonyl-15-hydroxy-4-methyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

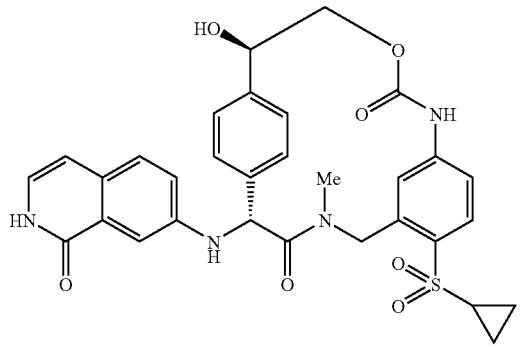

To acetonitrile (2.0 mL) and MeOH (2.0 mL) was added conc. HCl (60 μL) pH was check to be close to 1.0. To Example 39 (17.8 mg, 0.028 mmol) was added the above prepared solution (2.0 mL). The reaction was stirred at 65° C. for 30 min in a microwave reactor. The crude residue was purified using a preparative HPLC equipped with a C18 Phenomenex Luna AXIA column (30 mm×75 cm, 5μ with the UV detector set at 220 nm. The separations were performed using a gradient method: 10-65% B in 10 mins; then 90% B in 2 mins with a flow rate of 40 mL/min. Solvent B is 90% acetonitrile-10% water-0.1% TFA and solvent A is 10% acetonitrile-90% water-0.1% TFA. RT=6.1 min. The desired fractions were collected to give Example 71 (10 mg, 63% yield): $^1$H NMR (400 MHz, methanol-$d_4$) δ ppm 0.91-1.07 (m, 3H) 1.17-1.27 (m, 1H) 2.79-2.88 (m, 1H) 3.35 (s, 3H) 4.01 (dd, J=10.55, 4.83 Hz, 1H) 4.26 (d, J=17.58 Hz, 1H) 4.53 (t, J=10.33 Hz, 1H) 4.69 (dd, J=10.11, 4.83 Hz, 1H) 5.70-5.78 (m, 2H) 6.45 (s, 1H) 6.54 (d, J=7.03 Hz, 1H) 6.84 (dd, J=8.35, 2.20 Hz, 1H) 6.93 (d, J=7.03 Hz, 1H) 7.04 (d, J=7.03 Hz, 1H) 7.18-7.27 (m, 2H) 7.42 (d, J=8.79 Hz, 1H) 7.49 (s, 1H) 7.69-7.74 (m, 2H) 7.84 (d, J=6.59 Hz, 1H). MS (ESI) m/z 603 (M+H)$^+$. Analytical HPLC (Method A): Col A: 5.48 min, 93%; Col B: 5.38 min, 93%.

Example 72

(R)-7-Cyclopropanesulfonyl-4,17,20-trimethyl-2-(3-oxo-2,3-dihydro-1H-isoindol-5-ylamino)-4,11-diaza-tricyclo[14.2.2.1$^{6,10}$]henicosa-1(19),6,8,10(21),16(20),17-hexaene-3,12-dione trifluoroacetate

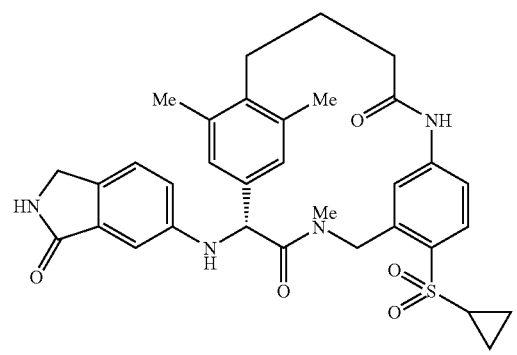 [SMILES: Cc1cc2cc(C)c1CCCC(=O)Nc1ccc(S(=O)(=O)C3CC3)c(c1)CN(C)C(=O)[C@@H]2Nc1ccc2c(c1)C(=O)NC2]

72A

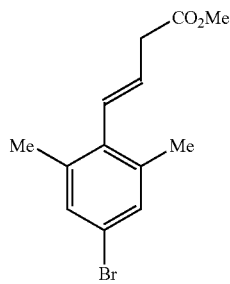 [SMILES: COC(=O)C/C=C/c1c(C)cc(Br)cc1C]

A mixture of 5-bromo-2-iodo-1,3-dimethylbenzene (2.500 g, 8.04 mmol), methyl 3-butenoate (1.714 mL, 16.08 mmol), Tri-o-tolylphosphine (0.367 g, 1.206 mmol), palladium(II) acetate (0.090 g, 0.402 mmol), DIEA (1.755 mL, 10.05 mmol) in MeCN (15 mL) was degassed (3×, Ar) and heated at 110° C. in a microwave reactor for 10 min. The reaction was diluted with EtOAc and filtered through a membrane filter, then the solvent was removed under reduced pressure. The residue was dissolved in EtOAc (100 mL), washed with NaHCO$_3$ (aq.), water (2×), brine (1×) and dried (Na$_2$SO$_4$). The reaction sequence was repeated twice. EtOAc was removed under reduced pressure and the residue was purified by flash chromatography: (120 g) 0-15% EtOAc/hex. The product eluted at ~9% EtOAc as two overlapping peaks corresponding to both isomers. Fractions were combined and concentrated under reduced pressure to give 72A (0.752 g, 2.66 mmol, 66.1% yield) as a mixture (~4:1 by NMR) of alkene isomers as a yellow oil. MS (ESI) m/z 283.0 (M+H)$_j$.

72B

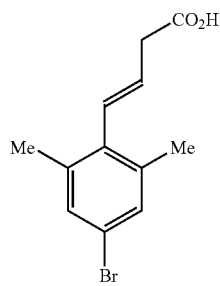 [SMILES: Cc1cc(Br)cc(C)c1/C=C/CC(=O)O]

To a solution of 72A (2.59 g, 9.15 mmol) in THF (30 mL), water (10 mL) and MeOH (5 mL), was added 1M aq. LiOH (15 mL, 15.00 mmol) to give a clear solution. The mixture was stirred at rt for 4 h. The volatiles were evaporated and water (50 mL) was added. The solution was washed with Et$_2$O. The aqueous phase was acidified with 1N HCl, then was extracted with EtOAc (2×). The combined organic extract was washed with brine, dried (Na$_2$SO$_4$) and concentrated to afford 72B (2.38 g, 8.84 mmol, 97% yield) as an off-white solid (mixture of alkene isomers). MS (ESI) m/z 269.0 (M+H)$^+$. (~1:3 mixture of alkene isomers)

72C

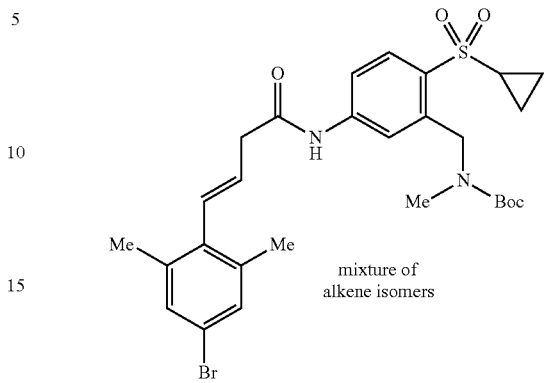

mixture of alkene isomers

To a solution of 72B (0.500 g, 1.857 mmol) in DCM (10 mL) at rt was added oxalyl chloride (0.195 mL, 2.229 mmol), followed by 2 drops of DMF. The mixture was stirred at rt for 1 h, then concentrated. The residue was co-evaporated with toluene. To a solution of Intermediate 11 (0.569 g, 1.671 mmol) in DCM (6 mL) and pyridine (2 mL) at 0° C., was added DMAP (0.023 g, 0.186 mmol) and a solution of the acid chloride prepared above in 2 mL DCM. The reaction was stirred min at 0° C., then diluted with EtOAc and washed with H$_2$O (2×), 1N HCl and brine, dried (Na$_2$SO$_4$) and concentrated. The crude product was dissolved in chloroform, loaded onto a 40 g column and eluted with a gradient from 0 to 100% ethyl acetate/hexanes to afford 72C (981 mg, 1.658 mmol, 99% yield) as a colorless solid, a mixture of alkene isomers. MS (ESI) m/z 591.1 (M+H)$^+$.

72D

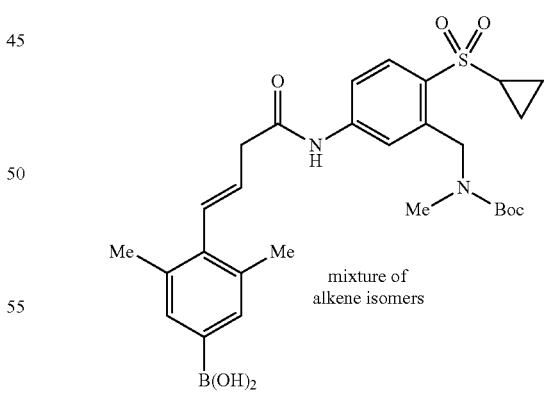

mixture of alkene isomers

Using a procedure analogous to that used to prepare 29B, 72C (980 mg, 1.657 mmol) was reacted with bis(neopentyl glycolato)diboron), potassium acetate and (1,1'-bis(diphenylphosphino)ferrocene)-dichloropalladium(11). The crude was purified by flash chromatography and preparative HPLC (CH₃CN/H₂O, 0.1% TFA) to afford 72D (619 mg, 1.112 mmol, 67.1% yield) as a pale yellow solid. MS (ESI) m/z 557.3 (M+H)⁺.

72E

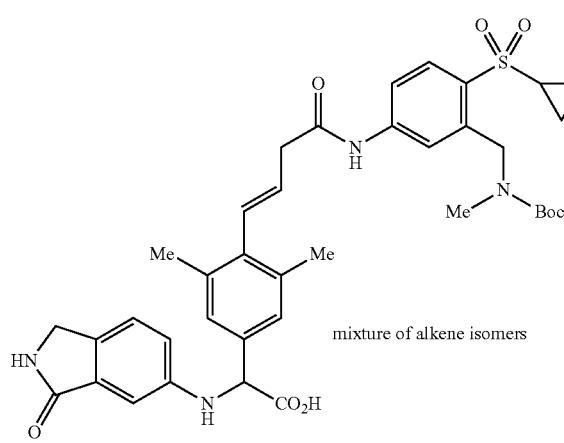

mixture of alkene isomers

Using a procedure analogous to that used to prepare IE, 72D (300 mg, 0.539 mmol), Intermediate 2, and glyoxylic acid monohydrate were reacted (two batches on this scale) and purified by flash chromatography (1% to 20% MeOH in CH₂Cl₂) to afford 72E (440 mg, 56.9% yield, average yield based upon 2 combined batches) as a yellow solid. MS (ESI) m/z 717.2 (M+H)⁺.

72F

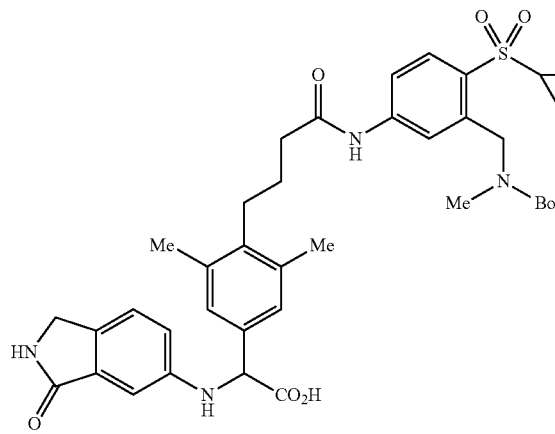

To a solution of 72E (440 mg, 0.614 mmol) in methanol (10 mL), 10% Pd/C (50 mg, 0.047 mmol) was added. The mixture was stirred under H₂ (60 psi) for 28 h, then was filtered and concentrated to afford 72F (368 mg, 0.512 mmol, 83% yield) as an off-white solid. MS (ESI) m/z 719.2 (M+H)⁺.

72G

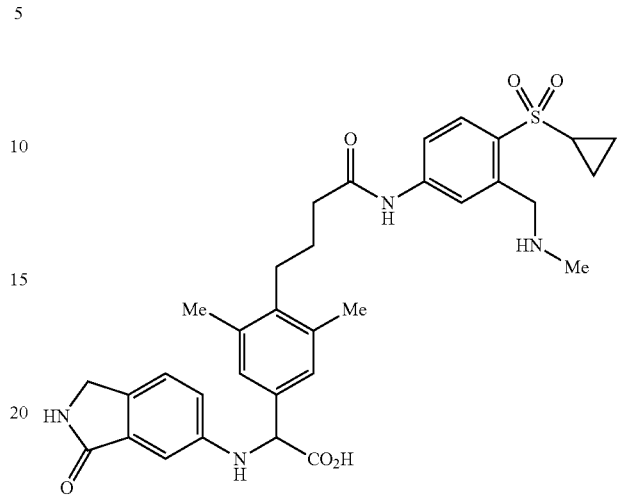

To a suspension of 72F (360 mg, 0.501 mmol) in ethyl acetate (10 mL), was added 4N HCl in dioxane (10.00 mL, 329 mmol). The mixture was stirred for 1 h, then was concentrated. The product was coevaporated with CH₃CN (2×) and toluene (1×) to afford 72G (370 mg, 0.503 mmol, 100% yield) as a colorless solid. MS (ESI) m/z 619.2 (M+H)⁺. ¹H NMR (400 MHz, CD₃OD) δ ppm 8.17 (d, J=2.20 Hz, 1H) 7.96 (d, J=8.79 Hz, 1H) 7.76-7.83 (m, 2H) 7.48-7.51 (m, J=8.79 Hz, 1H) 7.28-7.32 (m, 2H) 7.09-7.13 (m, 2H) 5.21 (s, 1H) 4.51 (s, 2H) 4.47-4.55 (m, 1H) 4.39 (s, 2H) 2.86-2.92 (m, 1H) 2.80 (s, 3H) 2.69-2.75 (m, 2H) 2.56 (t, J=7.25 Hz, 2H) 2.33 (s, 6H) 1.84 (dd, J=9.01, 6.37 Hz, 2H) 1.23-1.29 (m, 2H) 1.08-1.16 (m, 2H).

72H

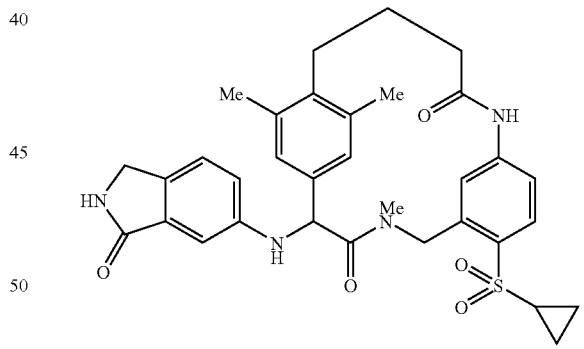

To a solution of BOP (221 mg, 0.500 mmol) and DMAP (153 mg, 1.251 mmol) in DCM (50 mL) and DMF (5 mL) at 40° C., was added a solution of 72G (173 mg, 0.250 mmol) and DIEA (0.087 mL, 0.500 mmol) in DMF (5 mL), dropwise via a syringe pump over 5 h. The mixture was stirred 30 min, then 2 mL H₂O was added and the mixture was concentrated. The crude product was purified by prep HPLC: Phenomenex Luna 5 μm C18 30X250 (0% to 70% B, 20 min grad, 30 mL/min); solvent A=10% CH₃CN/90% H₂O/0.1% TFA; solvent B=90% CH₃CN/10% H₂O/0.1% TFA. The resultant product was suspended in 2 mL MeOH, then heated and sonicated. The precipitate was allowed to settle, the methanol was decanted and the solid was dried in vacuo to afford 72H (36 mg, 0.050 mmol, 20.14% yield) as a white solid. MS (ESI) m/z 601.2 (M+H)⁺. ¹H NMR (400 MHz, D₆-DMSO) δ ppm 9.94 (s, 1H) 8.31 (s, 1H) 7.68 (d, J=8.25 Hz, 1H) 7.36 (s, 1H) 7.19 (d, J=8.25 Hz, 1H) 7.01 (d, J=8.24 Hz, 1H) 6.94 (s, 1H) 6.84 (d, J=8.79 Hz, 1H) 6.72 (s, 1H) 6.38 (s, 1H) 5.56-5.68 (m, 2H) 4.09-4.20 (m, 3H) 2.93-3.02 (m, 1H) 2.78 (d, J=10.99 Hz, 1H) 2.67 (t, J=11.27 Hz, 1H) 2.40 (s, 3H) 2.25-2.37 (m, 3H) 2.19 (s, 3H) 1.81-1.92 (m, 1H) 1.01-1.12 (m, 3H). A second batch of starting material (173 mg, 0.250 mmol) produced additional 72H (47 mg, 0.066 mmol, 26.3% yield), that was identical to the material prepared above.

Example 72

Racemic 72H (81 mg) was dissolved in a small amount of DMSO, then was diluted with MeOH and 50% (MeOH/EtOH)/heptane. The solution was separated in 15 injections on a chiral column: (R,R-Whelko (21.1×250 mm); 50% (EtOH/MeOH 1:1) in heptane 20 mL/min; peak #1: RT=13 min (S-stereoisomer); peak #2: RT=16.0 min (R-stereoisomer)). The R-stereoisomer was repurified by preparative HPLC (Axia Luna 5 μm C18 30X100 (20% to 70% B, 10 min grad, 40 mL/min); solvent A=10% CH$_3$CN/90% H$_2$O/0.1% TFA; solvent B=90% CH$_3$CN/10% H$_2$O/0.1% TFA) to afford Example 72 (23.5 mg, 0.033 mmol, 58.0% yield) as a white powder. MS (ESI) m/z 601.2 (M+H)$^+$. Analytical HPLC (Method A): Col A: 9.29 min, 98%; Col B: 9.45 min, 98%.

Example 73

4-Methyl-2-(4-oxo-3,4-dihydro-quinazolin-6-ylamino)-7-(propane-2-sulfonyl)-4,11-diaza-tricyclo[14.2.2.1$^{6,10}$]henicosa-1(19),6,8,10(21),16(20),17-hexaene-3,12-dione trifluoroacetate

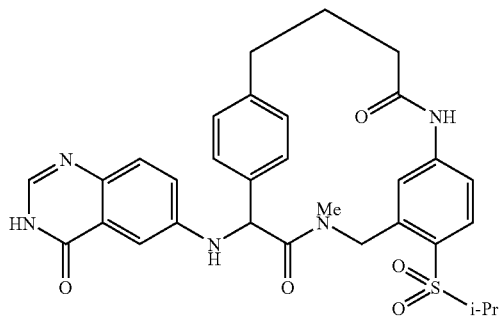

73A

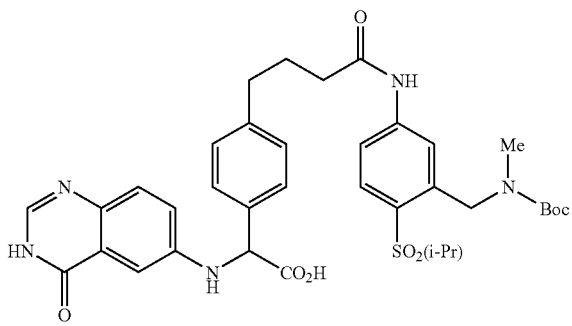

Using a procedure analogous to that used to prepare 1E, 3G (141 mg, 0.265 mmol), Intermediate 4, and glyoxylic acid monohydrate were reacted and purified by flash chromatography (1% to 20% MeOH in CH$_2$Cl$_2$) to afford 73A (150 mg, 0.213 mmol, 80% yield) as an off-white solid. A second batch of 3G (309 mg, 0.580 mmol), afforded additional 73A ((360 mg, 0.510 mmol, 88% yield). MS (ESI) m/z 706.2 (M+H)$^+$. $^1$H NMR (400 MHz, CD$_3$OD) δ ppm 7.81-7.86 (m, 2H) 7.65-7.77 (m, 2H) 7.47 (dd, J=8.52, 4.67 Hz, 3H) 7.29 (dd, J=8.79, 2.75 Hz, 1H) 7.21 (d, J=8.24 Hz, 2H) 7.16 (d, J=2.75 Hz, 1H) 5.12 (s, 1H) 4.82 (s, 2H) 2.96 (s, 3H) 2.67 (t, J=7.42 Hz, 2H) 2.39 (t, J=7.42 Hz, 2H) 1.98 (qd, J=7.51, 7.15 Hz, 2H) 1.48-1.38 (m, 9H) 1.22-1.28 (d, J=6.60 Hz, 6H).

73B

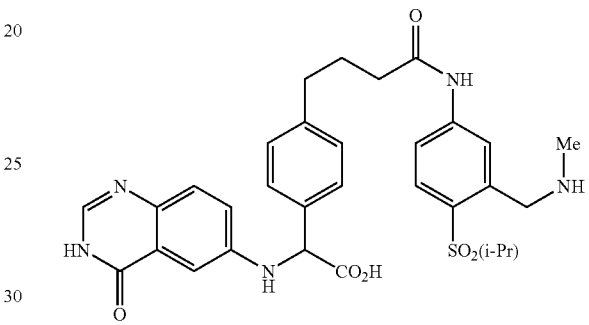

To a suspension of 73A (505 mg, 0.715 mmol) in dichloromethane (5 mL) and ethyl acetate (5 mL), was added 4N HCl in dioxane (10.00 mL, 329 mmol). The suspension was stirred at rt for 30 min, then was concentrated. The resultant solid was co-evaporated with toluene, then was dried o.n. under vacuum to afford 73B (478 mg, 0.704 mmol, 98% yield) as an off-white solid. MS (ESI) m/z 606.2 (M+H)$^+$. $^1$H NMR (400 MHz, CD$_3$OD) δ ppm 8.96 (s, 1H) 8.15 (d, J=2.20 Hz, 1H) 7.96 (d, J=8.79 Hz, 1H) 7.80 (dd, J=8.79, 2.20 Hz, 1H) 7.50-7.54 (m, 1H) 7.48 (d, J=8.25 Hz, 2H) 7.41-7.45 (m, 1H) 7.22-7.27 (m, 3H) 5.20 (s, 1H) 4.42 (s, 2H) 3.41 (dt, J=13.60, 6.66 Hz, 1H) 2.78 (s, 3H) 2.70 (t, =7.70 Hz, 2H) 2.46 (t, J=7.42 Hz, 2H) 1.96-2.05 (m, 2H) 1.28 (d, J=6.60 Hz, 6H).

Example 73

To a solution of BOP (130 mg, 0.295 mmol) and DMAP (90 mg, 0.737 mmol) in DCM (50 mL) and DMF (5 mL) at 40° C., was added a solution of 73B and DIEA (0.051 mL, 0.295 mmol) in DMF (5 mL), dropwise via a syringe pump over 5 h. The reaction mixture was stirred for 30 min, then 2 mL H$_2$O was added and the mixture was concentrated. The crude product was purified by prep HPLC: Column #1: (Phenomenex Luna 5 μm C18 30X250 (20% to 60% B, 20 min grad, 30 mL/min); solvent A=10% CH$_3$CN/90% H$_2$O/0.1% TFA; solvent B=90% CH$_3$CN/10% H$_2$O/0.1% TFA); Column #2: (Axia Luna 5 μm C18 30X100 (20% to 60% B, 10 min grad, 40 mL/min); solvent A=10% CH$_3$CN/90% H$_2$O/0.1% TFA; solvent B=90% CH$_3$CN/10% H$_2$O/0.1% TFA) Purification afforded Example 73 (13 mg, 0.019 mmol, 13% yield) as an off-white powder. MS (ES) m/z 588.2 (M+H)$^+$. $^1$H NMR (400 MHz, CD$_3$OD) δ ppm 8.64 (s, 1H) 7.77 (d, J=8.24 Hz, 1H) 7.72 (dd, J=7.97, 1.92 Hz, 1H) 7.43-7.49 (m, 1H) 7.35-7.41 (m, J=6.32, 2.75, 2.47 Hz, 2H) 7.32 (d, J=2.75 Hz, 1H) 7.09 (dd, J=7.97, 1.37 Hz, 1H) 6.97 (dd, J=7.97, 1.92

Hz, 1H) 6.91 (dd, J=8.24, 1.65 Hz, 1H) 6.58 (d, J=1.65 Hz, 1H) 5.68 (s, 1H) 5.62 (d, J=17.04 Hz, 1H) 4.12 (d, J=17.04 Hz, 1H) 3.61 (dt, J=13.60, 6.66 Hz, 1H) 3.42 (s, 3H) 2.93-3.01 (m, 1H) 2.38-2.55 (m, 3H) 2.29 (qd, J=10.90, 2.47 Hz, 1H) 1.98-2.09 (m, 1H) 1.34 (d, J=6.60 Hz, 3H) 1.21 (d, J=7.15 Hz, 3H). Analytical HPLC (Method A): Col A: 7.83 min, 99%; Col B: 8.33 min, 99%.

Example 74

7-Cyclopropanesulfonyl-4,17,20-trimethyl-2-(1-oxo-1,2-dihydro-isoquinolin-7-ylamino)-4,11-diaza-tricyclo[14.2.2.1$^{6,10}$]henicosa-1(19),6,8,10(21),16(20),17-hexaene-3,12-dione trifluoroacetate

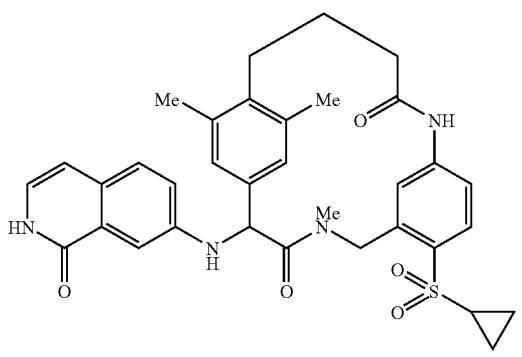

According to the sequence for the preparation of Example 72, replacement of Intermediate 2 with Intermediate 3 affords Example 74. MS (ESI) m/z 613.1 (M+H)$^+$. $^1$H NMR (400 MHz, CD$_3$OD/DMSO-d$_6$ (9:1)) δ ppm 7.75 (d, J=8.25 Hz, 1H) 7.40-7.45 (m, 3H) 7.24 (dd, J=8.79, 2.20 Hz, 1H) 6.93 (d, J=6.60 Hz, 1H) 6.85-6.90 (m, 2H) 6.58 (d, J=1.65 Hz, 1H) 6.55 (d, J=7.15 Hz, 1H) 5.78 (d, J=17.04 Hz, 1H) 5.57 (s, 1H) 4.23 (d, J=17.04 Hz, 1H) 3.45 (s, 3H) 2.94 (ddd, J=12.64, 7.70, 4.95 Hz, 2H) 2.77-2.87 (m, 1H) 2.51 (s, 3H) 2.40-2.49 (m, 3H) 2.29 (s, 3H) 1.92-2.00 (m, 1H) 1.22-1.30 (m, 1H) 1.04-1.15 (m, 3H) Analytical HPLC (Method A): Col A: 9.60 min, 97%; Col B: 9.65 min, 95%.

Example 75

7-Cyclopropanesulfonyl-4,17,20-trimethyl-2-(4-oxo-3,4-dihydro-quinazolin-6-ylamino)-4,11-diaza-tricyclo[14.2.2.1$^{6,10}$]henicosa-1(19),6,8,10(21),16(20),17-hexaene-3,12-dione trifluoroacetate

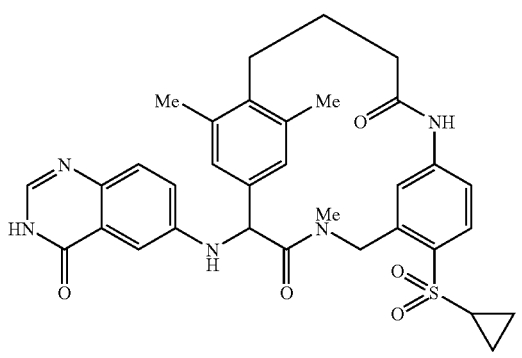 [SMILES: Cc1cc2cc(C)c1CCCC(=O)Nc1ccc(S(=O)(=O)C3CC3)c(c1)CN(C)C(=O)C2Nc1ccc2nc[nH]c(=O)c2c1]

According to the sequence for the preparation of Example 72, replacement of Intermediate 2 with Intermediate 4 affords Example 75. MS (ESI) m/z 614.2 (M+H)$^+$. Analytical HPLC (Method A): Col A: 8.21 min, 99%; Col B: 8.70 min, 98%.

Example 76

(2R,15R)-7-Cyclopropanesulfonyl-4,15,17-trimethyl-2-(4-oxo-3,4-dihydro-quinazolin-6-ylamino)-13-oxa-4,11-diaza-tricyclo[14.2.2.1$^{6,10}$]henicosa-1(19),6,8,10(21),16(20),17-hexaene-3,12-dione trifluoroacetate

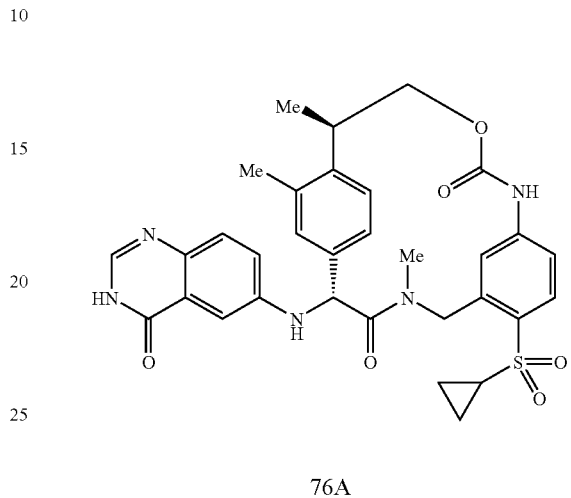

76A

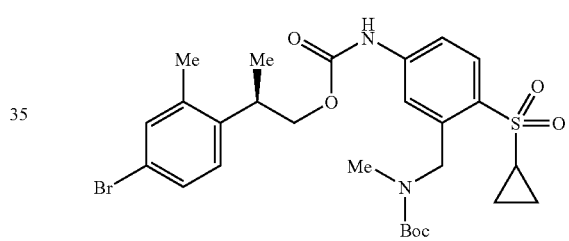

Using a procedure analogous to that used to prepare 29A, Intermediate 11 was reacted with sodium bicarbonate and phosgene followed by Intermediate 8 (565 mg, 2.467 mmol) and TEA. The crude product was added to a silica gel column (40 g) and was eluted with EtOAc/hexanes (0-50%) to afford 76A (1.10 g, 1.847 mmol, 90% yield) as a colorless foam. MS (ESI) m/z 595.2 (M+H)$^+$. $^1$H NMR (400 MHz, CDCl$_3$) δ ppm 7.87 (d, J=8.79 Hz, 1H) 7.56-7.65 (m, 1H) 7.29-7.34 (m, 2H) 7.06-7.13 (m, 1H) 6.77-6.89 (m, 1H) 4.93 (s, 2H) 4.25-4.30 (m, 1H) 4.18-4.23 (m, 1H) 3.33-3.44 (m, J=7.15, 7.15, 7.15, 7.15, 7.15 Hz, 1H) 2.94 (s, 3H) 2.52 (d, J=8.25 Hz, 1H) 2.35 (s, 3H) 1.35-1.54 (m, 9H) 1.28 (d, J=6.60 Hz, 3H) 1.27-1.31 (m, 2H) 0.98-1.05 (m, 2H).

76B

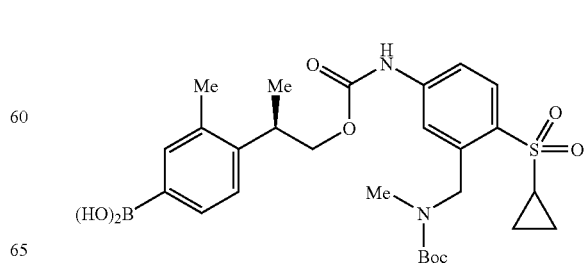

Using a procedure analogous to that used to prepare 29B, 76A (0.32 g, 0.633 mmol) was reacted with bis(neopentyl glycolato)diboron), potassium acetate and (1,1′-bis(diphenylphosphino)ferrocene)-dichloropalladium(II). The crude was purified by preparative HPLC (CH$_3$CN/H$_2$O, 0.1% TFA) to give 76B (766 mg, 1.367 mmol, 79% yield) as a tan solid. MS (ESI) m/z 561.2 (M+H)$^+$.

76C

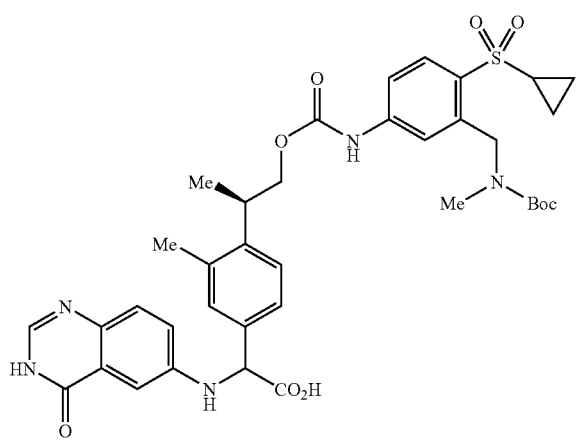 [SMILES: Cc1cc(C(Nc2ccc3nc[nH]c(=O)c3c2)C(=O)O)ccc1[C@@H](C)COC(=O)Nc1ccc(S(=O)(=O)C2CC2)c(CN(C)C(=O)OC(C)(C)C)c1]

Using a procedure analogous to that used to prepare 1E, 76B (85 mg, 0.152 mmol) Intermediate 4, and glyoxylic acid monohydrate were reacted and purified by flash chromatography (1% to 20% MeOH in CH$_2$Cl$_2$) to afford 76C (93 mg, 0.127 mmol, 83% yield) as an off-white glass. MS (ESI) m/z 734.3 (M+H)$^+$. $^1$H NMR (400 MHz, CD$_3$OD) δ ppm 7.83 (s, 1H) 7.78 (d, J=8.79 Hz, 1H) 7.58 (s, 1H) 7.42-7.53 (m, 2H) 7.33-7.41 (m, 2H) 7.25-7.32 (m, 2H) 7.17 (t, J=3.02 Hz, 1H) 5.08 (s, 1H) 4.18-4.29 (m, 2H) 3.40-3.50 (m, 1H) 2.94 (s, 3H) 2.76 (s, 1H) 2.37 (s, 3H) 1.44 (d, J=48.37 Hz, 9H) 1.28 (d, J=5.50 Hz, 3H) 1.16-1.21 (m, 2H) 1.02-1.10 (m, 2H).

76D

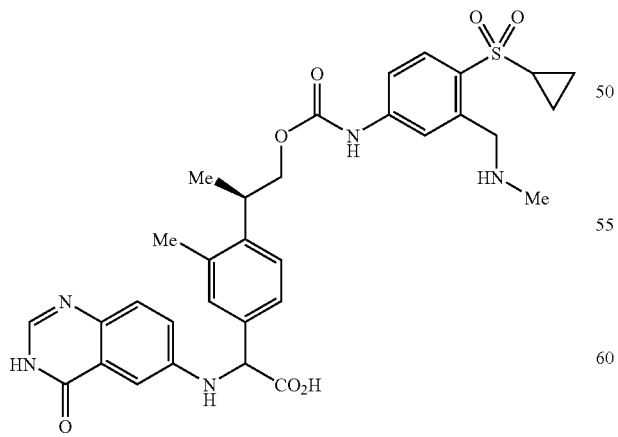

To a suspension of 76C (93 mg, 0.127 mmol) in DCM (2 mL) and ethyl acetate (2 mL), was added 4 N HCl in dioxane (4 mL, 16.00 mmol). The gelatinous mixture was stirred at rt for 30 min, then was concentrated to afford 76D (90 mg, 0.127 mmol, 100% yield) as an off-white solid. MS (ESI) m/z 634.3 (M+H)$^+$.

Example 76

To a solution of BOP (113 mg, 0.255 mmol) and DMAP (78 mg, 0.637 mmol) in DCM (40 mL) and DMF (10 mL) at 40° C., was added a solution of 76D (90 mg, 0.127 mmol) and DIEA (0.044 mL, 0.255 mmol) in DMF (4 mL), dropwise via a syringe pump over 3.75 h. The reaction was removed from the heating bath and stirred for 45 min. 1 mL H$_2$O was added and the reaction mixture was concentrated. The crude product was purified by prep HPLC (Phenomenex Luna 5 μm C18 30x250 (20% to 70% B, 20 min grad, 30 mL/min); solvent A=10% CH$_3$CN/90% H$_2$O/0.1% TFA; solvent B=90% CH$_3$CN/10% H$_2$O/0.1% TFA). Two peaks were isolated: Peak #1: rt=11.48 min (desired product, Example 76), Peak #2: rt=11.81 min ((S)-phenylglycine diastereomer). Example 76 (13.1 mg, 0.018 mmol, 14.1% yield) was isolated as a white powder. MS (ESI) m/z 616.2 (M+H)$^+$. $^1$H NMR (400 MHz, CD$_3$OD) δ ppm 9.45 (s, 1H) 8.45 (s, 1H) 7.72 (d, J=8.79 Hz, 1H) 7.66 (dd, J=8.24, 1.65 Hz, 1H) 7.43-7.49 (m, 2H) 7.36-7.41 (m, 1H) 7.34 (d, J=2.20 Hz, 1H) 7.11 (s, 1H) 6.82 (dd, J=8.52, 1.92 Hz, 1H) 6.41 (d, J=2.20 Hz, 1H) 5.75 (d, J=17.59 Hz, 1H) 5.66 (s, 1H) 4.63 (t, J=10.99 Hz, 1H) 4.28 (d, J=17.59 Hz, 1H) 3.97 (dd, J=10.72, 4.12 Hz, 1H) 3.43-3.53 (m, 1H) 3.39 (s, 3H) 2.81-2.89 (m, 1H) 2.29 (s, 3H) 1.32 (d, J=7.15 Hz, 3H) 1.21-1.28 (m, J=10.44, 4.95 Hz, 1H) 1.09-1.15 (m, 1H) 1.00-1.09 (m, 2H). Analytical HPLC (Method A): Col A: 8.52 min, 99%; Col B: 8.92 min, 99%.

Example 77

(2R,15R)-7-Cyclopropanesulfonyl-15-ethyl-4,17-dimethyl-2-(4-oxo-3,4-dihydro-quinazolin-6-ylamino)-13-oxa-4,11-diaza-tricyclo[14.2.2.1$^{6,10}$]henicosa-1(19),6,8,10 (21),16(20),17-hexaene-3,12-dione trifluoroacetate

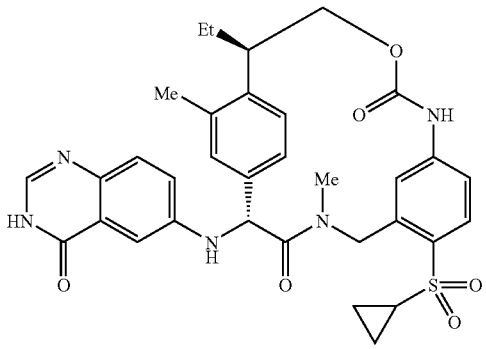

77A

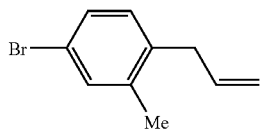

To a solution of 4-bromo-1-iodo-2-methylbenzene (5 g, 16.84 mmol) in THF (100 mL) at −20° C., was added Isopropylmagnesium chloride (2M, THF) (15 mL, 30.0 mmol). (added 10 mL iPrMgCl, stirred 15 min. iPrMgCl (5 mL, 10.0 mmol) was added, and the reaction mixture was stirred 30 min at −20° C. A solution of lithium chloride (1.713 g, 40.4 mmol) and Copper(I) cyanide (1.810 g, 20.21 mmol) in THF (40 mL) was added. The pale green solution was stirred for 10 min at −10° C., then allyl bromide (4.37 mL, 50.5 mmol) was added. The mixture was stirred at −10° C. for 30 min. The reaction was quenched with sat. $NH_4Cl$, then was diluted with EtOAc. The organic phase was washed with $H_2O$, 1N HCl and brine. The organic phase was dried ($Na_2SO_4$), filtered through a 1" pad of $SiO_2$ and concentrated to afford 77A (3.55 g, 16.82 mmol, 100% yield) as a pale yellow oil. $^1$H NMR (400 MHz, $CDCl_3$) δ ppm 7.24-7.31 (m, 2H) 7.00 (d, J=7.91 Hz, 1H) 5.86-5.96 (m, J=16.81, 10.33, 6.21, 6.21 Hz, 1H) 5.07 (dd, J=10.11, 1.32 Hz, 1H) 4.97 (dd, J=17.14, 1.32 Hz, 1H) 3.31 (d, J=6.15 Hz, 2H) 2.26 (s, 3H).

77B

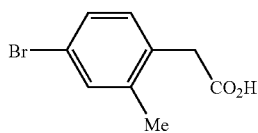

To a solution of 77A (3.55 g, 16.82 mmol) in $CCl_4$ (100 mL), water (150 mL) and acetonitrile (100 mL) at rt, was added Ruthenium (III) chloride hydrate (0.523 g, 2.52 mmol) and sodium periodate (17.98 g, 84 mmol). The suspension was stirred vigorously for 2.5 h, then was diluted with $H_2O$ and DCM. The mixture was filtered through celite. The phases were partitioned. The aqueous phase was extracted with DCM (2×). The combined organic extract was washed with $H_2O$ and brine, dried ($Na_2SO_4$) and concentrated. The resultant black solid was partitioned between $Et_2O$ and 0.1 N NaOH. The organic phase was extracted with $H_2O$, then the combined aqueous extract was acidified with 12 N HCl, giving a precipitate. The aqueous phase was extracted with EtOAc (3×). The combined organic extract was washed with $H_2O$ and brine, dried ($Na_2SO_4$), filtered through 1" $SiO_2$ and concentrated to afford 77B (3.26 g, 14.23 mmol, 85% yield) as an off-white solid. MS (ESI) m/z 229.2 (M+H)$^+$.

77C

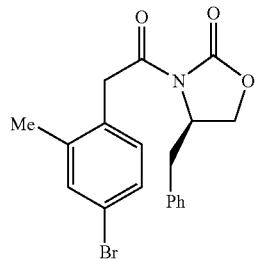 [SMILES: Cc1cc(Br)ccc1CC(=O)N1C(=O)OC[C@H]1Cc1ccccc1]

Using a procedure analogous to that used to prepare 17E, 77B (1.00 g, 4.37 mmol) was reacted with oxalyl chloride and DMF and concentrated. The crude acid chloride was reacted with (R)-4-benzyloxazolidin-2-one and purified by column chromatography (0 to 100% ethyl acetate/hexanes) to afford 77C (1.46 g, 3.76 mmol, 86% yield) as a white crystalline solid. MS (ESI) m/z 387.9 (M+H)$^+$. $^1$H NMR (400 MHz, $CD_3OD$) δ ppm 7.37 (d, J=1.65 Hz, 1H) 7.27-7.35 (m, 4H) 7.16-7.20 (m, 2H) 7.05 (d, J=8.24 Hz, 1H) 4.65-4.72 (m, 1H) 4.16-4.33 (m, 4H) 3.31 (dd, J=13.47, 3.02 Hz, 1H) 2.78 (dd, J=13.19, 9.89 Hz, 1H) 2.28 (s, 3H).

77D

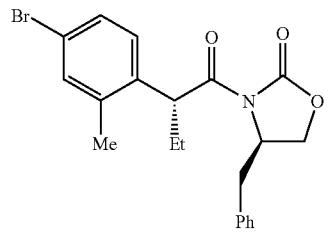 [SMILES: CC[C@@H](C(=O)N1C(=O)OC[C@H]1Cc1ccccc1)c1ccc(Br)cc1C]

Using a procedure analogous to that used to prepare 17F, 77C (2.00 g, 5.15 mmol) was reacted with NaHMDS and iodoethane and purified by column chromatography (0 to 35% ethyl acetate/hexanes) to afford 77D (1.27 g, 3.05 mmol, 59.2% yield) as a viscous colorless oil. MS (ESI) m/z 415.9 (M+H)$^+$. $^1$H NMR (400 MHz, $CDCl_3$) δ ppm 7.30-7.37 (m, 3H) 7.22-7.29 (m, 4H) 7.12 (d, J=8.35 Hz, 1H) 5.03 (dd, J=8.57, 5.93 Hz, 1H) 4.62-4.68 (m, J=9.89, 7.14, 2.91, 2.91 Hz, 1H) 4.05-4.15 (m, 2H) 3.37 (dd, J=13.18, 3.08 Hz, 1H) 2.80 (dd, J=13.18, 9.67 Hz, 1H) 2.40 (s, 3H) 2.11 (ddd, J=13.84, 8.35, 7.25 Hz, 1H) 1.70 (tt, J=13.62, 7.47 Hz, 1H) 0.99 (t, J=7.25 Hz, 3H).

77E

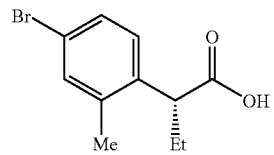 [SMILES: CC[C@@H](C(=O)O)c1ccc(Br)cc1C]

Using a procedure analogous to that used to prepare 17G, 77D (1.52 g, 3.65 mmol) was reacted with lithium peroxide to afford 77E (933 mg, 3.63 mmol, 99% yield) as a colorless oil. MS (ESI) m/z 257.3 (M+H)$^+$. $^1$H NMR (400 MHz, $CDCl_3$) δ ppm 7.29-7.34 (m, 2H) 7.18 (d, J=7.91 Hz, 1H) 3.70 (t, J=7.47 Hz, 1H) 2.36 (s, 3H) 2.05-2.16 (m, 1H) 1.70-1.81 (m, 1H) 0.91 (t, J=7.47 Hz, 3H).

77F

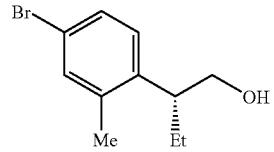 [SMILES: CC[C@@H](CO)c1ccc(Br)cc1C]

Using a procedure analogous to that used to prepare 17H, 77E (928 mg, 3.61 mmol) was reduced with Borane-THF (1 M, THF) to afford 77F (877 mg, 3.61 mmol, 100% yield) as a colorless oil. MS (ESI) m/z 225.1 (M+H)+. $^1$H NMR (400 MHz, CDCl$_3$) δ ppm 7.30-7.34 (m, 2H) 7.05 (d, J=9.23 Hz, 1H) 3.67-3.79 (m, 2H) 2.99-3.07 (m, 1H) 2.33 (s, 3H) 1.73-1.83 (m, 1H) 1.48-1.58 (m, 1H) 1.23-1.29 (m, 1H) 0.82 (t, J=7.47 Hz, 3H).

77G

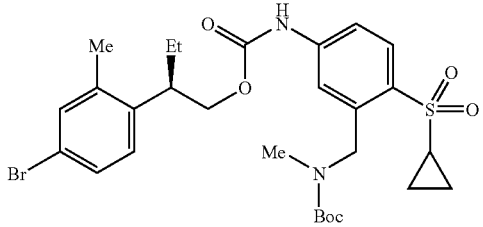 [SMILES: CC[C@@H](COC(=O)Nc1ccc(S(=O)(=O)C2CC2)c(CN(C)C(=O)OC(C)(C)C)c1)c1ccc(Br)cc1C]

Using a procedure analogous to that used to prepare 29A, Intermediate 11 was reacted with sodium bicarbonate and phosgene followed by 77F (600 mg, 2.467 mmol) and TEA. The crude product was added to a silica gel column (80 g) and was eluted with EtOAc/hexanes (0-50%) to give 77G (960 mg, 1.575 mmol, 77% yield) as a colorless foam. MS (ESI) m/z 611.2 (M+H)+. $^1$H NMR (400 MHz, CDCl$_3$) δ ppm 7.86 (d, J=8.79 Hz, 1H) 7.45-7.71 (m, 1H) 7.30-7.36 (m, 2H) 7.06 (d, J=9.34 Hz, 1H) 6.71-6.96 (m, 1H) 4.92 (s, 2H) 4.28-4.35 (m, 1H) 4.18-4.27 (m, 1H) 3.15-3.24 (m, 1H) 2.94 (s, 3H) 2.52 (s, 1H) 2.33 (s, 3H) 1.76-1.89 (m, 1H) 1.55-1.67 (m, 1H) 1.45 (d, J=48.37 Hz, 9H) 1.31 (d, J=2.20 Hz, 2H) 0.98-1.05 (m, 2H) 0.84 (t, J=7.42 Hz, 3H).

77H

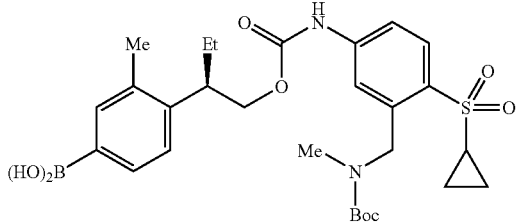 [SMILES: CC[C@@H](COC(=O)Nc1ccc(S(=O)(=O)C2CC2)c(CN(C)C(=O)OC(C)(C)C)c1)c1ccc(B(O)O)cc1C]

Using a procedure analogous to that used to prepare 29B, 77G (954 mg, 1.565 mmol) was reacted with bis(neopentyl glycolato)diboron, potassium acetate and (1,1'-bis(diphenylphosphino)ferrocene)-dichloropalladium(I). The crude was purified by preparative HPLC (CH$_3$CN/H$_2$O, 0.1% TFA) to afford 77H (735 mg, 1.279 mmol, 82% yield) as a white powder. MS (ESI) m/z 575.2 (M+H)+.

77I

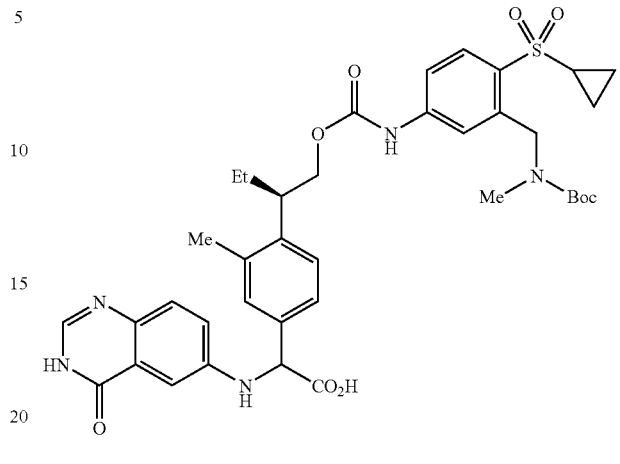

Using a procedure analogous to that used to prepare 1E, 77H (153 mg, 0.266 mmol), Intermediate 4, and glyoxylic acid monohydrate were reacted and purified by flash chromatography (1% to 25% MeOH in CH$_2$Cl$_2$) to afford 77I (123 mg, 0.164 mmol, 61.8% yield) as a pale yellow glass. MS (ESI) m/z 748.3 (M+H)+. $^1$H NMR (400 MHz, CD$_3$OD) δ ppm 7.85 (s, 1H) 7.77 (dd, J=8.52, 1.92 Hz, 1H) 7.53-7.63 (m, 1H) 7.47 (d, J=9.34 Hz, 1H) 7.42 (s, 1H) 7.35-7.42 (m, 2H) 7.25-7.31 (m, 2H) 7.19 (dd, J=5.50, 2.75 Hz, 1H) 5.11 (s, 1H) 4.89 (s, 2H) 4.32 (ddd, J=10.31, 6.73, 3.30 Hz, 1H) 4.18-4.26 (m, 1H) 3.26 (s, 1H) 2.94 (s, 3H) 2.70-2.79 (m, 1H) 2.36 (s, 3H) 1.86 (ddd, J=20.34, 13.19, 7.15 Hz, 1H) 1.58-1.70 (m, 1H) 1.50 (br. s, 4.5H) 1.38 (br. s, 4.5H) 1.15-1.21 (m, 2H) 1.05 (td, J=7.28, 4.67 Hz, 2H) 0.83 (t, J=7.42 Hz, 3H).

77J

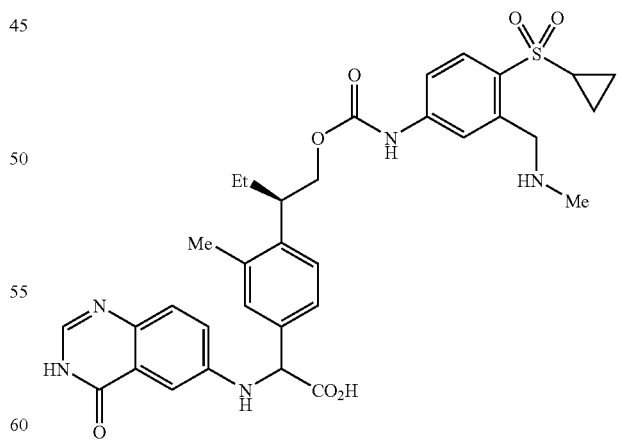

To a solution of 77I (117 mg, 0.156 mmol) in DCM (2 mL), was added 4N HCl in dioxane (3 mL, 12.00 mmol). The suspension was stirred at rt for 30 min, then concentrated to afford 77J (113 mg, 0.157 mmol, 100% yield) as a white powder. MS (ESI) m/z 648.3 (M+H)+. $^1$H NMR (400 MHz, CD$_3$OD) δ ppm 8.95 (s, 1H) 7.92 (s, 1H) 7.89 (d, J=8.79 Hz, 1H) 7.63 (d, J=8.79 Hz, 1H) 7.51-7.54 (m, 1H) 7.43 (dd, J=8.79, 2.75 Hz, 1H) 7.39 (s, 1H) 7.37 (s, 1H) 7.31 (d, J=6.05 Hz, 1H) 7.26-7.29 (m, 1H) 5.17 (s, 1H) 4.48 (s, 2H) 4.32-4.37 (m, 1H) 4.24-4.30 (m, 1H) 3.24-3.29 (m, 1H) 2.87 (ddd, J=12.64, 7.70, 4.95 Hz, 1H) 2.78 (s, 3H) 2.37 (d, J=6.60 Hz, 3H) 1.83-1.94 (m, 1H) 1.61-1.72 (m, 1H) 1.23-1.28 (m, 2H) 1.08-1.13 (m, 2H) 0.83 (t, J=7.42 Hz, 3H).

Example 77

To a solution of BOP (135 mg, 0.305 mmol) and DMAP (93 mg, 0.763 mmol) in DCM (40 mL) and DMF (10 mL) at 40° C., was added a solution of 77J (110 mg, 0.153 mmol) and DIEA (0.053 mL, 0.305 mmol) in DMF (5 mL), dropwise via a syringe pump over 4.5 h. The reaction was removed from the heating bath and stirred for 30 min. H$_2$O (1 mL) was added and the reaction mixture was concentrated. The reaction mixture was purified by preparative HPLC (Phenomenex Luna 5 μm C18 30×250 (20% to 70% B, 20 min grad, 30 mL/min); solvent A=10% CH$_3$CN/90% H$_2$O/0.1% TFA; solvent B=90% CH$_3$CN/10% H$_2$O/0.1% TFA; rt=12.81 min), chiral HPLC (R,R-Whelk-O column (21.1×250 mm, 60:40 (MeOH/EtOH 1:1)/heptane, 20 mL/min); rt=13.5 min), and a second preparative HPLC purification (YMC ODS-A S-5 uM 20×100 (20% to 100% B, 10 min grad); solvent A=10% CH$_3$CN/90% H$_2$O/0.1% TFA; solvent B=90% CH$_3$CN/10% H$_2$O/0.1% TFA) to afford Example 77 (17.8 mg, 15.7% yield) as a off-white powder. MS (ESI) m/z 630.3 (M+H)$^+$. $^1$H NMR (400 MHz, CD$_3$OD) δ ppm 9.44 (s, 1H) 8.34 (s, 1H) 7.71 (d, J=8.79 Hz, 1H) 7.65 (dd, J=8.24, 1.65 Hz, 1H) 7.44-7.47 (m, 1H) 7.42 (d, J=7.70 Hz, 1H) 7.31-7.37 (m, 2H) 7.14 (s, 1H) 6.81 (dd, J=8.24, 2.20 Hz, 1H) 6.40 (d, J=2.20 Hz, 1H) 5.75 (d, J=17.59 Hz, 1H) 5.65 (s, 1H) 4.67 (t, J=10.99 Hz, 1H) 4.28 (d, J=17.59 Hz, 1H) 4.01 (dd, J=10.99, 3.85 Hz, 1H) 3.40 (s, 3H) 3.20-3.28 (m, 1H) 2.84 (ddd, J=12.78, 8.11, 4.95 Hz, 1H) 2.26 (s, 3H) 1.72-1.82 (m, 2H) 1.20-1.27 (m, 1H) 1.07-1.14 (m, 1H) 0.98-1.07 (m, 2H) 0.85-0.92 (m, 3H). Analytical HPLC (Method A): Col A: 8.84 min, 99%; Col B: 9.33 min, 99%.

Example 78

(2R,15R)-7-Cyclopropanesulfonyl-2-(7-fluoro-4-oxo-3,4-dihydro-quinazolin-6-ylamino)-4,15,17-trimethyl-13-oxa-4,1-diaza-tricyclo[14.2.2.1$^{6,10}$]henicosa-1(19),6,8,10(21),16(20),17-hexaene-3,12-dione

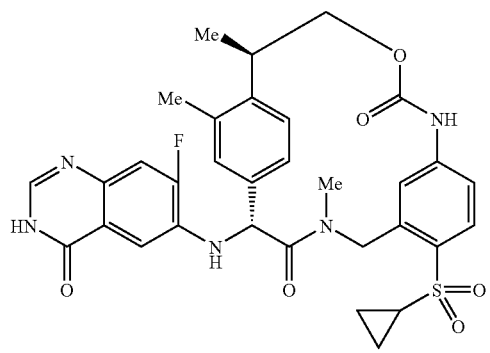 [SMILES: Cc1cc2ccc1[C@@H](C)COC(=O)Nc1ccc(S(=O)(=O)C3CC3)c(c1)CN(C)C(=O)[C@@H]2Nc1cc2c(=O)[nH]cnc2cc1F]

According to the sequence for the preparation of Example 76, replacement of Intermediate 4 with Intermediate 12 afforded Example 78. R,R-Whelk-O column (21.1×250 mm, 60:40 (MeOH/EtOH 1:1)/heptane, 20 mL/min); peak #2: rt=14.7 min. MS (ESI) m/z 634.3 (M+H)$^+$. 1H NMR (400 MHz, CD$_3$OD) δ ppm 7.88 (s, 1H) 7.69-7.74 (m, 2H) 7.46 (d, J=7170 Hz, 1H) 7.43 (d, J=9.34 Hz, 1H) 7.27 (d, J=12.09 Hz, 1H) 7.02 (s, 1H) 6.82 (dd, J=8.79, 2.20 Hz, 1H) 6.41 (d, J=2.20 Hz, 1H) 5.77 (d, J=17.59 Hz, 1H) 5.69 (s, 1H) 4.63 (t, J=10.99 Hz, 1H) 4.28 (d, J=17.59 Hz, 1H) 3.96 (dd, J=10.99, 4.40 Hz, 1H) 3.43-3.51 (m, 1H) 3.38 (s, 3H) 2.83-2.91 (m, 1H) 2.27 (s, 3H) 1.31 (d, J=7.15 Hz, 3H) 1.24-1.29 (min, 1H) 1.04-1.15 (m, 3H). Analytical HPLC (Method A): Col A: 9.45 min, 99%; Col B: 9.55 min, 99%.

Example 79

(2R,15R)-7-Cyclopropanesulfonyl-4,15,17-trimethyl-2-(1-oxo-1,2-dihydro-isoquinolin-7-ylamino)-13-oxa-4,1-diaza-tricyclo[14.2.2.1$^{6,10}$]henicosa-1(19),6,8,10(21),16(20),17-hexaene-3,12-dione

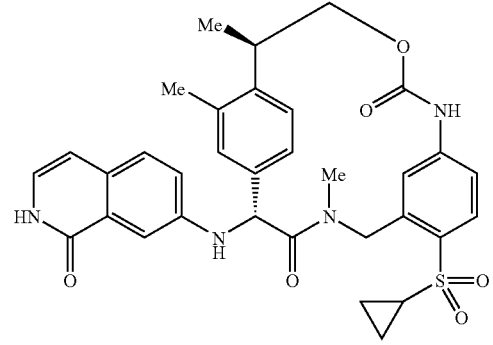 [SMILES: Cc1cc2ccc1[C@@H](C)COC(=O)Nc1ccc(S(=O)(=O)C3CC3)c(c1)CN(C)C(=O)[C@@H]2Nc1ccc2cc[nH]c(=O)c2c1]

According to the sequence for the preparation of Example 76, replacement of Intermediate 4 with Intermediate 3 afforded Example 79. R,R-Whelk-O column (21.1×250 mm, 60:40 (MeOH/EtOH 1:1)/heptane, 20 mL/min); peak #2: rt=13.0 min. MS (ESI) m/z 615.3 (M+H)$^+$. $^1$H NMR (400 MHz, CD$_3$OD) δ ppm 7.71 (d, J=8.79 Hz, 1H) 7.65 (dd, J=7.97, 1.92 Hz, 1H) 7.38-7.46 (m, 3H) 7.22 (dd, J=8.79, 2.20 Hz, 1H) 7.12 (d, J=1.65 Hz, 1H) 6.90 (d, J=7.15 Hz, 1H) 6.81 (dd, J=8.24, 2.20 Hz, 1H) 6.54 (d, J=6.60 Hz, 1H) 6.43 (d, J=1.65 Hz, 1H) 5.75 (d, J=17.59 Hz, 1H) 5.63 (s, 1H) 4.62 (t, J=11.27 Hz, 1H) 4.28 (d, J=17.59 Hz, 1H) 3.96 (dd, J=10.44, 4.40 Hz, 1H) 3.44-3.52 (m, 1H) 3.41 (s, 3H) 2.82-2.89 (m, 1H) 2.29 (s, 2H) 1.32 (d, J=7.15 Hz, 3H) 1.22-1.29 (m, 1H) 1.00-1.12 (m, 3H). Analytical HPLC (Method A): Col A: 9.96 min, 99%; Col B: 9.93 min, 99%.

Example 80

(2R,15R)-7-Cyclopropanesulfonyl-15-ethyl-4,17-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

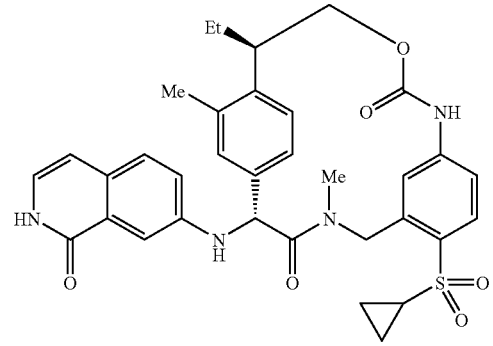 [SMILES: CC[C@H]1COC(=O)Nc2ccc(S(=O)(=O)C3CC3)c(c2)CN(C)C(=O)[C@H](Nc2ccc3cc[nH]c(=O)c3c2)c2ccc1c(C)c2]

According to the sequence for the preparation of Example 77, replacement of Intermediate 4 with Intermediate 3 afforded Example 80. R,R-Whelk-O column (21.1×250 mm, 60:40 (MeOH/EtOH 1:1)/heptane, 20 mL/min); Peak #2 RT=11.67 min. MS (ESI) m/z 629.3 (M+H)+. 1H NMR (500 MHz, CD3OD) δ ppm 7.71 (d, J=8.80 Hz, 1H) 7.66 (dd, J=8.25, 1.65 Hz, 1H) 7.39-7.43 (m, 3H) 7.23 (dd, J=8.52, 2.47 Hz, 1H) 7.17 (d, J=1.65 Hz, 1H) 6.91 (d, J=6.60 Hz, 1H) 6.81 (dd, J=8.25, 2.20 Hz, 1H) 6.55 (d, J=7.15 Hz, 1H) 6.43 (d, J=1.65 Hz, 1H) 5.75 (d, J=17.05 Hz, 1H) 5.63 (s, 1H) 4.67 (t, J=11.27 Hz, 1H) 4.30 (d, J=17.60 Hz, 1H) 4.00 (dd, J=10.72, 4.12 Hz, 1H) 3.42 (s, 3H) 3.22-3.28 (m, 1H) 2.82-2.87 (m, 1H) 2.27 (s, 3H) 1.78 (td, J=14.16, 6.87 Hz, 2H) 1.22-1.27 (m, 1H) 0.96-1.11 (m, 3H) 0.89 (t, J=7.42 Hz, 3H). Analytical HPLC (Method A): Col A: 10.34 min, 99%; Col B: 10.26 min, 99%.

Example 81

(2R,15R)-4,15,17-Trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

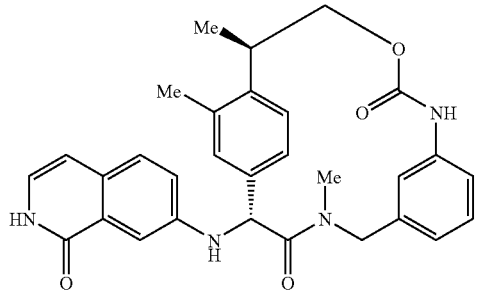

81A

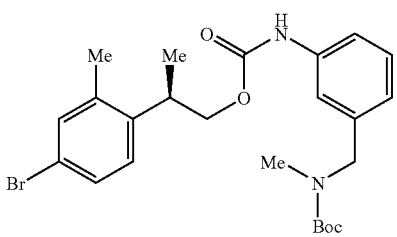 [SMILES: Cc1cc(Br)ccc1[C@@H](C)COC(=O)Nc1cccc(CN(C)C(=O)OC(C)(C)C)c1]

Using a procedure analogous to that used to prepare 29A, 171 (643 mg, 2.72 mmol) was reacted with sodium bicarbonate and phosgene followed by Intermediate 8 (450 mg, 1.964 mmol) and TEA. The crude product was added to a silica gel column (80 g) and was eluted with EtOAc/hexanes (0-60%) to afford 81A (930 mg, 1.892 mmol, 96% yield) as a colorless foam. MS (ESI) m/z 435.2 (M+H)+.

81B

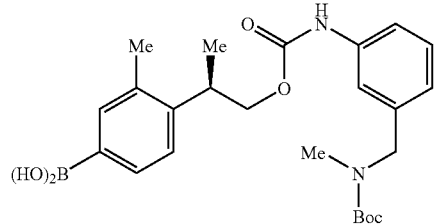 [SMILES: Cc1cc(B(O)O)ccc1[C@@H](C)COC(=O)Nc1cccc(CN(C)C(=O)OC(C)(C)C)c1]

Using a procedure analogous to that used to prepare 29B, 81A (970 mg, 1.629 mmol) was reacted with bis(neopentyl glycolato)diboron), potassium acetate and (1,1'-bis(diphenylphosphino)ferrocene)-dichloropalladium(II). The crude was purified by preparative HPLC (CH3CN/H2O, 0.1% TFA) to afford after lypholization 81B (712 mg, 1.270 mmol, 78% yield) as a off-white solid. MS (ESI) m/z 561.3 (M+H)+.

81C

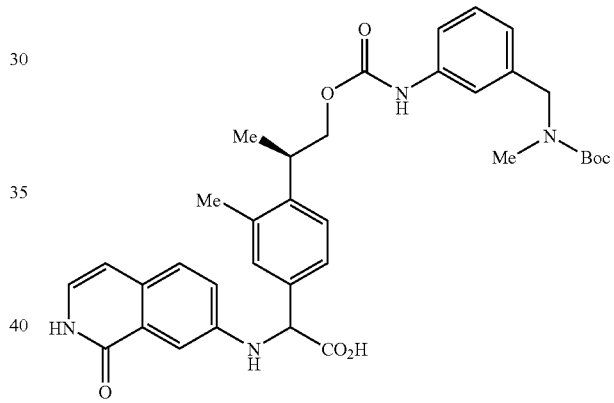

The following reaction was repeated 3 times and combined for purification. 81B (200 mg, 0.438 mmol) and Intermediate 3 (73.7 mg, 0.460 mmol) were dissolved in DMF (0.5 mL). Glyoxylic acid monohydrate (40.3 mg, 0.438 mmol) was added, followed by acetonitrile (2.0 mL). The resultant suspension was irradiated at 100° C. for 10 min in a microwave reactor. The combined reaction mixtures were purified by flash chromatography (gradient 1 to 20% MeOH/CH2Cl2) to afford 81C (520 mg, 63%) as a tan foam. MS (ESI) m/z 629.4 (M+H)+.

Example 81

To a solution of 81C (520 mg, 0.827 mmol) in ethyl acetate (5 mL) and DCM (5 mL), was added 4N HCl in dioxane (10 mL, 40.0 mmol). The resultant suspension was stirred at rt for 35 min, then was concentrated to afford the aminoacid.2HCl salt (595 mg, 100%) as a pale yellow solid. MS (ESI) m/z 529.3 (M+H)+. To a solution of BOP (732 mg, 1.654 mmol) and DMAP (505 mg, 4.14 mmol) in dichloromethane (200 mL) and DMF (50 mL) at 40° C., was added a solution of the amino acid.2HCl salt prepared above and DIEA (0.289 mL, 1.654 mmol) in DMF (10 mL), dropwise via a syringe pump over 3.5 h. The reaction mixture was stirred at 40° C. for 30 min. H$_2$O (5 mL) was added, and then the mixture was concentrated. The mixture was purified by preparative HPLC (3 injections; Phenomenex Luna 5 µm C18 30X250 (20% to 70% B, 20 min grad, 30 mL/min); solvent A=10% CH$_3$CN/ 90% H$_2$O/0.1% TFA; solvent B=90% CH$_3$CN/10% H$_2$O/ 0.1% TFA). The diastereomers were separated by chiral chromatography (R,R-Whelk-O column (21.1×250 mm, 60:40 (MeOH/EtOH 1:1)/heptane, 20 mL/min)) to afford Example 81 (93 mg, 0.182 mmol, 22.02% yield) as a white powder. MS (ESI) m/z 511.4 (M+H)$^+$. $^1$H NMR (400 MHz, METHANOL-d$_4$) δ ppm 7.62 (dd, J=7.70, 1.65 Hz, 1H) 7.43 (t, J=3.30 Hz, 2H) 7.40 (s, 1H) 7.22-7.28 (m, 2H) 7.18 (t, J=7.70 Hz, 1H) 6.91 (d, J=6.60 Hz, 2H) 6.69 (d, J=7.15 Hz, 1H) 6.55 (d, J=6.60 Hz, 1H) 5.95 (s, 1H) 5.66 (s, 1H) 5.45 (d, J=16.49 Hz, 1H) 4.64 (t, J=10.17 Hz, 1H) 3.99 (dd, J=10.72, 4.12 Hz, 1H) 3.90 (d, J=16.49 Hz, 1H) 3.48 (ddd, J=10.72, 6.87, 4.40 Hz, 1H) 2.34 (s, 3H) 1.30 (d, J=7.15 Hz, 3H). Analytical HPLC (Method A): Col A: 11.49 min, 99%; Col B: 11.28 min, 99%.

Example 82

(2R,15R)-7-Cyclopropanesulfonyl-17-methoxy-4, 15-dimethyl-2-(1-oxo-1,2-dihydro-isoquinolin-7-ylamino)-13-oxa-4,11-diaza-tricyclo[14.2.2.1$^{6,10}$] henicosa-1(19),6,8,10(21),16(20),17-hexaene-3,12-dione

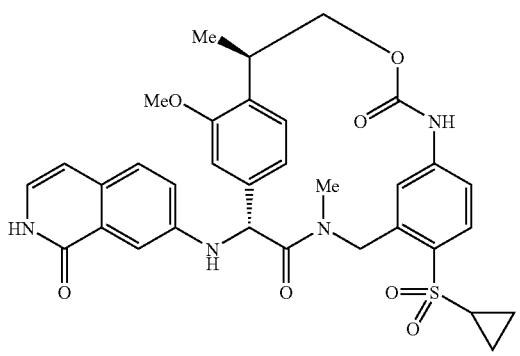 [SMILES: COc1cc2ccc1[C@@H](C)COC(=O)Nc1ccc(S(=O)(=O)C3CC3)c(c1)CN(C)C(=O)[C@@H]2Nc1ccc2cc[nH]c(=O)c2c1]

According to the sequence for the preparation of Example 76, replacement of Intermediate 8 with Intermediate 9 afforded Example 82. MS (ESI) m/z 631.4 (M+H)$^+$. $^1$H NMR (400 MHz, CD$_3$OD) δ ppm 9.43 (s, 1H) 7.72 (d, J=8.24 Hz, 1H) 7.38-7.44 (m, 4H) 7.25 (dd, J=8.52, 2.47 Hz, 1H) 6.89-6.93 (m, 2H) 6.83 (dd, J=8.24, 2.20 Hz, 1H) 6.55 (d, J=7.15 Hz, 1H) 6.51 (d, J=1.65 Hz, 1H) 5.76 (d, J=17.59 Hz, 1H) 5.67 (s, 1H) 4.48 (t, J=10.44 Hz, 1H) 4.34 (d, J=17.59 Hz, 1H) 4.01 (dd, J=10.99, 3.85 Hz, 1H) 3.75 (ddd, J=10.99, 7.15, 3.85 Hz, 1H) 3.60 (s, 3H) 3.40 (s, 3H) 2.86 (ddd, J=12.50, 7.83, 4.95 Hz, 1H) 1.28 (d, J=7.15 Hz, 3H) 1.21-1.26 (m, 1H) 1.08-1.15 (m, 1H) 0.99-1.08 (m, 2H). Analytical chiral HPLC: (R,R-Whelk-O column (4.6×250 mm, 10µ, 60:40 (MeOH/EtOH 1:1)/heptane, 1 mL/min) rt=9.18 min.

Example 83

(2R,15R)-17-Methoxy-4,15-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16 (20),17-hexaene-3,12-dione

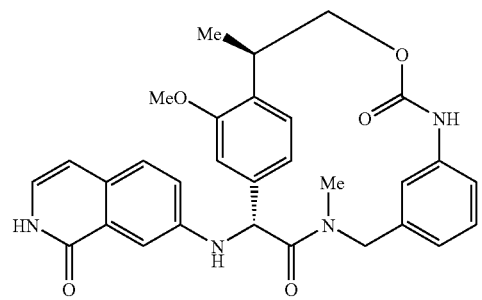

According to the sequence for the preparation of Example 81, replacement of Intermediate 8 with Intermediate 9 afforded Example 83. R,R-Whelk-O column (21.1×250 mm, 60:40 (MeOH/EtOH 1:1)/heptane, 20 mL/min), rt=7.20 min. MS (ESI) m/z 527.3 (M+H)$^+$. $^1$H NMR (400 MHz, CD$_3$OD) δ ppm 7.50 (s, 1H) 7.44-7.47 (m, 1H) 7.28-7.35 (m, 3H) 7.17 (t, J=7.70 Hz, 1H) 7.06 (s, 1H) 6.94 (d, J=7.15 Hz, 1H) 6.90 (d, J=8.25 Hz, 1H) 6.69 (d, J=7.70 Hz, 1H) 6.57 (d, J=6.60 Hz, 1H) 6.06 (s, 1H) 5.71 (s, 1H) 5.47 (d, J=15.94 Hz, 1H) 4.34-4.42 (m, 1H) 4.16-4.23 (m, 1H) 3.83-3.90 (m, 1H) 3.69 (s, 3H) 3.27 (s, 3H) 1.28 (d, J=7.15 Hz, 3H). Analytical HPLC (Method A): Col A: 9.63 min, 95%; Col B: 9.57 min, 95%.

Example 84

(2R,15R)-17-Chloro-7-cyclopropanesulfonyl-4,15-dimethyl-2-(1-oxo-1,2-dihydro-isoquinolin-7-ylamino)-13-oxa-4,11-diaza-tricycle [14.2.2.1$^{6,10}$] henicosa-1(19),6,8,10(21),16(20),17-hexaene-3,12-dione

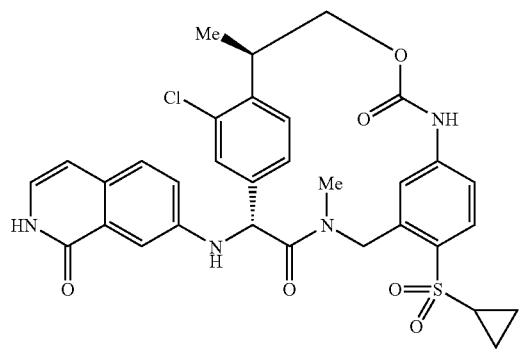 [SMILES: C[C@H]1COC(=O)Nc2ccc(S(=O)(=O)C3CC3)c(c2)CN(C)C(=O)[C@H](Nc2ccc3cc[nH]c(=O)c3c2)c2ccc1c(Cl)c2]

84A

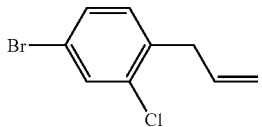

Using a procedure analogous to that used to prepare 77A, 4-bromo-2-chloro-1-iodobenzene (10.0 g, 31.5 mmol) was reacted with isopropylmagnesium chloride, lithium chloride, copper(I) cyanide and allyl bromide to give 84A (7.270 g, 31.4 mmol, 100% yield) as a colorless oil. $^1$H-NMR: (400 MHz, CDCl$_3$) δ ppm 3.44 (d, J=6.60 Hz, 2H) 5.00-5.16 (m, 2H) 5.85-5.99 (m, 1H) 7.09 (d, J=8.25 Hz, 1H) 7.33 (dd, J=7.97, 1.92 Hz, 1H) 7.52 (d, J=1.65 Hz, 1H).

84B

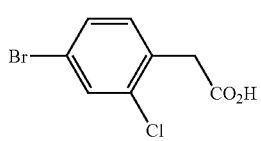 [SMILES: O=C(O)Cc1ccc(Br)cc1Cl]

Using a procedure analogous to that used to prepare 77B, 84A (7.270 g, 31.4 mmol) was reacted with osmium tetroxide and oxone to give 84B (4.61 g, 18.48 mmol, 58.8% yield) as a yellowish solid. MS (ESI) m/z 249.1 (M+H)$^+$. $^1$H-NMR: (400 MHz, CDCl$_3$) δ ppm 3.78 (s, 2H) 7.16 (d, J=7.91 Hz, 1H) 7.38 (dd, J=8.13, 1.98 Hz, 1H) 7.57 (d, J=1.76 Hz, 1H).

84C

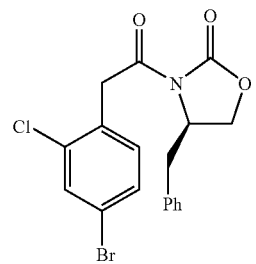 [SMILES: O=C(Cc1ccc(Br)cc1Cl)N1C(=O)OC[C@H]1Cc1ccccc1]

Using a procedure analogous to that used to prepare 17E, 84B (4.610 g, 18.48 mmol was reacted with oxalyl chloride and DMF and concentrated. The crude acid chloride was reacted with (R)-4-benzyloxazolidin-2-one and purified by column chromatography (0 to 35% ethyl acetate/hexanes) to give 84C (1.765 g, 4.32 mmol, 23.37% yield) as a white powder. MS (ESI) m/z 408.0 (M+H)$^+$. $^1$H-NMR: (400 MHz, CDCl$_3$) δ ppm 2.80 (dd, J=13.47, 9.62 Hz, 1H) 3.32 (dd, J=13.47, 3.02 Hz, 1H) 4.20-4.30 (m, 2H) 4.28-4.49 (m, 2H) 4.62-4.76 (m; 1H) 7.14 (d, J=8.25 Hz, 1H) 7.20 (d, J=6.60 Hz, 2H) 7.24-7.37 (m, 3H) 7.40 (dd, J=8.25, 2.20 Hz, 1H) 7.60 (d, J=2.20 Hz, 1H).

84D

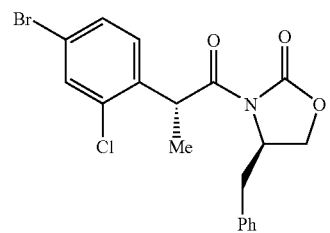 [SMILES: C[C@@H](C(=O)N1C(=O)OC[C@H]1Cc1ccccc1)c1ccc(Br)cc1Cl]

Using a procedure analogous to that used to prepare 17F, 84C (1.765 g, 4.32 mmol) was reacted with NaHMDS and iodomethane and purified by column chromatography (0-40% EtOAc/hex) to give 84D (1.182 g, 2.80 mmol, 64.7% yield) as a white foam. MS (ESI) m/z 422.0 (M+H)$^+$. $^1$H-NMR: (400 MHz, CDCl$_3$) δ ppm 1.56 (d, J=7.03 Hz, 3H) 2.81 (dd, J=13.18, 9.67 Hz, 1H) 3.32 (dd, J=13.18, 2.64 Hz, 1H) 4.19 (d, J=5.27 Hz, 2H) 4.61-4.75 (m, 1H) 5.32 (q, J=7.03 Hz, 1H) 7.16-7.25 (m, 3H) 7.25-7.45 (m, 4H) 7.55 (d, J=2.20 Hz, 1H).

84E

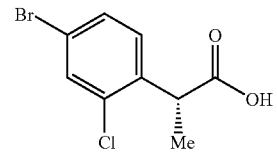

Using a procedure analogous to that used to prepare 17G, 84D (1.18 g, 2.79 mmol) was reacted with lithium peroxide to afford 84E (735 mg, 2.79 mmol, 100% yield) as a colorless crystalline solid. MS (ESI) m/z 263.1 (M+H)$^+$. $^1$H NMR (400 MHz, CDCl$_3$) δ ppm 7.56 (d, J=2.20 Hz, 1H) 7.40 (d.d, J=8.52, 1.92 Hz, 1H) 7.23 (d, J=8.24 Hz, 1H) 4.22 (q, J=7.51 Hz, 1H) 1.52 (d, J=7.15 Hz, 3H).

84F

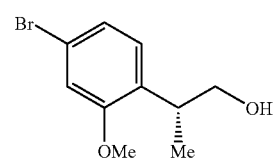 [SMILES: COc1cc(Br)ccc1[C@@H](C)CO]

Using a procedure analogous to that used to prepare 17H, 84E (730 mg, 2.77 mmol) was reduced with Borane-THF (1 M, THF) to afford 84F (683 mg, 2.74 mmol, 99% yield) as a colorless oil. MS (ESI) m/z 231.0 (M+H)$^+$. $^1$H NMR (400 MHz, CDCl$_3$) δ ppm 7.54 (d, J=2.20 Hz, 1H) 7.38 (d, J=8.52, 1.92 Hz, 1H) 7.17 (d, J=8.25 Hz, 1H) 3.75-3.81 (m, 1H) 3.68-3.74 (m, 1H) 3.48 (dq, J=13.60, 6.64 Hz, 1H) 1.33 (t, J=5.77 Hz, 1H) 1.28 (d, J=7.15 Hz, 3H).

84G

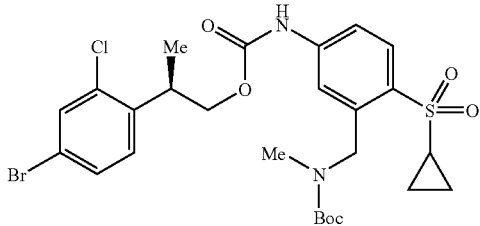 [SMILES: C[C@@H](COC(=O)Nc1ccc(S(=O)(=O)C2CC2)c(CN(C)C(=O)OC(C)(C)C)c1)c1ccc(Br)cc1Cl]

Using a procedure analogous to that used to prepare 29A, Intermediate 11 was reacted with sodium bicarbonate and phosgene followed by 84F (250 mg, 1.002 mmol) and TEA. The crude product was added to a silica gel column (40 g) and was eluted with EtOAc/hexanes (0-100%) to afford 84G (527 mg, 0.856 mmol, 85% yield) colorless foam. MS (ESI) m/z 615.2 (M+H)+. $^1$H NMR (400 MHz, CDCl$_3$) amide bond isomers δ ppm 7.87 (d, J=8.79 Hz, 1H) 7:70 (br s, 0.5H) 7.56 (d, J=1.32 Hz, 1H) 7.50 (br s, 0.5H) 7.40 (dd, J=8.35, 1.76 Hz, 1H) 7.31 (br s, 0.5H) 7.18 (d, J=8.35 Hz, 1H) 7.08 (brs, 0.5H) 7.00 (br s, 0.5H) 6.81 (brs, 0.5H) 4.92 (s, 2H) 4.26-4.35 (m, 2H) 3.64-3.73 (m, J=7.12, 7.12, 7.12, 7.12, 7.12 Hz, 1H) 2.94 (s, 3H) 2.52 (s, 1H) 1.51 (s, 4.5H) 1.39 (s, 4.5H) 1.28-1.34 (m, 5H) 1.02 (td, J=7.36, 5.49 Hz, 2H).

84H

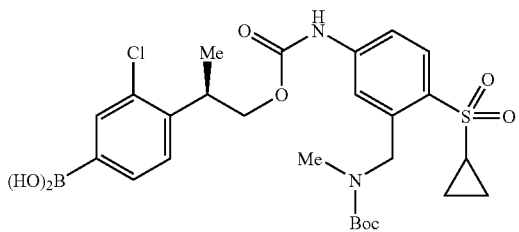 [SMILES: C[C@@H](COC(=O)Nc1ccc(S(=O)(=O)C2CC2)c(CN(C)C(=O)OC(C)(C)C)c1)c1ccc(B(O)O)cc1Cl]

Using a procedure analogous to that used to prepare 29B, 84G (522 mg, 0.847 mmol) was reacted with bis(neopentyl glycolato)diboron), potassium acetate and (1,1'-bis(diphenylphosphino)ferrocene)-dichloropalladium(II). The crude was filter through a silca plug, concentrated and preparative HPLC (CH$_3$CN/H$_2$O, 0.1% TFA) to give 84H (332 mg, 0.572 mmol, 67.4% yield) as a white powder. MS (ESI) m/z 581.3 (M+H)+.

84I

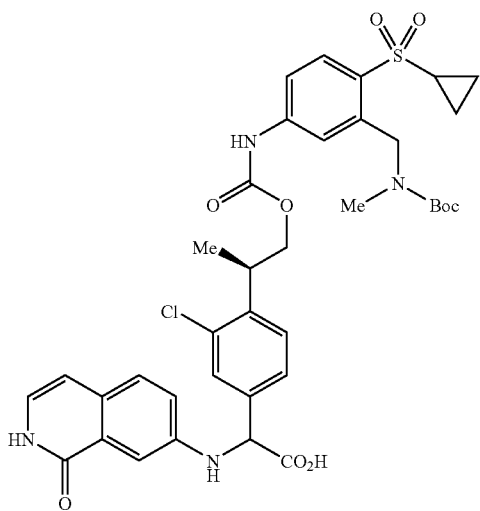 [SMILES: C[C@@H](COC(=O)Nc1ccc(S(=O)(=O)C2CC2)c(CN(C)C(=O)OC(C)(C)C)c1)c1ccc(C(Nc2ccc3cc[nH]c(=O)c3c2)C(=O)O)cc1Cl]

Using a procedure analogous to that used to prepare 1E, 84H (105 mg, 0.181 mmol), Intermediate 3, and glyoxylic acid monohydrate were reacted and purified by prep HPLC to afford 84I (120 mg, 0.159 mmol, 29.8% yield based on three combined runs) as a tan powder. MS (ESI) m/z 753.4 (M+H)+. $^1$H NMR (400 MHz, CD$_3$OD) δ ppm 7.77 (d, J=8.79 Hz, 1H) 7.47-7.63 (m, 4H) 7.43 (d, J=8.25 Hz, 2H) 7.28 (s, 1H) 7.21-7.26 (m, 1H) 6.91 (dd, J=7.15, 2.75 Hz, 1H) 6.55 (dd, J=7.15, 3.30 Hz, 1H) 5.20 (s, 1H) 4.26-4.38 (m, 2H) 3.68-3.77 (m, 1H) 2.94 (s, 3H) 1.50 (s, 4H) 1.33-1.44 (m, 5H) 1.27-1.32 (m, 3H) 1.18 (dt, J=7.15, 4.40 Hz, 2H) 1.02-1.09 (m, 2H).

Example 84

To a solution of 84I (115 mg, 0.153 mmol) in ethyl acetate (2 mL), was added a solution of 4 N HCl in dioxane (3 mL, 12.00 mmol). The resultant suspension was stirred at rt for 30 min, then was concentrated. The resultant residue was dissolved in DMF (4 mL), then was added to a solution of BOP (135 mg, 0.305 mmol) and DMAP (93 mg, 0.763 mmol) in DMF (10 ml) and DCM (40 mL) at 40° C., dropwise via a syringe pump over 2.25 h. The reaction was stirred for 15 min, then was quenched with H$_2$O (1 mL). The reaction mixture was concentrated then was purified by preparative HPLC (Phenomenex Luna 5 µm C18 30x250 (40% to 80% B, 20 min grad, 30 mL/min); solvent A=10% CH$_3$CN/90% H$_2$O/0.1% TFA; solvent B=90% CH$_3$CN/10% H$_2$O/0.1% TFA). The product containing fractions were repurified by chiral HPLC to separate diastereomers (R,R-Whelk-O column (21.1×250 mm, 60:40 (MeOH/EtOH 1:1)/heptane, 20 mL/min), rt=10.97 min) to afford Example 84 (7.0 mg, 0.011 mmol, 7.22% yield) as a white powder. MS (ESI) m/z 635.3 (M+H)+. $^1$H NMR (400 MHz, CD$_3$OD) δ ppm 7.80 (dd, J=8.24, 1.65 Hz, 1H) 7.72 (d, J=8.79 Hz, 1H) 7.58 (d, J=7.70 Hz, 1H) 7.43 (d, J=8.79 Hz, 1H) 7.41 (d, J=2.75 Hz, 1H) 7.36 (d, J=1.65 Hz, 1H) 7.25 (dd, J=8.79, 2.75 Hz, 1H) 6.92 (d, J=7.15 Hz, 1H) 6.84 (dd, J=8.24, 2.20 Hz, 1H) 6.53-6.57 (m, 2H) 5.75 (d, J=17.59 Hz, 1H) 5.72 (s, 1H) 4.60 (t, J=10.72 Hz, 1H) 4.32 (d, J=17.59 Hz, 1H) 4.03 (dd, J=10.72, 3.57 Hz, 1H) 3.76-3.86 (m, 1H) 3.42 (s, 3H) 2.88 (tt, J=7.90, 5.02 Hz, 1H) 1.34 (d, J=7.15 Hz, 3H) 1.25-1.31 (m, 1H) 1.02-1.14 (m, 3H). Analytical HPLC (Method A): Col A: 10.15 min, 93%; Col B: 10.12 min, 94%.

Example 85

[(2R,15R)-17-Methoxy-15-methyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-acetic acid trifluoroacetate

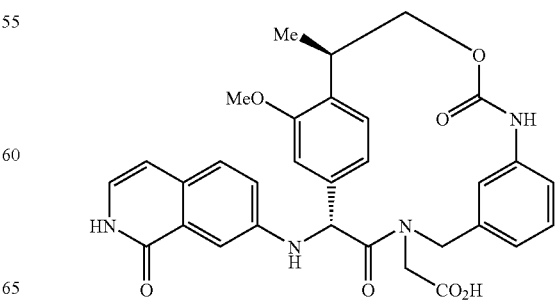

85A

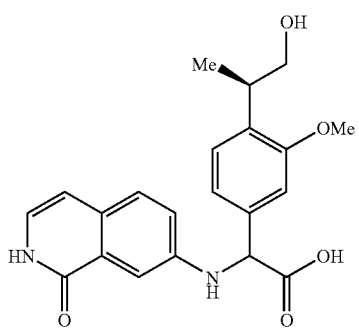 [SMILES: COc1cc(C(Nc2ccc3cc[nH]c(=O)c3c2)C(=O)O)ccc1[C@@H](C)CO]

Intermediate 13 (360 mg, 1.11 mmol), Intermediate 3 (178 mg, 1.11 mmol) and glyoxylic acid monohydrate (102 mg, 1.11 mmol) were suspended in acetonitrile (3.2 mL) and DMF (0.8 mL). The mixture was heated at 100° C. for 10 min in a microwave reactor. The reaction mixture was filtered and the collected solid was dried to afford 85A (166.5 mg, 0.435 mmol, 39.2% yield) as a tan solid. MS (ESI) m/z 383.2 (M+H)$^+$.

85B

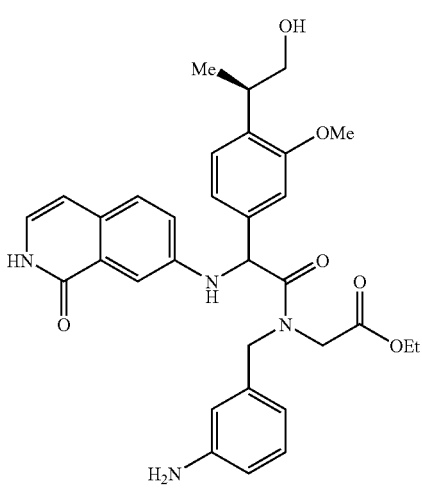 [SMILES: CCOC(=O)CN(Cc1cccc(N)c1)C(=O)C(Nc1ccc2cc[nH]c(=O)c2c1)c1ccc([C@@H](C)CO)c(OC)c1]

A solution of 85A (104.1 mg, 0.173 mmol) in MeOH (3 mL) was hydrogenated (1 atm) over 10% Pd—C (9.1 mg, 8.55 µmol) using a balloon for 20 h. The reaction was filtered and concentrated to afford 85B (105.4 mg, 0.184 mmol, 107% yield). MS (ESI) m/z 573.3 (M+H)$^+$.

85C

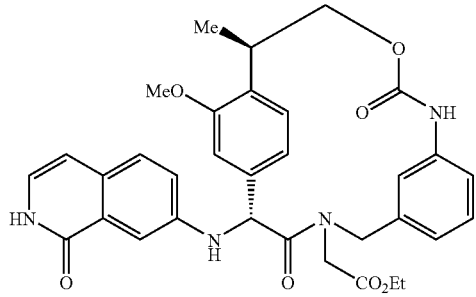 [SMILES: CCOC(=O)CN1Cc2cccc(c2)NC(=O)OC[C@H](C)c2ccc(cc2OC)[C@@H](Nc2ccc3cc[nH]c(=O)c3c2)C1=O]

Phosgene (20% solution in toluene) (0.111 mL, 0.212 mmol) was added dropwise to a solution of 85B (105.4 mg, 0.184 mmol) in acetonitrile (10 mL) at 0° C. After 30 min, additional phosgene (8 uL) was added. After 10 min, nitrogen was bubbled through the reaction mixture for 10 min to remove excess phosgene. This fine suspension was added dropwise in 1 mL aliquots to a solution of triethylamine (0.257 mL, 1.841 mmol) in dichloromethane (150 mL) at reflux over 3 h. Reflux was continued for 1 h after the addition was completed, and the reaction mixture was concentrated. The reaction mixture was purified by preparative HPLC (Phenomenex Luna 5 µm C18 30x250 (20% to 80% B, 20 min grad, 30 mL/min); solvent A=10% CH$_3$CN/90% H$_2$O/0.1% TFA; solvent B=90% CH$_3$CN/10% H$_2$O/0.1% TFA; rt=15.60 min). This material was purified twice chiral HPLC: #1: (R,R-Whelk-O column (21.1×250 mm, 60:40 (MeOH/EtOH 1:1)/heptane, 20 mL/min)); rt=8.23 min); #2: (R,R-Whelk-O column (21.1×250 mm, 50:50 (MeOH/EtOH 1:1)/heptane, 20 mL/min)); rt=7.92 min, to afford 85C (10.4 mg, 0.017 mmol, 9.44% yield) as an off-white solid. MS (ESI) m/z 599.2 (M±H)$^+$.

Example 85

To a solution of 85C (10.4 mg, 0.017 mmol) in THF (0.5 mL) and MeOH (0.250 mL), was added aq. LiOH (1 M) (0.017 mL, 0.017 mmol). The mixture was stirred at rt for 15 min, then was acidified with TFA and concentrated. The mixture was purified by preparative HPLC (YMC ODS-A S-5 uM C18 20×100 (20% to 100% B, 10 min grad, 20 mL/min); solvent A=10% CH$_3$CN/90% H$_2$O/0.1% TFA; solvent B=90% CH$_3$CN/10% H$_2$O/0.1% TFA) to afford Example 85 (11.8 mg, 0.017 mmol, 99% yield) as an off-white powder. MS (ESI) m/z 271.4 (M+H)$^+$. Analytical HPLC (Method A): Col A: 6.37 min, 88%; Col B 6.31 min, 91%.

Example 86

(2R,15R)-7-(1,1-Dioxo-1λ$^6$-perhydro-1,2-thiazin-2-yl)-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

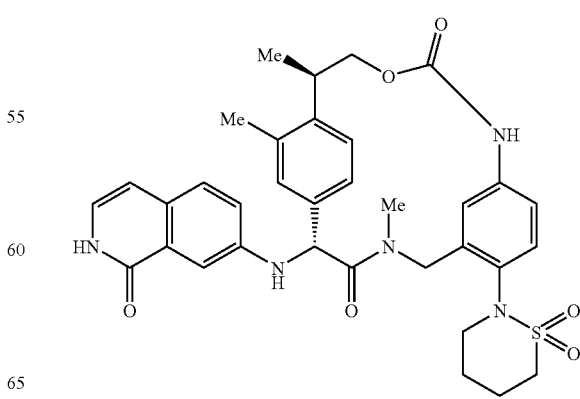

86A

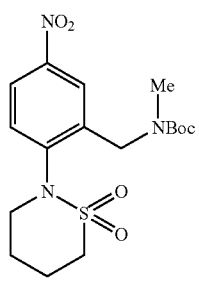

To sealed and degassed reaction vial containing Intermediate 18 (518 mg, 1.500 mmol), butanesultam (243 mg, 1.800 mmol), 9,9-Dimethyl-4,5-bis(diphenylphosphino)xanthene (130 mg, 0.225 mmol), Palladium(II) acetate (33.7 mg, 0.150 mmol), and cesium carbonate (733 mg, 2.250 mmol), was added toluene (5 mL). The mixture was stirred at 90° C. for 20 h, then was concentrated. The residue was diluted with water, extracted with DCM (3×20 mL). The combined organic layer was washed with 1N HCl. sat. $NaHCO_3$ and brine, dried ($Na_2SO_4$) and concentrated. The product was purified by flash chromatography (0-60% EtOAc in Hexanes) to afford 86A (380 mg, 0.951 mmol, 63.4% yield) as a yellow solid. MS (ESI) m/z 400.3 $(M+H)^+$.

86B

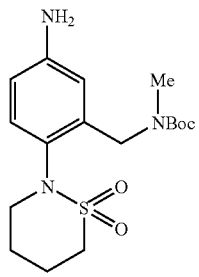

To a solution of 86A (380 mg, 0.951 mmol) in THF (10 mL), was added 10% Pd/C (ca. 50 mg). The mixture was hydrogenated at 40 psi for 2 h. The reaction mixture was filtered and concentrated. The product was purified by flash chromatography (0-80% EtOAc in Hexanes) to afford 86B (280 mg, 0.750 mmol, 79% yield) as a yellow foam. MS (ESI) m/z 370.3 $(M+H)^+$.

86C

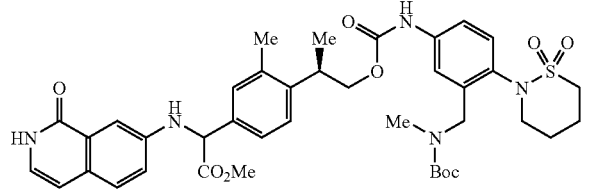 [SMILES: COC(=O)C(Nc1ccc2cc[nH]c(=O)c2c1)c1ccc([C@@H](C)COC(=O)Nc2ccc(N3CCCCS3(=O)=O)c(CN(C)C(=O)OC(C)(C)C)c2)c(C)c1]

To a flask containing 86B (107 mg, 0.289 mmol), sodium bicarbonate (121 mg, 1.446 mmol) in DCM (5 mL) at 0° C., phosgene (20% in toluene) (0.456 mL, 0.867 mmol) was added. The mixture was stirred 0° C. for 5 min and then rt for 2 h. The mixture was filtered and concentrated. The residue was dissolved in DCM (5 mL) and cooled to 0° C. TEA (0.121 mL, 0.867 mmol) was added, followed by Intermediate 16 (110 mg, 0.289 mmol). The mixture was stirred at rt for 16 h, then was concentrated. The product was purified by flash chromatography (0-80% EtOAc in Hexanes) to afford 86C (80 mg, 0.098 mmol, 33.9% yield) as a white solid. MS (ESI) m/z 776.4 $(M+H)^+$.

86D

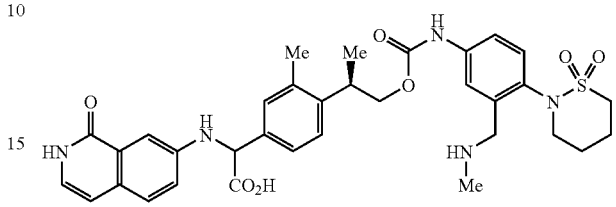

To a solution of 86C (75 mg, 0.097 mmol) in THF (3 mL), was added an aqueous solution of LiOH (1M, 2 mL). The mixture was stirred rt for 1 h, then was concentrated. Water was added, then the aqueous solution was acidified with 10% citric acid and extracted with EtOAc (3×20 mL). The combined organic phase was concentrated. To a solution of the residue in EtOAc (3.00 mL), was add 4N HCl in dioxane (2 ml). The mixture was stirred rt for 1 h, then was concentrated. The product was purified by preparative HPLC to afford 86D (30 mg, 0.045 mmol, 46.9% yield) as a white solid. MS (ESI) m/z 662.7 $(M+H)^+$.

Example 86

To a solution of BOP (40.1 mg, 0.091 mmol) and DMAP (27.7 mg, 0.227 mmol) in DCM (40 mL), was added a solution of 86D (30 mg, 0.045 mmol), N,N-Diisopropylethylamine (7.92 µL, 0.045 mmol) in DMF (10 mL) dropwise over h via a syringe pump. The reaction mixture was concentrated and purified via preparative HPLC. The diastereomers were separated by chiral chromatography (Chiralcel OD-H; 60% EtOH/40% Hep/0.1% DEA; 20 mL/min; peak #1 rt=7.2 min (Example 15), peak #2 rt=13 min (phenylglycine diastereomer)) to afford Example (9.1 mg, 36%) as a white powder. MS (ESI) m/z 644.2 $(M+H)^+$. Analytical HPLC (Method A): Col A: 7.56 min, 99%; Col B: 7.07 min, 99%.

Example 87

2R,15R)-7-Imidazol-1-yl-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

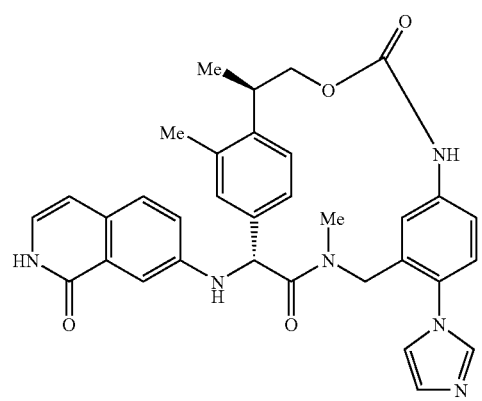 [SMILES: Cc1cc2ccc1[C@@H](C)COC(=O)Nc1ccc(-n3ccnc3)c(c1)CN(C)C(=O)[C@@H]2Nc1ccc2cc[nH]c(=O)c2c1]

87A

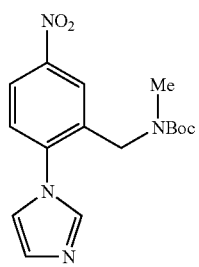

To a degassed reaction vial containing Intermediate 18 (690 mg, 2 mmol), N,N-dimethylglycine (41.2 mg, 0.400 mmol), potassium carbonate (553 mg, 4.00 mmol), imidazole (163 mg, 2.400 mmol), and copper(I) iodide (76 mg, 0.400 mmol), was added DMSO (2 mL). The mixture was stirred 110° C. for 40 h, then was quenched with water and extracted with EtOAc (3×10 mL). The combined organic layer was washed with brine, dried (Na$_2$SO$_4$). The product was purified by flash chromatography (0-100% EtOAc in Hexanes) to afford 87A (333 mg, 1.002 mmol, 50.1% yield) as a yellow solid. MS (ESI) m/z 333.2 (M+H)$^+$. 1H NMR (400 MHz, CD$_3$OD) δ ppm 1.39 (d, J=32.52 Hz, 9H) 2.78 (s, 3H) 4.39 (s, 2H) 7.60 (d, J=7.47 Hz, 1H) 8.00-8.37 (m, 2H).

87B

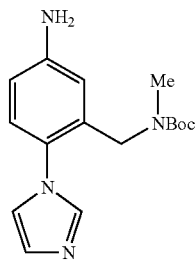 [SMILES: CN(Cc1cc([N+](=O)[O-])ccc1-n1ccnc1)C(=O)OC(C)(C)C]

To a solution of 87A (333 mg, 1.00 mmol) in MeOH (5 mL) and THF (1 mL), was added zinc (655 mg, 10.02 mmol) and ammonium chloride (1.07 g, 20.0 mmol). The mixture was stirred rt for 16 h. The reaction mixture was concentrated then was stirred with EtOAc and Na$_2$CO$_3$. The phases were separated, and the aqueous phase was extracted with EtOAc (2×). The combined organic phase was concentrated. The product was purified by flash chromatography (0-100% EtOAc in Hexanes) to afford 87B (305 mg, 0.978 mmol, 98% yield) as a white form. MS (ESI) m/z 303.4 (M+H)$^+$.

87C

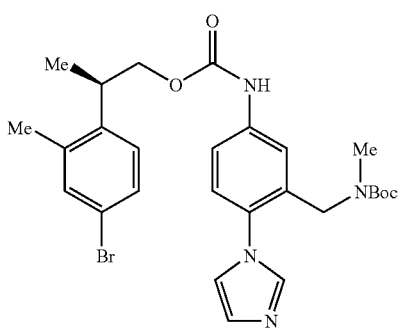

To a solution of Intermediate 8 (246 mg, 1.07 mmol) in DCM (3 mL) at 0° C. was added a 20% solution of phosgene in toluene (2.89 mL, 5.5 mmol). The solution was stirred rt for 17 h, then was bubbled with argon and then concentrated. The residue was dissolved in DCM (3 mL) and was cooled to 0° C. 87B (270 mg, 0.893 mmol) was added, followed by pyridine (0.146 mL, 1.79 mmol). The mixture was stirred rt for 1 h, then was concentrated. The product was purified by flash chromatography (0-90% EtOAc in Hexanes) to afford 87C (462 mg, 0.829 mmol, 93% yield) as a white foam. MS (ESI) m/z 557.4 (M+H)$^+$. $^1$H NMR (400 MHz, CD$_3$OD) δ ppm 1.27 (d, J=7.03 Hz, 3H) 1.41 (d, J=35.59 Hz, 9H) 2.34 (s, 3H) 2.75 (s, 3H) 3.42 (q, J=7.03 Hz, 1H) 4.14-4.30 (m, 4H) 7.13 (s, 1H) 7.16-7.25 (m, 3H) 7.27-7.33 (m, 2H) 7.43 (d, J=7.47 Hz, 1H) 7.54 (s, 1H) 7.74 (s, 1H).

87D

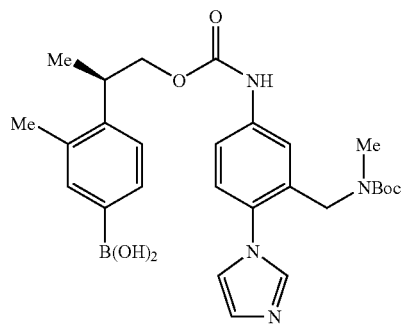 [SMILES: Cc1cc(B(O)O)ccc1[C@@H](C)COC(=O)Nc1ccc(-n2ccnc2)c(CN(C)C(=O)OC(C)(C)C)c1]

Using a procedure analogous to that used to prepare 29B, 87C (458 mg, 0.822 mmol) was reacted with bis(neopentyl glycolato)diboron), potassium acetate and (1,1'-bis(diphenylphosphino)ferrocene)-dichloropalladium(II). The crude was purified by preparative HPLC to afford 87D (429 mg, 100%). MS (ESI) m/z 523.2 (M+H)$^+$.

87E

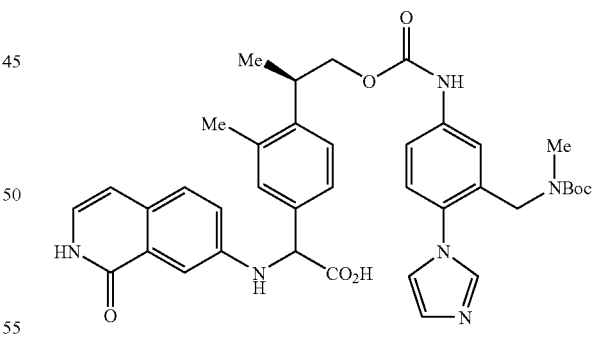

To a reaction vial containing 87D (446 mg, 0.854 mmol), Intermediate 3 (151 mg, 0.94 mmol), and glyoxylic acid monohydrate (79 mg, 0.854 mmol), were added CH$_3$CN (2 mL) and DMF (0.5 mL). The mixture was sealed and irradiated in a microwave reactor at 100° C. for 10 min. The reaction was quenched with water and extracted with EtOAc (3×10 mL). The combined organic layer was washed with water and brine, dried (Na$_2$SO$_4$) and concentrated. The crude product was purified by preparative reverse phase HPLC to afford 87E (292 mg, 41.8% yield) as a brown solid. MS (ESI) m/z 695.5 (M+H)$^+$.

87F

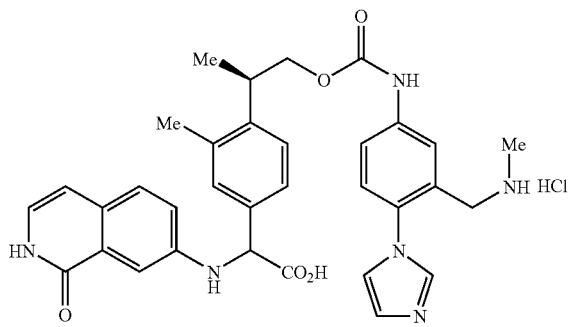 [SMILES: CNCc1cc(NC(=O)OC[C@H](C)c2ccc(C(Nc3ccc4cc[nH]c(=O)c4c3)C(=O)O)cc2C)ccc1-n1ccnc1 ; Cl]

87E (292 mg, 0.420 mmol) was mixed with 4 N HCl in dioxane (3 mL, 12 mmol). The mixture was stirred rt for 1 h, then was concentrated and purified via preparative HPLC to afford 87F (65 mg, 0.109 mmol, 26.0% yield) as a yellow solid. MS (ESI) m/z 595.5 (M+H)$^+$.

Example 87

To a solution of BOP (113 mg, 0.256 mmol) and DMAP (78 mg, 0.639 mmol) in DCM (40 mL) at rt, was added a solution of 87F (76 mg, 0.128 mmol) and N,N-Diisopropylethylamine (0.022 mL, 0.128 mmol) in DMF (10 mL) over 10 h via a syringe pump. The reaction was then concentrated and purified via preparative HPLC to give the cyclized product as a mixture of diastereomers. Diastereomers were separated by chiral chromatography (Chiralcel OD-H; 40% EtOH/60% Hep/0.1% DEA; 20 mL/min; peak #1 rt=7 min (Example 87), peak #2 rt=12.9 min (phenylglycine diastereomer)) to afford Example 87 (9.0 mg) as an off-white solid, MS (ESI) m/z 577.3 (M+H)$^+$. $^1$H NMR (400 MHz, METHANOL-d$_3$) δ ppm 7.99 (s, 1H) 7.63 (dd, J=8.25, 1.65 Hz, 1H) 7.44 (d, J=7.70 Hz, 1H) 7.39 (d, J=8.79 Hz, 1H) 7.35-7.38 (m, 2H) 7.18-7.24 (m, 3H) 7.16 (d, J=1.10 Hz, 1H) 6.89 (d, J=7.15 Hz, 1H) 6.82 (dd, J=8.24, 2.20 Hz, 1H) 6.53 (d, J=7.15 Hz, 1H) 6.28 (d, J=2.20 Hz, 1H) 5.61 (s, 1H) 5.01 (d, J=16.49 Hz, 1H) 4.66 (t, J=10.99 Hz, 1H) 3.98 (dd, J=10.72, 4.12 Hz, 1H) 3.76 (d, J=16.49 Hz, 1H) 3.43-3.54 (m, 1H) 3.36 (s, 3H) 2.31 (s, 3H) 1.31 (d, J=7.15 Hz, 3H). Analytical HPLC (Method A): Col A: 2.59 min, 99%; Col B: 3.63 min, 95%.

Example 88

(2R,15R)-7-Bromo-18-fluoro-20-methoxy-4,15-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

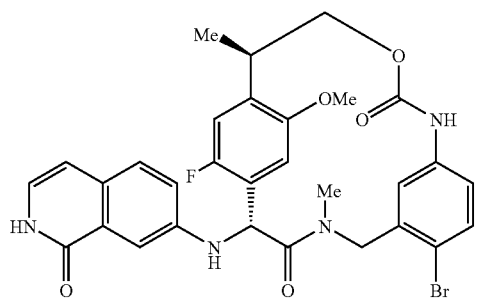 [SMILES: COc1cc2c(F)cc1[C@@H](C)COC(=O)Nc1ccc(Br)c(c1)CN(C)C(=O)[C@@H]2Nc1ccc2cc[nH]c(=O)c2c1]

88A

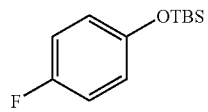 [SMILES: CC(C)(C)[Si](C)(C)Oc1ccc(F)cc1]

To a solution of 4-fluorophenol (30 g, 268 mmol) in DMF (200 mL) at 0° C., was added tert-butyldimethylchlorosilane (40.3 g, 268 mmol). The mixture was stirred until the reactant was fully dissolved, then imidazole (20.04 g, 294 mmol) was added in 4 portions over 5 min. The mixture was stirred at 0° C. for 1 h, then at rt for 1.5 h. Additional TBSCl (1.0 g, 6.6 mmol) was added and the mixture was stirred at rt. The mixture was stirred for 1 h, then was placed in a water bath and quenched with H$_2$O (300 mL). The mixture was stirred for 30 min. The mixture was extracted with hexanes (3×). The combined organic phase was washed with H$_2$O, 10% Na$_2$CO$_3$, H$_2$O and brine. The organic phase was dried (Na$_2$SO$_4$), filtered through a 1" pad of SiO$_2$, eluting with 5% EtOAc/hexanes (200 mL), and concentrated to afford 88A (60.2 g, 266 mmol, 99% yield) as a colorless oil.

88B

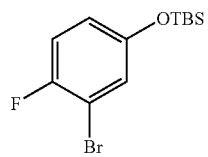 [SMILES: CC(C)(C)[Si](C)(C)Oc1ccc(F)c(Br)c1]

To a solution of 88A (31.3 g, 138 mmol) in THF (300 mL) at −78° C., was added a solution of sec-butyllithium (1.4 M, cyclohexane) (109 mL, 152 mmol), dropwise over 30 min. The stirrable, yellow suspension was stirred at −78° C. for 45 min. 1,2-dibromo-1,1,2,2-tetrafluoroethane (19.78 mL, 166 mmol) was added over 35 min. The mixture was stirred at −78° C. for 30 min, then was removed from the cooling bath and stirred for 1.5 h. The mixture was quenched with sat. NH$_4$Cl, then was diluted with hexanes and water. The phase were separated, then the organic phase was washed with brine, dried (Na$_2$SO$_4$), filtered through SiO$_2$, eluting with hexanes, and concentrated. The crude product was dissolved in hexanes, loaded onto a 330 g column and eluted with hexanes to afford 88B (24.6 g, 81 mmol, 58.3% yield) colorless oil. (~75% purity by NMR).

88C

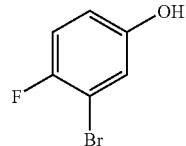

To a solution of 88B (24.4 g, 80 mmol) in THF (160 mL) at 0° C., was added TBAF, 1 M in THF (80 mL, 80 mmol). The mixture was stirred at 0° C. for 0.5 h. The mixture was concentrated to remove THF and TBS-F. The mixture was diluted with EtOAc/hexanes (1:1), then was washed with H$_2$O (3×) and brine, dried (Na$_2$SO$_4$), filtered through 1" SiO$_2$ and concentrated. The crude product was dissolved in hexanes, loaded onto a 330 g column and eluted with a gradient from 0 to 50% ethyl acetate/hexanes to afford 88C (12.5 g, 65.4 mmol, 82% yield) as a pale yellow oil. (~75% purity by NMR).

88D

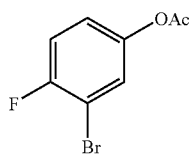

To a solution of 88C (12.5 g, 65.4 mmol) in DCM (150 mL), were added TEA (13.7 mL, 98 mmol), acetic anhydride (6.79 mL, 72.0 mmol) and DMAP (100 mg, 0.819 mmol). The mixture was stirred at rt for 17 h, then was concentrated. The crude product was dissolved in chloroform/hexanes (~1:2), loaded onto a 330 g column and eluted with a gradient from 0 to 20% ethyl acetate/hexanes to afford 88D (10.0 g, 42.9 mmol, 65.6% yield) as a white powder.

88E

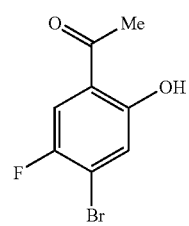

88D and another batch prepared in the same fashion (16.76 g total, 71.9 mmol) and aluminum trichloride (17.26 g, 129 mmol) were combined in a round-bottom flask. The mixture was lowered into an oil bath, then gradually heated to 1.65° C. to give a brown oil. The mix was stirred at 165° C. for 3 h. Upon cooling to rt, the reaction mixture solidified to a brown solid. The solid was broken up and suspended in DCM, then poured carefully into 2 N HCl, giving two phases and some insoluble solids. The layers were separated, then the aqueous phase was extracted with DCM (2×). The combined organic phase was washed with $H_2O$ and brine, dried ($Na_2SO_4$), filtered through $SiO_2$ and concentrated. The crude product was dissolved in chloroform, loaded onto a 330 g column and eluted with a gradient from 0 to 30% ethyl acetate/hexanes to afford 88E (14.9 g, 63.9 mmol, 89% yield) as an off-white solid. MS (ESI) m/z 256.3 (M+H)$^+$.

88F:
1-(4-bromo-5-fluoro-2-methoxyphenyl)ethanone

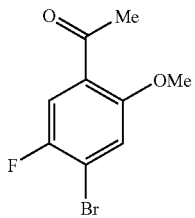 [SMILES: COc1cc(Br)c(F)cc1C(C)=O]

To a solution of 88E (14.9 g, 63.9 mmol) in Acetone (150 mL), were added potassium carbonate (10.60 g, 77 mmol) and iodomethane (8.00 mL, 128 mmol). The mixture was stirred at 50° C. for 2 h. The mixture was cooled to rt, diluted with 300 mL hexanes, then filtered through 1" $SiO_2$, eluting with 20% EtOAc/hexanes. The filtrate was concentrated. The crude product was dissolved in chloroform, loaded onto a 330 g column and eluted with a gradient from 0 to 40% ethyl acetate/hexanes to afford after concentration 88F (15.28 g, 61.8 mmol, 97% yield) as an off-white crystalline solid. MS (ESI) m/z 247.0 (M+H)$^+$.

88G

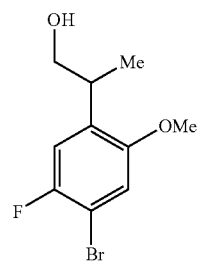 [SMILES: COc1cc(Br)c(F)cc1C(C)CO]

Using a procedures analogous to that used to prepare Intermediate 8C and Intermediate 8D, 88F and another batch prepared in the same fashion (16.05 g, 65.0 mmol) was reacted with (methoxymethyl)triphenylphosphonium chloride, HCl and then sodium borohydride. The crude was purified by column chromatography (0 to 50% ethyl acetate/hexanes) to afford 88G (16.1 g, 61.2 mmol, 94% yield) as a brown oil. MS (ESI) m/z 245.1 (M+H)$^+$.

88H

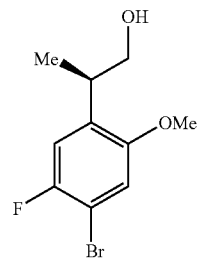 [SMILES: COc1cc(Br)c(F)cc1[C@@H](C)CO]

Chiral separation of 88G to afford 88H was accomplished by SFC using a Chiralpak IA 30×250 mm 5 micron column; $CO_2$/IPA: (95/5); Flow Rate: 65 ml/min @ 40° C.; RT$_1$: 16.0 min (S-stereoisomer) RT$_2$: 18.2 min (R-stereoisomer). MS (ESI) m/z 245.2 (M+H)$^+$.

88I

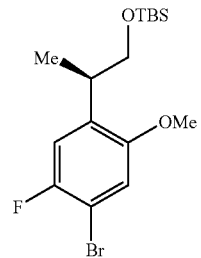 [SMILES: COc1cc(Br)c(F)cc1[C@@H](C)CO[Si](C)(C)C(C)(C)C]

To a solution of 88H (320 mg, 1.216 mmol) in DMF (6 mL) at rt, were added imidazole (124 mg, 1.824 mmol) and TBS-Cl (202 mg, 1.338 mmol). The mixture was stirred at rt for 22 h. The reaction mixture was diluted with water, then was extracted with hexanes (2×). The combined organic phase was washed with H$_2$O and brine, dried (Na$_2$SO$_4$) and concentrated. The crude product was dissolved in hexanes, loaded onto a 12 g column and eluted with a gradient from 0 to 5% ethyl acetate/hexanes to afford after concentration 88I (440 mg, 1.166 mmol, 96% yield) as a colorless oil. MS (ESI) m/z 245.2 (M+H)$^+$.

88J

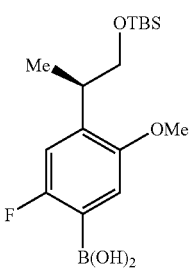 [SMILES: COc1cc(B(O)O)c(F)cc1[C@@H](C)CO[Si](C)(C)C(C)(C)C]

To a solution of 88I (435 mg, 1.153 mmol) at −78° C., was added 1.6 M BuLi in hexanes (1.081 mL, 1.729 mmol). The mixture was stirred at −78° C. for 15 min, then trimethyl borate (0.262 mL, 2.305 mmol) was added. The mixture was stirred −78° C. for 15 min, then was removed from the cooling bath and was stirred for 1.5 h. The reaction was diluted with EtOAc, then was washed with 1 N HCl, H$_2$O and brine, dried (Na$_2$SO$_4$), filtered through a 1" pad of SiO$_2$ and concentrated. The crude product was dissolved in hexanes, loaded onto a 12 g column and eluted with a gradient from 0 to 50% ethyl acetate/hexanes (monitored at 230 nm, eluted from 23-38% EtOAc) to afford after concentration 88J (287 mg, 0.838 mmol, 72.7% yield) as a white solid. MS (ESI) m/z 211.1 (M+H)$^+$.

88K

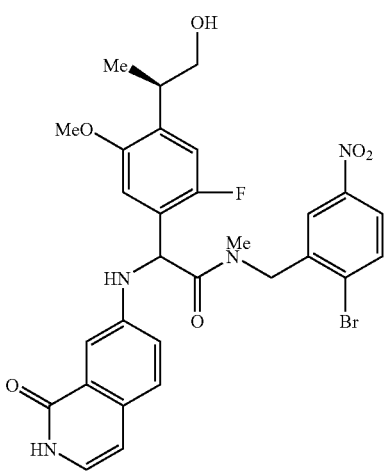 [SMILES: COc1cc(C(Nc2ccc3cc[nH]c(=O)c3c2)C(=O)N(C)Cc2cc([N+](=O)[O-])ccc2Br)c(F)cc1[C@@H](C)CO]

Using a procedure analogous to that used to prepare 41E, a mixture of 88J (284 mg, 0.830 mmol), Intermediate 3 and 2-oxoacetic acid hydrate were reacted. The resulting solution was reacted with Intermediate 17 (244 mg, 0.996 mmol) using BOP and DIEA. The crude product was purified by column chromatography (1 to 20% methanol/methylene chloride) to afford 88K (374 mg, 72%). MS (ESI) m/z 627.2 (M+H)$^+$.

88L

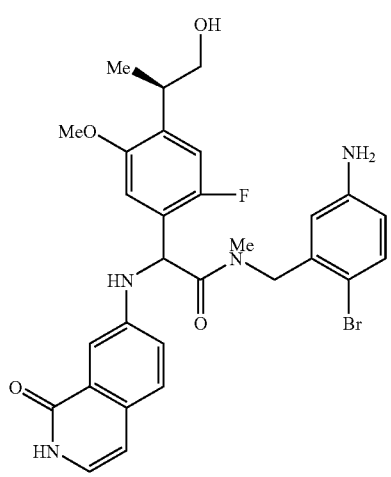 [SMILES: COc1cc(C(Nc2ccc3cc[nH]c(=O)c3c2)C(=O)N(C)Cc2cc(N)ccc2Br)c(F)cc1[C@@H](C)CO]

To a solution of 88K (370 mg, 0.590 mmol) dissolved in THF (5 mL), then methanol (10 mL) was added. To this solution, zinc (dust) (386 mg, 5.90 mmol) and ammonium chloride (631 mg, 11.79 mmol) were added. The resulting suspension was stirred at 50° C. for 2 h. The mixture was concentrated, then sat. Na$_2$CO$_3$ (30 mL) and EtOAc (50 mL) were added, and the suspension was stirred vigorously for 10 min. The layers were separated, then the aqueous phase was extracted with EtOAc. The combined organic extracts were washed with brine, dried (Na$_2$SO$_4$) and concentrated. The crude product was dissolved in dichloromethane, loaded onto a 40 g column and eluted with a gradient from 1 to 15% methanol/methylene chloride to afford after concentration to afford 88L (220 mg, 0.368 mmol, 62.4% yield) as a yellow glass. MS (ESI) m/z 597.2 (M+H)$^+$.

Example 88

To a solution of 88L (214 mg, 0.358 mmol) in acetonitrile (15 mL) and DCM (5 mL) at 0° C., was added a solution of phosgene (20% in toluene) (195 mg, 0.394 mmol). The resultant suspension was stirred at 0° C. for 30 min, then at rt for 30 min. The mixture was diluted with acetonitrile (20 mL), then was added drop wise via an addition funnel into a solution of TEA (0.499 mL, 3.58 mmol) in DCM (70 mL) at 40° C. over 1.5 h. The yellow solution was stirred at 40° C. for 30 min, then was concentrated. The crude product was purified by preparative HPLC (Phenomenex Axia Luna 5 μm C18 30X100 (20% to 80% B, 10 min grad, 40 mL/min); solvent A=10% CH$_3$CN/90% H$_2$O/0.1% TFA; solvent B=90% CH$_3$CN/10% H$_2$O/0.1% TFA; RT=7.68 min). The mixture of diastereomers was separated by chiral chromatography (R,R-Whelk-O column 21.1×250 mm, MeOH/EtOH (1:1), 20 mL/min; peak 1: rt=4.72 min—phenylglycine diastereomer); peak 2: rt=8.25 min—Example 88). Example 88 (44 mg, 39% yield) was isolated as an off-white solid. MS (ESI) m/z 623.2 (M+H)$^+$. $^1$H NMR (400 MHz, METHANOL-d$_3$) δ ppm 7.50

(d, J=2.20 Hz, 1H) 7.42 (dd, J=11.54, 8.79 Hz, 2H) 7.26 (dd., J=8.79, 2.75 Hz, 1H) 7.20 (d, J=10.44 Hz, 1H) 6.92 (d, J=7.15 Hz, 2H) 6.64 (dd, J=8.52, 2.47 Hz, 1H) 6.55 (d, J=6.60 Hz, 1H) 6.20 (d, J=2.20 Hz, 1H) 6.01 (s, 1H) 5.33 (d, J=17.04 Hz, 1H) 4.52 (t, J=10.72 Hz, 1H) 3.86-3.96 (m, 2H) 3.68-3.79 (m, 1H) 3.60 (s, 3H) 1.24 (d, J=7.15 Hz, 3H). Analytical HPLC (Method A): Col A: 10.55 min, 99%; Col B: 9.99 min, 98%.

Example 89

(2R,15R)-19-Fluoro-17-methoxy-4,15-dimethyl-2-(1-oxo-1,2-dihydro-isoquinolin-7-ylamino)-7-phenyl-13-oxa-4,11-diaza-tricyclo[14.2.2.1$^{6,10}$]henicosa-1(19),6,8,10(21),16(20),17-hexaene-3,12-dione trifluoroacetate

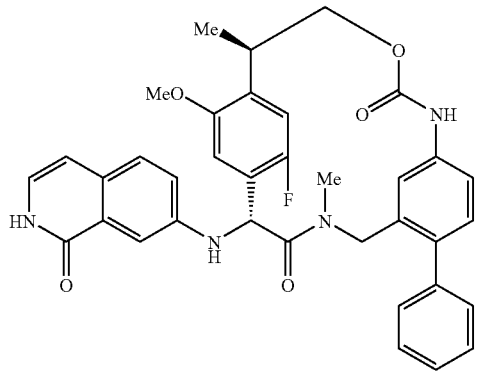 [SMILES: COc1cc2c(F)cc1[C@@H](C)COC(=O)Nc1ccc(-c3ccccc3)c(c1)CN(C)C(=O)[C@@H]2Nc1ccc2cc[nH]c(=O)c2c1]

To a sealable reaction vial containing Example 88 (36.7 mg, 0.059 mmol), 1,2,3,4,5-pentaphenyl-1-(di-t-butylphosphino)ferrocene (Q-phos) (12.66 mg, 0.018 mmol), phenylboronic acid (71.8 mg, 0.589 mmol), and potassium phosphate (205 mg, 1.177 mmol), was added dioxane (1 mL). The mixture was degassed by evacuation and flushing with argon (3×). Pd$_2$(dba)$_3$ (8.09 mg, 8.83 µmol) was added. The mixture was degassed (2×). The vial was sealed, then stirred at 105° C. for 2.5 h. The reaction mixture was diluted with DMSO (0.5 mL) and chloroform (3 mL), and filtered, the filter was rinsed with chloroform and methanol. Solvent was removed under reduced pressure. The crude product was purified by preparative HPLC (Phenomenex Axia Luna 5 µm C18 30X100 (20% to 80% B, 10 min grad, 40 mL/min); solvent A=10% CH$_3$CN/90% H$_2$O/0.1% TFA; solvent B=90% CH$_3$CN/10% H$_2$O/0.1% TFA; RT=7.40 min) to afford Example 89 (25.1 mg, 0.034 mmol, 58.0% yield) as a white powder. MS (ESI) m/z 621.3 (M+H)$^+$. 1H NMR (400 MHz, METHANOL-d$_4$) δ ppm 7.47 (d, J=2.20 Hz, 1H) 7.39-7.46 (m, 3H) 7.28-7.37 (m, 3H) 7.26 (dd, J=8.52, 2.47 Hz, 1H) 7.19 (d, J=10.44 Hz, 1H) 7.09 (d, J=8.25 Hz, 1H) 6.98 (d, J=6.05 Hz, 1H) 6.92 (d, J=7.15 Hz, 1H) 6.79 (dd, J=8.25, 2.20 Hz, 1H) 6.55 (d, J=7.15 Hz, 1H) 6.30 (d, J=2.20 Hz, 1H) 5.97 (s, 1H) 5.31 (d, J=16.49 Hz, 1H) 4.48 (t, J=10.72 Hz, 1H) 4.05 (d, J=8.25 Hz, 1H) 3.70-3.82 (m, 1H) 3.79 (d, J=16.49 Hz, 1H) 3.68 (s, 3H) 3.22 (s, 3H) 1.27 (d, J=7.15 Hz, 3H). Analytical HPLC (Method A): Col A: 9.09 min, 99%; Col B: 8.70 min, 99%.

Example 90

(2R,15R)-4,15,17-Trimethyl-2-(1-oxo-1,2-dihydro-isoquinolin-7-ylamino)-7-(2-oxo-piperidin-1-yl)-13-oxa-4,11-diaza-tricyclo[14.2.2.1$^{6,10}$]henicosa-1(19),6,8,10(21),16(20),17-hexaene-3,12-dione

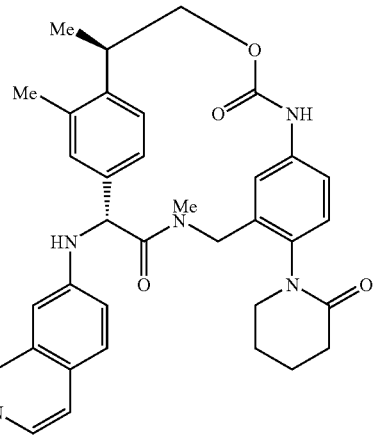

90A

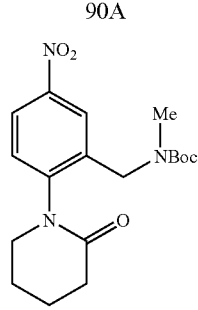

In a sealable reaction tube was mixed Intermediate 18 (500 mg, 1.448 mmol), piperidin-2-one (172 mg, 1.738 mmol), 9,9-Dimethyl-4,5-bis(diphenylphosphino)xanthene (126 mg, 0.217 mmol), Pd$_2$(dba)$_3$ (66.3 mg, 0.072 mmol), and cesium carbonate (661 mg, 2.028 mmol). The tube was sealed, then evacuated and filled with argon (3×). Dioxane (1.5 mL) was added. The mixture was degassed (3×), then was stirred at 100° C. for 18 h. The mixture was diluted with EtOAc (30 mL), then was filtered. The filtrate was concentrated. The crude product was dissolved in chloroform, loaded onto a 40 g column and eluted with a gradient from 0 to 100% ethyl acetate/hexanes. Product eluted at 100% EtOAc. The product containing fractions were concentrated to afford 90A (166 mg, 0.457 mmol, 31.5% yield) as an off-white foam. MS (ESI) m/z 364.2 (M+H)$^+$.

90B

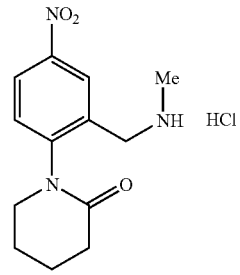 [SMILES: CNCc1cc([N+](=O)[O-])ccc1N1CCCCC1=O ; Cl]

To a solution of 90A (162 mg, 0.446 mmol) in ethyl acetate (1 mL), was added 4N HCl in dioxane (1 mL, 4.00 mmol). The mixture was stirred at rt for 1.5 h, then was concentrated to afford 90B (134 mg, 0.447 mmol, 100% yield) as a pale yellow foam. MS (ESI) rz/z 264.2 (M+H)+. 1H NMR (400 MHz, METHANOL-d4) δ ppm 8.54 (d, J=2.78 Hz, 1H) 8.42 (dd, J=8.84, 2.53 Hz, 1H) 7.72 (d, J=8.84 Hz, 1H) 4.15-4.28 (m, 1H) 4.06-4.14 (m, 1H) 3.88-4.00 (m, 1H) 3.47-3.59 (m, 0H) 2.81 (s, 3H) 2.65-2.77 (m, 1H) 2.54-2.65 (m, 0H) 1.98-2.10 (m, 4H).

90C

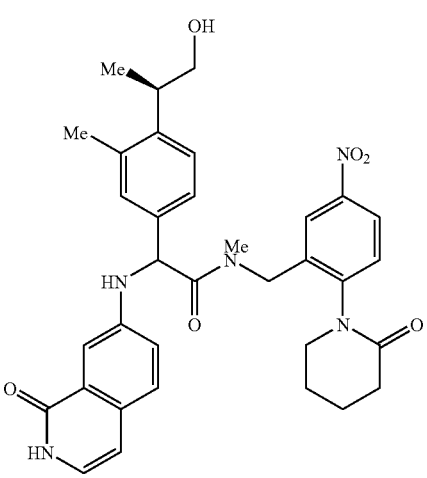 [SMILES: Cc1cc(C(Nc2ccc3cc[nH]c(=O)c3c2)C(=O)N(C)Cc2cc([N+](=O)[O-])ccc2N2CCCCC2=O)ccc1[C@@H](C)CO]

Using a procedure analogous to that used to prepare 41E, a mixture of Intermediate 10 (95 mg, 0.308 mmol), Intermediate 3 and 2-oxoacetic acid hydrate were reacted. The resulting solution was reacted with 90B (130 mg, 0.434 mmol) using BOP and DIEA. The crude product was purified column chromatography (1 to 15% methanol/methylene chloride) to afford 9° C. (103. mg, 0.168 mmol, 54.6% yield) as a yellow solid. MS (ESI) m/z 612.3 (M+H)+.

90D

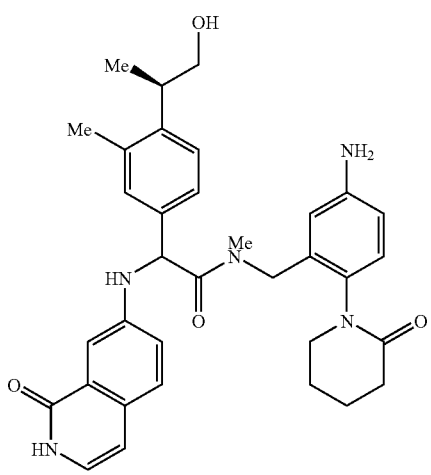 [SMILES: Cc1cc(C(Nc2ccc3cc[nH]c(=O)c3c2)C(=O)N(C)Cc2cc(N)ccc2N2CCCCC2=O)ccc1[C@@H](C)CO]

To a solution of 9° C. (103 mg, 0.168 mmol) in MeOH (5 mL), was added 10% Pd on carbon (20 mg, 0.019 mmol). The mixture was evacuated and flushed with H2, then was stirred under an atmosphere of H2 for 7.5 h. The reaction mixture was filtered and concentrated to afford 90D (88 mg, 0.151 mmol, 90% yield) as an off-white solid. MS (ESI) m/z 582.3 (M+H)+.

Example 90

A solution of 90D (88 mg, 0.151 mmol) in acetonitrile (3 mL) and DCM (2 mL), was cooled to 0° C., giving a suspension. To this suspension, was added phosgene (20% in toluene) (82 mg, 0.166 mmol), to give a very fine suspension. The mixture was stirred at 0° C. for 30 min. The mixture was bubbled with argon for 10 min to remove excess phosgene. The fine suspension was diluted with 3 mL acetonitrile, loaded into a 10 mL syringe and was added via a syringe pump over 1.5 h into a solution of TEA (0.211 mL, 1.513 mmol) in DCM (50 mL) at 40° C. The yellow solution was stirred for an additional 30 min, then was concentrated. The crude product was purified by preparative HPLC (Phenomenex Axia Luna 5 μm C18 30X100 (20% to 80% B, 20 min grad, 40 mL/min); solvent A=10% CH3CN/90% H2O/0.1% TFA; solvent B=90% CH3CN/10% H2O/0.1% TFA; RT=5.29 min). The diastereomers were separated by chiral chromatography (Chiralcel OD-H 250×20 mm (L X OD); 20 mL/min 50:50 (1:1 MeOH/EtOH)/heptane; RT=4.60 min (Example 90) and 7.65 min (phenylglycine diastereomer) to afford Example 90 (13.4 mg, 0.022 mmol, 29.2% yield) as a white powder. MS (ESI) m/z 608.3 (M+H)+. Analytical HPLC (Method A): Col A: 6.57 min, 99%; Col B: 6.60 min, 98%.

Example 91

(2R,15R)-4,15,17-Trimethyl-7-(1-oxo-3,4-dihydro-1H-isoquinolin-2-yl)-2-(1-oxo-1,2-dihydro-isoquinolin-7-ylamino)-13-oxa-4,11-diaza-tricyclo[14.2.2.1^{6,10}]henicosa-1(19),6,8,10(21),16(20),17-hexaene-3,12-dione

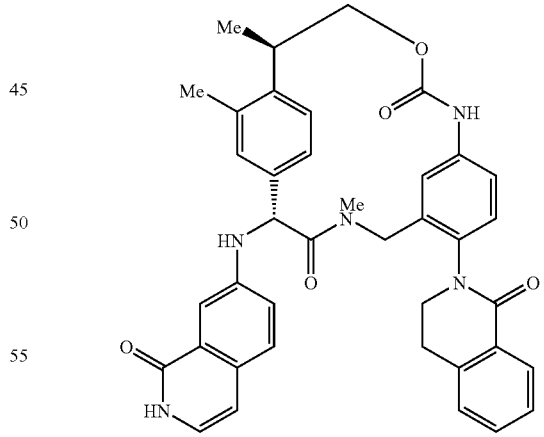

According to the sequence for the preparation of Example 90, replacement of piperidin-2-one with 3,4-dihydroisoquinolin-1(2H)-one afforded Example 91. Chiralcel OD-H 250×20 mm (L X OD); 20 mL/min 40:60 (1:1 MeOH/EtOH)/heptane RT=8.63 min (Example 91) and 13.78 min (phenylglycine diastereomer). MS (ESI) m/z 656.3 (M+H)+. Analytical HPLC (Method A): Col A: 7.17 min, 97%; Col B: 7.19 min, 97%.

Example 92

(2R,15R)-15-Ethyl-4,17-dimethyl-2-(1-oxo-1,2-di-hydro-isoquinolin-7-ylamino)-13-oxa-4,11-diaza-tricyclo[14.2.2.1⁶,¹⁰]henicosa-1(19),6,8,10(21),16(20),17-hexaene-3,12-dione

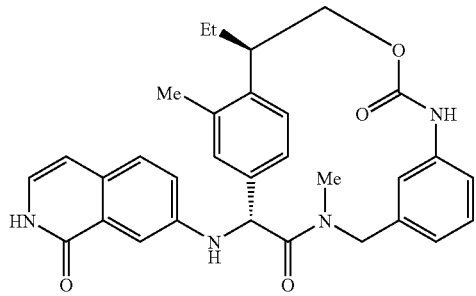 [SMILES: CC[C@H]1COC(=O)Nc2cccc(c2)CN(C)C(=O)[C@H](Nc2ccc3cc[nH]c(=O)c3c2)c2ccc1c(C)c2]

According to the sequence for the preparation of Example 81, replacement of Intermediate 8 with 77F afforded Example 92. MS (ESI) m/z 525.3 (M+H)⁺. ¹H-NMR (400 MHz, CD₃OD) δ ppm 0.92 (t, J=7.15 Hz, 3H) 1.84-2.01 (m, 2H) 2.46 (s, 3H) 3.05-3.19 (m, 1H) 3.25 (s, 3H) 3.87 (d, J=15.94 Hz, 1H) 4.05 (dd, J=11.27, 3.02 Hz, 1H) 4.81 (dd, J=10.99, 2.75 Hz, 1H) 5.41 (d, J=16.49 Hz, 1H) 5.62 (s, 1H) 6.09 (s, 1H) 6.55 (d, J=7.15 Hz, 1H) 6.68 (d, J=7.15 Hz, 1H) 6.90 (t, J=7.42 Hz, 1H) 7.16 (t, J=7.70 Hz, 1H) 7.21-7.27 (m, 3H) 7.39-7.46 (m, 2H) 7.56 (s, 1H).

Example 93

(2R,15R)-7-Fluoro-4,15,17-trimethyl-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaene-3,12-dione

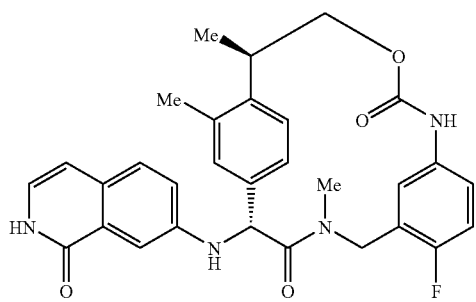 [SMILES: Cc1cc2ccc1[C@@H](C)COC(=O)Nc1ccc(F)c(c1)CN(C)C(=O)[C@@H]2Nc1ccc2cc[nH]c(=O)c2c1]

93A

Using procedures analogous to that used to prepare Intermediate 17 and Intermediate 18, 2-fluoro-5-nitrobenzaldehyde (3.0 g, 17.74 mmol) was reacted with methylamine and sodium borohydride (1.342 g, 35.5 mmol) followed by BOC-Anhydride (7.74 g, 35.5 mmol). The crude product was purified by flash chromatography: (120 g) 0-30% EtOAc/hexanes to give 93A (4.117 g, 14.48 mmol, 82% yield) as a yellow oil. MS (ESI) m/z 229.1 (M+H)⁺.-tBu.

93B

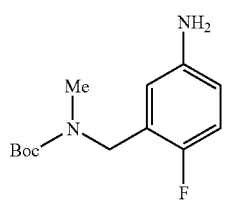 [SMILES: CN(Cc1cc(N)ccc1F)C(=O)OC(C)(C)C]

93A (4.117 g, 14.48 mmol) was dissolved in MeOH (100 mL), degassed (3× vacuum/argon). Pd—C (0.771 g, 0.724 mmol) was added, the suspension was degassed again (3×), and hydrogenated (1 atm) for 2 h. Pd—C was removed by filtration, and MeOH was removed under reduced pressure to give 93B (3.650 g, 14.35 mmol, 99% yield) as a brown oil. MS (ESI) m/z 255.2 (M+H)⁺.

93C: {3-[(tert-Butoxycarbonyl-methyl-amino)-methyl]-4-fluoro-phenyl}-carbamic acid (R)-2-(4-bromo-2-methyl-phenyl)-propyl ester

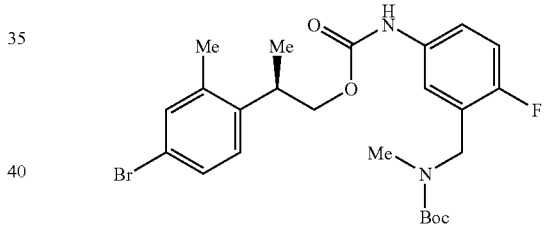

Using a procedure analogous to that used to prepare 29A, 93B (0.600 g, 2.359 mmol) was reacted with sodium bicarbonate and phosgene followed by Intermediate 8 (0.360 g, 1.573 mmol) and TEA. The crude product was added to a silica gel column (40 g) and was eluted with EtOAc/hexanes (0-75%) to give to give 93C (0.752 g, 1.476 mmol, 94% yield) as a white foam. MS (ESI) m/z 455.2 (M±H)⁺.-tBu.

93D

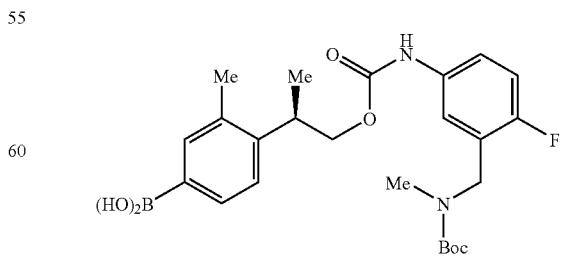

Using a procedure analogous to that used to prepare 29B, 93C (0.752 g, 1.476 mmol) was reacted with bis(neopentyl glycolato)diboron), potassium acetate and (1,1'-bis(diphenylphosphino)ferrocene)-dichloropalladium(II). The crude was filtered through a plug of silica gel, concentrated, and purified by preparative HPLC (CH$_3$CN/H$_2$O, 0.1% TFA) to give 93D (0.464 g, 0.978 mmol, 66.3% yield) as an off-white solid. MS (ESI) m/z 497.2 (M+Na)$^+$.

93E

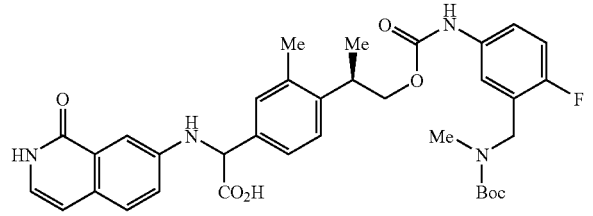 [SMILES: Cc1cc(C(Nc2ccc3cc[nH]c(=O)c3c2)C(=O)O)ccc1[C@@H](C)COC(=O)Nc1ccc(F)c(CN(C)C(=O)OC(C)(C)C)c1]

In a microwave reaction vial, 93D (0.464 g, 0.978 mmol), Intermediate 3 (0.157 g, 0.978 mmol), and glyoxylic acid monohydrate (0.090 g, 0.978 mmol) were dissolved in acetonitrile (4 mL) and DMF (2 mL) to give a solution. The mixture was irradiated in a microwave reactor at 100° C. for 10 min, then was concentrated. The crude product was dissolved in dichloromethane with a couple of drops of MeOH, loaded onto a 40 g column and eluted with a gradient from 1 to 20% methanol/methylene chloride. The product containing peak that eluted (~10% MeOH) was concentrated to give 93E (0.405 g, 0.626 mmol, 64.0% yield) as a yellow glass. MS (ESI) m/z 647.5 (M+H)$^+$.

93F

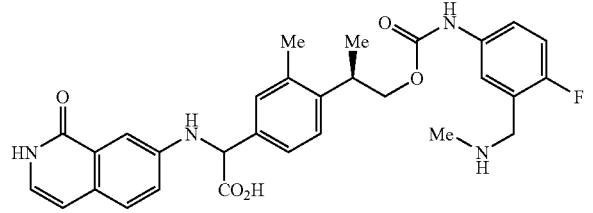 [SMILES: CNCc1cc(NC(=O)OC[C@H](C)c2ccc(C(Nc3ccc4cc[nH]c(=O)c4c3)C(=O)O)cc2C)ccc1F]

To a solution of 93E (405 mg, 0.626 mmol) in DCM (3 mL) and ethyl acetate (3 mL), was added a solution of 4 N HCl in dioxane (5 mL, 20.00 mmol). The resultant suspension was stirred at rt for 45 min, then concentrated. The resultant yellow solid was coevaporated with MeCN, then was dried under high vac to give 93F (360 mg, 0.617 mmol, 99% yield) as an orange solid. MS (ESI) m/z 547.4 (M+H)$^+$.

Example 93

To a solution of BOP (546 mg, 1.235 mmol) and DMAP (377 mg, 3.09 mmol) in DCM (200 mL) and DMF (40 mL) at 40° C., was added a solution of 93F (360 mg, 0.617 mmol) and DIEA (0.216 mL, 1.235 mmol) in DMF (5 mL), dropwise via a syringe pump 3 h addition. After addition was complete, the reaction was removed from the heating bath and stirred for 30 min. Then the reaction was quenched with H$_2$O (1 mL). The reaction was stored overnight at −20° C. Then, solvent was removed under reduced pressure, and the residue was purified by prep HPLC (Phenomenex Luna 5 μm C18 30×250 mm column; sol. A 10% MeCN −90% H$_2$O-0.1% TFA; sol. B 90% MeCN −10% H$_2$O-0.1% TFA; wavelength 220 nm; flow rate 30 mL/min; gradient time 20 min; start % B=20%, final % B=70%) 16.2-17.5 min (mixture of diastereomers). The diastereomers were separated by chiral chromatography (R,R-Whelk-O column (21.1×250 mm, 60:40 (MeOH/EtOH 1:1)/heptane, 20 mL/min); peak #1: rt 5.78 min (phenyglycine diastereomer); peak #2: rt 11.09 min (Example 93) to afford Example 22 (48 mg, 0.091 mmol, 29.4% yield) as an off-white solid. MS (ESI) m/z 529.3 (M+H)$^+$. $^1$H-NMR (400 MHz, DMSO-d$_6$) δ ppm 1.22 (d, J=7.15 Hz, 3H) 2.22 (s, 3H) 3.21 (s, 3H) 3.26-3.36 (m, 1H) 3.84-3.98 (m, 2H) 4.54 (t, J=10.99 Hz, 1H) 5.20 (d, J=17.04 Hz, 1H) 5.70 (s, 1H) 5.78 (dd, J=7.15, 2.20 Hz, 1H) 6.33 (d, J=6.60 Hz, 1H) 6.61-6.69 (m, 1H) 6.81 (t, J=6.05 Hz, 1H) 7.00 (t, J=8.79 Hz, 1H) 7.06 (s, 1H) 7.22-7.41 (m, 4H) 7.61 (d, J=7.70 Hz, 1H) 9.04 (s, 1H) 10.89 (d, J=4.95 Hz, 1H). Analytical HPLC (Method A): Col A: 7.81 min, 97%; Col B: 7.71 min, 95%.

Example 94

(R)-4,15,17-Trimethyl-2-(1-oxo-1,2-dihydro-isoquinolin-7-ylamino)-7-(2-oxo-pyrrolidin-1-yl)-13-oxa-4,11-diaza-tricyclo[14.2.2.1$^{6,10}$]henicosa-1(19),6,8,10(21),16(20),17-hexaene-3,12-dione

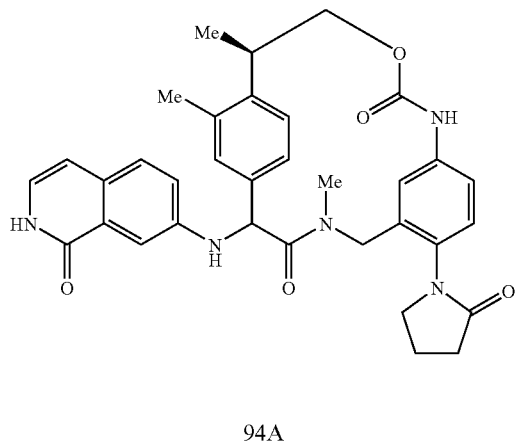

94A

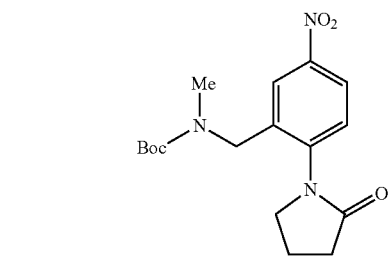 [SMILES: CN(Cc1cc([N+](=O)[O-])ccc1N1CCCC1=O)C(=O)OC(C)(C)C]

Intermediate 18 (0.100 g, 0.290 mmol), pyrrolidin-2-one (0.033 mL, 0.435 mmol), trans-N1,N2-dimethylcyclohexane-1,2-diamine (0.012 g, 0.087 mmol) were dissolved in Dioxane (1 mL). The solution was degassed using vacuo/argon (3×), and then potassium carbonate (0.080 g, 0.579 mmol) and copper(I) iodide (8.28 mg, 0.043 mmol) were added. The suspension was degassed again (3×), and heated at 100° C. overnight. The reaction mixture was diluted with EtOAc (15 mL), filtered through a glass filter and the solvent was removed under reduced pressure. The residue was purified by flash chromatography: (12 g) 0-100% EtOAc/hex. Product eluted at ~90% EtOAc. Fractions were combined and concentrated under reduced pressure to give 94A (0.060 g, 0.172 mmol, 59.3% yield) as a colorless syrup. MS (ESI) m/z 350.2 (M+H)+. 1H-NMR (400 MHz, CDCl3) δ ppm 1.33-1.58 (m, 9H) 2.29 (m, 2H) 2.61 (t, J=8.13 Hz, 2H) 2.93 (s, 3H) 3.82 (t, J=6.37 Hz, 2H) 4.33-4.50 (m, 2H) 7.35 (d, J=8.79 Hz, 1H) 8.11 (s, 1H) 8.17 (dd, J=8.57, 2.42 Hz, 1H)

94B

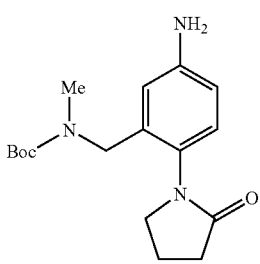 [SMILES: CN(Cc1cc(N)ccc1N1CCCC1=O)C(=O)OC(C)(C)C]

94A (0.263 g, 0.753 mmol) was dissolved in MeOH (10 mL) and degassed (3× vacuum/Ar). Pd—C (0.080 g, 0.075 mmol) was added, then the suspension was degassed again (3×) and hydrogenated (1 atm) for 1.5 h. Pd—C was removed by filtration and MeOH was removed under reduced pressure to give 94B (0.237 g, 0.742 mmol, 99% yield) as a colorless glass. MS (ESI) m/z 320.3 (M+H)+. 1H-NMR: (400 MHz, CDCl3) δ ppm 1.46 (d, J=19.24 Hz, 9H) 2.18 (s, 2H) 2.54 (t, J=8.25 Hz, 2H) 2.82 (d, J=22.54 Hz, 3H) 3.64 (s, 2H) 3.74 (s, 2H) 4.27 (s, 2H) 6.51 (s, 1H) 6.54-6.74 (m, 1H) 6.86-7.03 (m, 1H).

94C

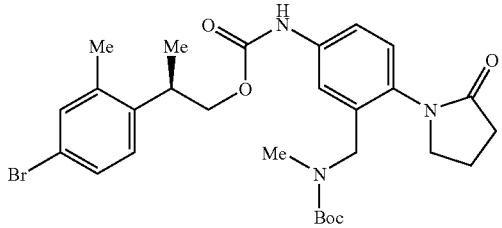 [SMILES: Cc1cc(Br)ccc1[C@@H](C)COC(=O)Nc1ccc(N2CCCC2=O)c(CN(C)C(=O)OC(C)(C)C)c1]

Using a procedure analogous to that used to prepare 29A, 94B (0.237 g, 0.742 mmol) was reacted with sodium bicarbonate and phosgene followed by Intermediate 8 (0.255 g, 1.113 mmol) and TEA. The crude product was added to a silica gel column (40 g) and was eluted with EtOAc/hexanes (0-100%) to give 94C (0.361 g, 0.628 mmol, 85% yield) as a colorless syrup. MS (ESI) m/z 574.6 (M+H)+. 1H-NMR: Rotamers. (400 MHz, CDCl3) δ ppm 1.26 (d, J=7.15 Hz, 3H) 1.35-1.58 (m, 9H) 2.20 (s, 2H) 2.34 (s, 3H) 2.54 (t, J=7.97 Hz, 2H) 2.69-2.91 (m, 3H) 3.28-3.44 (m, 1H) 3.67 (s, 2H) 4.14-4.26 (m, 2H) 4.30 (s, 2H) 6.92-7.15 (m, 4H) 7.32 (dd, J=4.12, 2.47 Hz, 2H).

94D

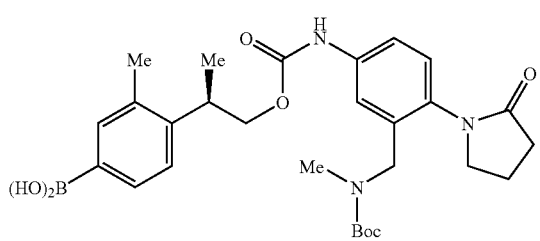 [SMILES: Cc1cc(B(O)O)ccc1[C@@H](C)COC(=O)Nc1ccc(N2CCCC2=O)c(CN(C)C(=O)OC(C)(C)C)c1]

Using a procedure analogous to that used to prepare 29B, 94C (0.361 g, 0.628 mmol) was reacted with bis(neopentyl glycolato)diboron), potassium acetate and (1,1'-bis(diphenylphosphino)ferrocene)-dichloropalladium(II). The crude was purified by flash chromatography and preparative HPLC (CH3CN/H2O, 0.1% TFA) to give 94D (0.1724 g, 0.320 mmol, 50.9% yield) as a white solid. MS (ESI) m/z 540.4 (M+H)+.

94E

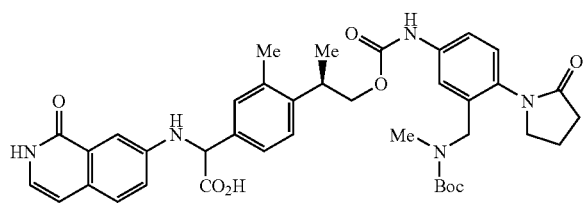 [SMILES: Cc1cc(C(Nc2ccc3cc[nH]c(=O)c3c2)C(=O)O)ccc1[C@@H](C)COC(=O)Nc1ccc(N2CCCC2=O)c(CN(C)C(=O)OC(C)(C)C)c1]

Using a procedure analogous to that used to prepare 1E, 94D (0.172 g, 0.319 mmol), Intermediate 3, and glyoxylic acid monohydrate were reacted and purified by flash chromatography (1% to 25% MeOH in CH2Cl2) to give 94E (0.175 g, 0.246 mmol, 77% yield) as a yellow glass. MS (ESI) m/z 712.5 (M+H)+. 1H-NMR: Rotamers (400 MHz, CD3OD) δ ppm 1.25-1.30 (m, 3H) 1.35-1.55 (m, 9H) 2.12-2.28 (m, 2H) 2.35 (s, 3H) 2.54 (t, J=7.97 Hz, 2H) 2.78 (d, J=15.39 Hz, 3H) 3.36-3.49 (m, 1H) 3.72 (s, 2H) 4.14-4.27 (m, 2H) 4.32 (s, 2H) 5.11 (s, 1H) 6.49-6.58 (m, 1H) 6.84-6.94 (m, 1H) 7.04-7.23 (m, 2H) 7.23-7.49 (m, 7H).

94F

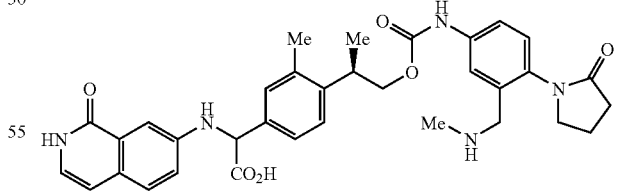

To a solution of 94E (175 mg, 0.246 mmol) in DCM (3 mL) and ethyl acetate (3 mL), was added a solution of 4 N HCl in dioxane (5 mL, 20.00 mmol). The resultant suspension was stirred at rt for 45 min, then concentrated. The resultant yellow solid was coevaporated with MeCN, then was dried under high vac to give 94F (158 mg, 0.244 mmol, 99% yield) as a yellowish solid. MS (ESI) m/z 612.4 (M+H)+. 1H-NMR: (400 MHz, CD3OD) δ ppm 1.28 (d, J=7.15 Hz, 3H) 2.22-2.31 (m, 2H) 2.65 (t, J=7.97 Hz, 2H) 2.76 (s, 3H) 3.46 (q, J=6.96

Hz, 1H) 3.55-3.60 (m, 1H) 3.67 (s, 1H) 3.71-3.77 (m, 1H) 3.88 (t, J=6.87 Hz, 2H) 4.03 (s, 2H) 4.18-4.33 (m, 2H) 5.26 (s, 1H) 6.62 (dd, J=7.15, 2.20 Hz, 1H) 6.74 (d, J=7.15 Hz, 1H) 7.04 (d, J=7.15 Hz, 1H) 7.26-7.35 (m, 2H) 7.36-7.48 (m, 2H) 7.53-7.60 (m, 2H) 7.68-7.91 (m, 2H) 8.30 (d, J=2.20 Hz, 1H).

Example 94

To a solution of BOP (216 mg, 0.488 mmol) and DMAP (149 mg, 1.219 mmol) in DCM (100 mL) and DMF (15 mL) at 40° C., was added a solution of 94F (158 mg, 0.244 mmol) and DIEA (0.085 mL, 0.488 mmol) in DMF (10 mL), dropwise via a syringe pump; 3 h addition. After addition was complete, the reaction was removed from the heating bath and stirred for 30 min. The reaction was quenched with H$_2$O (1 mL). The solvent was removed under reduced pressure, and the residue was purified by prep HPLC (Phenomenex Luna 5 µm C18 30×250 mm column; sol. A 10% MeCN –90% H$_2$O-0.1% TFA; sol. B 90% MeCN –10% H$_2$O-0.1% TFA; wavelength 220 nm; flow rate 30 mL/min; gradient time 20 min; start % B=0%, final % B=50%) peaks around 20.9-21.1 contained product (mixture of diastereomers). The product was repurified by HPLC (YMC-Pack ODS S-5 um 20×100 mm column; sol. A 10% MeOH –90% H$_2$O-0.1% TFA; sol. B 90% MeOH –10% H$_2$O-0.1% TFA; wavelength 220 nm; flow rate 20 mL/min; gradient time 10 min; start % B=20%, final % B=100%; rt 7.48 min) to afford Example 94 (3.09 mg, 5.20 µmol, 4.27% yield) as an off-white solid. MS (ESI) m/z 594.4 (M+H)$^+$. $^1$H-NMR: Mixture of phenylglycine diastereomers (400 MHz, CD$_3$OD) δ ppm 1.37 (dd, J=51.94, 6.87 Hz, 3H) 2.16-2.28 (m, 2H) 2.40 (d, J=63.76 Hz, 3H) 2.54 (t, J=7.97 Hz, 2H) 3.34 (s, 3H) 3.37-3.54 (m, 1H) 3.74-4.09 (m, 2H) 4.63 (t, J=10.72 Hz, 1H) 4.90-4.97 (m, 1H) 5.20 (t, J=17.31 Hz, 1H) 5.62 (d, J=8.79 Hz, 1H) 6.19 (d, J=39.03 Hz, 1H) 6.55 (d, J=7.15 Hz, 1H) 6.72-6.80 (m, 1H) 6.91 (d, J=7.15 Hz, 1H) 7.07-7.29 (m, 4H) 7.39-7.46 (m, 3H) 7.56 (s, 1H) 7.62 (d, J=7.70 Hz, 1H). Analytical HPLC (Method A): Col A: 9.45 min, 85%; Col B: 9.68 min, 88%.

Example 95

(2R,15R)-7-Chloro-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16 (20),17-hexaene-3,12-dione

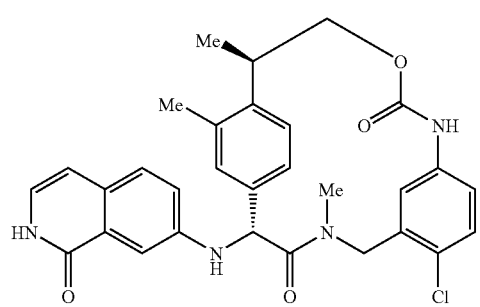

95A

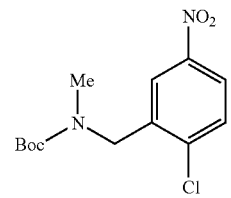

Using a procedure analogous to that used to prepare Intermediate 17 and Intermediate 18, 2-chloro-5-nitrobenzaldehyde (3.0 g, 16.17 mmol) was reacted with methylamine and sodium borohydride followed by BOC-Anhydride. The crude product was purified by flash chromatography: (120 g) 0-50% EtOAc/hexanes to give 95A (3.873 g, 12.88 mmol, 80% yield) as a white solid. MS (ESI) m/z 245.1 (M+H)$^+$-tBu.

95B

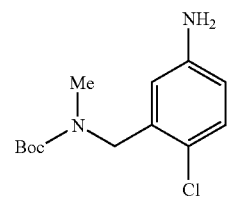 [SMILES: CN(Cc1cc(N)ccc1Cl)C(=O)OC(C)(C)C]

To a solution of 95A (1.500 g, 4.99 mmol) in methanol (25 mL) and THF (5 mL) was added zinc (dust) (3.26 g, 49.9 mmol) and ammonium chloride (5.34 g, 100 mmol). The resulting solution was stirred for 2 h at 60° C. MeOH was removed under reduced pressure, to the solid residue Na$_2$CO$_3$ (aq, 100 mL) and EtOAc (150 mL) were added, and the suspension was stirred vigorously for 10 min. Filtered through glass frit, solid residue was washed with EtOAc (3×150 mL). Combined EtOAc fractions were washed with water (2×50 mL), brine (1×50 mL) and dried (Na$_2$SO$_4$). EtOAc was removed under reduced pressure and the residue was purified by flash chromatography: (40 g column) 0-100% EtOAc/hex. Product eluted at ~50% EtOAc. Fractions were combined and concentrated under reduced pressure to give 95B (1.262 g, 4.66 mmol, 93% yield) as a colorless oil, which solidified upon standing. MS (ESI) m/z 215.2 (M+H)$^+$-tBu.

Example 95

According to the sequence for the preparation of Example 93, 95B was converted to Example 95. Purification by chiral chromatography (R,R-Whelk-O column (21.1×250 mm, 60:40 (MeOH/EtOH 1:1)/heptane, 20 mL/min); peak #1: rt 7.91 min (phenylglycine diastereomer); peak #2: rt 19.44 min (Example 95)) afforded Example 95. MS (ESI) m/z 545.3 (M+H)$^+$. $^1$H-NMR: (500 MHz, CD$_3$OD) a ppm 1.29 (d, J=6.6 Hz, 3H), 2.31 (s, 3H), 3.33 (s, 3H), 3.43-3.51 (m, 1H), 3.88-3.95 (m, 2H), 4.64 (t, J=11.0 Hz, 1H), 5.37 (d, J=17.6 Hz, 1H), 5.65 (s, 1H), 5.99 (s, 1H), 6.55 (d, J=7.1 Hz, 1H), 6.68 (dd, J=8.2, 2.7 Hz, 1H), 6.91 (d, J=7.1 Hz, 1H), 7.20-7.26 (m, 4H), 7.39-7.44 (m, 4H), 7.65 (dd, J=8.2, 1.6 Hz, 1H), 9.01 (s, 1H). Analytical HPLC (Method A): Col A: 7.66 min, 97%; Col B: 7.47 min, 96%.

Example 96

(2R,15R)-4,15,17-Trimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-7-carbonitrile

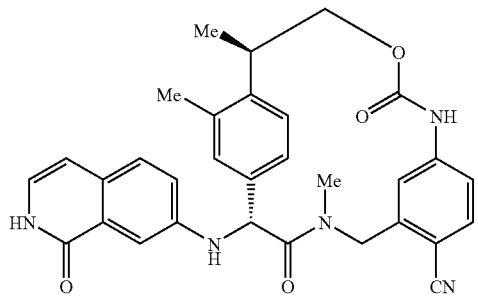 [SMILES: Cc1cc2ccc1[C@@H](C)COC(=O)Nc1ccc(C#N)c(c1)CN(C)C(=O)[C@@H]2Nc1ccc2cc[nH]c(=O)c2c1]

96A

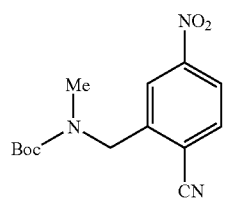 [SMILES: CN(Cc1cc([N+](=O)[O-])ccc1C#N)C(=O)OC(C)(C)C]

Intermediate 18 (0.867 g, 2.51 mmol), zinc cyanide (0.295 g, 2.51 mmol) and triphenylphosphine (0.132 g, 0.502 mmol) were dissolved in DMF (10 mL), degassed using vacuo/Ar (3×), and then palladium(II) acetate (0.056 g, 0.251 mmol) was added. The suspension was degassed again (3×), and heated at 100° C. for 1.5 days. The reaction mixture was diluted with EtOAc (150 mL), washed with water (3×100 mL), brine (1×100 mL) and dried (Na$_2$SO$_4$). EtOAc was removed under reduced pressure and the residue was purified by flash chromatography: (40 g) 0-40% EtOAc/hex. Eluted at ~25% EtOAc. Fractions were combined and concentrated under reduced pressure to give 96A (0.414 g, 1.421 mmol, 56.6% yield) as a yellow oil, which solidified upon standing. MS (ESI) m/z 192.2 (M+H)$^+$-Boc. $^1$H-NMR: (400 MHz, CDCl$_3$) δ ppm 1.48 (d, J=27.48 Hz, 9H) 2.98 (s, 3H) 4.73 (d, J=10.44 Hz, 2H) 7.87 (d, J=7.15 Hz, 1H) 8.22 (s, 2H).

96B

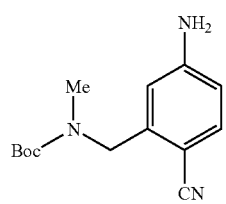 [SMILES: CN(Cc1cc(N)ccc1C#N)C(=O)OC(C)(C)C]

To a solution of 96A (0.414 g, 1.421 mmol) in methanol (10 mL) and THF (5 mL) was added zinc (dust) (0.929 g, 14.21 mmol) and ammonium chloride (1.520 g, 28.4 mmol). The resulting solution was stirred for 2 h at 60° C. MeOH was removed under reduced pressure, to the solid residue Na$_2$CO$_3$ (aq, 50 mL) and EtOAc (100 mL) were added, and the suspension was stirred vigorously for 10 min. Filtered through glass frit, solid residue was washed with EtOAc (3×150 mL). Combined EtOAc fractions were washed with water (2×50 mL), brine (1×50 mL) and dried (Na$_2$SO$_4$). EtOAc was removed under reduced pressure and the residue was purified by flash chromatography: (12 g) 0-100% EtOAc/hex. Fractions were combined and concentrated under reduced pressure to give 96B (0.179 g, 0.685 mmol, 48.2% yield) as a white solid. MS (ESI) m/z 162.2 (M+H)$^+$-Boc. $^1$H-NMR: Rotamers. (400 MHz, CDCl$_3$) δ ppm 1.47 (d, J=24.19 Hz, 9H) 2.89 (d, J=21.99 Hz, 3H) 4.17 (s, 2H) 4.55 (s, 2H) 6.41-6.68 (m, 2H) 7.40 (d, J=8.25 Hz, 1H).

Example 96

According to the sequence for the preparation of Example 93, 96B was converted to Example 96. MS (ESI) m/z 536.4 (M+H)$^+$. Chiral analytical HPLC: (Whelko-01 10 um 4.6×250 mm; sol. A Heptane; sol. B 50% MeOH −50% EtOH; wavelength 220 nm and 254 nm; flow rate 1 mL/min; isocratic time 30 min; % B=60%) 13.17 min. $^1$H-NMR: (400 MHz, CD$_3$OD) δ ppm 1.31 (d, J=7.1 Hz, 3H), 2.29 (s, 3H), 3.41 (s, 3H), 3.45-3.52 (m, J=7.0, 7.0, 4.1 Hz, 1H), 3.98 (dd, J=10.7, 4.1 Hz, 1H), 4.10 (d, J=17.6 Hz, 1H), 4.65 (t, J=10.7 Hz, 1H), 5.46 (d, J=17.0 Hz, 1H), 5.66 (s, 1H), 6.26 (s, 1H), 6.55 (d, J=7.1 Hz, 1H), 6.76 (d, J=8.2 Hz, 1H), 6.92 (d, J=7.1 Hz, 1H), 7.14 (s, 1H), 7.24 (dd, J=8.5, 2.5 Hz, 1H), 7.43 (t, J=8.0 Hz, 3H), 7.55 (d, J=8.2 Hz, 1H), 7.65 (d, J=6.0 Hz, 1H), 9.45 (s, 1H). Analytical HPLC (Method A): Col A: 7.02 min, 94%; Col B: 6.92 min, 95%.

Example 97

(2R,15R)-7-Bromo-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

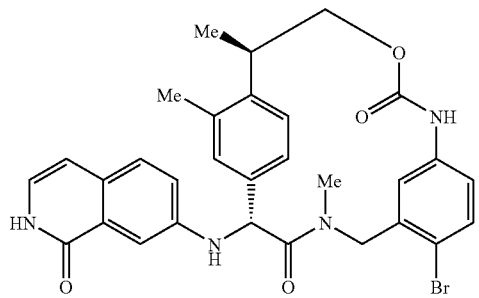

97A

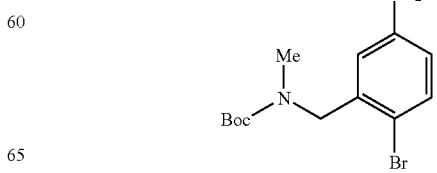

To a solution of tert-butyl Intermediate 18 (3.000 g, 8.69 mmol) in methanol (50 mL) and THF (10 mL) was added zinc (dust) (5.68 g, 87 mmol) and ammonium chloride (9.30 g, 174 mmol). The resulting solution was stirred at rt for 1 h (caution: slight exotherm observed) then overnight at 40° C. MeOH was removed under reduced pressure, to the solid residue $Na_2CO_3$ (aq, 100 mL) and EtOAc (150 mL) were added, and the suspension was stirred vigorously for 10 min. Filtered through glass frit, solid residue was washed with EtOAc (3×150 mL). Combined EtOAc fractions were washed with std. $Na_2CO_3$ (aq, 2×50 mL), water (2×50 mL), brine (1×50 mL) and dried ($Na_2SO_4$). EtOAc was removed under reduced pressure and the residue was purified by ISCO: (40 g) 0-100% EtOAc/hex. Fractions were combined and concentrated under reduced pressure to give 97A (2.687 g, 8.52 mmol, 98% yield) as a yellowish oil, which solidified upon standing. MS (ESI) m/z 259.1 $(M+H)^+$-tBu.

97B

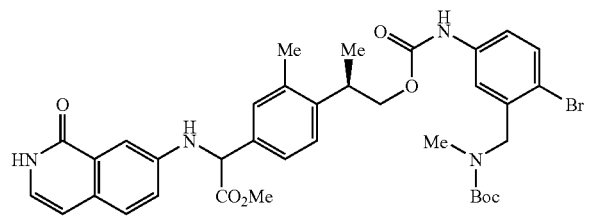 [SMILES: COC(=O)C(Nc1ccc2cc[nH]c(=O)c2c1)c1ccc([C@@H](C)COC(=O)Nc2ccc(Br)c(CN(C)C(=O)OC(C)(C)C)c2)c(C)c1]

Using a procedure analogous to that used to prepare 29A, 97A (0.249 g, 0.789 mmol) was reacted with sodium bicarbonate and phosgene followed by Intermediate 16 (0.200 g, 0.526 mmol) and TEA. The crude product was purified by flash chromatography: (40 g) 0-100% EtOAc/hex to give 97B (0.250 g, 0.346 mmol, 65.9% yield) as a yellowish glass. MS (ESI) m/z 721.5 $(M+H)^+$.

97C

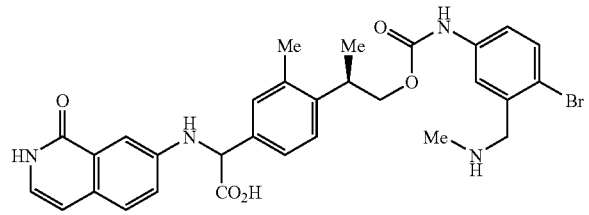 [SMILES: CNCc1cc(NC(=O)OC[C@H](C)c2ccc(C(Nc3ccc4cc[nH]c(=O)c4c3)C(=O)O)cc2C)ccc1Br]

97B (0.250 g, 0.346 mmol) was dissolved in THF (1.5 mL), then MeOH (1.5 mL) and water (1 mL) were added sequentially. To the resulting solution, cooled at 0° C., lithium hydroxide (0.041 g, 1.732 mmol) was added. The reaction mixture was allowed to stand at 0° C. for 1.5 h. The reaction mixture was diluted with water (15 mL), and most of MeOH and THF were removed under reduced pressure. Remaining solution was extracted with $Et_2O$ (1×15 mL). Then EtOAc (15 mL) was added, water phase was acidified to pH~3 with std. aqueous citric acid solution with stirring. The organic phase was separated, and water phase was extracted with EtOAc (5×10 mL). Combined organic phases were washed with water (3×25 mL) and dried ($Na_2SO_4$). The organic phase was filtered and concentrated under reduced pressure (co-evaporated with MeCN/benzene 3×) to give a hydrolyzed product (0.230 g) as a yellowish foam. The hydrolyzed product was dissolved in EtOAc (5 mL) and DCM (5 mL), then HCl (4 M in dioxane, 5 mL) was added. The reaction mixture was stirred for 1 h at rt. The solvent was removed under reduced pressure, and the residue was dried under high vacuum to give 97C (0.218 g, 0.339 mmol, 98% yield) as a yellow solid. MS (ESI) m/z 607.3 $(M+H)^+$.

Example 97

To a solution of BOP (299 mg, 0.677 mmol) and DMAP (207 mg, 1.693 mmol) in DCM (100 mL) and DMF (20 mL) at 40° C., was added a solution of 97C (218 mg, 0.339 mmol) and DIEA (0.118 mL, 0.677 mmol) in DMF (5 mL), dropwise via a syringe pump 3 h addition. After addition was complete, the reaction was removed from the heating bath and stirred for 30 min. The reaction progress was checked by LC-MS: complete. Then the reaction was quenched with $H_2O$ (1 mL) and solvent was removed under reduced pressure. The residue was purified by prep HPLC (Phenomenex Luna 5 μm C18 30×250 mm column; sol. A 10% MeCN −90% $H_2O$-0.1% TFA; sol. B 90% MeCN −10% $H_2O$-0.1% TFA; wavelength 220 nm; flow rate 30 mL/min; gradient time 20 min; start % B=20%, final % B=75%; 17.5-19.5 min (mixture of diastereomers). The diastereomers were separated by chiral chromatography (R,R-Whelk-O column (21.1×250 mm, 100% (MeOH/EtOH 1:1), mL/min); peak #1: rt 5.10 min (phenyglycine diastereomer); peak #2: rt 14.20 min (Example 97)) to afford Example 97 (34.15 mg, 0.058 mmol, 34.2% yield) as an off-white solid. MS (ESI) m/z 589.4 (M−H). $^1$H-NMR: (500 MHz, $CD_3OD$) δ ppm 1.29 (d, J=7.1 Hz, 4H), 2.31 (s, 3H), 3.33 (s, 3H), 3.46 (ddd, J=11.0, 6.9, 4.1 Hz, 1H), 3.84 (d, J=17.0 Hz, 1H), 3.93 (dd, J=10.7, 4.1 Hz, 1H), 4.63 (t, J=11.0 Hz, 1H), 5.32 (d, J=17.0 Hz, 1H), 5.64 (s, 1H), 5.99 (s, 1H), 6.54 (d, J=7.1 Hz, 1H), 6.62 (dd, J=8.2, 2.7 Hz, 1H), 6.90 (d, J=7.1 Hz, 1H), 7.20-7.25 (m, 2H), 7.37-7.44 (m, 4H), 7.64 (d, J=8.2 Hz, 1H), 9.00 (s, 1H). Analytical HPLC (Method A): Col A: 7.81 min, 99%; Col B: 7.57 min, 99%.

Example 98

(2R,15R)-4,15,17-Trimethyl-2-(1-oxo-1,2-dihydro-isoquinolin-7-ylamino)-7-phenyl-13-oxa-4,11-diaza-tricyclo[14.2.2.1$^{6,10}$]henicosa-1(19),6,8,10(21),16(20),17-hexaene-3,12-dione trifluoroacetate

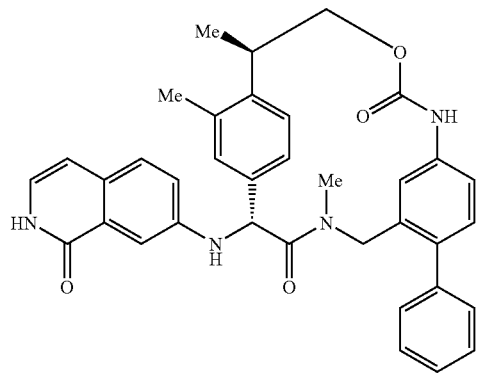 [SMILES: Cc1cc2ccc1[C@@H](C)COC(=O)Nc1ccc(-c3ccccc3)c(c1)CN(C)C(=O)[C@@H]2Nc1ccc2cc[nH]c(=O)c2c1]

Example 97 (74 mg, 0.126 mmol), Q-phos (27.0 mg, 0.038 mmol), phenylboronic acid (153 mg, 1.255 mmol), potassium phosphate (437 mg, 2.51 mmol) and $Pd_2$ $(dba)_3$ (17.24 mg, 0.019 mmol) were loaded into a reaction vial. The tube was capped, then degassed carefully (3× argon/vacuum). Toluene (1 mL) and dioxane (1 mL) were added through the cap, the reaction mixture was degassed again (3× argon/vacuum) and stirred at 105° C. for 14 h. The reaction mixture was diluted with DCM (20 mL) and filtered. Solvent was removed under reduced pressure, and the residue was purified by preparative HPLC (Phenomenex Luna 5 μm C18 30×250 mm column; sol. A 10% MeCN –90% H$_2$O-0.1% TFA; sol. B 90% MeCN –10% H$_2$O-0.1% TFA; wavelength 220 nm; flow rate 30 mL/min; gradient time 20 min; start % B=10%, final % B=100%; rt=17.427 min) to afford Example 98 (34.4 mg, 0.059 mmol, 46.7% yield) as an off-white solid. MS (ESI) m/z 587.4 (M+H)$^+$. Chiral analytical HPLC: (Whelko-01 10 um 4.6×250 mm; sol. A Heptane; sol. B 50% MeOH –50% EtOH; wavelength 220 nm and 254 nm; flow rate 1 mL/min; isocratic time 30 min; % B=60%) 6.95 min $^1$H-NMR: (500 MHz, CD$_3$OD) δ ppm 1.31 (d, J=7.1 Hz, 3H), 2.37 (s, 3H), 3.24 (s, 3H), 3.50 (ddd, J=11.1, 7.0, 4.4 Hz, 1H), 3.73 (d, J=17.0 Hz, 1H), 3.98 (dd, J=10.4, 4.4 Hz, 1H), 4.63 (t, J=10.7 Hz, 1H), 5.28 (d, J=16.5 Hz, 1H), 5.62 (s, 1H), 6.09 (s, 1H), 6.55 (d, J=7.1 Hz, 1H), 6.77 (dd, J=7.7, 2.2 Hz, 1H), 6.93 (d, J=7.1 Hz, 1H), 7.06 (d, J=8.2 Hz, 1H), 7.25-7.30 (m, 4H), 7.33 (t, J=7.4 Hz, 1H), 7.38-7.45 (m, 5H), 7.48 (d, J=2.2 Hz, 1H), 7.58 (d, J=6.0 Hz, 1H). Analytical HPLC (Method A): Col A: 8.42 min, 99%; Col B: 8.13 min, 99%.

Example 99

(2R,15R)-7-(2,6-Difluoro-phenyl)-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione trifluoroacetate

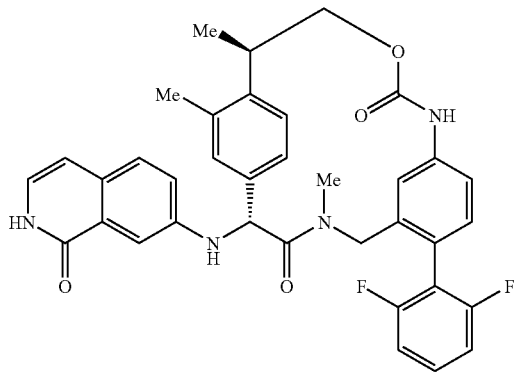 [SMILES: Cc1cc2ccc1[C@@H](C)COC(=O)Nc1ccc(-c3c(F)cccc3F)c(c1)CN(C)C(=O)[C@@H]2Nc1ccc2cc[nH]c(=O)c2c1]

Example 97 (15 mg, 0.025 mmol), Q-phos (5.47 mg, 7.63 μmol), 2,6-difluorophenylboronic acid (40.2 mg, 0.254 mmol), potassium phosphate (89 mg, 0.509 mmol) and Pd$_2$(dba)$_3$ (3.50 mg, 3.82 mol) were loaded in a reaction vial. The tube was capped, then degassed carefully (3× argon/vacuum). Toluene (1 mL) was added through the cap, then the reaction mixture was degassed again (3× Ar/vacuum) and stirred at 100° C. for 20 h. The reaction mixture was diluted with DMSO (0.5 mL) and DCM (3 mL), and filtered (membrane filter), the filter was rinsed with DCM (3×). Solvent was removed under reduced pressure, and the residue was purified by preparative HPLC (Phenomenex Luna 5 μm C18 30×250 mm column; sol. A 10% MeCN –90% H$_2$O-0.1% TFA; sol. B 90% MeCN –10% H$_2$O-0.1% TFA; wavelength 220 nm; flow rate 30 mL/min; gradient time 20 min; start % B=10%, final % B=100%; 17.329 min) to afford Example 99 (5.38 mg, 8.64 μmol, 34.0% yield) as an off-white solid. MS (ESI) m/z 623.5 (M+H)$^+$. Chiral analytical HPLC: (Whelko-01 10 um 4.6× 250 mm; sol. A Heptane; sol. B 50% MeOH –50% EtOH; wavelength 220 nm and 254 nm; flow rate 1 mL/min; isocratic time 30 min; % B=60%) 6.96 min. $^1$H-NMR: (500 MHz, CD$_3$OD) δ ppm 1.32 (d, J=7.1 Hz, 3H), 2.38 (s, 3H), 3.25 (s, 3H), 3.48-3.54 (m, 1H), 3.59 (d, J=17.0 Hz, 1H), 4.00 (dd, J=10.7, 4.1 Hz, 1H), 4.64 (t, J=11.0 Hz, 1H), 5.21 (d, J=17.0 Hz, 1H), 5.62 (s, 1H), 6.13 (s, 1H), 6.55 (d, J=7.1 Hz, 1H), 6.81 (dd, J=8.2, 2.2 Hz, 1H), 6.92 (d, J=7.1 Hz, 1H), 7.04-7.11 (m, 3H), 7.26 (dd, J=8.8, 2.2 Hz, 1H), 7.29 (s, 1H), 7.40-7.46 (m, 4H), 7.59 (d, J=8.2 Hz, 1H). Analytical HPLC (Method A): Col A: 8.41 min, 99%; Col B: 8.10 min, 99%.

Example 100

3-[(2R,15R)-4,15,17-Trimethyl-3,12-dioxo-2-(1-oxo-1,2-dihydro-isoquinolin-7-ylamino)-13-oxa-4, 11-diaza-tricyclo[14.2.2.1$^{6,10}$]henicosa-1(19),6,8,10 (21),16(20),17-hexaen-7-yl]-benzoic acid trifluoroacetate

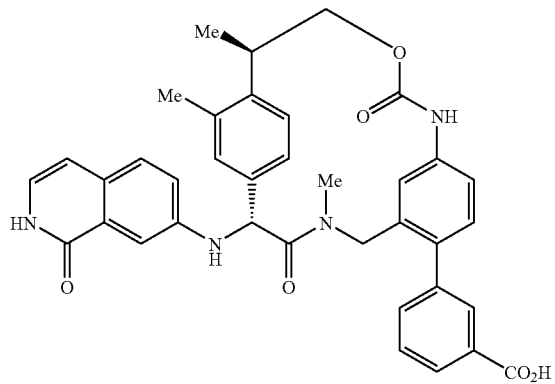 [SMILES: Cc1cc2ccc1[C@@H](C)COC(=O)Nc1ccc(-c3cccc(C(=O)O)c3)c(c1)CN(C)C(=O)[C@@H]2Nc1ccc2cc[nH]c(=O)c2c1]

Example 97 (30 mg, 0.051 mmol), Q-phos (10.94 mg, 0.015 mmol), 3-(methoxycarbonyl)benzeneboronic acid (45.8 mg, 0.254 mmol), potassium phosphate (89 mg, 0.509 mmol) and Pd$_2$(dba)$_3$ (6.99 mg, 7.63 μmol) were loaded into a reaction vial. The tube was capped, then degassed carefully (3× Ar/vacuum). Toluene (1 mL) was added through the cap, the reaction mixture was degassed again (3× Ar/vacuum) and stirred at 100° C. for 14 h. The reaction mixture was diluted with DMSO (0.5 mL) and DCM (3 mL), and filtered (membrane filter), the filter was rinsed with DCM (3×). Solvent was removed under reduced pressure, and the residue was purified by preparative HPLC (Phenomenex Luna 5 μm C18 30×250 mm column; sol. A 10% MeCN –90% H$_2$O-0.1% TFA; sol. B 90% MeCN –10% H$_2$O-0.1% TFA; wavelength 220 nm; flow rate 30 mL/min; gradient time 20 min; start % B=10%, final % B=100%; rt=17.154 min.). The solvent was removed, the residue (CO$_2$Me derivative; LC-MS: 1.328 min, [M+1]645.5) was dissolved in MeOH (0.40 mL), THF (0.40 mL) and water (0.20 mL). The solution was cooled down to 0° C., and lithium hydroxide (6.09 mg, 0.254 mmol) was added. The reaction was stirred for 1 h at 0° C. Additional lithium hydroxide (6.09 mg, 0.254 mmol) was added, and the reaction was let warm to rt and stir for 1 h. Additional lithium hydroxide (6.09 mg, 0.254 mmol) was added, and the reaction was stirred for 1 h. The reaction mixture was acidified to pH~3 with TFA, and the residue was purified by preparative HPLC (Axia Luna 5 μm C18 30×100 mm column; sol. A 10% MeCN –90% H$_2$O-0.1% TFA; sol. B 90% MeCN –10% H$_2$O-0.1% TFA; wavelength 220 nm; flow rate 40 mL/min; gradient time 10 min; start % B=10%, final % B=100%; rt=6.143 min) to afford Example 100 (10.3 mg, 0.016 mmol, 32.1% yield) as an off-white solid. MS (ESI) m/z 631.6 (M+H)$^+$. $^1$H-NMR: (500 MHz, CD$_3$OD) δ ppm 1.31 (d, J=7.1 Hz, 3H), 2.36 (s, 3H), 3.24 (s, 3H), 3.46-3.53 (m, 1H), 3.75 (d, J=16.5 Hz, 1H), 3.98 (dd, J=11.0, 4.4 Hz, 1H), 4.63 (t, J=11.0 Hz, 1H), 5.25 (d, J=16.5 Hz, 1H), 5.64 (s, 1H), 6.14 (d, J=1.6 Hz, 1H), 6.55 (d, J=7.1 Hz, 1H), 6.79 (dd, J=7.7, 2.2 Hz, 1H), 6.94 (d, J=7.1 Hz, 1H), 7.09 (d, J=8.2 Hz, 1H), 7.28 (s, 1H), 7.29 (d, J=2.7 Hz, 1H), 7.41-7.44 (m, 2H), 7.51-7.58 (m, 4H), 7.94 (s, 1H), 8.01 (ddd, J=6.9, 2.2, 1.9 Hz, 1H). Analytical HPLC (Method A): Col A: 7.12 min, 99%; Col B: 7.03 min, 99%.

Example 101

3-[(2R,15R)-4,15,17-Trimethyl-3,12-dioxo-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaen-7-yl]-benzoic acid methyl ester trifluoroacetate

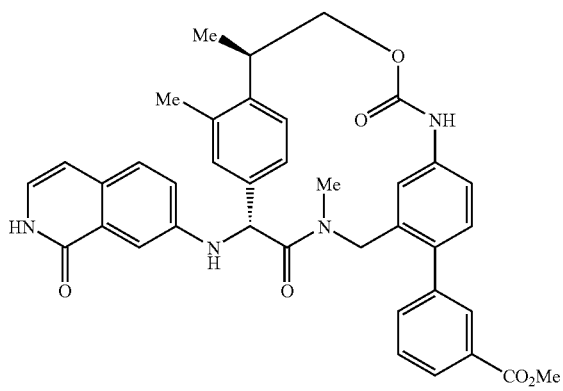 [SMILES: COC(=O)c1cccc(-c2ccc3cc2CN(C)C(=O)[C@H](Nc2ccc4cc[nH]c(=O)c4c2)c2ccc(c(C)c2)[C@@H](C)COC(=O)N3)c1]

According to the procedure for the preparation of Example 98, Example 97 (30 mg, 0.051 mmol) was coupled with 3-(methoxycarbonyl)benzeneboronic acid to afford after purification Example 101 (11.7 mg, 0.018 mmol, 35.7% yield) as an off-white solid. MS (ESI) m/z 645.6 (M+H)+. ¹H-NMR: (500 MHz, CD₃OD) δ ppm 1.30 (d, J=7.1 Hz, 3H), 2.35 (s, 3H), 3.25 (s, 3H), 3.49 (ddd, J=11.1, 7.0, 4.4 Hz, 1H), 3.73 (d, J=17.0 Hz, 1H), 3.90 (s, 3H), 3.97 (dd, J=10.4, 4.4 Hz, 1H), 4.63 (t, J=11.0 Hz, 1H), 5.23 (d, J=17.0 Hz, 1H), 5.62 (s, 1H), 6.14 (d, J=1.6 Hz, 1H), 6.53 (d, J=7.1 Hz, 1H), 6.79 (dd, J=7.7, 2.2 Hz, 1H), 6.92 (d, J=7.1 Hz, 1H), 7.08 (d, J=8.2 Hz, 1H), 7.24-7.29 (m, 2H), 7.41 (t, J=6.6 Hz, 2H), 7.48 (s, 1H), 7.51-7.60 (m, 3H), 7.93 (s, 1H), 8.00 (dt, J=7.1, 1.6 Hz, 1H). Analytical HPLC (Method A): Col A: 8.31 min, 99%; Col B: 8.00 min, 99%.

Example 102

4-Fluoro-3-[(2R,15R)-4,15,17-trimethyl-3,12-dioxo-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaen-7-yl]-benzoic acid trifluoroacetate

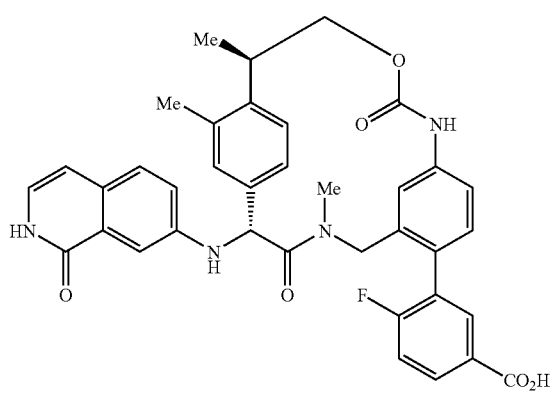 [SMILES: Cc1cc2ccc1[C@@H](C)COC(=O)Nc1ccc(-c3cc(C(=O)O)ccc3F)c(c1)CN(C)C(=O)[C@@H]2Nc1ccc2cc[nH]c(=O)c2c1]

According to the procedure for the preparation of Example 100, Example 97 (50 mg, 0.085 mmol) was coupled with 2-fluoro-5-(methoxycarbonyl)phenylboronic acid and the product was saponified to afford Example 102 (18.8 mg, 0.029 mmol, 34.2% yield) as an off-white powder. MS (ESI) m/z 649.6 (M+H)+. ¹H-NMR: (500 MHz, CD₃OD) δ ppm 1.30 (d, J=7.1 Hz, 3H), 2.34 (s, 3H), 3.24 (s, 3H), 3.48 (tt, J=11.3, 7.1 Hz, 1H), 3.65 (d, J=16.5 Hz, 1H), 3.97 (dd, J=10.7, 4.1 Hz, 1H), 4.63 (t, J=11.0 Hz, 1H), 5.19 (d, J=9.3 Hz, 1H), 5.63 (s, 1H), 6.14 (s, 1H), 6.52 (d, J=7.1 Hz, 1H), 6.81 (dd, J=8.0, 1.9 Hz, 1H), 6.92 (d, J=7.1 Hz, 1H), 7.10 (d, J=8.2 Hz, 1H), 7.24-7.31 (m, 3H), 7.40 (dd, J=10.4, 8.2 Hz, 3H), 7.49 (s, 1H), 7.58 (d, J=7.7 Hz, 1H), 7.94 (d, J=5.5 Hz, 1H), 8.08 (td, J=5.5, 2.2 Hz, 1H). Analytical HPLC (Method A): Col A: 10.70 min, 99%; Col B: 10.82 min, 98%.

Example 103

(2R,15R)-4,15,17-Trimethyl-2-(1-oxo-1,2-dihydro-isoquinolin-7-ylamino)-7-pyridin-2-yl-13-oxa-4,11-diaza-tricyclo[14.2.2.1⁶,¹⁰]henicosa-1(19),6,8,10(21),16(20),17-hexaene-3,12-dione bistrifluoroacetate

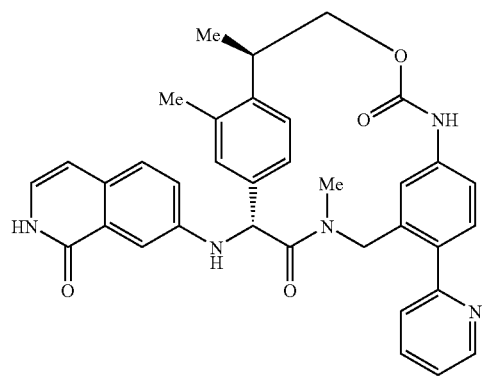 [SMILES: Cc1cc2ccc1[C@@H](C)COC(=O)Nc1ccc(-c3ccccn3)c(c1)CN(C)C(=O)[C@@H]2Nc1ccc2cc[nH]c(=O)c2c1]

Example 97 (30 mg, 0.051 mmol) and Pd(PPh₃)₄ (8.82 mg, 7.63 µmol) were loaded into a reaction vial. The tube was capped, then degassed carefully (3× Ar/vacuum). A solution of 2-(tributylstannyl)pyridine (94 mg, 0.254 mmol) in dioxane (1 mL) was added through the cap, then the reaction mixture was degassed again (3× Ar/vacuum) and heated at 105° C. overnight. MeOH was added to the reaction mixture, then the reaction mixture was filtered through a membrane filter and purified by preparative HPLC (Phenomenex Luna 5 µm C18 30×250 mm column; sol. A 10% MeCN −90% H₂O-0.1% TFA; sol. B 90% MeCN −10% H₂O-0.1% TFA; wavelength 220 nm; flow rate 30 mL/min; gradient time 20 min; start % B=10%, final % B=80%; rt=11.25 min) to afford Example 103 (19.4 mg, 0.024 mmol, 46.7% yield) as a yellow solid. MS (ESI) m/z 588.5 (M+H)+. ¹H-NMR: (500 MHz, CD₃OD) δ ppm 1.31 (d, J=7.1 Hz, 3H), 2.29 (s, 3H), 3.41 (s, 3H), 3.48 (tt, J=11.3, 7.1 Hz, 1H), 3.97-4.04 (m, 2H), 4.65 (t, J=11.0 Hz, 1H), 5.08 (d, J=16.5 Hz, 1H), 5.62 (s, 1H), 6.53 (d, J=7.1 Hz, 2H), 6.89-6.92 (m, 2H), 7.09 (s, 1H), 7.23 (dd, J=8.5, 2.5 Hz, 1H), 7.36-7.41 (m, 3H), 7.45 (d, J=7.7 Hz, 1H), 7.63 (dd, J=7.7, 1.6 Hz, 1H), 7.97 (td, J=6.9, 1.1 Hz, 1H), 8.11 (d, J=8.2 Hz, 1H), 8.57 (td, J=7.8, 1.4 Hz, 1H), 8.83 (d, J=6.0 Hz, 1H). Analytical HPLC (Method A): Col A: 4.99 min, 98%; Col B: 5.57 min, 99%.

Example 104

(2R,15R)-4,15,17-Trimethyl-2-(1-oxo-1,2-dihydro-isoquinolin-7-ylamino)-7-pyridin-3-yl-13-oxa-4,11-diaza-tricyclo[14.2.2.1$^{6,10}$]henicosa-1(19),6,8,10(21),16(20),17-hexaene-3,12-dione bistrifluoroacetate

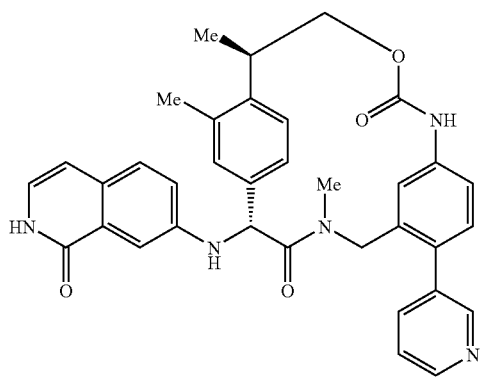 [SMILES: Cc1cc2ccc1[C@@H](C)COC(=O)Nc1ccc(-c3cccnc3)c(c1)CN(C)C(=O)[C@@H]2Nc1ccc2cc[nH]c(=O)c2c1]

According to the procedure for the preparation of Example 103, Example 97 (30 mg, 0.051 mmol) was coupled with 3-(tributylstannyl)pyridine (94 mg, 0.254 mmol) to afford Example 104 (19.7 mg, 0.024 mmol, 47.5% yield) as a yellow solid. MS (ESI) m/z 588.5 (M+H)$^+$. $^1$H-NMR: (500 MHz, CD$_3$OD) δ ppm 1.31 (d, J=7.1 Hz, 3H), 2.32 (s, 3H), 3.37 (s, 3H), 3.49 (ddd, J=11.1, 7.0, 4.4 Hz, 1H), 3.91 (d, J=16.5 Hz, 1H), 3.98 (dd, J=11.0, 4.4 Hz, 1H), 4.64 (t, J=11.0 Hz, 1H), 5.08 (d, J=16.5 Hz, 1H), 5.62 (s, 1H), 6.37 (d, J=2.2 Hz, 1H), 6.53 (d, J=7.1 Hz, 1H), 6.85 (dd, J=8.2, 2.2 Hz, 1H), 6.91 (d, J=7.1 Hz, 1H), 7.17 (s, 1H), 7.20 (d, J=8.2 Hz, 1H), 7.24 (dd, J=8.8, 2.7 Hz, 1H), 7.39-7.41 (m, 2H), 7.44 (d, J=7.7 Hz, 1H), 7.61 (dd, J=7.7, 1.6 Hz, 1H), 8.09 (dd, J=8.2, 6.0 Hz, 1H), 8.61 (d, J=8.2 Hz, 1H), 8.82 (d, J=5.5 Hz, 1H), 8.89 (s, 1H). Analytical HPLC (Method A): Col A: 4.95 min, 95%; Col B: 5.57 min, 95%.

Example 105

(2R,15R)-4,15,17-Trimethyl-2-(1-oxo-1,2-dihydro-isoquinolin-7-ylamino)-7-pyridin-4-yl-13-oxa-4,11-diaza-tricyclo[14.2.2.1$^{6,10}$]henicosa-1(19),6,8,10(21),16(20),17-hexaene-3,12-dione bistrifluoroacetate

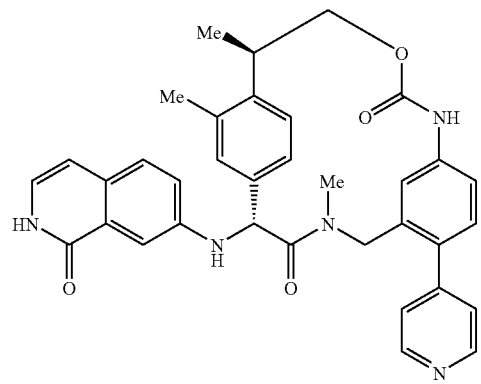 [SMILES: Cc1cc2ccc1[C@@H](C)COC(=O)Nc1ccc(-c3ccncc3)c(c1)CN(C)C(=O)[C@@H]2Nc1ccc2cc[nH]c(=O)c2c1]

According to the procedure for the preparation of Example 103, Example 97 (30 mg, 0.051 mmol) was coupled with 4-(tributylstannyl)pyridine (94 mg, 0.254 mmol) to afford Example 105 (8.02 mg, 9.83 μmol, 19.32% yield) as a yellow solid. MS (ESI) m/z 588.5 (M+H)$^+$. $^1$H-NMR: (500 MHz, CD$_3$OD) δ ppm 1.33 (d, J=7.1 Hz, 3H), 2.32 (s, 3H), 3.41 (s, 3H), 3.45-3.54 (m, 1H), 4.00 (dd, J=11.0, 4.4 Hz, 1H), 4.05 (d, J=16.5 Hz, 1H), 4.64 (t, J=11.0 Hz, 1H), 5.17 (d, J=16.5 Hz, 1H), 5.62 (s, 1H), 6.46 (s, 1H), 6.54 (d, J=7.1 Hz, 1H), 6.86-6.89 (m, 1H), 6.92 (d, J=7.1 Hz, 1H), 7.14 (s, 1H), 7.24 (dd, J=8.5, 2.5 Hz, 1H), 7.29 (d, J=8.2 Hz, 1H), 7.38-7.46 (am, 3H), 7.62 (d, J=7.7 Hz, 1H), 8.11 (d, J=7.1 Hz, 2H), 8.83 (d, J=7.1 Hz, 2H). Analytical HPLC (Method A): Col A: 4.94 min, 97%; Col B: 5.57 min, 99%.

Example 106

(2R,15R)-4,15,17-Trimethyl-7-(1-methyl-1H-imidazol-2-yl)-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione bistrifluoroacetate

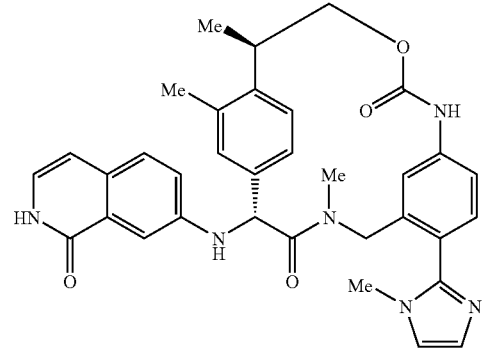 [SMILES: Cc1cc2ccc1[C@@H](C)COC(=O)Nc1ccc(-c3nccn3C)c(c1)CN(C)C(=O)[C@@H]2Nc1ccc2cc[nH]c(=O)c2c1]

According to the procedure for the preparation of Example 103, Example 97 (30 mg, 0.051 mmol) was coupled with 1-methyl-2-(tributylstannyl)-1H-imidazole (94 mg, 0.254 mmol) to afford Example 106 (6.1 mg, 7.45 μmol, 14.64% yield) as a yellow solid. MS (ESI) m/z 591.5 (M+H)$^+$. $^1$H-NMR: (500 MHz, CD$_3$OD) δ ppm 1.33 (d, J=6.6 Hz, 3H), 2.33 (s, 3H), 3.40 (s, 3H), 3.47-3.55 (m, 1H), 3.70 (s, 3H), 3.77 (d, J=17.0 Hz, 1H), 3.99 (dd, J=11.0, 4.4 Hz, 1H), 4.67 (t, J=11.0 Hz, 1H), 5.62 (s, 1H), 6.35 (d, J=2.2 Hz, 1H), 6.55 (d, J=6.6 Hz, 1H), 6.83 (dd, J=8.2, 2.2 Hz, 1H), 6.92 (d, J=7.1 Hz, 1H), 7.16 (d, J=1.6 Hz, 1H), 7.21-7.26 (m, 2H), 7.37 (d, J=2.2 Hz, 1H), 7.42 (d, J=8.8 Hz, 1H), 7.46 (d, J=8.2 Hz, 1H), 7.58 (d, J=1.6 Hz, 1H), 7.63 (dd, J=8.0, 1.9 Hz, 1H), 8.97 (d, J=1.1 Hz, 1H). Analytical HPLC (Method A): Col A: 4.88 min, 97%; Col B: 5.54 min, 99%.

Example 107

(2R,15R)-4,15,17-Trimethyl-2-(1-oxo-1,2-dihydro-isoquinolin-7-ylamino)-7-thiazol-2-yl-13-oxa-4,11-diaza-tricyclo[14.2.2.1$^{6,10}$]henicosa-1(19),6,8,10(21),16(20),17-hexaene-3,12-dione trifluoroacetate

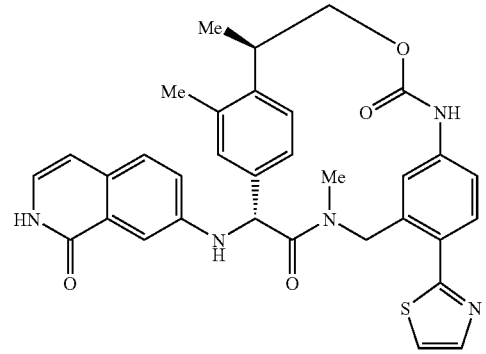 [SMILES: Cc1cc2ccc1[C@@H](C)COC(=O)Nc1ccc(-c3nccs3)c(c1)CN(C)C(=O)[C@@H]2Nc1ccc2cc[nH]c(=O)c2c1]

According to the procedure for the preparation of Example 103, Example 97 (30 mg, 0.051 mmol) was coupled with 2-(tributylstannyl)thiazole (76 mg, 0.204 mmol) at 100° C. for 2 h to afford Example 107 (12.4 mg, 0.018 mmol, 43.0% yield) as a white solid. MS (ESI) m/z 594.3 (M+H)$^+$. $^1$H-NMR: (500 MHz, CD$_3$OD) δ ppm 1.31 (d, J=7.1 Hz, 3H), 2.34 (s, 3H), 3.29 (s, 3H), 3.50 (ddd, J=11.1, 7.0, 4.4 Hz, 1H), 3.96 (dd, J=11.0, 4.4 Hz, 1H), 4.32 (d, J=−17.6 Hz, 1H), 4.61 (t, J=11.0 Hz, 1H), 5.60 (d, J=17.6 Hz, 1H), 5.70 (s, 1H), 6.27 (s, 1H), 6.57 (d, J=7. Hz, 1H), 6.80 (dd, J=8.2, 2.2 Hz, 1H), 6.99 (d, J=7.1 Hz, 1H), 7.26 (s, 1H), 7.33 (dd, J=8.5, 2.5 Hz, 1H), 7.45 (dd, J=18.4, 8.5 Hz, 2H), 7.55-7.62 (m, 3H), 7.64 (s, 1H), 7.89 (d, J=3.3 Hz, 1H). Analytical HPLC (Method A): Col A: 9.41 min, 95%; Col B: 9.29 min, 99%.

Example 108

(2R,15SR)-4,15,17-Trimethyl-7-oxazol-2-yl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione trifluoroacetate

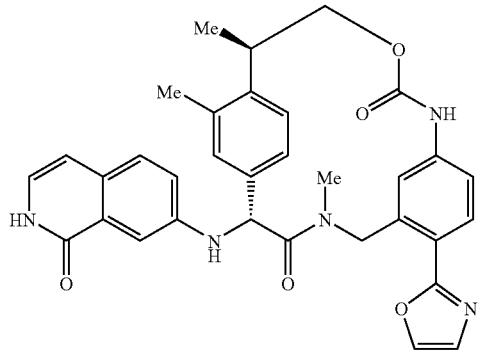 [SMILES: Cc1cc2ccc1[C@@H](C)COC(=O)Nc1ccc(-c3ncco3)c(c1)CN(C)C(=O)[C@@H]2Nc1ccc2cc[nH]c(=O)c2c1]

According to the procedure for the preparation of Example 103, Example 97 (25 mg, 0.042 mmol) was coupled with 2-(tributylstannyl)oxazole (76 mg, 0.212 mmol) at 100° C. for 2 h to afford Example 108 (12.7 mg, 0.018 mmol, 43.3% yield) as a white solid. MS (ESI) m/z 578.3 (M+H)$^+$. $^1$H-NMR: (500 MHz, CD$_3$OD) δ ppm 1.29 (d, J=7.1 Hz, 3H), 2.31 (s, 3H), 3.32 (s, 3H), 3.47 (ddd, J=11.3, 6.9, 4.4 Hz, 1H), 3.93 (dd, J=11.0, 4.4 Hz, 1H), 4.35 (d, J=18.1 Hz, 1H), 4.61 (t, J=11.3 Hz, 1H), 5.67 (s, 1H), 5.73 (d, J=18.1 Hz, 1H), 6.24 (d, J=1.6 Hz, 1H), 6.54 (d, J=7.1 Hz, 1H), 6.80 (dd., J=8.2, 2.2 Hz, 1H), 6.94 (d, J=7.1 Hz, 1H), 7.23 (d, J=1.1 Hz, 1H), 7.26-7.30 (m, 2H), 7.42 (d, J=8.2 Hz, 2H), 7.56 (d, J=2.2 Hz, 1H), 7.60 (dd, J=8.0, 1.9 Hz, 1H), 7.88 (d, J=8.8 Hz, 1H), 7.92 (s, 1H). Analytical HPLC (Method A): Col A: 7.10 min, 95%; Col B: 7.11 min, 95%.

Example 109

(2R,15R)-4,15,17-Trimethyl-2-(1-oxo-1,2-dihydro-isoquinolin-7-ylamino)-7-(2-trifluoromethoxy-phenyl)-13-oxa-4,11-diaza-tricyclo[14.2.2.1$^{6,10}$]henicosa-1(19),6,8,10(21),16(20),17-hexaene-3,12-dione trifluoroacetate

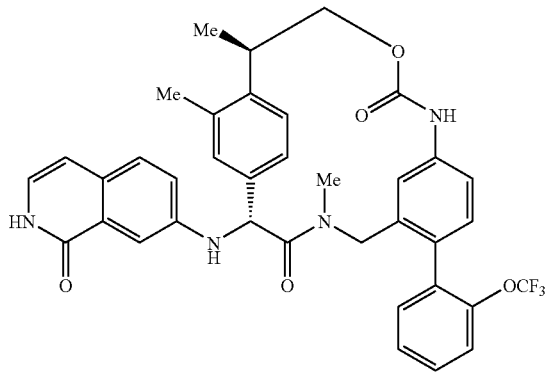 [SMILES: Cc1cc2ccc1[C@@H](C)COC(=O)Nc1ccc(-c3ccccc3OC(F)(F)F)c(c1)CN(C)C(=O)[C@@H]2Nc1ccc2cc[nH]c(=O)c2c1]

According to the procedure for the preparation of Example 98, Example 97 (30 mg, 0.051 mmol) was coupled with 2-(trifluoromethoxy)phenylboronic acid (87 mg, 0.424 mmol) at 100° C. for 2 h to afford after purification Example 109 (13.5 mg, 0.017 mmol, 40.6% yield) as an off-white solid. MS (ESI) m/z 671.3 (M+H)$^+$. $^1$H-NMR: (500 MHz, CD$_3$OD) δ ppm 1.30 (d, J=7.1 Hz, 3H), 2.34 (s, 2H), 2.38 (s, 1H), 3.12 (s, 1H), 3.27 (s, 2H), 3.45-3.53 (m, 2H), 3.94-4.03 (min, 1H), 4.58-4.67 (m, 1H), 5.00-5.39 (m, 1H), 5.62 (s, 1H), 6.00-6.18 (m, 1H), 6.53 (d, J=7.1 Hz, 1H), 6.77-6.83 (m, 1H), 6.92 (d, J=7.1 Hz, 1H), 7.02-7.10 (m, 1H), 7.24-7.31 (m, 2H), 7.35-7.43 (m, 5H), 7.43-7.52 (m, 3H), 7.52-7.61 (m, 1H). Analytical HPLC (Method A): Col A: 9.08 min, 97%; Col B: 8.52 min, 98%.

Example 110

(2R,15R)-7-(4-Hydroxy-phenyl)-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione trifluoroacetate

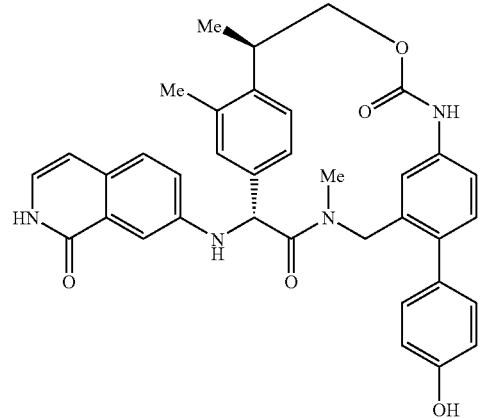 [SMILES: Cc1cc2ccc1[C@@H](C)COC(=O)Nc1ccc(-c3ccc(O)cc3)c(c1)CN(C)C(=O)[C@@H]2Nc1ccc2cc[nH]c(=O)c2c1]

According to the procedure for the preparation of Example 98, Example 97 (25 mg, 0.042 mmol) was coupled with 4-hydroxyphenylboronic acid (58.5 mg, 0.424 mmol) at 105° C. for 2 h to afford after purification Example 110 (16.43 mg, 0.023 mmol, 54.1% yield) as an off-white solid. MS (ESI) m/z 603.3 (M+H)$^+$. $^1$H-NMR: (400 MHz, CD$_3$OD) δ ppm 1.30 (d, J=7.1 Hz, 3H), 2.36 (s, 3H), 3.22 (s, 3H), 3.44-3.53 (m, 1H), 3.73 (d, J=17.0 Hz, 1H), 3.97 (dd, J=10.4, 4.4 Hz, 1H), 4.62 (t, J=11.0 Hz, 1H), 5.30 (d, J=17.0 Hz, 1H), 5.61 (s, 1H), 6.04 (d, J=2.2 Hz, 1H), 6.54 (d, J=7.1 Hz, 1H), 6.73 (dd, J=7.7, 2.2 Hz, 1H), 6.81 (d, J=8.8 Hz, 2H), 6.92 (d, J=7.1 Hz, 1H), 7.03 (d, J=8.2 Hz, 1H), 7.10 (d, J=8.2-1 Hz, 2H), 7.23-7.28 (m, 2H), 7.38-7.46 (m, 4H), 7.58 (dd, J=8.2, 1.6 Hz, 1H). Analytical HPLC (Method A): Col A: 7.65 min, 97%; Col B: 7.56 min, 95%.

Example 111

17,20-Dimethyl-2-(4-oxo-3,4-dihydro-quinazolin-6-ylamino)-7-(propane-2-sulfonyl)-4,11,14-triaza-tricyclo[14.2.2.1^{6,10}]henicosa-1(19),6,8,10(21),16(20),17-hexaene-3,12-dione bistrifluoroacetate

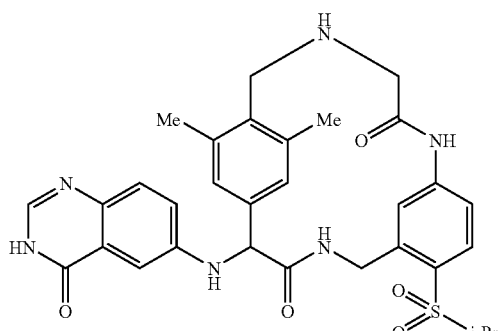

111A

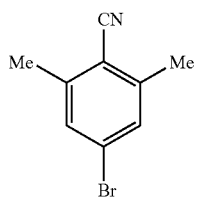

4-Bromo-2,6-dimethylaniline (4.49 g, 22.44 mmol) was taken up in water (25 mL) and conc. HCl (8 mL, 261 mmol) was added. The mixture was sonicated to form a fine suspension and then cooled to 0° C. A solution of sodium nitrite (1.67 g, 24.20 mmol) in water (5 mL) was added dropwise so as to maintain the temperature between 0-5° C. The mixture was stirred 0° C. for 30 min and then neutralized by addition of solid NaHCO$_3$. The resulting solution was then added portionwise to a solution of copper cyanide (2.42 g, 27.0 mmol) and potassium cyanide (3.65 g, 56.1 mmol) in water (25 mL) at 70° C. The mixture was stirred at 70° C. for 30 min. The reaction mixture was extracted with toluene (2×30 mL). The organic phase was washed with water, brine, and dried (MgSO$_4$). Purification via flash chromatography (0-5% EtOAc in Hexane) afforded 111A (3.0 g, 63%) as a tan solid. MS (ESI) m/z 209.9 (M+H)$^+$. $^1$H NMR: (400 MHz, CDCl$_3$) δ ppm 2.48 (s, 6H) 7.28 (s, 2H).

111B

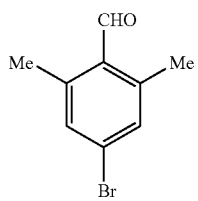 [SMILES: Cc1cc(Br)cc(C)c1C=O]

Diisobutylaluminum hydride (1M in THF, 13.00 mL, 13.00 mmol) was added to a solution of 111A (2.1 g, 10.00 mmol) in dry benzene (20 mL) at 4° C. After the mixture was stirred 1 h at rt, 5% H$_2$SO$_4$ (10 mL) was added at 4° C. The reaction mixture was extracted with ether (2×30 mL). The combined organic phase was washed with brine, dried (Na$_2$SO$_4$) and concentrated. Purification via flash chromatography (0-5% EtOAc in Hexanes) afforded 111B (1.9 g, 88%) as a tan solid. MS (ESI) m/z 212.9 (M+H)$^+$. $^1$H NMR: (400 MHz, CDCl$_3$) δ ppm 2.57 (s, 6H) 7.26 (s, 2H), 10.54 (s, 1H).

111C

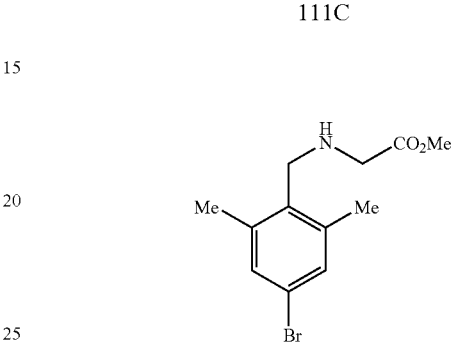

To a round bottom flask containing methyl 2-aminoacetate hydrochloride (326 mg, 2.60 mmol), triethylamine (263 mg, 2.60 mmol) in MeOH (5 ml) at 0° C., was added 111B (426 mg, 2 mmol). The mixture was stirred rt for 12 h. NaBH$_4$ (76 mg, 2.064 mmol) was added slowly at 0° C. The mixture was stirred 0° C. for 2 h, then at rt for 2 h. The mixture was acidified with 10% NaHSO$_4$, extracted with ether (2×20 ml). The water layer was basified with Na$_2$CO$_3$, and extracted with ether (2×30 ml), dried (Na$_2$SO$_4$). Concentration afforded 111C (503 mg, 87% yield) as a colorless oil. MS (ESI) m/z 286.0 (M+H)$^+$. $^1$H NMR (400 MHz, CD$_3$OD) d ppm 2.38 (s, 3H) 3.45 (s, 2H) 3.73 (s, 5H) 7.17 (s, 2H).

111D

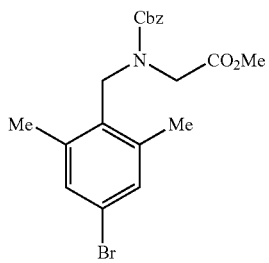 [SMILES: COC(=O)CN(Cc1c(C)cc(Br)cc1C)C(=O)OCc1ccccc1]

To a round bottom flask was added 111C (303 mg, 1.059 mmol), N,N-Diisopropylethylamine (411 mg, 3.18 mmol), and N-(Benzyloxycarbonyloxy) succinimide (290 mg, 1.165 mmol), in DMF (10 mL). The solution was stirred rt overnight. The mixture was diluted with EtOAc (50 mL). The organic phase was washed with 1N HCl, sat NaHCO$_3$, and brine, dried (Na$_2$SO$_4$), and concentrated. Purification through flash chromatography (0-25% EtOAc in Hexanes) afforded 111D (360 mg, 80% yield) as a colorless oil. MS (ESI) m/z 420.0 (M+H)$^+$.

111E

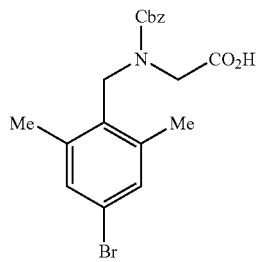 [SMILES: Cc1cc(Br)cc(C)c1CN(CC(=O)O)C(=O)OCc1ccccc1]

To a solution of 111D (360 mg, 0.857 mmol) in THF (5 mL), was added aqueous LiOH (1M, 8 mL). The solution was stirred rt overnight. The reaction mixture was concentrated, then purified by preparative HPLC to afford 111E (318 mg, 90% yield). MS (ESI) m/z 406.3 (M+H)+.

111F

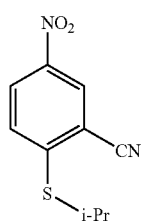

To a round bottom flask contained 2-fluoro-5-nitrobenzonitrile (10.07 g, 60.6 mmol) and N,N-Diisopropylethylamine (16.90 ml, 97 mmol) in DMF (25 ml), was added propane-2-thiol (6.76 ml, 72.7 mmol). The mixture was stirred rt for 3 h. The reaction was quenched with water. The mixture was extracted with EtOAc (3×30 ml). The combined organic layer was filtered through silica gel and concentrated. Purification via flash chromatography (0-20% EtOAc in Hexanes) affords 111F (13.2 g, 96% yield) as a yellow solid. MS (ESI) m/z 223.0 (M+H)+.

111G

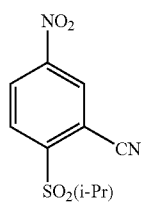

To a round bottom flask contained 111F (6.67 g, 30 mmol) in DCM (60 ml), was added m-CPBA (11.39 g, 66.0 mmol) at 0° C. The mixture was stirred at rt for 4 h. The reaction was quenched with water and extracted with EtOAc (3×30 ml). The organic layer was washed with sat. NaHCO3 and brine, dried (Na2SO4) and concentrated. Purification via flash chromatography (0-30% EtOAc in Hexanes) afforded 111G (7.0 g, 90% yield) as a white solid. MS (ESI) m/z 255.0 (M+H)+.

111H

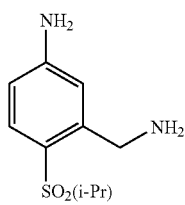

To a solution of 111G (2 g, 7.87 mmol) and conc. hydrochloric acid (0.631 g, 17.30 mmol) in MeOH (60 mL), was added 10% Pd/C (ca. 150 mg). The mixture was hydrogenated at 60 psi for 60 h. The reaction mixture was filtered. The residue was redissolved in MeOH (60 mL), then Hydrochloric acid (0.631 g, 17.30 mmol) and 10% Pd/C (ca. 150 mg) were added. The mixture was hydrogenated at 50 psi for 24 h. The reaction was filtered and concentrated to afford 111H (1.98 g, 79% yield) as a yellow solid. MS (ESI) m/z 229.3 (M+H)+.

111I

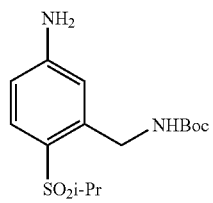

To a round bottom flask was added 111H (404 mg, 1.341 mmol) in THF (5 mL), and sodium bicarbonate (563 mg, 6.71 mmol) in water (5.00 mL), di-tert-butyl dicarbonate (0.324 mL, 1.408 mmol) was added at 0° C. The mixture was stirred rt for 30 min. The reaction mixture was extracted with EtOAc (2×20 mL). The combined organic phase was washed withed brine, dried (Na2SO4) and concentrated. Purification via flash chromatography (0-50% EtOAc in Hexanes) afford 111I (389 mg, 87% yield) as a white solid. MS (ESI) m/z 229.0 (M+H)+-Boc.

111J

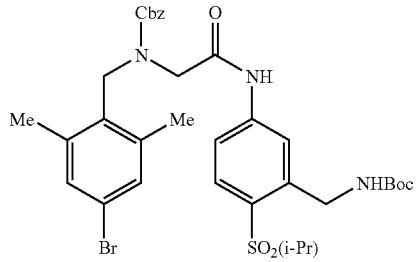

To a round bottom flask with 111E (248 mg, 0.610 mmol) in CH2Cl2 (6 mL), was added oxalyl chloride (0.5 mL, 1.0 mmol), and DMF (1 drop). The mixture was stirred rt for 1 h.

111M

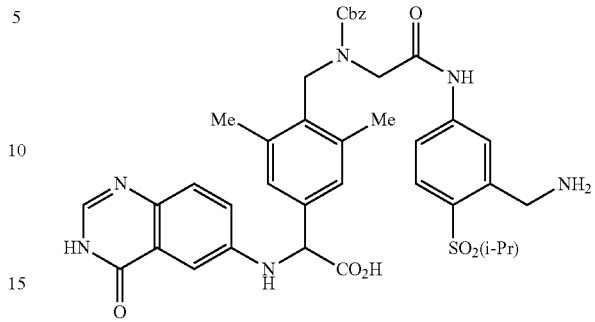

The reaction mixture was concentrated, then dried under vacuum for 30 min. The residue was dissolved in DCM (2 mL), and added to a r.b. flask containing 111I (221 mg, 0.671 mmol) and pyridine (290 mg, 3.66 mmol) in CH$_2$Cl$_2$ (6 mL) at 0° C. The mixture was stirred rt for 1 h, then was quenched with water. EtOAc (30 mL) was added, and the organic phase was washed with 0.5 HCl (2×10 mL) and brine, dried (Na$_2$SO$_4$) and concentrated. Purification via flash chromatography (0-50% EtOAc in Hexanes) afforded 111J (285 mg, 64.5% yield) as a white solid. MS (ESI) m/z 616.1 (M+H)$^+$.

111K

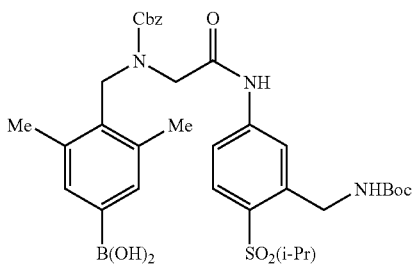

Using a procedure analogous to that used to prepare 29B, 111J (230 mg, 0.321 mmol) was reacted with bis(neopentyl glycolato)diboron), potassium acetate and (1,1'-bis(diphenylphosphino)ferrocene)-dichloropalladium(11). The crude was purified by flash chromatography and preparative HPLC to afford 111K (121 mg, 54.2% yield) as a white solid. MS (ESI) m/z 682.4 (M+H)$^+$.

111L

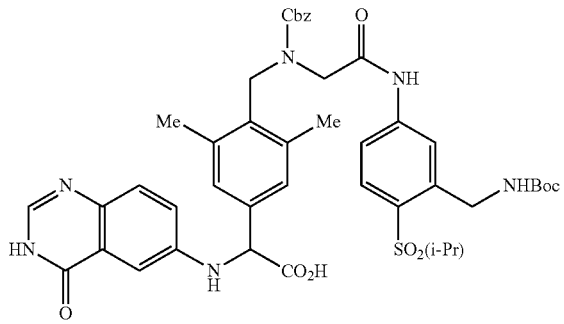

To a round bottom flask containing 111K (116 mg, 0.170 mmol), Intermediate 4 (27.4 mg, 0.170 mmol) and glyoxylic acid monohydrate (15.66 mg, 0.170 mmol), were added CH$_3$CN (3 mL) and DMF (0.5 mL). The mixture was irradiated in a microwave reactor at 100° C. for 10 min, then was concentrated. The crude product was purified by preparative HPLC to afford 111L (110 mg, 75% yield) as a yellow solid MS (ESI) m/z 855.4 (M+H)$^+$.

To a solution of 111L (109 mg, 0.127 mmol) in EtOAc (2 mL), was added 4 N hydrogen chloride in dioxane (0.637 mL, 2.55 mmol). The reaction mixture was stirred at rt for 2 h, then was concentration to afford 111M (89 mg, 85% yield) as a yellow solid. MS (ESI) m/z 755.3 (M+H)$^+$. $^1$H NMR: (500 MHz, CD$_3$OD) δ ppm 1.27 (d, J=6.60 Hz, 6H) 2.20 (s, 3H) 2.24 (s, 3H) 3.33-3.43 (m, 1H) 3.70 (d, J=17.04 Hz, 1H) 3.83-3.97 (m, 1H) 4.36 (s, 2H) 4.72 (s, 2H) 4.93 (d, J=8.24 Hz, 1H) 5.19 (d, J=32.98 Hz, 2H) 7.08 (s, 1H) 7.17-7.45 (m, 8H) 7.69-7.82 (m, 3H) 7.90 (d, J=8.25 Hz, 1H).

111N

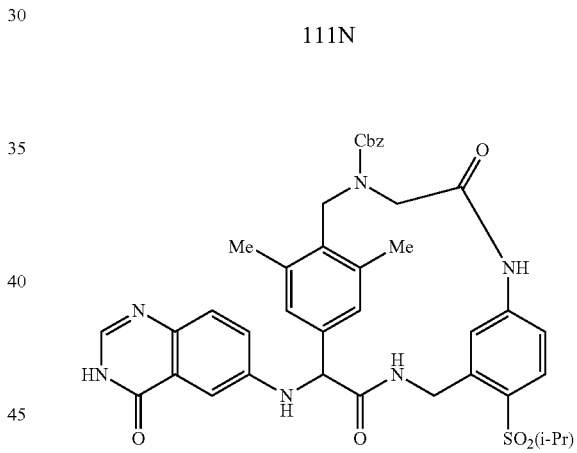

To a solution of BOP (105 mg, 0.202 mmol) and DMAP (9.88 mg, 0.081 mmol) in CH$_2$Cl$_2$ (40 mL) and DMF (10 mL), was added a solution of 111M (32 mg, 0.040 mmol) and TEA (8.18 mg, 0.081 mmol) in DMF (10 mL) dropwise via a syringe pump over 4 h. The mixture was stirred rt for 20 h. The reaction was quenched with water, then extracted with EtOAc (3×30 mL). The organic layer was washed with 1N HCl, sat. NaHCO$_3$ and brine, dried (Na$_2$SO$_4$). Purification via preparative HPLC afforded 111N (10.2 mg, 29.9% yield) as a tan solid. MS (ESI) m/z 737.4 (M+H)$^+$. $^1$HNMR: (400 MHz, CD$_3$OD) δ ppm 1.20 (d, J=6.60 Hz, 3H) 1.31 (d, J=7.15 Hz, 3H) 2.30 (d, J=14.29 Hz, 3H) 2.42-2.51 (m, 3H) 3.45-3.57 (m, 1H) 3.85 (d, J=17.04 Hz, 1H) 4.28 (d, J=15.94 Hz, 1H) 4.38-4.56 (m, 2H) 4.96-5.13 (m, 3H) 5.15-5.30 (m, 2H) 6.41-6.54 (m, 1H) 6.90 (d, J=8.24 Hz, 1H) 6.98 (d, J=13.19 Hz, 1H) 7.19-7.51 (m, 7H) 7.74 (d, J=8.24 Hz, 1H) 8.59 (s, 1H) 8.91 (s, 1H).

Example 111

To a solution of 111N (10.2 mg, 0.012 mmol) in MeOH (5 mL), was added Pd/C (10%, ca 5 mg). The mixture was hydrogenated with a balloon of $H_2$ for 2 h. The reaction mixture was filtered, concentrated, and purified via preparative HPLC to afford Example 111 (8.4 mg, 85% yield) as a white solid. MS (ESI) m/z 603.3 $(M+H)^+$. $^1$H NMR: (500 MHz, $CD_3OD$) δ ppm 1.22 (d, J=6.60 Hz, 3H) 1.34 (d, J=6.60 Hz, 3H) 2.40 (s, 3H) 2.66 (s, 3H) 3.51-3.61 (m, 1H) 3.88 (d, J=16.49 Hz, 1H) 4.11 (d, J=15.94 Hz, 1H) 4.29 (dd, J=17.04, 4.95 Hz, 1H) 4.44 (d, J=14.29 Hz, 1H) 4.60 (d, J=14.29 Hz, 1H) 5.06 (dd, J=17.31, 5.77 Hz, 1H) 5.13 (s, 1H) 6.67 (s, 1H) 6.90-6.96 (m, 1H) 7.07 (s, 1H) 7.21 (d, J=2.75 Hz, 1H) 7.35-7.41 (m, 1H) 7.49 (d, J=8.79 Hz, 1H) 7.57 (s, 1H) 7.80 (d, J=8.25 Hz, 1H) 8.58 (s, 1H) 8.98 (t, J=5.77 Hz, 1H). Analytical HPLC (Method A): Col A: 4.29 min, 99%; Col B: 4.87 min, 99%.

Example 112

3,17,18-Trimethyl-14-(4-oxo-3,4-dihydro-quinazolin-6-ylamino)-9-(propane-2-sulfonyl)-3,5,12-triazatricyclo[13.2.2.1$^{6,10}$]icosa-1(18), 6(20),7,9,15(19),16-hexaene-4,13-dione trifluoroacetate

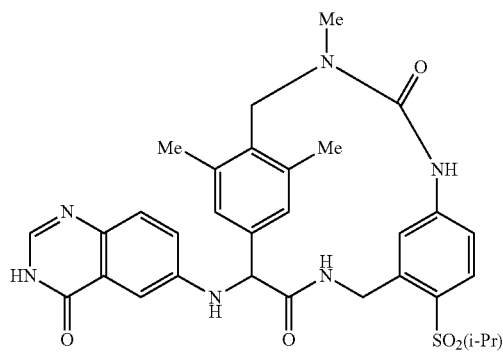

112A

To a solution of 111B (213 mg, 1.00 mmol) in MeOH (6 mL), methylamine, 2 M in THF (1 mL, 2.0 mmol) was added dropwise. The reaction mixture was stirred at rt for 1 h. The reaction mixture was cooled to 0° C., then sodium borohydride (113 mg, 3.00 mmol) was added. The reaction mixture was stirred at rt for 2 h, then was concentrated. The residue was taken up in EtOAc (20 mL). The organic phase was washed with water, and brine, dried ($Na_2SO_4$) and concentrated to afford 112A (223 mg, 94% yield) as a yellow oil. MS (ESI) m/z 228.3 $(M+H)^+$.

112B

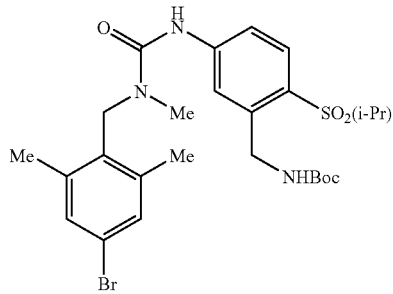

Using a procedure analogous to that used to prepare 29A, 111I (311 mg, 0.947 mmol) was reacted with sodium bicarbonate and phosgene followed by 112A (346 mg, 1.515 mmol) and TEA. Purification via flash chromatography (0-60% EtOAc in Hexanes) afforded 112B (484 mg, 87% yield) as a white solid. MS (ESI) m/z 582.3 $(M+H)^+$.

112C

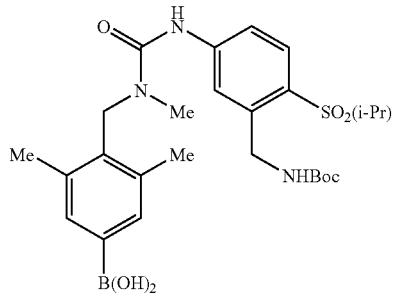

Using a procedure analogous to that used to prepare 29B, 112B (377 mg, 0.647 mmol) was reacted with bis(neopentyl glycolato)diboron), potassium acetate and (1,1'-bis(diphenylphosphino)ferrocene)-dichloropalladium(II). The crude was purified by flash chromatography and preparative HPLC to afford 112C (192 mg, 54% yield) as a tan solid. MS (ESI) m/z 548.3 $(M+H)^+$.

112D

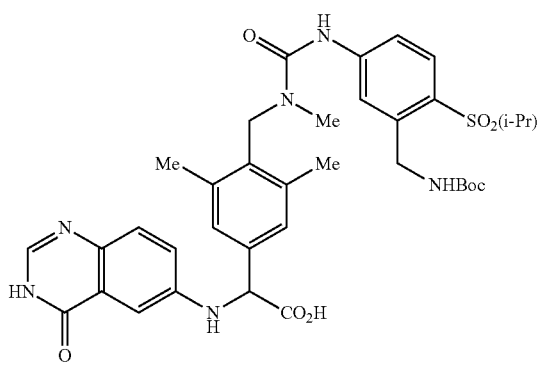

To a round bottom flask was added 112C (84 mg, 0.153 mmol), Intermediate 4 (24.73 mg, 0.153 mmol), glyoxylic acid monohydrate (14.12 mg, 0.153 mmol) in $CH_3CN$ (3 mL) and DMF (0.5 mL). The mixture irradiated in a microwave reactor at 100° C. for 10 min. Purification via preparative HPLC afforded 112D (58 mg, 52% yield) as a yellow solid. MS (ESI) m/z 721.4 $(M+H)^+$.

112E

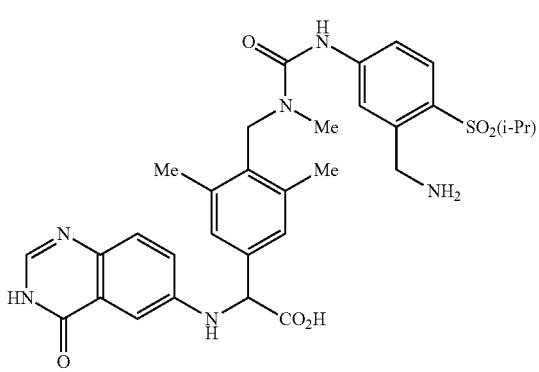

112D (55 mg, 0.076 mmol) was dissolved in EtOAc (2 mL), 4N HCl in dioxane (1 mL, 4.00 mmol) was added. The mixture was stirred at rt for 2 h, then was concentrated to afford 112E (46 mg, 91% yield) as a light yellow solid. MS (ESI) m/z 621.3 (M+H)$^+$.

Example 112

To a solution of BOP (93 mg, 0.210 mmol), DMAP (17.10 mg, 0.140 mmol), and TEA (21.25 mg, 0.210 mmol) in DCM (30 mL) and DMF (10 mL), was added a solution of 112E (46 mg, 0.070 mmol) in DMF (10 mL) dropwise over 8 h via a syringe pump. The mixture was stirred rt for 20 h. The reaction was quenched with water and extracted with DCM (3×20 mL). The combined organic layer was washed with 1N HCl, sat. NaHCO$_3$ and brine, dried (Na$_2$SO$_4$) and concentrated. Purification via preparative HPLC afforded Example 112 (5.5 mg, 9.03 µmol, 12.91% yield). MS (ESI) m/z 603.4 (M+H)$^+$. $^1$H NMR (400 MHz, CD$_3$OD) δ ppm 1.19 (d, J=6.60 Hz, 3H) 1.27 (d, J=7.15 Hz, 3H) 2.24 (s, 3H) 2.53 (s, 3H) 3.29 (s, 3H) 3.31-3.41 (m, 1H) 4.30-4.39 (m, 1H) 4.58 (d, J=115.39 Hz, 1H) 4.76-4.83 (m, 1H) 4.95 (dd, J=17.59, 7.15 Hz, 1H) 5.04 (s, 1H) 5.19 (s, 1H) 7.29 (d, J=2.75 Hz, 1H) 7.36 (s, 1H) 7.42-7.48 (m, 1H) 7.50-7.55 (m, 1H) 7.65-7.78 (m, 3H) 8.43 (s, 1H) 8.79 (dd, J=7.42, 4.67 Hz, 1H), Analytical HPLC (Method A): Col A: 5.87 min, 92%; Col B: 6.26 min, 95%.

Example 113

14-(7-Fluoro-4-oxo-3,4-dihydro-quinazolin-6-ylamino)-3,17,18-trimethyl-9-(propane-2-sulfonyl)-3,5,12-triaza-tricyclo[13.2.2.1$^{6,10}$]icosa-1(18),6(20),7,9,15(19),16-hexaene-4,13-dione trifluoroacetate

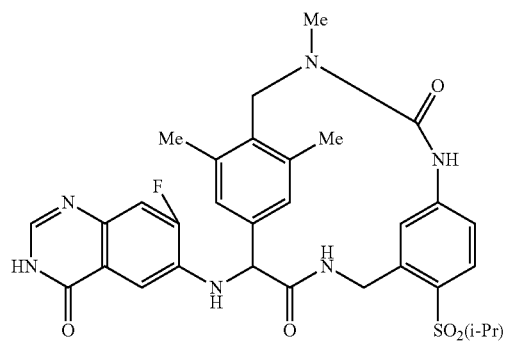

According to the procedure for the preparation of Example 112, substitution of Intermediate 4 with Intermediate 12 afforded Example 113. MS (ESI) m/z 621.1 (M+H)$^+$. $^1$H NMR (400 MHz, CD$_3$OD) δ ppm 1.19 (d, J=6.60 Hz, 3H) 1.29 (d, J=7.15 Hz, 3H) 2.22 (s, 3H) 2.55 (s, 3H) 3.15 (s, 3H) 3.32-3.41 (m, 1H) 4.32 (dd, J=17.31, 4.12 Hz, 1H) 4.56 (d, J=15.39 Hz, 1H) 4.82 (d, J=15.39 Hz, 1H) 4.96-5.03 (m, 1H) 5.04 (s, 1H) 5.26 (s, 1H) 7.24 (s, 1H) 7.32 (d, J=8.79 Hz, 1H) 7.39 (d, J=12.09 Hz, 1H) 7.65-7.69 (m, 1H) 7.72 (s, 1H) 7.75 (s, 1H) 8.24 (s, 1H) 8.83 (dd, J=7.70, 4.40 Hz, 1H). Analytical HPLC (Method A): Col A: 6.78 min, 94%; Col B; 6.82 min, 97%.

Example 114

14-(7-Fluoro-4-oxo-3,4-dihydro-quinazolin-6-ylamino)-3,17-dimethyl-9-(propane-2-sulfonyl)-3,5,12-triaza-tricyclo[13.2.2.1$^{6,10}$]icosa-1(18),6(20),7,9,15(19),16-hexaene-4,13-dione trifluoroacetate

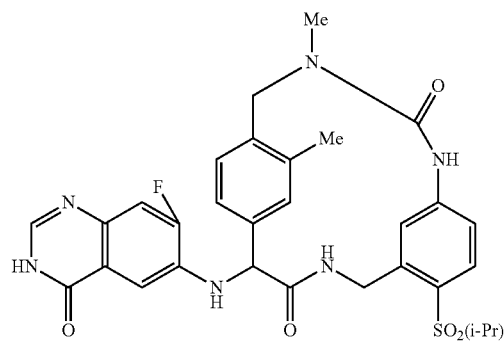

114A

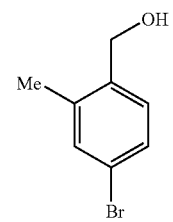

To a solution of 4-bromo-2-methylbenzoic acid (4.30 g, 20 mmol) in THF (20 mL) at 0° C., was added BH$_3$ (2 M in THF, 20.0 mL, 40.0 mmol). The mixture was stirred rt for 2 h, then was quenched with 1N HCl and extracted with EtOAc (3×20 mL). The combined organic layer was washed with 1N HCl, H$_2$O, sat. NaHCO$_3$, and brine, then dried (Na$_2$SO$_4$) and concentrated to afford 114A (4.0 g, 19.50 mmol, 97% yield). MS (ESI) m/z 183.0 (M+H)$^+$.

114B

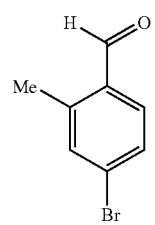

To a solution of 114A (0.885 g, 4.4 mmol) in DCM (15 mL) at 0° C., was added Dess-Martin periodinane (2.05 g, 4.83 mmol). The mixture was stirred rt for 1 h, then was quenched with water. The mixture was extracted with DCM (3×20 mL). The combined organic layer was washed with 1N HCl, sat. NaHCO$_3$ and brine, dried (Na$_2$SO$_4$) and concentrated. The crude material was added to a 120 g column and was eluted with 0-10% EtOAc in Hexanes. Concentration of product containing fraction provided 114B (835 mg, 4.15 mmol, 94% yield).

114C

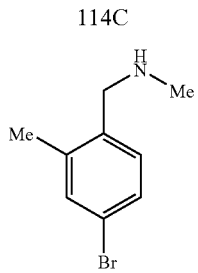

To a solution of 114B (773 mg, 3.88 mmol) in MeOH (10 mL) at 0° C., was added a solution of MeNH$_2$ (2 M in MeOH, 3.88 mL, 7.77 mmol). The mixture was stirred rt for 1 h, then was recooled to 0° C. Sodium borohydride (294 mg, 7.77 mmol) was added. The mixture was stirred rt for 1 h, then was concentrated. The residue was dissolved in DCM (60 mL). The organic layer was washed with sat. NaHCO$_3$ and brine, dried (Na$_2$SO$_4$) and concentrated to afford 114C (528 mg, 2.219 mmol, 57.2% yield). MS (ESI) m/z 214.3 (M+H)$^+$.

114D

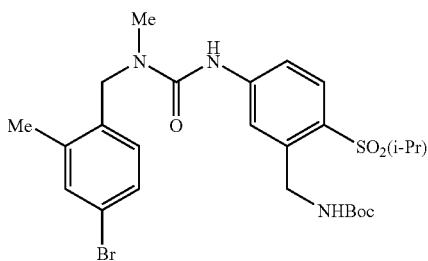

Using a procedure analogous to that used to prepare 29A, 1111 (680 mg, 2.070 mmol) was reacted with sodium bicarbonate and phosgene followed by 114C (532 mg, 2.485 mmol), and TEA. The crude material was added to a 80 g column and was eluted with 0-100% EtOAc in Hexanes to afford 114D (1.06 g, 1.809 mmol, 87% yield). MS (ESI) m/z 568.2 (M+H)$^+$.

114E

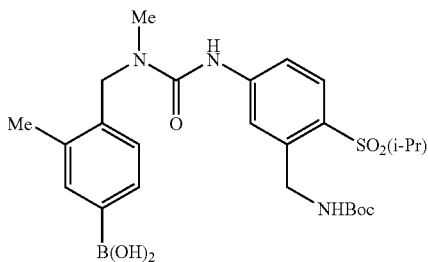

Using a procedure analogous to that used to prepare 29B, 114D (682 mg, 1.2 mmol) was reacted with bis(neopentyl glycolato)diboron, potassium acetate and (1,1'-bis(diphenylphosphino)ferrocene)-dichloropalladium(II). The crude was purified by flash chromatography and preparative HPLC (CH$_3$CN/H$_2$O, 0.1% TFA) to afford 114E (555 mg, 1.030 mmol, 86% yield) as a white solid. MS (ESI) m/z 533.4 (M+H)$^+$.

114F

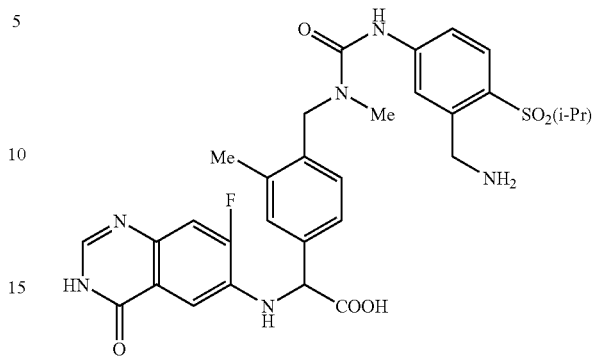

Using a procedure analogous to that used to prepare 1E, 114E (106 mg, 0.199 mmol), Intermediate 12, and glyoxylic acid monohydrate were reacted and purified by prep HPLC to afford 114F (50 mg, 0.079 mmol, 39.9% yield). MS (ESI) m/z 625.3 (M+H)$^+$.

Example 114

To a solution of BOP (170 mg, 0.384 mmol), DMAP (46.9 mg, 0.384 mmol) and TEA (23.33 mg, 0.231 mmol) in DCM (30 mL), and DMF (5 mL), was added a solution of 114F (48 mg, 0.077 mmol) in DMF (10 mL) dropwise via a syringe pump over 8 h. The mixture was stirred rt for 20 h, then was quenched with water. The mixture was extracted with EtOAc (3×20 mL). The organic phase was washed with brine, dried (Na$_2$SO$_4$) and concentrated. The crude product was purified by preparative HPLC to afford Example 114 (8 mg, 0.013 mmol, 17% yield). MS (ESI) m/z 607.3 (M+H)$^+$. $^1$H NMR (400 MHz, Acetone-d) δ ppm 1.14 (d, J=6.60 Hz, 3H) 1.29 (d, J=7.15 Hz, 3H) 2.44 (s, 3H) 3.18 (s, 3H) 3.38-3.49 (m, 1H) 4.27 (dd, J=17.04, 4.40 Hz, 1H) 4.54 (d, J=16.49 Hz, 1H) 4.86 (d, J=15.94 Hz, 1H) 4.99 (s, 1H) 5.04 (dd, J=17.31, 7.97 Hz, 1H) 5.42 (s, 1H) 5.96 (s, 1H) 6.15 (s, 1H) 7.28 (s, 2H) 7.33 (d, J=3.85 Hz, 1H) 7.36 (d, J=7.15 Hz, 1H) 7.66 (d, J=8.25 Hz, 1H) 7.74 (dd, J=8.79, 2.20 Hz, 1H) 7.90 (s, 1H) 7.96 (s, 1H) 8.04 (dd, J=7.42, 4.67 Hz, 1H). Analytical HPLC (Method A): Col A: 6.48 min, 95%; Col B: 6.88 min, 93%.

Example 115

3,17-Dimethyl-14-(1-oxo-1,2-dihydro-isoquinolin-7-ylamino)-9-(propane-2-sulfonyl)-3,5,12-triaza-tricyclo[13.2.2.1$^{6,10}$]icosa-1(18),6(20),7,9,15(19),16-hexaene-4,13-dione trifluoroacetate

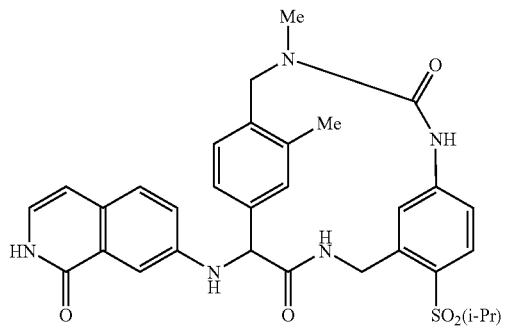

According to the procedure for the preparation of Example 114, replacement of Intermediate 12 with Intermediate 3 afforded Example 115. MS (ESI) m/z 588.2 (M+H)+. Analytical HPLC (Method A): Col A: 6.87 min, 95%; Col B: 6.89 min, 93%.

Example 116

14-Acetyl-17,20-dimethyl-2-(4-oxo-3,4-dihydro-quinazolin-6-ylamino)-7-(propane-2-sulfonyl)-4,11,14-triaza-tricyclo[14.2.2.1$^{6,10}$]henicosa-1(19),6,8,10(21),16(20),17-hexaene-3,12-dione trifluoroacetate

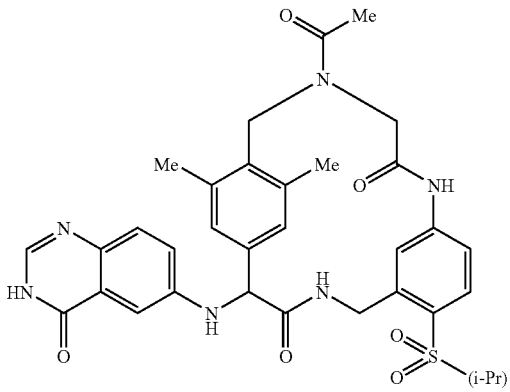

To a solution of Example 111 (8.7 mg, 0.014 mmol) in CH$_2$Cl$_2$ (1 mL) at 0° C., TEA (4.38 mg, 0.043 mmol) was added, followed by acetic anhydride (2.210 mg, 0.022 mmol). The mixture was stirred rt for 1 h. The reaction mixture was concentrated and purified via preparative HPLC [Phenomenex AXIA Luna 75×30 mm 5μ (10 min grad), A: 10% ACN-90% H$_2$O-0.1% TFA; B: 90% ACN-10% H$_2$O-0.1% TFA; 0-100% B; rt=4.25 min] to afford Example 116 (6.6 mg, 10.13 μmol, 70.2% yield). MS (ESI) m/z 645.4 (M+H)+. $^1$H NMR (500 MHz, CD$_3$OD) δ ppm 1.19-1.24 (m, 3H) 1.30-1.35 (m, 3H) 2.15 (s, 3H) 2.35 (s, 3H) 2.46 (s, 3H) 3.45-3.59 (m, 1H) 3.92-4.00 (m, 1H) 4.23-4.34 (m, 2H) 4.39 (d, J=17.59 Hz, 1H) 5.03 (dd, J=17.04, 6.05 Hz, 1H) 5.07-5.1.1 (m, 1H) 5.37 (d, J=14.84 Hz, 1H) 6.42-6.54 (m, 1H) 6.87-6.97 (m, 1H) 6.98-7.06 (m, 1H) 7.22 (d, J=2.20 Hz, 1H) 7.37 (dd, J=9.07, 2.47 Hz, 1H) 7.42-7.53 (m, 2H) 7.77 (d, J=8.25 Hz, 1H) 8.56-8.64 (m, 1H) 8.96 (t, J=5.77 Hz, 1H). Analytical HPLC (Method A): Col A: 5.06 min, 99%; Col B: 5.41 min, 99%.

Example 117

17,20-Dimethyl-3,12-dioxo-2-(4-oxo-3,4-dihydro-quinazolin-6-ylamino)-7-(propane-2-sulfonyl)-4,11,14-triaza-tricyclo[14.2.2.1$^{6,10}$]henicosa-1(19),6,8,10(21),16(20),17-hexaene-14-carboxylic acid methyl ester trifluoroacetate

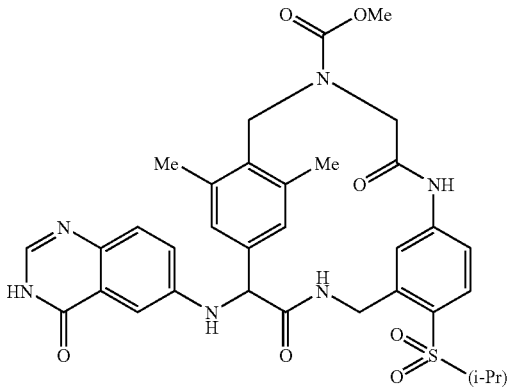

To a solution of Example 111 (6.9 mg, 9.86 μmol) in DCM (1 mL), pyridine (2.340 mg, 0.030 mmol) was added at 0° C., followed by methyl chloroformate (1.211 mg, 0.013 mmol). The reaction mixture was stirred at rt for 1 h. The reaction mixture was concentrated and purified via preparative HPLC [Phenomenex AXIA Luna 75×30 mm 5μ (10 min grad), A: 10% ACN-90% H$_2$O-0.1% TFA; B: 90% ACN-10% H$_2$O-0.1% TFA; 0-100% B; rt=4.4 min] to afford Example 117 (6.1 mg, 9.14 mmol, 93% yield). MS (ESI) m/z 661.2 (M+H)+. $^1$H NMR (400 MHz, CD$_3$OD) δ ppm 1.21 (d, J=7.15 Hz, 3H) 1.32 (d, J=7.15 Hz, 3H) 2.33 (s, 3H) 2.52 (s, 3H) 3.46-3.59 (m, 1H) 3.79 (d, J=36.83 Hz, 3H) 3.87 (s, 1H) 4.28 (d, J=17.04 Hz, 1H) 4.42 (d, J=17.04 Hz, 1H) 4.47 (s, 1H) 5.03 (dd, J=17.59, 6.05 Hz, 2H) 5.07 (s, 1H) 6.47 (s, 1H) 6.93 (d, J=6.60 Hz, 1H) 7.00 (s, 1H) 7.21 (d, J=2.75 Hz, 1H) 7.34 (dd, J=8.79, 2.75 Hz, 1H) 7.44 (s, 1H) 7.47 (d, J=8.79 Hz, 1H) 7.76 (d, J=8.79 Hz, 1H) 8.33 (s, 1H) 8.94 (t, J=5.50 Hz, 1H). Analytical HPLC (Method A): Col A: 5.55 min, 99%; Col B: 5.95 min, 99%.

Example 118

17,20-Dimethyl-2-(4-oxo-3,4-dihydro-quinazolin-6-ylamino)-7-(propane-2-sulfonyl)-14-propionyl-4,11,14-triaza-tricyclo[14.2.2.1$^{6,10}$]henicosa-1(19),6,8,10(21),16(20),17-hexaene-3,12-dione trifluoroacetate

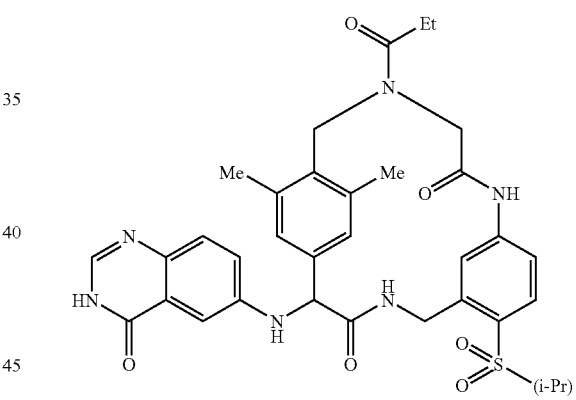

To a solution of Example 111 (6.0 mg, 9.96 μmol) in DCM (1 mL), TEA (3.02 mg, 0.030 mmol) was added, followed by propionic anhydride (1.296 mg, 9.96 μmol). The mixture was stirred at rt for 1 h. The reaction mixture was concentrated and purified via preparative HPLC [Phenomenex AXIA Luna 75×30 mm 5μ (10 min grad), A: 10% ACN-90% H$_2$O-0.1% TFA; B: 90% ACN-10% H$_2$O-0.1% TFA; 0-100% B; rt=4.5 min] to afford Example 118 (5.58 mg, 8.39 μmol, 84% yield). MS (ESI) m/z 659.2 (M+H)+. $^1$H NMR (400 MHz, CD$_3$OD) δ ppm 1.15 (t, J=7.42 Hz, 3H) 1.22 (d, J=6.60 Hz, 3H) 1.33 (d, J=7.15 Hz, 3H) 2.36 (s, 3H) 2.38-2.58 (m, 5H) 3.48-3.58 (m, 1H) 3.94 (d, J=17.59 Hz, 1H) 4.24-4.36 (m, 2H) 4.42 (d, J=17.59 Hz, 1H) 5.02 (dd, J=17.31, 5.77 Hz, 1H) 5.05-5.11 (m, 1H) 5.41 (d, J=14.84 Hz, 1H) 6.42-6.55 (m, 1H) 6.91 (t, J=8.52 Hz, 1H) 6.98-7.07 (m, 1H) 7.21 (d, J=2.75 Hz, 1H) 7.35 (dd, J=9.07, 2.47 Hz, 1H) 7.40-7.54 (m, 2H) 7.76 (t, J=7.97 Hz, 1H) 8.40-8.52 (m, 1H) 8.97 (t, J=5.77 Hz, 1H). Analytical HPLC (Method A): Col A: 5.41 min, 99%; Col B: 5.81 min, 99%.

Example 119

14,17,20-Trimethyl-2-(4-oxo-3,4-dihydro-quinazolin-6-ylamino)-7-(propane-2-sulfonyl)-4,11,14-triaza-tricyclo[14.2.2.1⁶,¹⁰]henicosa-1(19),6,8,10(21),16(20),17-hexaene-3,12-dione bistrifluoroacetate

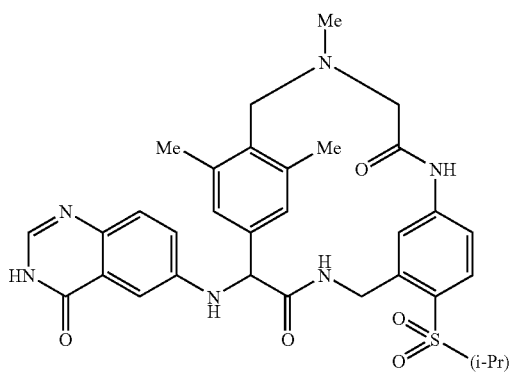

To a solution of Example 111 (6.9 mg, 0.011 mmol) in DCM (1 mL), TEA (1.2 mg, 0.011 mmol) was added, followed by formaldehyde (0.7 mg, 0.02 mmol), acetic acid (3.4 mg, 0.057 mmol), and Na(OAc)₃BH (4.85 mg, 0.023 mmol). The mixture was stirred rt for 1 h. The reaction mixture was concentrated and purified via preparative HPLC [Phenomenex AXIA Luna 75×30 mm 5µ (10 min grad), A: 10% ACN-90% H₂O-0.1% TFA; B: 90% ACN-10% H₂O-0.1% TFA; 0-100% B; rt=4.2 min] to afford Example 119 (4.92 mg, 7.98 µmol, 69.7% yield). MS (ESI) m/z 617.3 (M+H)⁺. ¹H NMR (400 MHz, CD₃OD) δ ppm 1.22 (d, J=7.15 Hz, 3H) 1.35 (d, J=6.60 Hz, 3H) 2.42 (s, 3H) 2.68 (s, 3H) 3.27 (s, 3H) 3.52-3.64 (m, 1H) 4.06-4.33 (m, 3H) 4.53-4.76 (m, 2H) 5.01-5.10 (m, 1H) 5.13 (s, 1H) 6.65 (s, 1H) 6.92 (d, J=8.24 Hz, 1H) 7.04 (d, 1H) 7.19 (d, J=2.75 Hz, 1H) 7.36 (d, J=7.70 Hz, 1H) 7.48 (d, J=9.34 Hz, 1H) 7.60 (s, 1H) 7.80 (d, J=8.25 Hz, 1H) 8.40-8.45 (m, 1H) 8.99 (s, 1H). Analytical HPLC (Method A): Col A: 4.24 min, 99%; Col B: 4.87 min, 99%.

Example 120

14-Isobutyryl-17,20-dimethyl-2-(4-oxo-3,4-dihydro-quinazolin-6-ylamino)-7-(propane-2-sulfonyl)-4,11,14-triaza-tricyclo[14.2.2.1⁶,¹⁰]henicosa-1(19),6,8,10(21),16(20),17-hexaene-3,12-dione trifluoroacetate

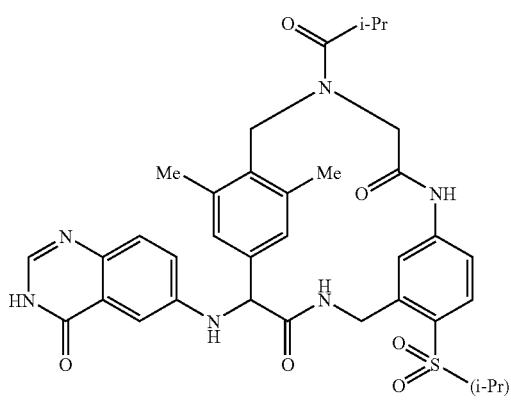

To a solution of Example 111 (6.5 mg, 10.78 µmol) in DCM (1 mL), TEA (3.3 mg, 0.032 mmol) was added, followed by isobutyric anhydride (2.6 mg, 0.016 mmol). The mixture was stirred rt for 1 h. The reaction mixture was concentrated and purified via preparative HPLC [Phenomenex AXIA Luna 75×30 mm 5µ (10 min grad), A: 10% ACN-90% H₂O-0.1% TFA; B: 90% ACN-10% H₂O-0.1% TFA; 0-100% B] to afford Example 120 (3.05 mg, 4.49 µmol, 41.6% yield). MS (ESI) m/z 673.3 (M+H)⁺. ¹H NMR (400 MHz, CD₃OD) δ ppm 1.13 (d, J=6.60 Hz, 3H) 1.16 (d, J=6.60 Hz, 3H) 1.22 (d, J=6.60 Hz, 3H) 1.33 (d, J=6.60 Hz, 3H) 2.36 (s, 3H) 2.44 (s, 3H) 2.82-2.95 (m, 1H) 3.46-3.59 (m, 1H) 3.96 (d, J=17.59 Hz, 1H) 4.23-4.34 (m, 2H) 4.49 (d, J=17.59 Hz, 1H) 5.02 (dd, J=17.59, 6.05 Hz, 1H) 5.06-5.11 (m, 1H) 5.42 (d, J=14.29 Hz, 1H) 6.46 (s, 1H) 6.90-6.96 (m, 1H) 6.99-7.05 (m, 1H) 7.22 (d, J=2.75 Hz, 1H) 7.33-7.39 (m, 1H) 7.43 (s, 1H) 7.48 (d, J=8.79 Hz, 1H) 7.77 (d, J=8.25 Hz, 1H) 8.49-8.57 (m, 1H) 8.96 (t, J=5.77 Hz, 1H). Analytical HPLC (Method A): Col A: 5.72 min, 99%; Col B: 6.12 min, 99%.

Example 121

14-Ethyl-17,20-dimethyl-2-(4-oxo-3,4-dihydro-quinazolin-6-ylamino)-7-(propane-2-sulfonyl)-4,11,14-triaza-tricyclo[14.2.2.1⁶,¹⁰]henicosa-1(19),6,8,10(21),16(20),17-hexaene-3,12-dione bistrifluoroacetate

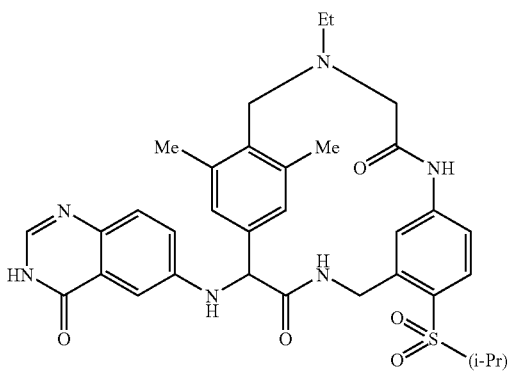

To a solution of Example 111 (8.5 mg, 0.014 mmol) in DCM (1 mL), TEA (1.4 mg, 0.014 mmol) was added, followed by acetaldehyde (1.2 mg, 0.028 mmol), acetic acid (4.2 mg, 0.071 mmol), and Na(OAc)₃BH (6.0 mg, 0.028 mmol). The mixture was stirred rt for 1 h. LC/MS shows about 10% conversion. Additional acetaldehyde (1.2 mg, 0.028 mmol), acetic acid (4.2 mg, 0.071 mmol) and Na(OAc)₃BH (6.0 mg, 0.028 mmol) were added and the reaction was stirred overnight at rt. The reaction mixture was concentrated and purified via preparative HPLC [Phenomenex AXIA Luna 75×30 mm 5 g (10 min grad), A: 10% ACN-90% H₂O-0.1% TFA; B: 90% ACN-10% H₂O-0.1% TFA; 0-100% B; rt=3.6 min] to afford Example 121 (6.0 mg, 9.42 mmol, 66.8% yield). MS (ESI) m/z 631.4 (M+H)⁺. ¹H NMR (400 MHz, CD₃OD) δ ppm 1.22 (d, J=6.60 Hz, 3H) 1.35 (d, J=7.15 Hz, 3H) 1.60 (t, J=7.15 Hz, 3H) 2.42 (s, 3H) 2.67 (s, 3H) 3.53-3.72 (m, 3H) 4.06 (s, 1H) 4.23 (s, 2H) 4.50 (s, 1H) 4.76 (d, J=23.09 Hz, 1H) 5.06 (d, 1H) 5.13 (s, 1H) 6.65 (s, 1H) 6.93 (d, J=8.25 Hz, 1H) 7.04 (d, 1H) 7.19 (d, J=2.75 Hz, 1H) 7.35 (d, J=8.79 Hz, 1H) 7.48 (d, J=9.34 Hz, 1H) 7.60 (s, 1H) 7.80 (d, J=8.25 Hz, 1H) 8.34-8.40 (m, 1H) 9.00 (s, 1H). Analytical HPLC (Method A): Col A: 4.35 min, 99%; Col B: 4.99 min, 99%.

Example 122

[17,20-Dimethyl-3,12-dioxo-2-(4-oxo-3,4-dihydro-quinazolin-6-ylamino)-7-(propane-2-sulfonyl)-4,11,14-triaza-tricyclo[14.2.2.1$^{6,10}$]henicosa-1(19),6,8,10(21),16(20),17-hexaen-14-yl]-acetic acid bistrifluoroacetate

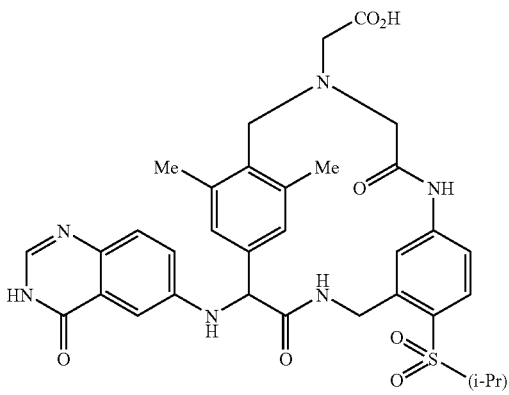

To a solution of Example 111 (6.6 mg, 11 μmol) in DCM (1 mL), TEA (1.1 mg, 11 μmol) was added, followed by 2-oxoacetic acid (1.6 mg, 0.022 mmol). The mixture was stirred rt for 1 h. The reaction mixture was concentrated and purified via preparative HPLC [Phenomenex AXIA Luna 75×30 mm 5μ (10 min grad), A: 10% ACN-90% H$_2$O-0.1% TFA; B: 90% ACN-10% H$_2$O-0.1% TFA; 0-100% B; rt=3.75 min] to afford Example 122 (1.26 mg, 1.869 μmol, 17% yield). MS (ESI) m/z 661.4 (M+H)$^+$. $^1$H NMR (400 MHz, CD$_3$OD) d ppm 1.21 (d, J=6.60 Hz, 3H) 1.35 (d, J=6.60 Hz, 3H) 2.32 (s, 3H) 2.60 (s, 3H) 3.11-3.27 (m, 2H) 3.62-3.69 (m, 1H) 3.72 (s, 1H) 3.95 (s, 1H) 4.16 (d, J=13.19 Hz, 1H) 4.22 (dd, J=16.76, 4.67 Hz, 1H) 4.31 (d, J=13.19 Hz, 1H) 5.03 (d, J=6.60 Hz, 1H) 5.06 (s, 1H) 6.44 (s, 1H) 6.92 (s, 1H) 7.05-7.10 (m, 1H) 7.22 (d, J=2.75 Hz, 1H) 7.34 (dd, J=8.79, 2.75 Hz, 1H) 7.43 (s, 1H) 7.47 (d, J=8.79 Hz, 1H) 7.76 (d, J=8.25 Hz, 1H) 8.29 (s, 1H) 8.95-9.02 (m, 1H). Analytical HPLC (Method A): Col A: 4.68 min, 98%; Col B: 4.96 min, 99%.

Example 123

17,20-Dimethyl-2-(4-oxo-3,4-dihydro-quinazolin-6-ylamino)-7-(propane-2-sulfonyl)-14-propyl-4,11,14-triaza-tricyclo[14.2.2.1$^{6,10}$]henicosa-1(19),6,8,10(21),16(20),17-hexaene-3,12-dione bistrifluoroacetate

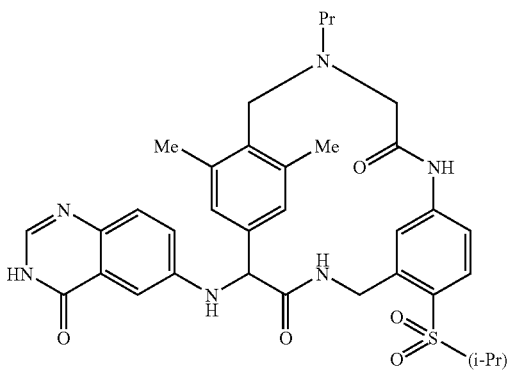

To a solution of Example 111 (8 mg, 0.013 mmol) in DCM (2 mL), TEA (1.3 mg, 0.013 mmol) was added, followed by methylacetaldehyde (1.5 mg, 0.027 mmol), acetic acid (4.0 mg, 0.066 mmol), and Na(OAc)$_3$BH (5.6 mg, 0.027 mmol). The mixture was stirred rt for 1 h. The reaction mixture was concentrated and purified via preparative HPLC to afford Example 123 (7.26 mg, 0.011 mmol, 84% yield). MS (ESI) m/z 645.3 (M+H)$^+$. $^1$H NMR (400 MHz, CD$_3$OD) δ ppm 1.11 (t, J=7.15 Hz, 3H) 1.22 (d, J=6.60 Hz, 3H) 1.34 (d, J=6.60 Hz, 3H) 1.97-2.12 (m, 2H) 2.41 (s, 3H) 2.67 (s, 3H) 3.42-3.64 (m, 3H) 4.08 (s, 1H) 4.24 (s, 2H) 4.53 (d, J=12.09 Hz, 1H) 4.73 (s, 1H) 5.00-5.11 (m, 1H) 5.13 (s, 1H) 6.64 (s, 1H) 6.93 (d, J=8.79 Hz, 1H) 7.05 (s, 1H) 7.19 (d, J=2.75 Hz, 1H) 7.35 (d, J=8.79 Hz, 1H) 7.48 (d, J=8.79 Hz, 1H) 7.59 (s, 1H) 7.80 (d, J=8.25 Hz, 1H) 8.39 (s, 1H) 8.99 (s, 1H). Analytical HPLC (Method A): Col A: 4.52 min, 99%; Col B: 5.23 min, 99%.

Example 124

14-Isopropyl-17,20-dimethyl-2-(4-oxo-3,4-dihydro-quinazolin-6-ylamino)-7-(propane-2-sulfonyl)-4,11,114-triaza-tricyclo[14.2.2.1$^{6,10}$]henicosa-1(19),6,8,10(21),06(20),17-hexaene-3,12-dione bistrifluoroacetate

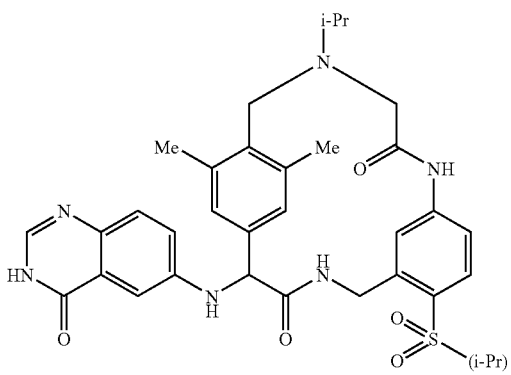

To a solution of Example 111 (8 mg, 0.013 mmol) in DCM (2 mL), TEA (1.3 mg, 0.013 mmol) was added, followed by propan-2-one (2.3 mg, 0.040 mmol), acetic acid (4.0 mg, 0.066 mmol), and Na(OAc)$_3$BH (5.63 mg, 0.027 mmol). The reaction mixture was concentrated and purified via preparative HPLC to afford Example 124 (4.0 mg, 6.14 μmol, 46.3% yield). MS (ESI) m/z 645.5 (M+H)$^+$. $^1$H NMR (400 MHz, CD$_3$OD) δ ppm 1.22 (d, J=6.60 Hz, 3H) 1.35 (d, J=6.05 Hz, 3H) 1.57 (d, J=4.95 Hz, 3H) 1.66 (d, 3H) 2.40 (s, 3H) 2.68 (s, 3H) 3.58 (s, 1H) 3.89 (s, 1H) 3.96-4.06 (m, 1H) 4.25 (s, 2H) 4.46 (d, J=9.34 Hz, 1H) 4.71 (d, 1H) 5.06 (d, 1H) 5.14 (s, 1H) 6.64 (s, 1H) 6.90-7.00 (m, 1H) 7.05 (s, 1-1) 7.17 (d, J=2.20 Hz, 1H) 7.34 (s, 1H) 7.47 (d, J=8.24 Hz, 1H) 7.64 (s, 1H) 7.82 (d, J=8.25 Hz, 1H) 8.18 (s, 1H) 9.01 (s, 1H). Analytical HPLC (Method A): Col A: 4.69 min, 97%; Col B: 5.16 min, 98%.

Example 125

(2R,15R)-7-Cyclopropanesulfonyl-4,15,20-trimethyl-3,12-dioxo-2-(1-oxo-1,2-dihydro-isoquinolin-7-ylamino)-4,11,14-triaza-tricyclo[14.2.2.1$^{6,10}$]henicosa-1(19),6,8,10(21),16(20),17-hexaene-14-carboxylic acid benzyl ester trifluoroacetate

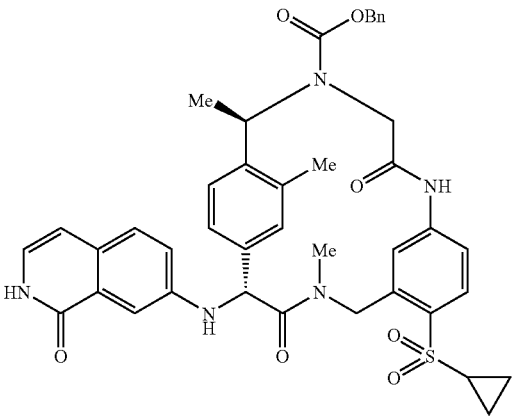

125A

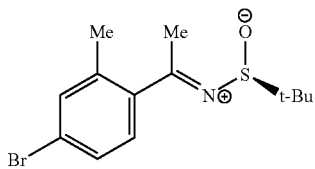

To a solution of Intermediate 8B (960 mg, 4.51 mmol) in THF (10 mL) at rt, were added Ti(OEt)$_4$ (1.869 mL, 9.01 mmol) and (S)-2-methylpropane-2-sulfinamide (601 mg, 4.96 mmol). The mixture was stirred at 65° C. for 20 h. The reaction mixture was cooled to rt, then poured into well-stirred brine (10 mL). The mixture was filtered through a pad of Celite®, and then rinsed with EtOAc. The filtrate was concentrated, then purified by flash chromatography (120 g column; 0-10% EtOAc in Hexanes) to afford 125A (1.3 g, 4.07 mmol, 90% yield) as a yellow oil.

125B

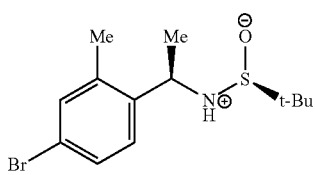

To a solution of 125A (1.29 g, 4.08 mmol) in THF (10 mL) at 0° C., was added L-Selectride (6.12 mL, 12.24 mmol). The mixture was stirred and allowed to warm rt and stir for 2 h. The reaction was quenched with water at 0° C., then was extracted with EtOAc (3×20 mL). The combined organic layer was washed with H$_2$O, sat. NaHCO$_3$ and brine, dried (Na$_2$SO$_4$), and concentrated to afford 125B (2.5 g), which was used without further purification. MS (ESI) m/z 318.2 (M+H)$^+$.

125C

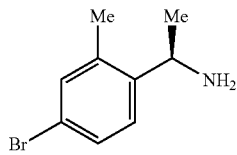 [SMILES: Cc1cc(Br)ccc1[C@@H](C)N]

To a solution of 125B (1.44 g, 4.51 mmol) in EtOAc (15 mL), was added 4 N HCL in dioxane (10 mL, 40.0 mmol). The mixture was stirred rt for 1 h, then concentrated. The residue was dissolved in water (50 mL) and washed with Et$_2$O (3×20 mL). The water layer was basified with 1N NaOH, then was extracted with DCM (3×20 mL). The combined organic layer was washed with brine, dried (Na$_2$SO$_4$) and concentrated to give the 125C (818 mg, 3.67 mmol, 81% yield). MS (ESI) m/z 197.3 (M+H)$^+$.

125D

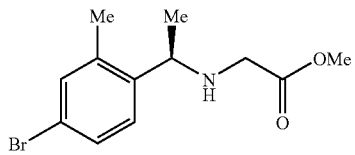

To a solution of 125C (745 mg, 3.48 mmol) in DMF (5 mL), was added N,N-Diisopropylethylamine (0.790 mL, 4.52 mmol), and methyl 2-bromoacetate (559 mg, 3.65 mmol) at rt. The mixture was stirred rt for 1 h. The reaction was quenched with water and extracted with EtOAc (2×20 mL). The combined organic layer was washed with water and brine, dried (Na$_2$SO$_4$) and concentrated to give 125D (950 mg, 3.15 mmol, 91% yield) colorless oil. MS (ESI) m/z 286.2 (M+H)$^+$.

125E

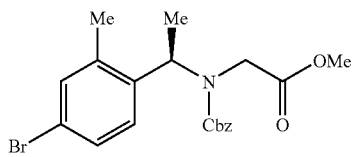 [SMILES: COC(=O)CN(C(=O)OCc1ccccc1)[C@H](C)c1ccc(Br)cc1C]

To a solution of 125D (960 mg, 3.35 mmol) in THF (15 mL) at 0° C., was added Na$_2$CO$_3$ (711 mg, 6.71 mmol) in water (6 mL), followed by benzyl chloroformate (687 mg, 4.03 mmol). The mixture was stirred 0° C. for 1 h, then was poured into 1N HCl and extracted with EtOAc (2×20 mL). The combined organic layer was washed with brine, dried (Na$_2$SO$_4$) and concentrated to afford 125E (1.43 g, 3.16 mmol, 94% yield) as a colorless oil. MS (ESI) m/z 420.4 (M+H)$^+$.

125F

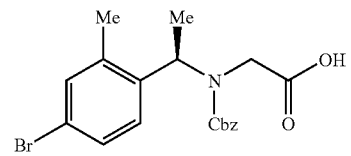 [SMILES: Cc1cc(Br)ccc1[C@@H](C)N(CC(=O)O)C(=O)OCc1ccccc1]

To a solution of 125E (1.43 g, 3.40 mmol) in THF (20 mL), was added 1M aq. LiOH (15 mL, 15 mmol). The mixture was stirred rt for 3 h. The reaction mixture was concentrated. The residue was diluted with water, acidified with 1N HCl, the extracted with EtOAc (3×30 mL). The combined organic layer was washed with brine, dried (Na$_2$SO$_4$) and concentrated to afford 125F (1.26 g, 2.95 mmol, 87% yield) as a colorless solid. MS (ESI) m/z 406.1 (M+H)$^+$.

125G

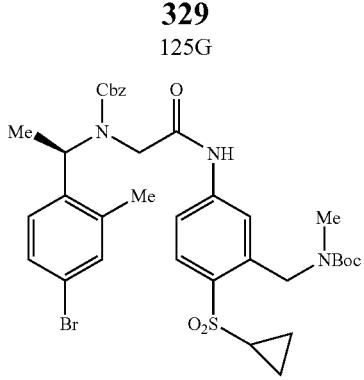

To a solution of 125F (211 mg, 0.520 mmol) in DCM (3 mL), was added oxalyl chloride (0.286 mL, 0.572 mmol) and DMF (1 drop). The mixture was stirred rt for 1 h, then was concentrated. The residue was dissolved in DCM (2 mL), and added to a round bottom flask containing a solution of Intermediate 11 (177 mg, 0.520 mmol) and pyridine (206 mg, 2.60 mmol) in DCM (3 mL) at 0° C. The mixture was stirred rt for 1 h, then was quenched with water. EtOAc (30 mL) was added, then the organic phase was washed with 1N HCl (2×10 mL) and brine, dried ($Na_2SO_4$) and concentrated. The crude product was purified by flash chromatography (0-55% EtOAc in Hexane) to afford 125G (218 mg, 0.296 mmol, 57.0% yield). MS (ESI) m/z 728.3 $(M+H)^+$.

125H

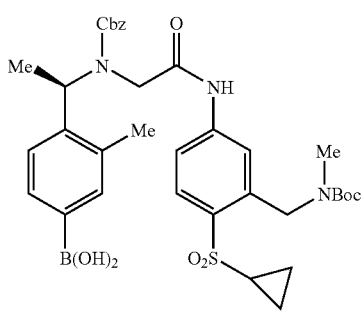 [SMILES: Cc1cc(B(O)O)ccc1[C@@H](C)N(CC(=O)Nc1ccc(S(=O)(=O)C2CC2)c(CN(C)C(=O)OC(C)(C)C)c1)C(=O)OCc1ccccc1]

Using a procedure analogous to that used to prepare 29B, 125G (178 mg, 0.244 mmol) was reacted with bis(neopentyl glycolato)diboron), potassium acetate and (1,1'-bis(diphenylphosphino)ferrocene)-dichloropalladium(II). The crude was purified by flash chromatography and preparative HPLC to afford 125H (118 mg, 0.168 mmol, 68.9% yield). MS (ESI) m/z 694.3 $(M+H)^+$.

125I

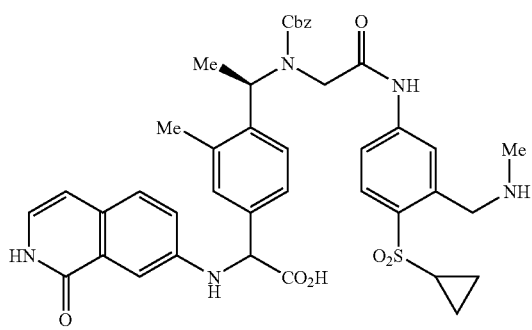 [SMILES: CNCc1cc(NC(=O)CN(C(=O)OCc2ccccc2)[C@H](C)c2ccc(C(Nc3ccc4cc[nH]c(=O)c4c3)C(=O)O)cc2C)ccc1S(=O)(=O)C1CC1]

A mixture of 125H (117 mg, 0.169 mmol), Intermediate 3 (29.8 mg, 0.186 mmol), and glyoxylic acid monohydrate (17.07 mg, 0.186 mmol) in $CH_3CN$ (3 mL) and DMF (0.5 mL) was irradiated in a microwave reactor at 100° C. for 10 min. The reaction was quenched with water, then extracted with EtOAc (3×10 mL). The combined organic layer was washed with water and brine, dried ($Na_2SO_4$) and concentrated. The product was purified by preparative HPLC. The resultant product was dissolved in EtOAc (5 mL), and treated with HCl (4M, 1 mL, 4 mmol). The mixture was stirred at rt for 1 h, then was concentrated to afford 125I (63 mg, 0.076 mmol, 44.9% yield) as a yellow solid. MS (ESI) m/z 766.5 $(M+H)^+$.

Example 125

To a solution of BOP (86 mg, 0.165 mmol) and DMAP (9.88 mg, 0.081 mmol), in DCM (40 mL) and DMF (10 mL), a solution of 125I (63 mg, 0.082 mmol) and DIEA (20.81 mg, 0.206 mmol) in DMF (10 mL) was added dropwise via a syringe pump over 8 h. The mixture was stirred rt for 10 h. The reaction was quenched with water, then was extracted with EtOAc (3×20 mL). The combined organic layer was washed with water and brine, dried ($Na_2SO_4$) and concentrated. Purification via preparative HPLC afforded first the phenyglycine diastereomer, followed by the desired product 125J (15 mg, 0.020 mmol, 24% yield). MS (ESI) m/z 748.5 $(M+H)^+$. Chiral analytical HPLC: Whelko-01 micro 4.6×250 mm, Sol A=Hep; Sol B=EtOH/MeOH (50/50); 60% B, 1 mL/min; rt=16.53 min. Analytical HPLC (Method A): Col A: 7.55 min, 99%; Col B: 7.62 min, 99%.

Example 126

(2R,15R)-7-Cyclopropanesulfonyl-4,15,20-trimethyl-2-(1-oxo-1,2-dihydro-isoquinolin-7-ylamino)-4,11,14-triaza-tricyclo[14.2.2.1$^{6,10}$]henicosa-1(19),6,8,10(21),16(20),17-hexaene-3,12-dione bistrifluoroacetate

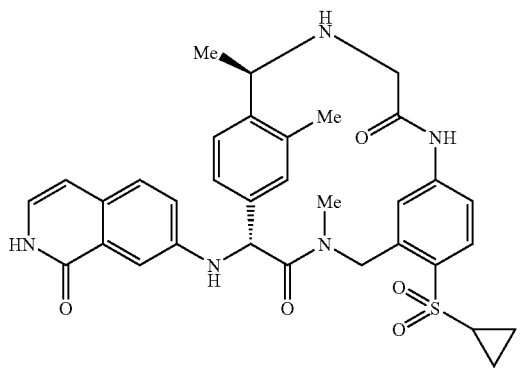 [SMILES: Cc1cc2ccc1[C@@H](C)NCC(=O)Nc1ccc(S(=O)(=O)C3CC3)c(c1)CN(C)C(=O)[C@@H]2Nc1ccc2cc[nH]c(=O)c2c1]

To a solution of Example 125 (16 mg, 0.021 mmol) in MeOH (3 mL), was added Pd/C (ca. 10 mg). The mixture was stirred rt for 1 h under hydrogen balloon. The reaction mixture was filtered, concentrated and purified via preparative HPLC to give Example 126 (6.3 mg, 9.8 μmol, 46% yield) as a yellow solid. MS (ESI) m/z 614.4 $(M+H)^+$. 1H NMR (400 MHz, $CD_3OD$) δ ppm 1.03-1.35 (m, 4H) 1.77 (d, J=7.15 Hz, 3H) 2.34 (s, 3H) 2.88-2.96 (m, 1H) 3.10-3.19 (m, 1H) 3.48 (s, 3H) 3.80 (d, J=16.49 Hz, 1H) 4.13 (d, J=16.49 Hz, 1H) 4.31 (d, J=17.59 Hz, 1H) 4.76-4.81 (m, 1H) 5.75 (s, 1H) 5.78 (d, J=17.59 Hz, 1H) 6.48 (s, 1H) 6.54 (d, J=7.15 Hz, 1H) 6.88-6.95 (m, 2H) 7.18-7.26 (m, 2H) 7.36-7.44 (m, 2H) 7.77 (d, J=7.70 Hz, 1H) 7.80 (d, J=8.79 Hz, 1H) 7.87 (d, J=8.25 Hz, 1H). Analytical HPLC (Method A): Col A: 5.25 min, 96%; Col B: 5.98 min, 94%.

Example 127

(2R,15R)-14-Acetyl-7-cyclopropanesulfonyl-4,15,20-trimethyl-2-(1-oxo-1,2-dihydro-isoquinolin-7-ylamino)-4,11,14-triaza-tricyclo[14.2.2.1⁶,¹⁰]henicosa-1(19),6,8,10(21),16(20),17-hexaene-3,12-dione trifluoroacetate

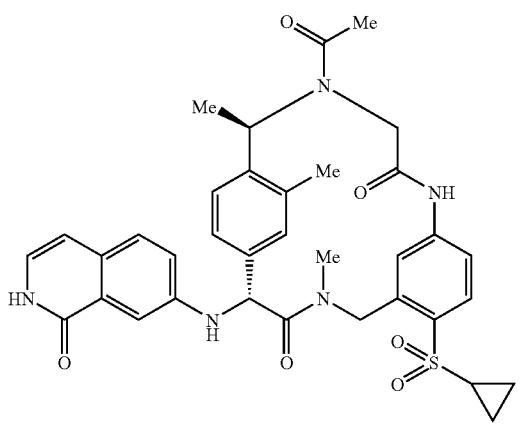 [SMILES: CC(=O)N1CC(=O)Nc2ccc(S(=O)(=O)C3CC3)c(c2)CN(C)C(=O)[C@H](Nc2ccc3cc[nH]c(=O)c3c2)c2ccc(c(C)c2)[C@H]1C]

To a mixture of Example 126 (3.7 mg, 6.03 µmol) in DCM (1 mL) at 0° C., TEA (1.8 mg, 0.018 mmol) was added, followed by acetic anhydride (0.9 mg, 9 µmol). The mixture was stirred at rt for 1 h. The reaction mixture was concentrated and purified via preparative HPLC [Phenomenex AXIA Luna 75×30 mm 5 g (10 min grad), A: 10% ACN-90% H₂O-0.1% TFA; B: 90% ACN-10% H₂O-0.1% TFA; 0-100% B; rt=4.25 min] to afford Example 127 (2.4 mg, 3.59 µmol, 59.5% yield). MS (ESI) m/z 656.4 (M+H)⁺. Analytical HPLC (Method A): Col A: 5.72 min, 99%; Col B: 5.66 min, 98%.

Example 128

14-Acetyl-17,20-dimethyl-2-(1-oxo-1,2-dihydro-isoquinolin-7-ylamino)-7-(propane-2-sulfonyl)-4,11,14-triaza-tricyclo[14.2.2.1⁶,¹⁰]henicosa-1(19),6,8,10(21),16(20),17-hexaene-3,12-dione trifluoroacetate

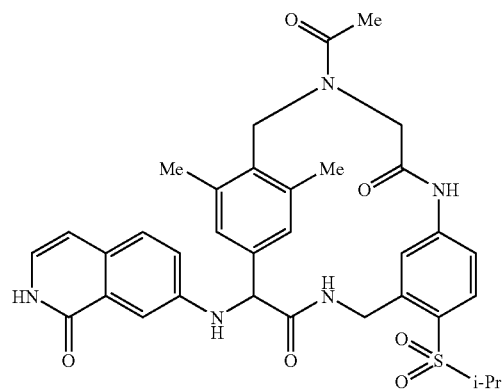 [SMILES: CC(=O)N1CC(=O)Nc2ccc(S(=O)(=O)C(C)C)c(c2)CNC(=O)C(Nc2ccc3cc[nH]c(=O)c3c2)c2cc(C)c(c(C)c2)C1]

According to the procedure for the preparation of Example 116, replacement of Intermediate 4 with Intermediate 3 afforded Example 128. MS (ESI) m/z 656.4 (M+H)⁺. Analytical HPLC (Method A): Col A: 6.28 min, 99%; Col B: 6.36 min, 99%.

Example 129

(2R,15R)-7-Cyclopropanesulfonyl-4,15,20-trimethyl-3,12-dioxo-2-(1-oxo-1,2-dihydro-isoquinolin-7-ylamino)-4,11,14-triaza-tricyclo[14.2.2.1⁶,¹⁰]henicosa-1(19),6,8,10(21),16(20),17-hexaene-14-carboxylic acid methyl ester trifluoroacetate

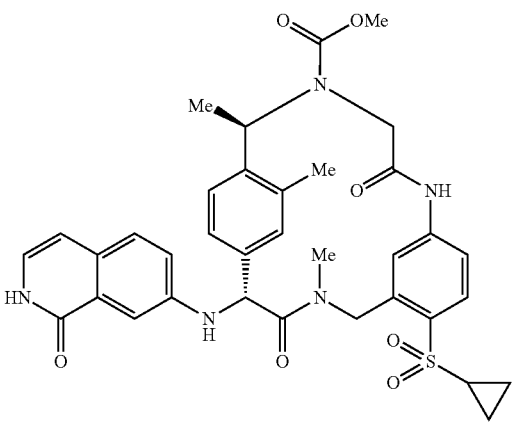 [SMILES: COC(=O)N1CC(=O)Nc2ccc(S(=O)(=O)C3CC3)c(c2)CN(C)C(=O)[C@H](Nc2ccc3cc[nH]c(=O)c3c2)c2ccc(c(C)c2)[C@H]1C]

According to the procedure for the preparation of Example 125, replacement of benzyl chloroformate with methyl chloroformate afforded Example 129. MS (ESI) m/z 672.3 (M+H)⁺. ¹H NMR (400 MHz, CD₃OD) b ppm 0.95-1.16 (m, 3H) 1.21-1.31 (m, 1H) 1.53 (s, 3H) 2.17 (d, J=10.99 Hz, 3H) 2.85 (s, 1H) 3.42 (s, 3H) 3.74-3.90 (m, 3H) 4.22-4.55 (m, 2H) 5.56-5.84 (m, 3H) 6.04 (d, J=39.03 Hz, 1H) 6.52 (d, J=7.15 Hz, 1H) 6.90 (d, J=7.15 Hz, 1H) 7.03 (dd, J=27.76, 7.97 Hz, 1H) 7.16-7.28 (m, 2H) 7.35-7.41 (m, 2H) 7.54 (d, J=8.25 Hz, 1H) 7.66 (d, J=6.05 Hz, 1H) 7.76 (d, J=8.25 Hz, 1H). Chiral analytical HPLC: Whelko-01 10 micron 4.6×250 mm; Sol A=hep, Sol B=EtOH/MeOH (50/50); Percent B: 60; Flow Rate=1 ml/min; wavelength 1=254 m, wavelength 2=220 nm; 14.08 min. Analytical HPLC (Method A): Col A: 6.28 min, 99%; Col B: 6.23 min, 99%.

Example 130

(2R,15R)-4,15,17-Trimethyl-2-(1-oxo-1,2-dihydro-isoquinolin-7-ylamino)-7-(1,1,2,2-tetrafluoro-ethoxy)-13-oxa-4,11-diaza-tricyclo[14.2.2.1⁶,¹⁰]henicosa-1(19),6,8,10(21),16(20),17-hexaene-3,12-dione

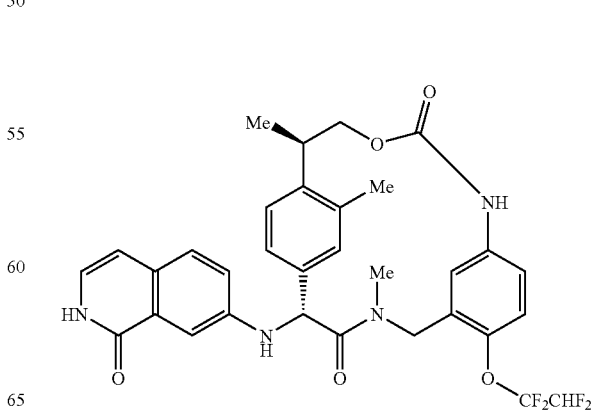

130A

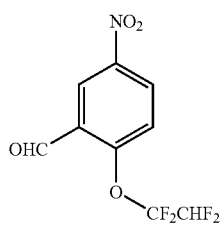

To a mixture of nitric acid (1.6 mL, 35.8 mmol) and sulfuric acid (8 mL, 150 mmol) at 0° C., was added 2-(1,1,2,2-tetrafluoroethoxy)benzaldehyde (2.5 g, 11.25 mmol), dropwise over 5 min. The brown mixture was stirred at 0° C. for 1 h, then was poured onto 100 mL ice, giving an oil. The oil was diluted with EtOAc (50 mL), washed with H$_2$O and brine, dried (Na$_2$SO$_4$) and concentrated to afford 130A (2.90 g, 10.86 mmol, 96% yield) as a yellow oil. $^1$H NMR (400 MHz, CHLOROFORM-d) δ ppm 10.35 (s, 1H) 8.82 (d, J=2.93 Hz, 1H) 8.52 (dd, J=9.29, 2.93 Hz, 1H) 7.63 (dt, J=8.93, 1.65 Hz, 1H) 6.09 (dt, J=52.7, 2.20 Hz, 1H).

130B

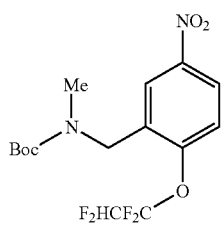

Using a procedure analogous to that used to prepare Intermediate 18 and Intermediate 19, 130A (1 g, 3.74 mmol) was reacted with methylamine and sodium borohydride followed by BOC-anhydride. The crude product was purified by flash chromatography: (0 to 40% ethyl acetate/hexanes) to afford 130B (1.17 g, 3.06 mmol, 82% yield) as a pale yellow oil. MS (ESI) m/z 327.2 (M−(t-Bu)+2H)$^+$. $^1$H NMR (400 MHz, CHLOROFORM-d) δ ppm 8.11-8.23 (m, 2H) 7.47 (d, J=9.29 Hz, 1H) 5.81-6.27 (m, 1H) 4.46-4.58 (m, 2H) 2.85-2.97 (m, 3H) 1.42-1.54 (m, 9H).

130C

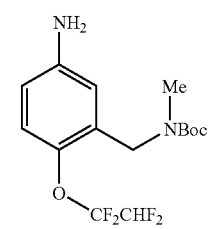

To a solution of 130B (700 mg, 1.831 mmol) in MeOH (10 mL), was added 10% Pd/C. The mixture was hydrogenated under an H$_2$ balloon overnight, then was filtered and concentrated to afford 13° C. (582 mg, 1.652 mmol, 90% yield) as a tan oil. MS (ESI) m/z 353.3 (M+H)$^+$. $^1$H NMR (400 MHz, CDCl$_3$) δ ppm 1.44 (d, J=20.34 Hz, 9H) 2.66-2.90 (m, 3H) 3.67 (s, 2H) 4.37 (s, 2H) 5.72-6.18 (m, 1H) 6.40-6.60 (m, 2H) 7.00 (d, J=8.25 Hz, 1H).

130D

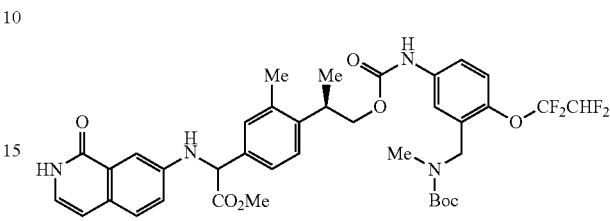

Using a procedure analogous to that used to prepare 29A, 13° C. (222 mg, 0.63 mmol) was reacted with sodium bicarbonate and phosgene followed by Intermediate 16 (113 mg, 0.297 mmol) and TEA. The crude product was purified by flash chromatography (0-100% EtOAc in Hexanes) to afford 130D (162 mg, 0.214 mmol, 71.9% yield) as a yellow solid. MS (ESI) m/z 759.3 (M+H)$^+$. $^1$H NMR (400 MHz, CD$_3$OD) d ppm 1.20-1.25 (m, 3H) 1.43 (d, J=32.98 Hz, 9H) 2.32 (s, 3H) 2.73-2.88 (m, 3H) 3.34-3.44 (m, 1H) 3.67 (s, 3H) 4.09-4.24 (m, 2H) 4.42 (s, 2H) 5.1.7 (s, 1H) 5.46 (s, 1H) 6.18-6.40 (m, 1H) 6.49 (d, J=7.15 Hz, 1H) 6.87 (d, J=6.60 Hz, 1H) 7.09-7.50 (m, 9H).

130E

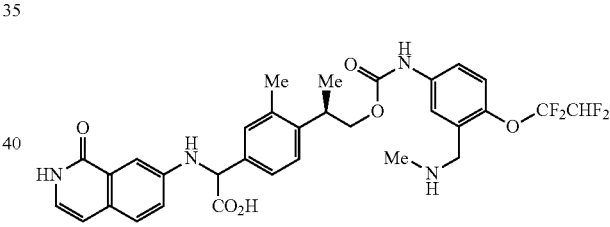

To a solution of 130D (159 mg, 0.210 mmol) in THF (5 mL) was added aq. LiOH (1 mL, 1M). The mixture was stirred rt for 2 h, then was concentrated. Water (20 mL) was added, and then was acidified with 10% citric acid, and extracted with EtOAc (2×10 mL) and ether (2×10 mL). The combined organic phase was dried (Na$_2$SO$_4$), and concentrated to afford the carboxylic acid. This product was dissolved in EtOAc (5 mL), then was treated with 4N HCl in dioxane (2 mL) and stirred rt for 3 h. The reaction mixture was concentrated and purified via preparative HPLC to afford 130E (105 mg, 0.163 mmol, 78% yield) as a yellow solid. MS (ESI) m/z 645.4 (M+H)$^+$.

Example 130

To a solution of BOP (144 mg, 0.326 mmol) and 4-Dimethylaminopyridine (99 mg, 0.814 mmol) in DCM (40 mL), was added a solution of 130E (105 mg, 0.163 mmol) and N,N-Diisopropylethylamine (0.028 mL, 0.163 mmol) in DMF (10 mL) via a syringe pump over 10 h. The reaction mixture was concentrated and purified by preparative HPLC to afford the cyclized product (50 mg, 48.5%). The diastereomers were separated by chiral chromatography (R,R-

Whelk-O column (21.1×250 mm, 60:40 (MeOH/EtOH 1:1)/heptane, 20 mL/min)) to afford the phenylglycine diastereomer (RT=6 min), followed by Example 130 (RT=11 min) (22.8 mg, 0.036 mmol, 90% yield). MS (ESI) m/z 627.5 (M+H)+. Analytical HPLC (Method A): Col A: 7.71 min, 99%; Col B: 7.97 min, 99%.

Example 131

(2R,15R)-4,15,17-Trimethyl-2-(1-oxo-1,2-dihydro-isoquinolin-7-ylamino)-7-trifluoromethoxy-13-oxa-4,11-diaza-tricyclo[14.2.2.1$^{6,10}$]henicosa-1(19),6,8,10(21),16(20),17-hexaene-3,12-dione

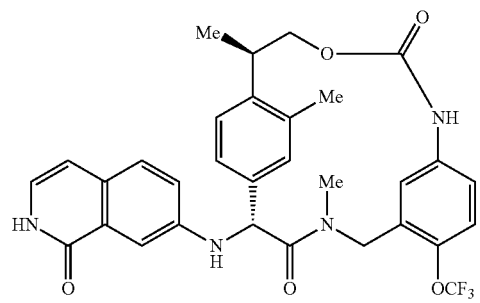 [SMILES: Cc1cc2ccc1[C@@H](C)COC(=O)Nc1ccc(OC(F)(F)F)c(c1)CN(C)C(=O)[C@@H]2Nc1ccc2cc[nH]c(=O)c2c1]

131A

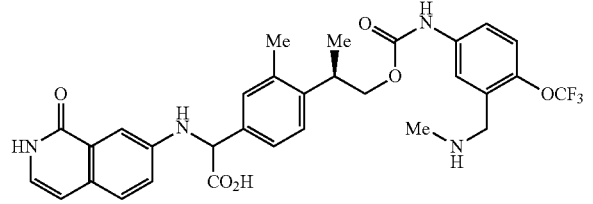 [SMILES: CNCc1cc(NC(=O)OC[C@H](C)c2ccc(C(Nc3ccc4cc[nH]c(=O)c4c3)C(=O)O)cc2C)ccc1OC(F)(F)F]

Using a procedure analogous to that used to prepare 29A, 70B (154 mg, 0.48 mmol) was reacted with sodium bicarbonate and phosgene followed by Intermediate 16 (121 mg, 0.318 mmol) and TEA. The crude product was purified by flash chromatography (0-100% EtOAc in Hexanes) to afford 131A (145 mg, 0.176 mmol, 55.2% yield) as a yellow solid. MS (ESI) m/z 727.4 (M+H)+.

131B

To a solution of 131A (144 mg, 0.198 mmol) in THF (5 mL), was added aq. LiOH (1 mL, 1 M). The mixture was stirred it for 2 h, then was concentrated. Water (20 mL) was added, then the mixture was acidified with 10% citric acid, and extracted with EtOAc (2×10 mL) and ether (2×10 mL), dried (Na$_2$SO$_4$) and concentrated to give the acid. To a solution of this product in EtOAc (5 mL), was added 4N HCl (2 mL). The mixture was stirred rt for 3 h, then was concentrated. The crude product was purified by preparative HPLC to afford 131B (75 mg, 0.122 mmol, 61.8% yield.) as a yellow solid. MS (ESI) m/z 613.4 (M+H)+.

Example 131

To a solution of BOP (85 mg, 0.193 mmol) and 4-Dimethylaminopyridine (58.8 mg, 0.482 mmol) in DCM (40 mL), was added a solution of 131B (59 mg, 0.096 mmol) and N,N-Diisopropylethylamine (0.017 mL, 0.096 mmol) in DMF (10 mL) via a syringe pump over 10 h. The reaction mixture was concentrated and purified by preparative HPLC to afford the cyclized product (39 mg, 0.065 mmol, 67.4% yield). The diastereomers were separated by chiral chromatography (R,R-Whelk-O column (21.1×250 mm, 60:40 (MeOH/EtOH 1:1)/heptane, 20 mL/min)) to afford the phenylglycine diastereomer (RT=5 min), followed by Example 131 (RT=11 min) (17.8 mg, 0.030 mmol, 90% yield). MS (ESI) m/z 627.5 (M+H)+. Chiral analytical HPLC: Whelko-01 10 micron 4.6×250 mm; Sol A=hep, Sol B=EtOH/MeOH (50/50); Percent B: 50%; Flow Rate=1 ml/min; wavelengh1=254, wavelengh2=220; 11.93 min. $^1$H NMR (400 MHz, METHANOL-d$_3$) δ ppm 7.64 (dd, J=8.25, 1.65 Hz, 1H) 7.42 (s, 1H) 7.42 (t, J=7.15 Hz, 2H) 7.24 (dd, J=8.79, 2.75 Hz, 1H) 7.22 (d, J=1.65 Hz, 1H) 7.14 (dd, J=8.25, 1.65 Hz, 1H) 6.91 (d, J=7.15 Hz, 1H) 6.77 (dd, J=8.52, 2.47 Hz, 1H) 6.55 (d, J=7.15 Hz, 1H) 6.06 (d, J=2.75 Hz, 1H) 5.65 (s, 1H) 5.43 (d, J=17.59 Hz, 1H) 4.65 (t, J=10.99 Hz, 1H) 3.89-3.99 (m, 2H) 3.48 (tt, J=11.27, 7.15 Hz, 1H) 3.34 (s, 3H) 2.32 (s, 3H) 1.30 (d, J=7.15 Hz, 3H). Analytical HPLC (Method A): Col A: 7.85 min, 99%; Col B: 8.04 min, 99%.

Example 132

(2R,15R)-7-Difluoromethoxy-4,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexane-3,12-dione

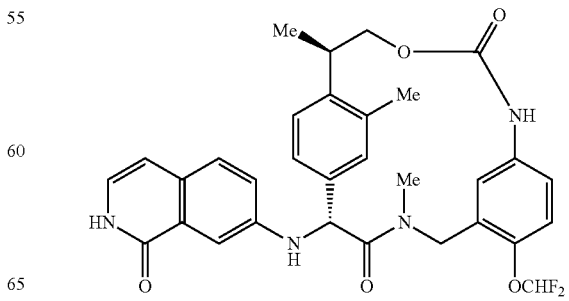

132A

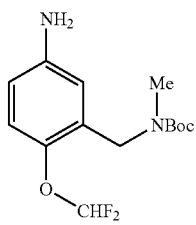 [SMILES: CN(Cc1cc(N)ccc1OC(F)F)C(=O)OC(C)(C)C]

To a solution of Intermediate 15 (500 mg, 1.505 mmol) in MeOH (10 mL), was added 10% Pd/C. The mixture was hydrogenated under an H₂ balloon overnight, then was filtered and concentrated to afford 132A (386 mg, 1.264 mmol, 84% yield) as a tan oil. MS (ESI) m/z 325.3 (M+H)⁺. ¹H NMR (400 MHz, CDCl₃) δ ppm 1.43 (s, 9H) 2.80 (d, J=17.59 Hz, 3H) 3.62 (s, 2H) 4.40 (s, 2H) 6.43-6.59 (m, 2H) 6.89 (d, J=8.79 Hz, 1H).

132B

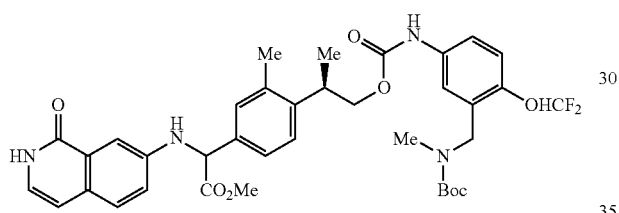

Using a procedure analogous to that used to prepare 29A, 132A (134 mg, 0.442 mmol) was reacted with sodium bicarbonate and phosgene followed by Intermediate 16 (112 mg, 0.294 mmol) and TEA. The crude product was purified by preparative HPLC to afford 132B (158 mg, 0.223 mmol, 76% yield) as a yellow solid. MS (ESI) m/z 709.3 (M+H)⁺. ¹H NMR (400 MHz, CD₃OD) δ ppm 1.22-1.28 (m, 3H) 1.44 (d, J=25.93 Hz, 9H) 2.34 (s, 3H) 2.69-2.85 (m, 3H) 3.41 (q, J=7.03 Hz, 1H) 3.69 (s, 3H) 4.09-4.27 (m, 2H) 4.44 (s, 2H) 5.19 (s, 1H) 6.54 (t, J=6.59 Hz, 2H) 6.71-7.09 (m, 2H) 7.16-7.45 (m, 8H).

132C

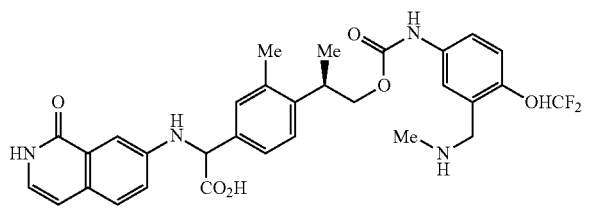

To a solution of 132B (150 mg, 0.212 mmol) in THF (5 mL) was added aq. LiOH (1 mL, 1M). The mixture was stirred rt for 2 h, then was concentrated. The residue was taken up in water (20 mL), then was acidified with 10% citric acid and extracted with EtOAc (2×10 mL). The organic phase was dried (Na₂SO₄) and concentrated to give the acid. To a solution of the acid EtOAc (5 mL), was added 4N HCl (2 mL), the mixture was stirred at rt for 3 h, then was concentrated. Purification by preparative HPLC afforded the 132C (22 mg, 0.037 mmol, 17.48% yield). MS (ESI) m/z 595.4 (M+H)⁺.

Example 132

To a solution of BOP (31 mg, 0.071 mmol) and 4-Dimethylaminopyridine (22 mg, 0.177 mmol) in DCM (40 mL), was added a solution of 132C (21 mg, 0.035 mmol) and N,N-diisopropylethylamine (6.2 µL, 0.035 mmol) in DMF (10 mL) via a syringe pump over 10 h. The reaction mixture was concentrated and purified by preparative HPLC to afford the cyclized product (15 mg, 0.026 mmol, 72.9% yield). The diastereomers were separated by chiral chromatography (R,R-Whelk-O column (21.1×250 mm, 60:40 (MeOH/EtOH 1:1)/heptane, 20 mL/min)) to afford the phenylglycine diastereomer (RT=5 min), followed by Example 132 (RT=14 min) (6.52 mg, 0.011 mmol, 93% yield). MS (ESI) m/z 577.5 (M+H)⁺. Chiral analytical HPLC: Whelko-01 10 micron 4.6× 250 mm; Sol A=hep, Sol B=EtOH/MeOH (50/50); Percent B: 50%; Flow Rate=1 ml/min; wavelengh1=254, wavelengh2=220; 15.83 min, 100% purity. Analytical HPLC (Method A): Col A: 7.26 min, 97%; Col B: 7.42 min, 99%.

Example 133

(2R,15R)-4,15,17-Trimethyl-2-(1-oxo-1,2-dihydro-isoquinolin-7-ylamino)-7-pyrazol-1-yl-13-oxa-4,11-diaza-tricyclo[14.2.2.1⁶,¹⁰]henicosa-1(19),6,8,10(21),16(20),17-hexaene-3,12-dione

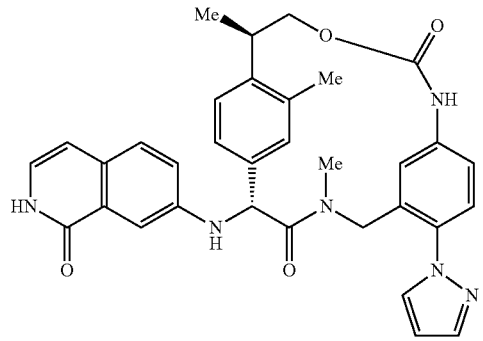 [SMILES: Cc1cc2ccc1[C@@H](C)COC(=O)Nc1ccc(-n3cccn3)c(c1)CN(C)C(=O)[C@@H]2Nc1ccc2cc[nH]c(=O)c2c1]

133A

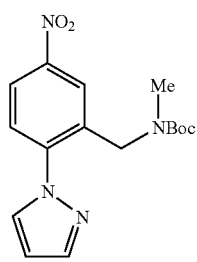 [SMILES: CN(Cc1cc([N+](=O)[O-])ccc1-n1cccn1)C(=O)OC(C)(C)C]

Intermediate 18 (690 mg, 2.0 mmol), N,N-dimethylglycine (41.2 mg, 0.400 mmol), potassium carbonate (553 mg, 4.00 mmol), pyrazole (150 mg, 2.20 mmol), and copper(I) iodide (76 mg, 0.4 mmol) were sealed in a reaction vial. The tube was degassed and filled with argon. DMSO (2 mL) was added. The mixture was stirred 110° C. for 20 h, then was quenched with water and extracted with EtOAc (3× mL). The combined organic layer was washed with brine, dried (Na$_2$SO$_4$) and concentrated. The crude material was added to a 35 g column and was eluted with 0-20% EtOAc in Hexanes to afford 133A (545 mg, 1.623 mmol, 81% yield) yellow oil. MS (ESI) m/z 333.2 (M+H)$^+$. $^1$H NMR (400 MHz, CD$_3$OD) d ppm 1.44 (d, J=41.23 Hz, 9H) 2.80 (s, 3H) 4.58 (s, 2H) 6.59 (s, 1H) 7.65 (d, J=8.25 Hz, 1H) 7.82 (s, 1H) 8.04 (d, J=2.20 Hz, 1H) 8.20 (d, J=12.64 Hz, 1H) 8.28 (d, J=8.79 Hz, 1H).

133B

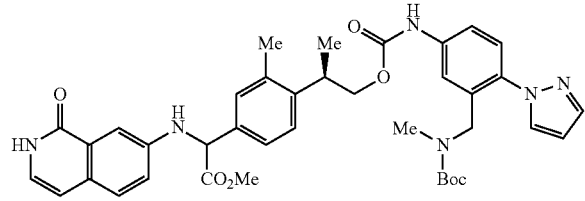 [SMILES: COC(=O)C(Nc1ccc2cc[nH]c(=O)c2c1)c1ccc([C@@H](C)COC(=O)Nc2ccc(-n3cccn3)c(CN(C)C(=O)OC(C)(C)C)c2)c(C)c1]

133A was reduced to the corresponding aniline using Pd/C and H$_2$. Using a procedure analogous to that used to prepare 29A, the aniline (124 mg, 0.41 mmol) was reacted with sodium bicarbonate and phosgene followed by Intermediate 16 (103 mg, 0.271 mmol) and TEA. The crude product was purified to afford 133B (103 mg, 0.144 mmol, 53.1% yield) as a yellow solid. MS (ESI) m/z 709.7 (M+H)$^+$.

133C

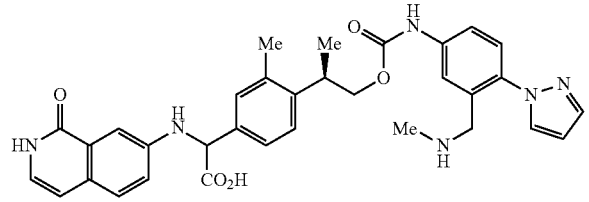 [SMILES: CNCc1cc(NC(=O)OC[C@H](C)c2ccc(C(Nc3ccc4cc[nH]c(=O)c4c3)C(=O)O)cc2C)ccc1-n1cccn1]

To a solution of 133B (103 mg, 0.145 mmol) in THF (3 mL), was added aq. LiOH (2 mL, 1M). The mixture was stirred at rt for 1 h, then was concentrated. Water (10 mL) was added, then was acidified with 10% citric acid. The aqueous phase was extracted with EtOAc (2×10 mL). The combined organic phase was concentrated to give the acid intermediate. To a solution of this product in EtOAc (3 mL), was added 4N HCl in dioxane (2 mL). The mixture was stirred rt for 1 h, then was concentrated. The crude product was purified by preparative HPLC to afford 133C (40 mg, 0.067 mmol, 46.3% yield) as a yellow solid. MS (ESI) m/z 595.6 (M+H)$^+$. $^1$H NMR (400 MHz, CD$_3$OD) δ ppm 1.24 (t, J=6.15 Hz, 3H) 2.32 (d, J=20.65 Hz, 3H) 2.70 (s, 3H) 3.40 (q, J=6.74 Hz, 1H) 3.90 (s, 2H) 4.21-4.30 (m, 2H) 6.47 (d, J=7.03 Hz, 1H) 6.56 (d, J=2.20 Hz, 1H) 6.82 (d, J=7.03 Hz, 1H) 7.09 (dd, J=8.57, 2.42 Hz, 1H) 7.16-7.44 (m, 8H) 7.61 (s, 1H) 7.80 (s, 1H) 8.02 (s, 1H).

Example 133

To a solution of BOP (59.5 mg, 0.135 mmol) and 4-Dimethylaminopyridine (41.1 mg, 0.336 mmol) in DCM (40 mL), was added a solution of 133C (40 mg, 0.067 mmol) and N,N-Diisopropylethylamine (0.012 mL, 0.067 mmol) in DMF (10 mL) via a syringe pump over 10 h. The reaction mixture was concentrated and purified by preparative HPLC to afford the cyclized product (36 mg, 0.058 mmol, 86% yield). The diastereomers were separated by chiral chromatography (R,R-Whelk-O column (21.1×250 mm, 60:40 (MeOH/EtOH 1:1)/heptane, 20 mL/min)) to afford the phenylglycine diastereomer (rt=6 min), followed by Example 133 (rt=11 min) (15.8 mg, 0.027 mmol, 88% yield). MS (ESI) m/z 577.5 (M+H)$^+$. Chiral analytical HPLC: Whelko-01 10 micron 4.6×250 mm; Sol A=hep, Sol B=EtOH/MeOH (50/50); Percent B: 50%; Flow Rate=1 ml/min; wavelengh1=254, wavelengh2=220; 10.13 min. $^1$H NMR (400 MHz, CD$_3$OD) δ ppm 1.30 (d, J=7.03 Hz, 3H) 2.31 (s, 3H) 3.31 (s, 3H) 3.42-3.51 (m, 1H) 3.84 (d, J=17.14 Hz, 1H) 3.97 (dd, J=10.77, 4.17 Hz, 1H) 4.63 (t, J=10.99 Hz, 1H) 5.11 (d, J=17.14 Hz, 1H) 5.59 (s, 1H) 6.22 (s, 1H) 6.49 (d, J=2.20 Hz, 1H) 6.52 (d, J=7.03 Hz, 1H) 6.80 (d, J=8.35 Hz, 1H) 6.88 (d, J=7.03 Hz, 1H) 7.19 (d, J=3.08 Hz, 2H) 7.21 (s, 1H) 7.35-7.40 (m, 2H) 7.42 (d, J=7.91 Hz, 2H) 7.63 (d, J=7.91 Hz, 1H) 7.70 (s, 1H) 7.82 (s, 1H). Analytical HPLC (Method A): Col A: 6.69 min, 99%; Col B: 6.71 min, 99%.

Example 134

(2R,15S)-17-Methoxy-4,15-dimethyl-2-(1-oxo-1,2-dihydro-isoquinolin-7-ylamino)-7-trifluoromethoxy-4,11-diaza-tricyclo[14.2.2.16,10]henicosa-1(19),6,8,10(21),16(20),17-hexaene-3,12-dione

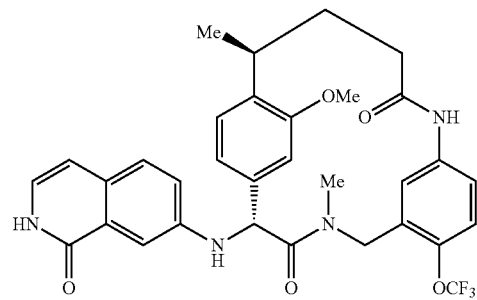 [SMILES: COc1cc2ccc1[C@@H](C)CCC(=O)Nc1ccc(OC(F)(F)F)c(c1)CN(C)C(=O)[C@@H]2Nc1ccc2cc[nH]c(=O)c2c1]

134A

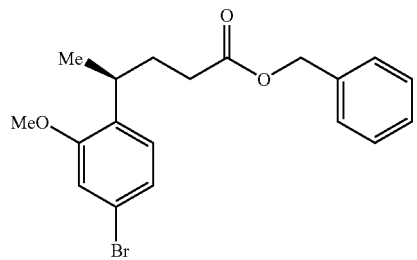 [SMILES: COc1cc(Br)ccc1[C@@H](C)CCC(=O)OCc1ccccc1]

A mixture of 47D (0.94 g, 3.27 mmol) and sodium bicarbonate (1.100 g, 13.09 mmol) in DMF (8.0 mL) was stirred at rt for 10 min. Then benzyl bromide (1.363 mL, 11.46 mmol) was added and the reaction was stirred at 65° C. for 15 h. It was diluted with diethyl ether, washed with water, brine and dried over Na₂SO₄. After evaporation of solvent, the crude in small amount of CHCl₃/hexanes was charged to a 40 g silica gel column, eluted with hexanes for 8 min and then with ethyl acetate in hexanes from 0-13% in 13 min gradient time to give 134A (0.82 g, 2.173 mmol, 66.4% yield) as a clear oil. ¹H NMR (400 MHz, methanol-d₄) δ ppm 1.20 (d, J=7.07 Hz, 3H) 1.85-1.95 (m, 2H) 2.22-2.28 (m, 2H) 3.13-3.22 (m, 1H) 3.76 (s, 3H) 5.06 (s, 2H) 7.05 (s, 3H) 7.30-7.39 (m, 5H); LC-MS 399 [M+Na]⁺.

134B

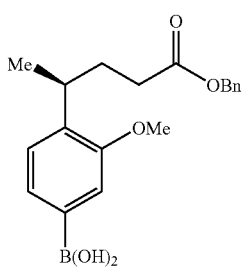 [SMILES: COc1cc(B(O)O)ccc1[C@@H](C)CCC(=O)OCc1ccccc1]

Using a procedure analogous to that used to prepare 29B, 134A (0.81 g, 2.147 mmol) was reacted with bis(neopentyl glycolato)diboron), potassium acetate and (1,1'-bis(diphenylphosphino)ferrocene)-dichloropalladium(II). The crude was purified by flash chromatography (EtOAc/hexanes 0% to 30%) and preparative HPLC (CH₃CN/H₂O, 0.1% TFA) to give 134B (0.47 g, 64% yield) as a viscous oil. ¹H NMR (400 MHz, methanol-d₄) δ ppm 1.09-1.16 (m, 3H) 1.77-1.89 (m, 2H) 2.10-2.20 (m, 2H) 3.10-3.20 (m, 1H) 3.69 (s, 3H) 4.96 (s, 2H) 7.00-7.13 (m, 3H) 7.17-7.33 (m, 5H); LCMS (m/z) 281.4.

134C

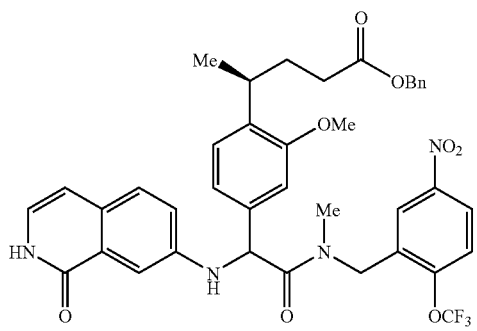

Using a procedure analogous to that used to prepare 41E, a mixture of 134B (0.156 g, 0.456 mmol), Intermediate 3 and 2-oxoacetic acid hydrate were reacted. The resulting solution was reacted with 42D (0.144 g, 0.501 mmol) using BOP and DIEA. The crude product was purified by column chromatography (0-10% dichloromethane/methanol) to give 134C (0.3 g, 88% yield) as a solid. LCMS (m/z) 747.7 [M+H]⁺.

134D

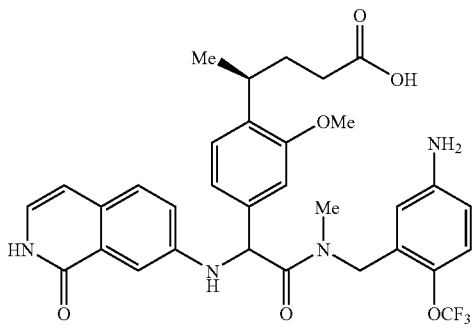 [SMILES: COc1cc(C(Nc2ccc3cc[nH]c(=O)c3c2)C(=O)N(C)Cc2cc(N)ccc2OC(F)(F)F)ccc1[C@@H](C)CCC(=O)O]

To 134C (0.3 g, 0.402 mmol) and Pd/C (0.1 g, 0.094 mmol) was added MeOH (5 mL), water (2.00 mL) and ethyl acetate (2.00 mL). The flask was purged with nitrogen and degassed (3×). Then hydrogen balloon was introduced and the system was purged and degassed (3×). A drop of 6N HCl was added and reaction was stirred at rt for 5 h. The catalyst was filtered over celite and washed with methanol. The filtrates were combined and evaporated to give 134D (0.25 g, 99% yield) as a solid. LCMS 627.6 [M+H]⁺.

Example 134

To a solution of BOP (0.353 g, 0.798 mmol) and DMAP (0.195 g, 1.596 mmol) in CH₂Cl₂ (60 mL) and DMF (6 mL) at rt was added a solution of 134D (0.25 g, 0.399 mmol) and DIEA (0.209 ml, 1.197 mmol) in DMF (5.0 mL) via a syringe pump over 5 h. To the reaction mixture was added 0.5 N HCl (30 mL), stirred for 10 min. The organic layer was collected and aqueous was extracted with CH₂Cl₂. The organic layers were washed with brine and dried over sodium sulfate. After evaporation of solvent, the crude residue was dissolved in 90% acetonitrile-10% water-0.1% TFA and purified (4 injections) by preparative HPLC equipped with a C18 Phenomenex Luna column (30 mm×100 mm, 5µ) with the UV detector set at 254 nm. The separations were performed using a gradient method: 10-100% B in 10 mins; then 100% B in 2 min with a flow rate of 40 mL/min. Solvent B is 90% acetonitrile-10% water-0.1% TFA and solvent A is 10% acetonitrile-90% water-0.1% TFA. The desired fractions were collected and further purified and separated using a preparative HPLC equipped with a Whelko-01 column. The residue was dissolved in MeOH/EtOH with 10% DMSO. The separations were performed using an isocratic method of 40% 1:1 ethanol/methanol: heptane for 40 min with a flow rate of 20 mL/min. The second peak (33 mg, 14% yield) was confirmed to be Example 134: ¹H NMR (400 MHz, methanol-d₄) δ ppm 1.14-1.33 (m, 3H) 1.74-1.87 (m, 1H) 2.06-2.19 (m, 1H) 2.25-2.41 (m, 2H) 3.26-3.32 (m, 1H) 3.34-3.39 (m, 3H) 3.48 (s, 3H) 3.82 (d, J=16.93 Hz, 1H) 5.34 (d, J=16.93 Hz, 1H) 5.58 (s, 1H) 6.13 (d, J=2.53 Hz, 1H) 6.48 (d, J=7.07 Hz, 1H) 6.66-6.76 (m, 2H) 6.84 (d, J=7.07 Hz, 1H) 7.09 (dd, J=8.59, 1.52 Hz, 1H) 7.17 (dd, J=8.84, 2.53 Hz, 1H) 7.24-7.31 (m, 2H) 7.33-7.39 (m, 2H), ¹⁹F NMR (376 MHz, MeOD) δ ppm −59.61 (3F). LCMS (m/z) 609.6 [M+H]⁺. Analytical HPLC (Method A): Col A: 7.18 min, 86%; Col B: 7.28 min, 86%.

Example 135

(2R,15S)-7-Difluoromethoxy-17-methoxy-4,15-dimethyl-2-(1-oxo-1,2-dihydro-isoquinolin-7-ylamino)-4,11-diaza-tricyclo[14.2.2.16,10]henicosa-1(19),6,8,10(21),16(20),17-hexaene-3,12-dione

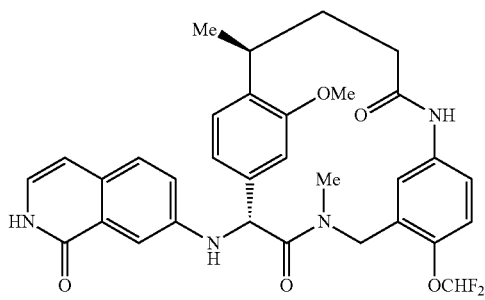 [SMILES: COc1cc2ccc1[C@@H](C)CCC(=O)Nc1ccc(OC(F)F)c(c1)CN(C)C(=O)[C@@H]2Nc1ccc2cc[nH]c(=O)c2c1]

135A

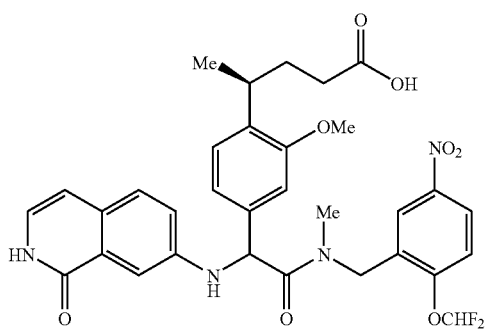 [SMILES: COc1cc(C(Nc2ccc3cc[nH]c(=O)c3c2)C(=O)N(C)Cc2cc([N+](=O)[O-])ccc2OC(F)F)ccc1[C@@H](C)CCC(=O)O]

Using a procedure analogous to that used to prepare 41E, a mixture of 134B (0.156 g, 0.456 mmol), Intermediate 3 and 2-oxoacetic acid hydrate were reacted. The resulting solution was reacted with 50A (0.135 g, 0.501 mmol) using BOP and DIEA. The crude product was purified column chromatography (0-10% dichloromethane/methanol) to give 135A (0.28 g, 84% yield). LCMS (m/z) 729.7 [M+H]$^+$.

135B

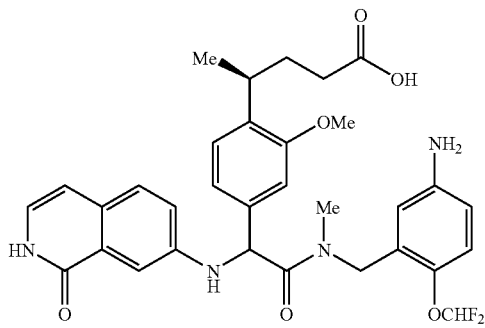 [SMILES: COc1cc(C(Nc2ccc3cc[nH]c(=O)c3c2)C(=O)N(C)Cc2cc(N)ccc2OC(F)F)ccc1[C@@H](C)CCC(=O)O]

To 135A (0.28 g, 0.384 mmol) and Pd/C (0.1 g, 0.094 mmol) was added MeOH (5 mL), water (2 mL) and ethyl acetate (2.00 mL). The flask was purged with nitrogen and degassed (3×). Then hydrogen balloon was introduced and the system was purged and degassed (3×). A drop of 6N HCl was added and reaction was stirred at rt for 5 h. The catalyst was filtered over celite and washed with methanol. The filtrates were combined and evaporated to give 135B (0.24 g, 100% yield) as a solid. LCMS (m/z) 609.6 [M+H]$^+$.

Example 135

To a solution of BOP (0.349 g, 0.789 mmol) and DMAP (0.193 g, 1.577 mmol) in CH$_2$Cl$_2$ (60 mL) and DMF (6 mL) at rt was added a solution of 135B (0.24 g, 0.394 mmol) and DIEA (0.207 mL, 1.183 mmol) in DMF (5.0 mL) via a syringe pump over 5 h. To the reaction mixture was added 0.5 N HCl (30 mL), stirred for 10 min. The organic layer was collected and aqueous was extracted with CH$_2$Cl$_2$. The organic layers were washed with brine and dried over sodium sulfate. After evaporation of solvent, the crude residue was dissolved in 90% acetonitrile-10% water-0.1% TFA and purified (4 injections) by preparative HPLC equipped with a C18 Phenomenex Luna column (30 mm×100 mm, 5μ) with the UV detector set at 254 nm. The separations were performed using a gradient method: 10-100% B in 10 mins; then 100% B in 2 min with a flow rate of 40 mL/min. Solvent B is 90% acetonitrile-10% water-0.1% TFA and solvent A is 10% acetonitrile-90% water-0.1% TFA. The desired fractions were collected and further purified and separated using a preparative HPLC equipped with a Whelko-01 column. The residue was dissolved in MeOH/EtOH with 10% DMSO. The separations were performed using an isocratic method of 50% 1:1 ethanol/methanol: heptane for 40 min with a flow rate of 20 mL/min. The second peak (33 mg, 14% yield) was confirmed to be Example 135: $^1$H NMR (400 MHz, methanol-d$_4$) δ ppm 1.12-1.33 (m, 3H) 1.73-1.86 (m, 1H) 2.05-2.20 (m, 1H) 2.21-2.41 (m, 2H) 3.26-3.32 (m, 1H) 3.33-3.38 (m, 3H) 3.48 (s, 3H) 3.80 (d, J=16.93 Hz, 1H) 4.82 (dd, J=5.56, 3.54 Hz, 1H) 5.30 (d, J=16.93 Hz, 1H) 5.56-5.63 (m, 1H) 6.03 (d, J=2.27 Hz, 1H) 6.47 (d, J=7.07 Hz, 1H) 6.64-6.72 (m, 2H) 6.75 (d, J=1.26 Hz, 1H) 6.83 (d, J=7.07 Hz, 1H) 6.95 (d, J=8.59 Hz, 1H) 7.13-7.19 (m, 1H) 7.24-7.31 (m, 2H) 7.31-7.39 (m, 2H); $^{19}$F NMR (376 MHz, MeOD) δ ppm −84.52-81.59 (m, 2F); LCMS (m/z) 591.6 [M+H]$^+$ Analytical HPLC (Method A): Col A: 6.81 min, 89%; Col B: 6.95 min, 89%.

Example 136

(2R,15S)-17-Methoxy-4,15-dimethyl-2-(1-oxo-1,2-dihydro-isoquinolin-7-ylamino)-7-pyrazol-1-yl-4,11-diaza-tricyclo[14.2.2.16,10]henicosa-1(19),6,8,10(21),6(20),17-hexaene-3,12-dione

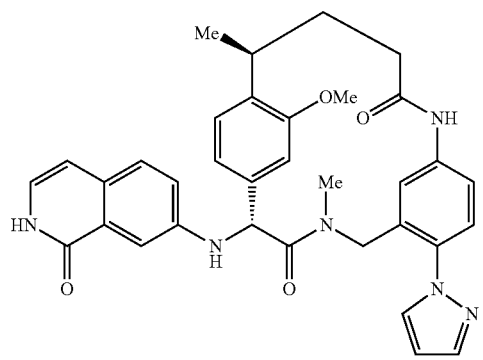 [SMILES: COc1cc2ccc1[C@@H](C)CCC(=O)Nc1ccc(-n3cccn3)c(c1)CN(C)C(=O)[C@@H]2Nc1ccc2cc[nH]c(=O)c2c1]

136A

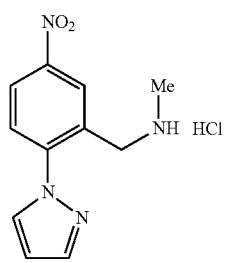 [SMILES: CNCc1cc([N+](=O)[O-])ccc1-n1cccn1 ; Cl]

To 133A (0.28 g, 0.842 mmol) was added 4.0 M HCl in dioxane (3 mL, 12.00 mmol). The reaction was stirred at rt for 2 h. The solvent was removed and the residue was dried under high vacuum to give 136A (0.2 g, 88% yield) as a yellow solid. $^1$H NMR (400 MHz, methanol-$d_4$) δ ppm 2.79 (s, 3H) 4.25 (s, 2H) 6.62-6.67 (m, 1H) 7.83 (d, J=8.84 Hz, 1H) 7.90 (d, J=1.77 Hz, 1H) 8.30 (d, J=2.27 Hz, 1H) 8.42 (dd, J=8.97, 2.65 Hz, 1H) 8.54 (d, J=2.78 Hz, 1H); LCMS (m/z) 233.3 [M+H]$^+$.

136B

Using a procedure analogous to that used to prepare 41E, a mixture of 134B (0.156 g, 0.456 mmol), Intermediate 3 and 2-oxoacetic acid hydrate were reacted. The resulting solution was reacted with 136A (0.122 g, 0.456 mmol) (0.191 g, 0.680 mmol) using BOP and DIEA. The crude product was purified column chromatography (0-10% dichloromethane/methanol) to give 136B (0.33 g, 99% yield) as a solid. LCMS (m/z) 729.8 [M+H]$^+$.

136C

To 136B (0.33 g, 0.453 mmol) and Pd/C (0.1 g, 0.094 mmol) was added MeOH (5 mL). The flask was purged with nitrogen and degassed (3x). Then hydrogen balloon was introduced and the system was purged and degassed (3x). A drop of 6N HCl was added and reaction was stirred at rt for 5 h. The catalyst was filtered over celite and washed with methanol. The filtrates were combined and evaporated to give 136C (0.27 g, 88% yield) as a solid. LCMS (m/z) 609.6 [M+H]$^+$.

Example 136

To a solution of BOP (0.392 g, 0.887 mmol) and DMAP (0.217 g, 1.774 mmol) in CH$_2$Cl$_2$ (60 mL) and DMF (6 mL) at rt was added a solution of 136C (0.27 g, 0.444 mmol) and DIEA (0.232 mL, 1.331 mmol) in DMF (5.0 mL) via a syringe pump over 5 h. To the reaction mixture was added 0.5 N HCl (30 mL), stirred for 10 min. The organic layer was collected and aqueous was extracted with CH$_2$Cl$_2$. The organic layers were washed with brine and dried over sodium sulfate. After evaporation of solvent, the crude residue was dissolved in 90% acetonitrile-10% water-0.1% TFA and purified (4 injections) by preparative HPLC equipped with a C18 Phenomenex Luna column (30 mm×100 mm, 5μ) with the UV detector set at 254 nm. The separations were performed using a gradient method: 0-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected and further purified using a preparative HPLC equipped with a Whelko-01 column. The residue was dissolved in MeOH/EtOH with heptanes, During the separation the sample precipitated out-few drops of DMSO was added. The separations were performed using an isocratic method of 20% 1:1 ethanol/methanol: heptane for 40 min with a flow rate of 20 mL/min. The second peak (21 mg, 8% yield) was confirmed to be Example 136: $^1$H NMR (400 MHz, methanol-$d_4$) δ ppm 1.17 (d, J=7.07 Hz, 3H) 1.74-1.90 (m, 1H) 2.06-2.20 (m, 1H) 2.24-2.44 (m, 2H) 3.28-3.34 (m, 1H) 3.34-3.38 (m, 3H) 3.48 (s, 3H) 3.83 (d, J=16.93 Hz, 1H) 4.90 (d, J=16.67 Hz, 1H) 5.53 (s, 1H) 6.32-6.40 (m, 1H) 6.42 (t, J=2.15 Hz, 1H) 6.46 (d, J=7.07 Hz, 1H) 6.69 (s, 1H) 6.74-6.86 (m, 2H) 7.10-7.20 (m, 2H) 7.26-7.37 (m, 4H) 7.63 (d, J=1.52 Hz, 1H) 7.77-7.83 (m, 1H); LCMS (m/z) 591.6 [M+H]$^+$. Analytical HPLC (Method A): Col A: 6.1.7 min, 87%; Col B 6.23 min, 93%.

Example 137

(2R,15R)-2-(6-Fluoro-3-oxo-2,3-dihydro-1H-isoindol-5-ylamino)-4,13,15,17-tetramethyl-7-trifluoromethoxy-4,11,13-triaza-tricyclo[14.2.2.16,10]henicosa-1(19),6,8,10(21),16(20), 17-hexaene-3,12-dione

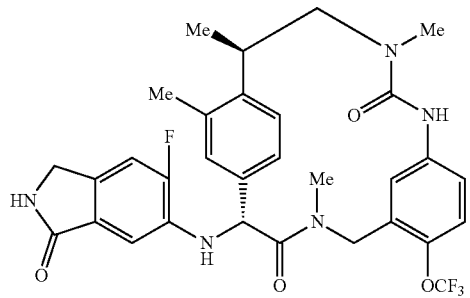 [SMILES: Cc1cc2ccc1[C@@H](C)CN(C)C(=O)Nc1ccc(OC(F)(F)F)c(c1)CN(C)C(=O)[C@@H]2Nc1cc2c(cc1F)CNC2=O]

137A

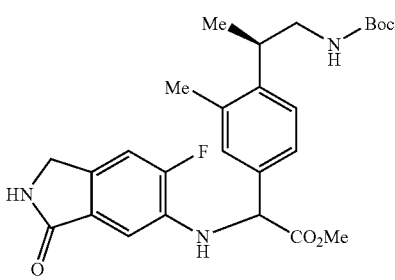 [SMILES: COC(=O)C(Nc1cc2c(cc1F)CNC2=O)c1ccc([C@@H](C)CNC(=O)OC(C)(C)C)c(C)c1]

To a 5 mL microwave flask was added 7° C. (500 mg, 1.628 mmol), Intermediate 7 (297 mg, 1.790 mmol), glyoxylic acid monohydrate (157 mg, 1.709 mmol), DMF (0.25 mL) and acetonitrile (2 mL). The mixture was heated in a microwave reactor at 100° C. for 10 min. Then MeOH (1 ml) and trimethylsilyldiazomethane (0.977 ml, 1.953 mmol) were added to the mixture and stirred for 1 h. Additional trimethylsilyldiazomethane (0.5 mL) was added and stirred for 30 min. The mixture was diluted by EtOAc and washed with water, brine. The organic layer was dried with $MgSO_4$ and concentrated. The residue was dissolved in a small amount of dichloromethane, added to a 40 g ISCO column and eluted with 0-100% EtOAc/hexanes for 30 min followed with pure EtOAc for 20 min. The desired fractions were collected to give 137A (310 mg, 38% yield) as a yellow oil. LCMS 500 [M+1]$^+$.

137B

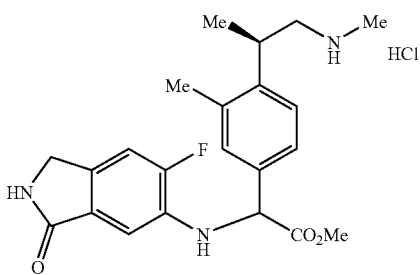 [SMILES: CNC[C@H](C)c1ccc(C(Nc2cc3c(cc2F)CNC3=O)C(=O)OC)cc1C ; Cl]

To 137A (310 mg) in EtOAc (8.0 mL) was added 4.0 N HCl in dioxane (8.14 mL, 32.6 mmol). The mixture was stirred at rt for 2 h. After evaporation of solvent, 137B (213 mg) was obtained as a solid. LCMS 400 [M+1]$^+$.

137C

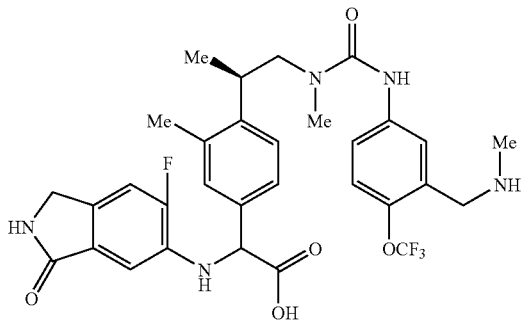 [SMILES: CNCc1cc(NC(=O)N(C)C[C@H](C)c2ccc(C(Nc3cc4c(cc3F)CNC4=O)C(=O)O)cc2C)ccc1OC(F)(F)F]

Using a procedure analogous to that used to prepare 70E and 70F, 70B (80 mg, 0.250 mmol) was reacted with Phosgene and sodium bicarbonate followed by 137B and triethylamine. The crude product was purified by column chromatography (0-100% EtOAc/hexanes). The intermediate was dissolved in 2.0 mL of THF and was treated with 1.0 M LiOH (1.001 mL, 1.001 mmol) at rt for 3 h. The reaction was quenched by 1.0 N HCl and extracted with EtOAc. The organic layer was washed with water, brine, dried over $MgSO_4$, and concentrated to an oil. The crude was diluted in 3 mL of EtOAc and 4.0 N HCl in dioxane (2.503 mL, 10.01 mmol) was added. The mixture was stirred at rt for 2 h. After solvent evaporation, 137C (160 mg, 96% yield) was obtained as a solid, LCMS 632 [M+1]$^+$.

Example 137

To a solution of BOP (212 mg, 0.479 mmol) and DMAP (117 mg, 0.958 mmol) in $CH_2Cl_2$ (50 mL) and DMF (3 mL) at rt was added a solution of 137C (160 mg, 0.239 mmol) and DIEA (0.084 mL, 0.479 mmol) in DMF (5.0 mL) via a syringe pump over 10 h at rt. Solvent was completely removed and the crude was purified by prep HPLC using AXIA column (4 injections) eluting with 90% water to 20% water in MeOH with 0.1% TFA. The desired fractions were collected and further purified by chrial semi-prep HPLC: 2 injections on Whelko-01 column eluted by 60% MeOH/EtOH)/heptane at 20 mL/min. The second peak (RT=13.5 min) was identified to be Example 137: $^1$H NMR (400 MHz, methanol-d$_4$) δ ppm 0.84-1.03 (m, 3H) 1.08-1.26 (m, 1H) 2.14-2.23 (m, 3H) 2.31-2.42 (m, 3H) 2.67-2.90 (m, 2H) 2.99-3.15 (m, 1H) 3.26-3.33 (m, 3H) 3.98 (s, 1H) 4.17 (d, J=18.02 Hz, 1H) 4.84-5.00 (m, J=3.95 Hz, 1H) 5.40-5.49 (m, 1H) 5.55-5.70 (m, 1H) 6.35 (s, 1H) 6.41-6.47 (m, 1H) 6.71 (dd, J=8.35, 1.76 Hz, 1H) 6.77-6.83 (m, 1H) 6.86 (s, 1H) 7.07-7.15 (m, 1H) 7.27-7.33 (m, 2H) 7.35 (s, 1H) 7.57-7.62 (m, 1H). LCMS 614 (M+H)$^+$. Analytical HPLC (Method A): Col A: 6.74 min, 99%; Col B: 6.75 min, 99%.

Example 138

(2R,15R)-7-Difluoromethoxy-4,13,15,17-tetramethyl-2-(1-oxo-1,2-dihydro-isoquinolin-7-ylamino)-4,11,13-triaza-tricyclo[14.2.2.16,10]henicosa-1(19),6,8,10(21),16(20),17-hexaene-3,12-dione

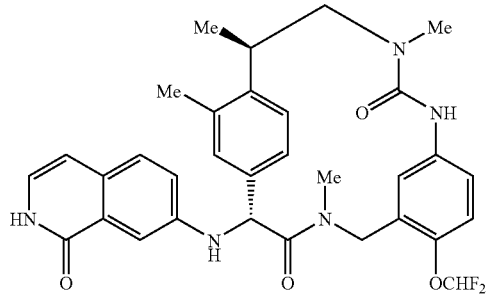 [SMILES: Cc1cc2ccc1[C@@H](C)CN(C)C(=O)Nc1ccc(OC(F)F)c(c1)CN(C)C(=O)[C@@H]2Nc1ccc2cc[nH]c(=O)c2c1]

138A

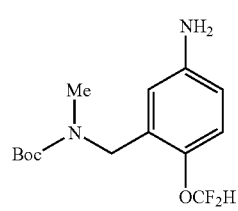

To Intermediate 15 (270 mg, 0.813 mmol) in MeOH (5.0 mL) was added 10% Pd/C (90 mg, 0.813 mmol). The mixture was hydrogenated with a hydrogen balloon for 3.0 h. Pd/C was removed by filtration. The filtrate was concentrated to give 138A (240 mg, 0.794 mmol, 98% yield) as a viscous oil. LCMS 303 [M+H]+.

138B

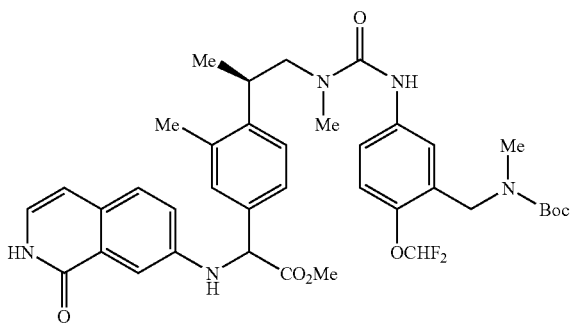 [SMILES: COC(=O)C(Nc1ccc2cc[nH]c(=O)c2c1)c1ccc([C@@H](C)CN(C)C(=O)Nc2ccc(OC(F)F)c(CN(C)C(=O)OC(C)(C)C)c2)c(C)c1]

Using a procedure analogous to that used to prepare 70E and 70F, 138A (127 mg, 0.419 mmol) was reacted with Phosgene and sodium bicarbonate followed by 70D and triethylamine. The crude product was purified by column chromatography (0-100% EtOAc/hexanes). The desired fractions were collected to give 138B (270 mg) as a clear oil.

138C

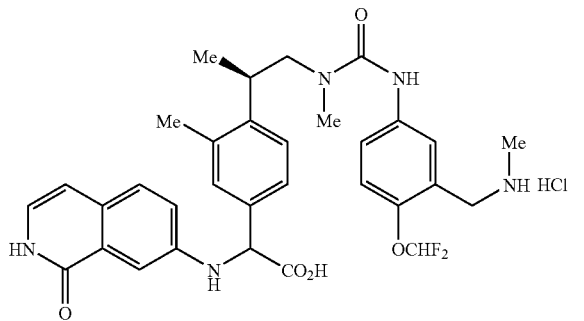 [SMILES: CNCc1cc(NC(=O)N(C)C[C@H](C)c2ccc(C(Nc3ccc4cc[nH]c(=O)c4c3)C(=O)O)cc2C)ccc1OC(F)F ; "HCl"]

To 138B (270 mg) in 2 ml of THF was added 1.0 M LiOH (1.396 mL, 1.396 mmol). The mixture was stirred at rt for 3 h. The reaction was quenched by addition of 1.0 N HCl and extracted with EtOAc, the organic layer was washed with water and brine, dried with MgSO$_4$ and concentrated to an oil. The residue was diluted in 3 mL of EtOAc and treated with 4.0 N HCl in dioxane (3.49 mL, 13.96 mmol) for 2.0 h. 138C (210 mg, 93% yield) was obtained after removal of solvent. LCMS 608 [M+1].

Example 138

To a solution of BOP (288 mg, 0.652 mmol) and DMAP (159 mg, 1.304 mmol) in CH$_2$Cl$_2$ (50 mL) and DMF (3 mL) at rt was added a solution of 138C (210 mg, 0.326 mmol) and DIEA (0.114 mL, 0.652 mmol) in DMF (5.0 mL) via a syringe pump over 10 h at rt. Solvent was completely removed and the crude was purified by a prep HPLC using AXIA column (4 injections) eluting with 90% water to 20% water in acetonitrile with 0.1% TFA. The desired fractions were collected and further purified by chrial semi-prep HPLC on Whelko-01 column eluted by 60% MeOH/EtOH/heptane at 20 mL/min. The second peak (31 mg, RT=11.04 min) was identified to be Example 138: $^1$H NMR (400 MHz, methanol-d$_4$) δ ppm 1.15 (d, J=6.59 Hz, 3H) 1.91 (s, 3H) 2.88 (s, 3H) 3.13-3.24 (m, 5H) 3.73-3.91 (m, 2H) 5.28 (d, J=16.70 Hz, 1H) 5.58 (s, 1H) 6.40 (d, J=23.73 Hz, 1H) 6.59-6.92 (m, 4H) 7.01-7.40 (m, 6H) 7.54 (s, 1H); LCMS 590 [M+1]+. Analytical HPLC (Method A): Col A: 7.00 min, 99%; Col B: 7.12 min, 99%.

Example 139

(S)-4,15,17-Trimethyl-2-(1-oxo-1,2-dihydro-isoquinolin-7-ylamino)-7-(pyrrolidine-1-carbonyl)-4,11-diaza-tricyclo[14.2.2.110]henicosa-1(19),6,8,10(21),16(20),17-hexaene-3,12-dione

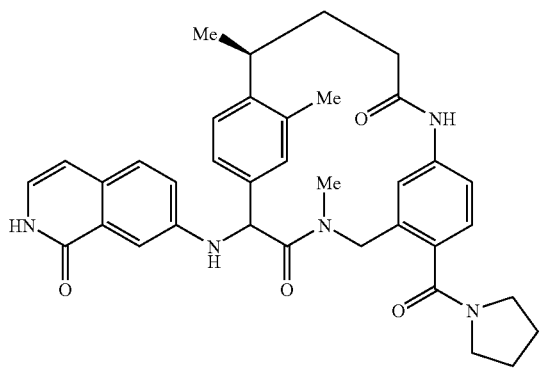 [SMILES: Cc1cc2ccc1[C@@H](C)CCC(=O)Nc1ccc(C(=O)N3CCCC3)c(c1)CN(C)C(=O)C2Nc1ccc2cc[nH]c(=O)c2c1]

139A

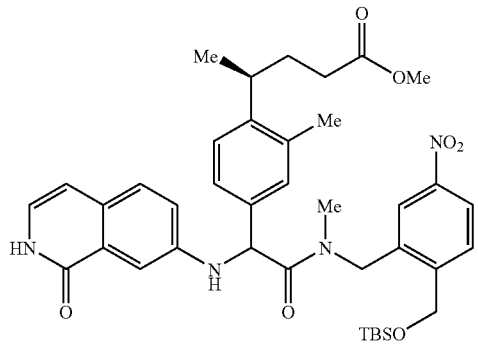 [SMILES: COC(=O)CC[C@H](C)c1ccc(C(Nc2ccc3cc[nH]c(=O)c3c2)C(=O)N(C)Cc2cc([N+](=O)[O-])ccc2CO[Si](C)(C)C(C)(C)C)cc1C]

Using a procedure analogous to that used to prepare 41E, a mixture of 41D (620 mg, 2.479 mmol), Intermediate 3 and 2-oxoacetic acid hydrate were reacted. The resulting solution was reacted with 21D (770 mg, 2.479 mmol using BOP and DIEA. The crude product was purified by column chromarography (0 to 20% MeOH in CH$_2$Cl$_2$) to yield 139A (1100 mg, 1.539 mmol, 62.1% yield).

139B

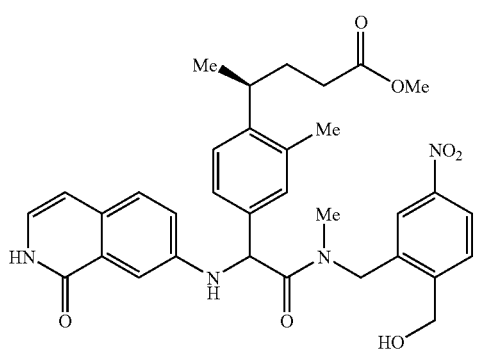

TBAF (1399 µL, 1.399 mmol) was added to a solution of 139A (500 mg, 0.699 mmol) in THF (3.5 mL) and stirred for 4 h at rt. The reaction was diluted with EtOAc (100 mL), washed with H$_2$O and brine (50 mL each), dried over Na$_2$SO$_4$ and concentrated. The crude product was purified by flash chromatography (0% to 20% methanol in dichloromethane) to yield 139B (380 mg, 0.633 mmol, 90% yield) as an oil. MS (ESI) m/z 601.6 (M+H)$^+$.

139C

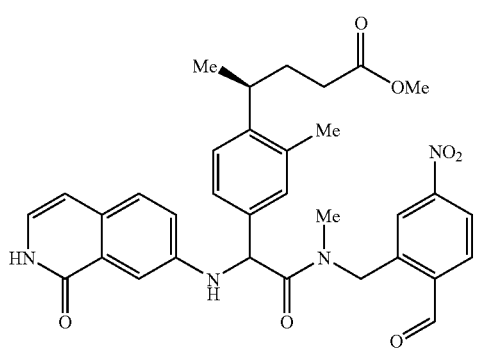 [SMILES: COC(=O)CC[C@H](C)c1ccc(C(Nc2ccc3cc[nH]c(=O)c3c2)C(=O)N(C)Cc2cc([N+](=O)[O-])ccc2C=O)cc1C]

A solution of 139B (245 mg, 0.41 mmol) in THF (15 mL) was stirred with IBX polystyrene (1.1 mg, 1.2 mmol) overnight at rt. The mixture was filtered and the polystyrene was washed with THF 5 times. The combined organics were concentrated to yield 139C (175 mg, 0.29 mmol, 72% yield) an oil. MS (ESI) m/z 599.6 (M+H)$^+$.

139D

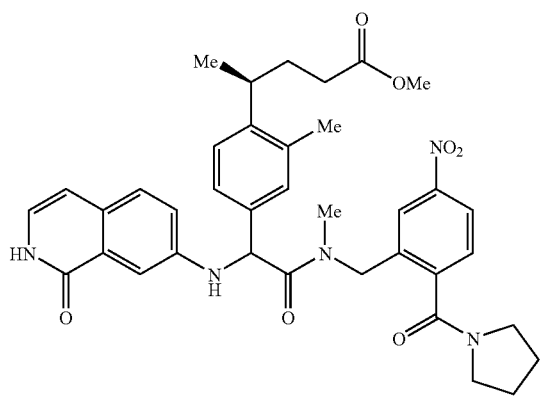 [SMILES: COC(=O)CC[C@H](C)c1ccc(C(Nc2ccc3cc[nH]c(=O)c3c2)C(=O)N(C)Cc2cc([N+](=O)[O-])ccc2C(=O)N2CCCC2)cc1C]

Acetone cyanohydrin (26.8 µL, 0.292 mmol) was added to a solution of 139C (175 mg, 0.292 mmol), pyrrolidine (72.0 µL, 0.877 mmol) and TEA (61.1 µL, 0.438 mmol) in acetonitrile (585 uL) and stirred overnight at rt. BOP (129 mg, 0.292 mmol) was added and mixture was stirred for 1 h at rt. The crude mixture was purified by prep HPLC to yield 139D (75 mg, 0.112 mmol, 38.4% yield) as an oil. MS (ESI) m/z 668.7 (M+H)$^+$.

139E

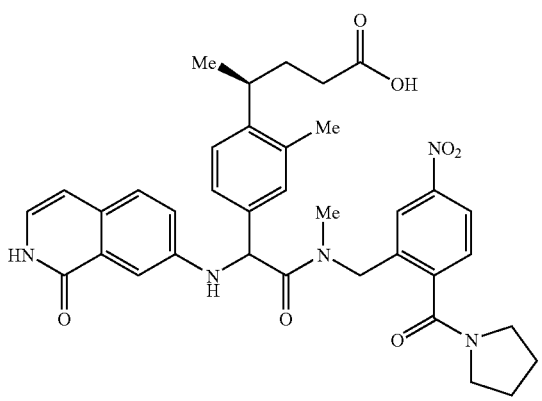 [SMILES: Cc1cc(C(Nc2ccc3cc[nH]c(=O)c3c2)C(=O)N(C)Cc2cc([N+](=O)[O-])ccc2C(=O)N2CCCC2)ccc1[C@@H](C)CCC(=O)O]

To a solution of 139D (75 mg, 0.112 mmol) in THF (1.0 mL) and was added 1.0 N LiOH (0.5 mL, 0.5 mmol). The mixture was stirred at rt for 2 h. The reaction mixture was acidified with 1.0 mL 1.0 N HCl (0.6 mL) and extracted with EtOAc. The combined organics were washed with brine, dried over Na$_2$SO$_4$ and concentrated to yield 139E (65 mg, 0.1 mmol, 83% yield). MS (ESI) min/z 654.7 (M+H)$^+$.

139F

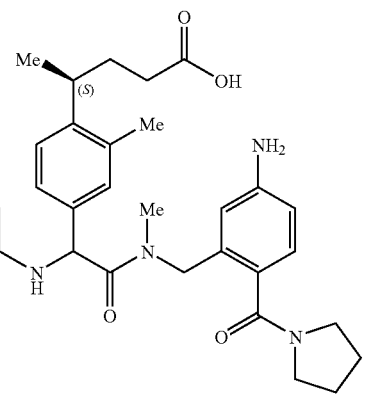

A solution of 139E (65 mg, 0.099 mmol) in MeOH (1 mL) with Pd/C (10.58 mg, 9.94 µmol) and HCl (99 µL, 0.099 mmol) was stirred under H$_2$ (1 atm) for 4 h. The reaction was filtered, concentrated, and purified by prep HPLC to yield 139F (33 mg, 0.053 mmol, 53.2% yield).

Example 139

Using a procedure analogous to that used to prepare Example 41, 139F 33 mg, 0.053 mmol) was cyclized with BOP, DMAP, and DIEA and purified by prep HPLC to yield Example 139 (3 mg, 4.95 μmol, 9.36% yield) as an off-white solid. MS (ESI) m/z 606.7 (M+H)+. Analytical HPLC (Method A): Col A: 5.87 min, 96%; Col B: 5.79, 5.84 min (distereomers), 96%.

Example 140

(2R,15R)-7-(1,1-Dioxo-1λ6-isothiazolidin-2-yl)-4,15,17-trimethyl-2-(1-oxo-1,2-dihydro-isoquinolin-7-ylamino)-13-oxa-4,11-diaza-tricyclo[14.2.2.1^6]henicosa-1(19),6,8,10(21),16(20),17-hexaene-3,12-dione

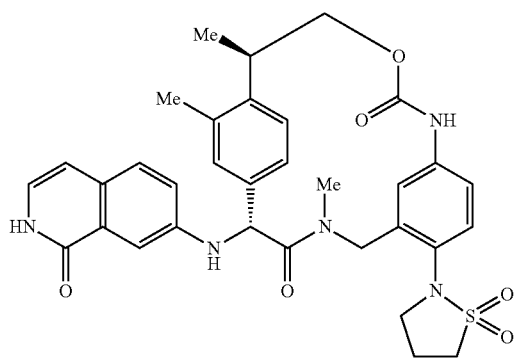 [SMILES: Cc1cc2ccc1[C@@H](C)COC(=O)Nc1ccc(N3CCCS3(=O)=O)c(c1)CN(C)C(=O)[C@@H]2Nc1ccc2cc[nH]c(=O)c2c1]

140A

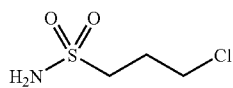

A solution of 3-chloropropane-1-sulfonyl chloride (13.50 g, 76 mmol) in DCM (50 mL) was bubbled with NH$_3$ (g) for 20 min. The mixture was stirred rt for 1 h, then was filtered and concentrated. Recrystallization from CHC$_3$ afforded 140A (11.61 g, 97% yield) as a white solid. $^1$H NMR (400 MHz, CDCl$_3$) δ ppm 2.26-2.37 (m, 2H) 3.30 (t, 2H) 3.68 (t, J=6.15 Hz, 2H), 5.03 (s, 2H).

140B

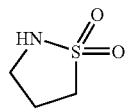

To degassed ethanol (100 mL), Na (206 mg) was added, followed by 140A (2.00 g, 12.69 mmol). The solution was refluxed for 2 h, then concentrated. The mixture was diluted with water, and extracted with chloroform. The organic phase was concentrated to afford 140B (1.40 g, 91% yield) as a colorless oil, which was used in the following step without purification. $^1$H NMR (400 MHz, CDCl$_3$) d ppm 2.29-2.45 (m, 2H) 3.02 (t, J=7.47 Hz, 2H) 3.34 (t, J=6.59 Hz, 2H) 4.24 (s, 1H).

140C

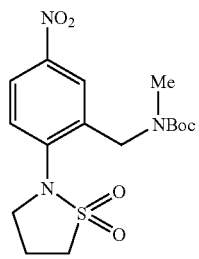

Intermediate 18 (518 mg, 1.5 mmol), 140B (363 mg, 3.00 mmol), 9,9-dimethyl-4,5-bis(diphenylphosphino)xanthene (260 mg, 0.450 mmol), Pd(OAc)$_2$ (67.4 mg, 0.300 mmol), and cesium carbonate (977 mg, 3.00 mmol) were combined in a sealed reaction vial. The mixture was degassed and filled with N$_2$. Toluene (5 mL) was added. The mixture was stirred at 90° C. for 20 h, then concentrated. Water was added, then the mixture extracted with DCM (3×20 mL). The combined organic layer was washed with 1N HCl. sat. NaHCO$_3$, and brine, dried (Na$_2$SO$_4$) and concentrated. The crude product was purified by flash chromatography (0-60% EtOAc in hexanes) to afford 14° C. (503 mg, 80% yield) as a yellow solid. MS (ESI) m/z 386.3 (M+H)+.

Example 140

According to the procedure for the preparation of Example 130, replacement of 130B with 14° C. afforded Example 140. The diastereomers were separated by chiral chromatography (Chiralcel OD-H, 20 mm× 250 mm, 10% heptane 90% (EtOH/MeOH (1:1), 20 mL/min) to afford Example 140, followed by the phenylglycine diastereomer. MS (ESI) m/z 630.6 (M+H)+. $^1$H NMR (400 MHz, CD$_3$OD) δ ppm 7.55-7.61 (m, 1H) 7.51 (d., J=2.20 Hz, 1H) 7.39-7.47 (m, 2H) 7.26-7.31 (m, 2H) 7.24 (s, 1H) 6.94 (d, J=7.03 Hz, 1H) 6.75 (dd, J=8.35, 2.64 Hz, 1H) 6.56 (d, J=7.03 Hz, 1H) 6.08 (d, J=2.20 Hz, 1H) 5.66 (s, 1H) 5.46 (d, J=17.14 Hz, 1H) 4.61 (t, J=10.77 Hz, 1H) 4.10 (d, J=17.14 Hz, 1H) 3.93-4.00 (m, 1H) 3.58-3.72 (m, 2H) 3.43-3.52 (m, 1H) 3.33-3.39 (m, 2H) 3.28 (s, 3H) 2.42-2.55 (m, 2H) 2.32 (s, 3H) 1.25-1.34 (m, 3H). Analytical HPLC (Method A): Col A: 6.52 min, 83%, 16% (rotomers); Col B: 6.87 min, 83%, 16% (rotomers).

Example 141

(2R,15R)-7-(1,1-Dioxo-1,3-dihydro-1λ6-1,2-benzisothiazol-2-yl)-4,15,17-trimethyl-2-(1-oxo-1,2-dihydro-isoquinolin-7-ylamino)-13-oxa-4,11-diaza-tricyclo[14.2.2.1^{6,10}]henicosa-1(19),6,8,10(21),16(20),17-hexaene-3,12-dione

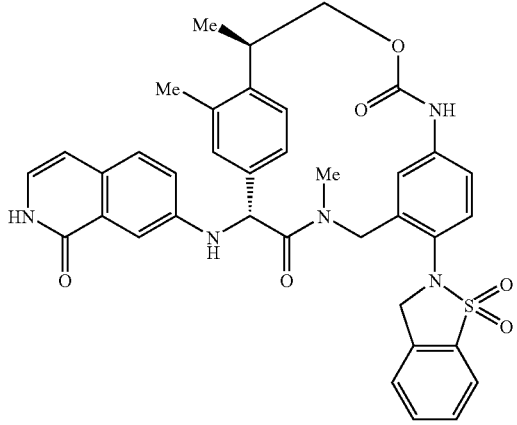 [SMILES: Cc1cc2ccc1[C@@H](C)COC(=O)Nc1ccc(N3Cc4ccccc4S3(=O)=O)c(c1)CN(C)C(=O)[C@@H]2Nc1ccc2cc[nH]c(=O)c2c1]

141A

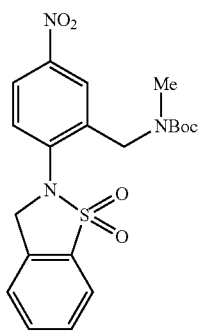

Intermediate 18 (518 mg, 1.5 mmol), 2,3-dihydro-1,1-dioxo-1,2-benzothiazole (254 mg, 1.50 mmol), 9,9-dimethyl-4,5-bis(diphenylphosphino)xanthene (260 mg, 0.450 mmol), Pd(OAc)$_2$ (50.5 mg, 0.225 mmol), and cesium carbonate (1026 mg, 3.15 mmol) were sealed in a reaction vial. The vial was degassed and filled with N$_2$. Toluene (5 mL) was added. The mixture was stirred at 90° C. for 60 h. The mixture was concentrated. Water was added and the mixture was extracted with DCM (3×20 mL). The combined organic layer was washed with 1N HC., sat. NaHCO$_3$, and brine, dried (Na$_2$SO$_4$) and concentrated. The crude product was purified by flash chromatography (0-60% EtOAc in Hex) to afford 141A (388 mg, 59.1% yield) as a white solid. MS (ESI) m/z 434.4 (M+H)$^+$. $^1$H NMR (400 MHz, CDCl$_3$) δ ppm 1.26-1.51 (m, 9H) 2.93 (s, 3H) 4.70 (s, 2H) 4.77 (s, 2H) 7.47 (d, J=7.47 Hz, 1H) 7.54-7.77 (m, 3H) 7.87 (d, J=7.91 Hz, 1H) 8.06-8.31 (m, 2H).

Example 141

According to the procedure for the preparation of Example 130, replacement of 130B with 141A afforded Example 141. The diastereomers were separated by chiral chromatography (Chiralcel OD-H, 20 mm×250 mm (ID X L), 10% heptane 90% (EtOH/MeOH (1:1), 20 mL/min) to afford Example 141, followed by the phenylglycine diastereomer. MS (ESI) m/z 678.7 (M+H)$^+$. $^1$H NMR (400 MHz, CD$_3$OD) δ ppm 7.82 (d, J=7.91 Hz, 1H) 7.70 (t, J=7.25 Hz, 1H) 7.61 (t, J=8.13 Hz, 2H) 7.55 (d, J=7.91 Hz, 1H) 7.34-7.50 (m, 4H) 7.20-7.28 (m, 2H) 6.90 (d, J=7.03 Hz, 1H) 6.81 (dd, J=8.13, 2.42 Hz, 1H) 6.51 (d, J=7.03 Hz, 1H) 6.18 (d, J=2.20 Hz, 1H) 5.64 (s, 1H) 5.46 (d, J=16.70 Hz, 1H) 4.71-4.87 (m, 2H) 4.56-4.67 (m, 1H) 4.11 (d, J=17.14 Hz, 1H) 3.97 (dd, J=10.77, 4.17 Hz, 1H) 3.46 (s, 1H) 3.30 (s, 3H) 2.30 (s, 3H) 1.29 (d, J=7.03 Hz, 3H). Analytical HPLC (Method A): Col A: 7.42 min, 98%; Col B: 7.41 min, 98%.

Example 142

(2R,15R)-4,15,17-Trimethyl-2-(1-oxo-1,2-dihydro-isoquinolin-7-ylamino)-7-phenoxy-13-oxa-4,11-diaza-tricyclo[14.2.2.1$^{6,10}$]henicosa-1(19),6,8,10(21),16(20),17-hexaene-3,12-dione

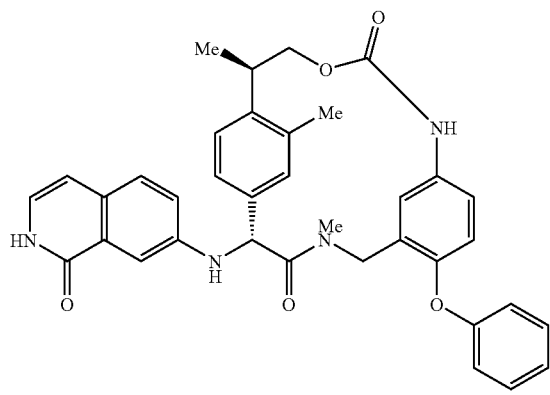 [SMILES: Cc1cc2ccc1[C@@H](C)COC(=O)Nc1ccc(Oc3ccccc3)c(c1)CN(C)C(=O)[C@@H]2Nc1ccc2cc[nH]c(=O)c2c1]

142A

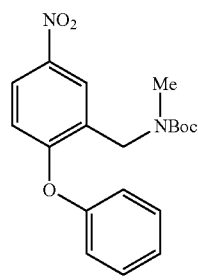

A mixture of Intermediate 18 (518 mg, 1.5 mmol), ethyl 2-oxocyclohexanecarboxylate (51.1 mg, 0.300 mmol), CuI (28.6 mg, 0.150 mmol), cesium carbonate (1026 mg, 3.15 mmol), and phenol (169 mg, 1.800 mmol) in DMSO (5 mL), was degassed and flushed with N$_2$. The mixture was irradiated in a microwave reactor at 90° C. for 20 min. The reaction mixture was diluted with water and extracted with EtOAc (3×20 mL). The combined organic layer was washed with brine, dried (Na$_2$SO$_4$), and concentrated. The crude product was purified by prep HPLC to afford 142A (430 mg, 80% yield). MS (ESI) m/z 359.3 (M+H)$^+$. $^1$H NMR (400 MHz, CDCl3) d ppm 1.46 (d, J=19.33 Hz, 9H) 2.97 (s, 3H) 4.58 (d, J=-25.93 Hz, 2H) 6.77 (d, J=8.79 Hz, 1H) 6.97-7.17 (m, 2H) 7.16-7.28 (m, 1H) 7.34-7.50 (m, 2H) 7.96-8.41 (m, 2H).

Example 142

According to the procedure for the preparation of Example 130, replacement of 130B with 142A afforded Example 142. The diastereomers were separated by chiral chromatography (R,R-Whelk-0 column 21.1×250 mm, 90% (MeOH/EtOH (1:1)), 10% heptane, 20 mL/min) to afford the phenylglycine diastereomer, followed by Example 142. MS (ESI) m/z 603.6 (M+H)$^+$. $^1$H NMR (400 MHz, CD$_3$OD) δ ppm 7.63 (d, J=6.59 Hz, 1H) 7.37-7.43 (m, 3H) 7.21-7.32 (m, 4H) 7.05 (t, J=7.47 Hz, 1H) 6.87-6.92 (m, 3H) 6.68-6.74 (m, 2H) 6.52 (d, J=7.03 Hz, 1H) 5.96 (s, 1H) 5.63 (s, 1H) 5.35 (d, J=17.14 Hz, 1H) 4.66 (t, J=10.99 Hz, 1H) 3.94 (dd, J=10.77, 4.17 Hz, 1H) 3.84 (d, J=17.14 Hz, 1H) 3.47 (ddd, J=10.99, 7.03, 4.39 Hz, 1H) 3.29 (s, 3H) 2.33-2.36 (m, 3H) 1.29 (d, J=7.03 Hz, 4H). Analytical HPLC (Method A): Col A: 8.14 min, 99%; Col B: 8.40 min, 99%.

Example 143

(2R,15R)-4,15,17-Trimethyl-2-(1-oxo-1,2-dihydro-isoquinolin-7-ylamino)-7-(2-oxo-2H-pyridin-1-yl)-13-oxa-4,11-diaza-tricyclo[14.2.2.1$^{6,10}$]henicosa-1(19),6,8,10(21),16(20),17-hexaene-3,12-dione

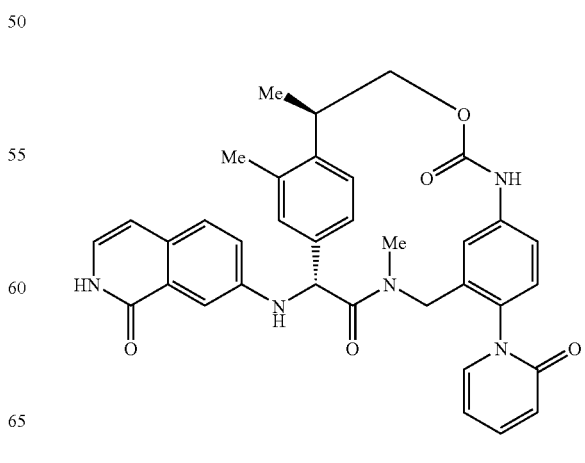

143A

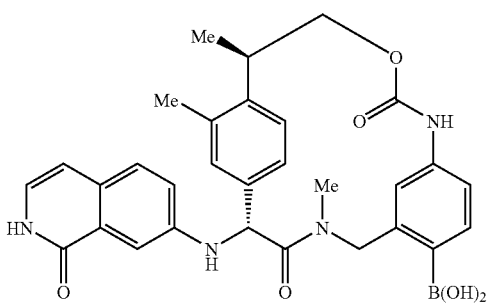 [SMILES: Cc1cc2ccc1[C@@H](C)COC(=O)Nc1ccc(B(O)O)c(c1)CN(C)C(=O)[C@@H]2Nc1ccc2cc[nH]c(=O)c2c1]

In a reaction vial, 97 (100 mg, 0.170 mmol), bis(neopentyl glycolato)diboron (42.2 mg, 0.187 mmol), potassium acetate (41.6 mg, 0.424 mmol) and (1,1'-bis(diphenylphosphino)ferrocene)-dichloropalladium(II) (14 mg, 0.017 mmol) were combined and degassed by evacuating and flushing with argon (4×). DMSO (1 mL) was added and the mixture was degassed (3×). The reaction was stirred at 80° C. for 3 h. The reaction mixture was filtered and purified by preparative HPLC to afford 143A (61 mg, 64.9% yield) as an off-white solid. MS (ESI) m/z 555.5 (M+Na)+.

Example 143

To 143A (0.061 g, 0.110 mmol), pyridin-2(1H)-one (0.209 g, 2.201 mmol), DMAP (0.067 g, 0.550 mmol), MS 4A (0.075 g, 0.110 mmol) and copper(II) acetate monohydrate (0.022 g, 0.110 mmol) was added DCM (3 mL). The reaction mixture was placed stirred vigorously at rt for 18 h under an air atmosphere. The reaction mixture was diluted with MeOH, filtered and concentrated. The crude product was purified by preparative HPLC to afford Example 143 (8.9 mg, 13% yield) as an off-white solid. MS (ESI) m/z 604/7 (M+H)+. $^1$H-NMR: (500 MHz, CD$_3$OD) δ ppm 1.30 (dd, J=6.9, 4.1 Hz, 3H), 2.33 (d, J=11.5 Hz, 3H), 3.15-3.37 (m, 3H), 3.42-3.55 (m, 1H), 3.69-3.94 (m, 1H), 3.92-4.01 (m, 1H), 4.57-4.69 (m, 1H), 5.41 (dd, J=16.8, 4.1 Hz, 1H), 5.67 (d, J=14.8 Hz, 1H), 5.99-6.30 (m, 1H), 6.45-6.65 (m, 2H), 6.67-6.89 (m, 1H), 6.92-7.00 (m, 1H), 7.08-7.20 (m, 1H), 7.22-7.36 (m, 2H), 7.39-7.67 (m, 5H). Analytical HPLC (Method A): Col A: 6.06 min, 79%; Col B: 6.09 min, 69% (Purities for major rotomers).

Example 144

3-[17,20-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20), 17-hexaen-4-yl]-propionic acid ethyl ester

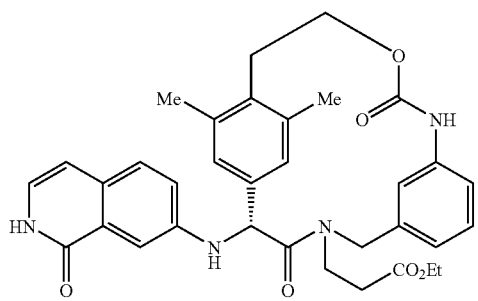 [SMILES: CCOC(=O)CCN1Cc2cccc(c2)NC(=O)OCCc2c(C)cc(cc2C)[C@@H](Nc2ccc3cc[nH]c(=O)c3c2)C1=O]

144A

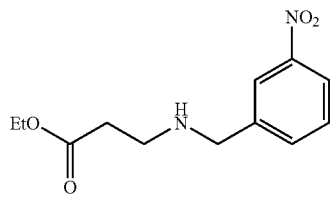 [SMILES: CCOC(=O)CCNCc1cccc([N+](=O)[O-])c1]

A mixture of 3-nitrobenzaldehyde (453 mg, 3.00 mmol), ethyl 3-aminopropanoate hydrochloride (507 mg, 3.30 mmol), acetic acid (0.172 mL, 3.00 mmol), and sodium triacetoxyborohydride (1.27 g, 6.00 mmol) was stirred at rt for two days. The reaction was quenched with water and extracted with EtOAc (2×). The combined organic layers were washed with brine, concentrated and purified by flash chromatography (gradient, 30 to 90% EtOAc/Hexane) to obtain 144A (173 mg, 23%) as a yellow oil.

144B

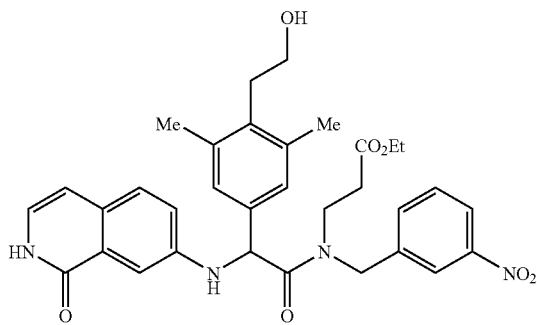

A solution of 144A (68.8 mg, 0.273 mmol) and triethylamine (0.228 mL, 1.64 mmol) in DMF (1.5 mL) was added to a solution of 8A (100 mg, 0.273 mmol) and 1-hydroxy-7-azabenzotriazole (37.1 mg, 0.273 mmol) and EDCI (105 mg, 0.546 mmol) in DMF (1 mL). The reaction mixture was stirred for 18 h at rt. The reaction mixture was concentrated, triturated with water, and the residue was purified by flash chromatography (gradient, 0 to 20% MeOH in DCM) to yield 144B (113 mg, 68.9%) as a yellow foam. MS (ESI) m/z 601.0 [M+H]+.

144C

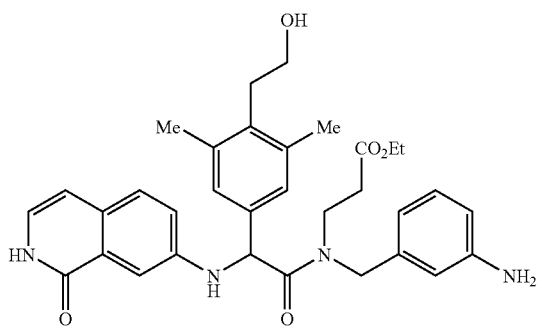 [SMILES: CCOC(=O)CCN(Cc1cccc([N+](=O)[O-])c1)C(=O)C(Nc1ccc2cc[nH]c(=O)c2c1)c1cc(C)c(CCO)c(C)c1]

A suspension of 144B (113 mg, 0.188 mmol) and palladium on carbon (40 mg, 0.038 mmol, 10%) in MeOH (20 mL) was hydrogenated (20 psi) for 3 h. The reaction mixture was filtered, concentrated, and purified by flash chromatography (gradient, 0 to 5% methanol/DCM) to give 144C (77.4 mg, 72%) as a clear oil. MS (ESI) m/z 571.2 [M+H]$^+$.

Example 144

Phosgene solution in toluene (0.078 ml, 0.148 mmol) was added dropwise to a solution of 144C (77.4 mg, 0.136 mmol) in acetonitrile (10 ml) at 0° C. The reaction mixture was stirred for 4 h at 0° C. Nitrogen was bubbled through the reaction mixture for 10 min to remove any unreacted phosgene, and then this solution was added portionwise (0.5-1.0 mL aliquots every 15-30 min) into refluxing dichloromethane (30 mL) containing triethylamine (0.190 ml, 1.36 mmol). The reaction was then concentrated and the residue was purified by preparative HPLC (Method A, Gradient: 20 to 100% Solvent B in 15 min) to give 144D (25.8 mg, 31.9%). $^1$H NMR (400 MHz, methanol-d$_4$) a ppm 1.22 (t, J=7.03 Hz, 3H) 2.28-2.42 (m, 1H) 2.36 (s, 3H) 2.46 (s, 3H) 2.68-2.96 (m, 3H) 3.15-3.26 (m, 1H) 3.34-3.45 (m, 1H) 4.01-4.08 (m, 2H) 4.12 (q, J=7.03 Hz, 2H) 4.28-4.40 (m, 1H) 5.01 (br. s., 1H) 5.23 (d, J=16.70 Hz, 1H) 5.86 (s, 1H) 6.03 (s, 1H) 6.58 (d, J=7.03 Hz, 1H) 6.68 (d, J=7.47 Hz, 1H) 6.90 (d, J=7.47 Hz, 1H) 6.99 (d, J=7.03 Hz, 1H) 7.14 (s, 1H) 7.17 (t, J=7.69 Hz, 1H) 7.36 (dd, J=8.57, 2.42 Hz, 1H) 7.43 (s, 1H) 7.50 (d, J=8.79 Hz, 1H) 7.67 (s, 1H). MS (ESI) m/z 597.0 [M+H]$^-$. Analytical HPLC (Method A): Col A: 12.47 min, 91%; Col B: 12.17 min, 90%.

Example 145

3-[17,20-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-propionic acid

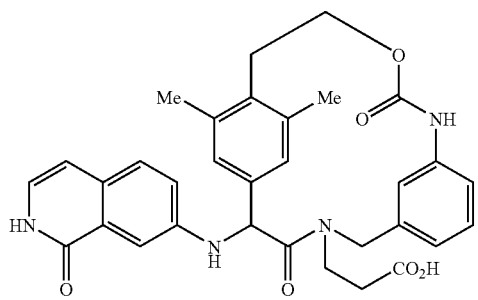 [SMILES: Cc1cc2cc(C)c1CCOC(=O)Nc1cccc(c1)CN(CCC(=O)O)C(=O)C2Nc1ccc2cc[nH]c(=O)c2c1]

Lithium hydroxide solution (0.5 mL, 0.500 mmol, IM) was added to a solution of 144D (10.1 mg, 0.014 mmol) in a mixture of THF (0.5 mL) and MeOH (0.5 mL). The reaction mixture was stirred at rt for 1.5 h. HCl (0.5 mL, 1M) was added and the mixture was concentrated. The residue was purified by preparative HPLC (Method A, Gradient: 20 to 100% Solvent B in 15 min) to give Example 145 (3.99 mg, 41.1% yield) as a white solid. $^1$H NMR (400 MHz, methanol-d$_4$) δ ppm 2.36 (s, 3H) 2.46 (s, 3H) 2.65-2.74 (m, 1H) 2.74-2.85 (m, 1H) 2.91 (d, J=14.06 Hz, 1H) 3.14-3.25 (m, 1H) 3.39 (ddd, J=14.83, 5.60, 5.49 Hz, 1H) 4.08 (d, J=16.70 Hz, 2H) 4.38 (ddd, J=15.05, 7.69, 7.58 Hz, 1H) 5.01 (br. s., 1H) 5.26 (d, J=16.70 Hz, 1H) 5.84 (s, 1H) 6.04 (s, 1H) 6.57 (d, J=7.03 Hz, 1H) 6.68 (d, J=7.91 Hz, 1H) 6.90 (d, J=7.91 Hz, 1H) 6.96 (d, J=7.03 Hz, 1H) 7.13 (s, 1H) 7.17 (t, J=7.69 Hz, 1H) 7.32 (dd, J=8.57, 2.42 Hz, 1H) 7.41 (s, 1H) 7.46 (d, J=8.35 Hz, 1H) 7.58 (br. s., 1H). MS (ESI) m/z 569.0 [M+H]$^+$. Analytical HPLC (Method A): Col A: 11.07 min, 95%; Col B: 10.94 min, 95%.

Example 146

[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-acetic acid

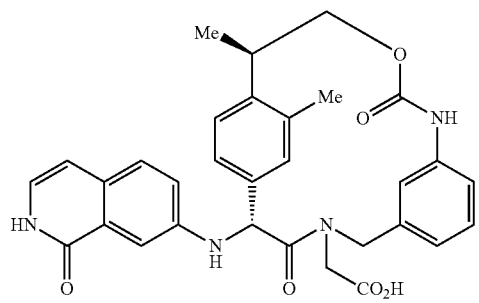 [SMILES: Cc1cc2ccc1[C@@H](C)COC(=O)Nc1cccc(c1)CN(CC(=O)O)C(=O)[C@@H]2Nc1ccc2cc[nH]c(=O)c2c1]

146A

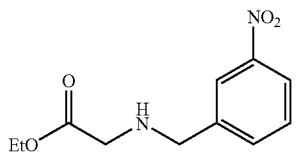 [SMILES: CCOC(=O)CNCc1cccc([N+](=O)[O-])c1]

A solution of 3-nitrobenzaldehyde (453 mg, 3.00 mmol), ethyl 2-aminoacetate hydrochloride (460 mg, 3.30 mmol) and triethylamine (0.50 mL, 3.6 mmol) in methanol (10 mL) was stirred at rt for 1 h. The reaction mixture was cooled to 0° C. and sodium borohydride (227 mg, 6.00 mmol) was added in small portions. The reaction was stirred at rt overnight. The reaction was quenched with water and extracted with EtOAc (2×). The combined organic layers were washed with brine, concentrated, and purified by flash chromatography (gradient 0 to 20% MeOH, DCM) to give 146A (454 mg, 64%). MS (ESI) m/z 239.1 [M+H]$^+$.

146B

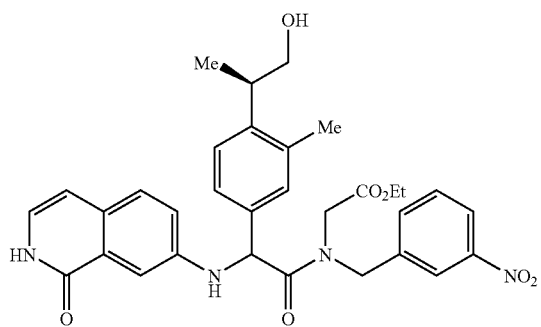 [SMILES: CCOC(=O)CN(Cc1cccc([N+](=O)[O-])c1)C(=O)C(Nc1ccc2cc[nH]c(=O)c2c1)c1ccc([C@@H](C)CO)c(C)c1]

To a solution of 211 (100 mg, 0.273 mmol), 1-hydroxy-7-azabenzotriazole (37.1 mg, 0.273 mmol) and EDC (105 mg, 0.546 mmol) in DMF (2 mL) was added 146A (65.0 mg, 0.273 mmol) followed by triethylamine (0.23 ml, 1.64 mmol). The reaction mixture was stirred for 17 h at rt. The reaction mixture was concentrated and the residue was purified by preparative HPLC (Method A, Gradient: to 100% Solvent B in 10 min, RT=8.5 min) to give Example 146B (63 mg, 39%) as a yellow foam. MS (ESI) m/z 587.0 [M+H]$^+$.

146C

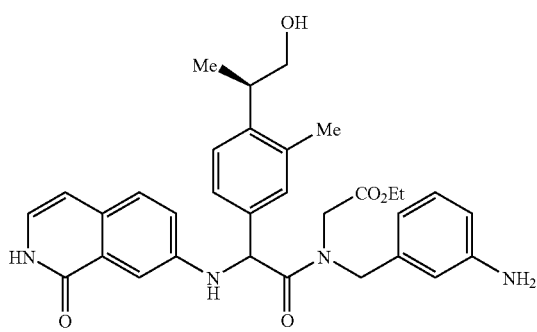 [SMILES: CCOC(=O)CN(Cc1cccc(N)c1)C(=O)C(Nc1ccc2cc[nH]c(=O)c2c1)c1ccc([C@@H](C)CO)c(C)c1]

Using a procedure analogous to that used for preparation of 144C, 146B (63 mg, 0.107 mmol) was hydrogenated to give 146C (54 mg, 90%) as a pale yellow glass. MS (ESI) m/z 557.1 [M+H]$^+$.

146D

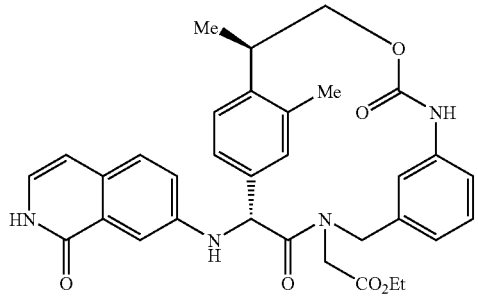

Phosgene in toluene (0.056 ml, 0.107 mmol) was added dropwise to a solution of 146C (54 mg, 0.097 mmol) in acetonitrile (10 ml) at 0° C. The reaction mixture was stirred for 2 h at 0° C. Nitrogen was bubbled through the reaction mixture for 15 min to remove any unreacted phosgene, and then this solution was added dropwise into dichloromethane (30 mL) containing triethylamine (0.14 ml, 0.97 mmol) at 40° C. over 1 h. The reaction was concentrated and the residue was purified by preparative HPLC (Method A, gradient 20 to 100% Solvent B in 10 min). This material was further purified by preparative chiral HPLC (Whelko (R,R) 250×21.1 mm column, eluted with 6:4 (1:1 MeOH:EtOH):heptane at 20 mL/min. RT 6.2 min for undesired diastereoner, 7.8 min for 146D) to give 146D (10 mg, 18%). MS (ESI) m/z 583.0 [M+H]$^+$.

Example 146

Using a procedure analogous to that used for preparation of Example 2, 146D (10 mg, 0.017 mmol) was hydrolyzed and purified by preparative HPLC to give Example 146 (7.5 mg, 65%) as a white solid. MS (ESI) m/z 555.1 [M+H]$^+$. Analytical HPLC (Method A): Col A: 5.52 min, 100%; Col B: 5.85 min, 100%.

Example 147

4-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-butyric acid

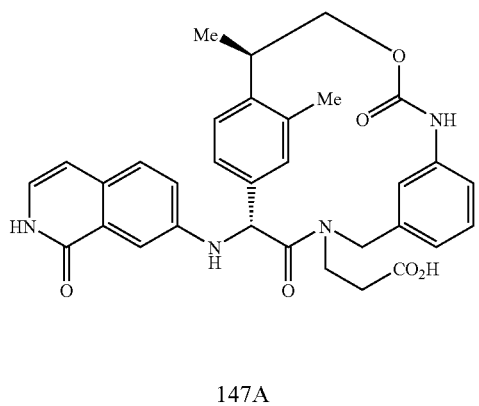

147A

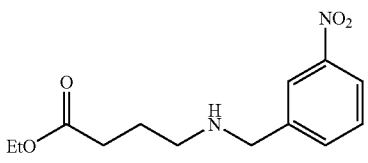 [SMILES: CCOC(=O)CCCNCc1cccc([N+](=O)[O-])c1]

A solution of 3-nitrobenzaldehyde (453 mg, 3.00 mmol), ethyl 4-aminobutanoate hydrochloride (553 mg, 3.30 mmol) and triethylamine (0.50 mL, 3.6 mmol) in methanol (10 mL) was stirred at rt for 1 h. The reaction mixture was cooled to 0° C. and sodium borohydride (227 mg, 6.00 mmol) was added in small portions. The reaction mixture was stirred at rt overnight. The reaction was quenched with water and extracted with EtOAc (2×). The combined organic layers were washed with brine, concentrated and purified by flash chromatography (gradient, 0 to 15% MeOH/DCM) to obtain 147A (470 mg, 58.9) as a yellow oil. MS (ESI) m/z 267.1 [M+H]$^+$.

147B

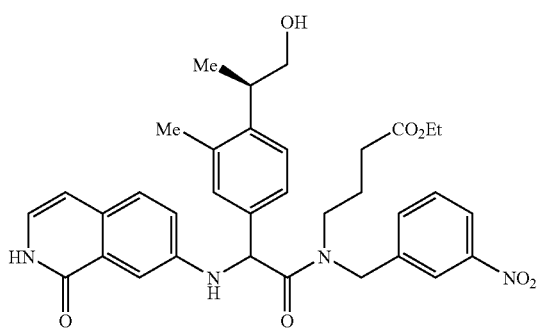 [SMILES: CCOC(=O)CCCN(Cc1cccc([N+](=O)[O-])c1)C(=O)C(Nc1ccc2cc[nH]c(=O)c2c1)c1ccc([C@@H](C)CO)c(C)c1]

Using a procedure analogous to that used for preparation of 146B, 147A (100 mg, 0.273 mmol) was reacted with 21I, 1-hydroxy-7-azabenzotriazole, and EDC to give 147B (105 mg, 0.171 mmol, 62.6% yield) as a yellow foam. MS (ESI) m/z 615.0 [M+H]⁺.

147C

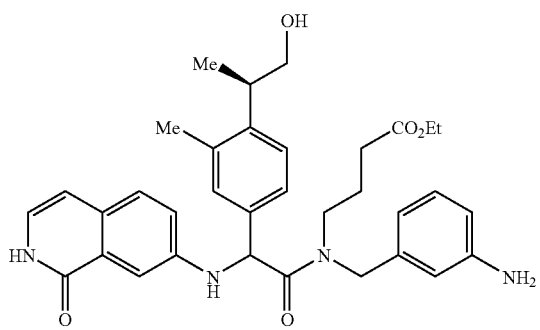 [SMILES: CCOC(=O)CCCN(Cc1cccc(N)c1)C(=O)C(Nc1ccc2cc[nH]c(=O)c2c1)c1ccc([C@@H](C)CO)c(C)c1]

Using a procedure analogous to that used for preparation of 144C, 147B (105 mg, 0.171 mmol) was hydrogenated to give 147C (80 mg, 80%) as a pale yellow glass. MS (ESI) m/z 585.1 [M+H]⁺.

147D

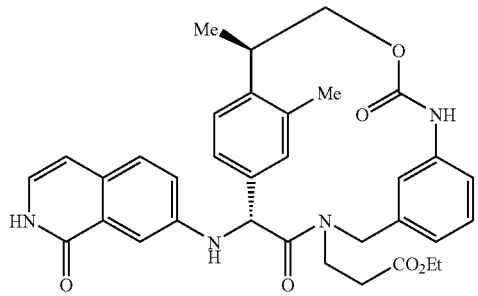

Using a procedure analogous to that used for preparation of 146D, 147C (80 mg, 0.137 mmol) was reacted with phosgene to give 147D (12 mg, 14%). Chiral HPLC (Whelko (R,R) 250×21.1 mm column, eluted with 6:4 (1:1 MeOH:EtOH):heptane at 20 mL/min, RT 6.2 min for undesired diastereoner, 7.7 min for 147D).

Example 147

Using a procedure analogous to that used for preparation of Example 2, 147D (12 mg, 0.020 mmol) was hydrolyzed and purified by preparative HPLC to give Example 147 (5.2 mg, 65%) as a white solid. ¹H NMR (400 MHz, methanol-d4) δ ppm 1.28 (d, J=7.03 Hz, 3H), 1.97-2.11 (m, 2H), 2.34 (s, 3H), 2.38 (t, J=3.52 Hz, 1H), 2.47-2.60 (m, 1H), 2.88-3.02 (m, 1H), 3.42-3.55 (m, 1H), 3.89-3.99 (m, 1H), 4.03 (s, 1H), 4.04-4.16 (m, 1H), 4.60 (t, J=11.21 Hz, 1H), 5.25 (d, J=16.70 Hz, 1H), 5.85 (s, 1H), 6.00 (s, 1H), 6.57 (d, J=7.03 Hz, 1H), 6.66 (d, J=7.91 Hz, 1H), 6.89 (d, J=7.91 Hz, 1H), 6.98 (d, J=7.03 Hz, 1H), 7.16 (t, J=7.69 Hz, 1H), 7.29 (s, 1H), 7.38 (d, J=7.91 Hz, 2H), 7.45-7.52 (m, 1H), 7.59 (d, J=7.91 Hz, 1H), 7.71 (d, J=2.20 Hz, 1H). MS (ESI) m/z 583.1 [M+H]⁺. Analytical HPLC (Method A): Col A: 5.56 min, 100%; Col B: 5.89 min, 100%.

Example 148

{2-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaen-4-yl]-ethyl}-carbamic acid tert-butyl ester

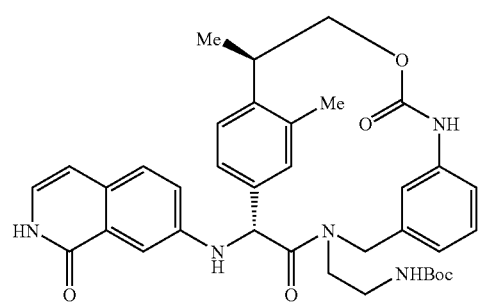 [SMILES: Cc1cc2ccc1[C@@H](C)COC(=O)Nc1cccc(c1)CN(CCNC(=O)OC(C)(C)C)C(=O)[C@@H]2Nc1ccc2cc[nH]c(=O)c2c1]

148A

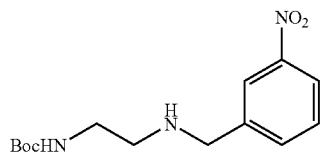 [SMILES: CC(C)(C)OC(=O)NCCNCc1cccc([N+](=O)[O-])c1]

Using a procedure analogous to that used for preparation of 147A, tert-butyl N-(2-aminoethyl)carbamate (0.520 mL, 3.30 mmol) was reacted with 3-nitrobenzaldehyde and sodium borohydride to give 148A (800 mg, 90%) as a yellow oil. ¹H NMR (400 MHz, chloroform-d) d ppm 1.45 (s, 9H), 2.77 (t, J=5.93 Hz, 2H), 3.26 (q, J=5.57 Hz, 8H), 3.91 (s, 2H), 7.50 (t, J=7.91 Hz, 1H), 7.67 (d, J=7.47 Hz, 1H), 8.12 (d, J=7.91 Hz, 1H), 8.22 (s, 1H). MS (ESI) m/z 296.2 [M+H]⁺.

148B

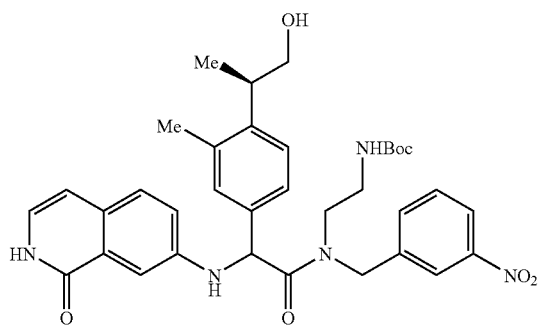 [SMILES: Cc1cc(C(Nc2ccc3cc[nH]c(=O)c3c2)C(=O)N(CCNC(=O)OC(C)(C)C)Cc2cccc([N+](=O)[O-])c2)ccc1[C@@H](C)CO]

Using a procedure analogous to that used for preparation of 146B, 148A (106 mg, 0.360 mmol) was reacted with 21I, 1-hydroxy-7-azabenzotriazole, and EDC to give 148B (115 mg, 49.6%) as a yellow foam. MS (ESI) m/z 644.1 [M+H]⁺.

148C

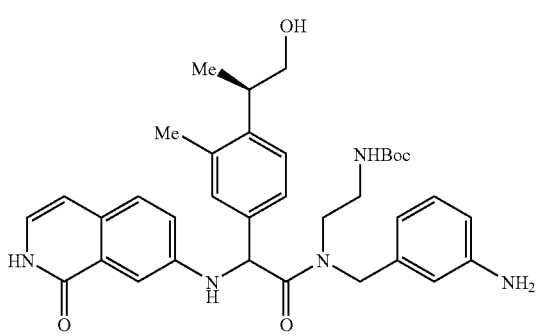 [SMILES: Cc1cc(C(Nc2ccc3cc[nH]c(=O)c3c2)C(=O)N(CCNC(=O)OC(C)(C)C)Cc2cccc(N)c2)ccc1[C@@H](C)CO]

Using a procedure analogous to that used for preparation of 144C, 148B (115 mg, 0.179 mmol) was hydrogenated to give 148C (100 mg, 91%) as a yellow oil. MS (ESI) m/z 614.2 [M+H]⁺.

Example 148

Using a procedure analogous to that used for preparation of 146D, 148C (100 mg, 0.163 mmol) was reacted with phosgene to give Example 148 (9.8 mg, 8%) as a white amorphous solid. Chiral HPLC (Whelko (R,R) 250×21.1 mm column, eluted with 3:7 (1:1 MeOH:EtOH):heptane at 20 mL/min. RT 10.7 min for undesired diastereomer, 13 min for Example 148). $^1$H NMR (400 MHz, methanol-d4) δ ppm 7.55-7.64 (m, 2H), 7.45 (d, J=8.79 Hz, 1H), 7.41 (d, J=7.91 Hz, 1H), 7.31 (dd, J=8.57, 2.42 Hz, 1H), 7.27 (s, 1H), 7.16 (t, J=7.69 Hz, 1H), 6.95 (d, J=7.03 Hz, 1H), 6.89 (d, J=8.35 Hz, 1H), 6.66 (d, J=7.03 Hz, 1H), 6.57 (d, J=7.03 Hz, 1H), 6.00 (s, 1H), 5.59 (s, 1H), 5.25 (d, J=16.70 Hz, 1H), 4.62 (t, J=11.21 Hz, 1H), 4.26-4.36 (m, 1H), 4.07 (d, J=17.14 Hz, 1H), 3.94 (dd, J=10.99, 4.39 Hz, 1H), 3.33-3.54 (m, 3H), 2.96-3.03 (m, 1H), 2.35 (s, 3H), 1.30 (d, J=7.03 Hz, 3H), 1.21 (s, 9H). MS (ESI) m/z 640.4 [M+H]⁺.

Example 149

(2R,15R)-4-(2-Amino-ethyl)-15,17-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10 (21),16(20),17-hexaene-3,12-dione

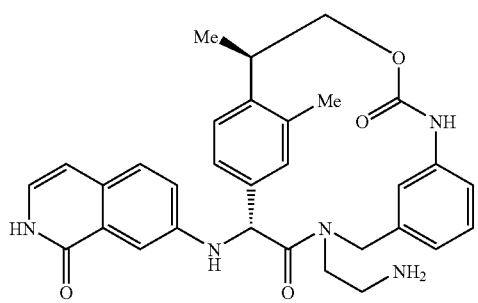 [SMILES: Cc1cc2ccc1[C@@H](C)COC(=O)Nc1cccc(c1)CN(CCN)C(=O)[C@@H]2Nc1ccc2cc[nH]c(=O)c2c1]

Example 148 was dissolved in EtOAc (1 mL) was treated with HCl (1.5 mL, 4N in dioxanes) and stirred overnight. The reaction mixture was concentrated and the residue purified by preparative HPLC to give Example 149 (18 mg) as an off-white amorphous solid. $^1$H NMR (400 MHz, methanol-d$_4$) δ ppm 7.60-7.68 (m, 1H), 7.41-7.47 (m, 2H), 7.33-7.38 (m, 1H), 7.25-7.33 (m, 3H), 7.15-7.21 (m, 1H), 6.89-6.98 (m, 2H), 6.69 (d, J=7.91 Hz, 1H), 6.58 (t, J=6.37 Hz, 1H), 5.96 (s, 1H), 5.60 (s, 1H), 5.35 (d, J=17.14 Hz, 1H), 4.62 (t, J=10.77 Hz, 1H), 4.33 (s, 1H), 4.05 (d, J=17.14 Hz, 1H), 3.97 (dd, J=10.77, 4.17 Hz, 1H), 3.60-3.75 (m, 1H), 3.44-3.54 (m, 1H), 3.32-3.43 (m, 3H), 2.34 (s, 3H), 1.30 (d, J=7.03 Hz, 3H). MS (ESI) m/z 540.4 [M+H]⁺. Analytical HPLC (Method A): Col A: 5.61 min, 99%; Col B: 6.23 min, 99%.

Example 150

(2R,15R)-4-Ethyl-15,17-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

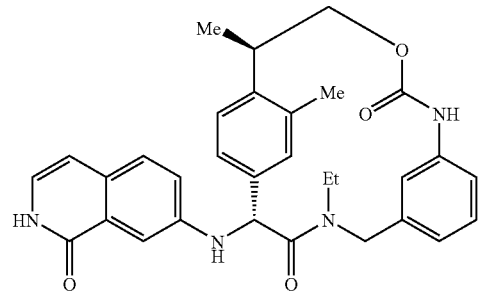 [SMILES: CCN1Cc2cccc(c2)NC(=O)OC[C@H](C)c2ccc(cc2C)[C@@H](Nc2ccc3cc[nH]c(=O)c3c2)C1=O]

150A

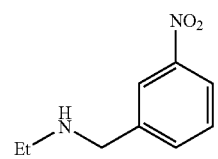

A solution of 3-Nitrobenzaldehyde (453 mg, 3.00 mmol), ethanamine (1.499 mL, 3.00 mmol, 2M in MeOH), and triethylamine (0.501 mL, 3.60 mmol) in methanol (10 mL) was stirred at rt for 1 h. The reaction mixture was cooled to 0° C. and sodium borohydride (227 mg, 6.00 mmol) was added in small portions. The reaction was slowly warmed to rt and stirred overnight. The reaction was quenched with water and extracted with EtOAc (2×). The combined organic layers were washed with brine, concentrated then purified by flash chromatography (gradient from 0-20% MeOH/DCM) to give 150A (468 mg, 87% yield) as a yellow oil. $^1$H NMR (400 MHz, chloroform-d) δ ppm 1.16 (t, J=7.03 Hz, 3H), 2.70 (q, J=7.18 Hz, 2H), 3.91 (s, 2H), 7.49 (t, J=7.91 Hz, 1H), 7.69 (d, J=7.91 Hz, 1H), 8.11 (d, J=7.91 Hz, 1H), 8.22 (s, 1H). MS (ESI) m/z 181.2 [M+H]$^+$.

150B

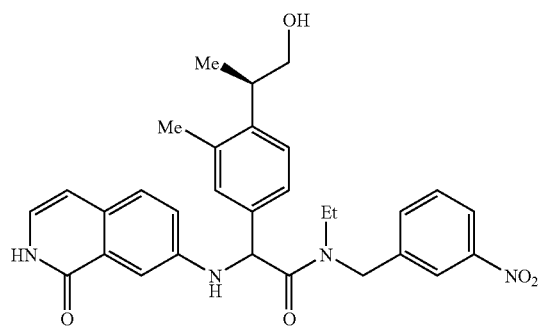 [SMILES: CCN(Cc1cccc([N+](=O)[O-])c1)C(=O)C(Nc1ccc2cc[nH]c(=O)c2c1)c1ccc([C@@H](C)CO)c(C)c1]

To 150A (42.8 mg, 0.237 mmol), 211 (87 mg, 0.237 mmol) and BOP (105 mg, 0.237 mmol) in DMF (1 mL) was added N-methylmorpholine (0.040 mL, 0.364 mmol). The reaction mixture was stirred 40 min at rt. The reaction was concentrated in vacuo to remove most solvent. Water was added, and the resulting precipitate was filtered and washed with water. The solid was purified by flash chromatography (gradient from 0-20% MeOH/DCM) to give 150B (75 mg, 59.8% yield). MS (ESI) m/z 529.1 [M+H]$^+$.

150C

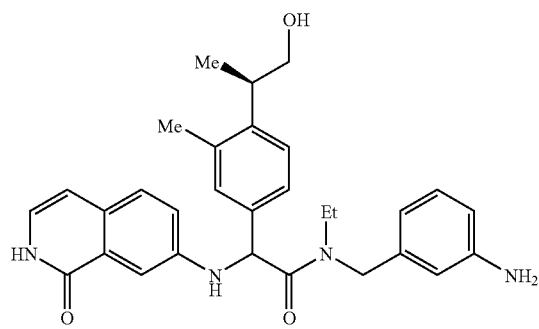 [SMILES: CCN(Cc1cccc(N)c1)C(=O)C(Nc1ccc2cc[nH]c(=O)c2c1)c1ccc([C@@H](C)CO)c(C)c1]

A solution of 150B (100 mg, 0.199 mmol) in MeOH (20 mL) was hydrogenated (20 psi) over palladium (58 mg, 0.054 mmol, 10% on carbon). The reaction mixture was filtered and concentrated to give 15° C. (100 mg, 100%). MS (ESI) m/z 499.3 [M+H]$^+$.

Example 150

Using a procedure analogous to that used for preparation of 146D, 15° C. (100 mg, 0.21 mmol) was reacted with phosgene to give Example 150 (11 mg, 10%). Chiral HPLC (Whelko (R,R) 250×21.1 mm column, eluted with 1:1 (1:1 MeOH:EtOH):heptane at 20 mL/min. RT 6.9 min for undesired diastereomer, 9.4 min for Example 150). $^1$H NMR (400 MHz, methanol-d$_4$) b ppm 7.59-7.68 (m, 1H), 7.45-7.50 (m, 1H), 7.40 (d, J=8.35 Hz, 2H), 7.32 (s, 1H), 7.20-7.26 (m, 2H), 7.12-7.20 (m, 1H), 6.91 (t, J=6.37 Hz, 1H), 6.66 (d, J=7.47 Hz, 1H), 6.49-6.58 (m, 1H), 6.01 (s, 1H), 5.59 (s, 1H), 5.24 (d, J=16.70 Hz, 1H), 4.62 (t, J=10.99 Hz, 1H), 4.08-4.16 (m, 1H), 4.03 (d, J=16.70 Hz, 1H), 3.41-3.54 (m, 3H), 3.10-3.25 (m, 3H), 2.32 (s, 3H), 1.41 (t, J=7.03 Hz, 3H), 1.29 (d, J=7.03 Hz, 3H). MS (ESI) m/z 525.3 [M+H]$^+$.

Example 151

(2R,15R)-4-(2-Hydroxy-ethyl)-15,17-dimethyl-2-(1-oxo-1,2-dihydro-isoquinolin-7-ylamino)-13-oxa-4, 11-diaza-tricyclo[14.2.2.1$^{6,10}$]henicosa-1(19),6,8,10 (21),16(20),17-hexaene-3,12-dione

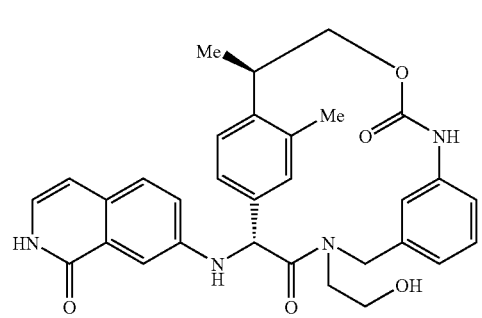 [SMILES: Cc1cc2ccc1[C@@H](C)COC(=O)Nc1cccc(c1)CN(CCO)C(=O)[C@@H]2Nc1ccc2cc[nH]c(=O)c2c1]

151A

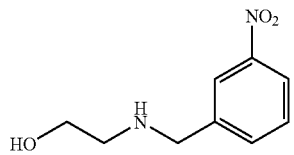

Using a procedure analogous to that used for 150A, 2-aminoethanol (201 mg, 3.30 mmol) was reacted with 3-nitrobenzaldehyde and sodium borohydride to give 151A (457 mg, 78%) as an off-white solid. MS (ESI) m/z 197.1 [M+H]$^+$.

151B

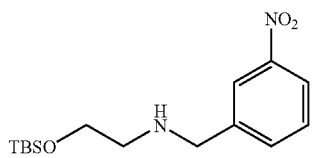 [SMILES: CC(C)(C)[Si](C)(C)OCCNCc1cccc([N+](=O)[O-])c1]

TBS-Cl (151 mg, 0.999 mmol) was added to a solution of 151A (196 mg, 0.999 mmol) and imidazole (102 mg, 1.498 mmol) in DCM (10 mL) and stirred at rt for 2 days. The reaction was diluted with DCM (25 mL), washed with 0.5 M HCl (30 mL), water, and brine, dried over Na₂SO₄ and concentrated to yield 151B (270 mg, 87%) as a white solid.

151C

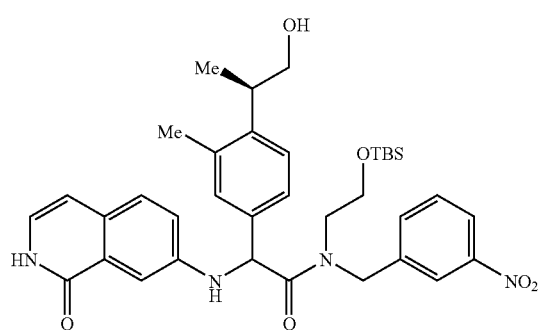 [SMILES: Cc1cc(C(Nc2ccc3cc[nH]c(=O)c3c2)C(=O)N(CCO[Si](C)(C)C(C)(C)C)Cc2cccc([N+](=O)[O-])c2)ccc1[C@@H](C)CO]

Using a procedure analogous to that used for preparation of 150B, 151B (155 mg, 0.500 mmol) was coupled to 211 (183 mg, 0.5 mmol) using BOP and N-methylmorpholine to give 151C (75 mg, 23%). MS (ESI) m/z 659.5 [M+H]⁺.

151D

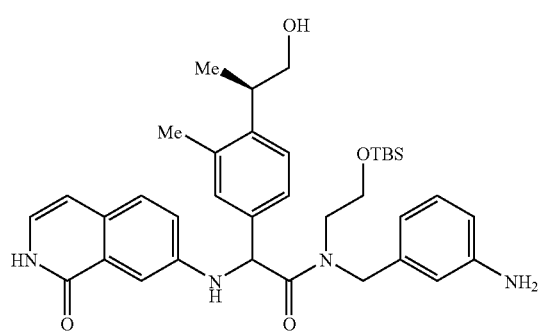 [SMILES: Cc1cc(C(Nc2ccc3cc[nH]c(=O)c3c2)C(=O)N(CCO[Si](C)(C)C(C)(C)C)Cc2cccc(N)c2)ccc1[C@@H](C)CO]

Using a procedure analogous to that used for preparation of 15° C., 151C (75 mg, 0.11 mmol) was hydrogenated to give 151D (69 mg, 96%). MS (ESI) m/z 629.5 [M+H]⁺.

Example 151

Using a procedure analogous to that used for preparation of 146D, 151D (69 mg, 0.110 mmol) was reacted with phosgene to give Example 151 (11 mg, 18%). Chiral HPLC (Whelko (R,R) 250×21.1 mm column, eluted with 1:1 (1:1 MeOH: EtOH):heptane at 20 mL/min. RT 6.4 min for undesired diastereomer, 7.4 min for Example 151). ¹H NMR (400 MHz, methanol-d₄) δ ppm 7.60-7.69 (m, 1H), 7.53 (d, J=2.20 Hz, 1H), 7.37-7.47 (m, 2H), 7.31-7.35 (m, 1H), 7.23-7.30 (m, 2H), 7.11-7.19 (m, 1H), 6.91 (t, J=6.37 Hz, 2H), 6.67 (d, J=9.23 Hz, 1H), 6.54 (d, J=7.03 Hz, 1H), 6.04 (s, 1H), 5.78 (s, 1H), 5.31 (d, J=16.70 Hz, 1H), 4.63 (t, J=10.99 Hz, 1H), 4.21-4.34 (m, 1H), 4.10 (d, J=16.70 Hz, 1H), 3.91-3.99 (m, 1H), 3.82-3.93 (m, 2H), 3.41-3.53 (m, 1H), 3.01-3.16 (m, 1H), 2.33 (s, 3H), 1.27-1.35 (m, 3H). MS (ESI) m/z 541.4 [M+H]⁺.

Example 152

(2R,15R)-4-(2-Methoxy-ethyl)-15,17-dimethyl-2-(1-oxo-1,2-dihydro-isoquinolin-7-ylamino)-13-oxa-4,11-diaza-tricyclo[14.2.2.1⁶,¹⁰]henicosa-1(19),6,8,10(21),16(20),17-hexaene-3,12-dione

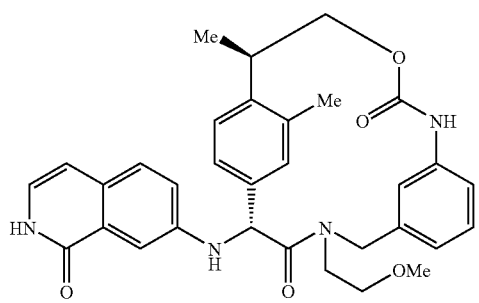 [SMILES: COCCN1Cc2cccc(c2)NC(=O)OC[C@H](C)c2ccc(cc2C)[C@@H](Nc2ccc3cc[nH]c(=O)c3c2)C1=O]

152A

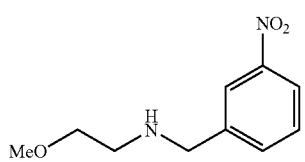 [SMILES: COCCNCc1cccc([N+](=O)[O-])c1]

Using a procedure analogous to that used for 150A, 2-methoxyethanamine (0.287 ml, 3.30 mmol) was reacted with 3-nitrobenzaldehyde and sodium borohydride to give 152A (570 mg, 90%) as a yellow oil. MS (ESI) m/z 211.2 [M+H]⁺.

152B

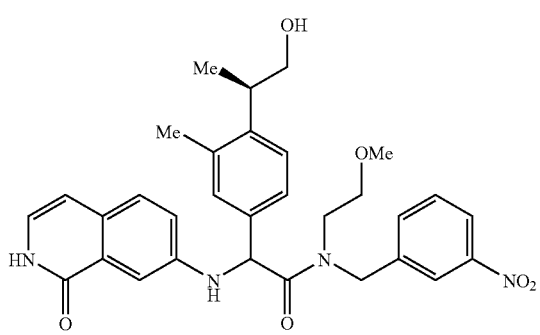 [SMILES: COCCN(Cc1cccc([N+](=O)[O-])c1)C(=O)C(Nc1ccc2cc[nH]c(=O)c2c1)c1ccc([C@@H](C)CO)c(C)c1]

Using a procedure analogous to that used for preparation of 150B, 152A (105 mg, 0.500 mmol) was coupled to 211 (183 mg, 0.5 mmol) using BOP and N-methylmorpholine to give 152B (100 mg, 35.8%) as a yellow foam. MS (ESI) m/z 559.2 [M+H]⁺.

152C

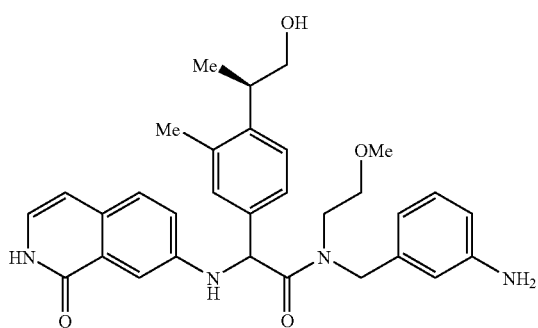

Using a procedure analogous to that used for preparation of 15° C., 152B (100 mg, 0.18 mmol) was hydrogenated to give 152C (77 mg, 81%) as an oil. MS (ESI) m/z 529.3 [M+H]$^+$.

Example 152

Using a procedure analogous to that used for preparation of 146D, 152C (77 mg, 0.146 mmol) was reacted with phosgene to give Example 152 (14 mg, 17%). Chiral HPLC (Whelko (R,R) 250×21.1 mm column, eluted with 2:3 (1:1 MeOH: EtOH):heptane at 20 mL/min. RT 9.5 min for undesired diastereomer, 11.8 min for Example 152). $^1$H NMR (400 MHz, methanol-d$_4$) δ ppm 7.61 (d, J=6.36 Hz, 1H), 7.51 (d, J=2.45 Hz, 1H), 7.41 (d, J=8.31 Hz, 2H), 7.27 (dd, J=8.80, 2.45 Hz, 1H), 7.22 (s, 1H), 7.16 (t, J=7.83 Hz, 1H), 6.90 (d, J=7.34 Hz, 2H), 6.67 (d, J=7.82 Hz, 1H), 6.54 (d, J=6.85 Hz, 1H), 6.02 (s, 1H), 5.79 (s, 1H), 5.29 (d, J=16.63 Hz, 1H), 4.54-4.65 (m, 2H), 4.27-4.43 (m, 1H), 4.08 (d, 1H), 3.92-4.00 (m, 1H), 3.59-3.78 (m, 2H), 3.39-3.54 (m, 4H), 3.08-3.19 (m, 1H), 2.33 (s, 3H), 1.30 (d, J=6.85 Hz, 3H). MS (ESI) m/z 555.4 [M+H]$^+$. Analytical HPLC (Method A): Col A: 7.25 min, 90%; Col B: 7.07 min, 90%.

Example 153

{2-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-ethyl}-carbamic acid methyl ester

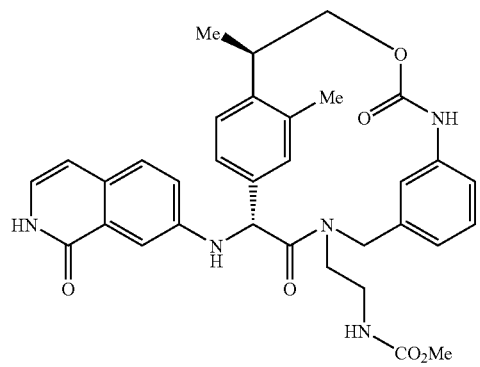 [SMILES: COC(=O)NCCN1Cc2cccc(c2)NC(=O)OC[C@H](C)c2ccc(cc2C)[C@@H](Nc2ccc3cc[nH]c(=O)c3c2)C1=O]

A solution of Example 149 (10 mg, 0.013 mmol) and DIEA (10 μL, 0.057 mmol) in THF (1 mL) was cooled in an ice bath. Methyl chloroformate (20 μL of a solution of 20 μL methyl chloroformate in 200 μL THF, 0.02 mmol) was added and the reaction mixture was stirred at rt for 30 min and then concentrated. The residue was purified by preparative HPLC to give Example 153 (6.8 mg, 73%) as a pale yellow solid. $^1$H NMR (400 MHz, methanol-d$_4$) δ ppm 7.62 (d, J=7.82 Hz, 1H), 7.56 (s, 1H), 7.40-7.47 (m, 2H), 7.27-7.34 (m, 2H), 7.24 (s, 1H), 7.17 (t, J=7.82 Hz, 1H), 6.92 (dd, J=15.41, 7.58 Hz, 2H), 6.67 (d, J=7.83 Hz, 1H), 6.56 (d, J=7.34 Hz, 1H), 6.00 (s, 1H), 5.67 (s, 1H), 5.26 (d, J=16.63 Hz, 1H), 4.62 (t, J=11.00 Hz, 1H), 4.24 (dd, J=14.92, 7.58 Hz, 1H), 4.05 (d, J=16.63 Hz, 1H), 3.96 (dd, J=10.76, 3.91 Hz, 1H), 3.53 (s, 3H), 3.44-3.51 (m, 1H), 3.36-3.44 (m, 1H), 3.01-3.14 (m, 1H), 2.33 (s, 3H), 1.30 (d, J=6.85 Hz, 3H). MS (ESI) m/z 598.5 [M+H]$^+$. Analytical HPLC (Method A): Col A: 6.81 min, 100%; Col B: 6.74 min, 96%.

Example 154

3-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-propionic acid ethyl ester

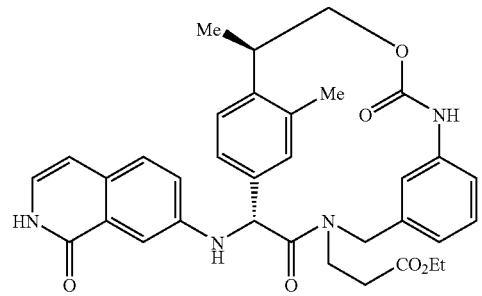 [SMILES: CCOC(=O)CCN1Cc2cccc(c2)NC(=O)OC[C@H](C)c2ccc(cc2C)[C@@H](Nc2ccc3cc[nH]c(=O)c3c2)C1=O]

154A

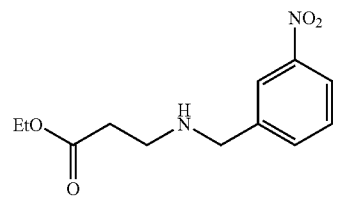 [SMILES: CCOC(=O)CCNCc1cccc([N+](=O)[O-])c1]

Using a procedure analogous to that used for 150A, ethyl 3-aminopropanoate HCl salt (1.014 g, 6.60 mmol) was reacted with 3-nitrobenzaldehyde and sodium borohydride to give 154A (1.37 g, 91%) as a yellow oil. MS (ESI) m/z 253.2 [M+H]+.

154B

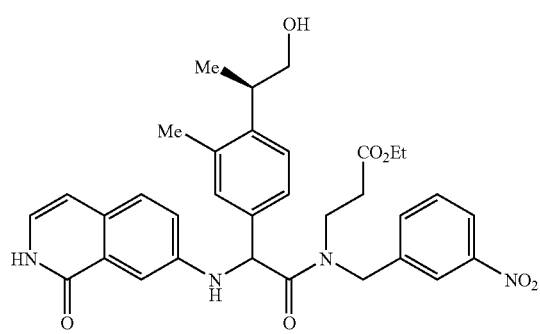 [SMILES: CCOC(=O)CCN(Cc1cccc([N+](=O)[O-])c1)C(=O)C(Nc1ccc2cc[nH]c(=O)c2c1)c1ccc([C@@H](C)CO)c(C)c1]

Using a procedure analogous to that used for preparation of 150B, 154A (245 mg, 0.972 mmol) was coupled to 211 (356 mg, 0.972 mmol) using BOP and N-methylmorpholine to give 154B (272 mg, 39%). MS (ESI) m/z 601.4 [M+H]+.

154C

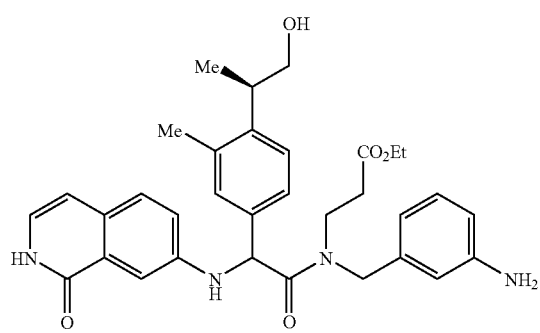 [SMILES: CCOC(=O)CCN(Cc1cccc(N)c1)C(=O)C(Nc1ccc2cc[nH]c(=O)c2c1)c1ccc([C@@H](C)CO)c(C)c1]

Using a procedure analogous to that used for preparation of 15° C., 154B (272 mg, 0.381 mmol) was hydrogenated to give 154C (231 mg, 100%) as an oil. MS (ESI) m/z 571.3 [M+H]+.

Example 154

Using a procedure analogous to that used for preparation of 146D, 154C (231 mg, 0.405 mmol) was reacted with phosgene to give Example 154 (45 mg, 19%). Chiral HPLC (Whelko (R,R) 250×21.1 mm column, eluted with 2:3 (1:1 MeOH:EtOH):heptane at 20 mL/min. RT 10.5 min for undesired diastereomer, 13.6 min for Example 154). $^1$H NMR (400 MHz, methanol-$d_4$) δ ppm 7.67 (d, J=8.31 Hz, 1H), 7.47 (d, J=2.45 Hz, 1H), 7.41 (d, J=7.83 Hz, 2H), 7.14-7.32 (m, 4H), 6.90 (d, J=6.85 Hz, 2H), 6.67 (d, J=7.83 Hz, 1H), 6.53 (d, J=7.34 Hz, 1H), 5.98 (s, 1H), 5.81 (s, 1H), 5.23 (d, J=17.12 Hz, 1H), 4.62 (t, J=10.76 Hz, 1H), 4.43-4.52 (m, 1H), 4.14 (d, J=5.87 Hz, 1H), 4.07 (d, J=16.63 Hz, 1H), 3.97 (dd, J=10.76, 3.91 Hz, 1H), 3.33-3.49 (m, 2H), 2.75-2.90 (m, 2H), 2.32 (s, 3H), 1.28 (s, 3H), 1.23 (t, J=7.34 Hz, 3H). MS (ESI) m/z 597.3 [M+H]+. Analytical HPLC (Method A): Col A: 7.69 min, 87%; Col B: 7.48 min, 87%.

Example 155

3-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-propionic acid

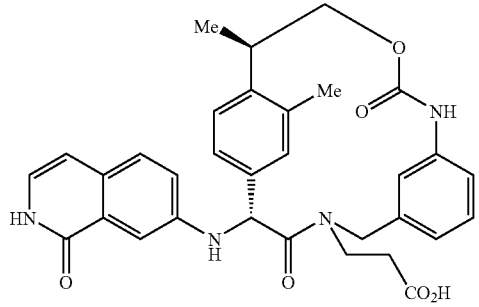 [SMILES: Cc1cc2ccc1[C@@H](C)COC(=O)Nc1cccc(c1)CN(CCC(=O)O)C(=O)[C@@H]2Nc1ccc2cc[nH]c(=O)c2c1]

To a solution of Example 154 (42 mg, 0.070 mmol) in MeOH (0.5 mL) and THF (2 mL) was added aqueous lithium hydroxide solution (0.5 mL, 0.5 mmol, 1M). The suspension was stirred at rt for 1 h, acidified with hydrochloric acid (1M), and extracted with EtOAc (2×). The combined organic layers were dried, concentrated, and purified by preparative HPLC to give Example 155. $^1$H NMR (400 MHz, methanol-$d_4$) δ ppm 7.63 (s, 1H), 7.59 (d, J=1.63 Hz, 1H), 7.48 (d, J=8.57 Hz, 1H), 7.41 (d, J=7.75 Hz, 1H), 7.34 (dd, J=8.98, 2.45 Hz, 1H), 7.28 (s, 1H), 7.17 (t, J=7.75 Hz, 2H), 6.98 (d, J=7.34 Hz, 1H), 6.91 (d, J=7.75 Hz, 1H), 6.68 (d, J=7.75 Hz, 1H), 6.58 (d, J=7.34 Hz, 1H), 6.00 (s, 1H), 5.93 (s, 1H), 5.26 (d, J=16.73 Hz, 1H), 4.34-4.47 (m, 1H), 4.09 (d, J=16.73 Hz, 1H), 3.96 (dd, J=10.81, 4.28 Hz, 1H), 3.44-3.55 (m, 1H), 2.77-2.88 (m, 1H), 2.65-2.75 (m, 1H), 2.35 (s, 3H), 1.30 (d, J=6.94 Hz, 3H). MS (ESI) m/z 569.3 [M+H]+. Analytical HPLC (Method A): Col A: 10.03 min, 98%; Col B: 10.14 min, 97%.

Example 156

3-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-propionamide

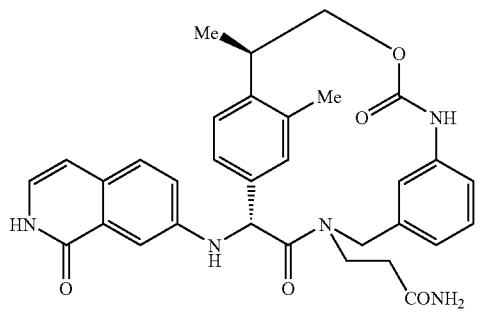 [SMILES: Cc1cc2ccc1[C@@H](C)COC(=O)Nc1cccc(c1)CN(CCC(N)=O)C(=O)[C@@H]2Nc1ccc2cc[nH]c(=O)c2c1]

Ammonium hydroxide (0.1 mL, saturated aqueous solution) was added to a solution of Example 155 (14 mg, 0.025 mmol), PyBOP (19 mg, 0.037 mmol), and DMAP (6 mg, 0.05 mmol) in DMF (1 mL) and the reaction mixture was stirred at rt overnight. The reaction mixture was concentrated and the residue was purified by preparative HPLC to give Example 156 (8.2 mg, 49%) as an amorphous off-white solid. $^1$H NMR (400 MHz, methanol-d$_4$) δ ppm 7.57-7.62 (m, 2H), 7.47-7.51 (m, 1H), 7.43 (d, J=7.75 Hz, 1H), 7.36 (dd, J=8.57, 2.45 Hz, 1H), 7.29 (s, 1H), 7.17 (t, J=7.75 Hz, 1H), 6.98 (d, J=6.94 Hz, 1H), 6.89 (s, 1H), 6.67 (d, J=8.57 Hz, 1H), 6.58 (d, J=7.34 Hz, 1H), 6.01 (s, 1H), 5.86 (s, 1H), 5.26 (d, J=16.73 Hz, 1H), 4.27-4.38 (m, 1H), 4.07 (d, J=16.73 Hz, 1H), 3.88-3.99 (m, 1H), 3.39-3.57 (m, 2H), 2.62-2.71 (m, 2H), 2.37 (s, 3H), 1.31 (d, J=6.94 Hz, 3H). MS (ESI) m/z 568.3 [M+H]$^+$. Analytical HPLC (Method A): Col A: 9.3 min, 98%; Col B: 9.45 min, 98%.

Example 157

3-[(2R,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaen-4-yl]-N-methyl-propionamide

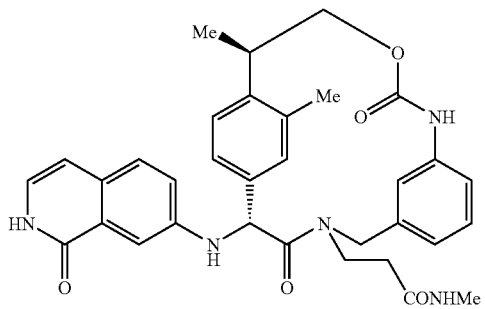

Using a procedure analogous to that used to prepare Example 156, 155 (14 mg, 0.025 mmol) was reacted with methylamine to give Example 157 (7 mg, 41%) as an amorphous off-white solid. $^1$H NMR (400 MHz, methanol-d$_4$) δ ppm 7.63 (d, J=2.04 Hz, 1H), 7.53 (d, J=2.45 Hz, 1H), 7.46-7.48 (m, 1H), 7.43 (d, J=7.75 Hz, 1H), 7.33 (dd, J=8.77, 2.24 Hz, 1H), 7.29 (s, 1H), 7.16 (t, J=7.96 Hz, 1H), 6.96 (d, J=6.94 Hz, 1H), 6.88 (d, J=7.75 Hz, 1H), 6.67 (d, J=7.75 Hz, 1H), 6.57 (d, J=7.34 Hz, 1H), 5.99 (s, 1H), 5.78 (s, 1H), 5.24 (d, J=17.14 Hz, 1H), 4.22-4.31 (m, 1H), 4.01 (dd, 1H), 3.96 (dd, J=10.81, 4.28 Hz, 1H), 3.60-3.69 (m, 1H), 3.45-3.56 (m, 1H), 2.59-2.70 (m, 2H), 2.55 (s, 3H), 2.36 (s, 3H), 1.31 (d, J=7.34 Hz, 3H). MS (ESI) m/z 582.3 [M+H]$^+$. Analytical HPLC (Method A): Col A: 6.17 min, 100%; Col B: 6.18 min, 100%.

Example 158

(2R,5R,15R)-5,5,17-Trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

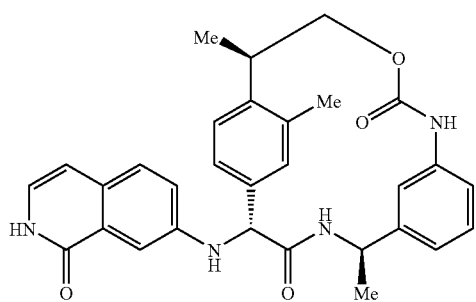 [SMILES: Cc1cc2ccc1[C@@H](C)COC(=O)Nc1cccc(c1)[C@@H](C)NC(=O)[C@@H]2Nc1ccc2cc[nH]c(=O)c2c1]

158A

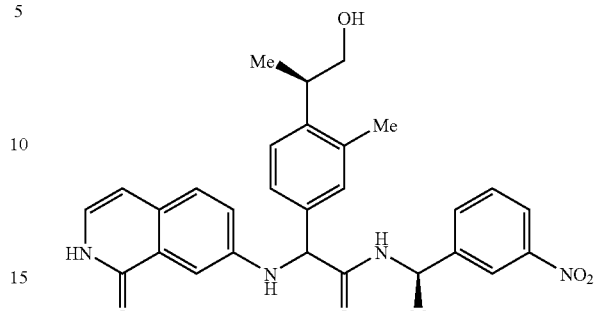

Using a procedure analogous to that used for preparation of 150B, (R)-1-(3-nitrophenyl)ethanamine hydrochloride salt (101 mg, 0.500 mmol) was coupled to 211 using BOP to give 158A. MS (ESI) m/z 515.2 [M+H]$^+$. $^1$H NMR (400 MHz, methanol-d$_4$) δ ppm 7.79-8.20 (m, 2H), 7.46-7.75 (m, 1H), 7.27-7.46 (m, 5H), 7.12-7.25 (m, 2H), 6.93 (t, J=7.34 Hz, 1H), 6.53 (d, J=7.34 Hz, 1H), 5.00-5.17 (m, 2H), 3.64 (dd, J=10.76, 6.36 Hz, 1H), 3.46-3.59 (m, 1H), 3.08-3.23 (m, 1H), 2.32 (d, J=7.83 Hz, 3H), 1.43 (dd, J=44.99, 6.85 Hz, 3H), 1.21 (d, J=6.85 Hz, 3H).

158B

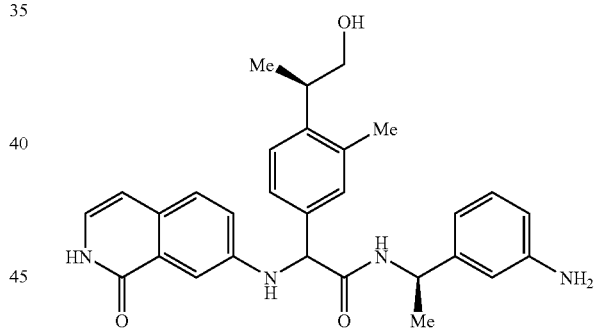

Using a procedure analogous to that used for preparation of 15° C., 158A (237 mg, 0.377 mmol) was hydrogenated to give 158B (170 mg, 93%) as a yellow foam. MS (ESI) m/z/z 485.2 [M+H]$^+$.

Example 158

Using a procedure analogous to that used for preparation of 146D, 158B (170 mg, 0.351 mmol) was reacted with phosgene to give Example 158 (14 mg, 6.4%). H NMR (400 MHz, methanol-d$_4$) δ ppm 8.60 (d, J=4.40 Hz, 1H), 7.55 (d, J=7.83 Hz, 1H), 7.39-7.48 (m, 3H), 7.25 (d, J=8.80 Hz, 1H), 7.08-7.18 (m, 2H), 6.91 (dd, J=12.72, 7.34 Hz, 2H), 6.62 (d, J=7.82 Hz, 1H), 6.55 (d, J=7.34 Hz, 1H), 6.21 (s, 1H), 5.16 (s, 1H), 4.69 (t, J=10.76 Hz, 1H), 3.94-4.10 (m, 1H), 3.41-3.53 (m, 1H), 2.30 (s, 3H), 1.45 (d, J=7.34 Hz, 3H), 1.28 (d, J=6.85 Hz, 3H). MS (ESI) m/z 511.2 [M+H]$^+$.

Example 159

[(2R,15R)-15,17-Dimethyl-3,12-dioxo-2-(1-oxo-1,2-dihydro-isoquinolin-7-ylamino)-7-phenyl-13-oxa-4,11-diaza-tricyclo[14.2.2.1[6,10]]henicosa-1(19),6,8,10(21),16(20),17-hexaen-4-yl]-acetic acid

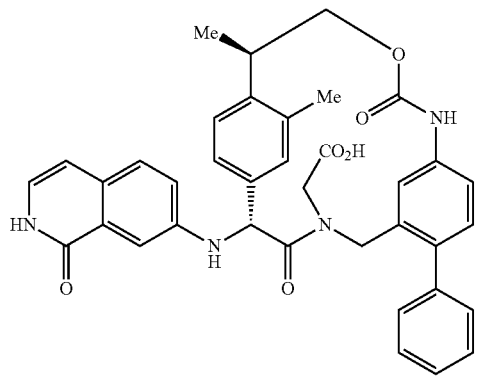 [SMILES: Cc1cc2ccc1[C@@H](C)COC(=O)Nc1ccc(-c3ccccc3)c(c1)CN(CC(=O)O)C(=O)[C@@H]2Nc1ccc2cc[nH]c(=O)c2c1]

159A

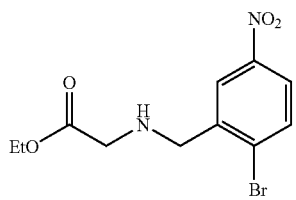 [SMILES: CCOC(=O)CNCc1cc([N+](=O)[O-])ccc1Br]

A solution of glycine ethyl ester hydrochloride (0.660 g, 4.73 mmol), 2-bromo-5-nitrobenzaldehyde (920 mg, 4.00 mmol) and triethylamine (0.557 mL, 4.00 mmol) in EtOH (100 mL) was heated at 45° C. for 40 min. The reaction was cooled to 0° C. and sodium cyanoborohydride (0.377 g, 6.00 mmol) was added in one portion. The reaction was stirred 10 min at 0° C. and then 1 h at rt. Most of the EtOH was removed in vacuo, and the reaction was diluted with water and extracted with DCM (2×). The organic extracts were dried and concentrated, and the residue was purified by flash chromatography (gradient from 0 to 40% EtOAc/Hexanes) to give 159A (0.97 g, 76%) as a white solid. $^1$H NMR (400 MHz, chloroform-d) δ ppm 8.38 (d, J=2.93 Hz, 1H), 7.99 (dd, J=8.56, 2.69 Hz, 1H), 7.73 (d, J=8.31 Hz, 1H), 4.22 (q, J=6.85 Hz, 2H), 3.97 (s, 2H), 3.48 (s, 2H), 1.30 (t, J=7.09 Hz, 3H). MS (ESI) m/z 319.0 [M+H]$^+$.

159B

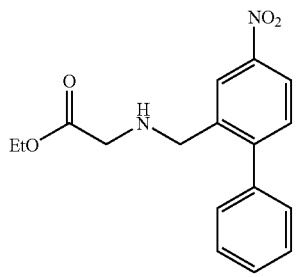 [SMILES: CCOC(=O)CNCc1cc([N+](=O)[O-])ccc1-c1ccccc1]

PdCl$_2$(dppf)-CH$_2$Cl$_2$ adduct (51.5 mg, 0.063 mmol) was added to a mixture of 159A (200 mg, 0.631 mmol), phenyl-boronic acid (154 mg, 1.261 mmol) and tribasic potassium phosphate (268 mg, 1.261 mmol) in dioxane (4 mL, degassed by sparging with nitrogen for 5 min). The reaction mixture was heated by microwave for 10 min at 150° C. The reaction was degassed again, an additional portion of palladium catalyst was added (72 mg), and the reaction mixture was heated by microwave for 10 min at 180° C. The reaction was filtered and then purified by flash chromatography to give 159B (112 mg, 56.5%). $^1$H NMR (400 MHz, chloroform-d) δ ppm 8.47 (s, 1H), 7.97-8.24 (m, 1H), 7.19-7.66 (m, 8H), 4.13 (q, J=7.17 Hz, 2H), 3.80 (s, 2H), 3.33 (s, 2H), 1.22 (t, J=7.09 Hz, 3H). MS (ESI) m/z 315.2 [M+H]$^+$.

159C

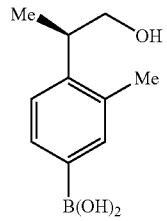

A 300 mL pressure tube was charged with Intermediate 10A (4.65 g, 14.12 mmol), potassium acetate (3.46 g, 35.3 mmol), bis(neopentyl glycolato)diboron (3.83 g, 16.94 mmol) and dioxane (75 mL). The reaction mixture was degassed by sparging with nitrogen for 5 min. PdCl$_2$ (dppf)-CH$_2$Cl$_2$ adduct (1.15 g, 1.41 mmol) was added, and the reaction mixture was heated at 80° C. for 3.5 h. The mixture was diluted with water and extracted with ether (2×). The combined organic layers were washed with water and brine, dried (MgSO$_4$), and concentrated. The residue was purified by flash chromatography (gradient from 0 to 100% EtOAc/hexanes) to give a boronic ester intermediate (4.76 g, 13.14 mmol, 93% yield) as a yellow oil. $^1$H NMR (400 MHz, chloroform-d) δ ppm 7.60-7.65 (m, 2H), 7.21 (d, J=7.34 Hz, 1H), 3.79 (s, 4H), 3.71 (dd, J=9.78, 5.87 Hz, 1H), 3.57-3.62 (m, 1H), 3.17-3.26 (m, 1H), 2.39 (s, 3H), 1.29 (d, J=6.85 Hz, 3H), 1.05 (s, 6H), 0.89 (s, 9H), 0.01 (s, 3H), −0.00 (s, 3H). A portion of this material (1.8 g) was purified by preparative HPLC to give the free boronic acid 159C (0.793 g, 89%) as a colorless foam.

159D

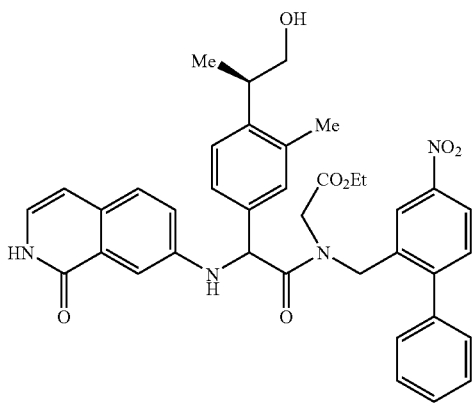 [SMILES: CCOC(=O)CN(Cc1cc([N+](=O)[O-])ccc1-c1ccccc1)C(=O)C(Nc1ccc2cc[nH]c(=O)c2c1)c1ccc([C@@H](C)CO)c(C)c1]

A solution of 159C (32.1 mg, 0.178 mmol), Intermediate 3 (28.5 mg, 0.178 mmol) and glyoxylic acid monohydrate (16.4 mg, 0.178 mmol) in a mixture of DMF (0.4 mL) and acetonitrile (1 mL) was heated by microwave for 10 min at 100° C. The resulting brown solution was cooled in an ice bath and HATU (67.7 mg, 0.178 mmol) was added, followed by 159B (112 mg, 0.356 mmol) and 4-methylmorpholine (18.0 mg, 0.178 mmol). The reaction mixture was stirred at rt overnight. The mixture was concentrated and purified by preparative HPLC to give 159D. MS (ESI) m/z 663.3 [M+H]$^+$.

159E

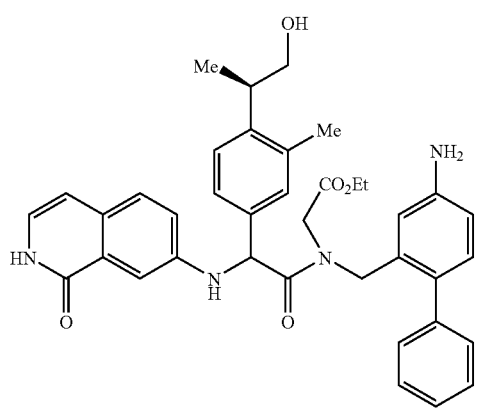

Using a procedure analogous to that used for preparation of 15° C., 159D (82 mg, 0.124 mmol) was hydrogenated to give 159E (80 mg, 100%). MS (ESI) m/z 633.3 [M+H]$_+$.

159F

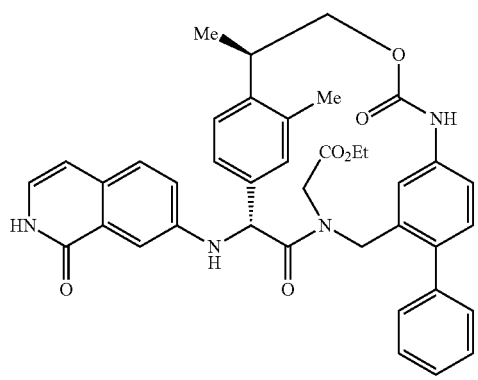 [SMILES: CCOC(=O)CN1Cc2cc(ccc2-c2ccccc2)NC(=O)OC[C@H](C)c2ccc(cc2C)[C@@H](Nc2ccc3cc[nH]c(=O)c3c2)C1=O]

Using a procedure analogous to that used for preparation of 146D, 159E (80 mg, 0.126 mmol) was reacted with phosgene to give 159F (20 mg, 24%). Chiral HPLC (AD-H 250×21.1 mm column, eluted with 2:8 MeOH:EtOH, 0.1% diethylamine at 20 mL/min. RT 6 min for undesired diastereomer, 11 min for 159F). MS (ESI) m/z 659.3 [M+H]$^+$.

Example 159

Using a procedure analogous to that used for preparation of Example 155, 159F (20 mg, 0.03 mmol) was hydrolyzed with lithium hydroxide to give Example 159 (11 mg, 49%). $^1$H NMR (400 MHz, methanol-d$_4$) δ ppm 7.63 (d, J=9.29 Hz, 1H), 7.55 (d, J=2.45 Hz, 1H), 7.43-7.49 (m, 1H), 7.37-7.43 (m, 3H), 7.33 (d, J=7.34 Hz, 1H), 7.24-7.30 (m, 3H), 7.21-7.24 (m, 1H), 7.06 (d, J=7.82 Hz, 1H), 6.91 (d, J=6.85 Hz, 1H), 6.77 (dd, J=8.07, 2.20 Hz, 1H), 6.52 (d, J=6.85 Hz, 1H), 6.16 (d, J=1.96 Hz, 1H), 5.38 (s, 1H), 5.25 (d, J=17.12 Hz, 1H), 4.75-4.87 (m, 1H), 4.64 (t, J=11.00 Hz, 1H), 3.96 (dd, J=10.76, 4.40 Hz, 1H), 3.70-3.85 (m, 2H), 3.43-3.56 (m, 1H), 2.34 (s, 3H), 1.30 (d, J=6.85 Hz, 3H). MS (ESI) m/z 631.3 [M+H]$^+$.

Example 160

(2R,15R)-2-(4-Chloro-1-oxo-1,2-dihydro-isoquinolin-7-ylamino)-7-cyclopropanesulfonyl-4,15,17-trimethyl-13-oxa-4,11-diaza-tricyclo[14.2.2.1$^{6,10}$]henicosa-1(19),6,8,10(21),16(20),17-hexaene-3,12-dione

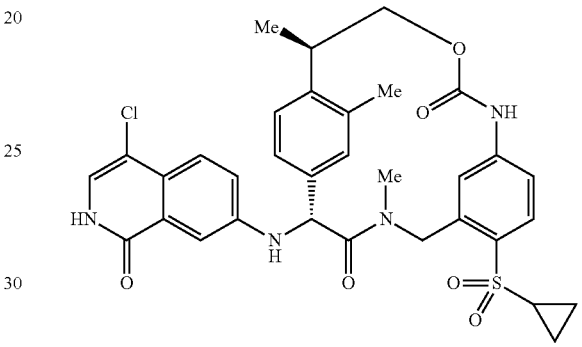

160A

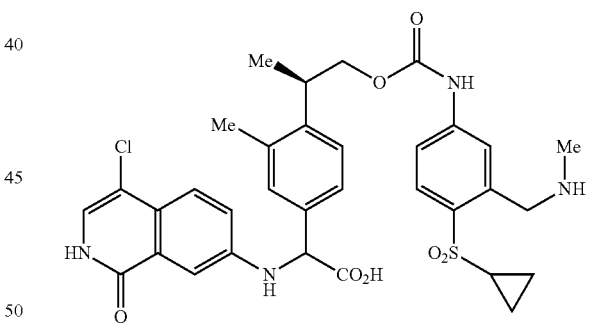

A suspension of Intermediate 76B (171 mg, 0.305 mmol), Intermediate 5 (59.4 mg, 0.305 mmol), and glyoxylic acid monohydrate (28.1 mg, 0.305 mmol) in a mixture of acetonitrile (1.6 mL) and DMF (0.4 mL) was heated by microwave for 10 min at 100° C. The solution was immediately purified by flash chromatography (gradient from 0 to 20% MeOH/DCM). The residue was dissolved in DCM (4 mL) and hydrogen chloride (4 mL, 4N solution in dioxane) was added. The reaction was stirred for 1 h at rt, concentrated to give 160A (155 mg, 68.6%) as an orange solid. MS (ESI) m/z 667.4 [M+H]$^+$.

Example 160

To a solution of BOP (206 mg, 0.465 mmol) and DMAP (142 mg, 1.162 mmol) in DCM (40 mL) and DMF (10 mL) at 40° C., was added a solution of 160A (155 mg, 0.232 mmol) and DIEA (0.090 mL, 0.515 mmol) in DMF (5 mL) and DCM (10 ml), dropwise via addition funnel over 2 h. The reaction was concentrated and the residue was purified by preparative HPLC, followed by chiral chromatography (Whelko (R,R) 250×21.1 mm column, eluted with 2:3 (1:1 MeOH:EtOH): heptane at 20 mL/min. RT 8.7 min for undesired diastereomer, 12 min for Example 160) to give Example 160 (24 mg, 16%) as an amorphous pale yellow solid. $^1$H NMR (400 MHz, methanol-d$_4$) δ ppm 7.71 (d, J=8.31 Hz, 1H), 7.65-7.68 (m, 1H), 7.64 (d, J=8.80 Hz, 2H), 7.42-7.51 (m, 2H), 7.31 (dd, J=8.80, 2.45 Hz, 1H), 7.12 (s, 1H), 7.04 (s, 1H), 6.82 (dd, J=8.31, 1.96 Hz, 1H), 6.43 (s, 1H), 5.76 (d, J=17.61 Hz, 2H), 5.65 (s, 1H), 4.62 (t, J=11.00 Hz, 1H), 4.29 (d, J=17.61 Hz, 1H), 3.96 (dd, J=10.51, 4.16 Hz, 1H), 3.44-3.53 (m, 1H), 3.40 (s, 3H), 2.80-2.95 (m, 2H), 2.27 (s, 3H), 1.32 (d, J=6.85 Hz, 3H), 1.19-1.26 (m, 1H), 0.89-1.15 (m, 3H). MS (ESI) m/z 649.4 [M+H]$^+$. Analytical HPLC (Method A): Col A: 7.06 min, 99%; Col B: 7.79 min, 98%.

Example 161

(2R,5S,15R)-15,17-Dimethyl-3,12-dioxo-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-5-carboxylic acid

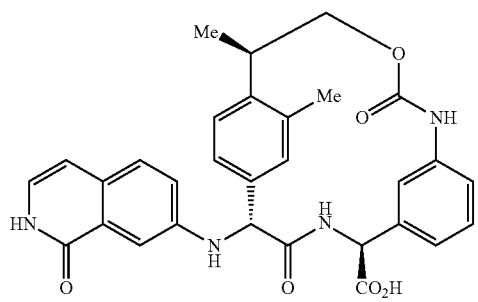 [SMILES: Cc1cc2ccc1[C@@H](C)COC(=O)Nc1cccc(c1)[C@@H](C(=O)O)NC(=O)[C@@H]2Nc1ccc2cc[nH]c(=O)c2c1]

161A

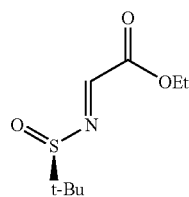 [SMILES: CCOC(=O)/C=N/[S@](=O)C(C)(C)C]

Ethyl glyoxalate (1.21 g, 5.93 mmol, 50% solution in toluene) was heated at 50° C. for 1 min under N$_2$. The mixture was cooled to rt and DCM (100 mL) was added, followed by (S)-2-methylpropane-2-sulfinamide (0.718 g, 5.93 mmol) and molecular sieves (35 g, activated at 350° C.). The reaction mixture was stirred at rt overnight. The reaction was filtered, concentrated, and the residue was purified by flash chromatography (gradient from 0-30% EtOAc/hexanes) to give 161A (448 mg, 36.8%) as a clear oil. $^1$H NMR (400 MHz, chloroform-d) δ ppm 8.01 (s, 1H), 4.39 (q, J=7.01 Hz, 2H), 1.39 (t, J=7.09 Hz, 3H), 1.28 (s, 9H).

161B

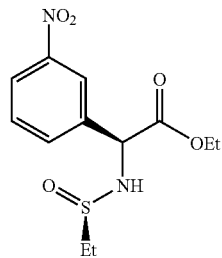 [SMILES: CCOC(=O)[C@@H](N[S@](=O)CC)c1cccc([N+](=O)[O-])c1]

A solution of 3-nitrophenylboronic acid (334 mg, 2.001 mmol) and 161A (205 mg, 1 mmol) in dioxane (4 mL) was sparged with nitrogen. Acetylacetonatobis(cyclooctene)-rhodium(I) (42 mg, 0.1 mmol) and 1,2-bis(diphenylphosphino)benzene (25 mg, 0.12 mmol) were added and the reaction mixture was heated by microwave at 140° C. for 10 min. The reaction mixture was diluted with EtOAc, washed with water, dried, concentrated, and purified by flash chromatography (gradient from 0 to 80% EtOAc/hexanes) to give 161B (170 mg, 51.8%) as a brown oil. $^1$H NMR (400 MHz, chloroform-d) δ ppm 8.30 (s, 1H), 8.21 (dd, J=8.07, 2.20 Hz, 1H), 7.77 (d, J=7.82 Hz, 1H), 7.58 (t, J=8.07 Hz, 1H), 5.22 (d, J=3.91 Hz, 1H), 4.84 (d, J=3.91 Hz, 1H), 4.06-4.32 (m, 2H), 1.29 (s, 9H), 1.20-1.23 (m, 3H). MS (ESI) m/z 329.1 [M+H]$^+$.

161C

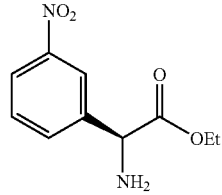 [SMILES: CCOC(=O)[C@@H](N)c1cccc([N+](=O)[O-])c1]

Hydrogen chloride (1.0 ml, 4.0 mmol, 4N solution in dioxane) was added to a solution of 161B (263 mg, 0.801 mmol) in ethanol (5 mL). The reaction mixture was stirred at rt for 4 h, and then concentrated. The residue was triturated with ether (2×) to give 161C (170 mg, 81%) as a brown foam. $^1$H NMR (400 MHz, methanol-d$_4$) δ ppm 8.44 (s, 1H), 8.36-8.40 (m, 1H), 7.90 (d, J=7.82 Hz, 1H), 7.78 (t, J=8.07 Hz, 1H), 5.44 (s, 1H), 4.28-4.35 (m, 2H), 1.23 (t, J=7.09 Hz, 3H). MS (ESI) m/z 329.1 [M+H]$^+$=225.2.

161D

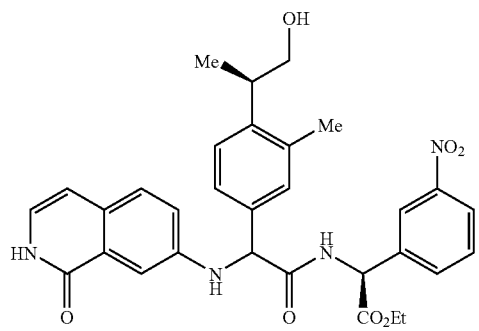 [SMILES: CCOC(=O)[C@@H](NC(=O)C(Nc1ccc2cc[nH]c(=O)c2c1)c1ccc([C@@H](C)CO)c(C)c1)c1cccc(N)c1]

A solution of 159C (0.127 g, 0.652 mmol), Intermediate 3 (0.104 g, 0.652 mmol) and glyoxylic acid monohydrate (0.060 g, 0.652 mmol) in a mixture of DMF (1 mL) and acetonitrile (1 mL) was heated by microwave for 10 min at 100° C. A solution of 161C (0.170 g, 0.652 mmol) and DIEA (0.110 mL, 0.630 mmol) in 1 m: DMF and was added to the microwaved solution, followed by BOP (0.288 g, 0.652 mmol). The reaction mixture was stirred at rt overnight. The mixture was concentrated and purified by preparative HPLC to give 161D (145 mg, 32.4%). $^1$H NMR (400 MHz, methanol-$d_4$) δ ppm 7.97-8.31 (m, 2H), 7.46-7.84 (m, 2H), 7.29-7.46 (m, 4H), 7.15-7.28 (m, 2H), 6.95 (d, J=6.85 Hz, 1H), 6.54 (dd, J=7.09, 3.67 Hz, 1H), 5.69 (d, J=10.76 Hz, 1H), 5.19 (d, J=12.23 Hz, 1H), 4.11-4.24 (m, 1H), 4.02-4.12 (m, 3H), 3.58-3.72 (m, 1H), 3.48-3.57 (m, 1H), 3.10-3.26 (m, 1H), 2.33 (t, J=6.11 Hz, 3H), 1.20 (dd, J=6.85, 2.93 Hz, 3H), 0.99-1.18 (m, 3H). MS (ESI) m/z 573.3 [M+H]$^+$.

161E

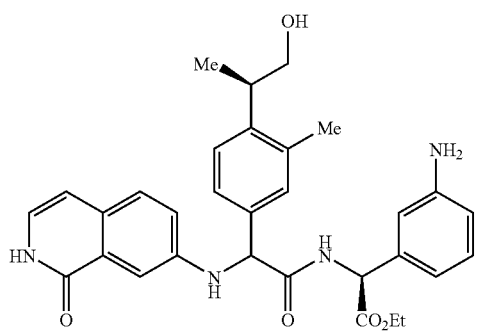

Using a procedure analogous to that used for preparation of 15° C., 161D (144 mg, 0.251 mmol) was hydrogenated to give 161E (115 mg, 84%) as a yellow glass. MS (ESI) m/z 543.3 [M+H]$^+$.

161F

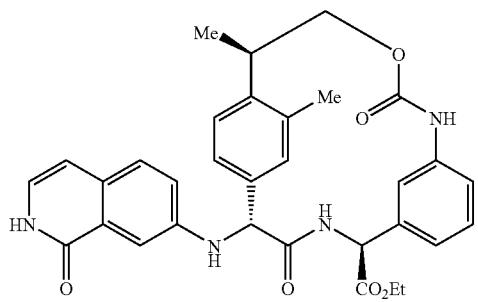 [SMILES: CCOC(=O)[C@H]1NC(=O)[C@H](Nc2ccc3cc[nH]c(=O)c3c2)c2ccc(c(C)c2)[C@@H](C)COC(=O)Nc2cccc1c2]

Using a procedure analogous to that used for preparation of 146D, 161E (115 mg, 0.212 mmol) was reacted with phosgene to give 161F (20 mg, 17%). Chiral HPLC (Whelko (R,R) 250×21.1 mm column, eluted with 2:3 (1:1 MeOH:EtOH): heptane at 20 mL/min. RT 12 min, 15 min, and 22 min for undesired diastereomers, 19 min for 161F). MS (ESI) m/z 569.3 [M+H]$^+$.

Example 161

Using a procedure analogous to that used for preparation of Example 155, 161F (20 mg, 0.035 mmol) was hydrolyzed with lithium hydroxide to give Example 161 (10 mg, 43%). $^1$H NMR (400 MHz, methanol-$d_4$) δ ppm 7.61 (d, J=7.83 Hz, 1H), 7.42 (dd, J=7.58, 3.67 Hz, 3H), 7.23 (dd, J=8.80, 2.45 Hz, 1H), 7.15 (d, J=4.89 Hz, 1H), 7.09 (s, 1H), 6.91 (d, J=7.34 Hz, 1H), 6.68 (d, J=2.93 Hz, 1H), 6.35 (s, 1H), 5.44-5.56 (m, 1H), 5.38 (s, 1H), 4.66 (s, 1H), 3.87-4.13 (m, 1H), 3.38-3.56 (m, 1H), 2.28 (s, 3H), 1.29 (t, J=7.34 Hz, 3H). MS (ESI) m/z 541.3 [M+H]$^+$.

Example 162

(2R,5R,15S)-20-Methoxy-5,15-dimethyl-2-(1-oxo-1,2-dihydro-isoquinolin-7-ylamino)-7-trifluoromethoxy-4,11-diaza-tricyclo[14.2.2.16,10]henicosa-1(19),6,8,10(21.),16(20),17-hexaene-3,12-dione

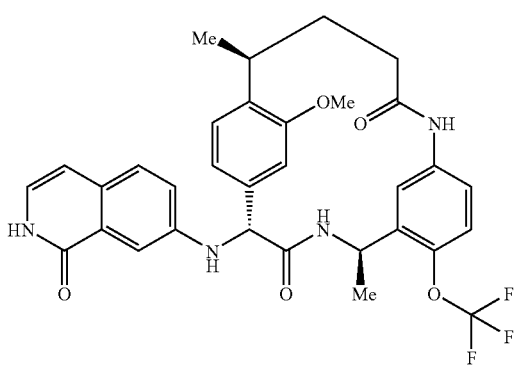 [SMILES: COc1cc2ccc1[C@@H](C)CCC(=O)Nc1ccc(OC(F)(F)F)c(c1)[C@@H](C)NC(=O)[C@@H]2Nc1ccc2cc[nH]c(=O)c2c1]

162A

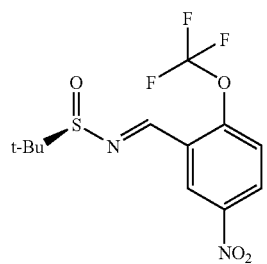 [SMILES: CC(C)(C)[S@@](=O)/N=C/c1cc([N+](=O)[O-])ccc1OC(F)(F)F]

To Intermediate 14A (1.0 g, 4.25 mmol) in THF (10 mL) was added (R)-2-methylpropane-2-sulfinamide (0.52 g, 4.25 mmol) followed by titanium(IV) ethoxide (1.783 mL, 8.51 mmol). The reaction mixture was stirred at 80° C. for 4 h. After cooling to rt, the reaction was quenched by slow addition of saturated sodium bicarbonate. EtOAc (100 mL) was added and the mixture was filtered and washed through Celite®. The phases were separated and the organic layer was washed with brine, dried over sodium sulfate and concentrated. The crude product was purified by column chromatography (0-25% ethyl acetate/hexanes) to obtain 162A (1.26 g, 88% yield). $^1$H NMR (400 MHz, methanol-$d_4$) δ ppm 1.23 (s, 9H) 7.69 (dd, J=9.09, 1.77 Hz, 1H) 8.47 (dd, J=9.09, 3.03 Hz, 1H) 8.81 (s, 5H) 8.83 (d, J=2.78 Hz, 1H). MS (ESI) m/z 339.3 (M+H)$^+$.

162B

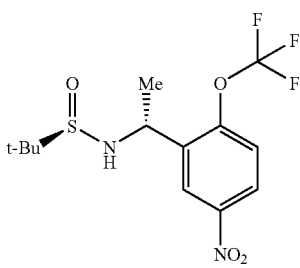 [SMILES: C[C@@H](N[S@](=O)C(C)(C)C)c1cc([N+](=O)[O-])ccc1OC(F)(F)F]

To a flame-dried flask under argon was added 162A (0.7 g, 2.069 mmol) in THF (10 mL). The resulting solution was cooled to −78° C. and methyllithium (1.940 mL, 3.10 mmol) was added dropwise. The solution turned dark red. Stirring was continued for 1 h at −78° C. The reaction was quenched with ammonium chloride, warmed to rt and diluted with ethyl acetate. The organic layer was washed with brine and dried over sodium sulfate. The crude product was purified by column chromatography (0-80% ethyl acetate in hexanes) to obtain 162B (0.32 g, 44% yield). $^1$H NMR (400 MHz, methanol-$d_4$) δ ppm 1.13-1.24 (m, 9H) 1.45 (d, J=7.07 Hz, 3H) 4.79-4.86 (m, 1H) 6.01 (d, J=8.08 Hz, 1H) 7.44-7.53 (m, 1H) 8.19 (dd, J=9.09, 2.78 Hz, 1H) 8.53 (d, J=2.78 Hz, 1H). MS (ESI) m/z 355.3 (M+H)$^+$.

162C

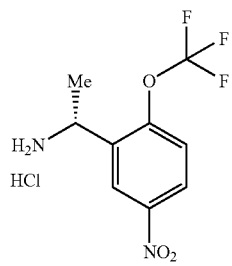 [SMILES: C[C@@H](N)c1cc([N+](=O)[O-])ccc1OC(F)(F)F ; Cl]

To 162B (0.32 g, 0.903 mmol) in MeOH (2 mL) was added HCl (4M in dioxane, 0.226 mL, 0.903 mmol). The reaction was stirred at rt for 1 h. The solvent was removed and residue was dried under vacuo to give 162C (0.25 g, 97%) as an orange solid. $^1$H NMR (400 MHz, methanol-$d_4$) δ ppm 1.60 (d, J=7.07 Hz, 3H) 4.83 (t, J=6.82 Hz, 1H) 7.59-7.69 (m, 1H) 8.37 (dd, J=9.09, 2.78 Hz, 1H) 8.53 (d, J=2.78 Hz, 1H). MS (ESI) m/z 251.2 (M+H)$^+$.

162D

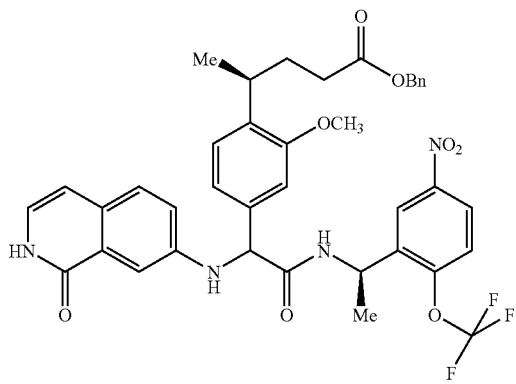 [SMILES: COc1cc(C(Nc2ccc3cc[nH]c(=O)c3c2)C(=O)N[C@H](C)c2cc([N+](=O)[O-])ccc2OC(F)(F)F)ccc1[C@@H](C)CCC(=O)OCc1ccccc1]

Using a procedure analogous to that used to prepare 41E, a mixture of 134B (0.25 g, 0.731 mmol), Intermediate 3 (0.117 g, 0.731 mmol) and 2-oxoacetic acid hydrate (0.067 g, 0.731 mmol) were reacted. The resulting solution was reacted with 162C using BOP and DIEA. The crude product was purified by column chromatography (0-10% dichloromethane/methanol) to obtain 162D (0.54 g, 99%) as a brown solid. $^1$H NMR showed rotamers and diastereomeric mixture; MS (ESI) m/z 747.6 (M+H)$^+$.

162E

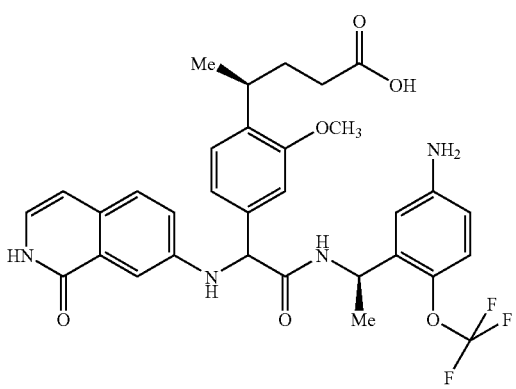 [SMILES: COc1cc(C(Nc2ccc3cc[nH]c(=O)c3c2)C(=O)N[C@H](C)c2cc(N)ccc2OC(F)(F)F)ccc1[C@@H](C)CCC(=O)O]

To 162D (0.54 g, 0.723 mmol) and 10% Pd/C (0.1 g) was added MeOH (5 mL) and water (2 mL) under nitrogen. The flask was purged with $N_2$. A few drops of 1.0 N HCl were added. Then $H_2$ balloon was introduced and the system was purged and degassed (3×). The reaction was stirred at rt for 6 h. The catalyst was filtered over Celite® and washed with methanol. The filtrates were combined, evaporated and lyophilized to give 162E (0.45 g, 99%) as a yellow solid. $^1$H NMR showed rotamers and diastereomeric mixture; MS (ESI) m/z 627.5 (M+H)$^+$.

Example 162

To a solution of BOP (0.635 g, 1.436 mmol) and DMAP (0.351 g, 2.87 mmol) in $CH_2Cl_2$ (60 mL) and DMF (6 mL) at rt was added a solution of 162E (0.45 g, 0.718 mmol) and DIEA (0.376 ml, 2.154 mmol) in DMF (5.0 mL) via a syringe pump over 10 h. To the reaction mixture was added 0.5 N HCl (30 mL), stirred for 10 min. The organic layer was collected and aqueous was extracted with $CH_2Cl_2$. The organic layers were washed with brine and dried over sodium sulfate. After evaporation of the solvent, the crude residue was dissolved in 90% acetonitrile-10% water-0.1% TFA and purified (3 injections) by preparative HPLC equipped with a C18 Phenomenex Luna column (30 mm×100 mm, 5µ) with the UV detector set at 254 nm. The separations were performed using a gradient method: 20-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected and isomers were further purified and separated using a preparative HPLC equipped with a Chiral OD column. The residue was dissolved in 50% MeOH/EtOH in heptane. The separations were performed using an isocratic method of 10% 1:1 ethanol/methanol: 90% heptane with 0.1% DEA for 40 min with a flow rate of 20 mL/min. The first peak (RT=11.2 min, 30 mg, 7% yield) was confirmed to be Example 162: $^1$H NMR (400 MHz, methanol-d$_4$) δ ppm 3.50 (s, 3H) 5.05-5.18 (m, 2H) 6.49 (d, J=2.53 Hz, 1H) 6.53 (d, J=7.07 Hz, 1H) 6.64 (s, 1H) 6.73 (dd, J=8.84, 2.53 Hz, 1H) 6.89 (d, J=7.07 Hz, 1H) 7.09 (d, J=8.59 Hz, 1H) 7.18 (dd, J=8.59, 2.53 Hz, 1H) 7.29-7.46 (m, 4H). MS (ESI) m/z 609.5 (M+H)$^+$. Analytical HPLC (Method B): Col A: 8.05 min, 99%; Col B: 7.27 min, 95%.

Example 163

(2R,15S)-7-Cyclopropanesulfonyl-15-hydroxymethyl-4,20-dimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

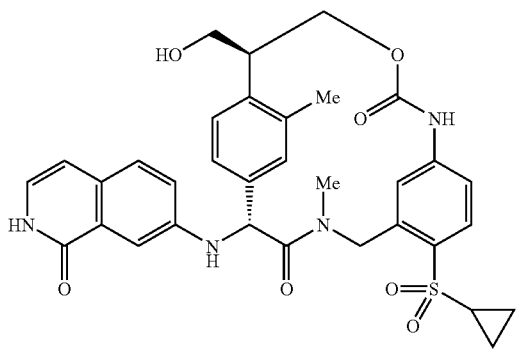 [SMILES: Cc1cc2ccc1[C@@H](CO)COC(=O)Nc1ccc(S(=O)(=O)C3CC3)c(c1)CN(C)C(=O)[C@@H]2Nc1ccc2cc[nH]c(=O)c2c1]

163A

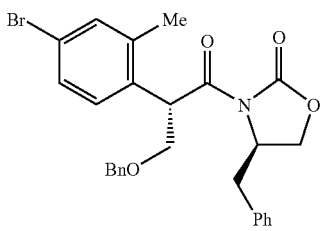 [SMILES: Cc1cc(Br)ccc1[C@@H](COCc1ccccc1)C(=O)N1C(=O)OC[C@H]1Cc1ccccc1]

To a solution of (R)-4-benzyl-3-(2-(4-bromo-2-methylphenyl)acetyl)oxazolidin-2-one (3.4 g, 8.76 mmol) in CH$_2$Cl$_2$ (30 mL) was added TiCl$_4$ (9.19 mL, 9.19 mmol) at 0° C. to form a yellow solution, then DIEA (1.682 mL, 9.63 mmol) was added at 0° C. to form a blue solution. The mixture was stirred at 0° C. for 1 h. Benzyl chloromethyl ether (2.74 g, 17.51 mmol) was added and stirring continued for 2 h at 0° C. The blue color faded away. The reaction was quenched by water and diluted by EtOAc. The organic layer was washed with saturated NaHCO$_3$, brine and dried over MgSO$_4$. The crude product was purified by column chromatography (0 to 50% EtOAc in hexanes) to obtain 163A (3.9 g, 7.67 mmol, 88% yield) as a colorless oil. $^1$H NMR (400 MHz, CDCl$_3$) δ ppm 2.43 (s, 3H) 2.89 (dd, J=13.40, 9.01 Hz, 1H) 3.31 (dd, J=13.62, 2.64 Hz, 1H) 3.52 (dd, J=9.23, 4.39 Hz, 1H) 4.04-4.20 (m, 3H) 4.47-4.68 (m, 2H) 4.71 (t, J=8.35 Hz, 1H) 5.47 (dd, J=9.67, 4.39 Hz, 1H) 7.11 (d, J=8.35 Hz, 1H) 7.18-7.37 (m, 12H). MS (ESI) m/z 508 (M+H)$^+$.

163B

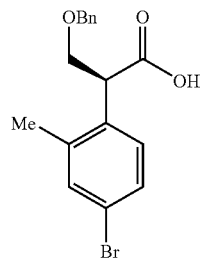 [SMILES: Cc1cc(Br)ccc1[C@@H](COCc1ccccc1)C(=O)O]

To 163A (4.15 g, 8.16 mmol) in THF (30 mL) and water (10.00 mL) at 0° C. was added a solution of lithium peroxide (prepared by adding hydrogen peroxide (4.17 mL, 40.8 mmol) to lithium hydroxide (0.293 g, 12.24 mmol) in water (8 mL) dropwise. The mixture was stirred at 0° C. for 1 h. The reaction was quenched with saturated sodium sulfite and the organic solvent was evaporated. The remaining solution was diluted by 50 mL of water and extracted with dichloromethane (2×20 mL). The aqueous layer was acidified using conc. HCl. The solution was then extracted with ethyl acetate (3×50 mL). The organic layers were combined, washed with brine and dried over MgSO$_4$. The solution was filtered and concentrated to give 163B (2.8 g, 8.02 mmol, 98% yield) as a yellow oil. $^1$H NMR (400 MHz, CDCl$_3$) δ ppm 2.31 (s, 3H) 3.56 (dd, J=9.23, 5.27 Hz, 1H) 4.02-4.15 (m, 2H) 4.34-4.65 (m, 2H) 7.10 (d, J=8.35 Hz, 1H) 7.16-7.53 (m, 7H).

163C

To a solution of 163B (2.8 g, 8.02 mmol) in THF (30 mL) at 0° C. was slowly added 1.0 M BH$_3$®THF in THF (11.23 mL, 11.23 mmol) in 10 min. The mixture was stirred from 0° C. to rt overnight. The reaction was quenched at 0° C. by addition of 5.0 mL of H$_2$O, diluted with EtOAc, washed with 10% Na$_2$CO$_3$. The aqueous was extracted with EtOAc. The combined organic was washed with sat. NaHCO$_3$, brine and dried over Na$_2$SO$_4$. After evaporation of solvent, 163C (2.5 g, 7.46 mmol, 93% yield) was obtained as a colorless liquid. $^1$H NMR (400 MHz, CDCl$_3$) δ ppm 2.32 (s, 3H) 3.32-3.41 (m, 1H) 3.60-3.89 (m, 4H) 4.47 (s, 2H) 7.13 (d, J=8.35 Hz, 1H) 7.20-7.34 (m, 7H).

163D

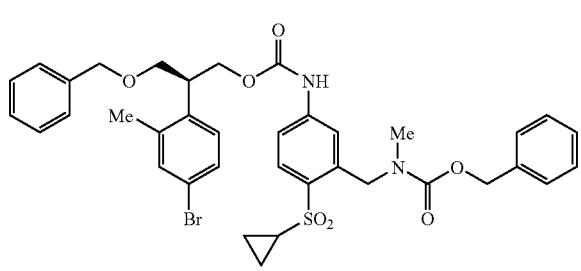 [SMILES: Cc1cc(Br)ccc1[C@@H](COCc1ccccc1)COC(=O)Nc1ccc(S(=O)(=O)C2CC2)c(CN(C)C(=O)OCc2ccccc2)c1]

Using a procedure analogous to that used to prepare 29A, 39E (300 mg, 0.801 mmol) was reacted with sodium bicarbonate and phosgene followed by 163C and TEA. The crude product was added to a silica gel column (40 g) and was eluted with EtOAc/hexanes (0-100%) to give to give 163D (0.54 g, 91% yield) as a colorless oil. $^1$H NMR (400 MHz, DMSO-$d_6$) $\delta$ ppm 0.80-1.05 (m, 4H) 2.27 (s, 3H) 2.46 (s, 3H) 2.85-3.01 (m, 4H) 3.47-3.78 (m, 3H) 4.30 (dd, J=10.55, 7.47 Hz, 1H) 4.38-4.50 (m, 3H) 5.01 (s, 1H) 5.11 (s, 1H) 7.03-7.15 (m, 1H) 7.15-7.49 (m, 13H) 7.61 (d, J=16.70 Hz, 1H) 7.71 (t, J=7.25 Hz, 1H). MS (ESI) m/z 735, 737 (M+H)$^+$.

163E

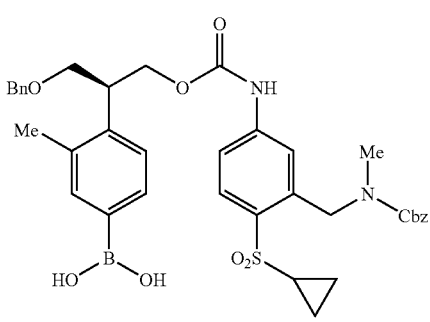 [SMILES: Cc1cc(B(O)O)ccc1[C@@H](COCc1ccccc1)COC(=O)Nc1ccc(S(=O)(=O)C2CC2)c(CN(C)C(=O)OCc2ccccc2)c1]

Using a procedure analogous to that used to prepare 29B, 163D (520 mg, 0.707 mmol) was reacted with bis(neopentyl glycolato)diboron), potassium acetate and. (1,1'-bis(diphenylphosphino)ferrocene)-dichloropalladium(II). The crude was purified by flash chromatography (EtOAc/hexanes 2% to 100%) and preparative HPLC (CH$_3$CN/H$_2$O, 0.1% TFA) to yield 163E (317 mg, 0.389 mmol, 55.1% yield) as a white solid. $^1$H NMR (400 MHz, methanol-$d_4$) $\delta$ ppm 0.79-0.92 (m, 1H) 1.01-1.24 (m, 3H) 2.36 (s, 3H) 3.01-3.09 (m, 4H) 3.65-3.73 (m, 2H) 3.74-3.82 (m, 1H) 4.40 (dd, J=10.55, 6.59 Hz, 1H) 4.49-4.58 (m, 3H) 4.91-4.99 (m, 2H) 5.07 (s, 1H) 5.18 (s, 1H) 7.05-7.62 (m, 15H) 7.76 (s, 1H). MS (ESI) m/z 701 (M+H)$^+$.

163F

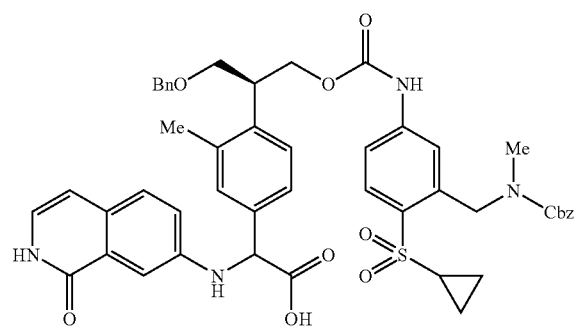 [SMILES: Cc1cc(C(Nc2ccc3cc[nH]c(=O)c3c2)C(=O)O)ccc1[C@@H](COCc1ccccc1)COC(=O)Nc1ccc(S(=O)(=O)C2CC2)c(CN(C)C(=O)OCc2ccccc2)c1]

Using a procedure analogous to that used to prepare 1E, 163E (300 mg, 0.368 mmol), Intermediate 3, and glyoxylic acid monohydrate were reacted and purified by flash chromatography (1% to 20% MeOH in CH$_2$Cl$_2$) to give 163F (300 mg, 0.344 mmol, 93% yield) as a slightly yellow solid. MS (ESI) m/z 873 (M+H)$^+$. $^1$HNMR indicated a mixture of diastereoisomers and rotomers.

163G

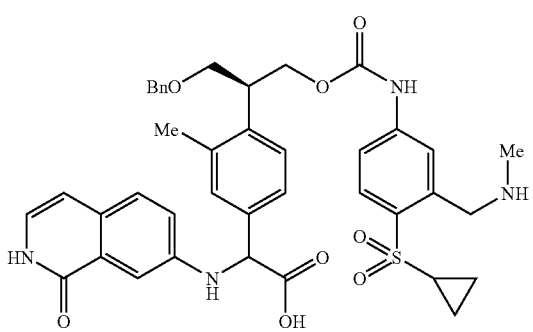 [SMILES: CNCc1cc(NC(=O)OC[C@H](COCc2ccccc2)c2ccc(C(Nc3ccc4cc[nH]c(=O)c4c3)C(=O)O)cc2C)ccc1S(=O)(=O)C1CC1]

To a solution of 163F (300 mg, 0.344 mmol) in EtOAc (10 mL) and MeOH (20 mL) was added Pd/C 10% (60 mg). The mixture was stirred under H$_2$ balloon for 2 h. Pd/C was filtered. The filtrate was concentrated to give 163G. MS (ESI) m/z 739 (M+H)$^+$. $^1$HNMR indicated a mixture of diastereoisomers.

Example 163

To a solution of BOP (192 mg, 0.433 mmol) and DMAP (106 mg, 0.866 mmol) in CH$_2$Cl$_2$ (60 mL) and DMF (6 mL) at it was added a solution of 163G (160 mg, 0.217 mmol) and DIEA (0.076 mL, 0.433 mmol) in DMF (5.0 mL) via a syringe pump over 10 h. To the reaction mixture was added 0.5 N HCl (30 mL), stirred for 10 min. The organic layer was collected and aqueous was extracted with CH$_2$Cl$_2$. The organic layers were washed with brine and dried over sodium sulfate. After evaporation of solvent, the crude residue was purified by a preparative HPLC equipped with a C18 Phenomenex Luna column (30 mm×100 mm, 5 g) with the UV detector set at 254 nm. The separations were performed using a gradient method: 20-100% B in 10 mins; then 100% B in 2 mins with a flow rate of 40 mL/min. Solvent B is 90% acetonitrile-10% water-0.1% TFA and solvent A is 10% acetonitrile-90% water-0.1% TFA. The desired fractions were collected and isomers were further purified and separated using a preparative HPLC equipped with a Regis Whelk-01 (R,R), 250×4.6 mm column using an isocratic method of 50% (50/50 Methanol-Ethanol): 50% Heptane, UV Detection: 254 nm with a flow rate of 20 mL/min. The peak eluted at retention time of 16.98 min was concentrated to give Example 163 (4.3 mg, 12% yield) as a white lyophilate: $^1$H NMR (400 MHz, CD$_3$OD) $\delta$ ppm 0.98-1.10 (m, 2H) 1.19-1.36 (m, 2H) 2.28 (s, 3H) 2.74-2.93 (m, 1H) 3.41 (s, 3H) 3.49-3.60 (m, 1H) 3.82-3.90 (m, 1H) 3.89-4.01 (m, 1H) 4.18-4.35 (m, 2H) 4.75 (t, J=10.77 Hz, 1H) 5.65 (s, 1H) 5.76 (d, J=17.58 Hz, 1H) 6.41 (s, 1H) 6.54 (d, J=7.03 Hz, 1H) 6.80-6.85 (m, 1H) 6.90 (d, J=7.03 Hz, 1H) 7.16 (s, 1H) 7.20-7.25 (m, 1H) 7.36-7.43 (m, 3H) 7.66 (d, J=7.47 Hz, 1H) 7.71 (d, J=8.79 Hz, 1H). MS (ESI) m/z 631 (M+H)$^+$; Analytical HPLC (Method A): Col A: 5.82 min, 96%; Col B: 5.75 min, 95%.

Example 164

(2R,15R)-7-Cyclopropanesulfonyl-15-hydroxy-4,17-dimethyl-2-(1-oxo-1,2-dihydro-isoquinolin-7-ylamino)-13-oxa-4,11-diaza-tricyclo[14.2.2.2.16,10]henicosa-1(19),6,8,10(21),16(20),17-hexaene-3,12-dione

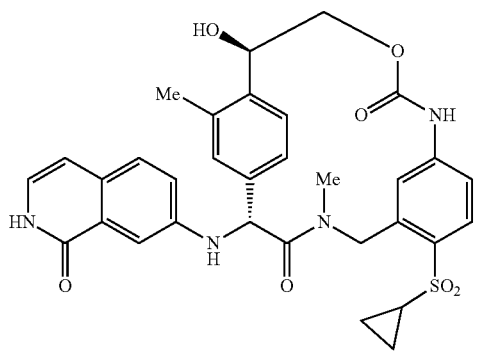 [SMILES: Cc1cc2ccc1[C@@H](O)COC(=O)Nc1ccc(S(=O)(=O)C3CC3)c(c1)CN(C)C(=O)[C@@H]2Nc1ccc2cc[nH]c(=O)c2c1]

164A

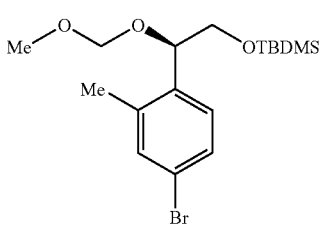 [SMILES: COCO[C@@H](CO[Si](C)(C)C(C)(C)C)c1ccc(Br)cc1C]

To 40E (2.8 g, 8.11 mmol) in dichloromethane (40 mL) was added DMAP (0.099 g, 0.811 mmol) and DIEA (7.08 mL, 40.5 mmol), followed by MeOCH$_2$Cl (1.848 mL, 24.32 mmol). The mixture was heated at 65° C. for 3.0 h. After it cooled to rt, the reaction mixture was washed with 0.5 N HCl, the organic layers were washed with sat. NaHCO$_3$, brine and dried over Na$_2$SO$_4$. The crude product was purified by column chromatography (0 to 30% EtOAc in hexanes) to obtain 164A (2.82 g, 7.24 mmol, 89% yield) as a clear liquid. $^1$H NMR (400 MHz, CDCl$_3$) δ ppm −0.02 (s, 3H) 0.01 (s, 3H) 0.86 (s, 9H) 2.33 (s, 3H) 3.35 (s, 3H) 3.62 (dd, J=10.99, 4.39 Hz, 1H) 3.76 (dd, J=10.77, 7.69 Hz, 1H) 4.52 (d, J=6.59 Hz, 1H) 4.64 (d, J=6.59 Hz, 1H) 4.90 (dd, J=7.69, 4.17 Hz, 1H) 7.27 (d, J=9.23 Hz, 2H) 7.30-7.35 (m, 1H).

164B Br

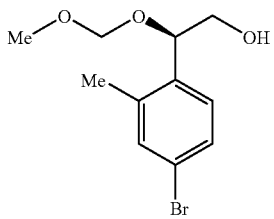 [SMILES: COCO[C@@H](CO)c1ccc(Br)cc1C]

To 164A (2.8 g, 7.19 mmol) in THF (20 mL) at 0° C. was added 1.0N TBAF in THF (10.79 mL, 10.79 mmol). The mixture was stirred at rt for 1.0 h. It was diluted with EtOAc and quenched with sat. NH$_4$Cl. The organic layers were washed with brine and dried over Na$_2$SO$_4$. The crude product was purified by column chromatography (0 to 50% EtOAc in hexanes) to obtain 164B (1.9 g, 6.91 mmol, 96% yield) as a viscous oil. $^1$H NMR (400 MHz, CD$_3$OD) δ ppm 2.32 (s, 3H) 3.40 (s, 3H) 3.52-3.71 (m, 2H) 4.57-4.61 (m, 1H) 4.61-4.67 (m, 1H) 4.89 (dd, J=8.35, 3.52 Hz, 1H) 7.21-7.28 (m, 1H) 7.28-7.36 (m, 2H).

164C

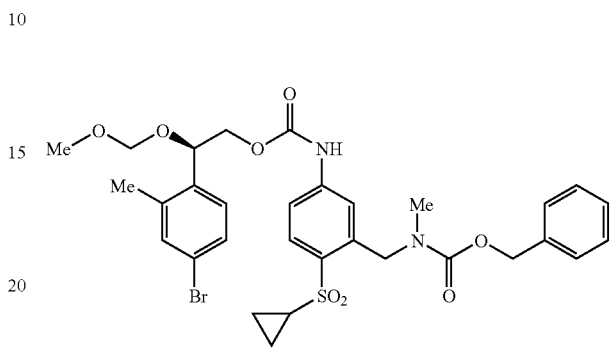

Using a procedure analogous to that used to prepare 29A, 39E (300 mg, 0.801 mmol) was reacted with sodium bicarbonate and phosgene followed by 164B and TEA. The crude product was added to a silica gel column (40 g) and was eluted with EtOAc/hexanes (0-100%) to give to give 164C (510 mg, 0.755 mmol, 94% yield) as a white solid. $^1$H NMR (400 MHz, DMSO-d$_6$) δ ppm 0.83-0.95 (m, 1H) 1.03 (d, J=11.86 Hz, 3H) 2.34 (s, 3H) 2.91-3.02 (m, 4H) 3.21 (s, 3H) 4.16-4.32 (m, 2H) 4.45 (s, 1H) 4.60 (d, J=6.59 Hz, 1H) 4.88 (s, 2H) 4.98-5.10 (m, 2H) 5.15 (s, 1H) 7.11-7.46 (m, 8H) 7.50 (d, J=7.91 Hz, 1H) 7.61-7.70 (m, 1H) 7.76 (t, J=7.69 Hz, 1H); MS (ESI) m/z 675, 677 (M+H)$^+$.

164D

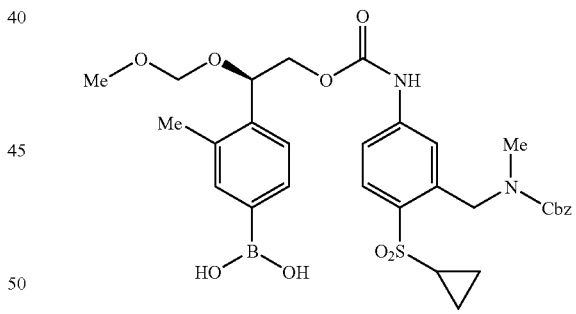

Using a procedure analogous to that used to prepare 29B, 164C (500 mg, 0.740 mmol) was reacted with bis(neopentyl glycolato)diboron), potassium acetate and. (1,1'-bis(diphenylphosphino)ferrocene)-dichloropalladium(II). The crude was purified by flash chromatography (EtOAc/hexanes 2% to 100%) and preparative HPLC (CH$_3$CN/H$_2$O, 0.1% TFA) to yield 164D (298 mg, 0.395 mmol, 53.4% yield) as a white solid. $^1$H NMR (400 MHz, acetonitrile-d$_3$) d ppm 0.80-1.35 (m, 4H) 2.40 and 2.49 (s, 3H) 2.51-2.73 (m, 1H) 3.02 (s, 3H) 3.30 and 3.32 (s, 3H) 4.24-4.34 (m, 2H) 4.49 and 4.54 (d, J=6.59 Hz, 1H) 4.61 and 4.65 (d, J=6.59 Hz, 1H) 4.91 (s, 2H) 5.06 (s, 1H) 5.12-5.27 (m, 2H) 7.12 (s, 1H) 7.23 (s, 2H) 7.32-7.49 (m, 3H) 7.60 (q, J=7.62 Hz, 3H) 7.80 (d, J=6.59 Hz, 1H) 7.91-8.04 (m, 1H) 8.21 (s, 1H); MS (ESI) m/z 641 (M+H)$^+$.

164E

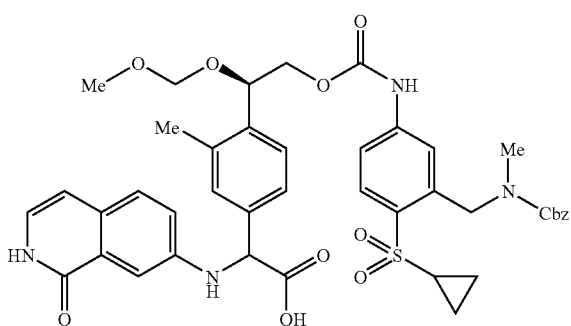 [SMILES: COCO[C@@H](COC(=O)Nc1ccc(S(=O)(=O)C2CC2)c(CN(C)C(=O)OCc2ccccc2)c1)c1ccc(C(Nc2ccc3cc[nH]c(=O)c3c2)C(=O)O)cc1C]

Using a procedure analogous to that used to prepare 1E, 164D (290 mg, 0.384 mmol), Intermediate 3, and glyoxylic acid monohydrate were reacted and purified by flash chromatography (1% to 20% MeOH in $CH_2Cl_2$) to give 164E (150 mg, 0.221 mmol, 57.5% yield) as a slightly yellow solid. MS (ESI) m/z 831 (M+H)+. $^1$H NMR indicated a mixture of diastereoisomers and rotamers.

164F

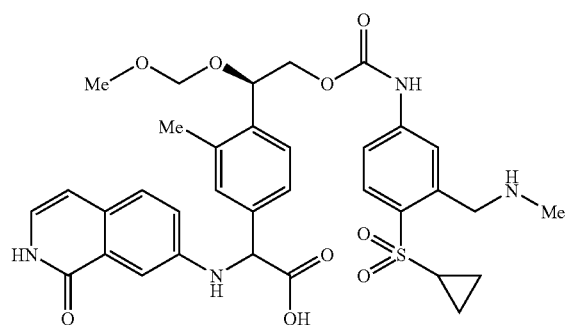 [SMILES: CNCc1cc(NC(=O)OC[C@H](OCOC)c2ccc(C(Nc3ccc4cc[nH]c(=O)c4c3)C(=O)O)cc2C)ccc1S(=O)(=O)C1CC1]

Using a procedure analogous to that used to prepare 163G, 164E was hydrogenated to give 164F. MS (ESI) m/z 679 (M+H)+. $^1$H NMR indicated a mixture of diastereoisomers.

164G

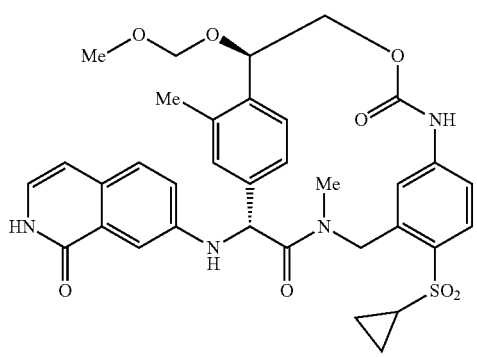 [SMILES: COCO[C@H]1COC(=O)Nc2ccc(S(=O)(=O)C3CC3)c(c2)CN(C)C(=O)[C@H](Nc2ccc3cc[nH]c(=O)c3c2)c2ccc1c(C)c2]

To a solution of BOP (195 mg, 0.442 mmol) and DMAP (108 mg, 0.884 mmol) in $CH_2Cl_2$ (50 mL) and DMF (3 mL) at rt was added a solution of 164F (150 mg, 0.221 mmol) and DIEA (0.077 mL, 0.442 mmol) in DMF (5.0 mL) via a syringe pump over 10.0 h at rt. The reaction was quenched by $H_2O$, the organic layer was washed by brine and dried over $MgSO_4$. The crude was purified by prep HPLC ($CH_3CN$/$H_2O$, 0.1% TFA) and then by a Chiral Regis Whelk-10 (R,R), 250×20 mm column eluting with 60% (50/50 Methanol-Ethanol): 40% Heptane at 20 mL/min to obtain the first peak (RT=6.21 min) and the second peak (RT=12.4 min). The second peak was confirmed to be 164G. $^1$H NMR (400 MHz, methanol-$d_4$) δ ppm 1.15 (d, J=6.59 Hz, 3H) 1.91 (s, 3H) 2.88 (s, 3H) 3.13-3.24 (m, 5H) 3.73-3.91 (m, 2H) 5.28 (d, J=16.70 Hz, 1H) 5.58 (s, 1H) 6.40 (d, J=23.73 Hz, 1H) 6.59-6.92 (m, 4H) 7.01-7.40 (m, 6H) 7.54 (s, 1H). MS (ESI) m/z 661 (M+H)+.

Example 164

To MeOH (4 mL) and MeCN (4.00 mL) was added conc. HCl (120 μL). To 164G (8 mg, 0.012 mmol) was added the above prepared solution (1.0 mL). The reaction was stirred at 65° C. for 30 min in a microwave reactor. The reaction mixture was concentrated. The residue was purified using a preparative HPLC equipped with a C18 Phenomenex Luna AXIA column (30 mm×75 cm, 5 m) with the UV detector set at 254 nm. The separations were performed using a gradient method: 10-90% B in 10 mins; then 90% B in 2 mins with a flow rate of 40 mL/min. Solvent B is 90% acetonitrile-10% water-0.1% TFA and solvent A is 10% acetonitrile-90% water-0.1% TFA. RT=5.49 min. Example 164 (7 mg, 9.58 mol, 79% yield) was obtained as a white lyophilate. Chiral HPLC: Column: Regis Whelk-Ol (R,R), 250×4.6 mm ID; 10 μm, Mobile Phase: 60% (50/50 Methanol-Ethanol): 40% Heptane, UV Detection: 254 nm, Retention Time 5.96 min. $^1$H NMR (400 MHz, $CD_3OD$) δ ppm 1.03-1.28 (m, 4H) 2.38 (s, 3H) 2.83-2.92 (m, 1H) 3.24 (s, 3H) 4.05-4.18 (m, 1H) 4.31 (d, J=17.14 Hz, 1H) 4.56 (t, J=10.33 Hz, 1H) 5.19 (dd, J=10.33, 5.05 Hz, 1H) 5.80 (d, J=17.14 Hz, 1H) 5.89 (s, 1H) 6.41 (d, J=1.76 Hz, 1H) 6.66 (d, J=6.59 Hz, 1H) 6.81-6.88 (m, 1H) 7.17 (d, J=7.03 Hz, 1H) 7.29 (s, 1H) 7.44 (d, J=7.91 Hz, 1H) 7.55-7.62 (m, 1H) 7.67 (dd, J=8.13, 4.17 Hz, 2H) 7.72-7.76 (m, 1H) 8.01 (s, 1H). MS (ESI) m/z 617 (M+H)+. Analytical HPLC (Method B): Col A: 5.87 min, 100%; Col B: 5.80 min, 94%.

Example 165

(2R,15R)-4,15,17-Trimethyl-2-(1-oxo-1,2-dihydro-isoquinolin-7-ylamino)-7-(pyridin-2-yloxy)-13-oxa-4,11-diaza-tricyclo[14.2.2.1$^{6,10}$]henicosa-1(19),6,8,10(21),16(20),17-hexaene-3,12-dione

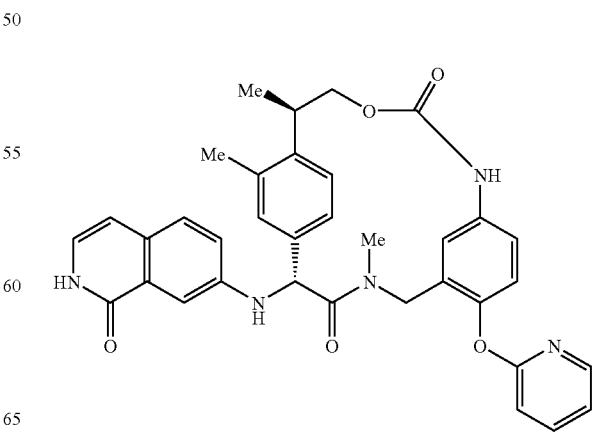

165A

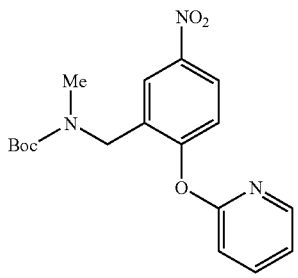

Intermediate 18 (1.000 g, 2.90 mmol), pyridin-2(1H)-one (0.275 g, 2.90 mmol), quinolin-8-ol (0.084 g, 0.579 mmol), copper(I) iodide (0.110 g, 0.579 mmol) and potassium carbonate (0.520 g, 3.77 mmol) were mixed in DMSO (2.90 mL). The reaction mixture was degassed (3× Ar/vacuum), sealed and heated at 100° C. overnight. The reaction mixture was poured into $NH_3$ (aq, 10%, 20 mL), and then EtOAc (50 mL) was added. The mixture was vigorously stirred for 10 min. The water phase was separated and extracted with EtOAc (3×). The combined organic phase was washed with water (2×), brine, dried ($Na_2SO_4$) and evaporated. The crude residue was purified by flash chromatography: 0-80% EtOAc/hex to afford 165A (0.360 g, 1.002 mmol, 34.6% yield) as a yellow oil. MS (ESI) m/z 360.1 $(M+H)^+$. $^1$H-NMR: (500 MHz, $CDCl_3$) δ ppm 8.12-8.30 (3H, m), 7.79 (1H, d, J=7.15 Hz), 7.19 (1H, d, J=8.25 Hz), 6.99-7.15 (2H, m), 4.43-4.61 (2H, m), 2.79-2.98 (3H, m), 1.47 (9H, d, J=18.15 Hz).

165B

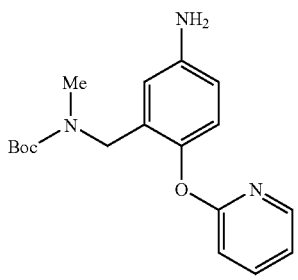 [SMILES: CN(Cc1cc([N+](=O)[O-])ccc1Oc1ccccn1)C(=O)OC(C)(C)C]

To a solution of 165A (0.360 g, 1.002 mmol) in methanol (10 mL) and THF (2 mL) was added zinc (dust) (0.655 g, 10.02 mmol) and ammonium chloride (1.072 g, 20.03 mmol). The resulting solution was stirred at 40° C. overnight. MeOH was removed under reduced pressure. To the solid residue, $Na_2CO_3$ (aq, 100 mL) and EtOAc (150 mL) were added, and the suspension was stirred vigorously for 10 min. The mixture was filtered and the solid residue was washed with EtOAc (3×). The combined organic phase was washed with water (2×) and brine, dried ($Na_2SO_4$), and evaporated. The crude product was purified by flash chromatography: 0-100% EtOAc/hex. to give 165B (0.288 g, 0.874 mmol, 87% yield) as a colorless syrup. MS (ESI) m/z 330.2 $(M+H)^+$. $^1$H-NMR: (500 MHz, $CDCl_3$) δ ppm 8.16 (1H, d, J=3.30 Hz), 7.63 (1H, d, J=5.50 Hz), 6.93 (1H, d, J=4.40 Hz), 6.88 (1H, d, J=8.25 Hz), 6.82 (1H, d, J=6.60 Hz), 6.53-6.69 (2H, m), 4.31 (2H, d, J=13.75 Hz), 3.63 (2H, br. s.), 2.71-2.89 (3H, m), 1.44 (9H, d, J=19.25 Hz).

165C

To a mixture of 165B (0.288 g, 0.874 mmol) and sodium bicarbonate (0.245 g, 2.91 mmol) in DCM (10 mL) at 0° C., was added phosgene (20% in toluene) (0.865 mL, 1.749 mmol). The mixture was stirred at 0° C. for 30 min, then was filtered. The filtrate was concentrated. The resultant oil was dissolved in DCM (5 mL) and cooled to 0° C., a solution of Intermediate 16 (0.222 g, 0.583 mmol) in DCM (2 mL) was added, followed by TEA (0.406 mL, 2.91 mmol). The mixture was stirred at 0° C. for 1 h, then at rt for 3 h. The solvent was evaporated and the resultant residue purified by flash chromatography 0-100% EtOAc/hexanes to afford 165C (0.139 g, 0.189 mmol, 32.4% yield) as a yellow glass. MS (ESI) m/z 736.3 $(M+H)^+$.

165D

To a solution of 165C (0.139 g, 0.189 mmol) in THF (1.5 mL), MeOH (1.5 mL) and water (1 mL) at 0° C., was added lithium hydroxide (0.023 g, 0.945 mmol). The reaction mixture was stirred at 0° C. for 1.5 h, then was diluted with water. The volatile solvents were removed under reduced pressure. The remaining aqueous phase was extracted with $Et_2O$. The aqueous phase was acidified to pH~3 with std. aq. citric acid, then was extracted with EtOAc (5×). The combined organic phase was washed with water (3×), dried ($Na_2SO_4$), and concentrated to give the carboxylic acid as a yellow foam. To a solution of this product in EtOAc (5 mL) and DCM (5 mL), was added HCl (4 M in dioxane, 5 mL). The reaction mixture was stirred for 1 h at rt, then was concentrated to afford 165D (0.114 g, 0.173 mmol, 92% yield) as a white solid. MS (ESI) m/z 622.2 $(M+H)^+$.

Example 165

To a solution of BOP (306 mg, 0.693 mmol) and DMAP (148 mg, 1.213 mmol) in DCM (75 mL) and DMF (10 mL) at 40° C., was added a solution of 165D (114 mg, 0.173 mmol) and DIEA (0.346 mmol) in DMF (5 mL), dropwise via a syringe pump; 3 h addition. The reaction was removed from the heating bath, stirred for 30 min, and then quenched with H$_2$O (1 mL) and concentrated. The residue was purified by prep HPLC (CH$_3$CN/H$_2$O+TFA). The diastereomers were separated by chiral HPLC (R,R-Whelk-0 column (21.1×250 mm, 100% (MeOH/EtOH 1:1), 20 mL/min) to afford the inactive diastereomer RT=5.06 min, followed by Example 165 (15.34 mg, 0.025 mmol, 29.3% yield.) RT=12.28 min. MS (ESI) a/z 604.3 (M+H)$^+$. $^1$H-NMR: (400 MHz, CD$_3$OD) δ ppm 8.09 (1H, d, J=3.85 Hz), 7.73-7.83 (1H, m), 7.63 (1H, d, J=8.24 Hz), 7.42 (1H, d, J=8.25 Hz), 7.39 (2H, dd, J=5.50, 2.75 Hz), 7.19-7.28 (2H, m), 7.07 (1H, dd, J=7.15, 4.95 Hz), 6.90 (3H, t, J=7.15 Hz), 6.76 (1H, dd, J=8.24, 2.75 Hz), 6.53 (1H, d, J=7.15 Hz), 6.02 (1H, d, J=2.75 Hz), 5.62 (1H, s), 5.30 (1H, d, J=17.04 Hz), 4.66 (1H, t, J=10.99 Hz), 3.96 (1H, dd, J=10.72, 4.12 Hz), 3.76 (1H, d, J=17.04 Hz), 3.42-3.54 (1H, m), 3.28 (3H, s), 2.34 (3H, s), 1.30 (3H, d, J=6.60 Hz). Analytical HPLC (Method A): Col A: 7.14 min, 99%; Col B: 7.01 min, 99%.

Example 166

(2R,15R)-4,15,17-Trimethyl-7-(3-methyl-2-oxo-imidazolidin-1-yl)-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione To a mixture of Intermediate 18 (518 mg, 1.5 mmol), 1-methylimidazolidin-2-one (225 mg, 2.250 mmol), 9,9-dimethyl-4,5-bis(diphenylphosphino)xanthene (260 mg, 0.450 mmol), palladium(II) acetate (67.4 mg, 0.300 mmol), and cesium carbonate (977 mg, 3.00 mmol) in a degassed, N$_2$-filled, sealed tube, was added toluene (5 mL). The mixture was stirred at 90° C. for 60 h, then was quenched with water and extracted with DCM (3×). The combined organic layer was washed with 1N HCl, sat. NaHCO$_3$ and brine, dried (Na$_2$SO$_4$) and concentrated. The crude product was purified by flash chromatography (0 to 100% EtOAc/hexanes) to afford 166A (430 mg, 1.121 mmol, 74.7% yield). MS (ESI) m/z 365.4 (M+H)$^+$.

Example 166

A was used to prepare Example 166 according to the sequence for the preparation of Example 165. Chiralcel OD-H 250×20 mm (L X OD); 20 mL/min 70:30 (1:1 MeOH/EtOH)/heptane afforded Example 166, followed by the phenylglycine diastereomer. MS (ESI) m/z 609.5 (M+H)$^+$. $^1$H NMR (400 MHz, METHANOL-d$_4$) b ppm 7.37-7.62 (m, 4H) 7.26-7.32 (m, 1H) 7.22 (s, 1H) 7.09 (d, J=8.35 Hz, 1H) 6.92-6.97 (m, 1H) 6.70-6.76 (m, 1H) 6.56 (d, J=7.03 Hz, 1H) 6.10 (s, 1H) 5.66 (s, 1H) 5.30 (d, J=16.70 Hz, 1H) 4.61 (t, J=10.99 Hz, 1H) 3.84-3.99 (m, 2H) 3.67-3.78 (m, 2H) 3.42-3.56 (m, 3H) 3.34 (s, 3H) 2.77-2.88 (m, 3H) 2.33 (s, 3H) 1.30 (d, J=6.59 Hz, 3H).

Example 167

(2R,15R)-8-Fluoro-7-isopropoxy-4,15,15,17-trimethyl-2-(1-oxo-1,2-dihydro-isoquinolin-7-ylamino)-13-oxa-4,11-diaza-tricyclo[14.2.2.1$^{6,10}$]henicosa-1(19),6,8,10(21),16(20),17-hexaene-3,12-dione

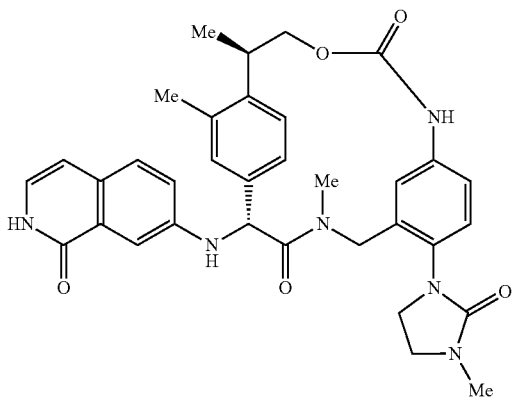 [SMILES: Cc1cc2ccc1[C@@H](C)COC(=O)Nc1ccc(N3CCN(C)C3=O)c(c1)CN(C)C(=O)[C@@H]2Nc1ccc2cc[nH]c(=O)c2c1]

166A

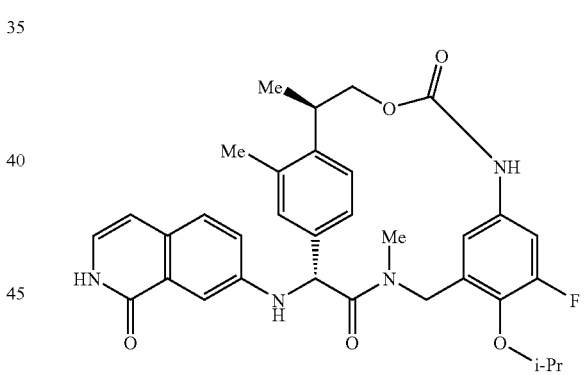

167A

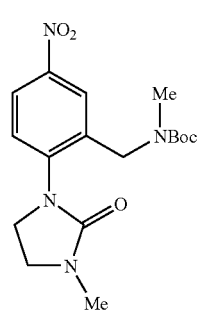 [SMILES: CN(Cc1cc([N+](=O)[O-])ccc1N1CCN(C)C1=O)C(=O)OC(C)(C)C]

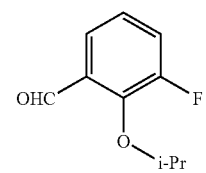 [SMILES: CC(C)Oc1c(F)cccc1C=O]

To a solution of 3-fluoro-2-hydroxybenzaldehyde (1.36 g, 9.71 mmol) in DMF (50 mL), was added 2-iodopropane (4.85 mL, 48.5 mmol). The mixture was stirred at 55° C. overnight, then was quenched with H$_2$O. The aqueous phase was extracted with EtOAc (3×). The combined organic layer was washed with water and brine, dried (Na$_2$SO$_4$) and concentrated. The crude material was purified by flash chromatography (0-10% EtOAc in hexanes) to afford 167A (1.58 g, 8.59 mmol, 88% yield) as a colorless oil. MS (ESI) m/z 183.2 (M+H)$^+$. $^1$H NMR (400 MHz, CDCl$_3$) δ ppm 10.32 (s, 1H) 7.52 (d, J=7.91 Hz, 1H) 7.18-7.26 (m, 1H) 6.96-7.04 (m, 1H) 4.49-4.62 (m, 1H) 1.28 (d, J=6.15 Hz, 6H).

167B

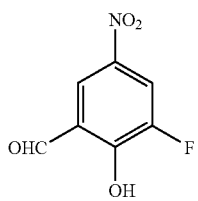 [SMILES: O=Cc1cc([N+](=O)[O-])cc(F)c1O]

Potassium nitrate (220 mg, 2.174 mmol) was added portion-wise to a solution of 167A (360 mg, 1.976 mmol) in sulfuric acid (2 mL, 37.5 mmol) at 0° C. over 10 min. The mixture was stirred at 0° C. for 1.75 h, then was poured over ice water. The aqueous phase was extracted with EtOAc (3×). The combined organic layer was washed with water and brine, dried (Na$_2$SO$_4$) and concentrated. The crude material was purified by flash chromatography (0-80% EtOAc in hexanes) to afford 167B (210 mg, 1.134 mmol, 57.4% yield) as a light yellow solid. $^1$H NMR (400 MHz, CHLOROFORM-D) δ ppm 11.62 (s, 1H) 10.02 (d, J=1.76 Hz, 1H) 8.41 (d, J=1.76 Hz, 1H) 8.23 (dd, J=10.11, 2.64 Hz, 1H).

167C

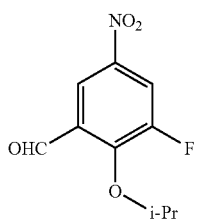 [SMILES: CC(C)Oc1c(F)cc([N+](=O)[O-])cc1C=O]

To a solution of 167B (188 mg, 1.016 mmol) in DMF (50 mL), was added 2-iodopropane (0.508 mL, 5.08 mmol). The mixture was stirred 55° C. overnight, then was quenched with H$_2$O. The aqueous phase was extracted with EtOAc (3×). The combined organic layer was washed with water and brine, dried (Na$_2$SO$_4$) and concentrated. The crude material was purified by flash chromatography (0-40% EtOAc in hexanes) to afford 167C (210 mg, 0.915 mmol, 90% yield) as a light yellow solid. $^1$H NMR (400 MHz, CHLOROFORM-D) δ ppm 10.39 (s, 1H) 8.49 (s, 1H) 8.18 (dd, J=11.64, 2.86 Hz, 1H) 4.96 (td, J=6.15, 1.76 Hz, 1H) 1.43 (d, J=6.15 Hz, 6H).

167D

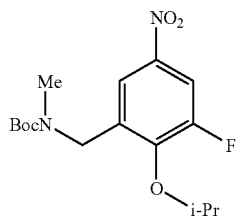

To a solution of 167C (210 mg, 0.924 mmol) in MeOH (6 mL), was added methylamine (2M, EtOH) (0.92 mL, 1.85 mmol). The mixture was stirred at rt for 1 h, then was cooled to 0° C. and sodium borohydride (105 mg, 2.77 mmol) was added. The mixture was stirred at rt for 1 h, then was concentrated. The residue was mixed with sodium bicarbonate (123 mg, 1.459 mmol) in water (5 mL) and THF (5 mL). (Boc)$_2$O (127 mg, 0.583 mmol) was added. The mixture was stirred rt for 1 h. The reaction mixture was extracted with EtOAc (3×). The combined organic phase was washed with water and brine, dried (Na$_2$SO$_4$), and concentrated. The crude material was purified by flash chromatography (0-50% EtOAc in hexanes) to afford 167D (322 mg, 0.875 mmol, 95% yield). MS (ESI) m/z 343.4 (M+H)$^+$.

Example 167

167D was used to prepare Example 167 according to the sequence for the preparation of Example 165. MS (ESI) m/z 587.5 (M+H)$^+$. $^1$H NMR (400 MHz, METHANOL-D$_4$) δ ppm 7.60 (d, J=7.91 Hz, 1H) 7.35-7.43 (m, 3H) 7.20-7.25 (m, 2H) 6.89 (d, J=7.03 Hz, 1H) 6.48-6.55 (m, 2H) 5.68 (s, 1H) 5.62 (s, 1H) 5.36 (d, J=17.14 Hz, 1H) 4.62 (t, J=10.99 Hz, 1H) 4.37-4.47 (m, 1H) 3.93 (dd, J=10.77, 4.17 Hz, 1H) 3.88 (d, J=17.14 Hz, 1H) 3.39-3.50 (m, 1H) 3.27 (s, 3H) 2.29 (s, 3H) 1.23-1.31 (m, 9H).

Example 168

(2R,15R)-4,15,17-Trimethyl-7-(3-oxo-2-aza-bicyclo [2.2.2]oct-2-yl)-2-(1-oxo-1,2-dihydro-isoquinolin-7-ylamino)-13-oxa-4,11-diaza-tricyclo[14.2.2.1$^{6,10}$] henicosa-1(19),6,8,10(21),16(20),17-hexaene-3,12-dione

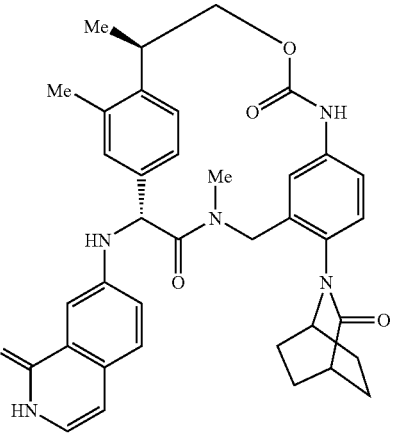

According to the sequence for the preparation of Example 90, replacement of piperidin-2-one with 2-azabicyclo[2.2.2] octan-3-one (Chung, J. Y. L. and Ho, G. J. Syn. Comm., 2002, 32, 1985-1995) afforded Example 168. Chiralcel OD-H 250× 20 mm (L × OD); 20 mL/min 50:50 (1:1 MeOH/EtOH)/ heptane RT=4.52 min (Example 168) and 6.32 min (phenylglycine diastereomer). MS (ESI) m/z 634.3 (M+H)$^+$. $^1$H NMR (400 MHz, METHANOL-d$_3$) δ ppm 7.39-7.63 (4H, m), 7.29 (1H, dd, J=8.79, 6.60 Hz), 7.18 (1H, s), 7.05-7.11 (1H, m), 6.93-7.00 (1H, m), 6.71-6.81 (1H, m), 6.56 (1H, d, J=6.60 Hz), 6.17 (0.7H, d, J=1.65 Hz), 6.02 (0.3H, s), 5.67 (1H, s), 5.57 (0.3H, d, J=17.04 Hz), 5.13 (0.7H, d, J=16.49 Hz), 4.63 (1H, t, J=10.99 Hz), 3.81-4.01 (2.7H, m), 3.66 (0.3H, d, J=16.49 Hz), 3.48 (1H, dd, J=18.14, 4.40 Hz), 3.36 (2H, s), 3.17 (1H, s), 2.61 (1H, br. s.), 2.36 (1H, s), 2.32 (2H, s), 2.09 (2H, d, J=6.05 Hz), 1.74-1.97 (6H, m), 1.31 (3H, d, J=7.15 Hz) atropisomers: ~2:1. Analytical HPLC (Method A): Col A: 6.31 min, 95.9%; Col B: 6.30 min, 97.5%.

Example 169

(2R,15R)-4,15,17-Trimethyl-2-(1-oxo-1,2-dihydro-isoquinolin-7-ylamino)-7-(2-oxo-perhydro-azepin-1-yl)-13-oxa-4,11-diaza-tricyclo[14.2.2.1$^{6,10}$]henicosa-1(19),6,8,10(21),16(20),17-hexaene-3,12-dione

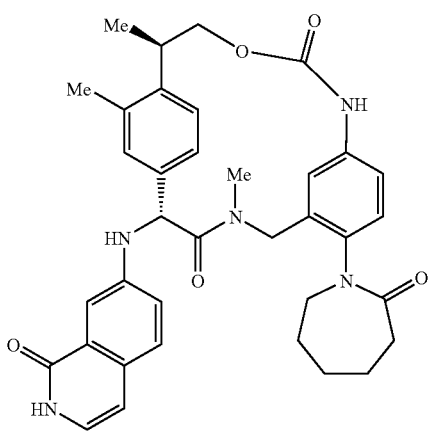 [SMILES: Cc1cc2ccc1[C@@H](C)COC(=O)Nc1ccc(N3CCCCCC3=O)c(c1)CN(C)C(=O)[C@@H]2Nc1ccc2cc[nH]c(=O)c2c1]

169A

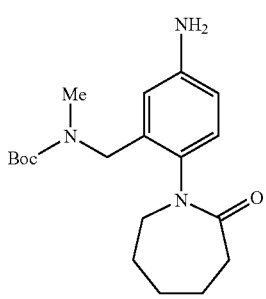 [SMILES: CN(Cc1cc(N)ccc1N1CCCCCC1=O)C(=O)OC(C)(C)C]

According to the sequence for the preparation of 90B, replacement of piperidin-2-one with azepan-2-one afforded 169A. MS (ESI) m/z 348.2 (M+H)$^+$. $^1$H-NMR (500 MHz, CDCl$_3$) δ ppm 6.88 (1H, d, J=8.25 Hz), 6.57 (1H, dd, J=8.52, 2.47 Hz), 6.48 (1H, br. s.), 4.28-4.71 (1H, m), 3.95-4.23 (1H, m), 3.68 (3H, s), 3.48 (2H, d, J=4.95 Hz), 2.61-2.91 (4H, m), 1.71-1.98 (6H, m), 1.38-1.57 (9H, m).

169B

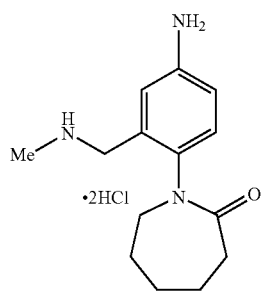 [SMILES: CNCc1cc(N)ccc1N1CCCCCC1=O ; "·2HCl"]

169A (0.328 g, 0.944 mmol) was dissolved in EtOAc (5 mL) and DCM (5 mL), then HCl (4 M in dioxane, 5 mL) was added. The reaction mixture was stirred for 1 h at it. The solvent was evaporated to give 169B (0.300 g, 0.937 mmol, 99% yield) as a pink solid. MS (ESI) m/z 248.2 (M+H)$^+$.

169C

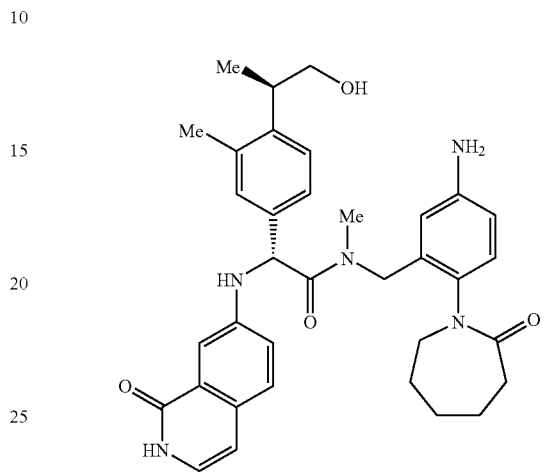

Using a procedure analogous to that used to prepare 41E, a mixture of Intermediate 10 (241 mg, 0.781 mmol), Intermediate 3 and 2-oxoacetic acid hydrate were reacted. The resulting solution was reacted with 168B (300 mg, 0.937 mmol) using BOP and DIEA. The crude product was purified column chromatography (1 to 15% methanol/methylene chloride) to afford 169C (224 mg, 0.376 mmol, 48.2% yield) as a yellow solid. MS (ESI) m/z 596.3 (M+H)$^+$.

Example 169

According to the procedure for the preparation of Example 90, 169C (0.227 g, 0.381 mmol) was cyclized to afford Example 169 (15.1 mg, 0.024 mmol, 12.75% yield) as a yellow powder. Chiralcel OD-H 250×20 mm (L X OD); 20 mL/min 50:50 (1:1 MeOH/EtOH)/heptane RT=4.60 min (Example 169) and 7.82 min (phenylglycine diastereomer). MS (ESI) m/z 622.3 (M+H)$^+$. $^1$H NMR (400 MHz, METHANOL-d$_4$) d ppm 7.51-7.63 (2H, m), 7.39-7.50 (2H, m), 7.27-7.35 (1.3H, m), 7.22 (0.7H, s), 6.99 (2H, dd, J=23.64, 7.70 Hz), 6.74 (1H, dd, J=8.25, 2.75 Hz), 6.56 (1H, d, J=7.15 Hz), 6.12 (0.7H, d, J=2.20 Hz), 5.99 (0.3H, d, J=2.20 Hz), 5.68 (1H, s), 5.43 (0.3H, d, J=17.04 Hz), 5.23 (0.7H, d, J=17.04 Hz), 4.62 (1H, t, J=10.72 Hz), 3.96 (1H, dd, J=10.44, 3.85 Hz), 3.69-3.86 (3H, m), 3.57-3.67 (1H, m), 3.42-3.57 (2H, m), 3.18 (1H, s), 2.72 (1H, d, J=10.44 Hz), 2.61 (1H, dd, J=14.02, 7.97 Hz), 2.34 (1H, s), 2.32 (2H, s), 1.85 (6H, d, J=18.14 Hz), 1.30 (3H, d, J=7.15 Hz) atropisomers. Analytical HPLC (Method A): Col A: 6.33 min, 98.0%; Col B: 6.33 min, 100%.

Example 170

(2R,15R)-4,15,17-Trimethyl-2-(1-oxo-1,2-dihydro-isoquinolin-7-ylamino)-7-(2-oxo-oxazolidin-3-yl)-13-oxa-4,11-diaza-tricyclo[14.2.2.1$^{6,10}$]henicosa-1(19),6,8,10(21),16(20),17-hexaene-3,12-dione

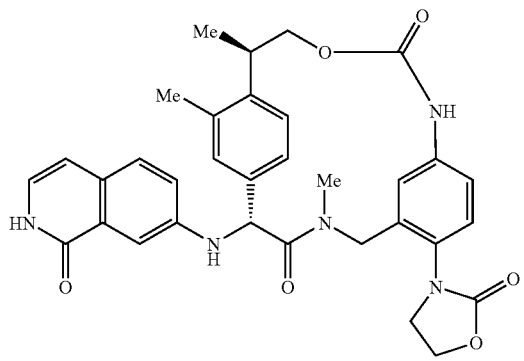 [SMILES: Cc1cc2ccc1[C@@H](C)COC(=O)Nc1ccc(N3CCOC3=O)c(c1)CN(C)C(=O)[C@@H]2Nc1ccc2cc[nH]c(=O)c2c1]

170A

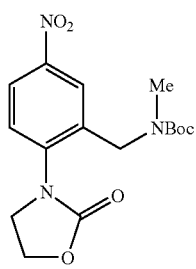

According to the procedure for the preparation of 166A, replacement of 1-methylimidazolidin-2-one with 2-oxazolidone afforded 170A. MS (ESI) m/z 352.3 (M+H)$^+$.

Example 170

According to the sequence for the preparation of Example 165, 170A was used to prepare Example 170. Chiralcel OD-H 250×20 mm (L X OD); 20 mL/min 25:75 (1:1 MeOH/EtOH)/heptane+0.1% DEA (Example 170), followed by the phenylglycine diastereomer. MS (ESI) m/z 596.5 (M+H)$^+$. $^1$H NMR (400 MHz, METHANOL-D4) δ ppm 7.59 (d, J=7.91 Hz, 1H) 7.50 (d, J=2.20 Hz, 1H) 7.43 (t, J=8.13 Hz, 2H) 7.28 (d.d, J=8.57, 2.42 Hz, 1H) 7.18-7.23 (m, 2H) 6.94 (d, J=7.03 Hz, 1H) 6.76 (dd, J=8.35, 2.20 Hz, 1H) 6.55 (d, J=7.03 Hz, 1H) 6.15 (d, J=2.20 Hz, 1H) 5.66 (s, 1H) 5.32 (d, J=16.70 Hz, 1H) 4.62 (t, J=10.99 Hz, 1H) 4.51 (t, J=7.91 Hz, 2H) 3.86-4.05 (m, 4H) 3.43-3.53 (m, 1H) 3.32 (s, 3H) 2.32 (s, 3H) 1.30 (d, J=7.03 Hz, 3H). Analytical HPLC (Method A): Col A: 6.24 min, 89.0%; Col B: 6.17 min, 97.3%.

Example 171

(2R,15R)-4,15,17-Trimethyl-7-((1S,4R)-3-oxo-2-aza-bicyclo[2.2.1]hept-2-yl)-2-(1-oxo-1,2-dihydro-isoquinolin-7-ylamino)-13-oxa-4,11-diaza-tricyclo[14.2.2.1$^{6,10}$]henicosa-1(19),6,8,10(21),16(2),0),17-hexaene-3,12-dione

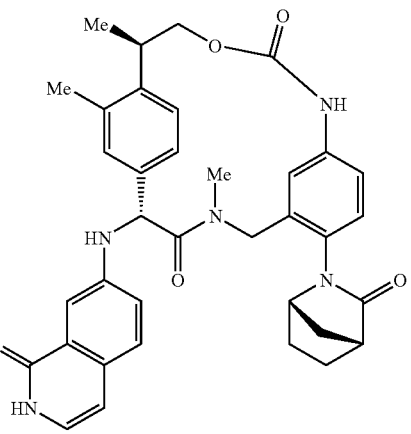

According to the sequence for the preparation of Example 90, replacement of piperidin-2-one with (1S,4R)-2-azabicyclo[2.2.1]heptan-3-one afforded Example 171. Chiralcel OD-H 250×20 mm (L X OD); 20 mL/min 60:40 (1:1 MeOH/EtOH)/heptane RT=4.48 min (Example 171) and 6.22 min (phenylglycine diastereomer). MS (ESI) m/z 620.2 (M+H)$^+$. $^1$H-NMR (500 MHz, CD$_3$OD) δ ppm 7.54-7.60 (2H, m), 7.42 (2H, dd, J=11.55, 8.25 Hz), 7.30 (1H, dd, J=8.52, 2.47 Hz), 7.24 (1H, s), 6.96 (2H, t, J=8.52 Hz), 6.72 (1H, dd, J=8.25, 2.75 Hz), 6.55 (1H, d, J=6.60 Hz), 6.13 (1H, d, J=2.75 Hz), 5.69 (1H, s), 5.28 (1H, d, J=17.05 Hz), 4.60 (1H, t, J=11.00 Hz), 4.17 (1H, s), 3.95 (1H, dd, J=10.72, 4.12 Hz), 3.82 (1H, d, J=16.50 Hz), 3.46 (1H, ddd, J=11.13, 7.01, 4.40 Hz), 3.28 (3H, s), 2.86 (1H, d, J=2.75 Hz), 2.31 (3H, s), 2.13 (1H, d, J=9.35 Hz), 2.01-2.10 (1H, m), 1.88-1.96 (2H, m), 1.66-1.75 (1H, m), 1.56 (1H, d, J=9.35 Hz), 1.29 (3H, d, J=7.15 Hz). Analytical HPLC (Method A): Col A: 5.22 min, 99%; Col B: 5.60 min, 99%.

Example 172

(2R,15R)-8-Fluoro-4,15,17-trimethyl-2-(1-oxo-1,2-dihydro-isoquinolin-7-ylamino)-7-[(S)-(tetrahydro-furan-3-yl)oxy]-13-oxa-4,11-diaza-tricyclo[14.2.2.1$^{6,10}$]henicosa-1(19),6,8,10(21),16(20),17-hexaene-3,12-dione

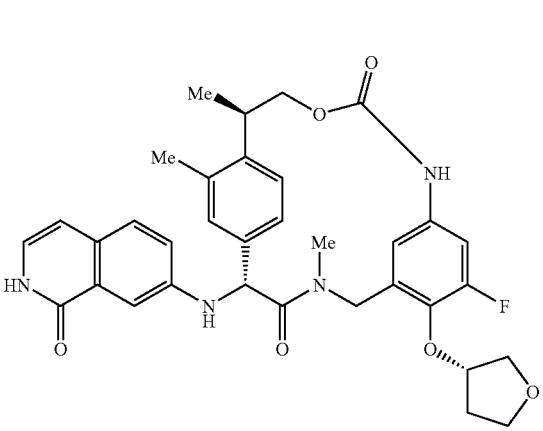 [SMILES: Cc1cc2ccc1[C@@H](C)COC(=O)Nc1cc(F)c(O[C@H]3CCOC3)c(c1)CN(C)C(=O)[C@@H]2Nc1ccc2cc[nH]c(=O)c2c1]

172A

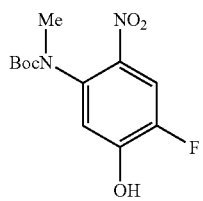 [SMILES: CN(C(=O)OC(C)(C)C)c1cc(O)c(F)cc1[N+](=O)[O-]]

To a round bottom flask with 167B (90 mg, 0.486 mmol) in MeOH (6 mL), methylamine, 2M (30.2 mg, 0.972 mmol) was added dropwise and stirred rt for 1 h. The mixture was cooled to 0° C., then sodium borohydride (55.2 mg, 1.459 mmol) was added. The mixture was stirred rt for 1 h, then was concentrated. The residue was mixed with sodium bicarbonate (123 mg, 1.459 mmol) in water (5 mL) and THF (5 mL). (Boc)$_2$O (127 mg, 0.583 mmol) was added, then the mixture was stirred rt for 1 h. The mixture was extracted with EtOAc (3×). The combined organic layer was washed with brine, dried (Na$_2$SO$_4$) and concentrated. The crude material was purified by flash chromatography (0-50% EtOAc in Hexane) to afford 172A (96 mg, 0.317 mmol, 65.1% yield) as a yellow solid. MS (ESI) m/z 301.2 (M+H)$^+$. $^1$H NMR (400 MHz, CHLOROFORM-D) d ppm 7.91 (dd, J=10.1.1, 2.64 Hz, 1H) 7.87 (s, 1H) 4.36 (s, 2H) 2.92 (s, 3H) 1.46 (s, 9H).

172B

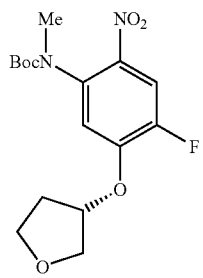

To a solution of 172A (150 mg, 0.5 mmol), (R)-tetrahydrofuran-3-ol (97 mg, 1.100 mmol), triphenylphosphine (289 mg, 1.100 mmol) in THF (5 mL) at 0° C., was added diisoproyl azodicarboxylate. The mixture was stirred rt for 3 h, then was concentrated and the crude product was purified by preparative HPLC to afford 172B (93 mg, 0.251 mmol, 50.2% yield). MS (ESI) m/z 371.3 (M+H)$^+$. $^1$H NMR (400 MHz, CD$_3$OD) δ ppm 8.04 (d, J=11.86 Hz, 1H) 7.86 (d, J=18.02 Hz, 1H) 5.38 (s, 1H) 4.49 (d, J=5.71 Hz, 2H) 3.95-4.14 (m, 2H) 3.76-3.93 (m, 2H) 2.93 (s, 3H) 2.24 (s, 2H) 1.36-1.59 (m, 9H).

Example 172

According to the sequence for the preparation of Example 165, 172B was used to prepare Example 172. R,R-Whelk-O column (21.1×250 mm, 100% (MeOH/EtOH 1:1), 20 mL/min) afforded the inactive diastereomer, followed by Example 172. MS (ESI) m/z 615.5 (M+H)$^+$. Analytical HPLC (Method A): Col A: 7.04 min, 94.9%; Col B: 7.15 min, 94.2%.

Example 173

(2R,15R)-4,15,17-Trimethyl-2-(1-oxo-1,2-dihydro-isoquinolin-7-ylamino)-7-(2-oxo-pyrrolidin-1-yl)-13-oxa-4,11-diaza-tricyclo[14.2.2.1$^{6,10}$]henicosa-1(19),6,8,10(21),16(20),17-hexaene-3,12-dione

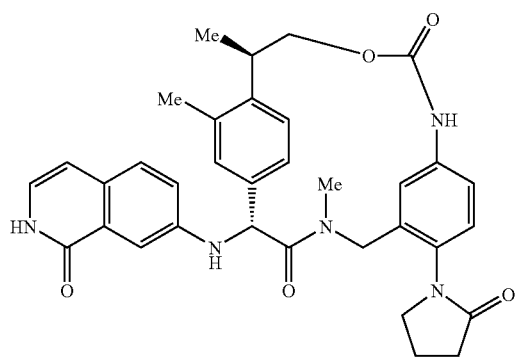 [SMILES: Cc1cc2ccc1[C@@H](C)COC(=O)Nc1ccc(N3CCCC3=O)c(c1)CN(C)C(=O)[C@@H]2Nc1ccc2cc[nH]c(=O)c2c1]

173A

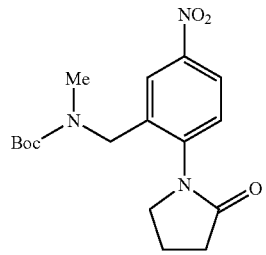

According to the sequence for the preparation of 90A, replacement of piperidin-2-one with pyrrolidin-2-one afforded 173A. MS (ESI) m/z 350.1 (M+H)$^+$. $^1$H NMR (400 MHz, METHANOL-d$_4$) δ ppm 8.23 (dd, J=8.79, 2.75 Hz, 1H) 8.13 (br. s., 1H) 7.56 (d, J=8.79 Hz, 1H) 4.45 (s, 2H) 3.88 (t, J=6.60 Hz, 2H) 2.83 (br. s., 3H) 2.61 (t, J=7.97 Hz, 2H) 2.29 (quin, J=7.56 Hz, 2H) 1.51 (br. s., 5H) 1.41 (br. s., 4H).

173B

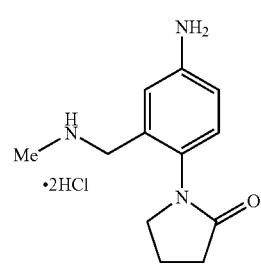 [SMILES: CNCc1cc(N)ccc1N1CCCC1=O ; "·2HCl"]

To a solution of 173A (960 mg, 2.75 mmol) in methanol (10 mL), was added 10% Pd—C (40 mg, 0.038 mmol). The mixture was evacuated and flushed with $H_2$ (3×), then was stirred under an atmosphere of $H_2$ for 20 h. The reaction mixture was filtered and concentrated. The resultant foam was dissolved in ethyl acetate (5 mL) and DCM (3 mL), then was treated with 4N HCl in dioxane (5 mL, 20.00 mmol). The resultant suspension was stirred at rt for 3 h. The mixture was concentrated, then was coevaporated with EtOAc (2×) to afford 173B (800 mg, 2.74 mmol, 100% yield) as an off-white solid, MS (ESI) m/z 220.2 $(M+H)^+$. $^1$H NMR (400 MHz, METHANOL-$d_4$) δ ppm 7.76 (d, J=2.75 Hz, 1H) 7.61-7.65 (m, 1H) 7.54-7.58 (m, 1H) 4.15 (s, 2H) 3.96 (t, J=7.15 Hz, 2H) 2.81 (s, 3H) 2.67 (t, J=7.97 Hz, 2H) 2.31 (quin, J=7.56 Hz, 2H) rotomers.

173C

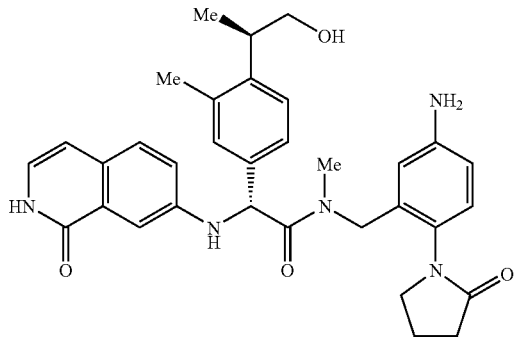 [SMILES: Cc1cc([C@@H](Nc2ccc3cc[nH]c(=O)c3c2)C(=O)N(C)Cc2cc(N)ccc2N2CCCC2=O)ccc1[C@@H](C)CO]

Using a procedure analogous to that used to prepare 41E, a mixture of Intermediate 10 (240 mg, 0.778 mmol), Intermediate 3 and 2-oxoacetic acid hydrate were reacted. The resulting solution was reacted with 173B (398 mg, 1.090 mmol) using BOP and DIEA. The crude product was purified column chromatography (1 to 15% methanol/methylene chloride) to afford 173C (262 mg, 0.462 mmol, 59.3% yield) as an off-white solid. MS (ESI) m/z 568.2 $(M+H)^+$.

Example 173

According to the procedure for the preparation of Example 90, 173C (0.262 g, 0.462 mmol) was cyclized to afford Example 173 (32.8 mg, 20% yield) as a yellow powder. Chiralcel OD-H 250×20 mm (L X OD); 20 mL/min 50:50 (1:1 MeOH/EtOH)/heptane, RT=7.40 min (Example 173) and 11.63 min (phenylglycine diastereomer). MS (ESI) m/z 594.2 $(M+H)^+$. $^1$H-NMR (400 MHz, $CD_3OD$) δ ppm 7.57 (2H, d, J=2.78 Hz), 7.37-7.47 (2H, m), 7.30 (1H, dd, J=8.72, 2.40 Hz), 7.23 (1H, d, J=1.52 Hz), 7.09 (1H, d, J=8.34 Hz), 6.95 (1H, d, J=7.07 Hz), 6.75 (1H, dd, J=8.21, 2.40 Hz), 6.54 (1H, d, J=7.07 Hz), 6.13 (1H, d, J=2.02 Hz), 5.67 (1H, s), 5.24 (1H, d, J=16.93 Hz), 4.61 (1H, t, J=10.99 Hz), 3.94 (1H, dd, J=10.86, 4.29 Hz), 3.72-3.84 (3H, m), 3.40-3.53 (1H, m), 3.28 (3H, s), 2.52 (2H, t, J=7.96 Hz), 2.30 (3H, s), 2.14-2.25 (2H, m), 1.28 (3H, d, J=7.07 Hz). Analytical HPLC (Method A): Col A: 5.92 min, 99.7%; Col B: 5.95 min, 93.5%.

Table 1 below lists Factor VIIa $K_i$ values for the following examples of this invention measured in the Factor VIIa assay described above.

TABLE 1

| Example Number | Factor VIIa $K_i$ (nM) |
|---|---|
| 13 | 24.0, 40.4 |
| 14 | 1520 |
| 18 | 0.96 |
| 40 | 1.57 |
| 42 | 27.6 |
| 65 | 29.4, 34.0 |
| 76 | 0.69, 0.86, 0.87, 0.96, 1.14, 1.22 |
| 78 | 1.35, 1.38 |
| 79 | 0.88 |
| 82 | 0.61 |
| 84 | 1.44 |
| 86 | 1.95 |
| 117 | 21.9 |
| 118 | 28.1 |
| 121 | 23.6 |
| 124 | 33.2 |
| 128 | 26.6 |
| 144 | 3100 |
| 145 | 1300 |
| 148 | 2530 |
| 149 | 1210 |
| 151 | 1120 |
| 152 | 1060 |
| 153 | 1460 |
| 154 | 1000 |
| 158 | 27.1, 97.5 |
| 168 | 0.88 |

While the foregoing specification teaches the principles of the present invention, which examples provided for the purpose of illustration, it will be understood that the practice of the invention encompasses all of the usual variations, adaptations and/or modifications as come within the scope of the following claims and their equivalents.

What is claimed is:

1. A compound of Formula (I):

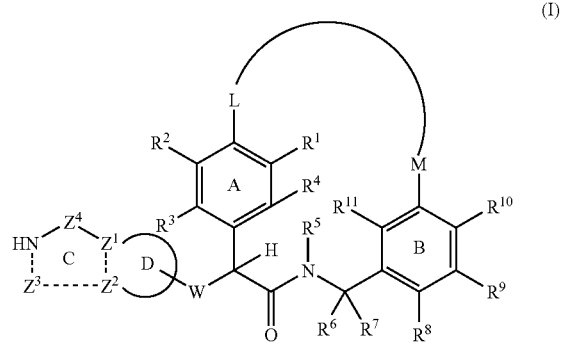

or a stereoisomer, a tautomer, or a pharmaceutically acceptable salt thereof, wherein:

ring A is phenyl or a pyridyl isomer defined by replacing one of $CR^1$, $CR^2$, $CR^3$, or $CR^4$ in ring A of formula (I) with N;

ring B is phenyl or a pyridyl isomer defined by replacing one of $CR^8$, $CR^9$, $CR^{10}$, or $CR^{11}$ in ring B of formula (I) with N;

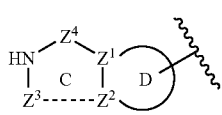

is selected from:

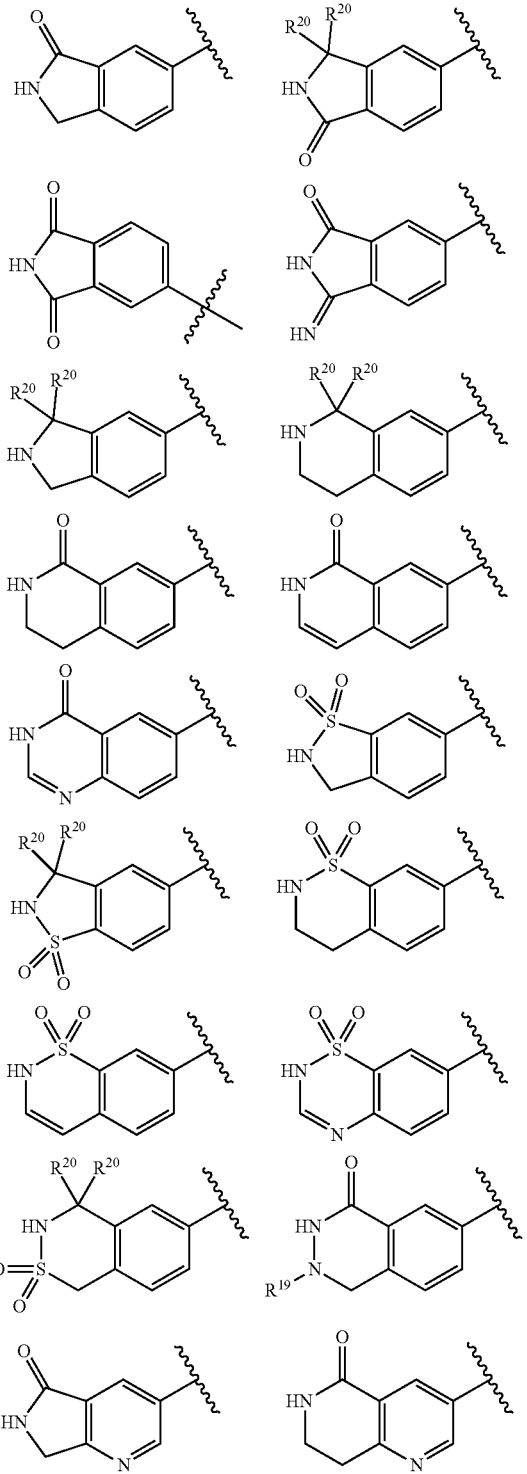

-continued

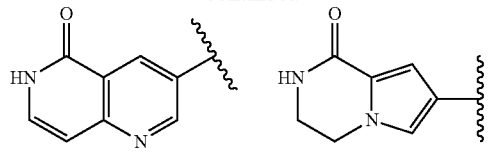
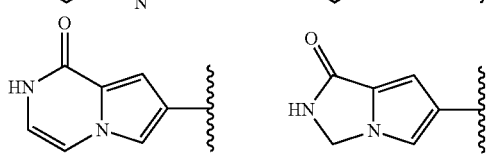
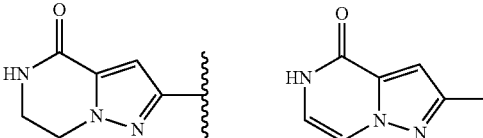
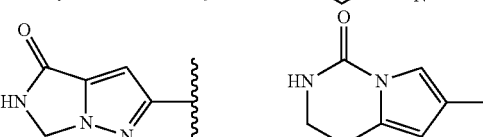
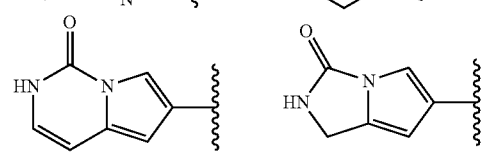
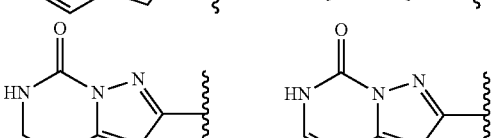
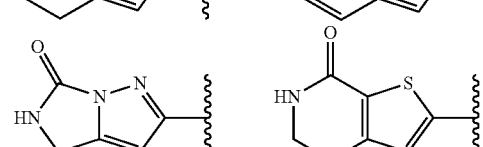
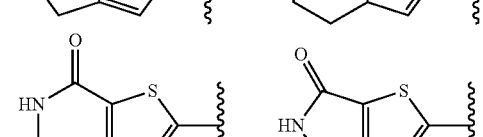
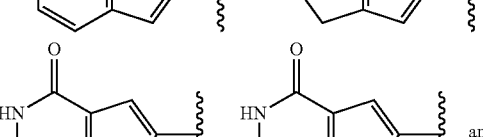

and

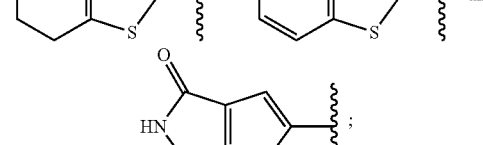

;

wherein ring C is substituted with 0-2 $R^{18}$; and ring D is substituted with 0-2 $R^{21}$:

for the definitions of L and M, as they are written from left to right, the atom connectivity is in the order (ring A)-L-M-(ring B);

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)$_y$—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, —C($R^{12}R^{13}$)C($R^{12}R^{13}$)Y—, —XC($R^{12}R^{13}$)Y—, —C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, —C($R^{12}R^{13}$)XC($R^{12}R^{13}$)C($R^{12}R^{13}$)—, —C($R^{12}R^{13}$)C($R^{12}R^{13}$)XC($R^{12}R^{13}$)—, —C($R^{12}R^{13}$)C($R^{12}R^{13}$)C($R^{12}R^{13}$)Y—, and —XC($R^{12}R^{13}$)C($R^{12}R^{13}$)Y—;

when M is —$SO_2NH$—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

when M is —NHCO—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

when M is —$NHSO_2$—, L is selected from —C($R^{12}R^{13}$)C($R^{12}R^{13}$)—, —C($R^{12}R^{13}$)C($R^{12}R^{13}$)C($R^{12}R^{13}$)—, XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)C($R^{12}R^{13}$)— and —C($R^{12}R^{13}$)XC($R^{12}R^{13}$)C($R^{12}R^{13}$)—;

W is NH or O;
X is O, S, or $NR^{16}$;
Y is O or $NR^{16}$;
$R^1$ is H, F, Cl, Br, I, $C_{1-4}$ alkyl substituted with 0-1 OH, $C_{1-4}$ fluoroalkyl, $C_{2-4}$ alkenyl, $C_{2-4}$ alkynyl, $C_{1-4}$ alkoxy, $C_{1-4}$ alkylthio, or $C_{3-6}$ cycloalkyl;
$R^2$ is H, F, Cl, Br, I, $OR^a$, $SR^b$, $CF_3$, $OCF_3$, $OCHF_2$, $OCH_2F$, CN, $NO_2$, —$NR^cR^d$, —C(O)$R^a$, —$CO_2R^a$, —$NR^cC(O)R^a$, —C(O)$NR^cR^d$, —$NR^cC(O)OR^b$, —$NR^cC(O)NR^cR^d$, —OC(O)$NR^cR^d$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, $C_{1-6}$ alkyl substituted with 0-2 $R^e$, $C_{1-4}$ fluoroalkyl, $C_{2-4}$ alkenyl substituted with 0-2 $R^e$, $C_{2-4}$ alkynyl substituted with 0-2 $R^e$, $C_{3-6}$ carbocycle substituted with 0-2 $R^f$, —$(CH_2)_s$-(5- to 6-membered heterocycle), —$NR^c$-(5- to 6-membered heterocycle), or —O-(5- to 6-membered heterocycle); wherein said heterocycle comprises carbon atoms and 1-3 heteroatoms selected from N, $NR^c$, O, and $S(O)_p$ and is substituted with 0-2 $R^g$;
$R^3$ is H, F, C, Br, I, $OR^a$, $SR^b$, $CF_3$, $OCF_3$, $OCHF_2$, $OCH_2F$, CN, $NO_2$, —$NR^cR^d$, —C(O)$R^a$, —$CO_2R^a$, —$NR^cC(O)R^a$, —C(O)$NR^cR^d$, $NR^cC(O)OR^b$, $NR^cC(O)NR^cR^d$, —OC(O)$NR^cR^d$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, —$O(CH_2)_nCO_2R^a$, —$SO_2NHCOR^b$, —$CONHSO_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, —O(benzyl substituted with $CO_2R^a$), or tetrazolyl;
$R^4$ is H, F, Cl, Br, I, or $C_{1-4}$ alkyl;
$R^5$ is H, $CH_2CH_2OR^a$, —$CH_2CH_2CH_2OR^a$, —$CH_2CO_2R^a$, —$CH_2H_2CO_2R^a$, —$CH_2CH_2CH_2CO_2R^a$, —$CH_2CH_2NHCO_2R^b$, —$CH_2CH_2NR^cR^d$, —$CH_2C(O)NR^cR^d$, —$CH_2CH_2C(O)NR^cR^d$, —$CH_2CONHSO_2R^b$, —$CH_2CH_2CONHSO_2R^b$, $C_{1-6}$ alkyl substituted with 0-2 $R^e$, —$(CH_2)_s$—$C_{3-6}$ carbocycle substituted with 0-2 $R^{f1}$, or —$(CH_2)_s$-5- to 6-membered heterocycle; wherein said heterocycle comprises carbon atoms and 1-3 heteroatoms selected from N, $NR^c$, O, and $S(O)_p$ and is substituted with 0-2 $R^{g1}$;

$R^6$ is H, $CH_2OR^a$, —$CH_2CH_2OR^a$, CN, —$CO_2R^a$, C(O)$NR^cR^d$, —$CH_2CO_2R^a$, —$CH_2C(O)NR^cR^d$, —$CONHSO_2R^b$, —$CH_2CONHSO_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, —$(CH_2)_s$—$C_{3-6}$ carbocycle substituted with 0-2 $R^{f1}$, or —$(CH_2)_s$-5- to 6-membered heterocycle; wherein said heterocycle comprises carbon atoms and 1-3 heteroatoms selected from N, $NR^c$, O, and $S(O)_p$ and is substituted with 0-2 $R^{g1}$;
alternatively, $R^5$ and $R^6$ can be joined to form a 2 to 5-membered alkylene chain, which may be substituted with 0-1 $R^{f1}$;
$R^7$ is H or $C_{1-6}$ alkyl;
alternatively, $R^6$ and $R^7$ can be joined to form a 3-7 membered carbocycle or heterocycle;
wherein said carbocycle may be substituted with 0-2 $R^{f1}$; and said heterocycle comprises carbon atoms and 1-3 heteroatoms selected from N, $NR^c$, O, and $S(O)_p$ and is substituted with 0-2 $R^{g1}$;
$R^8$ is H, F, Cl, Br, CN, $CH_2F$, $CHF_2$, —$(CH_2)_sCF_3$, —$(CH_2)_sCN$, —$(CH_2)_sNO_2$, $C_{1-6}$ alkyl, $C_{2-6}$ alkenyl, $C_{2-6}$ alkynyl, —$(CH_2)_n$—$OR^j$, —$(CH_2)_n$—$SR^j$, —$(CH_2)_n$—$NR^cR^d$, —$(CH_2)_sC(O)R^a$, —$(CH_2)_sCO_2R^a$, —$(CH_2)_sNR^cC(O)R^a$, —$(CH_2)_sCONR^cR^d$, —$(CH_2)_sSO_2R^j$, —$(CH_2)_sSO_2NR^cR^d$, —$(CH_2)_sNR^cC(O)OR^b$, —$(CH_2)_sOC(O)OR^b$, —$(CH_2)_sNR^cC(O)NR^cR^d$, —$(CH_2)_sOC(O)NR^cR^d$, —$(CH_2)_sNR^cSO_2NR^cR^d$, —$(CH_2)_sNR^cSO_2R^j$, —$(CH_2)_sNR^cSO_2CF_3$, —$(CH_2)_sSO_2CF_3$, —$O(CH_2)_nCO_2R^a$, —$(CH_2)_sSO_2NHCOR^b$, —$(CH_2)_sCONHSO_2R^j$, —O(benzyl substituted with $CO_2R^a$), —$(CH_2)_s$tetrazolyl, $C_{1-6}$ alkyl substituted with 0-3 $R^e$, $C_{1-4}$ fluoroalkyl, $C_{2-4}$ alkenyl substituted with 0-3 $R^e$, $C_{2-4}$ alkynyl substituted with 0-3 $R^e$, —$(CH_2)_s$—$C_{3-6}$ carbocycle substituted with 0-3 $R^f$, —$(CH_2)_n$-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$, or —O-5- to 10-membered heterocycle comprising: carbon atoms and 1-4 heteroatoms selected from N, $NR^c$, O, and $S(O)_p$, wherein said phenyl and heterocycle are substituted with 0-3 $R^{g1}$;
$R^9$ is H, F, Cl, Br, I, $C_{1-4}$ alkyl, or $C_{1-4}$ alkoxy;
$R^{10}$ and $R^{11}$ are, independently at each occurrence, H, F, Cl, Br, I, or $C_{1-4}$ alkyl;
$R^{12}$ and $R^{13}$ are, independently at each occurrence, H, F, Cl, $OR^a$, $SR^b$, $CF_3$, $OCF_3$, $OCHF_2$, $OCH_2F$, CN, $NO_2$, —$NR^cR^d$, —C(O)$R^a$, —$CO_2R^a$, —$NR^cC(O)R^a$, —C(O)$NR^cR^d$, —$NR^cC(O)OR^b$, —$NR^cC(O)NR^cR^d$, —OC(O)$NR^cR^d$, —OC(O)$OR^a$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, —$(CH_2)_s$—$C_{3-6}$ carbocycle substituted with 0-2 $R^{f1}$, —$(CH_2)_s$-(5- to 6-membered heterocycle), —$NR^c$-(5- to 6-membered heterocycle), or —O-(5- to 6-membered heterocycle); wherein said heterocycle comprises carbon atoms and 1-3 heteroatoms selected from N, $NR^c$, O, and $S(O)_p$ and is substituted with 0-2 $R^{g1}$;
alternatively, any two $R^{12}$ or $R^{13}$ attached to either the same carbon or to two adjacent carbons may combine to form a 3- to 7-membered carbocycle or heterocycle comprising: carbon atoms and 0-3 heteroatoms selected from N, NR$^c$, O, and S(O)$_p$, wherein said carbocycle or heterocycle is substituted with 0-3 R$^g$;

optionally, two R$^{12}$ or R$^{13}$ on adjacent carbon atoms in L may be replaced with a double bond between the two carbon atoms or four R$^{12}$ or R$^{13}$ on adjacent carbon atoms in L may be replaced with a triple bond between the two carbon atoms;

R$^{16}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —CH$_2$C(O)OR$^b$, —SO$_2$NR$^c$R$^d$, —SO$_2$CF$_3$, —S(O)$_2$R$^b$, or —(CH$_2$)$_s$-(5- to 6-membered heterocycle); wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{16a}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —CH$_2$C(O)OR$^b$, —SO$_2$NR$^c$R$^d$, —SO$_2$CF$_3$, —S(O)$_2$R$^b$, or 5- to 6-membered heterocycle; wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{17}$ is, independently at each occurrence, H or Me;

R$^{18}$ is, independently at each occurrence, H, F, Cl, Br, I, CF$_3$, OCF$_3$, OCHF$_2$, OCH$_2$F, CN, C$_{1-4}$ alkoxy, C$_{1-4}$ haloalkyl, C$_{1-4}$ alkyl, C$_{2-4}$ alkenyl, C$_{2-4}$ alkynyl, or C$_{3-6}$ cycloalkyl;

R$^{19}$ is, independently at each occurrence, is, independently at each occurrence, H, C$_{1-4}$ alkyl, C$_{2-4}$ alkenyl, or C$_{2-4}$ alkynyl;

R$^{20}$ is, independently at each occurrence, H, CF$_3$, C$_{1-6}$ alkyl substituted with 0-2 R$^e$, C$_{1-4}$ haloalkyl, C$_{2-4}$ alkenyl substituted with 0-2 R$^e$, C$_{2-4}$ alkynyl substituted with 0-2 R$^e$, or —(CH$_2$)$_s$-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^{21}$ is, independently at each occurrence, F, Cl, Br, I, CN, OH, CF$_3$, C$_{1-4}$ alkyl, C$_{1-4}$ haloalkyl, C$_{1-4}$ alkoxy, or C$_{3-6}$ cycloalkyl;

R$^a$ is, independently at each occurrence, H, C$_{1-4}$ alkyl, C$_{3-6}$ cycloalkyl, fluoroalkyl, phenyl, or benzyl; wherein said alkyl and cycloalkyl are optionally substituted with 0-2 R$^e$, and said phenyl and benzyl are optionally substituted with 0-2 R$^f$;

R$^b$ is, independently at each occurrence, C$_{1-4}$ alkyl, C$_{3-6}$ cycloalkyl, fluoroalkyl, phenyl, or benzyl; wherein said alkyl and cycloalkyl are optionally substituted with 0-2 R$^e$, and said phenyl and benzyl are optionally substituted with 0-2 R$^f$;

R$^c$ and R$^d$ are, independently at each occurrence, H, C$_{1-4}$ alkyl, C$_{3-6}$ cycloalkyl, fluoroalkyl, phenyl, or benzyl;

alternatively, R$^c$ and R$^d$, when attached to the same nitrogen atom, combine to form a 4- to 7-membered heterocycle comprising: carbon atoms and 0-2 additional heteroatoms selected from N, O, and S(O)$_p$; wherein said heterocycle is substituted with 0-2 RE;

R$^e$ is, independently at each occurrence, F, CF$_3$, OH, or C$_{1-3}$ alkoxy;

R$^f$ is, independently at each occurrence, F, Cl, Br, CF$_3$, OH, C$_{1-3}$ alkyl, or C$_{1-3}$ alkoxy;

R$^{f1}$ is, independently at each occurrence, R$^f$, —CO$_2$R$^a$, —C(O)NR$^c$R$^d$, —CONHSO$_2$R$^b$, or —CH$_2$CONHSO$_2$Rb;

R$^g$ is, independently at each occurrence, =O, F, Cl, Br, CF$_3$, OH, C$_{1-3}$ alkyl, C$_{1-3}$ fluoroalkyl, C$_{1-3}$alkoxy or C$_{1-3}$ fluoroalkoxy;

R$^{g1}$ is, independently at each occurrence, R$^g$, —CO$_2$R$^a$, —C(O)NR$^c$R$^d$, —CONHSO$_2$R$^b$, or —CH$_2$CONHSO$_2$R$^b$;

R$^h$ is, independently at each occurrence, H or C$_{1-3}$ alkyl;

R$^i$ is, independently at each occurrence, H, C$_{1-4}$ alkyl, C$_{3-6}$ cycloalkyl, phenyl, or benzyl;

wherein said alkyl and cycloalkyl are optionally substituted with 0-2 R$^k$ and 0-5 F; and said phenyl and benzyl are optionally substituted with 0-2 R$^f$;

R$^j$ is, independently at each occurrence, C$_{1-4}$ alkyl, C$_{3-6}$ cycloalkyl, phenyl, or benzyl; wherein said alkyl and cycloalkyl are optionally substituted with 0-2 R$^k$ and 0-5 F, and said phenyl and benzyl are optionally substituted with 0-2 R$^f$;

R$^k$ is, independently at each occurrence, CF$_3$, OH, or C$_{1-3}$ alkoxy;

n, at each occurrence, is selected from 0, 1, 2, 3, and 4;

p, at each occurrence, is selected from 0, 1, and 2;

q, at each occurrence is selected from 2 or 3;

r, at each occurrence is selected from 1, 2, or 3; and s, at each occurrence, is selected from 0, 1, and 2.

2. A compound according to claim 1, wherein:

ring A is phenyl or a pyridyl isomer defined by replacing one of CR$^1$, CR$^2$, CR$^3$, or CR$^4$ in ring A of formula (I) with N;

ring B is phenyl or a pyridyl isomer defined by replacing one of CR$^8$, CR$^9$, CR$^{10}$, or CR$^{11}$ in ring B of formula (I) with N;

with the proviso that when ring A is pyridyl, then ring B is not pyridyl;

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$), —C(R$^{12}$R$^{13}$)XC(R$^{12}$R$^{13}$)—, XC(R$^{12}$R$^{13}$)Y—, and —C(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)$_3$)—, —XC(R$^{12}$R$^{13}$)C(R$^{12}$R$^{13}$)(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)(R$^{12}$R$^{13}$)—, and —C(R$^{12}$R$^{13}$)XC(R$^{12}$R$^{13}$)C(R$^{12}$R$^{13}$)—;

W is NH or O; and

R$^4$ is H or F.

3. A compound according to claim 2, wherein:

ring A is phenyl;

ring B is phenyl;

M is —CONH— or —NHSO$_2$—;

when M is —CONH—, L is selected from —C(R¹²R¹³)C(R¹²R¹³)—, —XC(R¹²R¹³)—, —C(R¹²R¹³)Y—, —C(R¹²R¹³)C(R¹²R¹³)C(R¹²R¹³)—, —C(R¹²R¹³)XC(R¹²R¹³)—, and —C(R¹²R¹³)C(R¹²R¹³)Y—;

when M is —NHSO₂—, L is selected from —C(R¹²R¹³)C(R¹²R¹³)—, —C(R¹²R¹³)C(R¹²R¹³)C(R¹²R¹³)—, and —XC(R¹²R¹³)C(R¹²R¹³)—;

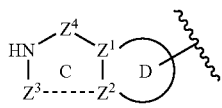

is selected from:

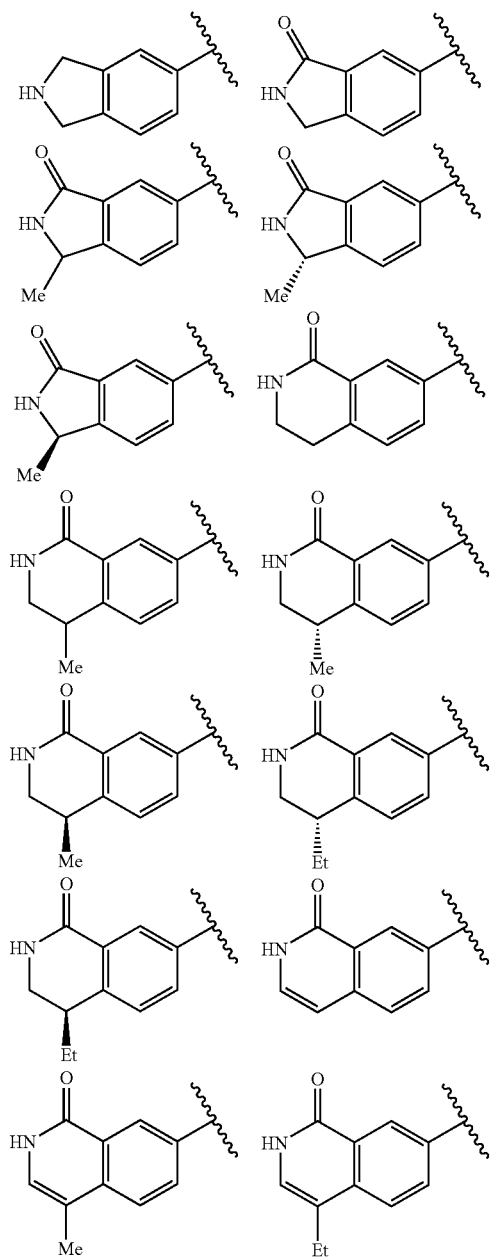

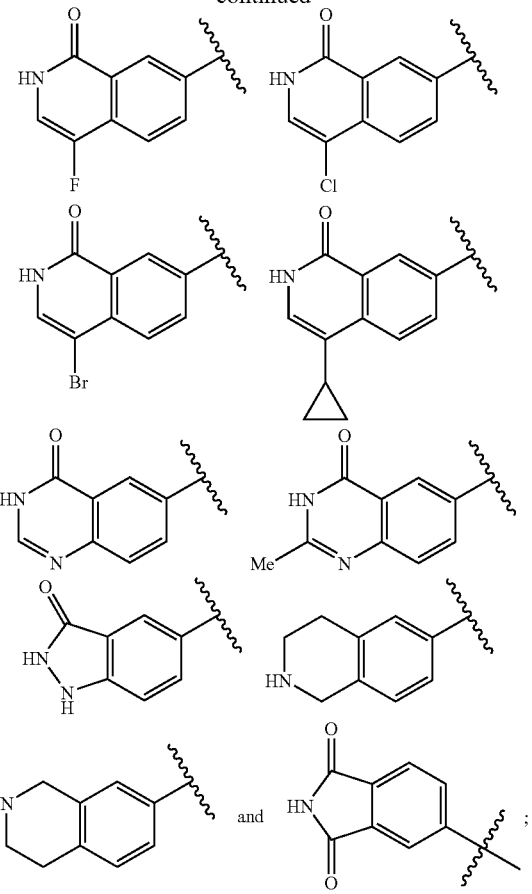

wherein ring D is optionally substituted with 0-1 F;

W is NH;

$R^1$ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl;

$R^2$ is H, F, Cl, $OR^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O-(5- to 6-membered heterocycle); wherein said heterocycle comprises carbon atoms and 1-3 heteroatoms selected from N, $NR^c$, O, and $S(O)_p$ and is substituted with 0-2 $R^g$;

$R^3$ is H, F, Cl, $OR^a$, —O(CH₂)$_n$CO₂$R^a$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, or —O(benzyl substituted with CO₂$R^a$);

$R^4$ is H;

$R^5$ is H, $C_{1-4}$ alkyl, —CH₂CH₂O$R^a$, —CH₂CH₂CH₂O$R^a$, —CH₂CO₂$R^a$, —CH₂CH₂CO₂$R^a$, —CH₂CH₂CH₂CO₂$R^a$, —CH₂CH₂NHCO₂$R^b$, —CH₂CH₂N$R^c R^d$, —CH₂C(O)N$R^c R^d$, or —CH₂CH₂C(O)N$R^c R^d$;

$R^6$ is H, —CH₂O$R^a$, —CH₂CH₂O$R^a$, CN, $C_{1-4}$ alkyl, —CO₂$R^a$, —C(O)N$R^c R^d$, —CH₂CO₂$R^a$, or —CH₂C(O)N$R^c R^d$;

$R^7$ is H;

$R^8$ is H, F, Cl, Br, CN, CH₂F, CHF₂, —(CH₂)$_s$CF₃, $C_{1-6}$ alkyl, $C_{2-6}$ alkenyl, $C_{2-6}$ alkynyl, —(CH₂)$_n$—O$R^i$, —(CH₂)$_n$—S$R^j$, —(CH₂)$_n$—N$R^c R^d$, —(CH₂)$_s$CO₂$R^a$, —(CH₂)$_s$N$R^c$C(O)$R^a$, —(CH₂)$_s$CONR$^c R^d$, —(CH₂)$_s$SO₂$R^j$, —(CH₂)$_s$SO₂N$R^c R^d$, N$R^c$SO₂$R^j$, NR$^c$SO$_2$CF$_3$, —SO$_2$CF$_3$, —O(benzyl substituted with CO$_2$R$^a$), C$_{1-6}$ alkyl substituted with 0-3 R$^e$, C$_{1-4}$ fluoroalkyl, C$_{2-4}$ alkenyl substituted with 0-3 R$^e$, C$_{2-4}$ alkynyl substituted with 0-3 R$^e$, —(CH$_2$)$_s$—C$_{3-6}$ carbocycle substituted with 0-3 R$^{f1}$, —(CH$_2$)$_n$-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$, or —O-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$; and R$^9$, R$^{10}$ and R$^{11}$ are, independently at each occurrence, H, F, or Cl.

4. A compound according to claim 3, wherein:

ring A is phenyl;

ring B is phenyl;

M is —CONH—;

L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$), —C(R$^{12}$R$^{13}$)XC(R$^{12}$R$^{13}$)—, and —C(R$^{12}$R$^{13}$)C(R$^{12}$R$^{13}$)Y—;

W is NH;

R$^1$ is H, Cl, Br, methyl, ethyl, vinyl, 2-propenyl, allyl, ethynyl, 1-propynyl, methoxy, ethoxy, or cyclopropyl;

R$^8$ is H, F, Cl, Br, CN, —(CH$_2$)$_n$—OR$^i$, —(CH$_2$)$_n$—SR$^j$, —(CH$_2$)$_n$—NR$^c$R$^d$, NR$^c$C(O)R$^a$, CONR$^c$R$^d$, —(CH$_2$)$_s$SO$_2$R$^j$, —(CH$_2$)$_s$SO$_2$NR$^c$R$^d$, NR$^c$SO$_2$R$^j$, NR$^c$SO$_2$CF$_3$, —SO$_2$CF$_3$, —O(benzyl substituted with CO$_2$R$^a$), C$_{1-6}$ alkyl substituted with 0-3 R$^e$, C$_{1-4}$ fluoroalkyl, C$_{2-4}$ alkenyl substituted with 0-3 R$^e$, C$_{2-4}$ alkynyl substituted with 0-3 R$^e$, —(CH$_2$)$_s$—C$_{3-6}$ carbocycle substituted with 0-3 R$^{f1}$, —(CH$_2$)$_n$-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$, or —O-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$.

5. A compound according to claim 4, wherein:

L is selected from —C(R$^{12}$R$^{13}$)C(R$^{12}$R$^{13}$)C(R$^{12}$R$^{13}$)—, —C(R$^{12}$R$^{13}$)NR$^{16}$C(R$^{12}$R$^{13}$)—, —C(R$^{12}$R$^{13}$)C(R$^{12}$R$^{13}$)Y—, —C(R$^{12}$R$^{13}$)C(R$^{12}$R$^{13}$)—, —C(R$^{12}$R$^{13}$)NR$^{16}$— or —OC(R$^{12}$R$^{13}$)—;

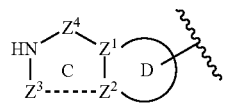

is selected from:

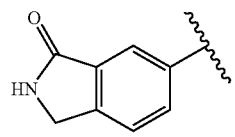 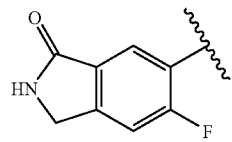

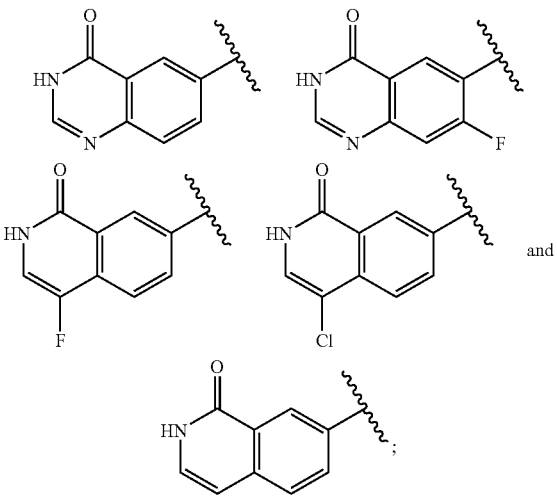

Y is O or NMe;

R$^1$ is H, Cl, Br, methyl, ethyl, vinyl, 2-propenyl, ethynyl, methoxy, or ethoxy;

R$^3$ is —I, F, Cl, Me, OCH$_2$CO$_2$H;

R$^5$ is H, C$_{1-4}$ alkyl, —CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$NR$^c$R$^d$, —CH$_2$C(O)NR$^c$R$^d$, or —CH$_2$CH$_2$C(O)NR$^c$R$^d$;

R$^6$ is H, C$_{1-4}$ alkyl, —CO$_2$R$^a$, —C(O)NR$^c$R$^d$, —CH$_2$CO$_2$R$^a$, or —CH$_2$C(O)NR$^c$R$^d$;

R$^{12}$ and R$^{13}$ are, independently at each occurrence, H, methyl, ethyl, propyl, isopropyl, cyclopropyl, t-butyl, methoxy, ethoxy, propoxy, isopropoxy, cyclopropoxy, OH, CH$_2$OH, OCH$_2$OMe, or NHCO$_2$Bn, with the proviso that no more than two of R$^{12}$ and R$^{13}$ mL are other than H; and R$^{16}$ is H, C$_{1-4}$ alkyl, —C(O)R$^a$, —C(O)NR$^c$R$^d$, —C(O)OR$^b$, —CH$_2$C(O)OR$^b$, or —S(O)$_2$R$^b$.

6. A compound according to claim 5, wherein:

L is —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)NR$^{16}$C(R$^{12}$R$^{13}$)—, —C(R$^{12}$R$^{13}$)C(R$^{12}$R$^{13}$)NH—, —C(R$^{12}$R$^{13}$)C(R$^{12}$R$^{13}$)NMe-, —C(R$^{12}$R$^{13}$)NHCH$_2$—, —C(R$^{12}$R$^{13}$)CH$_2$—, —CH$_2$NMe-, or —OCH$_2$—;

R$^1$ is H, Cl, Br, methyl, ethyl, methoxy, or ethoxy;

R$^2$ is H, Cl, Br, methyl, ethyl, methoxy, or ethoxy;

R$^3$ is H or F;

R$^5$ is H, C$_{1-4}$ alkyl, —CH$_2$CH$_2$OR$^a$, —CH$_2$CO$_2$R$^a$, —CH$_2$CH$_2$CO$_2$R$^a$, —CH$_2$CH$_2$CH$_2$CO$_2$R$^a$, —CH$_2$CH$_2$NHCO$_2$R$^b$, —CH$_2$CH$_2$NR$^c$R$^d$, —CH$_2$C(O)NR$^c$R$^d$, or —CH$_2$CH$_2$C(O)NR$^c$R$^d$;

R$^6$ is H, methyl, ethyl, —CO$_2$H or —CH$_2$CO$_2$H;

R$^7$ is H; and

R$^8$ is H, F, Cl, Br, CN, C$_{1-6}$ alkyl substituted with 0-3 R$^e$, OR$^i$, —CH$_2$OR$^i$, —CONR$^c$R$^d$, —SO$_2$R$^j$, —SO$_2$NR$^c$R$^d$, phenyl, O-phenyl, a 5- to 10-membered heterocycle selected from: morpholinyl, pyrrolidinyl, piperidinyl, pyrazolyl, oxazolyl, isoxazolyl, thiazolyl, imidazolyl, pyridyl, dihydroisoquinolinyl,

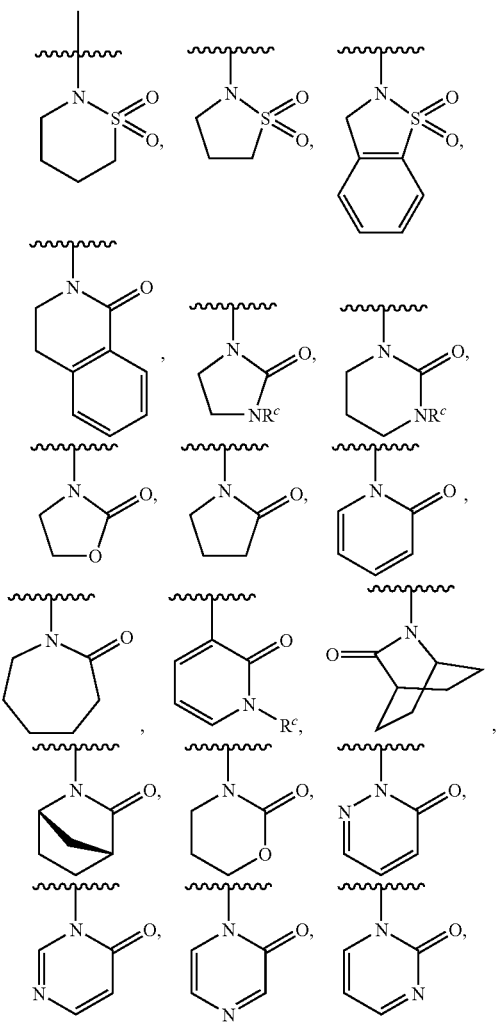

or O-5- to –10-membered heterocycle selected from: imidazolyl, oxadiazolyl, pyrazinyl, pyrazolyl, pyridazinyl, pyridyl, pyrimidinyl, pyrrolidinyl, pyrrolyl, tetrahydrofuranyl, thiadiazolyl, thiazolyl, thiophenyl, or triazolyl wherein said phenyl and heterocycle are substituted with 0-2 $R^g$; and $R^9$, $R^{10}$ and $R^{11}$ are, independently at each occurrence, H, F, or Cl.

7. A compound according to claim 6, wherein:
ring A is phenyl;
ring B is phenyl;
M is —CONH—;
L is —CH$_2$CH$_2$CH$_2$—, —CH(Me)CH$_2$CH$_2$—, —CH$_2$CH$_2$O—, —CHFCH$_2$O—, —CH(Me)CH$_2$O—, —CH(Et)CH$_2$O—, —CH(OH)CH$_2$O—, —CH(OMe)CH$_2$O—, —CH(OEt)CH$_2$O—, —CH(CH$_2$OH)CH$_2$O—, —CH(OCH$_2$OMe)CH$_2$O—, —CH(NHCO$_2$Bn)CH$_2$O—, —CH(Me)CH$_2$NH—, —CH(Me)CH$_2$N(Me)—, —CH$_2$N(Me)—, —CH$_2$NHCH$_2$—, —CH$_2$N(Me)CH$_2$—, —CH$_2$N(Et)CH$_2$—, —CH$_2$N(Pr)CH$_2$—, —CH$_2$N(i-Pr)CH$_2$—, —CH$_2$N(COMe)CH$_2$—, —CH$_2$N(COEt)CH$_2$—, —CH$_2$N(CO(i-Pr))CH$_2$—, —CH$_2$N(CO$_2$Me)CH$_2$—, —CH$_2$N(CH$_2$CO$_2$H)CH$_2$—, —CH(Me)NHCH$_2$—, —CH(Me)N(COMe)CH$_2$—, —CH(Me)N(CO$_2$Me)CH$_2$—, or —CH(Me)N(CO$_2$Bn)CH$_2$—;

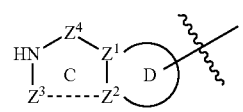

is selected from:

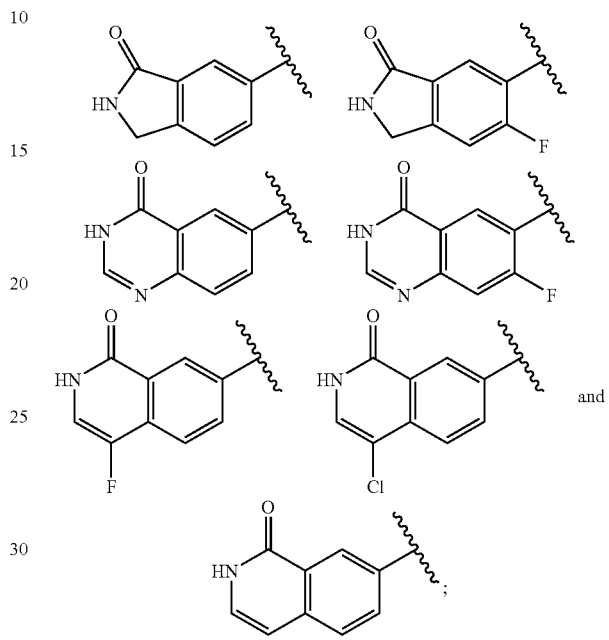

$R^1$ is H, Cl, Br, methyl, ethyl, methoxy, or ethoxy;
$R^2$ is H, Cl, Br, methyl, ethyl, methoxy, or ethoxy;
$R^3$ is H or F;
$R^4$ is H;
$R^5$ is H, methyl, ethyl, propyl, —CH$_2$CO$_2$H, —CH$_2$CH$_2$CO$_2$H, —CH$_2$CH$_2$CO$_2$Et, —CH$_2$CH$_2$CH$_2$CO$_2$H, —CH$_2$CH$_2$NHCO$_2$Me, —CH$_2$CH$_2$NHCO$_2$(t-Bu), —CH$_2$CH$_2$OH, —CH$_2$CH$_2$OMe, —CH$_2$CH$_2$NH$_2$, —CH$_2$CH$_2$CONH$_2$, or —CH$_2$CH$_2$CONHMe;
$R^6$ is H, methyl, ethyl, —CO$_2$H or —CH$_2$CO$_2$H;
$R^7$ is H;
$R^8$ is H, F, Cl, Br, CN, OH, —CH$_2$OH, —CH$_2$OMe, —OCF$_2$H, —OCF$_3$, —OCF$_2$CF$_2$H, CO$_2$H, —SO$_2$Et, —SO$_2$(i-Pr), —SO$_2$-cyclopropyl, phenyl, 2-OCF$_3$-phenyl, 3-CO$_2$H-phenyl, 3-CO$_2$Me-phenyl, 2,6-diF-phenyl, 2-F-5-CO$_2$H-phenyl, 1H-pyrazol-1-yl, 1-Me-1H-pyrazol-4-yl, 1-Me-1H-pyrazol-5-yl, 1-Et-1H-pyrazol-5-yl, oxazol-2-yl, 3,5-diMe-isoxazol-4-yl, 2-thiazolyl, 1H-imidazol-1-yl, 1-Me-1H-imidazol-2-yl, 1,2-dimethyl-1H-imidazol-5-yl, 2-pyridyl, 3-pyridyl, 4-pyridyl, -continued

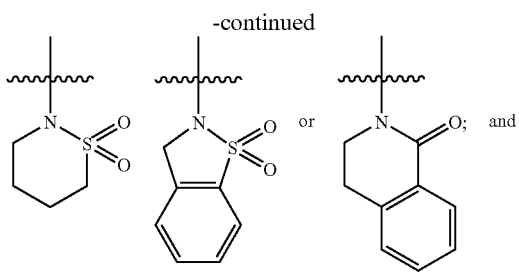

$R^9$, $R^{10}$, and $R^{11}$ are H.

8. A compound according to claim 7, wherein the compound is of Formula (Ia):

(Ia)

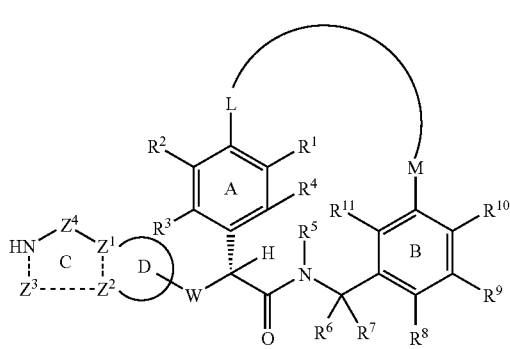

or a stereoisomer, a tautomer, or a pharmaceutically acceptable salt thereof.

9. A pharmaceutical composition, comprising: a pharmaceutically acceptable carrier and a compound of claim 1, or a stereoisomer, a tautomer, or a pharmaceutically acceptable salt thereof.

10. A method for the treatment of a thromboembolic disorder, comprising: administering to a patient in need thereof a therapeutically effective amount of a compound of claim 1, or a stereoisomer, a tautomer, or a pharmaceutically acceptable salt thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

12. A method according to claim 10, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

13. A method for the primary prophylaxis of a thromboembolic disorder, comprising: administering to a patient in need thereof a therapeutically effective amount of a compound of claim 1, or a stereoisomer, a tautomer, or a pharmaceutically acceptable salt thereof.

14. A method according to claim 13, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

15. A method according to claim 13, wherein the thromboembolic disorder is selected from unstable angina, an acute coronary syndrome, atrial fibrillation myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

16. A compound selected from:

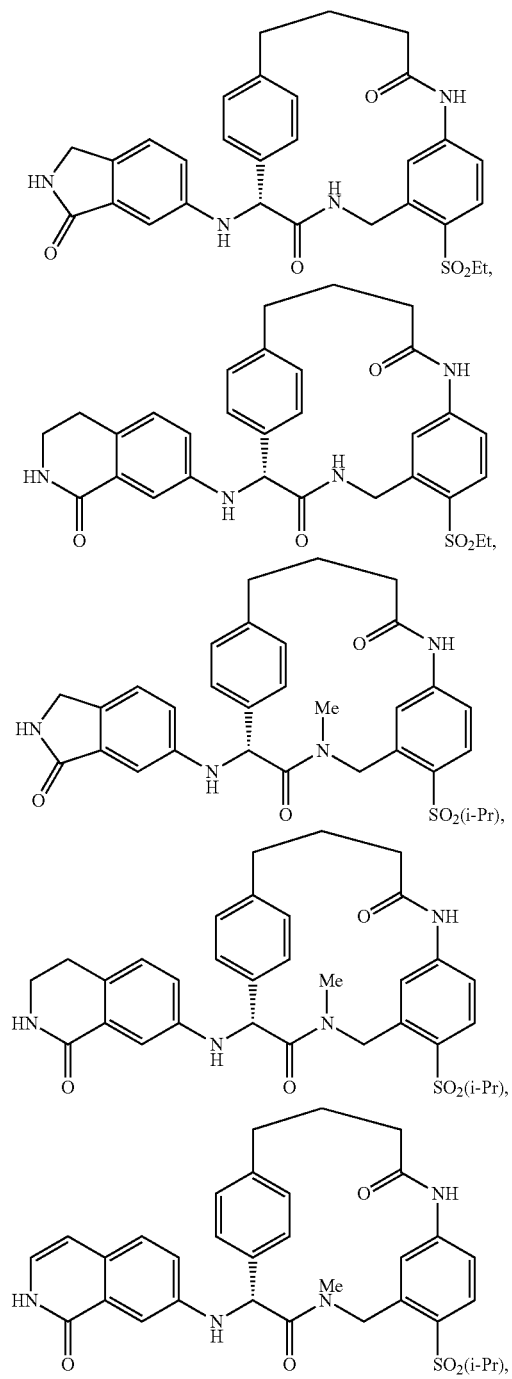

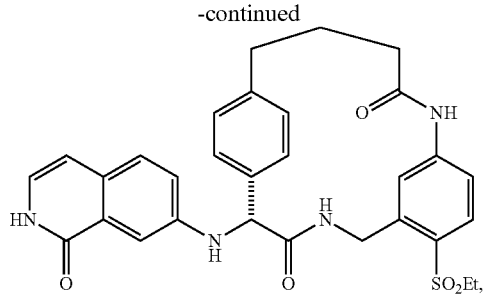
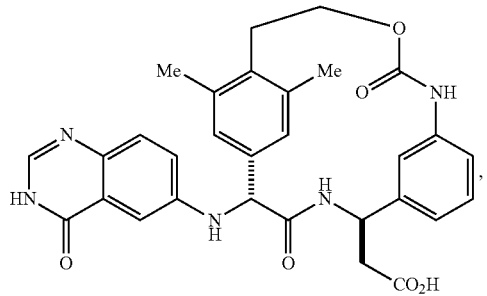
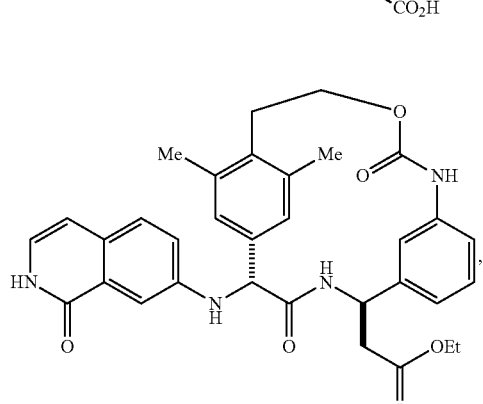
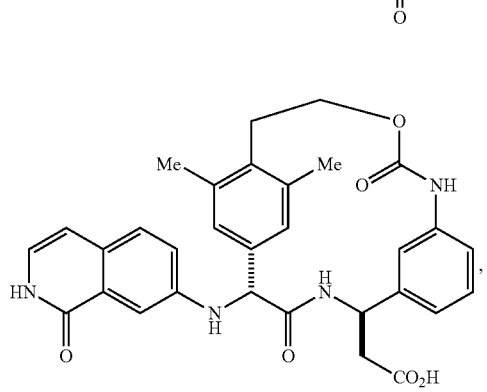
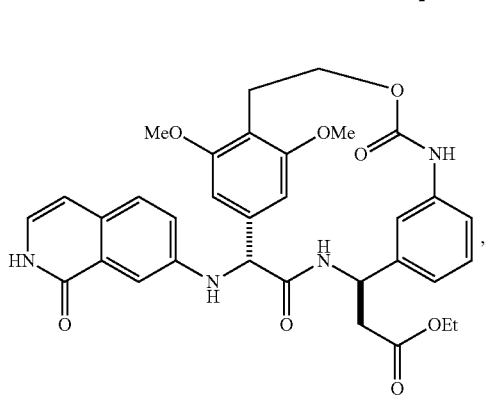
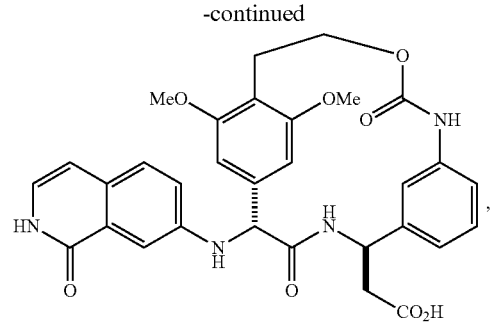
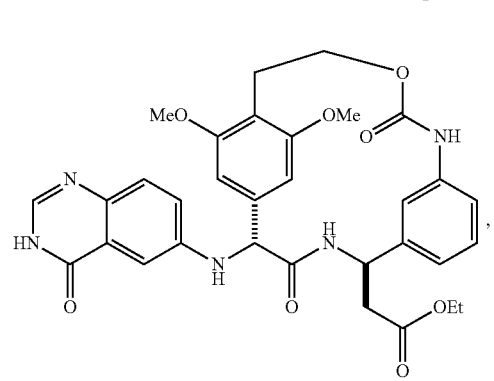
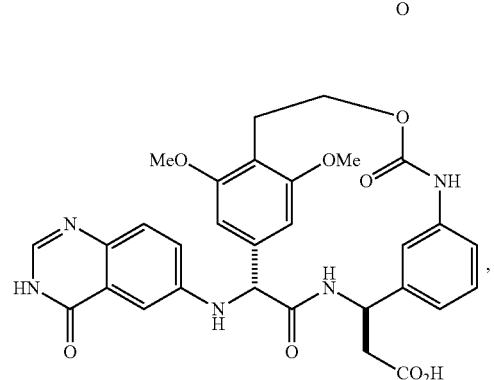
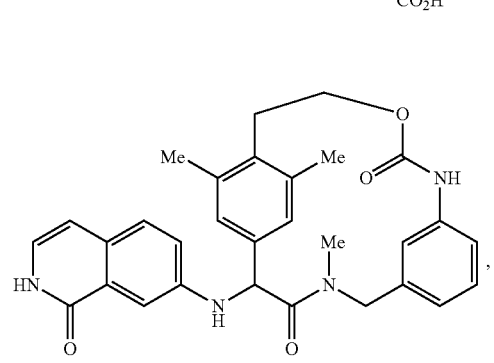
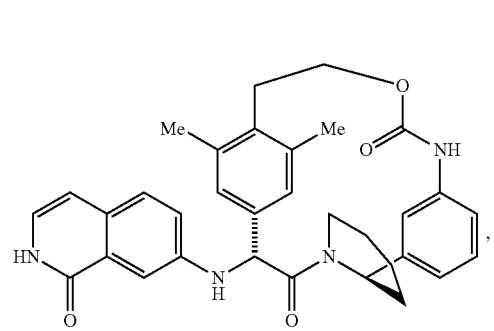

-continued
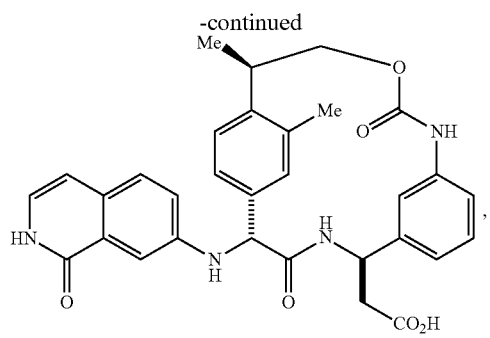
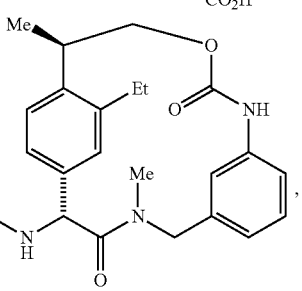
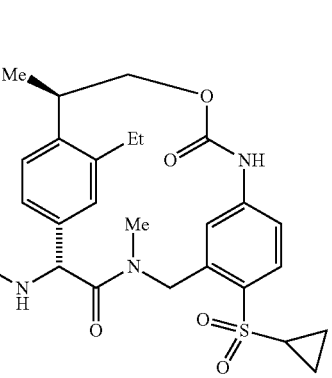
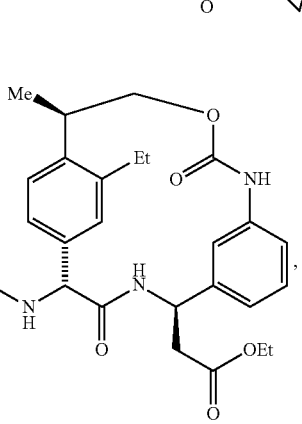
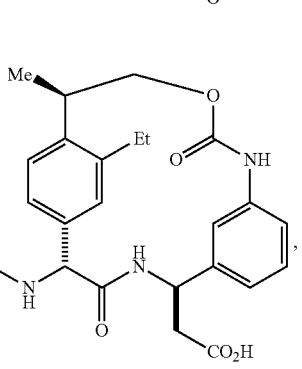
-continued
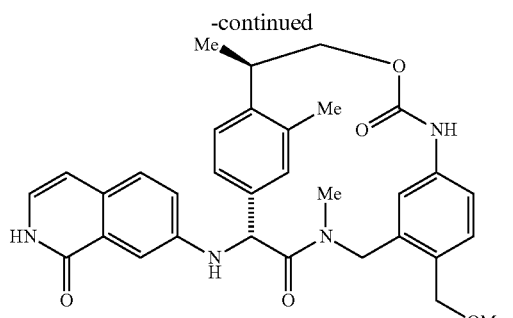
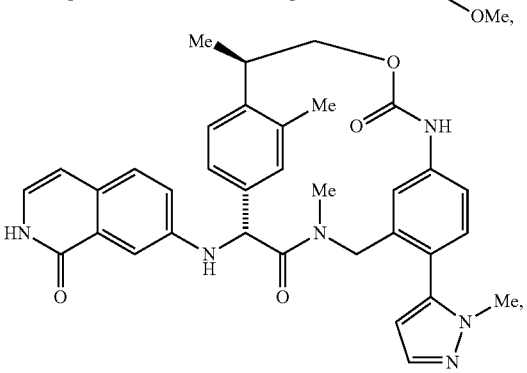
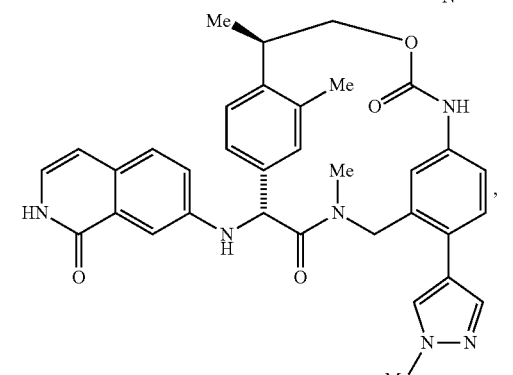
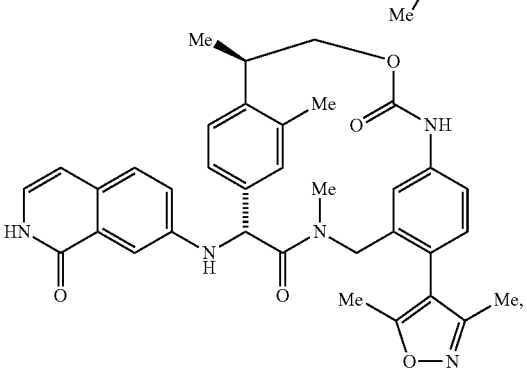
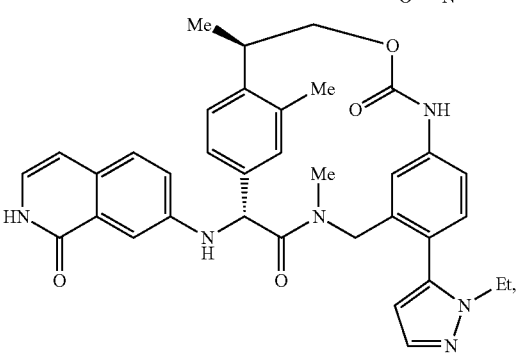

427
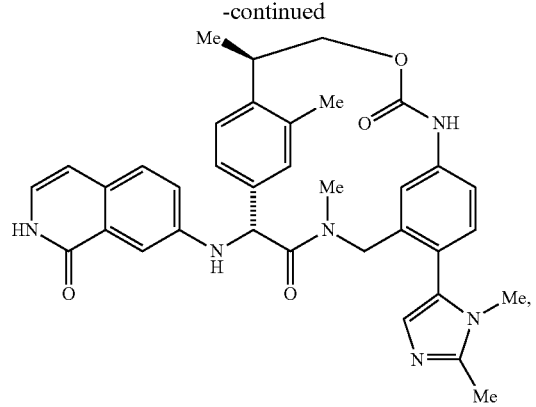
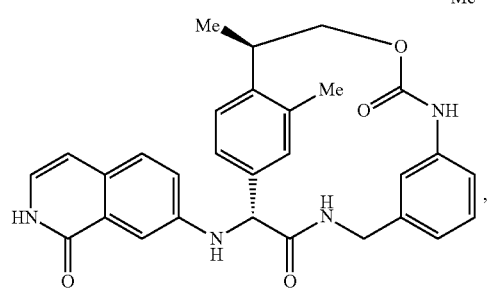
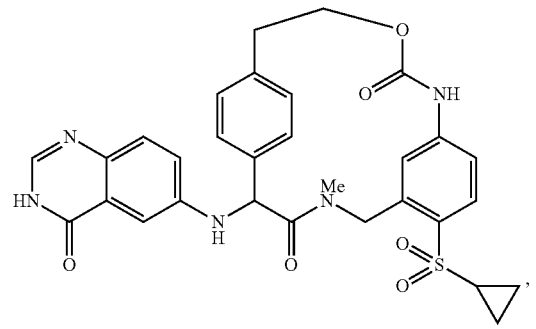
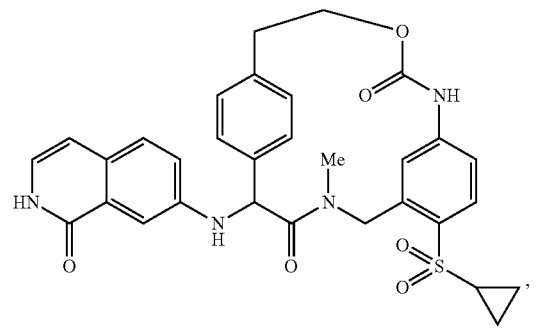
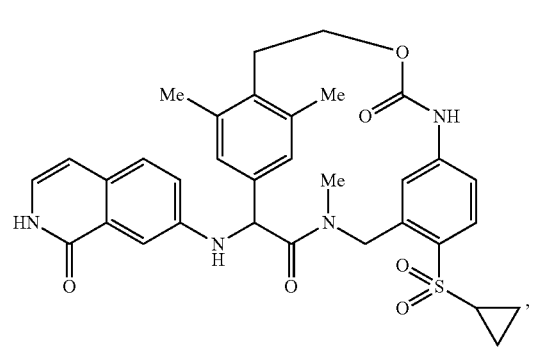
428
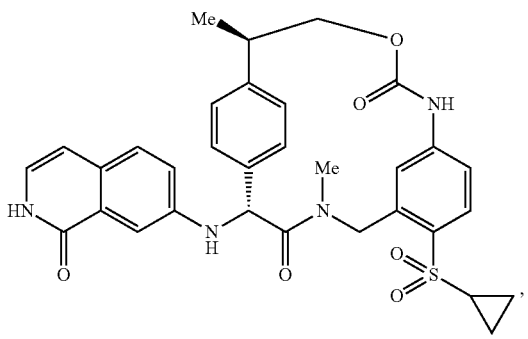
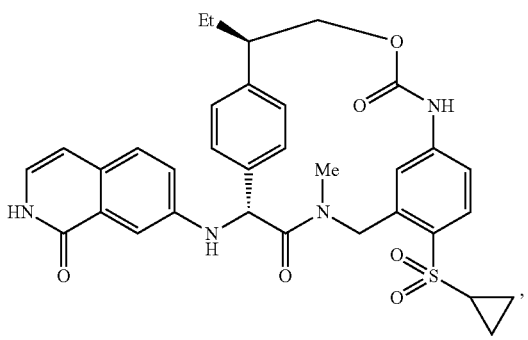
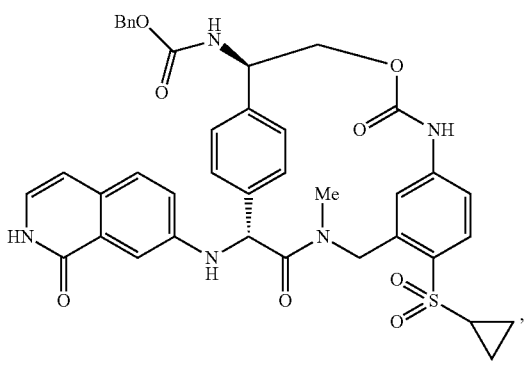
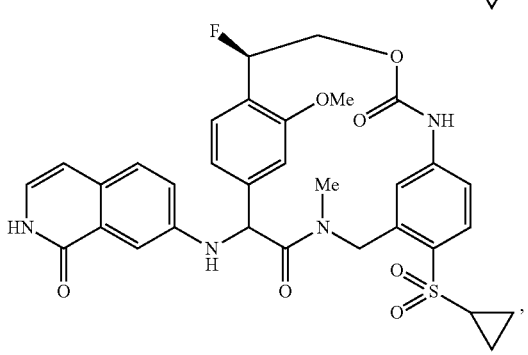
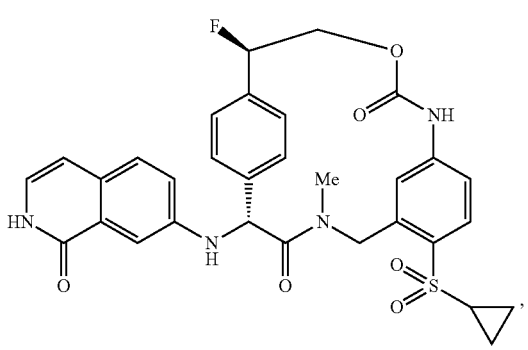

429
-continued
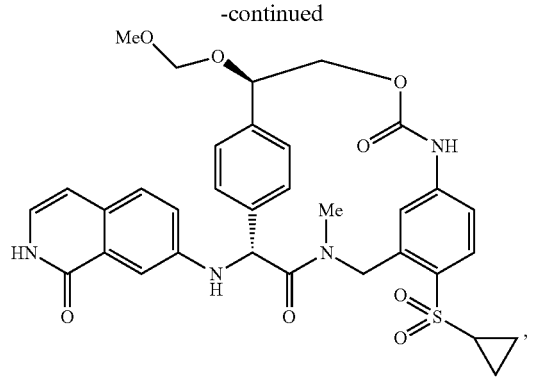
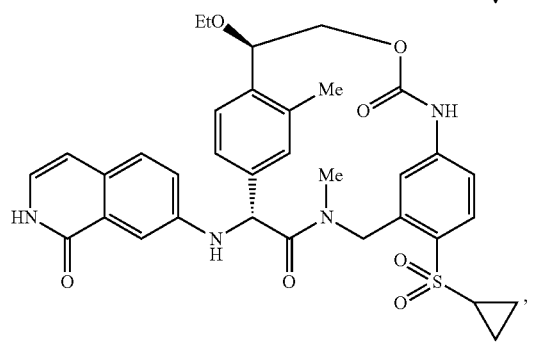
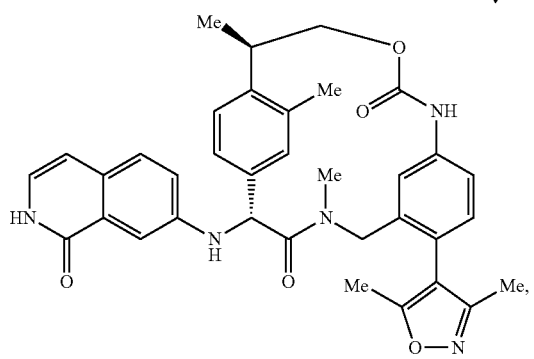
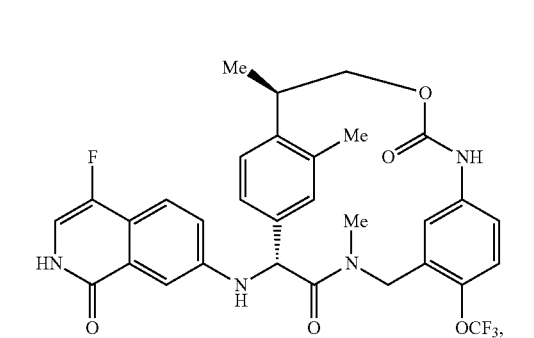
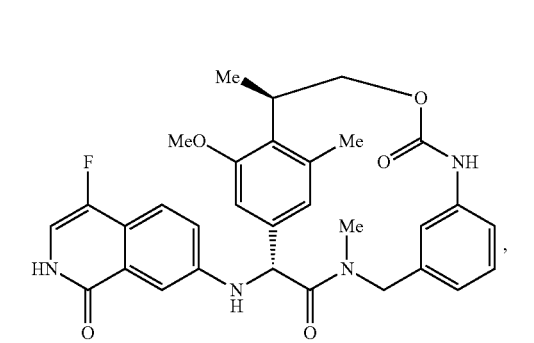
430
-continued
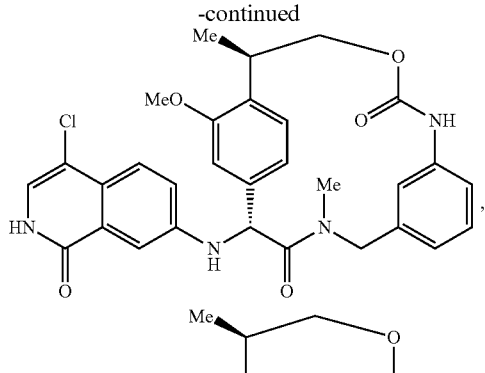
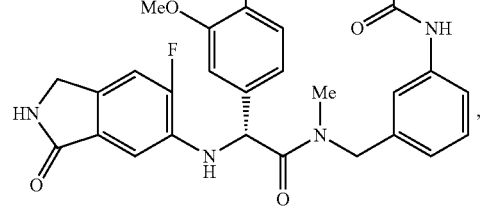
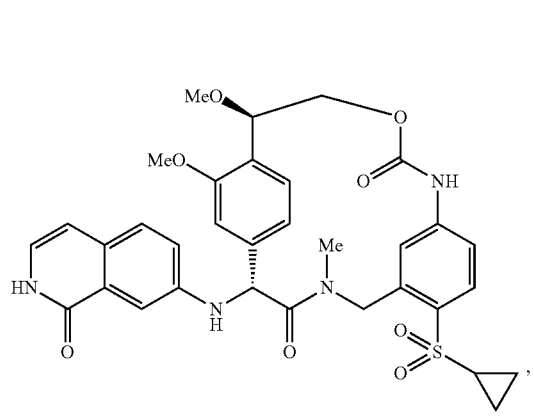
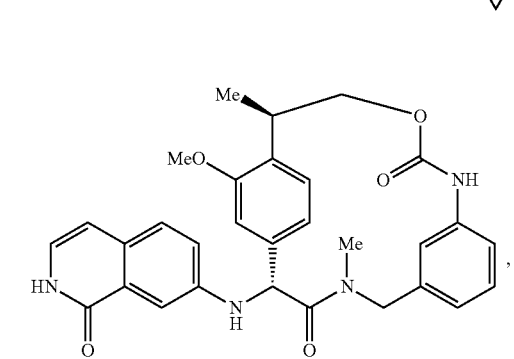
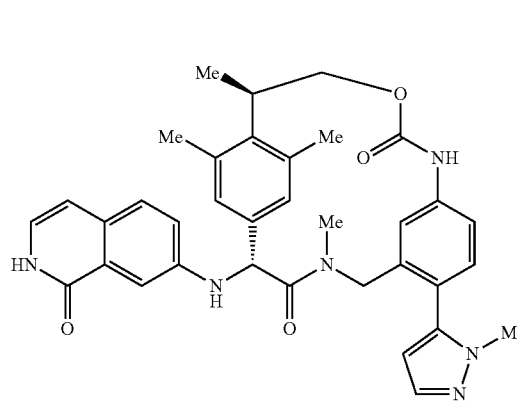

431
-continued
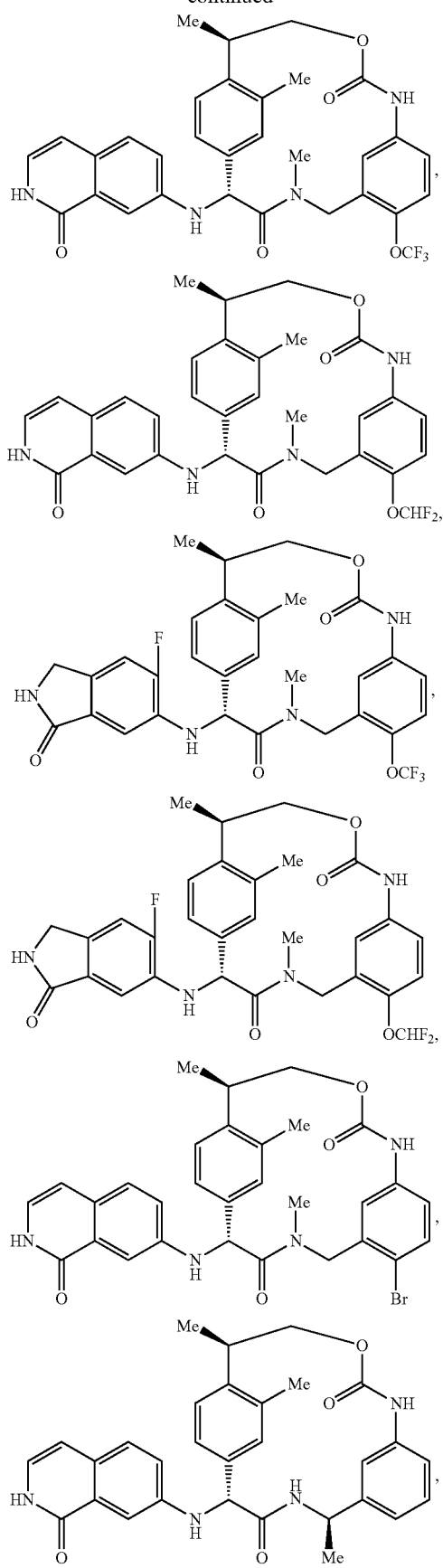
432
-continued
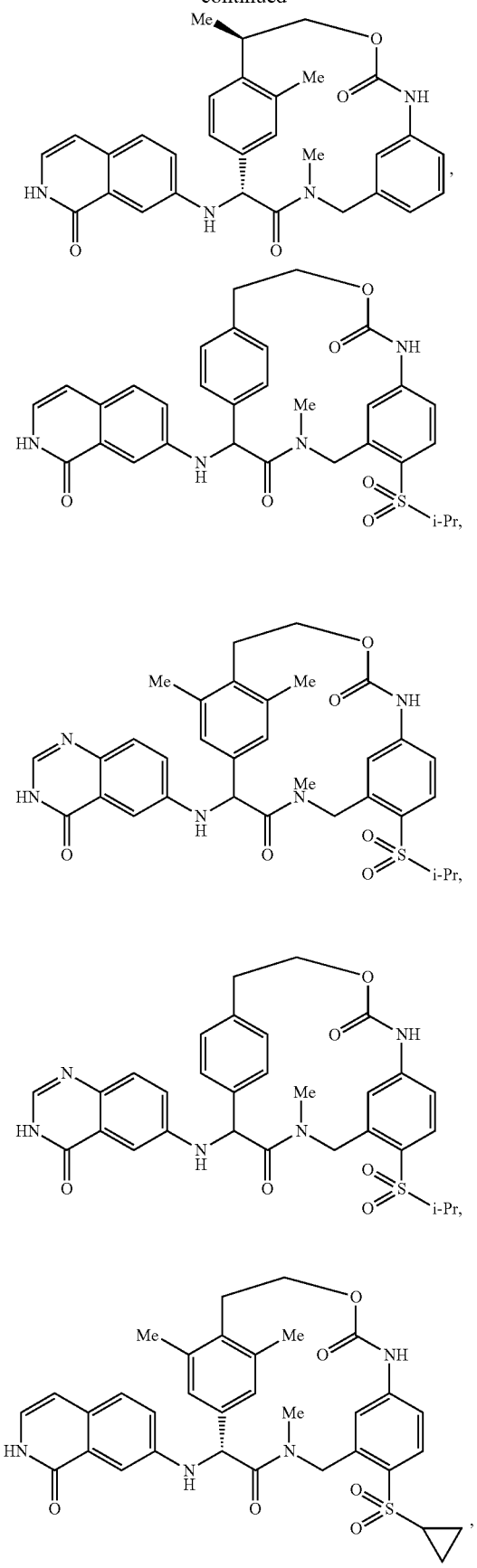

433
-continued
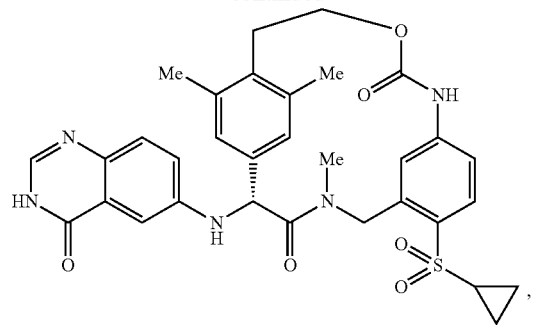
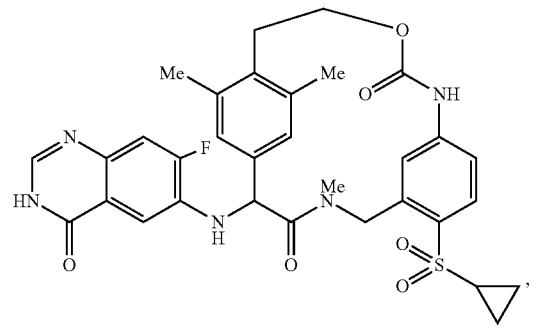
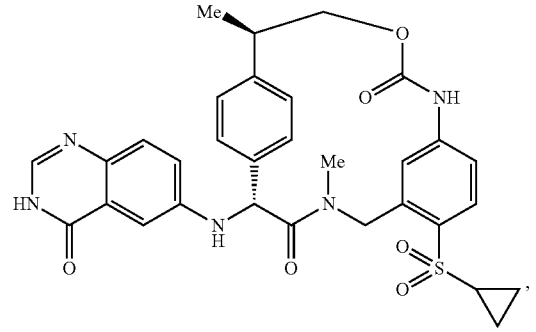
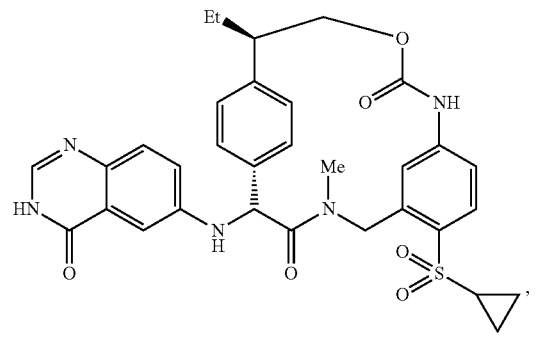
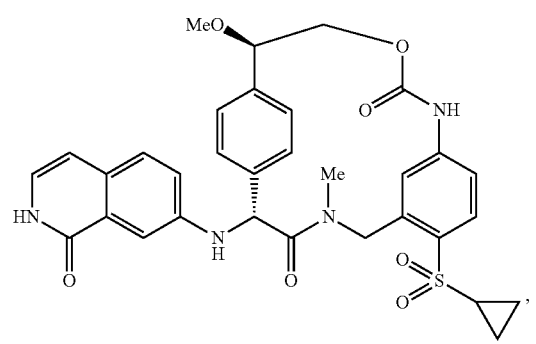
434
-continued
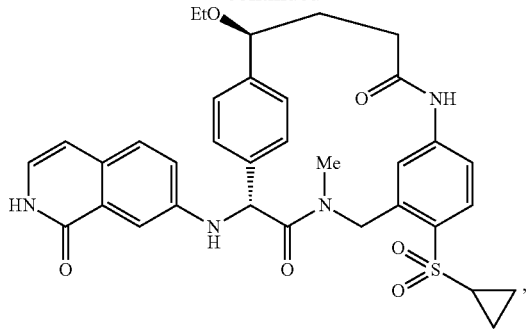
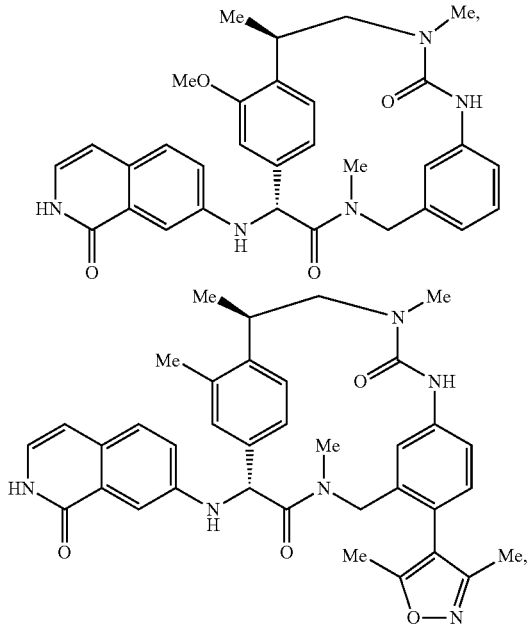
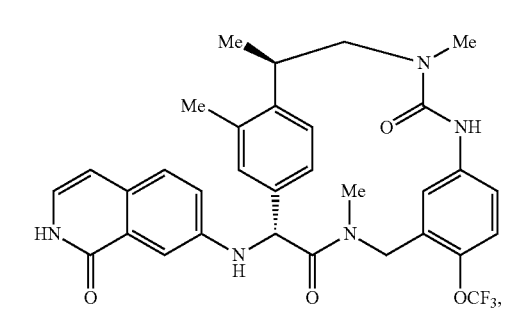
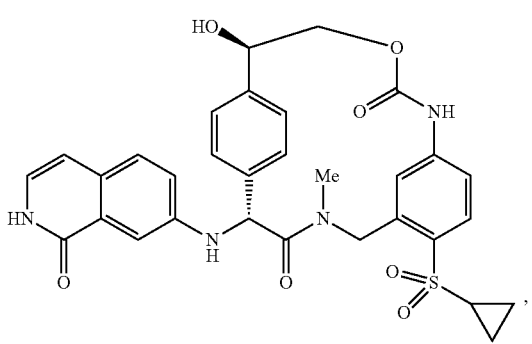

435
-continued
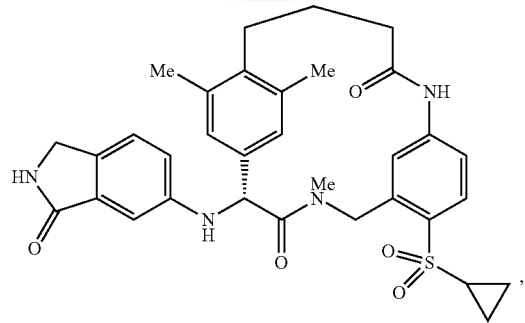
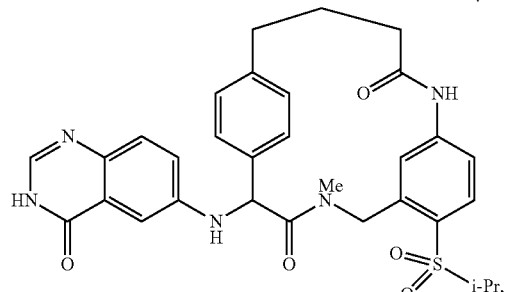
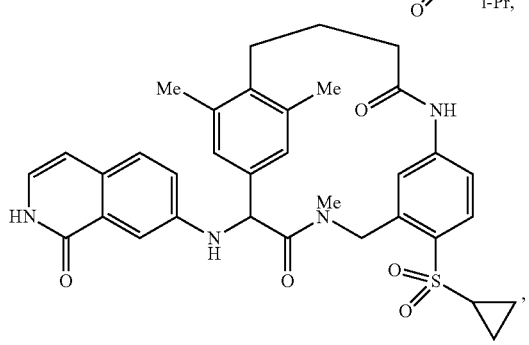
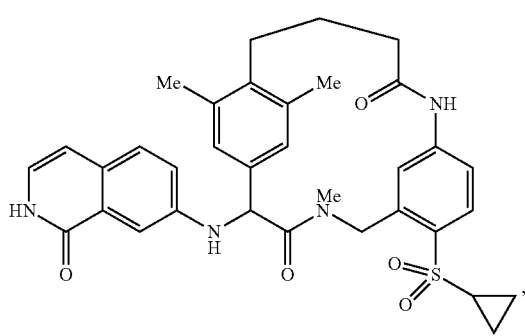
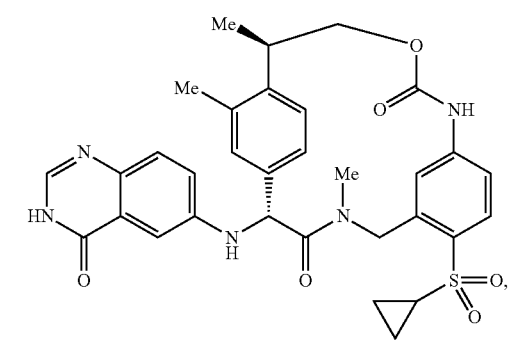
436
-continued
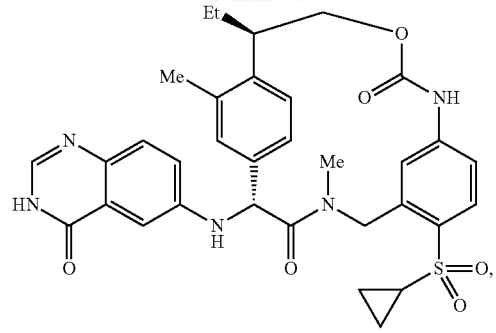
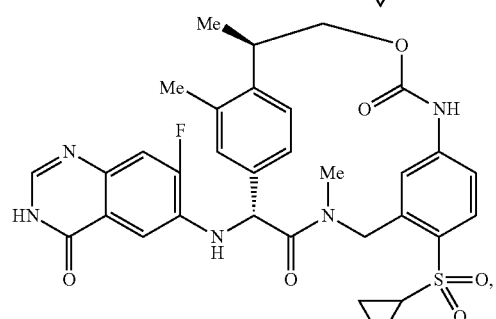
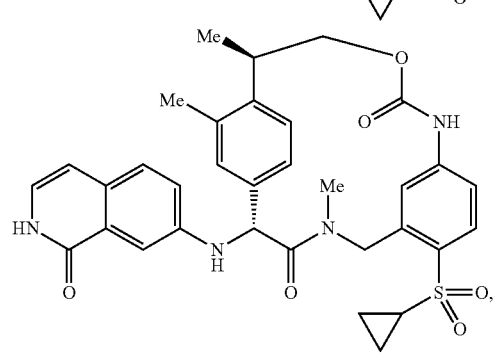
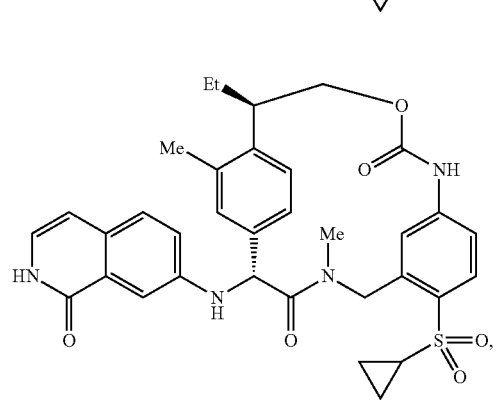
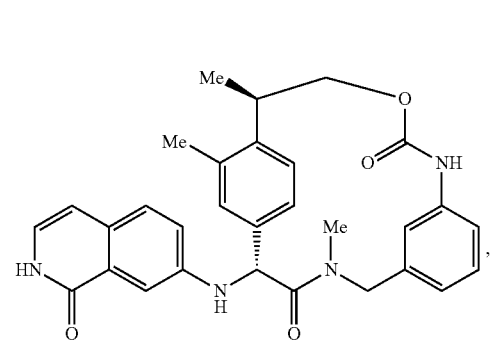

437
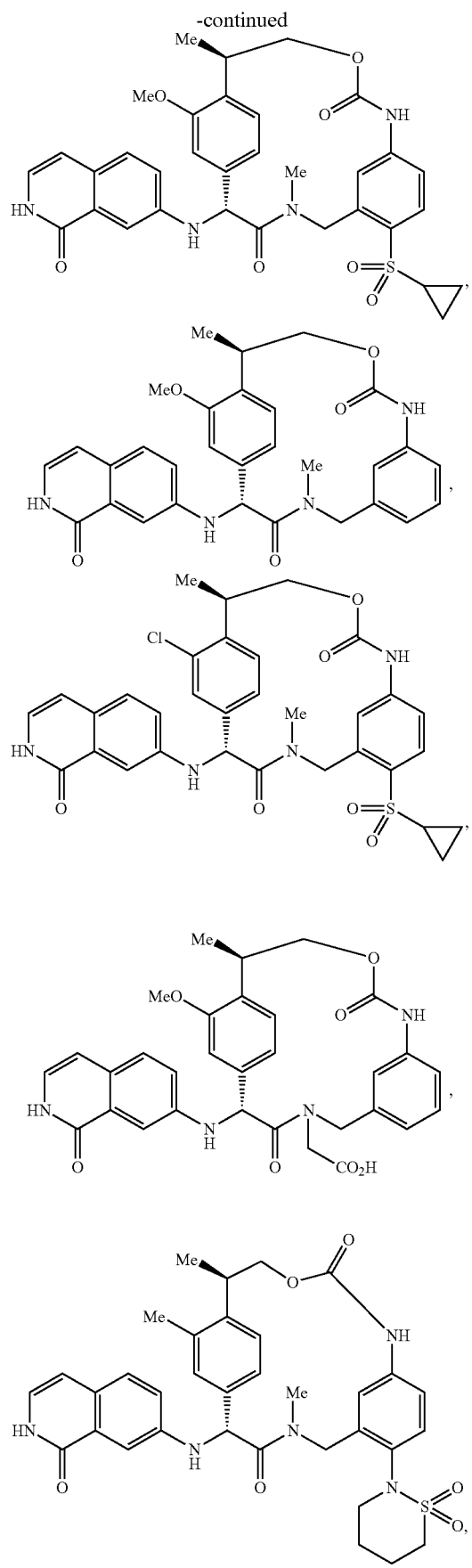
438
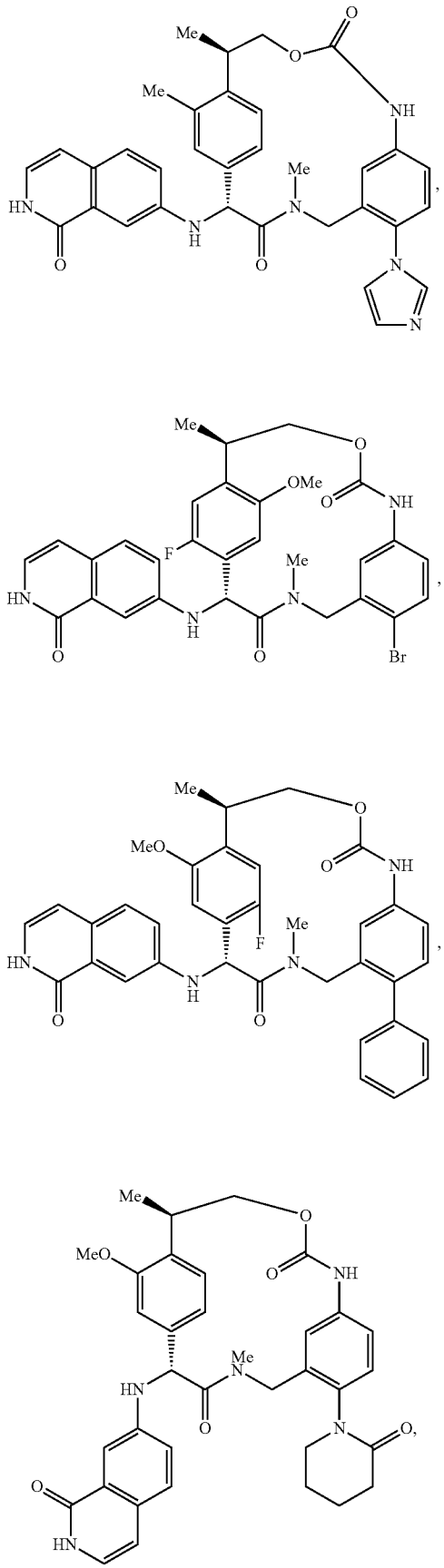

439
-continued
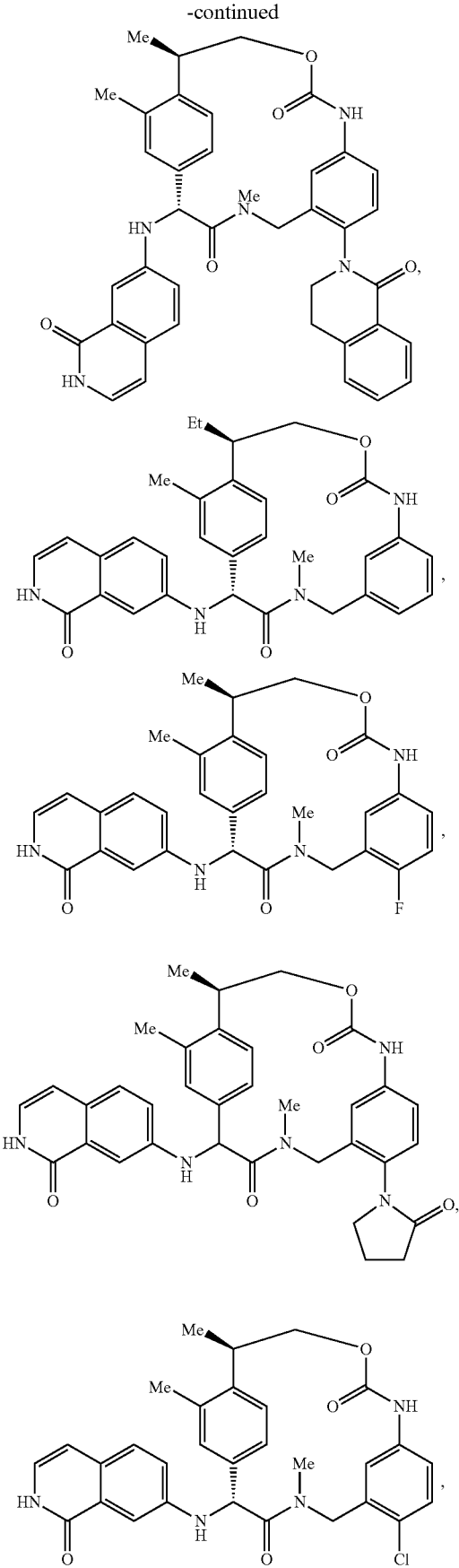
440
-continued
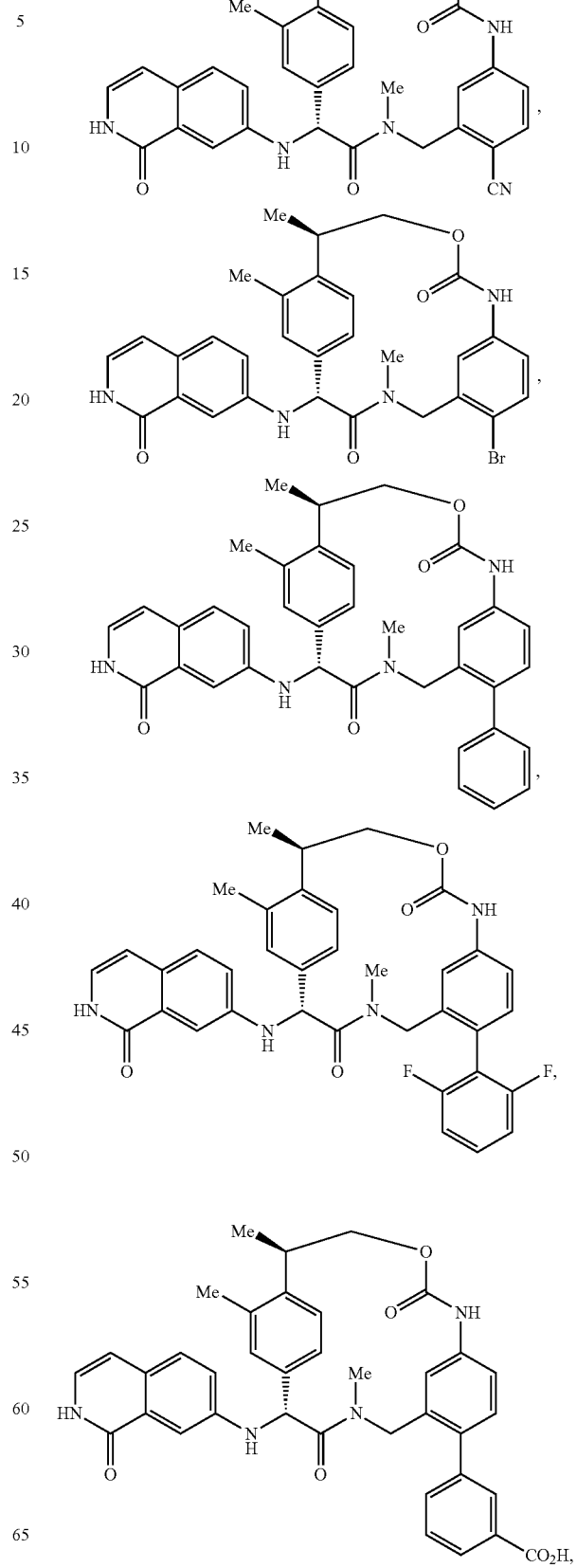

441
-continued
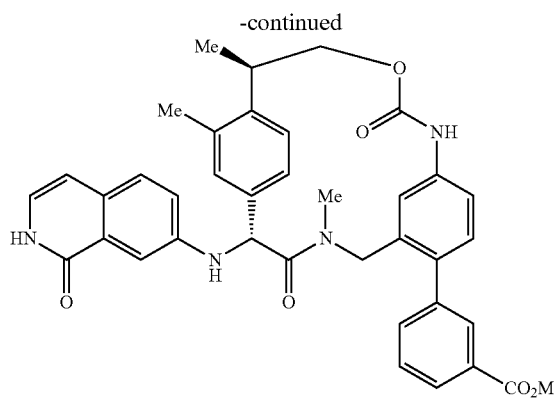
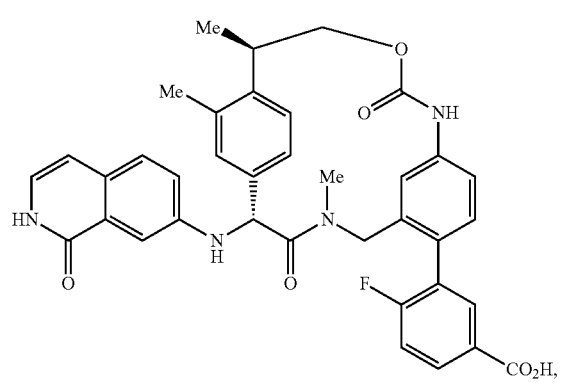
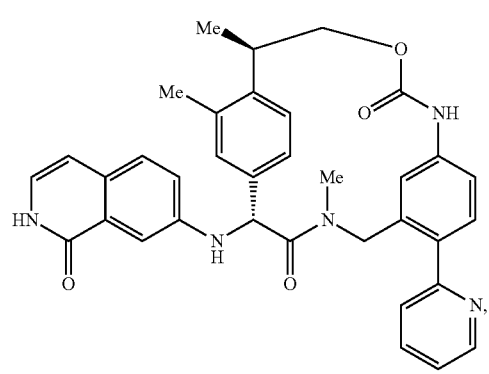
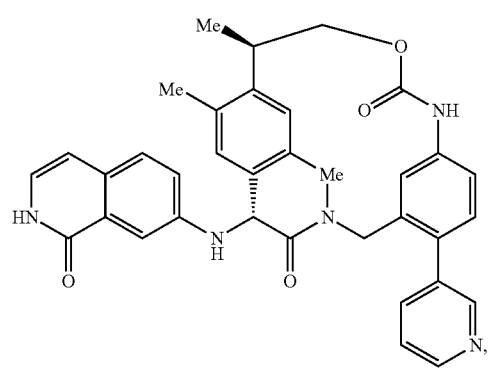
442
-continued
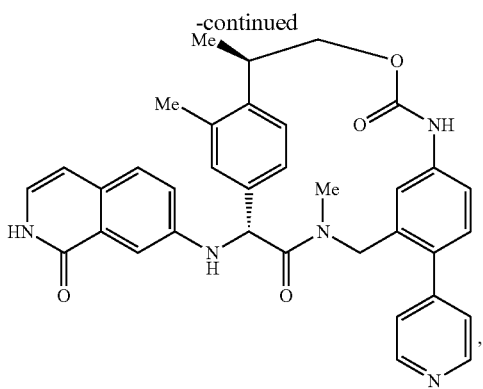
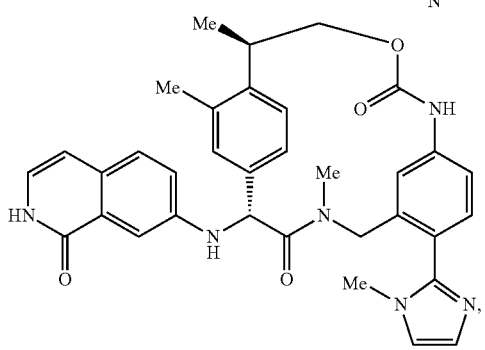
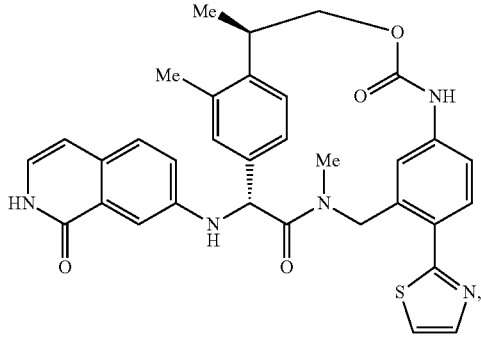
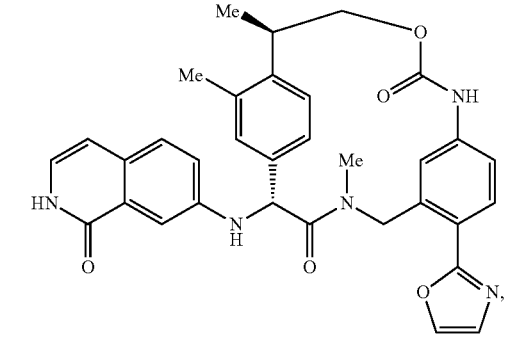
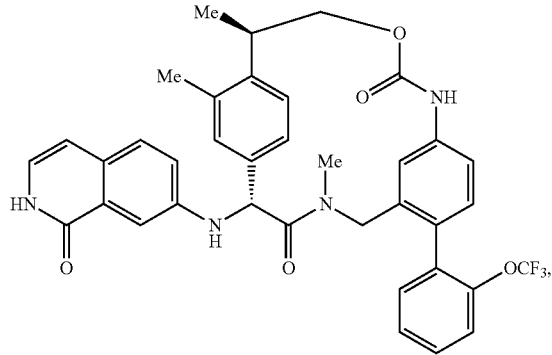

443
-continued
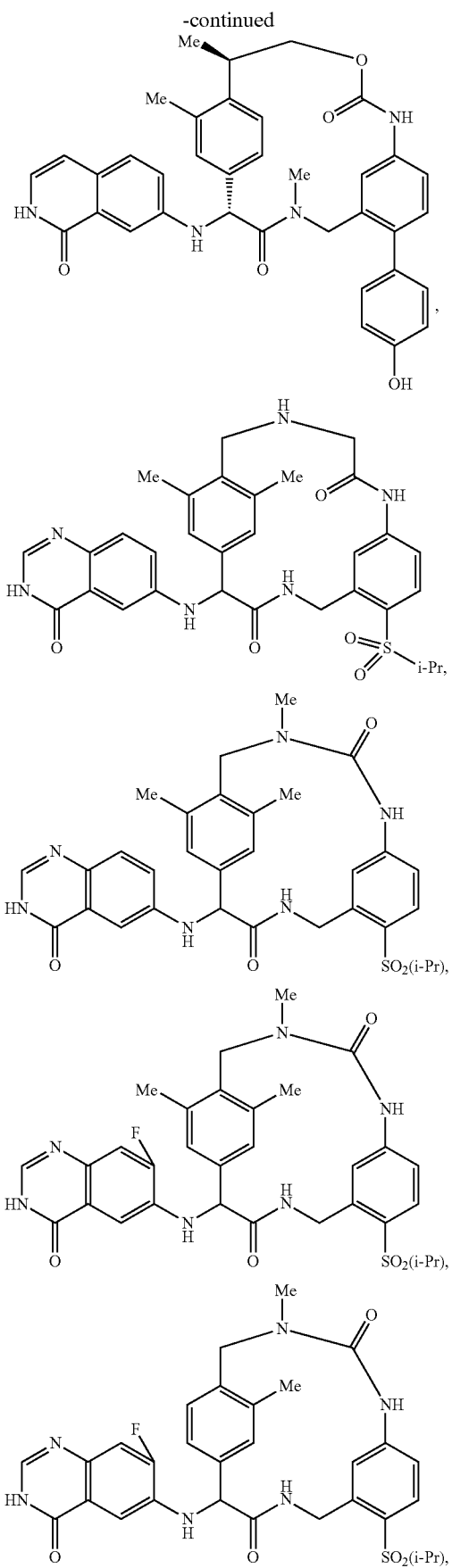
444
-continued
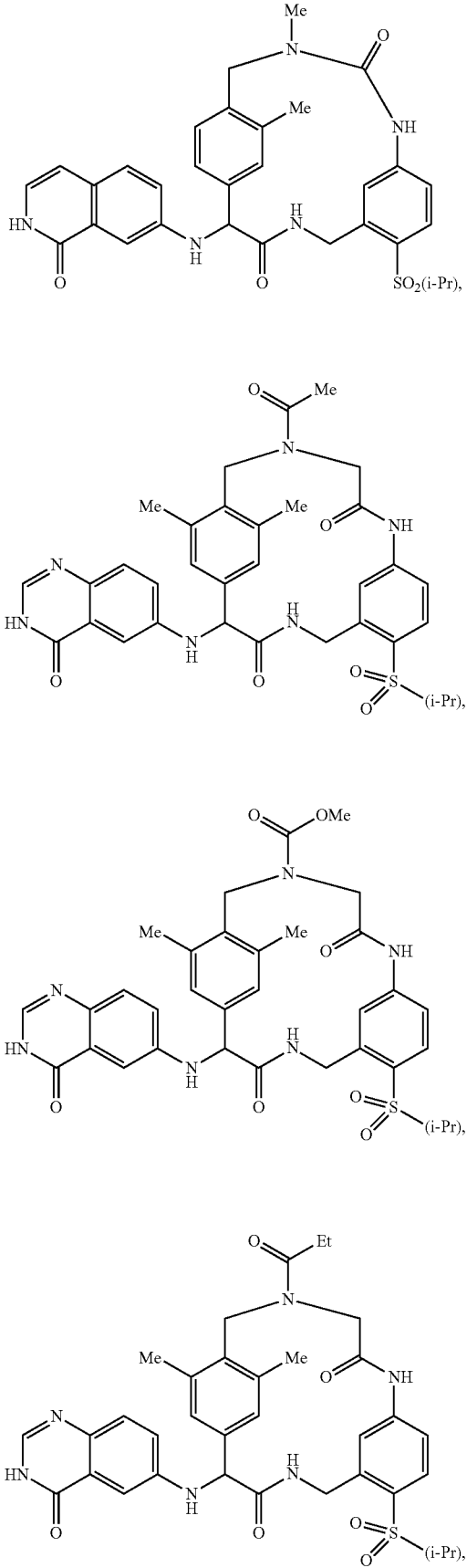

445
-continued
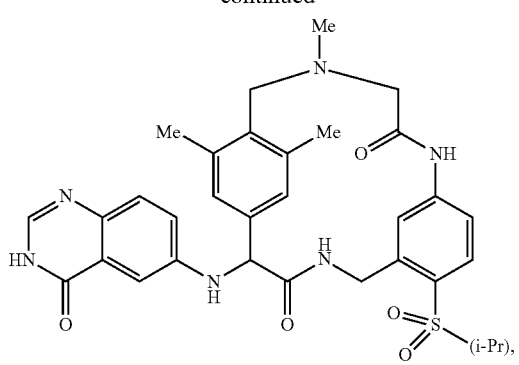
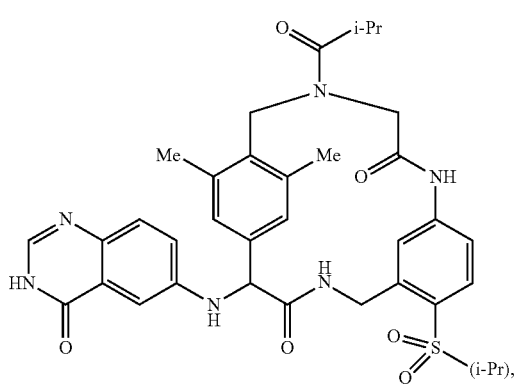
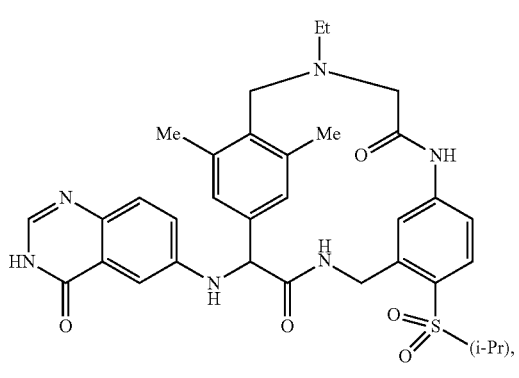
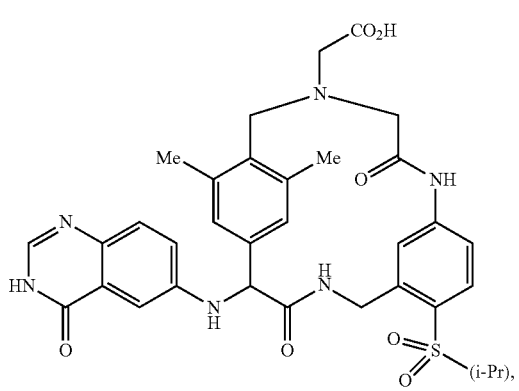
446
-continued
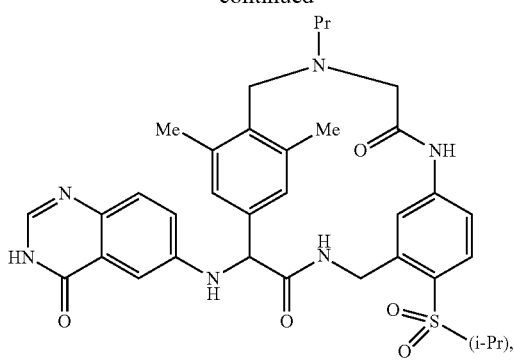
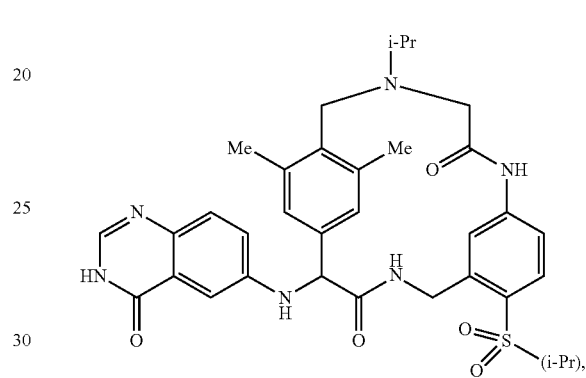
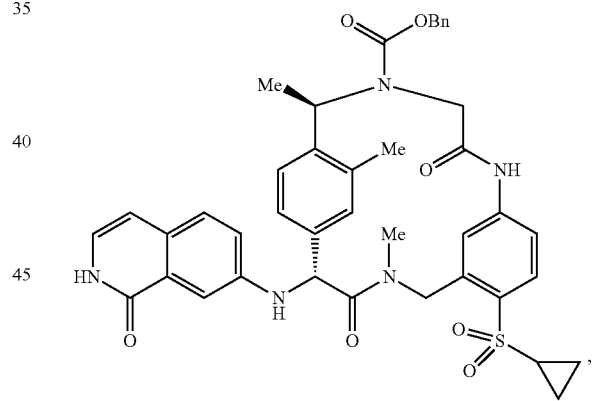
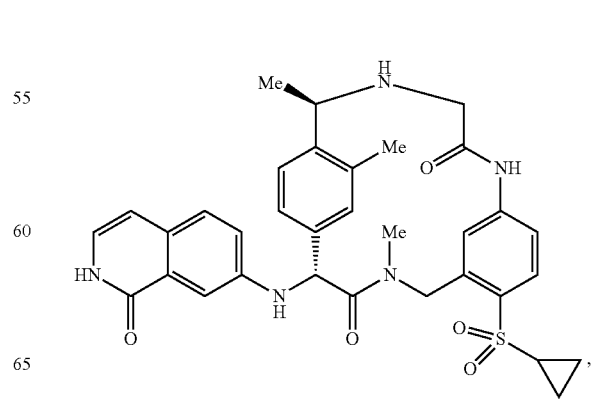

447
-continued
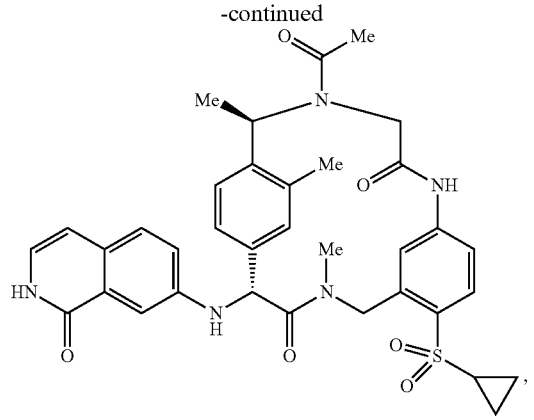
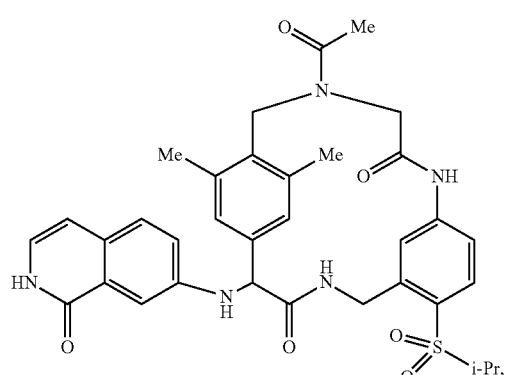
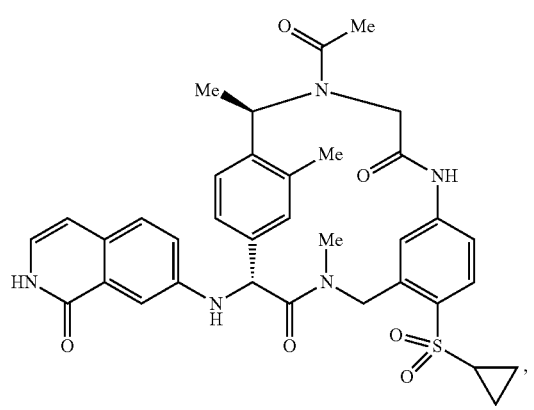
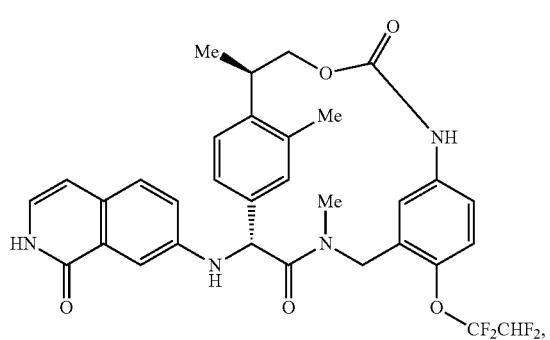
448
-continued
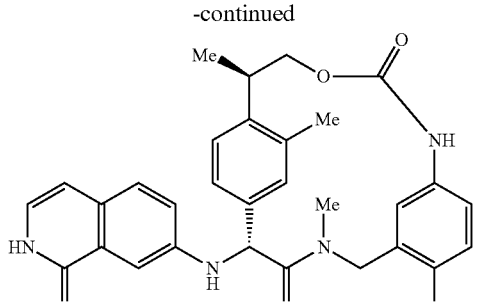
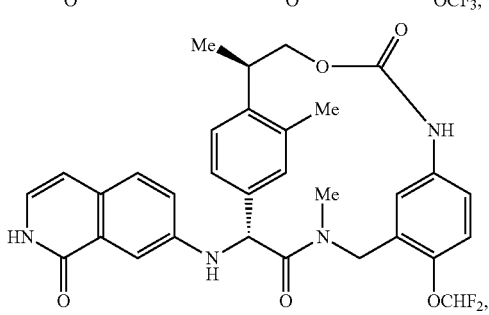
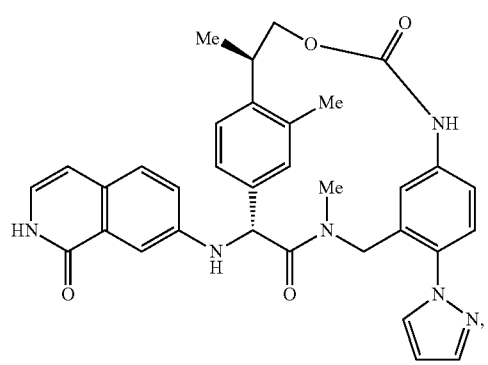
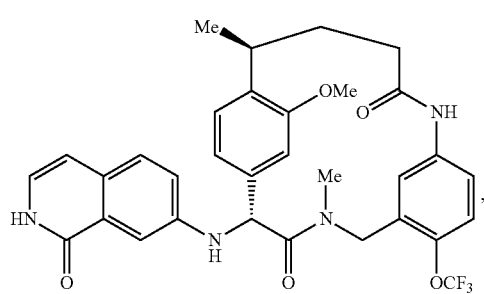
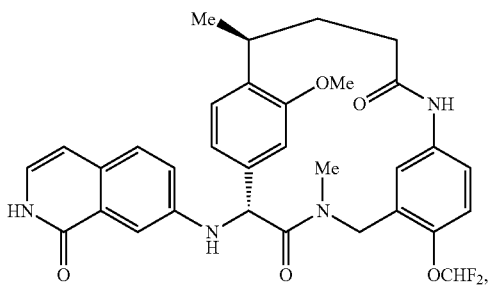

449

-continued

450

-continued

451
-continued
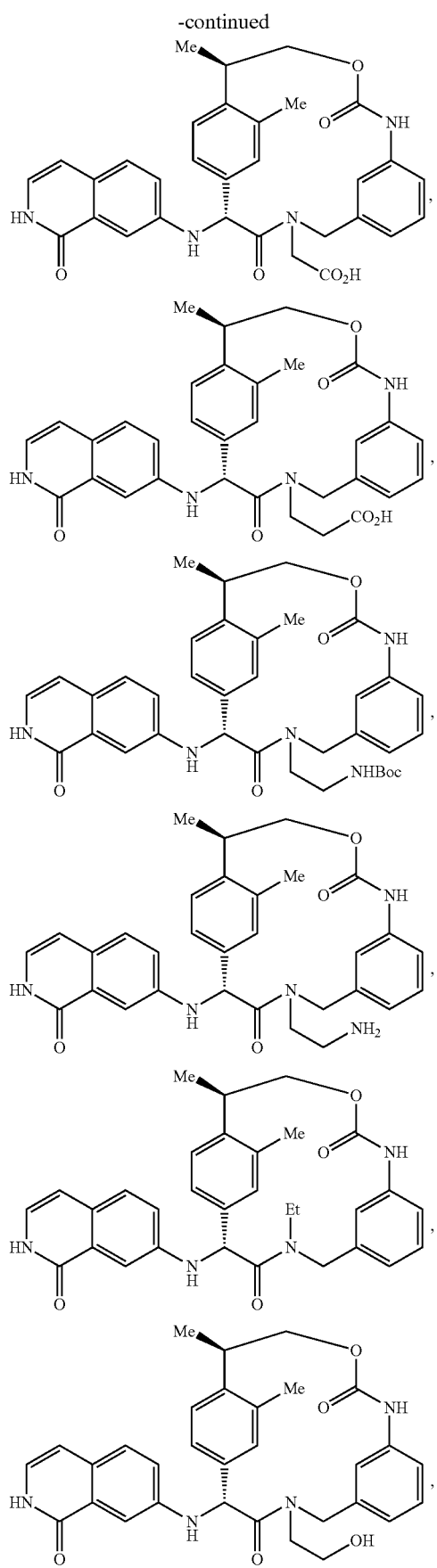
452
-continued
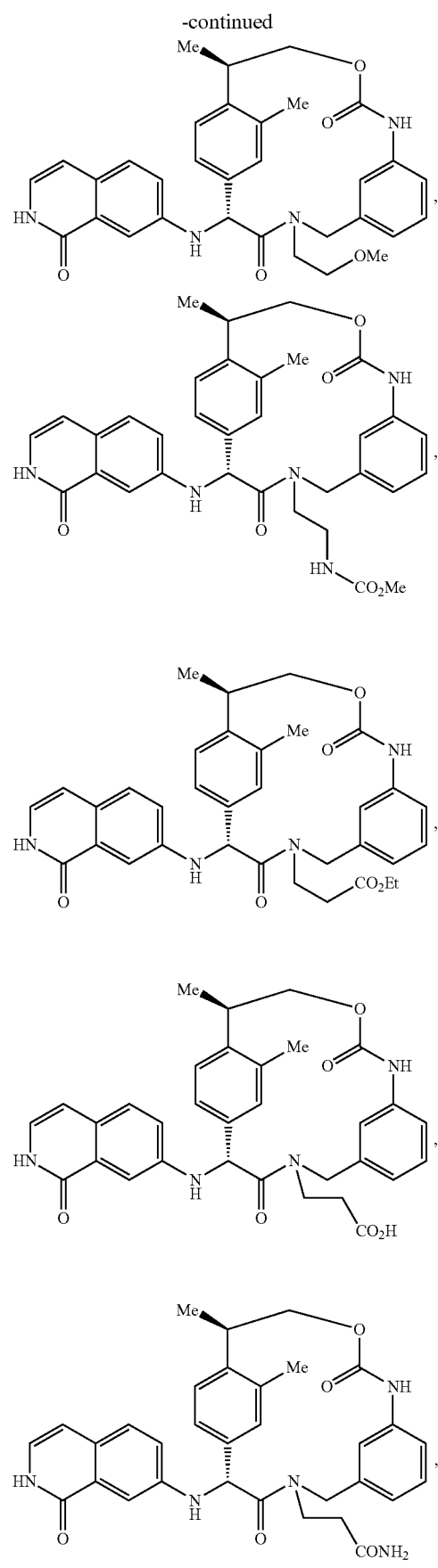

453
-continued
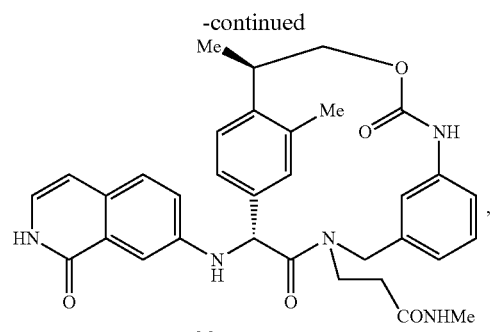
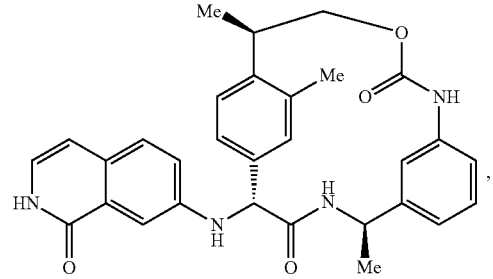
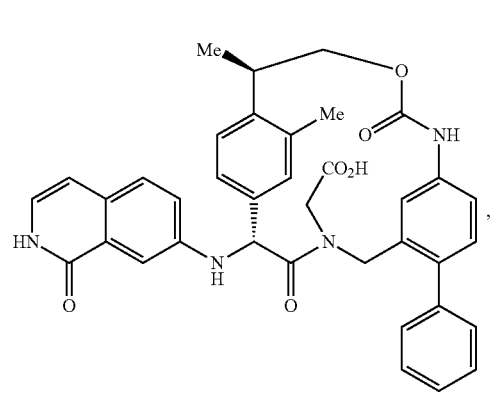
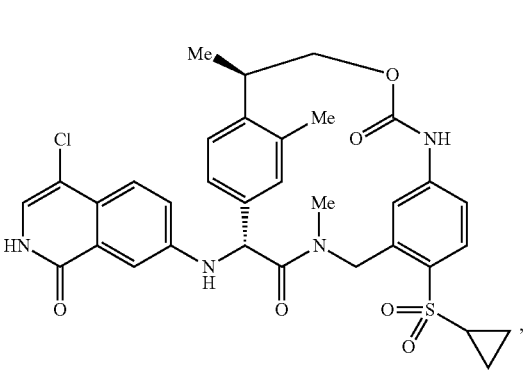
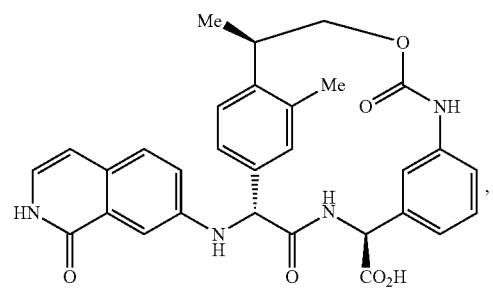
454
-continued
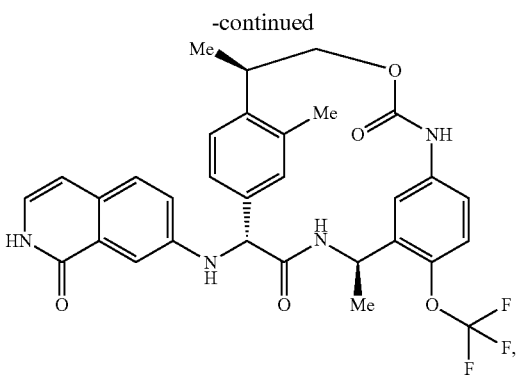
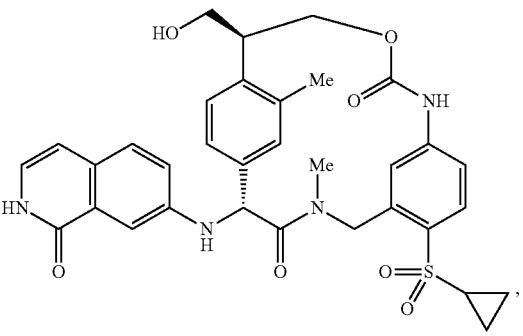
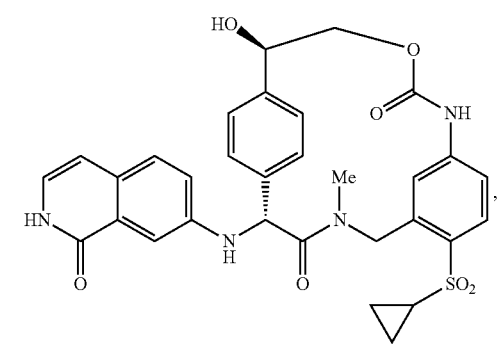
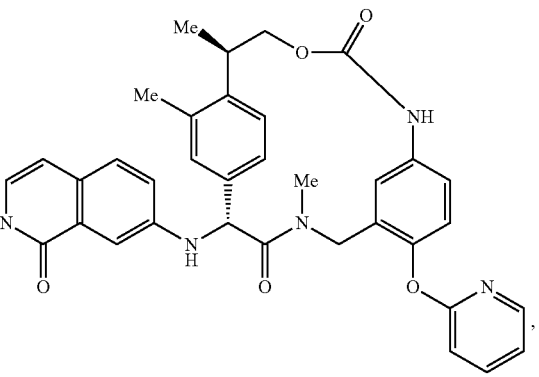

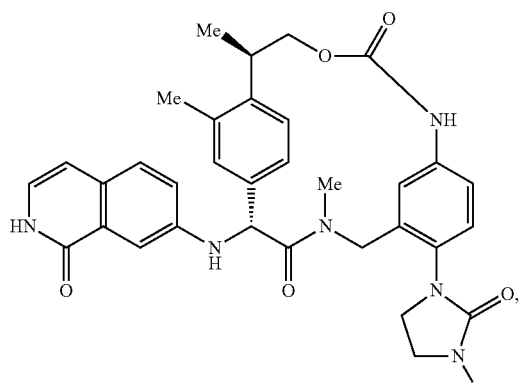
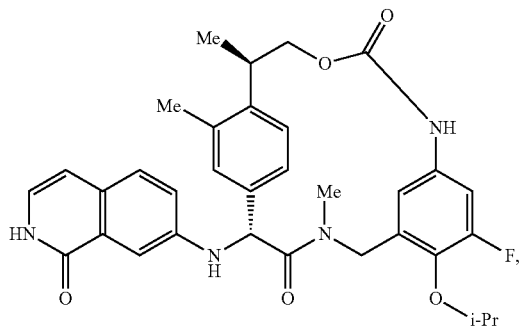
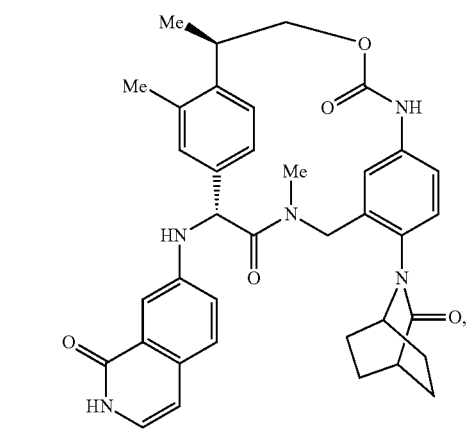
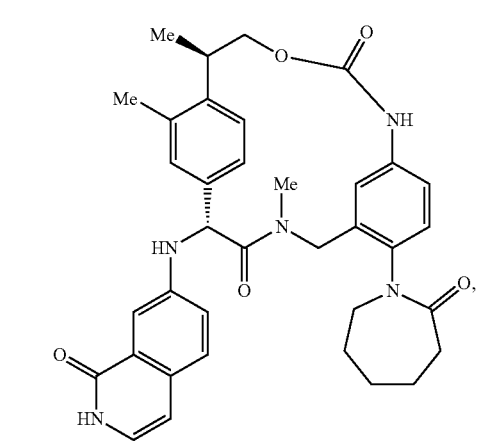
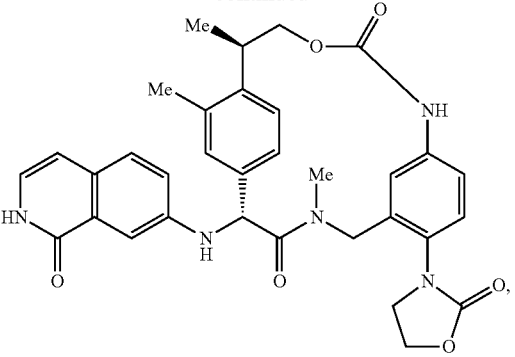
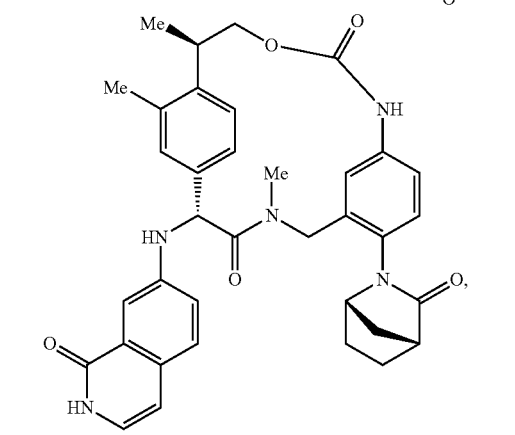
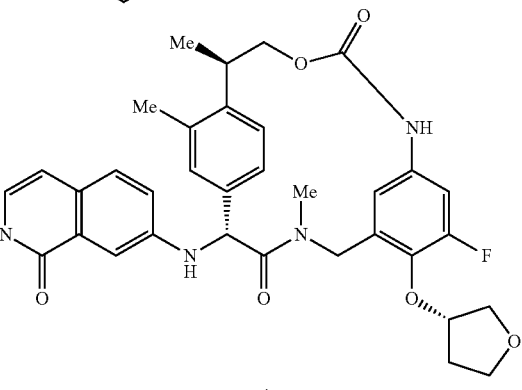
and
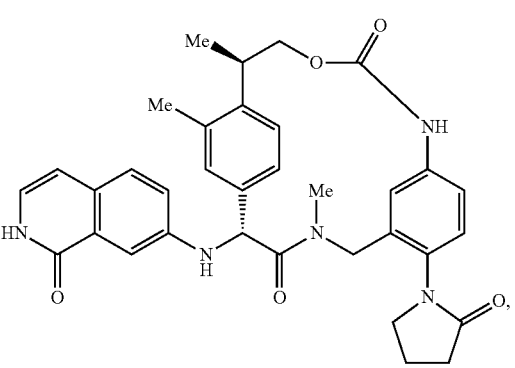
or a pharmaceutically acceptable salt thereof.
17. A pharmaceutical composition, comprising: a pharmaceutically acceptable carrier and a compound of claim 16.
* * * * *

UNITED STATES PATENT AND TRADEMARK OFFICE
CERTIFICATE OF CORRECTION

PATENT NO. : 8,420,830 B2
APPLICATION NO. : 12/519376
DATED : April 16, 2013
INVENTOR(S) : Nicholas Ronald Wurtz et al.

It is certified that error appears in the above-identified patent and that said Letters Patent is hereby corrected as shown below:

In the Claims:

Column 410
Line 59, "$R^{21}$:" should read -- $R^{21}$; --; and
Line 65, ")y" should read -- )Y --.

Column 411
Line 46, "C," should read -- Cl, --;
Line 57, "$CH_2CH_2OR^a$," should read -- -$CH_2CH_2OR^a$, --; and
Line 58, "-$CH_2H_2CO_2R^a$," should read -- -$CH_2CH_2CO_2R^a$, --.

Column 412
Line 1, "$CH_2OR^a$," should read -- -$CH_2OR^a$, --;
Line 1, "$C(O)NR^cR^d$," should read -- -$C(O)NR^cR^d$, --;
Line 22, "-$(CH_2)_5CN$," should read -- -$(CH_2)_5CN$, --; and
Line 37, "$R^f$," should read -- $R^{f1}$, --.

Column 413
Line 43, "$R^{g1}$:" should read -- $R^{g1}$; --; and
Line 63, "RE;" should read -- $R^g$; --.

Column 414
Line 47, ")$_3$)" should read -- ) --.

Column 418
Line 26, "—I," should read -- H, --; and
Line 39, "mL" should read -- in L --.

Signed and Sealed this
Fifteenth Day of October, 2013

Teresa Stanek Rea
*Deputy Director of the United States Patent and Trademark Office*

CERTIFICATE OF CORRECTION (continued)
U.S. Pat. No. 8,420,830 B2

Column 430
Lines 25-39 (approx.),

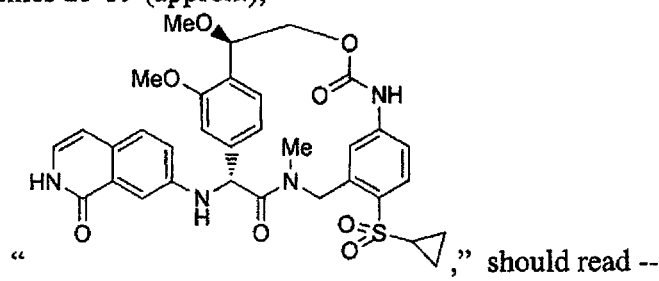 " should read -- 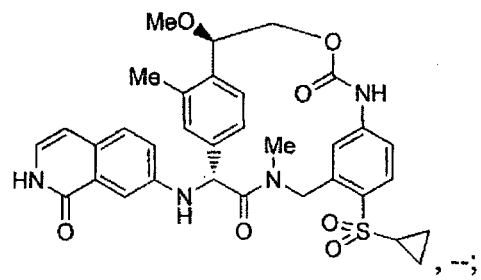 , --;

Lines 40-51 (approx.),

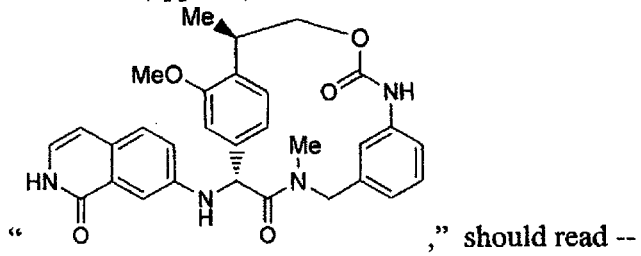 " should read -- 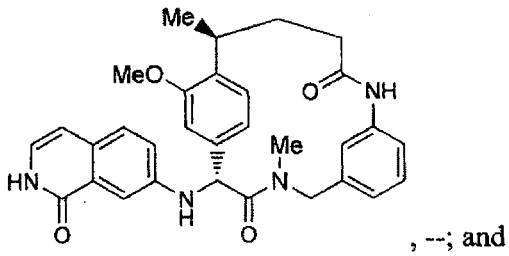 , --; and

Column 430 (cont.)
Lines 53-67 (approx.),

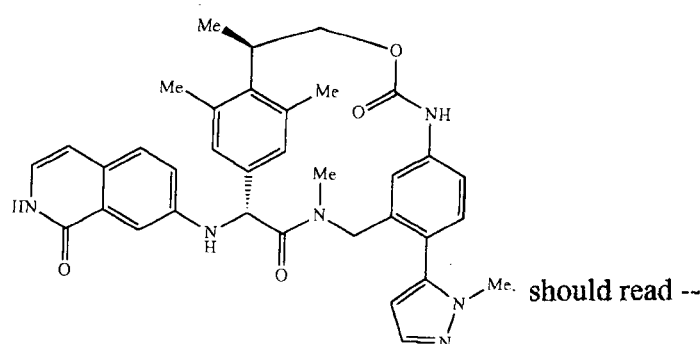 should read -- 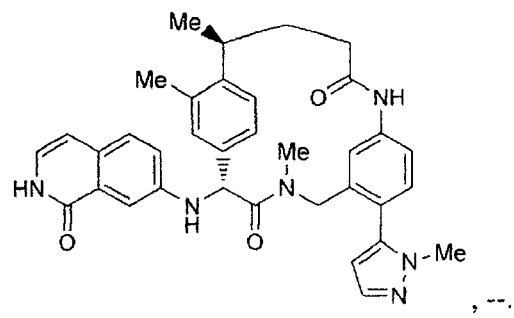 , --.

Column 431
Lines 1-12 (approx.),

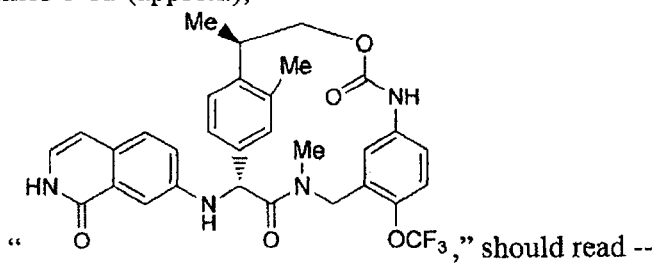 " should read -- 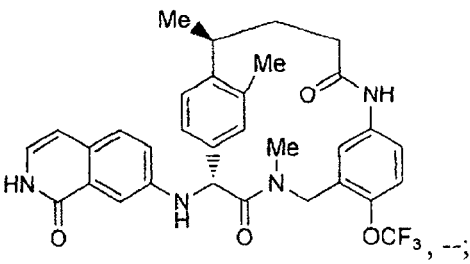 , --;

CERTIFICATE OF CORRECTION (continued)
U.S. Pat. No. 8,420,830 B2

Column 431 (cont.)
Lines 13-23 (approx.),
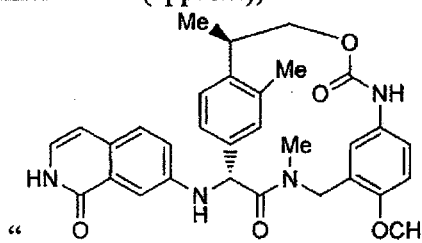 " should read -- 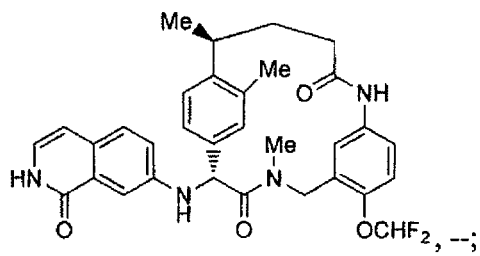 --;

Lines 24-34 (approx.),
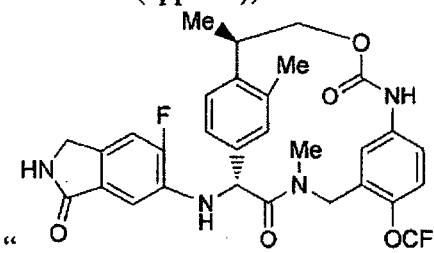 " should read -- 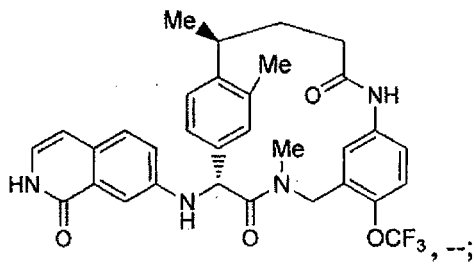 --;

Lines 35-45 (approx.),
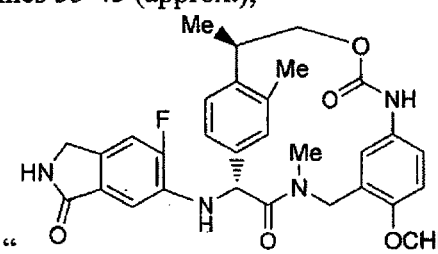 " should read -- 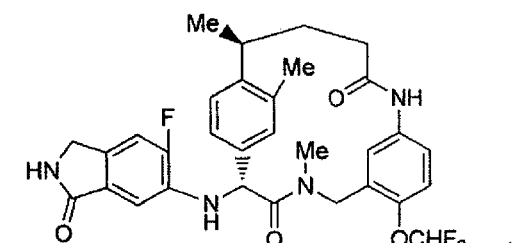 --;

Column 431 (cont.)
Lines 46-55 (approx.),
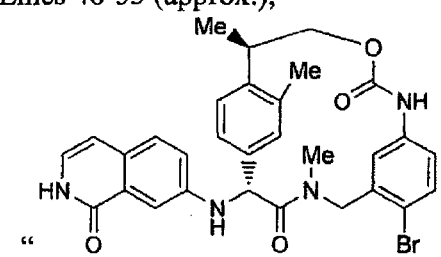 " should read -- 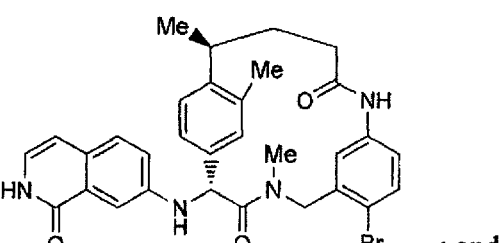 , --; and Lines 56-67 (approx.),
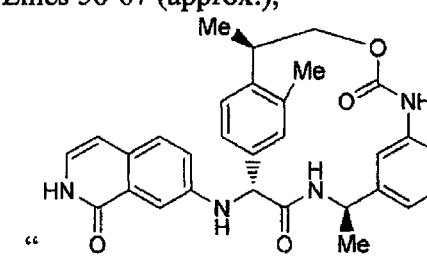 " should read -- 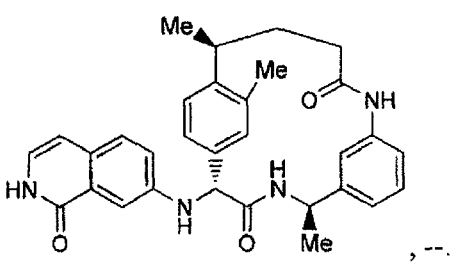 , --.

CERTIFICATE OF CORRECTION (continued)
U.S. Pat. No. 8,420,830 B2

Column 432
Lines 1-12 (approx.),
" 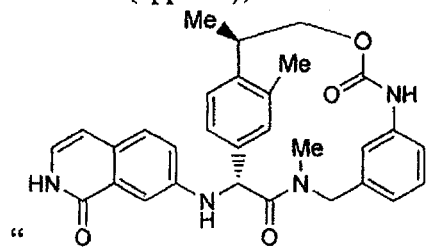 ," should read -- 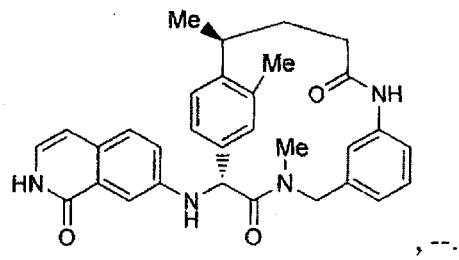 , --.

Column 434
Lines 1-14 (approx.),
" 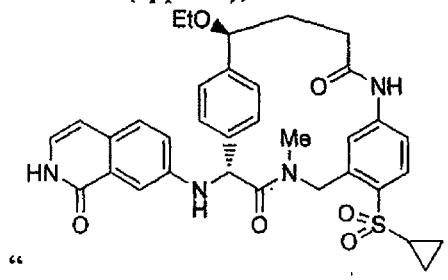 ," should read -- 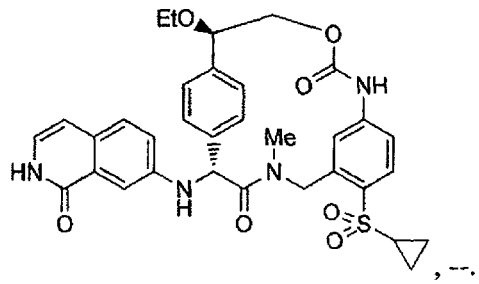 , --.

Column 449
Lines 15-25 (approx.),
" 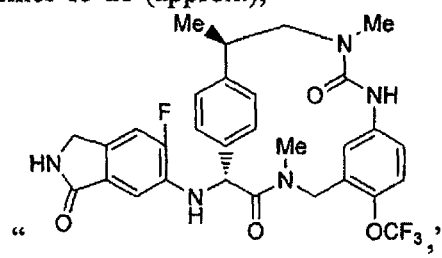 ," should read -- 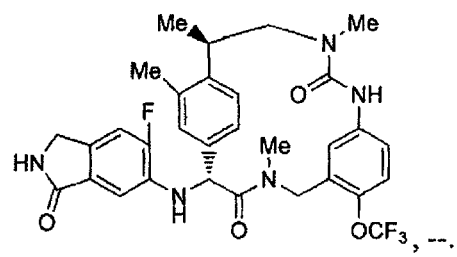 , --.

Column 454
Lines 1-15 (approx.),
" 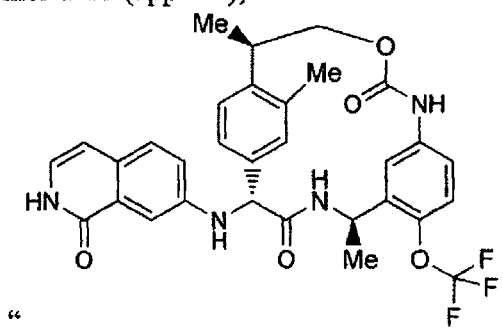 ," should read -- 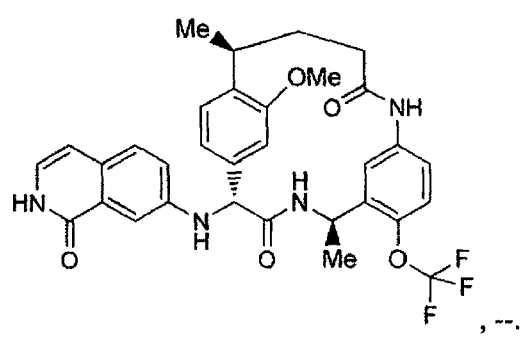 , --.

Column 454 (cont.)
Lines 35-47 (approx.),
" 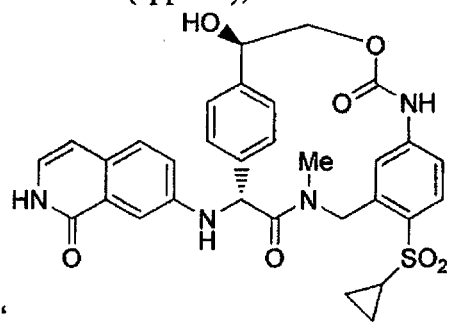 ," should read -- 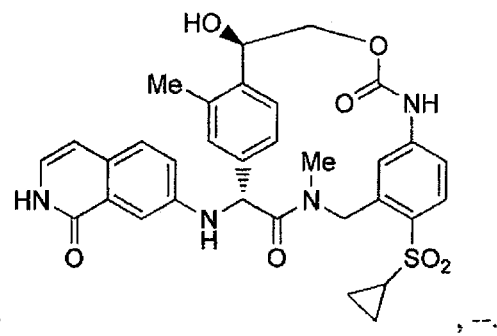 , --.